US007829694B2

(12) United States Patent
Kaemmerer

(10) Patent No.: US 7,829,694 B2
(45) Date of Patent: *Nov. 9, 2010

(54) TREATMENT OF NEURODEGENERATIVE DISEASE THROUGH INTRACRANIAL DELIVERY OF SIRNA

(75) Inventor: William F. Kaemmerer, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/852,997

(22) Filed: May 25, 2004

(65) Prior Publication Data

US 2004/0220132 A1 Nov. 4, 2004

(51) Int. Cl.
*C07H 21/04* (2006.01)
*C12N 15/00* (2006.01)

(52) U.S. Cl. ...................................... 536/24.5; 435/455

(58) Field of Classification Search ....................... None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,888,829 A | 12/1989 | Kleinerman et al. | |
| 4,965,188 A | 10/1990 | Mullis et al. | |
| 5,236,908 A | 8/1993 | Gruber et al. | |
| 5,354,326 A | 10/1994 | Comben et al. | |
| 5,534,350 A | 7/1996 | Liou | |
| 5,624,803 A | 4/1997 | Noonberg et al. | |
| 5,639,275 A | 6/1997 | Baetge et al. | |
| 5,702,716 A | 12/1997 | Dunn et al. | |
| 5,720,720 A | 2/1998 | Laske et al. | |
| 5,735,814 A | 4/1998 | Elsberry et al. | |
| 5,782,892 A | 7/1998 | Castle et al. | |
| 5,795,715 A * | 8/1998 | Livache et al. | 435/6 |
| 5,800,390 A | 9/1998 | Hayakawa et al. | |
| 5,814,014 A | 9/1998 | Elsberry et al. | |
| 5,840,059 A | 11/1998 | March et al. | |
| 5,882,561 A | 3/1999 | Barsoum et al. | |
| 5,925,310 A | 7/1999 | Nakayama et al. | |
| 5,942,455 A | 8/1999 | Barsoum et al. | |
| 5,968,059 A | 10/1999 | Ellis et al. | |
| 5,997,525 A | 12/1999 | March et al. | |
| 6,042,579 A | 3/2000 | Elsberry et al. | |
| 6,093,180 A | 7/2000 | Elsberry | |
| 6,110,459 A | 8/2000 | Mickle et al. | |
| 6,151,525 A | 11/2000 | Soykan et al. | |
| 6,180,613 B1 | 1/2001 | Kaplitt et al. | |
| 6,187,906 B1 | 2/2001 | Gluckman et al. | |
| 6,231,969 B1 | 5/2001 | Knight et al. | |
| 6,245,884 B1 | 6/2001 | Hook | |
| 6,281,009 B1 | 8/2001 | Boyce | |
| 6,291,243 B1 | 9/2001 | Fogarty et al. | |
| 6,294,202 B1 | 9/2001 | Burns et al. | |
| 6,300,539 B1 | 10/2001 | Morris | |
| 6,309,634 B1 | 10/2001 | Bankiewicz et al. | |
| 6,310,048 B1 | 10/2001 | Kumar | |
| 6,313,268 B1 | 11/2001 | Hook | |
| 6,319,905 B1 | 11/2001 | Mandel et al. | |
| 6,331,427 B1 * | 12/2001 | Robison | 435/226 |
| 6,343,233 B1 | 1/2002 | Werner et al. | |
| 6,372,250 B1 | 4/2002 | Pardridge | |
| 6,372,721 B1 | 4/2002 | Neuman et al. | |
| 6,376,471 B1 | 4/2002 | Lawrence, III et al. | |
| 6,436,392 B1 | 8/2002 | Engelhardt et al. | |
| 6,436,708 B1 | 8/2002 | Leone et al. | |
| 6,461,989 B1 | 10/2002 | El-Raghy et al. | |
| 6,468,524 B1 | 10/2002 | Chiorini et al. | |
| 6,551,290 B1 | 4/2003 | Elsberry et al. | |
| 6,594,880 B2 | 7/2003 | Elsberry | |
| 6,609,020 B2 | 8/2003 | Gill | |
| 6,632,671 B2 | 10/2003 | Unger | |
| 6,659,995 B1 | 12/2003 | Taheri | |
| 6,870,030 B2 * | 3/2005 | Powell et al. | 530/350 |
| 6,945,969 B1 | 9/2005 | Morris et al. | |

(Continued)

FOREIGN PATENT DOCUMENTS

WO WO9220400 11/1992

(Continued)

OTHER PUBLICATIONS

Paxinos et al. (2001) The Mouse Brain in Stereotaxic Coordinates. Academic Press, 2nd Ed. (selected pages).*

(Continued)

*Primary Examiner*—Louis Wollenberger
(74) *Attorney, Agent, or Firm*—Kenneth J. Collier; Gerard P. Norton; Fox Rothschild LLP

(57) ABSTRACT

The present invention provides devices, small interfering RNA, and methods for treating a neurodegenerative disorder comprising the steps of surgically implanting a catheter so that a discharge portion of the catheter lies adjacent to a predetermined infusion site in a brain, and discharging through the discharge portion of the catheter a predetermined dosage of at least one substance capable of inhibiting production of at least one neurodegenerative protein. The present invention also provides valuable small interfering RNA vectors, and methods for treating neurodegenerative disorders such as Alzheimer's disease, Parkinson's disease, Huntington's disease, Spinocerebellar Ataxia Type 1, Type 2, Type 3, and/or dentatorubral-pallidoluysian atrophy.

10 Claims, 13 Drawing Sheets

U.S. PATENT DOCUMENTS

| | | | | |
|---|---|---|---|---|
| 7,189,222 | B2 * | 3/2007 | Elsberry | 604/506 |
| 7,320,965 | B2 | 1/2008 | Sah et al. | |
| 2001/0027309 | A1 | 10/2001 | Elsberry | |
| 2001/0031947 | A1 | 10/2001 | Heruth | |
| 2002/0004038 | A1 | 1/2002 | Baugh et al. | |
| 2002/0068093 | A1 | 6/2002 | Trogolo et al. | |
| 2002/0114780 | A1 | 8/2002 | Bankiewicz | |
| 2002/0141980 | A1 | 10/2002 | Bankiewicz | |
| 2002/0187127 | A1 | 12/2002 | Bankiewicz | |
| 2003/0078229 | A1 | 4/2003 | Cooper et al. | |
| 2003/0088236 | A1 * | 5/2003 | Johnson et al. | 604/890.1 |
| 2003/0092003 | A1 | 5/2003 | Blatt et al. | |
| 2003/0095958 | A1 | 5/2003 | Bhisetti et al. | |
| 2003/0109476 | A1 | 6/2003 | Kmiec et al. | |
| 2003/0120282 | A1 | 6/2003 | Scouten et al. | |
| 2003/0143732 | A1 * | 7/2003 | Fosnaugh et al. | 435/325 |
| 2003/0152947 | A1 | 8/2003 | Crossman | |
| 2003/0175772 | A1 | 9/2003 | Wang | |
| 2003/0190635 | A1 * | 10/2003 | McSwiggen | 435/6 |
| 2003/0224512 | A1 * | 12/2003 | Dobie | 435/375 |
| 2004/0018520 | A1 | 1/2004 | Thompson | |
| 2004/0023390 | A1 | 2/2004 | Davidson | |
| 2004/0023855 | A1 | 2/2004 | John et al. | |
| 2004/0186422 | A1 | 9/2004 | Rioux | |
| 2004/0215164 | A1 | 10/2004 | Abott | |
| 2004/0220132 | A1 | 11/2004 | Kaemmerer | |
| 2004/0258666 | A1 | 12/2004 | Passini | |
| 2004/0259247 | A1 | 12/2004 | Tuschl | |
| 2004/0265849 | A1 | 12/2004 | Cargill | |
| 2004/0266707 | A1 | 12/2004 | Leake | |
| 2005/0032733 | A1 | 2/2005 | McSwiggen | |
| 2005/0042646 | A1 | 2/2005 | Davidson | |
| 2005/0048641 | A1 * | 3/2005 | Hildebrand et al. | 435/283.1 |
| 2005/0096284 | A1 | 5/2005 | McSwiggen | |
| 2005/0137134 | A1 | 6/2005 | Gill | |
| 2005/0153353 | A1 | 7/2005 | Meibohm | |
| 2005/0180955 | A1 | 8/2005 | Bankiewicz | |
| 2005/0202075 | A1 | 9/2005 | Pardridge | |
| 2005/0209179 | A1 | 9/2005 | McSwiggen | |
| 2005/0255086 | A1 | 11/2005 | Davidson | |
| 2005/0282198 | A1 | 12/2005 | Duff | |
| 2006/0009408 | A1 | 1/2006 | Davidson et al. | |
| 2006/0014165 | A1 | 1/2006 | Hackonarson | |
| 2006/0041242 | A1 | 2/2006 | Stypulkowski | |
| 2006/0150747 | A1 | 7/2006 | Mallett | |
| 2006/0210538 | A1 | 9/2006 | Kaplitt et al. | |
| 2006/0224411 | A1 | 10/2006 | Chang | |
| 2006/0257912 | A1 | 11/2006 | Kaemmerer | |
| 2007/0031844 | A1 | 2/2007 | Khvorova et al. | |
| 2007/0184029 | A1 | 8/2007 | Mishra | |
| 2008/0113351 | A1 | 5/2008 | Naito | |
| 2009/0022864 | A1 | 1/2009 | Steenhof | |

FOREIGN PATENT DOCUMENTS

| | | | | |
|---|---|---|---|---|
| WO | WO 93/23569 | | | 11/1993 |
| WO | WO9323569 | | | 11/1993 |
| WO | WO 94/02595 | | | 2/1994 |
| WO | WO9402595 | | | 2/1994 |
| WO | WO9618736 | | | 6/1996 |
| WO | WO 9618736 | | | 6/1996 |
| WO | WO 97/40874 | | | 11/1997 |
| WO | WO9740847 | | | 11/1997 |
| WO | WO9846273 | | | 10/1998 |
| WO | WO9846740 | | | 10/1998 |
| WO | WO9939744 | | | 8/1999 |
| WO | WO 99/50300 | A1 | | 10/1999 |
| WO | WO 99/50300 | A1 | | 10/1999 |
| WO | WO9950300 | | | 10/1999 |
| WO | WO 00/30567 | | | 6/2000 |
| WO | WO0030567 | | | 6/2000 |
| WO | WO 00/64505 | | | 11/2000 |
| WO | WO0064505 | | | 11/2000 |
| WO | WO 01/16312 | A2 | | 3/2001 |
| WO | WO0116312 | | | 3/2001 |
| WO | WO 01/49844 | A1 | | 7/2001 |
| WO | WO0149844 | | | 7/2001 |
| WO | WO 0149844 | A1 | * | 7/2001 |
| WO | WO 01/60794 | A2 | | 8/2001 |
| WO | WO0160794 | | | 8/2001 |
| WO | WO0170276 | | | 9/2001 |
| WO | WO0180840 | | | 11/2001 |
| WO | WO 01/91801 | A2 | | 12/2001 |
| WO | WO0191801 | | | 12/2001 |
| WO | WO 02/07810 | | | 1/2002 |
| WO | WO0205804 | | | 1/2002 |
| WO | WO0207810 | | | 1/2002 |
| WO | WO0222177 | | | 3/2002 |
| WO | WO03042385 | | | 5/2003 |
| WO | WO 03/047676 | A1 | | 6/2003 |
| WO | WO03047676 | | | 6/2003 |
| WO | WO 03/053516 | A1 | | 7/2003 |
| WO | WO03053516 | | | 7/2003 |
| WO | WO 03/070895 | A2 | | 8/2003 |
| WO | WO03070895 | | | 8/2003 |
| WO | WO 03/099298 | A1 | | 12/2003 |
| WO | WO03099298 | | | 12/2003 |
| WO | WO03102131 | | | 12/2003 |
| WO | WO2004007718 | | | 1/2004 |
| WO | WO 2004/013280 | | | 2/2004 |
| WO | WO2004010787 | | | 2/2004 |
| WO | WO2004013280 | | | 2/2004 |
| WO | WO2004013355 | | | 2/2004 |
| WO | WO2004/041101 | | | 5/2004 |
| WO | WO 2004/041101 | | | 5/2004 |
| WO | WO2004041101 | | | 5/2004 |
| WO | WO 2004/047872 | | | 6/2004 |
| WO | WO2004047872 | | | 6/2004 |
| WO | WO 2004/058940 | | | 7/2004 |
| WO | WO2004058940 | | | 7/2004 |
| WO | WO2004/084955 | | | 10/2004 |
| WO | WO 2004/084955 | | | 10/2004 |
| WO | WO2004084955 | | | 10/2004 |
| WO | WO2004/101063 | | | 11/2004 |
| WO | WO 2004/101063 | | | 11/2004 |
| WO | WO 2004/101787 | | | 11/2004 |
| WO | WO2004098648 | | | 11/2004 |
| WO | WO2004101063 | | | 11/2004 |
| WO | WO2005027980 | | | 3/2005 |
| WO | WO 2005/045034 | | | 5/2005 |
| WO | WO2005045034 | | | 5/2005 |
| WO | WO2005116204 | | | 8/2005 |
| WO | WO2005120581 | | | 12/2005 |
| WO | WO 2006006948 | A2 | * | 1/2006 |
| WO | WO2006022639 | | | 3/2006 |
| WO | WO2007039721 | | | 4/2007 |
| WO | WO2008005562 | | | 7/2007 |
| WO | WO2007087451 | | | 8/2007 |
| WO | WO2007139811 | | | 12/2007 |
| WO | WO2008004260 | | | 1/2008 |
| WO | WO2008021157 | | | 2/2008 |
| WO | WO2008046273 | | | 4/2008 |
| WO | WO2008143774 | | | 11/2008 |

OTHER PUBLICATIONS

Xia et al. (2002) Nature 20:1006-1010.*
Cahill et al. (1995) Atlas of Human Cross-sectional Anatomy, Wiley-Liss, 3rd ed. (selected pages).*
Whitesell et al. (1993) Proc. Natl. Acad. Sci. 90:4665-4669.*
Vassar et al. (1999) Science 286:735-741.*
Caplen et al. (2001) Proc. Natl. Acad. Sci. 98:9742-9747.*
Dorri et al. (1997) Exp. Neurology 147:48-54.*
Zhang et al. (1996) J. Mol. Neuroscience 7:13-28.*

Hooper et al. (1995) Neuroscience 63:917-924.*
Merriam-Webster OnLine dictionary entry for Catheter (1 page).*
The American Heritage Dictionary, 3rd Ed., selected definitions (2 pages).*
STIC-Biotech Sequence search results 1-3 (Db GeneSeq) (2 pages).*
Ezrin-Waters et al. (1986) Can J. Neurol. Sci. 13:8-14.*
Vickers et al. (2003) J. Biol. Chem. 278:7108-7118.*
Holen et al. (2002) Nucleic Acids Res. 30:1757-1766.*
Elbashir et al. (2002) Methods 26:199-213.*
Katahira et al. (2003) "Gene silencing in chick embryos with a vector-based small interfering RNA system" Develop. Growth Differ. 45: 361-367.*
Li et al, Predicting siRNA efficiency, Cellular and Molecular Life Sciences, 2007, pp. 1785-1792, vol. 64, Birkhauser Verlag, Basel, Switzerland.
Schwarz, Dianne S. et al, Designing siRNA that Distinguishes between Genes that Differ by a Single Nucleotide, PLoS Genetics, www.plosgenetics.org, Sep. 2006, pp. 1307-1318, vol. 2, Issue 9, e140.
Senn, Claudia et al, Central administration of small interfering RNAs in rats: A comparison with antisense oligonucleotides, European Journal of Pharmacology, 2005, pp. 30-37, vol. 522, Elsevier B.V.
Xu, Yunhe et al., Effective small interfering RNAs and phosphorothioate antisense DNAs have different preferences for target sites in the luciferase mRNAs, Biochemical and Biophysical Research Communications, 2003, pp. 712-717, vol. 306, Elsevier Science (USA).
Kashani-Sabet et al., Reversal of the Malignant Phenotype by an Anti-ras Ribozyme, Antisense Res. Dev., 2:3-15, 1992.
Kawarabayashi, T., et al, Age-Dependent Changes in Brain, CSF, and Plasma Amyloid β Protein in the Tg2576 Transgenic Mouse Model of Alzheimer's Disease, Journal of Neuroscience, 21(2):372-381, 2001.
King, D.L., et al, Behavioral Characterization of the Tg2576 Transgenic Model of Alzheimer's Disease Through 19 Months, Physiology & Behavior, 75:627-642, 2002.
Kitabwalla, Moiz, Ph.D., et al., RNA interference—a new weapon against HIV and beyond, New England Journal of Medicine, 347(17):1364-1367, 2002.
Klement, Ivan, et al., Ataxin-1 nuclear localization and aggregation: Role in polyglutamine-induced disease in SCA1 transgenic mice, Cell vol. 95:41-53, 1998.
L'Huillier, Phillip J., et al., Cytoplasmic delivery of ribozymes leads to efficient reduction in x-lactalbumin mRNA levels in C1271 mouse cells, EMBO Journal, 11(12):4411-4418, 1992.
Lisziewicz et al., Inhibition of human immunodeficiency virus type 1 replication by regulated expression of a polymeric Tat activation response RNA decoy as a strategy for gene therapy in AIDS, Proc. National Acad Sci USA, 90:8000-8004, 1993.
Matilla, A., et al., Mice lacking ataxin-1 display learning deficits and decreased hippocampal paired-pulse facilitation, Journal of Neuroscience, 18(14):5508-5516, 1998.
McGarry, Thomas J., et al., Inhibition of heat shock protein synthesis by heat-inducible antisense RNA, Proc. National Academy Science, USA, 83:399, 1986.
McManus, Michael T., Gene Silencing in Mammals by Small Interfering RNAs, Nature Reviews / Genetics, 3:737-747, 2002.
Miller, Victor M., Allele-specific silencing of dominant disease genes, PNAS, 100(12):7195-7200, 2003.
Naldini, Luigi, Efficient transfer, integration and sustained long-term expression of the transgene in adult rat brains injected with a lentiviral vector, Proc. National Academy Science, 93:11382-11388, 1996.
Noonberg, et al., In vivo generation of highly abundant sequence-specific oligonucleotides for antisense and triplex gene regulation, Nucleic Acid Research, 22(14):2830-2836, 1994.
Ohkawa, et al., Activities of HIV-RNA targeted riboyzmes transcribed from a shot-gun type riboyzme-trimming plasmid, Nucleic Acids Symp. Ser., 27:15-16, 1992.
Ojwang, Joshua O., et al., Inhibition of human immunodeficiency virus type-1 expressoin by a hairpin ribozyme, Proc. National Academy Science USA, 89:10802-10806, 1992.
Sarver, Nava et al., Ribozymes as potential anti-HIV-1 therapeutic agents, Science, 247:1222-1225, 1990.
Scanlon, K.J., et al., Ribozyme-mediated cleavage of c-fos mRNA rduces gene expression of DNA synthesis enzymes and metallothionein, Proc. National Academy Science USA, 88:10591-10595, 1991.
Stackman, Robert W., et al, Prevention of Age-Related Spatial Memory Deficits in a Transgenic Mouse Model of Alzheimer's Disease by Chronic Ginkgo biloba Treatment, Experimental Neurology, 184:510-520, 2003.
Sullenger, Bruce and Cech, Thomas R., Tethering Ribozymes to a Retroviral Packaging Signal for Destruction of Viral RNA, Science, 262:1566, 1993.
Taira, Kazunari, et al, Construction of a Novel RNA-Transcript-Trimming Plasmid which can be used Both in-vitro in Place of Run-off and (G)-Free Transcriptions and in vivo as Multi-Sequences Transcription Vectors, Nucleic Acids Research, 19(19):5125-5130, 1991.
Thompson, James D., et al., Improved accumulation and activity of ribozymes expressed from a tRNA-based RNA polymerase III promoter, Nucleic Acids Res., 23(12):2259, 1995.
Ventura, M., et al, Activation of HIV-Specific Ribozyme Activity by Self-Cleavage, Nucleic Acids Research, 21(14):3249-3255, 1993.
Weerasinghe, Migara et al., Resistance to human immunodeficiency virus type 1 (HIV-1) infection in human CD4 lymphocyte-derived cell lines conferred by using retroviral vectors expressing an HIG-1 RNA-specific ribozyme, Journal of Virology, 65(10):5531-5534, 1991.
Xia, et al., sIRNA-mediated gene silencing in vitro and in vivo, Nature Biotechnology 20:1006-1010, 2002.
Yamamoto, A, et al., Reversal of neuropathology and motor dysfunction in a conditional model of Huntington's Disease, Cell, 101:57-66, 2000.
Yu et al., A hairpin riboyzme inhibits expression of diverse strains of human immunodeficiency virus type 1, Proc. Natl. Acad Sci. USA, 90:6340-6344, 1993.
Yu, Jenn-Yah et al., RNA interference by expression of short-interfering RNAs and hairpin RNAs in mammalian cells, PNAS, 99(9):6047-6052, 2002.
Aebisher, Trends in Neurosci. 24(9) 553-540 (Sep. 2001).
Altschul et al., "Gapped Blast and PSO-BLAST: a new generation of protein database search prorams," Nucl. Acids Res., 25(17): 3389-3402 (1997).
Ambion Inc., pSilencer™ 1.0-U6 siRNA Expression Vector, Catalog # 7207-20 μg, Nov. 2004, Austin, TX, 6 pgs.
Ambion Technical Bulletin #506 (as published on Nov. 16, 2002) downloaded from www.archive.org.
Ambion, Inc., Silencer siRNA® Construction Kit, Cat. #1620, Instruction Manual, Aug. 2005, 36 pgs.
Ausubel et al., Eds., Current Protocols in Molecular Biology, vols. 1-3, John Wiley & Sons, Inc., New York, NY, 1994; title page, publisher's page and table of contents only, 14 pgs.
Basi et al., "Antagonistic Effects of β-site Amyloid Precursor Protein-cleaving Enzymes 1 and 2 on β- Amyloid Peptide Production in Cells," J. Bio. Chem., Published, JBC Papers in Press, Jun. 2003; 278(34): 31512-31520.
Bass et al., Nature 411: 428-429 (2001).
Bertrand et al., Biochem Biophys Res Comm 296: 1000-1004 (2002).
Bodendorf et al., J. Neurochem. 80(5), 799-806 (Mar. 2002).
Boillee et al., "Gene therapy for ALS deliver," Trends in Neurosciences, May 2004; 27(5): 235-238.
Bortolin, Susan et al., "Analytical validation of the tag-it high-throughout microsphere-based universal array genotyping platform. Application to the multiplex detection of a panel of thrombophilia-associates single-nucleotide polymorphisms." American Association for Clinical Chemistry vol. 50(11) 2028-2036 (2004).
Brentano et al., P.N.A.S. 89:4099-4103 (1992).
Brummelkamp et al., Science 296: 550-553 (2002).
Burger et al., Mol. Ther. 10(2) 302-317 (Aug. 2004).
Cahill et al Atlas of Human Cross-Sectional Anatomy Wiley-Liss, 3rd Ed. (1995).
Cai et al., Nat. Neurosci. 4(3) 233-234 (2004).
Callahan Am. J. Pathol. 158(3) 1173-1177 (2001).
Caplen et al, Human Mol. Genet. 11(2) 175-184 (2002).
Chen et al., Nucl. Acid. Res. 20, 4581-4589 (1992).

Chi et al., "Genomewide view of gene silencing by small interfering RNAs," Proc. Natl. Acad. Sci. USA, May 2003; 100 (11): 6343-6346.
Chowhira et al., J. Biol. Chem. 269, 25856-25863 (1994).
Christman, Tissue Engineering (10) 403-409 (2004).
Cioffi et al., Biochem J. 365: 833-840 (2002).
Clark et al., Annals Int. Med. 138 400-411 (2003).
Clark et al., J. Neurosci. 17(19) 7385-7395 (1997).
Cleary et al., Nat. Neurosci. 8(1) 79-84 (ePub Dec. 19, 2004).
Couture et al., Trends in Genetics, 12(12) 510-515 (Dec. 1996).
Dai et al., Developmental Biology 285:80-90 (2005).
Davidson et al., The Lancet, Neurology 3, 145-149 (2004).
Demetriades J. Neurolog. Sci. 203-204, 247-251 (2002).
Dineley, J, Biol. Chem. 277 (25) 22768-22780 (2002).
Dorri et al., Exp. Neurology 147 48-54 (1997).
Dropulic et al., J. Virol. 66(1) 1432-1441 (1992).
During et al., "Subthalamic GAD GeneTransfer in Parkinson's Disease Patients Who Are Candidates for Deep Brain Stimulation," Human Gene Therapy, Aug. 2001; I2(12): 1587-1598.
ElBashir, EMBOJ 20(23) 6877-6888 (2001).
Erzin-Walters et al., Can. J. Neurol. Sci. 13, 8-14 (1986).
Fu et al., Mo. Ther. 8(6) 911-917 (Dec. 2003).
Gau, Am. J. Pathol., 160(2) 731-738 (2002).
GeneDetect.com Limited, Code GD100X-RV, (GeneDetect rAVE™ gene delivery reagent), copyright 2000-2002, Auckland, New Zealand, 2 pgs.
Geraerts et al., Concise Review: Therapeutic Strategies for Parkinson Disease Based on Modulation of Adult Neurogenesis. Stem Cells, Nov. 2, 2006, vol. 25, No. 2, pp. 263-270.
Gerlai Behav. Brain Res. 95 191-203 (1998).
Glorioso, Curr. Opinion in Drug Discovery and Dev't 5(2) Pharma Press ISSN 1367-6733 (2002).
Good et al., Gene Ther. 4:45-54 (1997).
Goto et al., Neurology, 60(5) Suppl. 1 p. A286 (Mar. 11, 2003).
Harrison et al., Mol. Cel. Neurosci. 24(3) 646-655 (2003).
Hartlage-Rubsamen et al., Glia 41(2) 169-179 (Dec. 28, 2002).
Heale et al., Nucl. Acid. Res. 22(3), 2005.
Holen et al., Nucl. Acid Res. 30:1757-1766 (2002).
Hommel et al., "Local gene knockdown in the brain using viral-mediated RNA interference," Nature Medicine, Dec. 2003; 9(12); 1539-1544.
Hommel et al., Society for Neuroscience Abstract, 2003, Abstract 325.14 (2003).
Hooper et al., Neuroscience 63, 917-924 (1995).
Hsiao et al, Science 274 99-102(1996).
Huwyler et al., "Brain drug delivery of small molecules using immunoliposomes,"Proc. Natl. Acad., USA, Nov. 1996;93:14164-14169.
Invitrogen, pShooter™ Vector (pCMV/myc© vectors), For the intracellular targeting of recombinant proteins and antibodies, Catalog Nos. V820-20, V821-20, V822-20, V823-20, Version E, copyright 1998-2001, 35 pgs.
Invitrogen, pTRACER™-CMV2, Catalog Nos. V885-01, V885-20, Version C, copyright 1998-2001, 21 pgs.
Isacson et al., Scandinavian Physiol. Society 179 173-177 (2003).
Izant et al., Science 299 345 (1985).
Kaemmerer et al., Soc. Neurosci. Meeting (Oct. 26, 2004).
Kao et al., "BACE1 Suppression by RNA Interference in Primary Cortical Neurons," J. Bio. Chem., Published, JBC Papers in Press, Nov. 2003, 2004; 279(3): 1942-1949.
Kashani-Sabet et al., Antisense Res. Dev. 2: 3-15 (1992).
Katz et al., Bioessays 11(6): 181-185 (Dec. 1989).
Kawarabayashi et al., J. Neurosci. 372-381 (2001).
Kenderell et al., (2000) Nat. Biotech. 17, 896-898 (2000).
King et al., Physiology & Behavior, 75: 627-642, 2002.
Kitabwala et al., New England J. Med. 347(17) 1364-1367 (Oct. 24, 2002).
Kitazume J. Biol. Chem. 280(9) 8589-8595 (Mar. 4, 2005).
Klement et al., Cell 95 41-53 (1998).
L'Huillier et al., EMBO J. 11(12), 4411-4418 (1992).
Laird et al., J. Neurosci. 25, 11693-11709 (Dec. 14, 2005).
Le Gal La Salle et al, Science 259, 988-990 (1993).
Li et al., Mol. Cell Bio. 22 (5) 1277-1287 (2002).
Lisziewicz et al., Proc. Nat. Acad. Sci 90 8000-8004 (Sep. 1993).
Liu et al., Proc. Japan Academy, Series B, Physical and Biol. Sciences 79(10) 293-298 (Dec. 1993).
Luo et al., Neurobiol. Dis. 14(1), 81-88 (Oct. 2003).
Luo, Nat. Neurosci. 4, 231-232 (2001).
MacDonald, M. et al., "A novel gene containing a trinucleotide repeat that is expanded and unstable on huntington's disease chromosomes," Cell, vol. 72, 971-983 (1993).
Mas-Monteys, A. et al., "Allele-Specific silencing of mutant huntingtin for huntington's disease therapy", Molecular Therapy 13: S274-S275 (2006).
Matilla et al., J. Neurosci 18, 5508-5516 (1998).
McGarry et al., Proc. Natl Acad. Sci. 83, 399-403 (1986).
McManus et al., Nature Reviews/Genetics 3, 737-747 (Oct. 2002).
Menei et al Neurosurgery 34: 1058-1064 (1994).
Messier et al., Pharm. Biochem Behavior 63 313-318 (1999).
Miller et al Proc. Nat. Acad. Sci. 100(12) 7195-7200 (Jun. 10, 2003).
Mirus, TransIT-Neural® Transfection Reagent, Product Nos. MIR 2144, MIR 2140, MIR 2145, MIR 2146, Lit. # ML022, Rev. Mar. 2, 2005, 5 pgs.
Mirus, TransIT-TKO® Transfection Reagent, Product Nos. MIR 2154, MIR 2150, MIR 2155, MIR 2156, Lit. # ML015, Rev. Jul. 2004, 6 pgs.
Mogan et al., JECT 36: 191-196 (2004).
Morel et al., J. Comparative Neurology 387, 588-630 (1997).
Mucke et al., J. Neurosci. 20(11) 4050-4058 (Jun. 1, 2000).
Naldini et al., Proc. Nat. Acad. Sci. 93, 11382-11388 (Oct. 1996).
National Center for Biotechnology Information, National Library of Medicine, National Institutes of Health, "What does NCBI do?" [online]. Bethesda, MD [retrieved on Dec. 5, 2005], Revised Dec. 2005. Retrieved from the Internet: <URL:http://www.ncbi.nlm.nih.gov>; 2 pgs.
National Center for Biotechnology Information, National Library of Medicine, National Institutes of Health, GenBank Locus AF163864, Accession No. AF163864, "Homo sapiens SNCA isoform (SNCA) gene, complete cds, alternatively spliced, " [online]. Bethesda, MD [retrieved on Jun. 21, 2004]. Retrieved from the Internet: <URL:http://www.ncbi.nlm.nih.gov/entrez/viewer.fcgi?db=nucleotide&val=11118351>; 43 pgs.
National Center for Biotechnology Information, National Library of Medicine, National Institutes of Health, GenBank Locus AF163865, Accession No. AF163865, "Mus musculus alpha-synuclein (Snca) gene, complete cds," [online]. Bethesda, MD [retrieved on Jun. 21, 2004]. Retrieved from the Internet<URL:http://www.ncbi.nlm.nih.gov/entrez/viewer.fcgi?db=nucleotide&val=11118354>; 33 pgs.
National Center for Biotechnology Information, National Library of Medicine, National Institutes of Health, GenBank Locus AH003045, Accession No. AH003045, "Homo sapiens huntingtin (HD) gene, exon 1," [online]. Bethesda, MD [retrieved on Mar. 5, 2009]. Retrieved from the Internet<URL:http://www.ncbi.nlm.nih.gov/entrez/viewer.fcgi?db=nucleotide&val=663286>; 42 pgs.
National Center for Biotechnology Information, National Library of Medicine, National Institutes of Health, GenBank Locus NM_000027, Accession No. NM_000027, "Homo sapiens aspartylglucosaminidase (AGA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=32313568>; 4 pgs.
National Center for Biotechnology Information, National Library of Medicine, National Institutes of Health, GenBank Locus NM_000046, Accession No. NM_000046, "Homo sapiens arylsulfatase B (ARSB), transcript variant 1, mRNA," [online]. Bethesda, MD [retrieved on Mar. 5, 2009]. Retrieved from the Intemet<URL:http://www.ncbi.nlm.nih.gov/entrez/viewer.fcgi?db=nucleotide&val=38569404>; 4 pgs.
National Center for Biotechnology Information, National Library of Medicine, National Institutes of Health, GenBank Locus NM_000049, Accession No. NM_000049, "Homo sapiens aspartoacylase (aminoacylase 1, Canavan disease) (ASPA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4557334>; 4 pgs.
National Center for Biotechnology Information, National Library of Medicine, National Institutes of Health, GenBank Locus NM_000147, Accession No. NM_000147, “Homo sapiens fucosidase, alpha-L1, tissue (FUCA1), mRNA,” [online]. Bethesda, MD [retrieved on Mar. 5, 2009]. Retrieved from the Internet:<URL:http://www.ncbi.nlm.nih.gov/entrez/viewer. fcgi?db=nucleotide&val=24475878>; 3 pgs.

National Center for Biotechnology Information, National Library of Medicine, National Institutes of Health, GenBank Locus NM_000152, Accession No. NM_000152, “Homo sapiens glucosidase, alpha; acid (Pompe disease, glycogen storage disease type II) (GAA), mRNA,” [online]. Bethesda, MD [retrieved on Mar. 5, 2009]. Retrieved from the Internet: <URL:http://www.ncbi.nlm. nih.gov/entrez/viewer.fcgi?db=nucleotide&val=11496988>; 4 pgs.

National Center for Biotechnology Information, National Library of Medicine, National Institutes of Health, GenBank Locus NM_000153, Accession No. NM_000153, “Homo sapiens galactosylceramidase (Krabbe disease) (GALC), mRNA,” [online]. Bethesda, MD [retrieved on Mar. 5, 2009]. Retrieved from the Internet<URL:http://www.ncbi.nlm.nih.gov/entrez/viewer. fcgi?db=nucleotide&val=4557612>; 5 pgs.

National Center for Biotechnology Information, National Library of Medicine, National Institutes of Health, GenBank Locus NM_000157, Accession No. NM_000157, “Homo sapiens glucosidase, beta; acid (includes glucosylceramidase) (GBA), mRNA,” [online]. Bethesda, MD [retrieved on Mar. 5, 2009]. Retrieved from the Internet:<URL:http://www.ncbi.nlm.nih.gov/ entrez/viewer.fcgi?db=nucleotide&val=4503934>; 7 pgs.

National Center for Biotechnology Information, National Library of Medicine, National Institutes of Health, GenBank Locus NM_000158, Accession No. NM_000158, “Homo sapiens glucan (1, 4-alpha-), branching enzyme 1 (glucogen branching enzyme, Andersen disease, glycogen storage disease trype (IV)(GBE1), mRNA,” [online]. Bethesda, MD [retrieved on Mar. 5, 2009]. Retrieved from the Internet:<URL:http://www.ncbi.nlm.nih.gov/ entrez/viewer.fcgi?db=nucleotide&val=4557618>; 2 pgs.

National Center for Biotechnology Information, National Library of Medicine, National Institutes of Health, GenBank Locus NM_000181, Accession No. NM_000181, “Homo sapiens glucuronidase, beta (GUSB), mRNA,” [online]. Bethesda, MD [retrieved on Mar. 5, 2009]. Retrieved from the Internet<URL:http:// www.ncbi.nlm.nih.gov/entrez/viewer.fcgi?db=nucleotide &val=4504222>; 4 pgs.

National Center for Biotechnology Information, National Library of Medicine, National Institutes of Health, GenBank Locus NM_000199, Accession No. NM_000199, “Homo sapiens N-sulfoglucosamine sulfohydrolase (sulfamidase) (SGSH), mRNA,” [online]. Bethesda, MD [retrieved on Mar. 5, 2009]. Retrieved from the Internet<URL:http://www.ncbi.nlm.nih.gov/entrez/viewer. fcgi?db=nucleotide&val=31543619>; 3 pgs.

National Center for Biotechnology Information, National Library of Medicine, National Institutes of Health, GenBank Locus NM_000202, Accession No. NM_000202, “Homo sapiens iduronate 2-sulfatase (Hunter syndrome)(ID), transcript variant 1, mRNA,” [online]. Bethesda, MD [retrieved on Mar. 5, 2009]. Retrieved from the Internet<URL:http:// www.ncbi.nlm.nih.gov/ entrez/viewer.fcgi?db=nucleotide&val=5360215>; 8 pgs.

National Center for Biotechnology Information, National Library of Medicine, National Institutes of Health, GenBank Locus NM_000203, Accession No. NM_000203, “Homo sapiens iduronidase, alpha-L-(IDUA), mRNA,” [online]. Bethesda, MD [retrieved on Mar. 5, 2009]. Retrieved from the Internet<URL:http:// www.ncbi.nlm.nih.gov/entrez/viewer.fcgi?db=nucleotide &val=40354208>: 6 pgs.

National Center for Biotechnology Information, National Library of Medicine, National Institutes of Health, GenBank Locus NM_000235, Accession No. NM_000235, “Homo sapiens lipase A, lysosomal acid, cholesterol esterase (Wolman disease) (LIPA), mRNA,” [online]. Bethesda, MD [retrieved on Mar. 5, 2009]. Retrieved from the Internet: <URL:http://www.ncbi.nlm.nih.gov/ entrez/viewer.fcgi?db=nucleotide&val=4557720>: 4 pgs.

National Center for Biotechnology Information, National Library of Medicine, National Institutes of Health, GenBank Locus NM_000262, Accession No. NM_000262, “Homo sapiens N-acetylgalactosaminidase, alpha-(NAGA), mRNA,” [online]. Bethesda, MD [retrieved on Mar. 5, 2009]. Retrieved from the Internet<URL:http://www.ncbi.nlm.nih.gov/entrez/viewer. fcgi?db=nucleotide&val=4557780>; 4 pgs.

National Center for Biotechnology Information, National Library of Medicine, National Institutes of Health, GenBank Locus NM_000263, Accession No. NM_000263, “Homo sapiens N-acetylglucosaminidase, alpha-(Sanfilippo disease) (IIIB)(NAGLU), mRNA,” [online]. Bethesda, MD [retrieved on Mar. 5, 2009]. Retrieved from the Internet<URL:http:// www.ncbi.nlm. nih.gov/entrez/viewer.fcgi?db=nucleotide&val=40548380>: 4 pgs.

National Center for Biotechnology Information, National Library of Medicine, National Institutes of Health, GenBank Locus NM_000310, Accession No. NM_000310, “Homo sapiens palmitoyl-protein thioesterase 1 (ceroid-lipofuscinosis, neuronal 1, infantile) (PPT1), mRNA,” [online]. Bethesda, MD [retrieved on Mar. 5, 2009]. Retrieved from the Internet: <URL:http://www.ncbi. nlm.nih.gov/entrez/viewer.fcgi?db=nucleotide&val=4506030>; 4 pgs.

National Center for Biotechnology Information, National Library of Medicine, National Institutes of Health, GenBank Locus NM_000332, Accession No. NM_000332, “Homo sapiens spinocerebellar ataxia 1 (olivopontocerebellar ataxia 1, autosomal dominant, ataxin 1) (SCA1), mRNA,” [online]. Bethesda, MD [retrieved on Mar. 5, 2009]. Retrieved from the Internet<URL:http:// www.ncbi.nlm.nih.gov/entrez/viewer.fcgi?db=nucleotide &val=4506792>; 7 pgs.

National Center for Biotechnology Information, National Library of Medicine, National Institutes of Health, GenBank Locus NM_000345, Accession No. NM_000345, “Homo sapiens synuclein, alpha (nonA4 component of amyloid precursor) (SNCA), transcript variant NACP140, mRNA,” [online]. Bethesda, MD [retrieved on Mar. 5, 2009]. Retrieved from the Internet<URL:http:// www.ncbi.nlm.nih.gov/entrez/viewer.fcgi?db=nucleotide &val=6806896>; 6 pgs.

National Center for Biotechnology Information, National Library of Medicine, National Institutes of Health, GenBank Locus NM_000404, Accession No. NM_000404, “Homo sapiens glactosidase, beta 1 (GLB1), tranascript variant 179423, mRNA,” [online]. Bethesda, MD [retrieved on Mar. 5, 2009]. Retrieved from the Internet:<URL:http://www.ncbi.nlm.nih.gov/entrez/viewer. fcgi?db=nucleotide&val=10834965>: 5 pgs.

National Center for Biotechnology Information, National Library of Medicine, National Institutes of Health, GenBank Locus NM_000434, Accession No. NM_000434, “Homo sapiens sialidase 1 (lysosomal sialidase)(NEU1), mRNA,” [online]. Bethesda, MD [retrieved on Mar. 5, 2009]. Retrieved from the Internet<URL:http:// www.ncbi.nlm.nih.gov/entrez/viewer.fcgi?db=nucleotide &val=40806202>; 5 pgs.

National Center for Biotechnology Information, National Library of Medicine, National Institutes of Health, GenBank Locus NM_000487, Accession No. NM_000487, “Homo sapiens arysulfatase A (ARSA), mRNA,” [online]. Bethesda, MD [retrieved on Mar. 5, 2009 ]. Retrieved from the Internet:<URL:http://www. ncbi.nlm.nih.gov/entrez/viewer.fcgi?db=nucleotide &val=7262293>; 4 pgs.

National Center for Biotechnology Information, National Library of Medicine, National Institutes of Health, GenBank Locus NM_000512, Accession No. NM_000512, “Homo sapiens galactosamine (N-acetyl)-6-sulfate sulfatase (Morquio syndrome, mucopolysaccharidosis type IVA), (GALNS), mRNA,” [online]. Bethesda, MD [retrieved on Mar. 5, 2009 ]. Retrieved from the Internet<URL:http://www.ncbi.nlm.nih.gov/entrez/viewer. fcgi?db=nucleotide&val=9945384>: 4 pgs.

National Center for Biotechnology Information, National Library of Medicine, National Institutes of Health, GenBank Locus NM_000520, Accession No. NM_000520, “Homo sapiens hexosaminidase A (alpha polypeptide) (HEXA), mRNA,” [online]. Bethesda, MD [retrieved on Mar. 5, 2009 ]. Retrieved from the Internet<URL:http://www.ncbi.nlm.nih.gov/entrez/viewer. fcgi?db=nucleotide&val=13128865>; 5 pgs.

National Center for Biotechnology Information, National Library of Medicine, National Institutes of Health, GenBank Locus NM_000521, Accession No. NM_000521, “Homo sapiens hexosaminidase B (beta polypeptide) (HEXB), mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=13128866>; 6 pgs.

National Center for Biotechnology Information, National Library of Medicine, National Institutes of Health, GenBank Locus NM_000528, Accession No. NM_000528, "Homo sapiens mannosidase, alpha, class 2B, member 1 (MAN2B1), mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=10834967>; 4 pgs.

National Center for Biotechnology Information, National Library of Medicine, National Institutes of Health, GenBank Locus NM_000543, Accession No. NM_000543, "Homo sapiens sphingomyelin phosphodiesterase 1 acid lysosomal (acid sphingomyelinase) (SMPD1), mRNA," [online]. Bethesda, MD [retrieved on Mar. 5, 2009 ]. Retrieved from the Internet<URL:http://www.ncbi.nlm.nih.gov/entrez/viewer.fcgi?db=nucleotide &val=40254417>; 5 pgs.

National Center for Biotechnology Information, National Library of Medicine, National Institutes of Health, GenBank Locus NM_002076, Accession No. NM_002076, "Homo sapiens glucosamine (N-acetyl)-6-sulfatase (Sanfilippo disease)(IIID)(GNS), mRNA," [online]. Bethesda, Md [retrieved on Mar. 5, 2009 ]. Retrieved from the Internet:<URL: http://www.ncbi.nlm.nih.gov/entrez/viewer.fcgi?db=nucleotide&val=42490755>; 7 pgs.

National Center for Biotechnology Information, National Library of Medicine, National Institutes of Health, GenBank Locus NM_002778, Accession No. NM_0002778, Accession No. NM_000169, "Homo sapiens glactosidase, alpha (GLA), mRNA," [online]. Bethesda, MD [retrieved on Mar. 5, 2009 ]. Retrieved from the Internet<URL:http://www.ncbi.nlm.nih.gov/entrez/viewer.fcgi?db=nucleotide&val=4504008>; 4 pgs.

National Center for Biotechnology Information, National Library of Medicine, National Institutes of Health, GenBank Locus NM_002778, Accession No. NM_002778, "Homo sapiens prosaposin (variant Gaucher disease and variant metachromatic leukodystrophy) (PSAP), mRNA," [online]. Bethesda, MD [retrieved on Mar. 5, 2009 ]. Retrieved from the Internet: <URL:http://www.ncbi.nlm.nih.gov/entrez/viewer.fcgi?db=nucleotide&val=11386146>; 8 pgs.

National Center for Biotechnology Information, National Library of Medicine, National Institutes of Health, GenBank Locus NM_004315, Accession No. NM_004315, "Homo sapiens N-acylsphingosine amidohydrolase (acid ceramidase) 1 (ASAHI), transcript variant 2, mRNA," [online]. Bethesda, MD [retrieved on Mar. 5, 2009 ]. Retrieved from the Internet: <URL:http://www.ncbi.nlm.nih.gov/entrez/viewer.fcgi?db=nucleotide&val=30089929>; 5 pgs.

National Center for Biotechnology Information, National Library of Medicine, National Institutes of Health, GenBank Locus NM_004993, Accession No. NM_004993, "Homo sapiens Machado-Joseph disease (spinocerebellar ataxia 3, olivopontocerebellar ataxia 3, autosomal dominant, ataxin 3) (MJD), transcript variant 1, mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=13518018>; 9 pgs.

National Center for Biotechnology Information, National Library of Medicine, National Institutes of Health, GenBank Locus NM_005908, Accession No. NM_005908, "Homo sapiens mannosidase, beta A, lyosomal (MANBA), mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=24797157>; 4 pgs.

National Center for Biotechnology Information, National Library of Medicine, National Institutes of Health, GenBank Locus NM_007308, Accession No. NM_007308, "Homo sapiens synuclein, alpha (nonA4 component of amyloid precursor) (SNCA), transcript variant NACP112, mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=6806897>; 5 pgs.

National Center for Biotechnology Information, National Library of Medicine, National Institutes of Health, GenBank Locus NM_009124, Accession No. NM_009124, "Definition," [online]. Bethesda, MD [retrieved on Mar. 5, 2009 ]. Retrieved from the Internet: <URL:http://www.ncbi.nlm.nih.gov/entrez/viewer.fcgi?db=nucleotide&val=33636695>; 5 pgs.

National Center for Biotechnology Information, National Library of Medicine, National Institutes of Health, GenBank Locus NM_011792, Accession No. NM_011792, Version NM_011792.2, "Mus musculus beta-site APP cleaving enzyme 1 (Bace 1), mRNA," [online]. Bethesda, MD [retrieved on Mar. 5, 2009]. Retrieved from the Internet:<URL:http:// www.ncbi.nlm.nih.gov/entrez/viewer.fcgi?db=nucleotide&val=31981411>; 5 pgs.

National Center for Biotechnology Information, National Library of Medicine, National Institutes of Health, GenBank Locus NM_011792.2, Accession No. NM_011792, "Mus musculus beta-site APP cleaving enzyme (Bace), mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=6857758>; 4 pgs.

National Center for Biotechnology Information, National Library of Medicine, National Institutes of Health, GenBank Locus NM_012104, Accession No. NM_012104, "Homo sapiens beta-site APP-cleaving enzyme 1 (BACE1), transcript variant a, mRNA," [online]. Bethesda, MD [retrieved on Mar. 5, 2009 ]. Retrieved from the Internet:<URL:http://www.ncbi.nim.nih.gov/entrez/viewer.fcgi?db=nucleotide&val=46255011>; 8 pgs.

National Center for Biotechnology Information, National Library of Medicine, National Institutes of Health, GenBank Locus NM_012104, Accession No. NM_012104, Version NM_012104.2, "Homo sapiens beta-site APP-cleaving enzyme (BACE), transcript variant a, mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=21040369>; 10 pgs.

National Center for Biotechnology Information, National Library of Medicine, National Institutes of Health, GenBank Locus NM_013995, Accession No. NM_013995, "Homo sapiens lysosomal-associated membrane protein 2 (LAMP2), transcript variant LAMP2B, mRNA," [online]. Bethesda, MD [retrieved on Mar. 5, 2009 ]. Retrieved from the Internet: <URL:http://www.ncbi.nlm.nih.gov/entrez/viewer.fcgi?db=nucleotide&val=7669502>; 6 pgs.

National Center for Biotechnology Information, National Library of Medicine, National Institutes of Health, GenBank Locus NM_030660, Accession No. NM_030660, "Homo sapiens Machado-Joseph disease (spinocerebellar ataxia 3, olivopontocerebellar ataxia 3, autosomal dominant, ataxin 3) (MJD), transcript variant 2, mRNA," [online]. Bethesda, MD [retrieved on Mar. 5, 2009 ]. Retrieved from the Internet<URL:http://www.ncbi.nlm.nih.gov/entrez/viewer.fcgi?db=nucleotide&val=13518012>; 8 pgs.

National Center for Biotechnology Information, National Library of Medicine, National Institutes of Health, GenBank Locus NM_032520, Accession No. NM_032520, "Homo sapiens N-acetylglucosamine-1-phosphotransferase, gamma subunit (GNPTAG), mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=42476109>; 5 pgs.

National Center for Biotechnology Information, National Library of Medicine, National Institutes of Health, GenBank Locus NM_138971, Accession No. NM_138971, "Homo sapiens beta-site APP-cleaving enzyme 1 (BACE1), transcript variant c, mRNA," [online]. Bethesda, MD [retrieved on Mar. 5, 2009 ]. Retrieved from the Internet:<URL:http://www.ncbi.nlm.nih.gov/entrez/viewer.fcgi?db=nucleotide&val=46255012>; 8 pgs.

National Center for Biotechnology Information, National Library of Medicine, National Institutues of Health, GenBank Locus NM_138971, Accession No. NM_138971, Version NM_138971.1, "Homo sapiens beta-site APP-cleaving enzyme (BACE), transcript variant c, mRNA, " [online]. Bethesda, MD [retrieved on Mar. 5, 2009]. Retrieved from the Internet: <URL:http://www.ncbi.nlm.nih.gov/entrez/viewer.fcgi?db=nucleotide&val=21040363 >; 10 pgs.

National Center for Biotechnology Information, National Library of Medicine, National Institutues of Health, GenBank Locus NM_138972, Accession No. NM_138972, "Homo sapiens beta-site APP-cleaving enzyme 1 (BACE1), transcript variant b, mRNA, " [online]. Bethesda, MD [retrieved on Mar. 5, 2009]. Retrieved from the Internet: <URL:http://www.ncbi.nlm.nih.gov/entrez/viewer.fcgi?db=nucleotide&val=46255013 >; 8 pgs.

National Center for Biotechnology Information, National Library of Medicine, National Institutues of Health, GenBank Locus NM_138972, Accession No. NM_138972, Version NM_138972.1, "Homo sapiens beta-site APP-cleaving enzyme (BACE), transcript variant b, mRNA, " [online]. Bethesda, MD [retrieved on Mar. 5, 2009]. Retrieved from the Internet: <URL:http://www.ncbi.nlm.nih.gov/entrez/viewer.fcgi?db=nucleotide&val=21040365 >; 10 pgs.

National Center for Biotechnology Information, National Library of Medicine, National Institutues of Health, GenBank Locus NM_138973, Accession No. NM_138973, "Homo sapiens beta-site APP-cleaving enzyme 1 (BACE1), transcript variant d, mRNA, " [online]. Bethesda, MD [retrieved on Mar. 5, 2009]. Retrieved from the Internet: <URL:http://www.ncbi.nlm.nih.gov/entrez/viewer.fcgi?db=nucleotide&val=46255014 >; 8 pgs.

National Center for Biotechnology Information, National Library of Medicine, National Institutues of Health, GenBank Locus NM_138973, Accession No. NM_138973, Version NM_138973.1, "Homo sapiens beta-site APP-cleaving enzyme (BACE), transcript variant d, mRNA, " [online]. Bethesda, MD [retrieved on Mar. 5, 2009]. Retrieved from the Internet: <URL:http://www.ncbi.nlm.nih.gov/entrez/viewer.fcgi?db=nucleotide&val=21040367 >; 10 pgs.

National Center for Biotechnology Information, National Library of Medicine, National Institutues of Health, GenBank Locus U24233, Accession No. U24233 "*Mus musculus* huntingtin (Hd) mRNA, complete cds, " [online]. Bethesda, MD [retrieved on Mar. 5, 2009]. Retrieved from the Internet: <URL:http://www.ncbi.nlm.nih.gov/entrez/viewer.fcgi?db=nucleotide&val=902003 >; 5 pgs.

National Center for Biotechnology Information, National Library of Medicine, National Institutues of Health, GenBank Locus XM_032588, Accession No. XM_032588, "homo sapiens dentatorubral-pallidoluysian atrophy (atrophin-1) (DRAPLA), mRNA, " [online]. Bethesda, MD [retrieved on Mar. 5, 2009]. Retrieved from the Internet: <URL:http://www.ncbi.nlm.nih.gov/entrez/viewer.fcgi?db=nucleotide&val=20555988 >; 3 pgs.

National Center for Biotechnology Information, National Library of Medicine, National Institutues of Health, GenBank Locus XM_132846, Accession No. XM_132846, "Mus musculus dentatorubral pallidoluysian atrophy (Drpla), mRNA, " [online]. Bethesda, MD [retrieved on Mar. 5, 2009]. Retrieved from the Internet: <URL:http://www.ncbi.nlm.nih.gov/entrez/viewer.fcgi?db=nucleotide&val=20832263 >; 3 pgs.

Noonberg et al., Nucl. Acid Res. 22(14) 2830-2836 (1994).

Noordmans et al., Soc. Neurosci. Abstr. 27, Program 572.14 (2001).

Ohkawa Nucl. Acid. Symp. Ser. 27, 15-16 (1992).

Ohno et al., "BACEI Deficiency Rescues Memory Deficits and Cholinergic Dysfunction in a Mouse Model of Alzheimer's Disease," Neuron, Jan. 2004; 4I: 37-33.

Paxinos et al The Mouse Brain in Stereotactic Coordinates, Acad. Press 2nd Ed. (2001).

Potter, N. T. et al., "Technical standards and guidelines for huntington disease testing," Genetics in Medicine 6:61-65 (2004).

Promega Corporation, T4 DNA Ligase Blue/White Cloning Qualified, Part #9PIM180, Revised Apr. 2005, 2 pgs.

Promega Corporation, T4 DNA Polymerase(a) , Part#9PIM421, Revised May, 2004, 2 pgs.

Qiagen, Qiaex II Handbook, Feb. 1999, 24 pgs.

Qiagen, Rneasy Mini Handbook, 3rd Edition, Jun. 2001, 116 pgs.

R&D Systems, β-Secretase Activity Kit, Catalog No. FP002, Aug. 2002, 2 pgs.

Roberds et al., "BACE knockout mice are healthy despite lacking the primary β-secretase activity in brain: implications for Alzheimer's disease therapeutics," Human Molecular Genetics, Jun. 2001; 10(12): 1317-1324.

Ryu, Biomaterials 26: 319-326 (2005).

Salehi et al., J. Neural Transm. 106 955-986 (1999).

Sapru et al., Annual Meeting Soc. Neurosci. Abstract 297.9, XP001204566 (2003).

Sarver et al., Science 247, 1222-1225 (1990).

Scanlon et al., Proc. Nat. Acad. Sci. 88, 10591-10595 (1995).

Schenk, "Amyloid-β immunotherapy for Alzheimer's disease: the end of the beginning," Nature Reviews-Neuroscience, Oct. 2002; 3: 824-828.

Scherr et al., Cell Cycle 2(3) 251-257 (2003).

Serra et at., Medical Image Analysis 1(4) 317-329 (1996).

Singer et al., Nat. Neurosci. 8(10) 1343-1349 (ePub Aug. 28, 2005).

Stackman et al., Experimental Neurology 184, 510-520 (2003).

Strategene, AAV Helper-Free System, Instruction Manual, Catalog #240071, #240074, #240075, Revision #084007i, Aug. 2004, 50 pgs.

Strategene, pBluescript® II Phagemid Vectors, Instruction Manual, Catalog #212205, #212206, #212207, #212208, Revision #083001m, Aug. 2003, 35 pgs.

Sullenger, Science 262, p. 1566 (Dec. 3, 1993).

Taira et al., Nucl. Acid. Res. 19(19) 5125-5130 (1991).

Thompson et al., Nucl. Acid. Res. 23(12), 2259 (1995).

Timson et al., Biochem J 363:515-520 (2002).

Tuscjl Lab, "The siRNA user guide," Revised May 2004, [online]. Retrieved on Nov. 29, 2005. Retrieved from the Internet: <URL:rockefeller.edu/labheads/tuschl/sirna.html>; 6 pgs.

Valbonesi et al., Ttransf. And Apheresis Sci. 30: 153-156 (2004).

Van Bilsen et al., "Identification and allele-specific silencing of the mutant huntingtin allele in Huntington's disease patient-derived fibroblasts," Human Gene Therapy, vol. 19, pp. 710-718 (2008).

Vassar et al., Science 286 735-741 (1999).

Ventura et al., Nucl. Acid. Res. 21(14) 3249-3255 (1993).

Vickers, Journal of Bio. Chemistry, vol. 278, No. 9 7108-7118 (2003).

Watanabe et al., J. Mol. Cel. Card. 37 (3) 691-698 (2004).

Weerasinghe et al., J. Virol. 65(10), 5531-3334 (1991).

Whitesell et al., Proc. Nat. Acad. Sci. 90: 4665-4669 (1993).

Xia et al., Nat. Biotech. 20, 1006-1010 (2002).

Xia et al., Nat. Med. 10(8) 816-820 (2004).

Yamamoto et al., Cell 101, 57-66 (2000).

Yu et al., Proc. Nat. Acad. Sci. 90 6340-6344 (1993).

Yu et al., Proc. Nat. Acad. Sci. 99 6047-6052 (2002).

Zhang et al., "Global Non-Viral Gene Transfer to the Primate Brain Following Intravenous Administration," Molecular Therapy, Jan. 2003; 7(1): 11-18.

Zhang et al., "In vivo knockdown of gene expression in brain cancer with intravenous RNAi in adult rats, " J. Gene Med., 2003; 5:1039-1045; published online Aug. 4, 2003.

Zhang et al., "Intravenous RNA Interference Gene Therapy Targeting the Human Epidermal Growth Factor Receptor Prolongs Survival in Intracranial Brain Cancer," Clinical Cancer Research, Jun. 1, 2004; 10:3667-3677.

Zhang et al., 1996 J. Mol. Neurosci. 7: 13-28 (1996).

Zhao et al., J. Biol. Chem. 271(49), 31407-31411 (Dec. 1996).

Zlokovic et al., Neurosurgery 40 805-813 (1997).

Aebischer, Patrick, Recombinant proteins for neurodegenerative diseases: the delivery issue, Trends in Neurosciences, 24(9):533-540, 2001.

Callahan, Michael J., et al, Augmented Senile Plaque Load in Aged Female β-Amyloid Precursor Protein-Transgenic Mice, American Journal of Pathology, 158(3):1173-1177, 2001.

Caplen, Natasha J., et al.,, Rescue of polyglutamine-mediaed cytotoxicity by double-stranded RNA-mediated RNA interference, Human Molecular Genetics 11(2):175-184, 2002.

Chen et al., Multitasrget-ribozyme directed to cleave at up to nine highly conserved HIV-1 env RNA regions inhibits HIV-1 replication-potential effectiveness against most presently sequened HIV-1 isolates, Nucleic Acids Res., 20:4581-4589, 1992.

Chowrira et al., In vitro and in vivo comparison of Hammerhead, Hairpin and Hepatitis delta Virus Self-Processing Ribozyme Cassettes, Journal Biol. Chemistry, 269:25856-25863, 1994.

Clark, H., et al., Purkinji Cell Expression of a Mutant Allele of SCA1 in transgenic mice leads to disparate effects on motor behaviorsk, followed by a proigressive cerebellar dysfunction and histological alternations, Journal of Neuroscience, 17(19):7385-7395, 1997.

Couture, Larry A., et al, Anti-gene Therapy: The Use of Ribozymes to Inhibit Gene Function, Trends in Genetics, 12 (12):510-515, 1996.
Davidson, Beverly L., Molecular medicine for the brain: silencing of disease genes with RNA interference, The Lancet Neurology, 3:145-149, 2004.
Dineley, Kelly T., et al, Accelerated Plaque Accumulation, Associative Learning Deficits, and Up-regulation of α7 Nicotinic Receptor Protein in Transgenic Mice Co-expressing Mutant Human Presentilin 1 and Amyloid Precursor Proteins, Journal of Biological Chemistry, 277(25):22768-22780, 2002.
Dropulic et al., Functional characterization of a U5 Ribozyme: Intracellular Suppression of Human Immunodeficiency virus Type I Expression, Journal Virology., 66(1):1432-1441, 1992.
Gau, Jen-Tzer, et al, Stable β-Secretase Activity and Presynaptic Cholinergic Markers During Progressive Central Nervous System Amyloidogenesis in Tg2576 Mice, American Journal of Pathology, 160(2):731-738, 2002.
Glorioso, Joseph C., Use of HSV vectors to modify the nervous system, Current Opinion in Drug Discovery & Development, PharmaPress Ltd ISSN, 5(2):1367-6733, 2002.
Good, et al., Expression of small, therapeutic RNAs in human cell nuclei, Gene Therapy, 4:45-54, 1997.
Goto, J., et al., Suppression of Huntingtin Gene Expression by sIRNA: A Possible therapeutic Tool for Huntington's Disease, Neurology, Lippincoll Williams & Wilkins, Philadelphia, US, 60(5) Suppl 1, Mar. 11, 2003 p.A286.
Heale, et al., siRNA Target Site Secondary Structure Predictions Using Local Stable Substructures, Nucleic Acids Research, 33(3), 2005.
Hommel, J.D., et al., Local gene knockdown in the brain using viral-mediated RNA interference, Society for Neuroscience Abstract Viewer and Itinerary Planner 2003, vol. 2003, Abstract No. 325.14, Nov. 8-12, 2003.
Hsiao, Karen, et al, Correlative Memory Deficits, Aβ Elevation, and Amyloid Plaques in Transgenic Mice, Science, 274:99-102, 1996.
Isacson, et al., Lack of Efficacy of "Naked" Small Interfering RNA Applied Directly to Rat Brain, Scandinavian Physiiological Society, 179:173-177, 2003.
Izant, Jonathan G., et al., Constitutive and Conditional Suppression of Exogenous and Endogenous Genes by Anti-Sense RNA, Science, 229:345, 1985.
Kashani-Sabet et al., Reversal of the Malignant Phenotype by an Anti-ras Ribozyme, Antisense Res. Dev., 2:3-15, 1992.
Kawarabayashi, T., et al, Age-Dependent Changes in Brain, CSF, and Plasma Amyloid βProtein in the Tg2576 Transgenic Mouse Model of Alzheimer's Disease, Journal of Neuroscience, 21(2):372-381, 2001.
King, D.L., et al, Behavioral Characterization of the Tg2576 Transgenic Model of Alzheimer's Disease Through 19 Months, Physiology & Behavior, 75:627-642, 2002.
Kitabwalla, Moiz, Ph.D., et al., RNA interference—a new weapon against HIV and beyond, New England Journal of Medicine, 347(17):1364-1367, 2002.
Klement, Ivan, et al., Ataxin-1 nuclear localization and aggregation: Role in polyglutamine-induced disease in SCA1 transgenic mice, Cell vol. 95:41-53, 1998.
L'Huillier, Phillip J., et al., Cytoplasmic delivery of ribozymes leads to efficient reduction in x-lactalbumin mRNA levels in C1271 mouse cells, EMBO Journal, 11(12):4411-4418, 1992.
Lisziewicz et al., Inhibition of human immunodeficiency virus type 1 replication by regulated expression of a polymeric Tat activation response RNA decoy as a strategy for gene therapy in AIDS, Proc. National Acad Sci USA, 90:8000-8004, 1993.
Liu, et al., Specific inhibition of Huntington's disease gene expression by siRNAs in cultures cells., Proceedings of the Japan Academy, Series B, Physical and Biological Sciences, 79:10(pp293-298) Dec. 2003.
Matilla, A., et al., Mice lacking ataxin-1 display learning deficits and decreased hippocampal paired-pulse facilitation, Journal of Neuroscience, 18(14):5508-5516, 1998.
McGarry, Thomas J., et al., Inhibition of heat shock protein synthesis by heat-inducible antisense RNA, Proc. National Academy Science, USA, 83:399, 1986.
McManus, Michael T., Gene Silencing in Mammals by Small Interfering RNAs, Nature Reviews / Genetics, 3:737-747, 2002.
Miller, Victor M., Allele-specific silencing of dominant disease genes, PNAS, 100(12):7195-7200, 2003.
Naldini, Luigi, Efficient transfer, integration and sustained long-term expression of the transgene in adult rat brains injected with a lentiviral vector, Proc. National Academy Science, 93:11382-11388, 1996.
Noonberg, et al., In vivo generation of highly abundant sequence-specific oligonucleotides for antisense and triplex gene regulation, Nucleic Acid Research, 22(14):2830-2836, 1994.
Ohkawa, et al., Activities of HIV-RNA targeted riboyzmes transcribed from a shot-gun type riboyzme-trimming plasmid, Nucleic Acids Symp. Ser., 27:15-16, 1992.
Ojwang, Joshua O., et al., Inhibition of human immunodeficiency virus type-1 expressoin by a hairpin ribozyme, Proc. National Academy Science USA, 89:10802-10806, 1992.
Sapru, et al., Small interfering RNA (siRNA)-Mediated silencing of alpha-synuclein gene expression., Annual Meeting of the Society of Neuroscience, Abstract 297.9, XP001204566, 2003.
Sarver, Nava et al., Ribozymes as potential anti-HIV-1 therapeutic agents, Science, 247:1222-1225, 1990.
Scanlon, K.J., et al., Ribozyme-mediated cleavage of c-fos mRNA rduces gene expression of DNA synthesis enzymes and metal-lothionein, Proc. National Academy Science USA, 88:10591-10595, 1991.
Stackman, Robert W., et al, Prevention of Age-Related Spatial Memory Deficits in a Transgenic Mouse Model of Alzheimer's Disease by Chronic Ginkgo biloba Treatment, Experimental Neurology, 184:510-520, 2003.
Sullenger, Bruce and Cech, Thomas R., Tethering Ribozymes to a Retroviral Packaging Signal for Destruction of Viral RNA, Science, 262:1566, 1993.
Taira, Kazunari, et al, Construction of a Novel RNA-Transcript-Trimming Plasmid which can be used Both in-vitro in Place of Run-off and (G)-Free Transcriptions and in vivo as Multi-Sequences Transcription Vectors, Nucleic Acids Research, 19(19):5125-5130, 1991.
Thompson, James D., et al., Improved accumulation and activity of ribozymes expressed from a tRNA-based RNA polymerase III promoter, Nucleic Acids Res., 23(12):2259, 1995.
Ventura, M., et al, Activation of HIV-Specific Ribozyme Activity by Self-Cleavage, Nucleic Acids Research, 21(14):3249-3255, 1993.
Weerasinghe, Migara et al., Resistance to human immunodeficiency virus type 1 (HIV-1) infection in human CD4 lymphocyte-derived cell lines conferred by using retroviral vectors expressing an HIG-1 RNA-specific ribozyme, Journal of Virology, 65(10):5531-5534, 1991.
Xia, et al., sIRNA-mediated gene silencing in vitro and in vivo, Nature Biotechnology 20:1006-1010, 2002.
Xia, et al., RNAi suppresses polyglutamine-induced neurodegeneration in a model of spinocerebellar ataxia., Nature Medicine, 10:8(816-820) 2004.
Yamamoto, A, et al., Reversal of neuropathology and motor dysfunction in a conditional model of Huntington's Disease, Cell, 101:57-66, 2000.
Yu et al., A hairpin riboyzme inhibits expression of diverse strains of human immunodeficiency virus type 1, Proc. Natl. Acad Sci. USA, 90:6340-6344, 1993.
Yu, Jenn-Yah et al., RNA interference by expression of short-interfering RNAs and hairpin RNAs in mammalian cells, PNAS, 99(9):6047-6052, 2002.
Neurosciences, 24(9):533-540, 2001.
Callahan, Michael J., et al, Augmented Senile Plaque Load in Aged Female β-Amyloid Precursor Protein-Transgenic Mice, American Journal of Pathology, 158(3):1173-1177, 2001.
Caplen, Natasha J., et al.,, Rescue of polyglutamine-mediaed cytotoxicity by double-stranded RNA-mediated RNA interference, Human Molecular Genetics 11(2):175-184, 2002.
Chen et al., Multitasrget-ribozyme directed to cleave at up to nine highly conserved HIV-1 env RNA regions inhibits HIV-1 replication—potential effectiveness against most presently sequened HIV-1 isolates, Nucleic Acids Res., 20:4581-4589, 1992.

Chowrira et al., In vitro and in vivo comparison of Hammerhead, Hairpin and Hepatitis delta Virus Self-Processing Ribozyme Cassettes, Journal Biol. Chemistry, 269:25856-25863, 1994.
Clark, H., et al., Purkinji Cell Expression of a Mutant Allele of SCA1 in transgenic mice leads to disparate effects on motor behaviorsk, followed by a proigressive cerebellar dysfunction and histological alterations, Journal of Neuroscience, 17(19):7385-7395, 1997.
Couture, Larry A., et al, Anti-gene Therapy: The Use of Ribozymes to Inhibit Gene Function, Trends in Genetics, 12(12):510-515, 1996.
Davidson, Beverly L., Molecular medicine for the brain: silencing of disease genes with RNA interference, The Lancet Neurology, 3:145-149, 2004.
Dineley, Kelly T., et al, Accelerated Plaque Accumulation, Associative Learning Deficits, and Up-regulation of α7 Nicotinic Receptor Protein in Transgenic Mice Co-expressing Mutant Human Presenilin 1 and Amyloid Precursor Proteins, Journal of Biological Chemistry, 277(25):22768-22780, 2002.
Dropulic et al., Functional characterization of a U5 Ribozyme: Intracellular Suppression of Human Immunodeficiency virus Type I Expression, Journal Virology., 66(1):1432-1441, 1992.
Gau, Jen-Tzer, et al, Stable β-Secretase Activity and Presynaptic Cholinergic Markers During Progressive Central Nervous System Amyloidogenesis in Tg2576 Mice, American Journal of Pathology, 160(2):731-738, 2002.
Glorioso, Joseph C., Use of HSV vectors to modify the nervous system, Current Opinion in Drug Discovery & Development, PharmaPress Ltd ISSN, 5(2):1367-6733, 2002.
Good, et al., Expression of small, therapeutic RNAs in human cell nuclei, Gene Therapy, 4:45-54, 1997.
Goto, J., et al., Suppression of Huntingtin Gene Expression by sIRNA: A Possible therapeutic Tool for Huntington's Disease, Neurology, Lippincoll Williams & Wilkins, Philadelphia, US, 60(5) Suppl 1, Mar. 11, 2003 p. A286.
Heale, et al., siRNA Target Site Secondary Structure Predictions Using Local Stable Substructures, Nucleic Acids Research, 33(3), 2005.
Hommel, J.D., et al., Local gene knockdown in the brain using viral-mediated RNA interference, Society for Neuroscience Abstract Viewer and Itinerary Planner 2003, vol. 2003, Abstract No. 325.14, Nov. 8-12, 2003.
Hsiao, Karen, et al, Correlative Memory Deficits, Aβ Elevation, and Amyloid Plaques in Transgenic Mice, Science, 274:99-102, 1996.
lsacson, et al., Lack of Efficacy of "Naked" Small Interfering RNA Applied Directly to Rat Brain, Scandinavian Physiiological Society, 179:173-177, 2003.
Izant, Jonathan G., et al., Constitutive and Conditional Suppression of Exogenous and Endogenous Genes by Anti-Sense RNA, Science, 229:345, 1985.
Kashani-Sabet et al., Reversal of the Malignant Phenotype by an Anti-ras Ribozyme, Antisense Res. Dev., 2:3-15, 1992.
Kawarabayashi, T., et al, Age-Dependent Changes in Brain, CSF, and Plasma Amyloid β Protein in the Tg2576 Transgenic Mouse Model of Alzheimer's Disease, Journal of Neuroscience, 21(2):372-381, 2001.
King, D.L., et al, Behavioral Characterization of the Tg2576 Transgenic Model of Alzheimer's Disease Through 19 Months, Physiology & Behavior, 75:627-642, 2002.
Kitabwalla, Moiz, Ph.D., et al., RNA interference—a new weapon against HIV and beyond, New England Journal of Medicine, 347(17):1364-1367, 2002.
Klement, Ivan, et al., Ataxin-1 nuclear localization and aggregation: Role in polyglutamine-induced disease in SCA1 transgenic mice, Cell vol. 95:41-53, 1998.
L'Huillier, Phillip J., et al., Cytoplasmic delivery of ribozymes leads to efficient reduction in x-lactalbumin mRNA levels in C1271 mouse cells, EMBO Journal, 11(12):4411-4418, 1992.
Lisziewicz et al., Inhibition of human immunodeficiency virus type 1 replication by regulated expression of a polymeric Tat activation response RNA decoy as a strategy for gene therapy in AIDS, Proc. National Acad Sci USA, 90:8000-8004, 1993.
Matilla, A., et al., Mice lacking ataxin-1 display learning deficits and decreased hippocampal paired-pulse facilitation, Journal of Neuroscience, 18(14):5508-5516, 1998.
McGarry, Thomas J., et al., Inhibition of heat shock protein synthesis by heat-inducible antisense RNA, Proc. National Academy Science, USA, 83:399, 1986.
McManus, Michael T., Gene Silencing in Mammals by Small Interfering RNAs, Nature Reviews / Genetics, 3:737-747, 2002.
Miller, Victor M., Allele-specific silencing of dominant disease genes, PNAS, 100(12):7195-7200, 2003.
Naldini, Luigi, Efficient transfer, integration and sustained long-term expression of the transgene in adult rat brains injected with a lentiviral vector, Proc. National Academy Science, 93:11382-11388, 1996.
Noonberg, et al., In vivo generation of highly abundant sequence-specific oligonucleotides for antisense and triplex gene regulation, Nucleic Acid Research, 22(14):2830-2836, 1994.
Ohkawa, et al., Activities of HIV-RNA targeted riboyzmes transcribed from a shot-gun type riboyzme-trimming plasmid, Nucleic Acids Symp. Ser., 27:15-16, 1992.
Ojwang, Joshua O., et al., Inhibition of human immunodeficiency virus type-1 expressoin by a hairpin ribozyme, Proc. National Academy Science USA, 89:10802-10806, 1992.
Sarver, Nava et al., Ribozymes as potential anti-HIV-1 therapeutic agents, Science, 247:1222-1225, 1990.
Scanlon, K.J., et al., Ribozyme-mediated cleavage of c-fos mRNA rduces gene expression of DNA synthesis enzymes and metallothionein, Proc. National Academy Science USA, 88:10591-10595, 1991.
Stackman, Robert W., et al, Prevention of Age-Related Spatial Memory Deficits in a Transgenic Mouse Model of Alzheimer's Disease by Chronic Ginkgo biloba Treatment, Experimental Neurology, 184:510-520, 2003.
Sullenger, Bruce and Cech, Thomas R., Tethering Ribozymes to a Retroviral Packaging Signal for Destruction of Viral RNA, Science, 262:1566, 1993.
Taira, Kazunari, et al, Construction of a Novel RNA-Transcript-Trimming Plasmid which can be used Both in-vitro in Place of Run-off and (G)-Free Transcriptions and in vivo as Multi-Sequences Transcription Vectors, Nucleic Acids Research, 19(19):5125-5130, 1991.
Thompson, James D., et al., Improved accumulation and activity of ribozymes expressed from a tRNA-based RNA polymerase III promoter, Nucleic Acids Res., 23(12):2259, 1995.
Ventura, M., et al, Activation of HIV-Specific Ribozyme Activity by Self-Cleavage, Nucleic Acids Research, 21(14):3249-3255, 1993.
Weerasinghe, Migara et al., Resistance to human immunodeficiency virus type 1 (HIV-1) infection in human CD4 lymphocyte-derived cell lines conferred by using retroviral vectors expressing an HIG-1 RNA-specific ribozyme, Journal of Virology, 65(10):5531-5534, 1991.
Xia, et al., sIRNA-mediated gene silencing in vitro and in vivo, Nature Biotechnology 20:1006-1010, 2002.
Yamamoto, A, et al., Reversal of neuropathology and motor dysfunction in a conditional model of Huntington's Disease, Cell, 101:57-66, 2000.
Yu et al., A hairpin riboyzme inhibits expression of diverse strains of human immunodeficiency virus type 1, Proc. Natl. Acad Sci. USA, 90:6340-6344, 1993.
Yu, Jenn-Yah et al., RNA interference by expression of short-interfering RNAs and hairpin RNAs in mammalian cells, PNAS, 99(9):6047-6052, 2002.

* cited by examiner

293H Cells Transfected with Anti-Ataxin1 Ribozyme (A1364A) and Anti-ataxin siRNA (AT0945)

293H Cells Transfected with Control siRNA (GAPDH) and Anti-ataxin siRNA (AT1671)

Small interfering RNA Treatment of Neurodegenerative Diseases

| Disease | Location | Gene Product |
|---|---|---|
| Parkinson's Disease | Sub Nigra | alpha-synuclein |
| Alzheimer's Disease | Basalis of Meynert<br>Cerebral Cortex<br>Hippocampus | BACE1 (including variants thereof, e.g. variants A, B, C, and D) |
| Huntington's Disease | Striatum:<br>Caudate Nucleus<br>Putamen, Striatum | Huntingtin<br>IT15 |
| Spinocerbellar Ataxia<br>Type 1<br>Type 2<br>Type 3 (Machado Joseph) | Deep Cerebellar Nuclei:<br>Dentate nucleus<br>Emboliform nucleus<br>Globose nucleus<br>Fastigial nucleus<br>Cerebellar cortex | Ataxin 1<br>Ataxin 2<br>Ataxin 3 |
| Dentatorubral-pallidoluysian atrophy | Red Nucleus<br>Globose Pilidus | Atrophin 1 |

Fig. 6

Figure 10: Immunostaining revealing BACE1 protein in the normal mouse hippocampus

Brown = peroxidase visualization of BACE1
Green = methyl green counterstaining of cell nuclei

Figure 11A

Alignment of our sheep Huntington gene sequence with the human Huntington gene sequence available in Genbank (NM_002111.3)

The first row of each couplet below is the human Huntington gene sequence, and the second is the sequence of the sheep gene SEQ ID NO.: 48 that is homologous to the human Huntington gene. The third row, when present, indicates with an asterisk (*) the nucleotide positions for which the sheep and human DNA sequences are the same. This alignment was computed by the CLUSTAL W (1.82) multiple sequence alignment software service available on the Internet at: http://www.cbi.ac.uk/clustalw/. Note that only the first 1500 nucleic acids from the human Huntington sequence (NM_002111.3) are shown (SEQ ID NO.: 56).

```
humanHD-NM_002111.3    TTGCTGTGTGAGGCAGAACCTGCAGGGGGCAGGGGCGGGGCTTGGTTCCCTTGGCCAGCCATTG   60
sheepHD                ----------------------------------------------------------------

humanHD-NM_002111.3    GCAGAGTCCGGCAGCTAGGGCTGTCAATCATGTCTGCCGGCGTGGCCCCGGCTCCGGCGG   120
sheepHD                ----------------------------------------------------------------

humanHD-NM_002111.3    CGGGGCCCCGCCTCCGCGGGCGCACGTCTGGGACGCAGGCGCAAGGCGCCTGGGGCGCTGGCGGGA   180
sheepHD                ----------------------------------------------------------------

humanHD-NM_002111.3    CGGGTCCAAGATGACGGCGCCCGCTCAGGTTCCTGCTTTTACGTGCGGCCCAGAGCCCCATTC   240
sheepHD                ----------------------------------------------------------------

humanHD-NM_002111.3    ATTGCCCCGGTGCTGTGAGCGGCCGGAGTCGGCCCAGGCCTCCGGGGACTGCCGACC   300
sheepHD                ----------------------------------------------------------------

humanHD-NM_002111.3    GGGCGGGAGACCGCCATGGCGACCCTGGAAAAGCTGATGAAGGCCTTCGAGTCCCTCAAG   360
sheepHD                ----------------------------------------------------------------

humanHD-NM_002111.3    TCCTTCCAGCAGCAGCAGCAGCAGCAGCAGCAGCAGCAGCAGCAGCAGCAGCACCAGCAG   420
sheepHD                ----------------------------------------------------------------

humanHD-NM_002111.3    CAGCAGCAGCAACAGCAGCCGCCACCGCCGCCGCCGCCGCCGCCTCCTCAGCTTCCTCAG   480
sheepHD                ------------ATGGCGACC--CTGGAAAAGCTGATGAAGGCCTTCGAGTCCCTCAAG    45
                                  *   *   ***  *****************************
```

Figure 11B

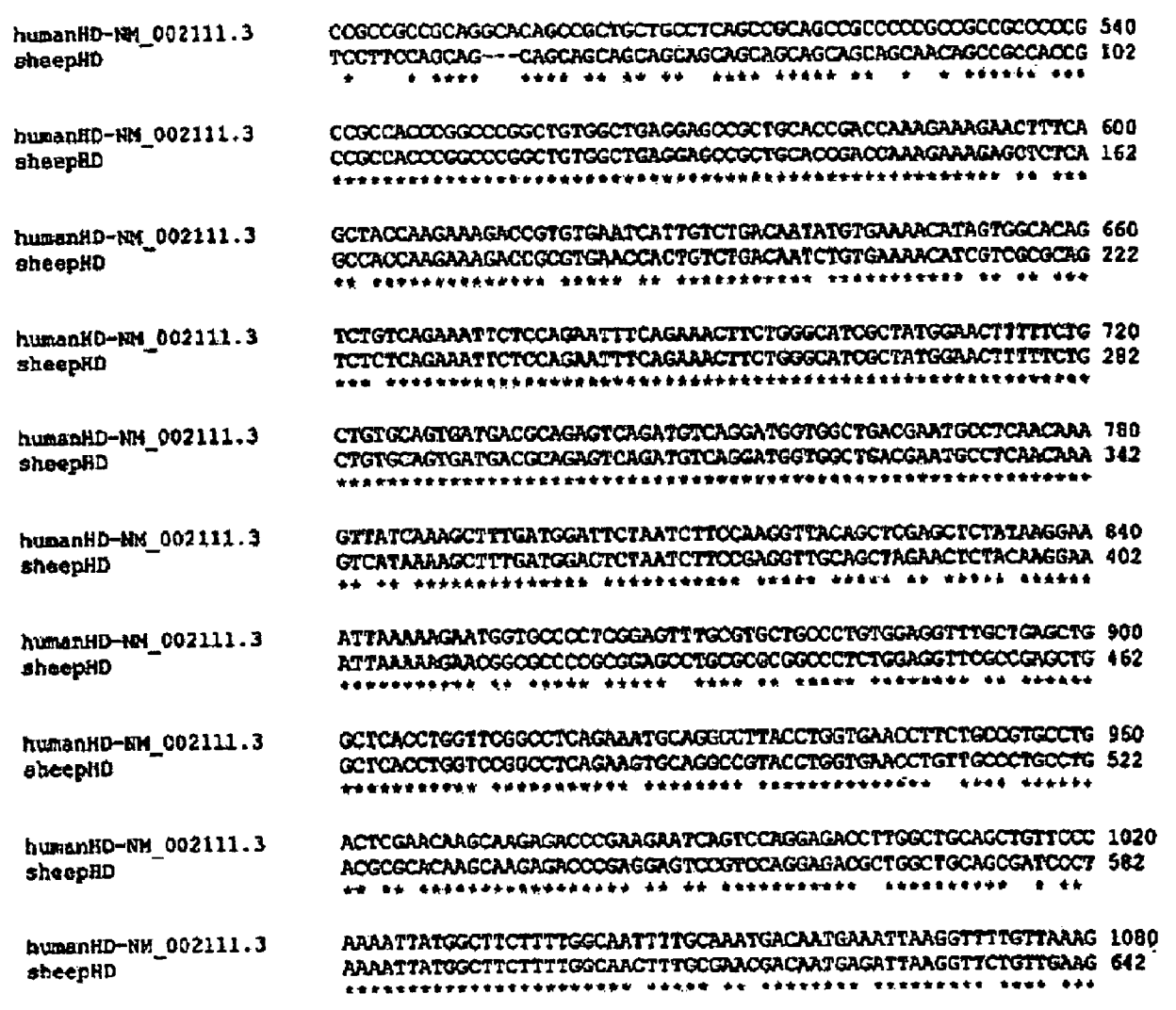

```
humanHD-NM_002111.3   CCGCCGCCGCAGGCACAGCCGCTGCTGCCTCAGCCGCAGCCGCCCCCGCCGCCGCCCCCG 540
sheepHD               TCCTTCCAGCAG---CAGCAGCAGCAGCAGCAGCAGCAGCAGCAGCAACAGCCGCCACCG 102
                       *     * ****    **** ** ** **   **** ***** **   *   * ****** ***

humanHD-NM_002111.3   CCGCCACCCGGCCCGGCTGTGGCTGAGGAGCCGCTGCACCGACCAAAGAAAGAACTTTCA 600
sheepHD               CCGCCACCCGGCCCGGCTGTGGCTGAGGAGCCGCTGCACCGACCAAAGAAAGAGCTCTCA 162
                      ***************************************************** ** ***

humanHD-NM_002111.3   GCTACCAAGAAAGACCGTGTGAATCATTGTCTGACAATATGTGAAAACATAGTGGCACAG 660
sheepHD               GCCACCAAGAAAGACCGCGTGAACCACTGTCTGACAATCTGTGAAAACATCGTCGCGCAG 222
                      ** ************** ***** ** *********** *********** ** ** ***

humanHD-NM_002111.3   TCTGTCAGAAATTCTCCAGAATTTCAGAAACTTCTGGGCATCGCTATGGAACTTTTTCTG 720
sheepHD               TCTCTCAGAAATTCTCCAGAATTTCAGAAACTTCTGGGCATCGCTATGGAACTTTTTCTG 282
                      *** ********************************************************

humanHD-NM_002111.3   CTGTGCAGTGATGACGCAGAGTCAGATGTCAGGATGGTGGCTGACGAATGCCTCAACAAA 780
sheepHD               CTGTGCAGTGATGACGCAGAGTCAGATGTCAGGATGGTGGCTGACGAATGCCTCAACAAA 342
                      ************************************************************

humanHD-NM_002111.3   GTTATCAAAGCTTTGATGGATTCTAATCTTCCAAGGTTACAGCTCGAGCTCTATAAGGAA 840
sheepHD               GTCATAAAAGCTTTGATGGACTCTAATCTTCCGAGGTTGCAGCTAGAACTCTACAAGGAA 402
                      ** ** *************** *********** ***** ***** ** ***** ******

humanHD-NM_002111.3   ATTAAAAAGAATGGTGCCCCTCGGAGTTTGCGTGCTGCCCTGTGGAGGTTTGCTGAGCTG 900
sheepHD               ATTAAAAAGAACGGCGCCCCGCGGAGCCTGCGCGCGGCCCTCTGGAGGTTCGCCGAGCTG 462
                      *********** ** ***** *****  **** ** ***** ******** ** ******

humanHD-NM_002111.3   GCTCACCTGGTTCGGCCTCAGAAATGCAGGCCTTACCTGGTGAACCTTCTGCCGTGCCTG 960
sheepHD               GCTCACCTGGTCCGGCCTCAGAAGTGCAGGCCGTACCTGGTGAACCTGTTGCCCTGCCTG 522
                      *********** *********** ******** **************  **** ******

humanHD-NM_002111.3   ACTCGAACAAGCAAGAGACCCGAAGAATCAGTCCAGGAGACCTTGGCTGCAGCTGTTCCC 1020
sheepHD               ACGCGCACAAGCAAGAGACCCGAGGAGTCCGTCCAGGAGACGCTGGCTGCAGCGATCCCT 582
                      ** ** ***************** ** ** ***********  ********** * **

humanHD-NM_002111.3   AAAATTATGGCTTCTTTTGGCAATTTTGCAAATGACAATGAAATTAAGGTTTTGTTAAAG 1080
sheepHD               AAAATTATGGCTTCTTTTGGCAACTTTGCGAACGACAATGAGATTAAGGTTCTGTTGAAG 642
                      *********************** ***** ** ********* ********* **** ***
```

Figure 11C

```
humanHD-NM_002111.3     GCCTTCATAGCGAACCTGAAGTCAAGCTCCCCCACCATTCGGCGGACAGCGGCTGGATCA 1140
sheepHD                 GCTTTCATCGCGAACCTGAAGTCCAGTTCCCCGACTGTGCGGCGGACCGCGGCGGGCTCA 702
                        ** ***** ************** ** ***** **   * ******** ***** ** ***

humanHD-NM_002111.3     GCAGTGAGCATCTGCCAGCACTCAAGAAGGACACAATATTTCTATAGTTGGCTACTAAAT 1200
sheepHD                 GTGGTCAGCATCTGCCAGCACTCCAGGAGGACGCAGTACTTTTACAGCTGGCTGCTCAGC 762
                        *  ** ***************** ** ***** ** ** ** ** ** ***** ** *

humanHD-NM_002111.3     GTGCTCTTAGGCTTACTCGTTCCTGTCGAGGATGAACACTCCACTCTGCTGATTCTTGGC 1260
sheepHD                 GTGCTCCTAGGTTTGCTGGTCCCCGTGGAGGAGGAGCACCCCACCCTGCTGATCCTCGGC 822
                        ****** **** ** ** ** ** ** ***** ** *** **** ******** ** ***

humanHD-NM_002111.3     GTGCTGCTCACCCTGAGGTATTTGGTGCCCTTGCTGCAGCAGCAGGTCAAGGACACAAGC 1320
sheepHD                 GTCCTGCTCACCCTGAGGTATCTG------------------------------------ 846
                        ** ****************** **

humanHD-NM_002111.3     CTGAAAGGCAGCTTCGGAGTGACAAGGAAAGAAATGGAAGTCTCTCCTTCTGCAGAGCAG 1380
sheepHD                 ------------------------------------------------------------

humanHD-NM_002111.3     CTTGTCCAGGTTTATGAACTGACGTTACATCATACACAGCACCAAGACCACAATGTTGTG 1440
sheepHD                 ------------------------------------------------------------

humanHD-NM_002111.3     ACCGGAGCCCTGGAGCTGTTGCAGCAGCTCTTCAGAACGCCTCCACCCGAGCTTCTGCAA 1500
sheepHD                 ------------------------------------------------------------
```

TREATMENT OF NEURODEGENERATIVE DISEASE THROUGH INTRACRANIAL DELIVERY OF SIRNA

FIELD OF INVENTION

This invention relates to devices, systems, and methods for treating neurodegenerative disorders by brain infusion of small interfering RNA or vectors containing the DNA encoding for small interfering RNA.

BACKGROUND OF THE INVENTION

This invention provides novel devices, systems, and methods for delivering small interfering RNA to targeted sites in the brain to inhibit or arrest the development and progression of neurodegenerative disorders. For several neurodegenerative diseases, such as Parkinson's disease, Alzheimer's disease, Huntington's disease, Spinocerebellar Ataxia Type 1, Type 2, and Type 3, and dentatorubral pallidoluysian atrophy (DRLPA), proteins involved in the overall pathogenic progression of the disease have been identified. There is currently no cure for these neurodegenerative diseases. These diseases are progressively debilitating and most are ultimately fatal.

Further problematic of these neurodegenerative diseases (especially Alzheimer's disease and Parkinson's disease) is that their prevalence continues to increase, thus creating a serious public health problem. Recent studies have pointed to alpha-synuclein (Parkinson's disease), beta-amyloid-cleaving enzyme 1 (BACE1 (including variants thereof, e.g. variants A, B, C, and D)) (Alzheimer's disease), huntingtin (Huntington's disease), and ataxin 1 (Spinocerebellar Ataxia Type 1) as major factors in the pathogenesis of each of these diseases, respectively.

The neurodegenerative process in Parkinson's disease and Alzheimer's disease is characterized by extensive loss of selected neuronal cell populations accompanied by synaptic injury and astrogliosis. Pathological hallmarks of Alzheimer's disease include formation of amyloid plaques, neurofibrillary tangles and neuropil thread formation; pathological hallmarks of Parkinson's diseases include the formation of intraneuronal inclusions called Lewy bodies and the loss of dopaminergic neurons in the substantia nigra. Although the mechanisms triggering cell dysfunction and death are unclear, the prevailing view is that neurodegeneration results from toxic effects subsequent to the accumulation of specific neuronal cell proteins, such as alpha-synuclein (Parkinson's disease) and amyloid precursor protein (APP) (Alzheimer's disease—processed into beta-amyloid by BACE1 (including variants thereof, e.g. variants A, B, C, and D)).

Alpha-synuclein has been implicated in Parkinson's disease because it is abundantly found in Lewy Bodies, its overexpression in transgenic mice leads to Parkinson's disease-like pathology, and mutations within this molecule are associated with familial Parkinson's disease. Alpha-synuclein, which belongs to a larger family of molecules including beta and gamma-synuclein, is a 140 amino acid non-amyloid synaptic protein which is a precursor of the 35 amino acid non-amyloid component protein found in amyloid plaques.

Alzheimer's disease is a progressive degenerative disorder of the brain characterized by mental deterioration, memory loss, confusion, and disorientation. Among the cellular mechanisms contributing to this pathology are two types of fibrillar protein deposits in the brain: intracellular neurofibrillary tangles composed of polymerized tau protein, and abundant extracellular fibrils comprised largely of beta-amyloid. Beta-amyloid, also known as Abeta, arises from the proteolytic processing of the amyloid precursor protein (APP) at the beta- and gamma-secretase cleavage sites giving rise to the cellular toxicity and amyloid-forming capacity of the two major forms of Abeta ($Abeta_{40}$ and $Abeta_{42}$). Thus, preventing APP processing into plaque-producing forms of amyloid may critically influence the formation and progression of the disease making BACE1 (including variants thereof, e.g. variants A, B, C, and D) a clinical target for inhibiting or arresting this disease. Similar reports suggest presenilins are candidate targets for redirecting aberrant processing.

Huntington's disease is a fatal, hereditary neurodegenerative disorder characterized by involuntary "ballistic" movements, depression, and dementia. The cause has been established to be a mutation in a single gene consisting of an excessively long series of C, A, G, C, A, G, . . . C, A, G, nucleotides in the DNA. The CAG repeat is in the region of the gene that codes for the protein the gene produces. Thus, the resulting huntingtin protein is also "expanded," containing an excessively long region made of the amino acid glutamine, for which "CAG" encodes. Shortly after this mutation was pinpointed as the cause of Huntington's disease, similar CAG repeat expansions in other genes were sought and found to be the cause of numerous other fatal, hereditary neurodegenerative diseases. The list of these so-called "polyglutamine" diseases now includes at least eleven more, including: spinocerebellar ataxia type 1, type 2, and type 3, spinobulbar muscular atrophy (SBMA or Kennedy's disease) and dentatorubral-pallidoluysian atropy (DRPLA). Although the particular gene containing the expanded CAG repeat is different in each disease, it is the production of an expanded polyglutamine protein in the brain that causes each one. Symptoms typically emerge in early to middle-aged adulthood, with death ensuing 10 to 15 years later. No effective treatments for these fatal diseases currently exist.

There is considerable evidence suggesting that shutting off production of the abnormal protein in neurons will be therapeutic in polyglutamine diseases. The cause of these diseases is known to be the gain of a new function by the mutant protein, not the loss of the protein's original function. Mice harboring the human, expanded transgene for spinocerebellar ataxia type 1 (SCA1) become severely ataxic in young adulthood (Clark, H., et al., *Journal of Neuroscience* 17: 7385-7395 (1997)), but mice in which the corresponding mouse gene has been knocked out do not suffer ataxia or display other major abnormalities (Matilla, A., et al., *Journal of Neuroscience* 18: 5508-5516 (1998)). Transgenic mice for SCA1 in which the abnormal ataxin1 protein is produced but has been genetically engineered to be incapable of entering the cell's nucleus do not develop ataxia (Klement, I., et al., *Cell* 95: 41-53 (1998)). Finally, a transgenic mouse model of Huntington's disease has been made in which the mutant human transgene has been engineered in a way that it can be artificially "turned off" by administering tetracycline (Normally, in mice and humans, administration of this antibiotic would have no effect on the disease). After these mice have begun to develop symptoms, shutting off production of the abnormal protein production by chronic administration of tetracyclin leads to an improvement in their behavior (Yamamoto, A., et al., *Cell* 101: 57-66 (2000)). This suggests that reducing expression of the abnormal huntingtin protein in humans might not only prevent Huntington's disease from progressing in newly diagnosed patients, but may improve the quality of life of patients already suffering from its symptoms.

Various groups have been recently studying the effectiveness of siRNAs. Caplen, et al. (*Human Molecular Genetics,* 11(2): 175-184 (2002)) assessed a variety of different double stranded RNAs for their ability to inhibit cell expression of mRNA transcripts of the human androgen receptor gene containing different CAG repeats. Their work found gene—specific inhibition occurred with double stranded RNAs containing CAG repeats only when flanking sequences to the CAG repeats were present in the double stranded RNAs. They were also able to show that constructed double stranded RNAs were able to rescue caspase-3 activation induced by expression of a protein with an expanded polyglutamine region. Xia, Mao, et al. (*Nature Biotechnology,* 20: 1006-1010 (2002)) demonstrated the inhibition of polyglutamine (CAG) expression of engineered neural PC12 clonal cell lines that express a fused polyglutamine-fluorescent protein using constructed recombinant adenovirus expressing siRNAs targeting the mRNA encoding green fluorescent protein.

The design and use of small interfering RNA complementary to mRNA targets that produce particular proteins is a recent tool employed by molecular biologists to prevent translation of specific mRNAs. Other tools used by molecular biologists to interfere with protein expression prior to translation involve cleavage of the mRNA sequences using ribozymes against therapeutic targets for Alzheimer's disease (see WO01/16312A2) and Parkinson's disease (see WO99/50300A1 and WO01/60794A2). However, none of the above aforementioned patents disclose methods for the specifically localized delivery of small interfering RNA vectors to targeted cells of the brain in a manner capable of local treatment of neurodegenerative diseases. The above patents do not disclose use of delivery devices or any method of delivery or infusion of small interfering RNA vectors to the brain. For example, the above patents do not disclose or suggest a method of delivery or infusion of small interfering RNA vectors to the brain by an intracranial delivery device.

Further, the foregoing prior art does not disclose any technique for infusing into the brain small interfering RNA vectors, nor does the prior art disclose whether small interfering RNA vectors, upon infusion into the brain, are capable of entering neurons and producing the desired small interfering RNA, which is then capable of reducing production of at least one protein involved in the pathogenesis of neurodegenerative disorders.

The prior art describes direct systemic delivery of ribozymes. This approach for treatment of neurodegenerative disorders would appear neither possible nor desirable. First, interfering RNAs are distinctly different than ribozymes. Second, small RNA molecules delivered systemically will not persist in vivo long enough to reach the desired target, nor are they likely to cross the blood-brain barrier. Further, the approach taken by the prior art may be impractical because of the large quantity of small interfering RNA that might have to be administered by this method to achieve an effective quantity in the brain. Even when the blood-brain barrier is temporarily opened, the vast majority of oligonucleotide delivered via the bloodstream may be lost to other organ systems in the body, especially the liver.

U.S. Pat. Nos. 5,735,814 and 6,042,579 disclose the use of drug infusion for the treatment of Huntington's disease, but the drugs specifically identified in these patents pertain to agents capable of altering the level of excitation of neurons, and do not specifically identify agents intended to enter the cell and alter protein production within cells.

The present invention solves prior problems existing in the prior art relating to systemic delivery of nucleic acids by directly delivering small interfering RNA in the form of DNA encoding the small interfering RNA to target cells of the brain using viral vectors. Directed delivery of the small interfering RNA vectors to the affected region of the brain infusion overcomes previous obstacles related to delivery. Further, use of viral vectors allows for efficient entry into the targeted cells and for efficient short and long term production of the small interfering RNA agents by having the cells' machinery direct the production of the small interfering RNA themselves. Finally, the present invention provides a unique targeting and selectivity profile by customizing the active small interfering RNA agents to specific sites in the mRNA coding sequences for the offending proteins.

SUMMARY OF THE INVENTION

The present invention provides devices, systems, and methods for delivering small interfering RNA for the treatment of neurodegenerative disorders.

A first objective of the described therapies is to deliver specifically tailored small interfering RNA as therapeutic agents for treatment of Parkinson's disease. Specifically tailored small interfering RNA for Parkinson's disease target the mRNA for the alpha-synuclein protein in order to reduce the amount of alpha-synuclein protein produced in neurological cells. In a related embodiment the present invention provides devices that specifically access the substantia nigra for delivery of anti-alpha-synuclein small interfering RNA.

A second objective of the described therapies is to deliver specifically tailored small interfering RNA as therapeutic agents for treatment of Alzheimer's disease. Specifically tailored small interfering RNA for Alzheimer's disease target the mRNA for BACE1 (including variants thereof, e.g. variants A, B, C, and D) in order to reduce the amount of BACE1 (including variants thereof, e.g. variants A, B, C, and D) protein produced in neurological cells and thereby interfere with the production of beta-amyloid. In a related embodiment the present invention provides devices that specifically access the nucleus basalis of Meynart and the cerebral cortex for delivery of anti-BACE1 (including variants thereof, e.g. variants A, B, C, and D) small interfering RNA.

A third objective of the described therapies is to deliver specifically tailored small interfering RNA as therapeutic agents for treatment of Huntington's disease. Specifically tailored small interfering RNA for Huntington's disease target the mRNA for huntingtin protein to reduce the amount of huntingtin protein produced in neurological cells. In a related embodiment the present invention provides devices that specifically access the caudate nucleus and putamen (collectively known as the striatum) for delivery of anti-huntingtin small interfering RNA.

A fourth objective of the described therapies is to deliver specifically tailored small interfering RNA as therapeutic agents for treatment of Spinocerebellar Ataxia Type 1 (SCA1). Specifically tailored small interfering RNA for Spinocerebellar Ataxia Type 1 target the mRNA for ataxin1 protein to reduce the amount of ataxin1 protein produced in neurological cells. In a related embodiment the present invention provides devices that specifically access the dentate nucleus, eboliform nucleus, globus nucleus, and fastigial nucleus of the cerebellum, (collectively known as the deep cerebellar nuclei), for delivery of anti-ataxin-1 small interfering RNA.

A fifth objective of the described therapies is to deliver specifically tailored small interfering RNA as therapeutic agents for treatment of Spinocerebellar Ataxia Type 3 (SCA3), also known as Machado-Joseph's Disease. Specifically tailored small interfering RNA for Spinocerebellar Ataxia Type 3 target the mRNA for ataxin3 protein to reduce the amount of ataxin3 protein produced in neurological cells. In a related embodiment the present invention provides devices that specifically access the dentate nucleus, eboliform nucleus, globus nucleus, and fastigial nucleus of the cerebellum, (collectively known as the deep cerebellar nuclei), the subthalamic region, and the substantia nigra for delivery of anti-ataxin-3-small interfering RNA.

A sixth objective of the described therapies is to deliver specifically tailored small interfering RNA as therapeutic agents for treatment of dentatorubral-pallidoluysian atrophy (DRPLA). Specifically tailored small interfering RNA for DRPLA target the mRNA for atrophin-1 protein to reduce the amount of atrophin-1 protein produced in neurological cells. In a related embodiment the present invention provides devices that specifically access the dentate nucleus, eboliform nucleus, globus nucleus, and fastigial nucleus of the cerebellum, (collectively known as the deep cerebellar nuclei), the globus pallidus, and the red nucleus for delivery of anti-DRPLA small interfering RNA.

The present invention provides a delivery system for a small interfering RNA vector therapy for neurodegenerative diseases that permits targeted delivery of small interfering RNA or vectors containing DNA encoding for small interfering RNA (small interfering RNA vectors) to targeted sites in the brain for brief durations of time or over an extended period of care for the patient.

In a main embodiment of the present invention, small interfering RNA vectors are infused into targeted sites of the brain wherein the small interfering RNA vectors are taken up by neurons and transported to the nucleus of targeted cells. The small interfering RNA vectors are then transcribed into RNA by the host cellular machinery to produce small interfering RNA that prevent production of the targeted neurodegenerative protein.

The present invention also provides methods of using neurosurgical devices to deliver therapeutic small interfering RNA vectors to selected regions of the brain. In particular, the present invention provides methods that use surgically implanted catheters for singular, repeated, or chronic delivery of small interfering RNA vectors to the brain. The small interfering RNA vectors introduced into the affected cells have the necessary DNA sequences for transcription of the required small interfering RNA by the cells, including a promoter sequence, the small interfering RNA sequence, and optionally flanking regions allowing defined ends of the therapeutic small interfering RNA to be produced, and optionally a polyadenylation signal sequence.

DESCRIPTION OF THE FIGURES

FIG. 6 illustrates the relation of various neurodegenerative diseases described herein, and the location of treatment with small interfering RNA vectors directed to their intended targeted gene product.

FIGS. 11A, 11B, and 11C is a sequence alignment of our sheep huntington gene sequence with the human Huntington gene sequence available in Genbank (NM_002111.3).

DETAILED DESCRIPTION OF THE PREFERRED EMBODIMENTS

Figure 1:
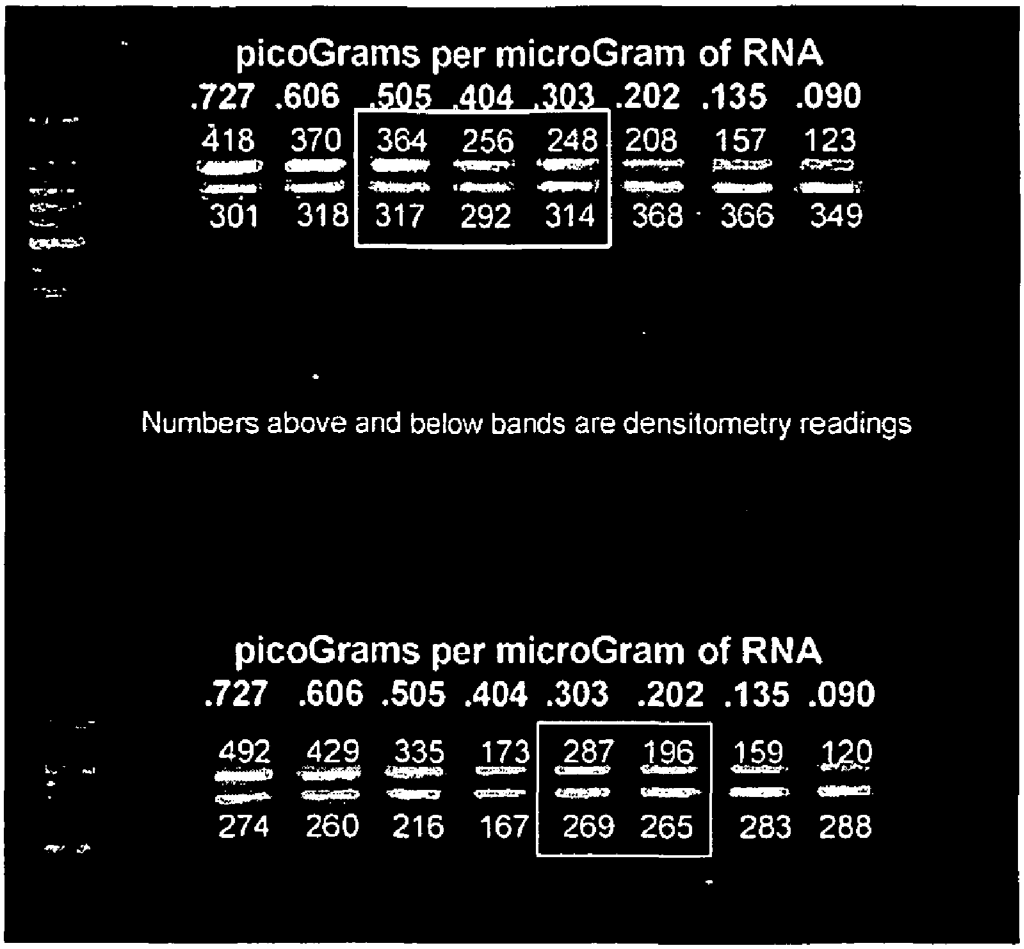
FIG. 1 shows the assay (using a quantitative RT-PCR method known to those practiced in the art) of the ataxin1 mRNA obtained from HEK293H cells that have been transfected with plasmid containing an anti-ataxin1 ribozyme (top lanes in FIG. 1) or with siRNA against ataxin1 (bottom lanes of FIG. 1).

The present invention solves two problems in the prior art at the same time: (1) the problem of how to treat neurodegenerative diseases caused by the production in neurons of a protein that has pathogenic properties and (2) the problem of delivery of therapeutic small interfering RNA to affected neurons.

In order to better understand the present invention, a list of terms and the scope of understanding of those terms is provided below.

Terminology

By "alpha-synuclein, BACE1 (including variants thereof, e.g. variants A, B, C, and D), huntingtin, ataxin-1, ataxin-3, and/or atrophin-1 proteins" is meant, a protein or a mutant protein derivative thereof, comprising the amino-acid sequence expressed and/or encoded by alpha-synuclein (Parkinson's disease), and beta-site APP-cleaving enzyme (BACE1 (including variants thereof, e.g. variants A, B, C, and D)) (Alzheimer's disease), huntingtin (Huntington's disease), and ataxin-1 (Spinocerebellar Ataxia Type 1), ataxin-3 (Spinocerebellar Ataxia Type 3 or Machado-Joseph's Disease), and/or dentatorubral-pallidoluysian atrophy (DRPLA) genes and/or the human genomic DNA respectively.

As used herein "cell" is used in its usual biological sense, and does not refer to an entire multicellular organism. The cell may be present in an organism which may be a human but is preferably of mammalian origin, e.g., such as humans, cows, sheep, apes, monkeys, swine, dogs, cats, and the like. However, several steps of producing small interfering RNA may require use of prokaryotic cells (e.g., bacterial cell) or eukaryotic cell (e.g., mammalian cell) and thereby are also included within the term “cell”.

By “complementarity” it is meant that a molecule comprised of one or more nucleic acids (DNA or RNA) can form hydrogen bond(s) with another molecule comprised of one or more nucleic acids by either traditional Watson-Crick pairing or other non-traditional types.

By “equivalent” DNA to alpha-synuclein, BACE1 (including variants thereof, e.g. variants A, B, C, and D), huntingtin, ataxin-1, ataxin-3, and/or atrophin-1 it is meant to include those naturally occurring DNA molecules having homology (partial or complete) to DNA encoding for alpha-synuclein, BACE1 (including variants thereof, e.g. variants A, B, C, and D), huntingtin, ataxin-1, ataxin-3 and/or atrophin-1 proteins or encoding for proteins with similar function as alpha-synuclein, BACE1 (including variants thereof, e.g. variants A, B, C, and D), huntingtin, ataxin-1, ataxin-3 and/or atrophin-1 in various organisms, including human, rodent, primate, rabbit, pig, and microorganisms. The equivalent DNA sequence also includes regions such as the 5'-untranslated region, the 3'-untranslated region, introns, intron-exon junctions, small interfering RNA targeted site and the like, optionally incorporated into the DNA of infective viruses, such as adeno-associated virus (AAV).

The term “functional equivalent” refers to any derivative that is functionally similar to the reference sequence or protein. In particular the term “functional equivalent” includes derivatives in which the nucleotide bases(s) have been added, deleted, or replaced without a significant adverse effect on biological function.

By “gene” it is meant a region of DNA that controls the production of RNA. In context of producing functional small interfering RNA, this definition includes the necessary DNA sequence information encompassing the DNA sequences encoding the small interfering RNA, noncoding regulatory sequence and any included introns. The present definition does not exclude the possibility that additional genes encoding proteins may function in association or in tandem with the genes encoding small interfering RNA.

The term “vector” is commonly known in the art and defines a plasmid DNA, phage DNA, viral DNA and the like, which can serve as a DNA vehicle into which DNA of the present invention can be inserted, and from which RNA can be transcribed. The term “vectors” refers to any of these nucleic acid and/or viral-based techniques used to deliver a desired nucleic acid. Numerous types of vectors exist and are well known in the art.

The term “expression” defines the process by which a gene is transcribed into RNA (transcription); the RNA may be further processed into the mature small interfering RNA.

The terminology “expression vector” defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

“Promoter” refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain “TATA” boxes and “CCAT” boxes. Prokaryotic promoters contain −10 and −35 consensus sequences, which serve to initiate transcription.

By “homology” it is meant that the nucleotide sequence of two or more nucleic acid molecules is partially or completely identical.

By “highly conserved sequence region” it is meant that a nucleotide sequence of one or more regions in a target gene does not vary significantly from one generation to the other or from one biological system to the other.

By the term “inhibit” or “inhibitory” it is meant that the activity of the target genes or level of mRNAs or equivalent RNAs encoding target genes is reduced below that observed in the absence of the provided small interfering RNA. Preferably the inhibition is at least 10% less, 25% less, 50% less, or 75% less, 85% less, or 95% less than in the absence of the small interfering RNA.

By “inhibited expression” it is meant that the reduction of alpha-synuclein, BACE1 (including variants thereof, e.g. variants A, B, C, and D), huntingtin, ataxin-1, ataxin-3 and/or atrophin-1 mRNA levels and thus reduction in the level of the respective protein to relieve, to some extent, the symptoms of the disease or condition.

By “RNA” is meant ribonucleic acid, a molecule consisting of ribonucleotides connected via a phosphate-ribose (sugar) backbone. By “ribonucleotide” is meant guanine, cytosine, uracil, or adenine or some a nucleotide with a hydroxyl group at the 2' position of a beta-D-ribo-furanose moiety. As is well known in the art, the genetic code uses thymidine as a base in DNA sequences and uracil in RNA. One skilled in the art knows how to replace thymidine with uracil in a written nucleic acid sequence to convert a written DNA sequence into a written RNA sequence, or vice versa.

By “patient” is meant an organism, which is a donor or recipient of explanted cells or the cells themselves. “Patient” also refers to an organism to which the nucleic acid molecules of the invention can be administered. Preferably, a patient is a mammal or mammalian cells, e.g., such as humans, cows, sheep, apes, monkeys, swine, dogs, cats, and the like, or cells of these animals used for transplantation. More preferably, a patient is a human or human cells.

The term “synuclein” may refer to alpha-synuclein (especially human or mouse) or beta-synuclein (especially human or mouse). The full nucleotide sequence encoding human alpha-synuclein is available under Accession No AF163864 (SEQ ID:7). Two variants of the human alpha-synuclein sequence are available under Accession No NM000345 (SEQ ID:14) and Accession No NM_007308 (SEQ ID:23). The mouse alpha-synuclein is available under Accession No. AF163865 (SEQ ID:10).

The term “BACE1” may refer to beta-site amyloid precursor protein cleaving enzyme type 1 (especially human or mouse). Several variants of BACE1 have been sequenced, including variants A, B, C, and D. In some scientific literature, BACE1 is also known as ASP2 and Memapsin2. The full nucleotide sequences encoding human BACE1, and variants related thereto, are available under Accession No. NM_138971 (SEQ ID:20), Accession No. NM_138972 (SEQ ID:19), Accession No. NM_138973 (SEQ ID:21), and Accession No. NM_012104 (SEQ ID:18). The sequence for a mouse homolog is available under accession number NM_011792 (SEQ ID:22).

The term “huntingtin” may refer to the protein product encoded by the Huntington’s Disease gene (IT-15) (especially human or mouse). The full nucleotide sequence encoding human IT-15 is available under Accession No AH003045 (SEQ ID:9). The mouse sequence is available under Accession No. U24233 (SEQ ID:12).

The term “ataxin-1” may refer to the protein product encoded by the Spinocerebellar Ataxia Type 1 gene (especially human or mouse). The full nucleotide sequence encoding human SCA1 is available under Accession No NM_000332 (SEQ ID:15). The mouse sca1 is available under Accession No. NM_009124 (SEQ ID:13).

The term “ataxin-3” may refer to the protein product encoded by the Spinocerebellar Ataxia Type 3 gene (especially human or mouse). The full nucleotide sequence encoding human SCA3 is available under Accession No NM_004993 (splice variant 1) (SEQ ID:16), and NM_030660 (splice variant 2) (SEQ ID:17). (The sequence for a mouse homolog is not yet available).

The term “atrophin-1” may refer to the protein product encoded by the dentatorubral-pallidolysian atrophy (DRPLA) gene (especially human or mouse). The full nucleotide sequence encoding human DRPLA is available under Accession No XM_032588 (SEQ ID:8). The mouse sequence is available under Accession No. XM_132846 (SEQ ID:11).

The term “modification” includes derivatives substantially similar to the reference sequence or protein.

By “nucleic acid molecule” as used herein is meant a molecule having nucleotides. The nucleic acid can be single, double, or multiple stranded and may comprise modified or unmodified nucleotides or non-nucleotides or various mixtures and combinations thereof. An example of a nucleic acid molecule according to the invention is a gene which encodes for a small interfering RNA, even though it does not necessarily have its more common meaning for encoding for the production of protein.

By “small interfering RNA” is meant a nucleic acid molecule which has complementarity in a substrate binding region to a specified gene target, and which acts to specifically guide enzymes in the host cell to cleave the target RNA. That is, the small interfering RNA by virtue of the specificity of its sequence and its homology to the RNA target, is able to cause cleavage of the RNA strand and thereby inactivate a target RNA molecule because it is no longer able to be transcribed. These complementary regions allow sufficient hybridization of the small interfering RNA to the target RNA and thus permit cleavage. One hundred percent complementarity often necessary for biological activity and therefore is preferred, but complementarity as low as 90% may also be useful in this invention. The specific small interfering RNA described in the present application are not meant to be limiting and those skilled in the art will recognize that all that is important in a small interfering RNA of this invention is that it have a specific substrate binding site which is complementary to one or more of the target nucleic acid regions.

Small interfering RNAs are double stranded RNA agents that have complementary to (i.e., able to base-pair with) a portion of the target RNA (generally messenger RNA). Generally, such complementarity is 100%, but can be less if desired, such as 91%, 92%, 93%, 94%, 95%, 96%, 97%, 98%, or 99%. For example, 19 bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences.

The small interfering RNA sequence needs to be of sufficient length to bring the small interfering RNA and target RNA together through complementary base-pairing interactions. The small interfering RNA of the invention may be of varying lengths. The length of the small interfering RNA is preferably greater than or equal to ten nucleotides and of sufficient length to stably interact with the target RNA; specifically 15-30 nucleotides; more specifically any integer between 15 and 30 nucleotides, such as 15, 16, 17, 18, 19, 20, 21, 22, 23, 24, 25, 26, 27, 28, 29, and 30. By “sufficient length” is meant an oligonucleotide of greater than or equal to 15 nucleotides that is of a length great enough to provide the intended function under the expected condition. By “stably interact” is meant interaction of the small interfering RNA with target nucleic acid (e.g., by forming hydrogen bonds with complementary nucleotides in the target under physiological conditions).

By “comprising” is meant including, but not limited to, whatever follows the word “comprising”. Thus, use of the term “comprising” indicates that the listed elements are required or mandatory, but that other elements are optional and may or may not be present.

By “consisting of” is meant including, and limited to, whatever follows the phrase “consisting of”. Thus, the phrase “consisting of” indicates that the listed elements are required or mandatory, and that no other elements may be present.

By “consisting essentially of” is meant including any elements listed after the phrase, and limited to other elements that do not interfere with or contribute to the activity or action specified in the disclosure for the listed elements. Thus, the phrase “consisting essentially of” indicates that the listed elements are required or mandatory, but that other elements are optional and may or may not be present depending upon whether or not they affect the activity or action of the listed elements.

The present invention provides the means and tools for treating polyglutamine diseases (such as Huntington’s disease and spinocerebellar ataxia type 1), Parkinson’s disease, and Alzheimer’s disease by intracranial delivery of vectors encoding small interfering RNAs designed to silence the expression of disease-causing or disease-worsening proteins, delivered through one or more implanted intraparenchymal catheters. In particular, the invention is (1) a method to treat Huntington’s disease by the intracranial delivery of a vector encoding a small interfering RNA designed to silence expression of huntingtin protein; (2) a method to treat spinocerebellar ataxia type 1 by the intracranial delivery of a vector encoding a small interfering RNA designed to silence expression of ataxin1 protein; (3) a method to treat Parkinson’s disease by the intracranial delivery of a vector encoding a small interfering RNA designed to silence expression of alpha-synuclein protein, and (4) a method to treat Alzheimer’s disease by the intracranial delivery of a vector encoding a small interfering RNA designed to silence expression of beta-amyloid cleaving enzyme 1 (BACE1).

As previously indicated, the small interfering RNA (or siRNA) described herein, is a segment of double stranded RNA that is from 15 to 30 nucleotides in length. It is used to trigger a cellular reaction known as RNA interference. In RNA interference, double-stranded RNA is digested by an intracellular enzyme known as Dicer, producing siRNA duplexes. The siRNA duplexes bind to another intracellular enzyme complex which is thereby activated to target whatever mRNA molecules are homologous (or complementary)

to the siRNA sequence. The activated enzyme complex cleaves the targeted mRNA, destroying it and preventing it from being used to direct the synthesis of its corresponding protein product. Recent evidence suggests that RNA interference is an ancient, innate mechanism for not only defense against viral infection (many viruses introduce foreign RNA into cells) but also gene regulation at very fundamental levels. RNA interference has been found to occur in plants, insects, lower animals, and mammals, and has been found to be dramatically more effective than other gene silencing technologies, such as antisense or ribozymes. Used as a biotechnology, siRNA involves introducing into cells (or causing cells to produce) short, double-stranded molecules of RNA similar to those that would be produced by the Dicer enzyme from an invading double-stranded RNA virus. The artificially-triggered RNA interference process then continues from that point.

To deliver a small interfering RNA to a patient's brain, a preferred method will be to introduce the DNA encoding for the siRNA, rather than the siRNA molecules themselves, into the cells of the brain. The DNA sequence encoding for the particular therapeutic siRNA can be specified upon knowing (a) the sequence for a small and accessible portion of the target mRNA (available in public human genome databases), and (b) well-known scientific rules for how to specify DNA that will result in production of a corresponding RNA sequence when the DNA is transcribed by cells. The DNA sequence, once specified, can be constructed in the laboratory from synthetic molecules ordered from a laboratory supplier, and inserted using standard molecular biology methods into one of several alternative "vectors" for delivery of DNA to cells. Once delivered into the neurons of the patient's brain, those neurons will themselves produce the RNA that becomes the therapeutic siRNA, by transcribing the inserted DNA into RNA. The result will be that the cells themselves produce the siRNA that will silence the targeted gene. The result will be a reduction of the amount of the targeted protein produced by the cell.

Small Interfering RNA and Small Interfering RNA Vectors

In accordance with the present invention, small interfering RNA against specific mRNAs produced in the affected cells prevent the production of the disease related proteins in neurons. In accordance with the present invention is the use of specifically tailored vectors designed to deliver small interfering RNA to targeted cells. The success of the designed small interfering RNA is predicated on their successful delivery to the targeted cells of the brain to treat the neurodegenerative diseases.

Small interfering RNA have been shown to be capable of targeting specific mRNA molecules in human cells. Small interfering RNA vectors can be constructed to transfect human cells and produce small interfering RNA that cause the cleavage of the target RNA and thereby interrupt production of the encoded protein.

A small interfering RNA vector of the present invention will prevent production of the pathogenic protein by suppressing production of the neuropathogenic protein itself or by suppressing production of a protein involved in the production or processing of the neuropathogenic protein. Repeated administration of the therapeutic agent to the patient may be required to accomplish the change in a large enough number of neurons to improve the patient's quality of life. Within an individual neuron, however, the change is longstanding enough to provide a therapeutic benefit. The desperate situation of many patients suffering from neurodegenerative disorders, such as Alzheimer's disease, Parkinson's disease, Huntington's disease, or Spinocerebellar Ataxia Type 1 provides a strong likelihood that the benefit from the therapy will outweigh the risks of the therapy delivery and administration. While it may be possible to accomplish some reduction in the production of neuropathogenic proteins with other therapeutic agents and routes of administration, development of successful therapies involving direct in vivo transfection of neurons may provide the best approach based on delivery of small interfering RNA vectors to targeted cells.

The preferred vector for delivery of foreign DNA to neurons in the brain is adeno-associated virus (AAV), such as recombinant adeno-associated virus serotype 2 or recombinant adeno-associated virus serotype 5. Alternatively, other viral vectors, such as herpes simplex virus, may be used for delivery of foreign DNA to central nervous system neurons. It is also possible that non-viral vectors, such as plasmid DNA delivered alone or complexed with liposomal compounds or polyethyleneamine, may be used to deliver foreign DNA to neurons in the brain.

It is important to note that the anti-ataxin-1 small interfering RNA, the anti-BACE1 small interfering RNA, and the anti-Huntington small interfering RNA illustrated here, as well as the other small interfering RNAs for treating neurodegenerative disorders, are just but some examples of the embodiment of the invention. Experimentation using neurosurgical methods with animals, known to those practiced in neuroscience, can be used to identify the candidate small interfering RNAs. The target site on the mRNA and the corresponding small interfering RNA identified by these empirical methods will be the one that will lead to the greatest therapeutic effect when administered to patients with the subject neurodegenerative disease.

In reference to the nucleic molecules of the present invention, the small interfering RNA are targeted to complementary sequences in the mRNA sequence coding for the production of the target protein, either within the actual protein coding sequence, or in the 5' untranslated region or the 3' untranslated region. After hybridization, the host enzymes guided by the siRNA are capable of cleavage of the mRNA sequence. Perfect or a very high degree of complementarity is needed for the small interfering RNA to be effective. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. However, it should be noted that single mismatches, or base-substitutions, within the siRNA sequence can substantially reduce the gene silencing activity of a small interfering RNA.

The small interfering RNA that target the specified sites in alpha-synuclein, BACE1 (including variants thereof, e.g. variants A, B, C, and D), huntingtin, ataxin-1, ataxin-3 and/or atrophin-1 RNAs represent a novel therapeutic approach to treat Parkinson's disease, Alzheimer's disease, Huntington's disease, Spinocerebellar 1, Spinocerebellar Ataxia Type 3, and/or dentatorubral-pallidoluysian atrophy in a cell or tissue.

In preferred embodiments of the present invention, a small interfering RNA is 15 to 30 nucleotides in length. In particular embodiments, the nucleic acid molecule is 15, 16, 17, 18, 19, 20, 21, 22, 23, 24, 25, 26, 27, 28, 29, or 30 nucleotides in length. In preferred embodiments the length of the siRNA sequence can be between 19-30 base pairs, and more preferably between 21 and 25 base pairs, and more preferably between 21 and 23 base pairs.

In a preferred embodiment, the invention provides a method for producing a class of nucleic acid-based gene inhibiting agents that exhibit a high degree of specificity for the RNA of a desired target. For example, the small interfering RNA is preferably targeted to a highly conserved sequence region of target RNAs encoding alpha-synuclein, BACE1 (including variants thereof, e.g. variants A, B, C, and D), huntingtin, ataxin-1, ataxin-3 and/or atrophin-1 RNA such that specific treatment of a disease or condition can be provided with either one or several nucleic acid molecules of the invention. Further, generally, interfering RNA sequences are selected by identifying regions in the target sequence that begin with a pair of adenine bases (AA) (see Examples). SiRNAs can be constructed in vitro or in vivo using appropriate transcription enzymes or expression vectors.

SiRNAs can be constructed in vitro using DNA oligonucleotides. These oligonucleotides can be constructed to include an 8 base sequence complementary to the 5' end of the T7 promoter primer included in the Silencer siRNA (Ambion Construction Kit 1620). Each gene specific oligonucleotide is annealed to a supplied T7 promoter primer, and a fill-in reaction with Klenow fragment generates a full-length DNA template for transcription into RNA. Two in vitro transcribed RNAs (one the antisense to the other) are generated by in vitro transcription reactions and then hybridized to each other to make double-stranded RNA. The double-stranded RNA product is treated with DNase (to remove the DNA transcription templates) and RNase (to polish the ends of the double-stranded RNA), and column purified to provide the siRNA that can be delivered and tested in cells.

Construction of siRNA vectors that express siRNAs within mammalian cells typically use an RNA polymerase III promoter to drive expression of a short hairpin RNA that mimics the structure of an siRNA. The insert that encodes this hairpin is designed to have two inverted repeats separated by a short spacer sequence. One inverted repeat is complementary to the mRNA to which the siRNA is targeted. A string of six consecutive thymidines added to the 3' end serves as a pol III transcription termination site. Once inside the cell, the vector constitutively expresses the hairpin RNA. The hairpin RNA is processed into an siRNA which induces silencing of the expression of the target gene, which is called RNA interference (RNAi).

In most siRNA expression vectors described to date, one of three different RNA polymerase III (pol III) promoters is used to drive the expression of a small hairpin siRNA (1-5). These promoters include the well-characterized human and mouse U6 promoters and the human H1 promoter. RNA pol III was chosen to drive siRNA expression because it expresses relatively large amounts of small RNAs in mammalian cells and it terminates transcription upon incorporating a string of 3-6 uridines.

The constructed nucleic acid molecules can be delivered exogenously to specific tissue or cellular targets as required. Alternatively, the nucleic acid molecules (e.g., small interfering RNA) can be expressed from DNA plasmid, DNA viral vectors, and/or RNA retroviral vectors that are delivered to specific cells.

The delivered small nuclear RNA sequences delivered to the targeted cells or tissues are nucleic acid-based inhibitors of alpha-synuclein, BACE1 (including variants thereof, e.g. variants A, B, C, and D), huntingtin, ataxin-1, ataxin-3 and/or atrophin-1 expression (e.g. translational inhibitors) that are useful for the prevention of the neurodegenerative diseases including Parkinson's disease, Alzheimer's disease, Huntington's disease, Spinocerebellar Ataxia Type 1, Spinocerebellar Ataxia Type 3, and DRPLA and any other diseases or conditions related to the level of alpha-synuclein, BACE1 (including variants thereof, e.g. variants A, B, C, and D), huntingtin, ataxin-1, ataxin-3 and/or atrophin-1 in a cell or tissue.

The nucleic acid-based inhibitors of the invention are added directly, or can be complexed with cationic lipids, packaged within liposomes, packaged within viral vectors, or otherwise delivered to target cells or tissues. The nucleic acid or nucleic acid complexes can be locally administered to relevant tissues ex vivo, or in vivo through injection, infusion pump or stent, with or without their incorporation in biopolymers. In preferred embodiments, the nucleic acid inhibitors comprise sequences which are a sufficient length and/or stably interact with their complementary substrate sequences identified in SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53. Examples of such small interfering RNA (siRNA) also are shown in SEQ IDS NOS: 1, 2, 3, 4, for SEQ IDS relating to siRNAs suppressing Ataxin1 mRNA (see also Examples 1-4). Examples of such small interfering RNA are shown in SEQ IDS NOS: 24, 25, 26, 27, 28, 29, 30, 31, 32, 33, 34, 35, 36, 37, 38, 39, or 40 relating to suppressing BACE1 mRNA (see also all of Example 5). Examples of such small interfering RNA are shown in SEQ IDS NOS: 41, 42, 43, 44, 45, 46, 47, 48, 49, 50, 51, 52, and 53 relating to siRNAs suppressing Huntington mRNA (see also all of Example 6).

In another aspect, the invention provides mammalian cells containing one or more nucleic acid molecules and/or expression vectors of this invention. The one or more nucleic acid molecules may independently be targeted to the same or different sites.

In another aspect of the invention, small interfering RNA molecules that interact with target RNA molecules and inhibit alpha-synuclein, BACE1 (including variants thereof, e.g. variants A, B, C, and D), huntingtin, ataxin-1, ataxin-3 and/or atrophin-1 RNA activity are expressed from transcription units inserted into DNA or RNA vectors. The recombinant vectors are preferably DNA plasmids or viral vectors. Small interfering RNA expressed from viral vectors could be constructed based on, but not limited to, the vector sequences of adeno-associated virus, retrovirus, or adenovirus. Preferably, the recombinant vectors capable of expressing the small interfering RNA are delivered as described above, and persist in target cells. Alternatively, viral vectors may be used that provide for transient expression of small interfering RNA. Such vectors might be repeatedly administered as necessary. Once expressed, the small interfering RNA bind to the target RNA and through use of the host machinery inhibit its expression and thereby its function. Delivery of small interfering RNA expressing vectors, or the small interfering RNA themselves, is by use of intracranial access devices.

The nucleic acid molecules of the instant invention, individually, or in combination or in conjunction with other drugs, can be used to treat diseases or conditions discussed above. For example, to treat a disease or condition associated with alpha-synuclein (Parkinson's Disease), and beta-site APP-cleaving enzyme (Alzheimer's Disease), huntingtin (Huntington's Disease), and Ataxin 1 (Spinocerebellar Ataxia), the patient may be treated, or other appropriate cells may be treated, as is evident to those skilled in the art, individually or in combination with one or more drugs under conditions suitable for the treatment.

In a further embodiment, the described small interfering RNA can be used in combination with other known treatments to treat conditions or diseases discussed above.

In another preferred embodiment, the invention provides nucleic acid-based inhibitors (e.g., small interfering RNA) and methods for their use to down-regulate or inhibit the expression of RNA (e.g., alpha-synuclein, BACE1 (including variants thereof, e.g. variants A, B, C, and D), huntingtin, ataxin-1, ataxin-3 and/or atrophin-1) coding for proteins involved in the progression and/or maintenance of Parkinson's disease, Alzheimer's disease, Huntington's disease, Spinocerebellar Ataxia Type 1, Spinocerebellar Ataxia Type 3, and dentatorubral-pallidoluysian atrophy.

The present invention also provides nucleic acid molecules that can be expressed within cells from known eukaryotic promoters (e.g., Izant and Weintraub, 1985, Science, -229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; propulic et al., 1992, J. Virol., 66, 1432-41; Weerasinghe et al., 1991, J Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45; all of these references are hereby incorporated herein, in their totalities, by reference). Those skilled in the art realize that any nucleic acid can be expressed in eukaryotic cells from the appropriate DNA/RNA vector. The activity of such nucleic acids can be augmented by their release from the primary transcript by ribozymes (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J Biol. Chem., 269, 25856; all of these references are hereby incorporated in their totality by reference herein).

In another aspect of the invention, RNA molecules of the present invention are preferably expressed from transcription units (see, for example, Couture et al., 1996, TIG., 12, 5 10) inserted into DNA or RNA vectors. The recombinant vectors are preferably DNA plasmids or viral vectors. Small interfering RNA expressing viral vectors could be constructed based on, but not limited to, adeno-associated virus, retrovirus, adenovirus, or alphavirus.

In one aspect, the invention features an expression vector comprising a nucleic acid sequence encoding at least one functional segment of the nucleic acid molecules of the instant invention. The nucleic acid sequence encoding the nucleic acid molecule of the instant invention is operably linked in a manner which allows expression of that nucleic acid molecule.

In another aspect the invention features an expression vector comprising: a) a transcription initiation region (e.g., eukaryotic pol I, II or III initiation region); b) a nucleic acid sequence encoding at least one of the nucleic acid agents of the instant invention; and c) a transcription termination region (e.g., eukaryotic pol I, II or III termination region); wherein said sequence is operably linked to said initiation region and said termination region, in a manner which allows expression and/or delivery of said nucleic acid molecule.

Transcription of the nucleic acid molecule sequences are driven from a promoter for eukaryotic RNA polymerase I (pol 1), RNA polymerase II (pol II), or RNA polymerase III (pol III) as is known and appreciated in the art. All of these references are incorporated by reference herein. Several investigators have demonstrated that RNA molecules can be expressed from such promoters can function in mammalian cells (e.g. Kashani-Sabet et al., 1992, Antisense Res. Dev., 2, 3-15; Ojwang et al., 1992, Proc. NatL Acad Sci. USA, 89, 10802-6; Chen et al., 1992, Nucleic Acids Res., 20, 4581-9; Yu et al., 1993, Proc. Natl. Acad Sci. USA, 90, 6340-4; L'Huillier et al., 1992, EMBO J, 11, 4411-8; Lisziewicz et al., 1993, Proc. Natl. Acad. Sci. U.S.A, 90, 8000-4; Thompson et al., 1995, Nucleic Acids Res., 23, 2259; Sullenger & Cech, 1993, Science, 262, 1566). More specifically, transcription units such as the ones derived from genes encoding U6 small nuclear (snRNA), transfer RNA (tRNA) and adenovirus VA RNA are useful in generating high concentrations of desired RNA molecules such as small interfering RNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96118736; all of these publications are incorporated by reference herein). The above small interfering RNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

It is also important to note that the targeting of ataxin1 mRNA for reduction using a small interfering RNA-based therapy for the disease Spinocerebellar Ataxia Type 1 is but one embodiment of the invention. Other embodiments include the use of an anti-huntingtin small interfering RNA administered to the striatum of the human brain, for the treatment of Huntington's disease, and the use of an anti-alpha-synuclein small interfering RNA administered to the substantia nigra of the human brain, for the treatment of Parkinson's disease.

It should be noted that the exemplified methods for constructing the small interfering RNA to be used as the therapeutic agents in the invention (that is, in vitro transcription from DNA templates and assembly into double-stranded RNA, or cloning the DNA coding for a hairpin structure of RNA into an adeno-associated viral expression vector) are only two possible means for making the therapeutic small interfering RNA. Other larger scale, more efficient methods for manufacturing small interfering RNA may be used to produce the clinical grade and clinical quantities used for treating human patients, without altering the essence of the invention.

Those of skill in the art are familiar with the principles and procedures discussed in widely known and available sources as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990) both of which are incorporated herein by reference.

In a preferred embodiment of the present invention, the composition comprising the siRNA agent or precursors or derivatives thereof is formulated in accordance with standard procedure as a pharmaceutical composition adapted for delivered administration to human beings and other mammals. Typically, compositions for intravenous administration are solutions in sterile isotonic aqueous buffer.

Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

In yet another preferred embodiment, therapeutics containing small interfering RNA or precursors or derivatives thereof can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

The amount of the therapeutic of the present invention which will be effective in the treatment of a particular disorder or condition will depend on the nature of the disorder or condition, and can be determined by standard clinical techniques, well established in the administration of therapeutics. The precise dose to be employed in the formulation will also depend on the route of administration, and the seriousness of the disease or disorder, and should be decided according to the judgment of the practitioner and the patient's needs. Suitable dose ranges for intracranial administration are generally about $10^3$ to $10^{15}$ infectious units of viral vector per microliter delivered in 1 to 3000 microliters of single injection volume. Addition amounts of infections units of vector per micro liter would generally contain about $10^4$, $10^5$, $10^6$, $10^7$, $10^8$, $10^9$, $10^{10}$, $10^{11}$, $10^{12}$, $10^{13}$, $10^{14}$ infectious units of viral vector delivered in about 10, 50, 100, 200, 500, 1000, or 2000 microliters. Effective doses may be extrapolated from dose-responsive curves derived from in vitro or in vivo test systems.

For the small interfering RNA vector therapy for neurodegenerative disease of the present invention, multiple catheters having access ports can be implanted in a given patient for a complete therapy. In a preferred embodiment, there is one port and catheter system per cerebral or cerebellar hemisphere, and perhaps several. Once the implantations are performed by a neurosurgeon, the patient's neurologist can perform a course of therapy consisting of repeated bolus injections of small interfering RNA expression vectors over a period of weeks to months, along with monitoring for therapeutic effect over time. The devices can remain implanted for several months or years for a full course of therapy. After confirmation of therapeutic efficacy, the access ports might optionally be explanted, and the catheters can be sealed and abandoned, or explanted as well. The device material should not interfere with magnetic resonance imaging, and, of course, the small interfering RNA preparations must be compatible with the access port and catheter materials and any surface coatings.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor. Laboratories) and Ausubel et al. (1994, Current Protocols in Molecular Biology, Wiley, New York).

The polymerase chain reaction (PCR) used in the construction of siRNA expression plasmids and/or viral vectors is carried out in accordance with known techniques. See, e.g., U.S. Pat. Nos. 4,683,195; 4,683,202; 4,800,159; and 4,965,188 (the disclosures of all three U.S. Patent are incorporated herein by reference). In general, PCR involves a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophoresis, or using a detectable label in accordance with known techniques, and the like. For a review on PCR techniques (see PCR Protocols, A Guide to Methods and Amplifications, Michael et al. Eds, Acad. Press, 1990).

Devices

Using the small interfering RNA vectors previously described, the present invention also provides devices, systems, and methods for delivery of small interfering RNA to target locations of the brain. The envisioned route of delivery is through the use of implanted, indwelling, intraparenchymal catheters that provide a means for injecting small volumes of fluid containing AAV or other vectors directly into local brain tissue. The proximal end of these catheters may be connected to an implanted, intracerebral access port surgically affixed to the patient's cranium, or to an implanted drug pump located in the patient's torso.

Figure 4:
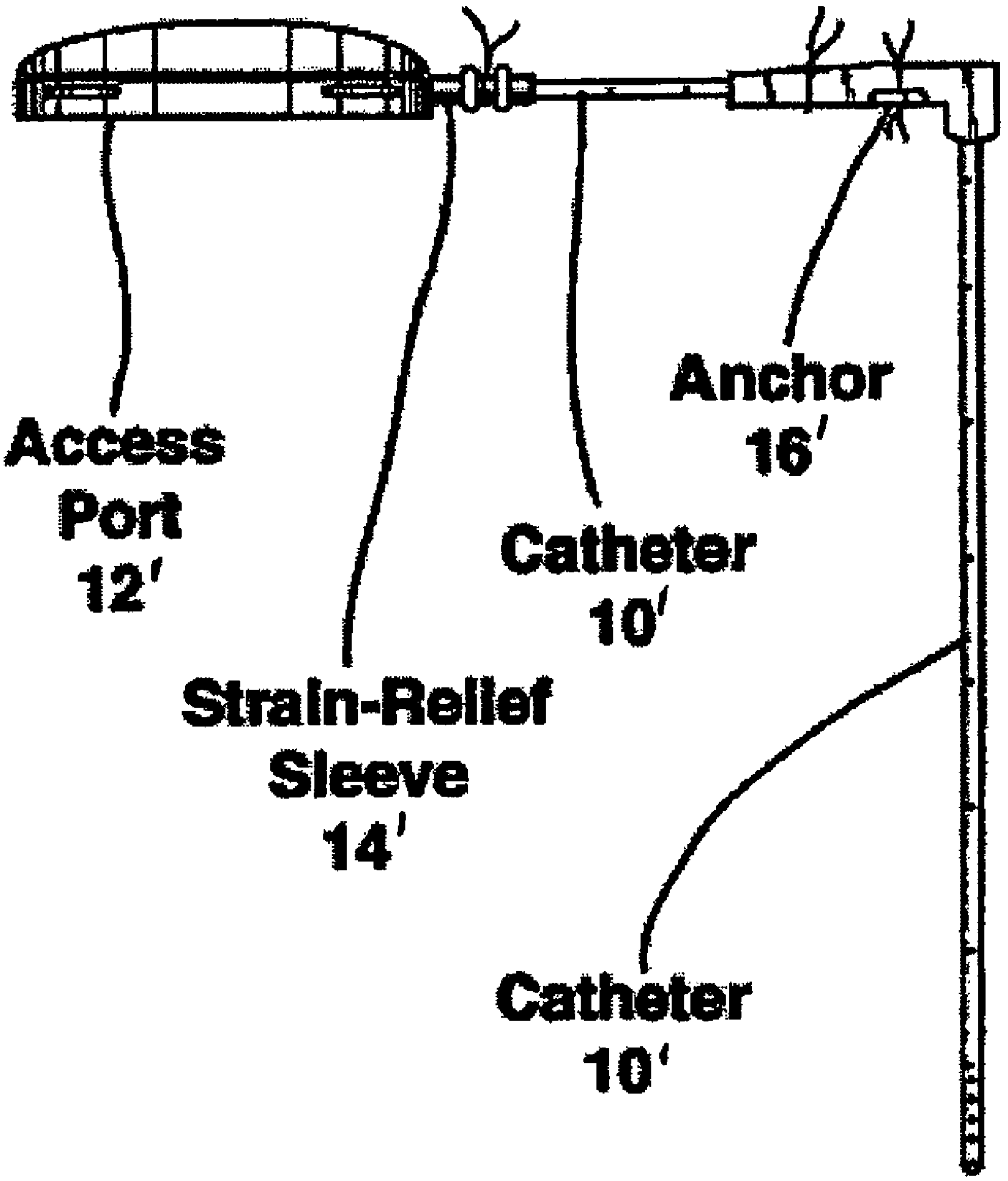
FIG. 4 illustrates an investigational device (by Medtronic, Inc. of Minneapolis, Minn. Model 8506), which can be implanted subcutaneously on the cranium, and provides an access port through which therapeutic agents may be delivered to the brain.
Figure 5:
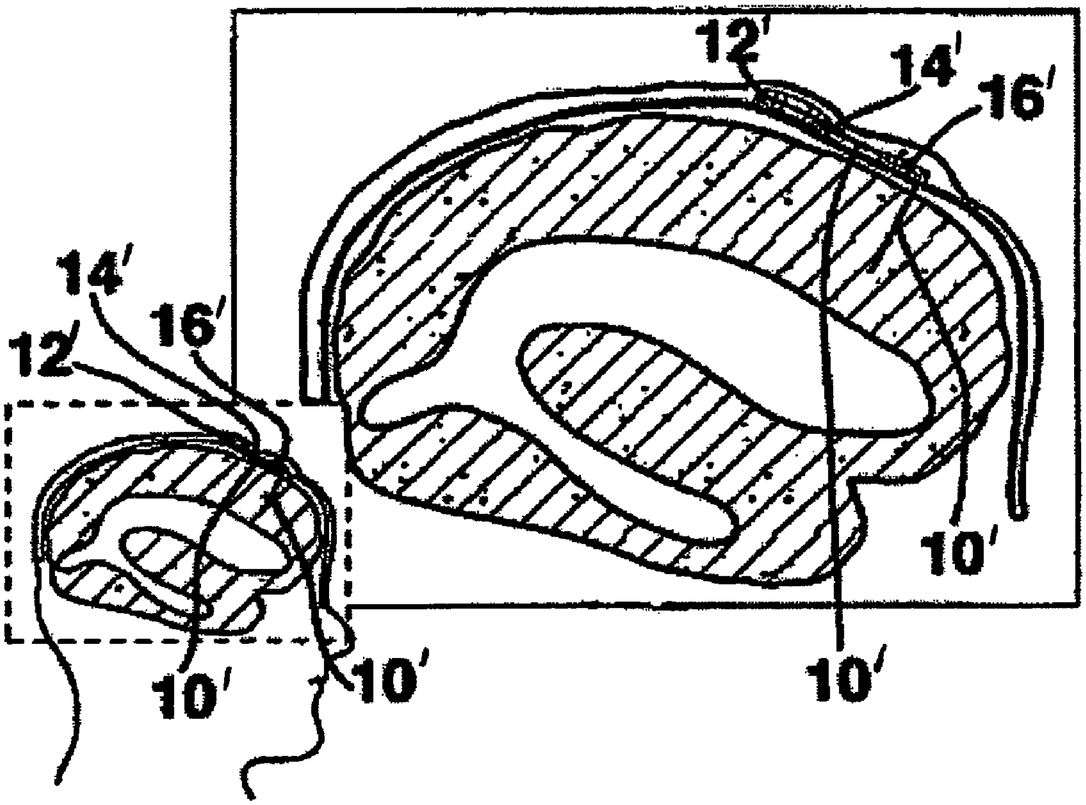
FIG. 5 illustrates an investigational device (by Medtronic, Inc. of Minneapolis, Minn.—schematic of Model 8506), which is implanted subcutaneously on the cranium, and provides an access port through which therapeutic agents may be delivered to the brain.

Examples of the delivery devices within the scope of the present invention include the Model 8506 investigational device (by Medtronic, Inc. of Minneapolis, Minn.), which can be implanted subcutaneously on the cranium, and provides an access port through which therapeutic agents may be delivered to the brain. Delivery occurs through a stereotactically implanted polyurethane catheter. The Model 8506 is schematically depicted in FIGS. 4 and 5. Two models of catheters that can function with the Model 8506 access port include the Model 8770 ventricular catheter by Medtronic, Inc., for delivery to the intracerebral ventricles, which is disclosed in U.S. Pat. No. 6,093,180, incorporated herein by reference, and the IPA1 catheter by Medtronic, Inc., for delivery to the brain tissue itself (i.e., intraparenchymal delivery), disclosed in U.S. Ser. Nos. 09/540,444 (U.S. Pat. No. 6,551,290) and 09/625,751 (U.S. Pat. No. 6,945,969), which are incorporated herein by reference. The latter catheter has multiple outlets on its distal end to deliver the therapeutic agent to multiple sites along the catheter path. In addition to the aforementioned device, the delivery of the small interfering RNA vectors in accordance with the present invention can be accomplished with a wide variety of devices, including but not limited to U.S. Pat. Nos. 5,735,814, 5,814,014, and 6,042,579, all of which are incorporated herein by reference.

Using the teachings of the present invention and those of skill in the art will recognize that these and other devices and systems may be suitable for delivery of small interfering RNA vectors for the treatment of neurodegenerative diseases in accordance with the present invention.

In one preferred embodiment, the method further comprises the steps of implanting a pump outside the brain, the pump coupled to a proximal end of the catheter, and operating the pump to deliver the predetermined dosage of the at least one small interfering RNA or small interfering RNA vector through the discharge portion of the catheter. A further embodiment comprises the further step of periodically refreshing a supply of the at least one small interfering RNA or small interfering RNA vector to the pump outside said brain.

Thus, the present invention includes the delivery of small interfering RNA vectors using an implantable pump and catheter, like that taught in U.S. Pat. Nos. 5,735,814 and 6,042,572, and further using a sensor as part of the infusion system to regulate the amount of small interfering RNA vectors delivered to the brain, like that taught in U.S. Pat. No. 5,814,014. Other devices and systems can be used in accordance with the method of the present invention, for example, the devices and systems disclosed in U.S. application Ser. Nos. 09/872,698 (filed Jun. 1, 2001) and 09/864,646 (filed May 23, 2001), which are incorporated herein by reference.

To summarize, the present invention provides methods to deliver small interfering RNA vectors to the human central nervous system, and thus treat neurodegenerative diseases by reducing the production of a pathogenic protein within neurons.

The present invention is directed for use as a treatment for neurodegenerative disorders and/or diseases, comprising Alzheimer's disease, Parkinson's disease, Huntington's disease, Spinocerebellar type 1, type 2, and type 3, and/or any neurodegenerative disease caused or aggravated by the production of a pathogenic protein, or any other neurodegenerative disease caused by the gain of a new, pathogenic function by a mutant protein.

EXAMPLES

Example 1

Construction of a Small Interfering RNA Targeting Human Ataxin1 mRNA

As an example of the embodiments of the invention, we have made a small interfering RNA that targets the mRNA for human ataxin1. This small interfering RNA reduces the amount of mRNA for human ataxin1 in human cells, in cell cultures. As a therapy for Spinocerebellar Ataxia Type 1 (SCA1), this same small interfering RNA or a similar small interfering RNA will be delivered to the cells of the cerebellum in the patient's brain, using implanted access ports and catheters. The result will be a reduction in the amount of ataxin1 protein in these cells, thereby slowing or arresting the progression of the patient's SCA1 disease.

The small interfering RNA against human ataxin1 was been constructed from the nucleotide sequence for human ataxin1. The sequence from human ataxin 1 was retrieved from the publicly-accessible nucleotide database provided by NCBI, retrievable as NCBI accession number NM_000332 (SEQ ID:15). A portion of the human mRNA sequence for ataxin1 was identified as a potential site for small interfering RNA cleavage and also predicted to be single-stranded by MFOLD analysis. In accession NM_000332 (SEQ ID:15), three pairs of anti ataxin1 siRNA targets were constructed:

1. Anti-ataxin1 siRNA targeting the mRNA sequence at sites numbered 945 through 965:

```
SEQ ID: 1        5'-AACCAAGAGCGGAGCAACGAA-3'

SEQ ID: 2        3'-GGTTCTCGCCTCGTTGCTTAA-5'
```

2. Anti-ataxin1 siRNA targeting the mRNA sequence at sites numbered 1671-through 1691:

```
SEQ ID: 3        5'-AACCAAGAGCGGAGCAACGAA-3'

SEQ ID: 4        3'-GGTTCTCGCCTCGTTGCTTAA-5'
```

3. Anti-ataxin1 siRNA targeting the mRNA sequence at sites numbered 2750-through 2770:

```
SEQ ID: 4        5'-AACCAGTACGTCCACATTTCC-3'

SEQ ID: 6        3'-GGTCATGCAGGTGTAAAGGAA-5'
```

A series of six deoxyoligonucleotide fragments were designed, ordered and purchased from the MWG Biotech, Inc., custom oligonucleotide synthesis service to provide the six fragments making up the three target sites. Additionally, these oligonucletides were constructed to include an 8 base sequence complementary to the 5' end of the T7 promoter primer included in an siRNA construction kit (Ambion, Inc. catalog number 1620). Each specific oligonucleotide was annealed to the supplied T7 promoter primer, and filled-in with Klenow fragment to generate a full-length DNA template for transcription into RNA. Two in vitro transcribed RNAs (one athe antisense to the other) were generated by in vitro transcription reactions then hybridized to each other to make double-stranded RNA. The double-stranded RNA product was treated with DNase (to remove the DNA transcription templates) and RNase (to polish the ends of the double-stranded RNA), and column purified to provide the three siRNAs that were delivered and tested in cells.

Example 2

Delivery of a Small Interfering RNA Targeting Human Ataxin1 mRNA

The constructed siRNA molecules 1-3 described in Example 1 were transfected into HEK293 cells. The RNA produced by the transfected cells was harvested and assayed to measure the amount of human ataxin1 mRNA.

FIG. 1 shows the results of a quantitative reverse-transcriptase polymerase chain reaction (qRT-PCR) assay for the amount of ataxin1 messenger RNA (mRNA) per microgram of total RNA from cultures of HEK 293H cells. Four cell populations were assayed. The first were 293H cells that had been transiently transfected with siRNA against GAPDH, a "housekeeping gene" with no known relationship to ataxin1 mRNA expression. (The siRNA against GAPDH was supplied as a standard control by Ambion, Inc., in their commercially-available kit for making and testing siRNA). The second were 293H cells that had been transiently transfected with siRNA against ataxin1 mRNA at location 1671 in the ataxin1 mRNA sequence. The third were 293H cells transiently transfected with a plasmid containing a ribozyme against ataxin1 mRNA (which cleaves ataxin1 mRNA at position 1364 in the ataxin1 mRNA sequence). The fourth were 293H cells transiently transfected with siRNA against ataxin1 mRNA at location 0945. All cell populations were harvested concurrently for total cellular RNA, at a time point 48 hours after transfection.

On the gels pictured, the amplified DNA products of the RT-PCR reaction were separated by molecular size, using gel electrophoresis, and are visible as bands of varying intensity. Each cell population described was assayed using a series of parallel reactions, shown as a set of lanes at the top or bottom of each gel. Each set of lanes contains two bands per lane. The top band is the DNA product amplified from a known quantity of DNA added to the reaction to compete with the endogenous cDNA reverse transcribed from the cellular mRNA. If the bands in a given lane are of the same intensity, then the amount of cellular mRNA in the original cell sample can be inferred to be equivalent to the amount of known quantity of DNA added to the reaction tube. From left to right across the lanes, the amount of known DNA standard added was decreased, in the picogram amounts shown. The assay is interpreted by looking for the set of lanes for which the intensity of the bands "crosses over" from being brightest for the DNA standard, to being brightest for the cellular product below it, indicating that the amount of DNA standard is now lower than the amount of cellular mRNA.

On the gel shown in FIG. 1, the top set of lanes is from the cells transfected with the ribozyme against ataxin1 mRNA. The comparison of the bands from this cellular sample to the bands from the DNA standards indicates that the amount of ataxin1 mRNA in these cells is between 0.505 and 0.303 picograms per microgram of total cellular RNA. The bottom set of lanes is from the cells transfected with siRNA against ataxin1 at position 0945. Analysis of these lanes indicates that the amount of ataxin1 mRNA in these cells is between 0.303 and 0.202 picograms per microgram of total cellular RNA.

Figure 2:
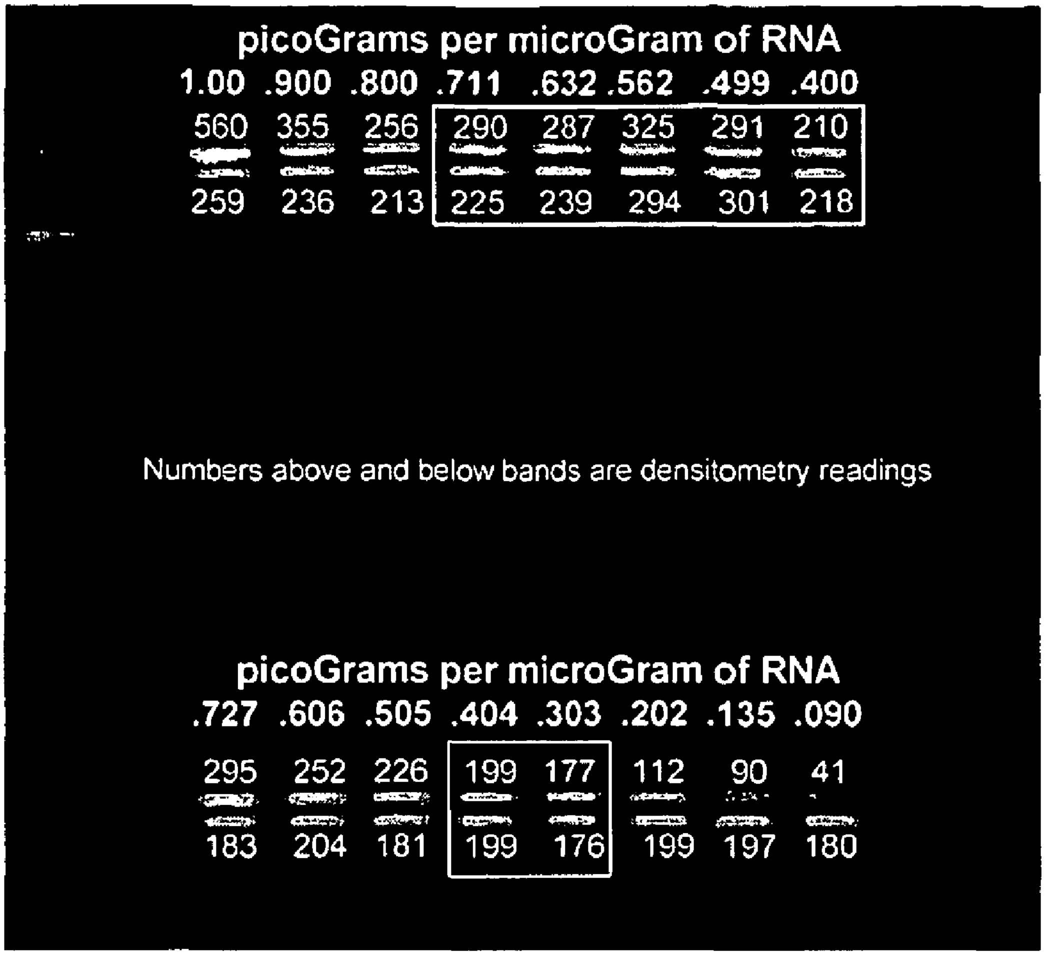
FIG. 2 shows the assay (using the same quantitative RT-PCR method known to those practiced in the art) of the ataxin-1 mRNA obtained from HEK293H cells that have been transfected with anti-ataxin-1 small interfering RNA (bottom lanes) compared to the mRNA obtained from HEK293H cells that have been transfected with a control siRNA that targets the mRNA for glyceraldehyde-3-phosphate dehydrogenase (GAPDH)

On the gel shown in FIG. 2, the top set of lanes is from the cells transfected with a control siRNA against GAPDH. Analysis of these lanes indicates that the amount of ataxin1 mRNA in these cells is between 0.711 and 0.400 picograms per microgram of total cellular RNA. Finally, the bottom set of lanes is from cells transfected with another siRNA against ataxin1, at position 1671. These lanes indicate that the amount of ataxin1 mRNA in these cells is between 0.404 and 0.303 picograms per microgram of total cellular RNA.

In summary, the results of this particular analysis were:

| | Amount of ataxin1 mRNA (picograms per microgram total cellular RNA) | | |
|---|---|---|---|
| Treatment | Lower bound | Upper bound | Midpoint Estimate |
| Control (GAPDH) | 0.400 | 0.711 | 0.555 |
| Ribozyme (A1364A) | 0.303 | 0.505 | 0.404 |
| siRNA (AT1671) | 0.303 | 0.404 | 0.353 |
| siRNA (AT0945) | 0.202 | 0.303 | 0.252 |

These data indicate that both the AT1671 and AT0945 siRNA against ataxin1 were effective at reducing the amount of ataxin1 mRNA in these cells within 48 hours after transfection, and that the siRNA were more effective at the reduction of ataxin1 mRNA than was this anti-ataxin1 ribozyme.

It should be noted that the exemplified method for constructing the small interfering RNA to be used as the therapeutic agents in the invention (that is, assembly from oligonucleotides using in vitro transcription and hybridization) is only one possible means for making the therapeutic small interfering RNA. Other larger scale, more efficient methods for manufacturing small interfering RNA may be used to produce the clinical grade and clinical quantities used for treating human patients, without altering the essence of the invention or departing from the spirit and scope of this invention, as set forth in the appended claims.

Example 3

Construction of Small, Interfering RNA Viral Vectors

Figure 3:
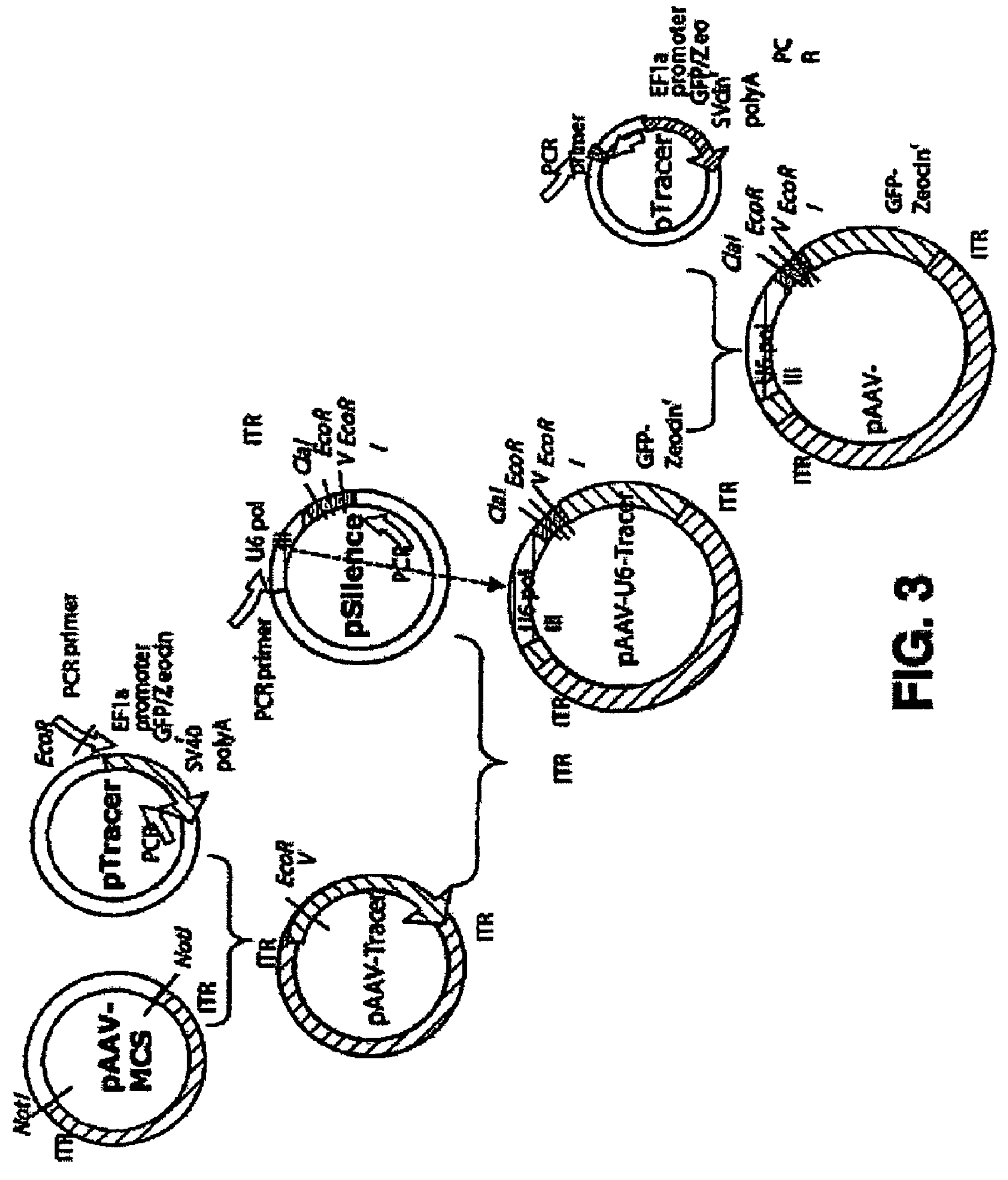
FIG. 3 shows the construction of the adeno-associated virus expression vector pAAV-siRNA.

We have constructed a selectable reporter plasmid, pAAV-U6-Tracer for cloning siRNA. (See FIG. 3). The plasmid pAAV-U6-Tracer was constructed to contain the inverted terminal repeats (ITR) of adeno-associated virus, flanking the U6 RNA polymerase III promoter from pSilencer (Ambion), and the EF1a promoter, green fluorescence protein, Zeocin$^r$ resistance, and SV40 poly A from pTracer (Invitrogen). The gene segments are cloned as shown in FIG. 3. Oligonucleotides for expressing siRNA are cloned into the multiple cloning region just downstream in the 3' direction from the U6 RNA polymerase III promoter.

HEK293 Cells are cotransfected with pAAV-siRNA, pHelper, and pAAV-RC to make viral producer cells, where the pAAV-RC and pHelper plasmids are part of the three plasmid AAV production system Avigen, Inc.). The producer 293 cells are grown in culture are used to isolate recombinant viruses, which is used to transfect cells for assessment of treatment effect, such as: HeLa Cells, DAOY cells, and SK-N-SH cells.

Example 4

Treatment of Alzheimer's Disease Using RNA Interference Targeting Beta-Amyloid Cleaving Enzyme Type 1 (BACE1)

As an example embodiment of the invention, we have developed and implemented a therapy for Alzheimer's disease. We have tested our therapy for Alzheimer's disease in a transgenic mouse model of the disease. This therapy uses a viral vector that encodes for an siRNA sequence that, upon uptake by a neuronal cell, reduces the amount of mRNA for beta-amyloid cleaving enzyme type 1 (BACE1) produced in that neuronal cell. Reducing the amount of BACE1 mRNA in cells will result in a reduction of the amount of the enzyme produced, and subsequently the amount of beta-amyloid fragments cleaved from the amyloid-precursor protein (APP) by the BACE1 enzyme. Reduction in the amount of beta-amyloid fragments in the brain is the biological mechanism by which Alzheimer's disease is treated by this therapy.

The steps involved in this work included (1) in vitro screening of candidate anti-BACE1 siRNA sequences for efficacy, (2) construction of a viral vector for in vivo delivery of DNA encoding for the anti-BACE1 siRNA to the mammalian brain, (3) neurosurgical administration of the vector to the mice, (4) testing of the behavior of the mice to assess the effect of the treatment, and (5) examination of the brain tissue of the mice to assess the effect of the treatment. These steps are described in detail below. Because Alzheimer's disease is an aging-related disorder, assessment of the treatment in these mice is on-going as the mice attain old age.

(1) Screening of Anti-BACE1 siRNA Sequences for In Vitro Efficacy

Identification of candidate anti-BACE1 siRNA sequences: In order to identify an siRNA sequence that is effective at reducing the expression of BACE1 mRNA in neuronal cells, we analyzed the human and mouse cDNA sequences for the BACE1 gene available in the Genbank database (National Center for Biotechnology Information, accession numbers NM_012104, NM_138971, NM_138972, and NM_138973 for human, and NM_011792 for mouse). The analysis consisted of identifying sections of the cDNA sequence beginning with two successive adenine nucleotides (AA) or with a cytosine and adenine (CA), and comprising those two nucleotides plus the nineteen successive nucleotides. These candidate sequences were tested for possible partial matches to other sequences in other genes, using the BLAST software program provided by the National Center for Biotechnology Information website (http://www.ncbi.nlm.nih.gov/BLAST/), and sequences with a high amount of partial matching to other genes (e.g., a match of more than 15 out of the 19 successive nucleotides following the AA or CA nucleotides) were eliminated from further consideration. Candidate sequences with an extreme percentage of guanine or cytosine (G or C) nucleotides in the sequence (e.g., greater than 65% or less than 35% of the 19 successive nucleotides were G or C rather than A or T) were also eliminated from consideration. From the remaining candidates, the following were selected for laboratory screening:

The set to be screened in the laboratory was selected to include candidates from a wide range of positions within the cDNA of the mouse BACE1 sequence. For purposes testing this therapy in a transgenic mouse model of Alzheimer's disease, it was essential that the siRNA sequence be effective at suppressing the native mouse BACE1 enzyme in these transgenic mice, not the human transgene that is overexpressed in this mice (which is the human gene for amyloid-precursor protein APP). Therefore, priority was given to candidate siRNA sequences corresponding to mouse cDNA regardless of the amount of homology to human BACE1 cDNA. However, some of the candidate siRNA sequences correspond 100% to human as well as mouse BACE1 cDNA. In particular, the candidate which we have found to be most effective, MB1749, targets a regions of BACE1 mRNA that is 100% identical across the human and mouse species, and thus constitutes a therapy component that is applicable to humans as well as mice.

Production of siRNA candidates for in vitro testing: We made double-stranded RNA corresponding to the MB0803, MB1663, MB1749, or MB3249 siRNA candidates by in vitro transcription from custom DNA oligonucleotides and other reagents using the Ambion Silencer™ siRNA Construction Kit (Ambion, Inc., Austin, Tex.; catalog number 1620) fol-

| SEQ ID: | Item | Name | Starting position within mouse BACE1 cDNA (Genbank Accession NM_011792) | DNA sequence corresponding to the therapeutic siRNA | Method used for production of siRNA for in vitro screening |
|---|---|---|---|---|---|
| SEQ ID: 24 | 1 | MB0803 | 0803 | AAGGGTGTGTATGTGCCCTAC | in vitro transcription |
| SEQ ID: 25 | 2 | MB1663 | 1663 | AATTGGCTTTGCTGTCAGCGC | in vitro transcription |
| SEQ ID: 26 | 3 | MB1749 | 1749 | AAGACTGTGGCTACAACATTC | in vitro transcription |
| SEQ ID: 27 | 4 | MB3249 | 3249 | AAGGCTGCCTGGAGAAAGGAT | in vitro transcription |
| SEQ ID: 28 | 5 | DhMB0918 | 0916 | caCTGAATCGGACAAGTTCTT | chemical synthesis |
| SEQ ID: 29 | 6 | DhMB1131 | 1129 | caTGATCATTGGTGGTATCGA | chemical synthesis |
| SEQ ID: 30 | 7 | DhMB1233 | 1231 | aaTCAATGGTCAAGATCTCAA | chemical synthesis |
| SEQ ID: 31 | 8 | DhMB1509 | 1507 | caTCCTTCCTCAGCAATACCT | chemical synthesis |
| SEQ ID: 32 | 9 | SEC0683 | 0683 | CAGACGCTCAACATCCTGGTG | expression cassette |
| SEQ ID: 33 | 10 | SEC1722 | 1722 | AAGGTCCGTTTGTTACGGCAG | expression cassette |
| SEQ ID: 34 | 11 | SEC2163 | 2163 | AATATCCTTAGACACCACAAA | expression cassette |
| SEQ ID: 35 | 12 | SEC2466 | 2466 | AAACAAGAACCTATGCGATGC | expression cassette |
| SEQ ID: 36 | 13 | SEC2473 | 2473 | AACCTATGCGATGCGAATGTT | expression cassette |

lowing the procedure recommended by the manufacturer. The custom DNA oligonucleotides used to produce our specific siRNA were as follows. The siRNA target sequences are listed in capital letters, while other oligonucleotides needed for the purposes of the in vitro transcription method are listed in lower case letters.

| SEQ ID: | siRNA | Sense oligonucleotide (DNA) | Antisense oligonucleotide (DNA) | SEQ ID antisense |
|---|---|---|---|---|
| 57 | MB0803 | aaGTAGGGCACATACACACCCcct-gtctc | AAGGGTGTGTATGTGCCCTACcctgtctc | 58 |
| 59 | MB1663 | aaGCGCTGACAGCAAAGCCAAcct-gtctc | AATTGGCTTTGCTGTCAGCGCcctgtctc | 60 |
| 61 | MB1749 | aaGAATGTTGTAGCCACAGTCcct-gtctc | AAGACTGTGGCTACAACATTCcctgtctc | 62 |
| 63 | MB3249 | aaATCCTTTCTCCAGGCAGCCcct-gtctc | AAGGCTGCCTGGAGAAAGGATcctgtctc | 64 |

We ordered chemically synthesized double-stranded RNA corresponding to the DhMB0918, DhMB1131, DhMB1233, and DhMB1509 siRNA candidates from Dharmacon, Inc. (Lafayette, Colo.). The sequences we specified that this supplier produce for us were as follows:

| SEQ ID: | siRNA | Sense oligonucleotide (RNA) | Antisense oligonucleotide (RNA) | SEQ ID Antisense |
|---|---|---|---|---|
| 65 | DhMB0918 | CUGAAUCGGACAAGUUCUUdTdT | AAGAACUUGUCCGAUUCAGdTdT | 66 |
| 67 | DhMB1131 | UGAUCAUUGGUGGUAUCGAdTdT | UCGAUACCACCAAUGAUCAdTdT | 68 |
| 69 | DhMB1233 | UCAAUGGUCAAGAUCUCAAdTdT | UUGAGAUCUUGACCAUUGAdTdT | 70 |
| 71 | DhMB1509 | UCCUUCCUCAGCAAUACCUdTdT | AGGUAUUGCUGAGGAAGGAdTdT | 72 |

We made DNA expression cassettes from which cells will transcribe RNA that forms a hairpin corresponding to the SEC0683, SEC1722, SEC2163, SEC2466, or SEC2473 siRNA candidates by polymerase chain reaction, using our custom DNA oligonucleotides plus reagents from the Ambion Silencer™ Express siRNA Expression Cassette Kit (Ambion, Inc., Austin, Tex.; catalog number 1682) following the procedure recommended by the manufacturer. The custom DNA oligonucleotides used to produce our specific siRNA expression cassettes were as follows. The siRNA target sequences are listed in capital letters, while other oligonucleotides needed for the purposes of the expression cassette method are listed in lower case letters.

| siRNA | strand | oligonucleotide (DNA) | SEQ ID: |
|---|---|---|---|
| SEC0683 | sense | ggtgaagcttgACCAGGATGTTGAGCGTCTGccggtgtttcgtcctttccacaag | SEQ ID: 73 |
| | antisense | cggcgaagcttttccaaaaaaCAGACGCTCAACATCCTGGTGaagcttgacca | SEQ ID: 74 |
| SEC1722 | sense | cagctacacaaaCTGCCGTAACAAACGGACCcggtgtttcgtcctttccacaag | SEQ ID: 75 |
| | antisense | cggcgaagcttttccaaaaAAGGTCCGTTTGTTACGGCAGctacacaaactgc | SEQ ID: 76 |
| SEC2163 | sense | aaactacacaaaTTTGTGGTGTCTAAGGATAccggtgtttcgtcctttccacaag | SEQ ID: 77 |
| | antisense | cggcgaagcttttccaaaaAATATCCTTAGACACCACAAActacacaaatttg | SEQ ID: 78 |
| SEC2466 | sense | tgcctacacaaaGCATCGCATAGGTTCTTGTcggtgtttcgtcctttccacaag | SEQ ID: 79 |
| | antisense | cggcgaagcttttccaaaaAAACAAGAACCTATGCGATGCctacacaaagcat | SEQ ID: 80 |
| SEC2473 | sense | gttgaagcttgAACATTCGCATCGCATAGGccggtgtttcgtcctttccacaag | SEQ ID: 81 |
| | antisense | cggcgaagcttttccaaaaAACCTATGCGATGCGAATGTTgaagcttgaaca | SEQ ID: 82 |

In vitro application of the siRNA candidates to neuronal cell cultures: To assess the effectiveness of each anti-BACE1 siRNA candidate in suppressing BACE1 mRNA in vitro, mouse neuronal cells of the Neuro2a cell line (American Type Culture Collection, catalog number CCL-131) were cultured using the standard cell culture conditions for these cells. Upon reaching 50-70% confluence, the cells were co-transfected with one of the siRNA candidates, and with a plasmid containing the cDNA for mouse BACE and for green fluorescent protein (GFP). This plasmid, called pTracerBace1, was constructed by us for this purpose by obtaining the mouse BACE cDNA from OpenBiosystems (Huntsville, Ala.; catalog number EMM1002-7007570), and transferring this cDNA into pTracer™-CMV2 (Invitrogen, Carlsbad, Calif.; catalog number V885-20) using standard molecular biology methods. In pTracerBace1, the cDNA for mouse BACE is inserted in the polylinker region downstream from the CMV promoter, and thus BACE mRNA is expressed from the CMV promoter. The GFP mRNA is expressed from a separate region of the plasmid following an EF-1a/EM7 promoter, as produced by the manufacturer.

The cell transfection procedure and reagents used to conduct the in vitro testing varied as appropriate for the form (RNA or DNA) in which the siRNA candidate was applied. For transfection of cells with plasmid plus siRNA candidates produced by in vitro transcription (MB0803, MB1663, MB1749, MB3249) or by direct chemical synthesis (DhMB0918, DhMB1131, DhMB1233, DhMB1509), first a mixture of pTracerBace1 plasmid in Transit-Neural transfection reagent (Mims, Inc. Madison, Wis.; catalog number 2144) was formed following the manufacturer's recommended procedures. Then, Transit-TKO transfection reagent (Minis, Inc., catalog number 2154) was added dropwise to the Transit-Neural mixture, and incubated at room temperature for 10 minutes. Next, the siRNA was added to the mixture, incubated to allow the siRNA to form complexes with the Transit-TKO, then finally added dropwise to the cells. In all cases, the amount of pTracerBace1 plasmid per cell culture well was 1 microgram per well (of a six-well culture plate) across the various conditions, and the final concentration of siRNA per cell culture well was 25 nanoMolar.

For transfection of cells with plasmid plus siRNA candidates in the form of DNA (Silencer Expression Cassettes SEC0683, SEC1722, SEC2163, SEC2466, SEC2473) the method was similar, but SiPort-XP1 transfection reagent (Ambion, Inc., Austin, Tex.; catalog number 4506) was used for transfection of the cells with the double-stranded DNA PCR products constituting the expression cassettes. In these cases, SiPort-XP1 reagent was added dropwise to Opti-MEM® reduced-serum medium (Invitrogen, Carlsbad, Calif.; catalog number 22600), vortexed, and incubated at room temperature for 15 minutes following the procedure recommended by Ambion, Inc. Then, pTracerBace1 plasmid was added to one aliquot of the SiPort-XP1 mixture, and siRNA expression cassette DNA was added to a separate aliquot of SiPort-XP1 mixture. Each aliquot was incubated at room temperature for 15 minutes to allow the DNA molecules to complex with the SiPort-XP1 reagent, then the two mixtures were combined and added dropwise to cells. The amount of pTracerBace1 plasmid per cell culture well was 1 migrogram per well across the various conditions, and the amount of siRNA expression cassette DNA added per well was 500 nanograms per well.

Assay of the effect of siRNA candidates on BACE1 mRNA levels in cells: To determine the effect of siRNA candidate on BACE1 mRNA levels in cells, the cells were harvested 48 to 72 hours after transfection with the siRNA and pTracerBace1 plasmid, and total cellular RNA was recovered from the cell lysate using the Qiagen RNeasy Mini Kit (Qiagen, Inc., Valencia, Calif.; catalog number 74106). The RNA was treated with DNase during this isolation, to eliminate genomic and plasmid DNA from the samples. The RNA samples were reverse transcribed to cDNA using the StrataScript First Strand cDNA Synthesis Kit (Stratagene, Inc., La Jolla, Calif.; catalog number 200420) following the manufacturer's protocol, and using oligo-dT to prime the cDNA synthesis. Parallel samples included in the same protocol, but omitting the inclusion of the reverse transcriptase enzyme, were used to verify the lack of genomic or plasmid DNA carryover to the PCR analysis.

The cDNA samples obtained from the reverse transcription reactions were then used to conduct real-time quantitative PCR analysis of relative amounts of BACE1 cDNA, GAPDH cDNA, and GFP cDNA in the samples. The assays for the various cDNA species were conducted in parallel on aliquots of the same sample, divided just before the addition of the pertinent PCR primers and fluorescent substrates for the PCR reactions. All reactions were performed in parallel in a Rotor-Gene 3000 real-time PCR machine (Corbett Research, Inc., Sydney, Australia) using TaqMan Universal PCR Mix without Amperase UNG (Applied Biosystems Foster City, Calif.; catalog number 4324018) as the polymerase and nucleotide reagent. The PCR assay for mouse BACE1 was performed using the BACE1 Assay on Demand (Applied Biosystems; catalog number Mm00478664_ml). The assay for rodent GAPDH used the TaqMan® Rodent Gapdh Control Reagents (Applied Biosystems; catalog number 4308313). The assay for GFP (introduced into transfected cells by the pTracerBace1 plasmid) used QuantiTect SYBR Green (Qiagen; catalog number 204143) and the following custom PCR primers: forward: 5'-TGGTGTTCAATGCTTTTCCC-3' (SEQ ID NO:55); reverse: 5'-GCGTCTTGTAGTTCCCGTCA-3' (SEQ ID NO:56), which produce an expected PCR product size of 128 basepairs.

To quantify the relative amounts of mRNA in various cell samples, a series of dilutions of cDNA from a sample of cells that was transfected with pTracerBace1 but not treated with any siRNA candidate was used to generate a standard curve relating PCR cycle threshold to cDNA quantity, ranging from 1 to 100 nanograms of mRNA per microliter of sample. Based on the standard curve for each mRNA target (BACE1, GAPDH, or GFP), the nanograms per microliter of mRNA of each gene product was obtained for each cell sample. Finally, the amount of BACE1 mRNA in the cell sample was normalized to the amount of GFP mRNA in the same sample. From these normalized amounts of BACE1 mRNA, the percentage reduction in BACE1 mRNA resulting from a given siRNA treatment relative to the untreated cells was calculated. The following table provides the results of one such assay, and illustrates the method.

Quantitative RT-PCR results from Neuro2a cells transfected with pTracerBace1 and various anti-Bace1 siRNA candidates.

| Sample Tube | Calculated amt of Bace1 mRNA | Calculated amt of Gapdh mRNA | Calculated amt of GFP mRNA | Bace1:GFP Ratio | % Suppression | Comment |
|---|---|---|---|---|---|---|
| 100 ng/ul | 101.142 | 122.670 | 93.721 | 1.079 | | |
| 50 ng/ul | 51.886 | 46.259 | 54.591 | 0.950 | | |
| 20 ng/ul | 19.064 | 16.968 | 18.387 | 1.037 | | |
| 10 ng/ul | 9.926 | 9.361 | 11.109 | 0.894 | | |
| 5 ng/ul | 4.871 | 4.687 | 4.796 | 1.016 | | |
| 1 ng/ul | 1.034 | 1.183 | 0.998 | 1.036 | | |
| | | | Average | 1.002 | | |
| | | | SD | 0.068 | | |
| MB0803 | 36.077 | 156.269 | 85.232 | 0.423 | 58% | |
| MB0803 no RT | 0.247 | 0.001 | 0.108 | | | no DNA contamination |
| MB1663 | 98.186 | 143.823 | 130.188 | 0.754 | 25% | |
| MB1663 no RT | 0.226 | 0.002 | 0.118 | | | no DNA contamination |
| MB1749 | 3.957 | 148.884 | 109.256 | 0.036 | 96% | Good anti-Bace1 effect |
| MB1749 no RT | 0.151 | 0.002 | 0.065 | | | no DNA contamination |
| MB3249 | 117.314 | 140.869 | 108.461 | 1.082 | −8% | Ineffective |
| MB3249 no RT | 0.153 | 0.001 | 0.078 | | | no DNA contamination |
| DhMB0918 | 5.906 | 164.022 | 75.280 | 0.078 | 92% | Good anti-Bace1 effect |
| DhMB0918 no RT | 0.515 | 0.004 | 0.187 | | | no DNA contamination |
| DhMB1131 | 8.125 | 176.968 | 82.778 | 0.098 | 90% | Good anti-Bace1 effect |
| DhMB1131 no RT | 0.208 | 0.001 | 0.094 | | | no DNA contamination |
| DhMB1233 | 9.014 | 137.025 | 73.113 | 0.123 | 88% | Good anti-Bace1 effect |
| DhMB1233 no RT | 0.327 | 0.003 | 0.136 | | | no DNA contamination |
| pTracerBace noRT | 0.184 | 0.001 | 0.080 | | | no DNA contamination |

Results

The cell transfections and quantitative real-time RT-PCR assays for BACE1 mRNA levels relative to GFP mRNA levels in transfected Neuro2a cells were repeated independently by at least two persons. The resulting percentage of BACE1 mRNA suppression for each siRNA candidate, averaged over the independent assays, is as shown in the following table.

| Item | siRNA Name | Percent suppression of BACE1 mRNA in Neuro2a (mouse neuronal) cells co-transfected with pTracer-Bace1 and the siRNA | 95% confidence interval based on two to four independent assays (by Student's T distribution) Lower bound | Upper bound |
|---|---|---|---|---|
| 1 | MB0803 | 57% | 44.3% | 69.7% |
| 2 | MB1663 | 42% | ≦0% | ≧100% |
| 3 | MB1749 | 97% | 90.2% | ≧100% |
| 4 | MB3249 | 0% | ≦0% | ≧100% |
| 5 | DhMB0918 | 79% | 17.0% | ≧100% |
| 6 | DhMB1131 | 85% | 59.1% | ≧100% |
| 7 | DhMB1233 | 82% | 47.8% | ≧100% |
| 8 | DhMB1509 | 57% | ≦0% | ≧100% |
| 9 | SEC0683 | 54% | 24.0% | 84.5% |
| 10 | SEC1722 | 50% | ≦0% | ≧100% |
| 11 | SEC2163 | 48% | 16.9% | 78.1% |
| 12 | SEC2466 | 42% | ≦0% | 94.5% |
| 13 | SEC2473 | 61% | 31.5% | 90.5% |

As this table shows, eight of the thirteen tested candidates suppress BACE1 mRNA to some statistically significant amount ($p<0.05$ based on lower bound of 95% confidence interval that is greater than zero), with MB1749 providing the greatest amount of suppression.

(2) Development of an AAV Vector Encoding for Anti-Bace1 siRNA:

To administer the MB1749 anti-BACE1 siRNA therapy to transgenic mice, the use of an adeno-associated viral (AAV) vector containing DNA encoding for the MB1749 siRNA was chosen. AAV is known to transduce neuronal cells in vivo in the rodent brain following surgical injection into the brain tissue, and produce long-lasting expression of the delivered DNA within transduced neuronal cells. To drive the expression of the MB1749 siRNA within transduced cells, we chose the mouse U6 RNA polymerase III promoter, provided by the pSilencer™ 1.0-U6 plasmid available from Ambion, Inc. (catalog number 7207). We genetically engineered the DNA encoding for a hairpin loop of RNA (consisting of the sequence for MB1749, a loop sequence, and the reverse complement of MB1749) into pSilencer™ between the ApaI and EcoRI restriction sites, using the following method.

Construction of the siRNA expression cassette using oligonucleotide condensation: In order to construct the DNA encoding for a hairpin loop of RNA corresponding to MB1749, we obtained the following four oligonucleotides from a synthesizing service:

| Oligo name | SEQ ID NO: | DNA sequence |
|---|---|---|
| MB1749A | SEQ ID NO: 37 | 5'-G<u>AAGACTGTGGCTACAACATTC</u>-3' |
| MB1749B | SEQ ID NO: 38 | 5'-TTCAAGAGA<u>GAATGTTGTAGCCACAGTCTTC</u>TTTTTTG-3' |
| MB1749C | SEQ ID NO: 39 | 5'-TCTCTTGAAGAATGTTGTAGCCACAGTCTTCGGCC-3' |
| MB1749D | SEQ ID NO: 40 | 5'-AATTCAAAAAAG<u>AAGACTGTGGCTACAACATTC</u>-3' |

In the above table, the portions of the oligonucleotide sequences that correspond to the effective siRNA sequence against BACE1 are underlined. Note that the reverse complement for oligonucleotide A is found within the sequence for oligonucleotide C, and all but the first four bases of oligonucleotide D is the reverse complement of the 3' end of oligonucleotide B. Thus, A and C are largely complementary to one another, and B and D are largely complementary to one another.

To construct the double-stranded DNA insert to be cloned into pSilencer™ 1.0-U6 to make pMB1749 plasmid, the four oligonucleotides were suspended in water to a concentration of 25 micromolar, then their ends were phosphorylated using T4 Polynucleotide Kinase enzyme. Next, in one tube, oligo MB1749A was mixed with oligo MB1749C, and in another tube, oligo MB1749B was mixed with oligo MB1749D. The mixtures were heated to 65 degrees Centigrade for 5 minutes then allowed to cool slowly to room temperature, to cause these complementary oligonucleotides to anneal into double-stranded form, with single-stranded overhangs. Next, a three-component ligation reaction was conducted by mixing oligosA/C and oligos B/D with pSilencer™ 1.0-U6 that had been linearized with ApaI and EcoRI restriction enzyme digestion, using standard molecular biology methods. The resulting ligation products were cloned into bacteria, and colonies screened to identify the desired plasmid product, which consists of the following construct inserted between the ApaI and EcoRI restrictions sites in pSilencer™ 1.0-U6:

After 48 hours, the total cellular RNA was harvested from these cells, and used to conduct a reverse transcription quantitative real-time PCR assay, as described above. The results showed that application of the plasmid pMB1749 to cells produced 94% suppression in the level of BACE1 mRNA (normalized for the amount of GFP mRNA as described above) compared to cells not treated with pMB1749. This compares favorably with the results previously obtained by applying MB1749 siRNA to cells in RNA form.

Verification of BACE1 mRNA expression by the MB1749 viral vector: To administer anti-BACE1 siRNA therapy to the brains of mice in vivo, we used an adeno-associated viral (AAV) vector as the means to deliver DNA encoding for the MB1749 siRNA to neurons in the brain, in the manner of the subject invention. To obtain a supply of the viral vector for this purpose, the pMB1749 plasmid we constructed was provided to GeneDetect, Ltd. (Auckland, New Zealand) who were commissioned to transfer the U6 promoter, our MB1749 construct, and the RNA polymerase III termination sequence (consisting of 6 thymines in succession) into their plasmid containing AAV inverted terminal repeats and a green fluorescent protein reporter gene expressed from a chicken beta-actin enhancer and CMV promoter. Our MB1749 expression cassette (U6 promoter, MB1749 construct, and termination sequence) was inserted following the 5' inverted terminal repeat for AAV, and before the GFP expression cassette. The resulting AAV plasmid was then used by GeneDetect to produce AAV-anti-BACE1-MB1749. In addition, we provided

```
        1749-A (SEQ ID NO: 37)        1749-B (SEQ ID NO: 38)
5'      GAAGACTGTGGCTACAACATTCTTCAAGAGAGAATGTTGTAGCCACAGTCTTCTTTTTTG         3'
3' CCGGCTTCTGACACCGATGTTGTAAGAAGTTCTCTCTTACAACATCGGTGTCAGAAGAAAAAACTTAA 5'
        1749-C (SEQ ID NO: 39)        1749-D (SEQ ID NO: 40)
```

We have found this strategy of assembling four oligonucleotides, rather than a single sense and antisense pair, necessary to efficiently clone the DNA coding for the MB1749 hairpin siRNA. Use of single sense and antisense strands (such as can be obtained by concatenating the sequence for MB1749A with MB1749B, making one longer sense strand oligonucleotide, and contatenating MB1749C and MB1749D, making one longer antisense strand) results in molecular strands that tend to form intramolecular hairpins, preventing annealing into a double-stranded DNA, and ligation into the plasmid.

Verification of BACE1 mRNA expression by the MB1749 plasmid: In order to verify that the pMB1749 plasmid, coding for a hairpin loop of RNA corresponding to MB1749, does in fact produce an siRNA that reduces the amount of BACE1 mRNA in cells, mouse Neuro2a neuronal cells were co-transfected with pTracerBace1 plasmid and pMB1749 plasmid, using the SiPort-XP1 transfection reagent as described above.

GeneDetect with another plasmid containing a scrambled sequence for MB1749, verified in vitro not to be active at suppressing BACE1 mRNA expression and not homologous to any known gene in Genbank, for production of AAV-control vector.

To verify in vitro that the resulting AAV-anti-BACE1-MB1749 vector, when used to infect cells, results in suppression of BACE1 mRNA, and the AAV-control vector does not, we transfected cells with pTracerB ace, then 24 hours later, infected them with AAV-anti-BACE1-MB1749 or AAV-control. In two separate cell cultures, we found that AAV-anti-BACE1-MB1749 resulted in a 72.8% and 57.6% (average, 65.2%) reduction in BACE1 mRNA, while AAV-control vector had no significant effect (16.2% and <0% reduction in two separate cultures).

(3) Neurosurgical Administration of the AAV Vector Encoding for Anti-Bace1 siRNA to Tg2576 Mice:

An accepted animal model of Alzheimer's disease is a transgenic mouse that overexpresses the human transgene for APP (Hsiao et al, 1996). The Tg2576 transgenic mouse line develops amyloid plaques containing beta-amyloid beginning at about 10 to 12 months of age (Gau et al, 2002). The plaques are particularly frequent in the cerebral cortex and hippocampus. They are readily detectable 15 months of age, and become more severe at 19 months of age and beyond (Kawarabayashi et al, 2001). Aged female Tg2576 mice deposit significantly more beta-amyloid in the brain than do aged male Tg2576 mice (Callahan et al, 2001). By 19 months of age, the Tg2576 mice exhibit behavioral and cognitive deficits on measures of balance, agility, and spatial memory (King and Arandash, 2002).

Based on these considerations, we have chosen to validate our invention by surgically injecting an AAV vector encoding for the MB1749 siRNA targeting murine BACE1 into the hippocampus of 12 month-old female Tg2576 mice, then assessing the mice for effects of the therapy at ages 15 months and beyond.

Pilot injections (to confirm stereotactic coordinates): To verify correct anatomical targeting of the mouse hippocampus in this age and strain of mouse, and to verify expression from the AAV vector, three nine-month old wildtype C57BL/6 female mice (the background strain for the Tg2576 transgenic line) were injected with 5 microliters of a standard AAV vector (at a concentration of approximately $2.3\times10^{12}$ viral particles per milliliter) containing the GFP reporter gene (rAVE-GFP ½, GeneDetect, Auckland, New Zealand). The injections were at the following stereotactic coordinates, expressed in millimeters from bregma, with the incisor bar at −5 mm: AP−2.70, ML±3.00, DV−2.25. The details of the neurosurgical procedure used to perform the injections are described are further described herein.

Thirteen days post-surgery, these mice were euthanized and transcardially perfused with saline followed by 4% paraformaldehyde to flush and fix their organ tissues. The brains were cut into 30 micron thick sections along the parasagittal planes, with serial sections were collected from throughout the entire left and right hemispheres. These sections were numbered sequentially with the lower numbers assigned to the lateral edge of the hemisphere, and higher numbers to the more medial sections of the hemisphere.

Figure 7:
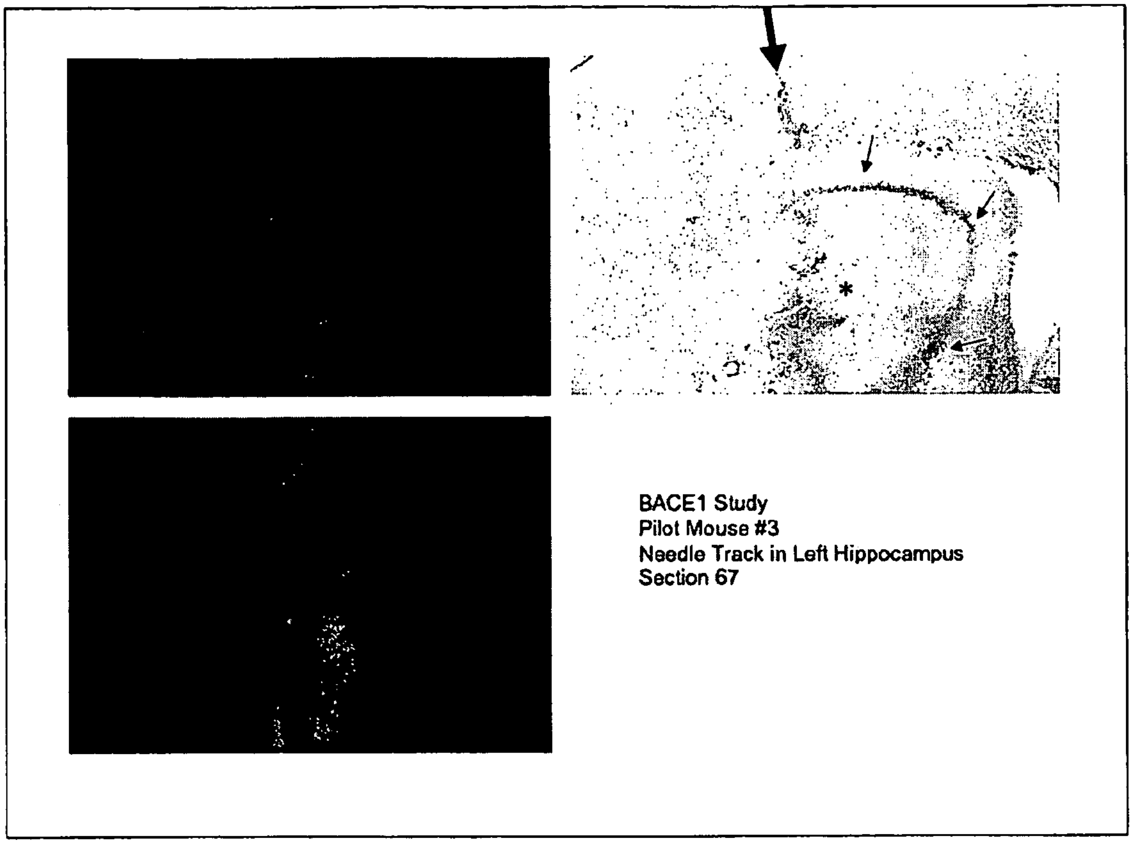
FIG. 7 contains three views of brain tissue section number 67 from a consecutive series of parasaggital brain tissue sections from the left hemisphere of mouse number three from administration of an AAV vector encoding for green fluorescent protein to a C57Bl/6 mouse.

FIG. 7 contains three views of brain tissue section number 67 from the left hemisphere of mouse number three from this pilot study. This section was stained with methyl green, and photographed under brightfield and fluorescence microscopy lighting conditions. As can be seen in the brightfield photograph in the upper right corner, the needle path is visible within this tissue section (vertical path indicated by the thick arrow), and correctly targets the middle of the hippocampus (the hilar region, marked by an asterisk) within the cornu ammonis (short arrows, CA1, CA2, and CA3 regions). Thus, this figure shows that our stereotactic coordinates correctly target the injection to the hippocampus in this age and strain of mouse.

Figure 8:
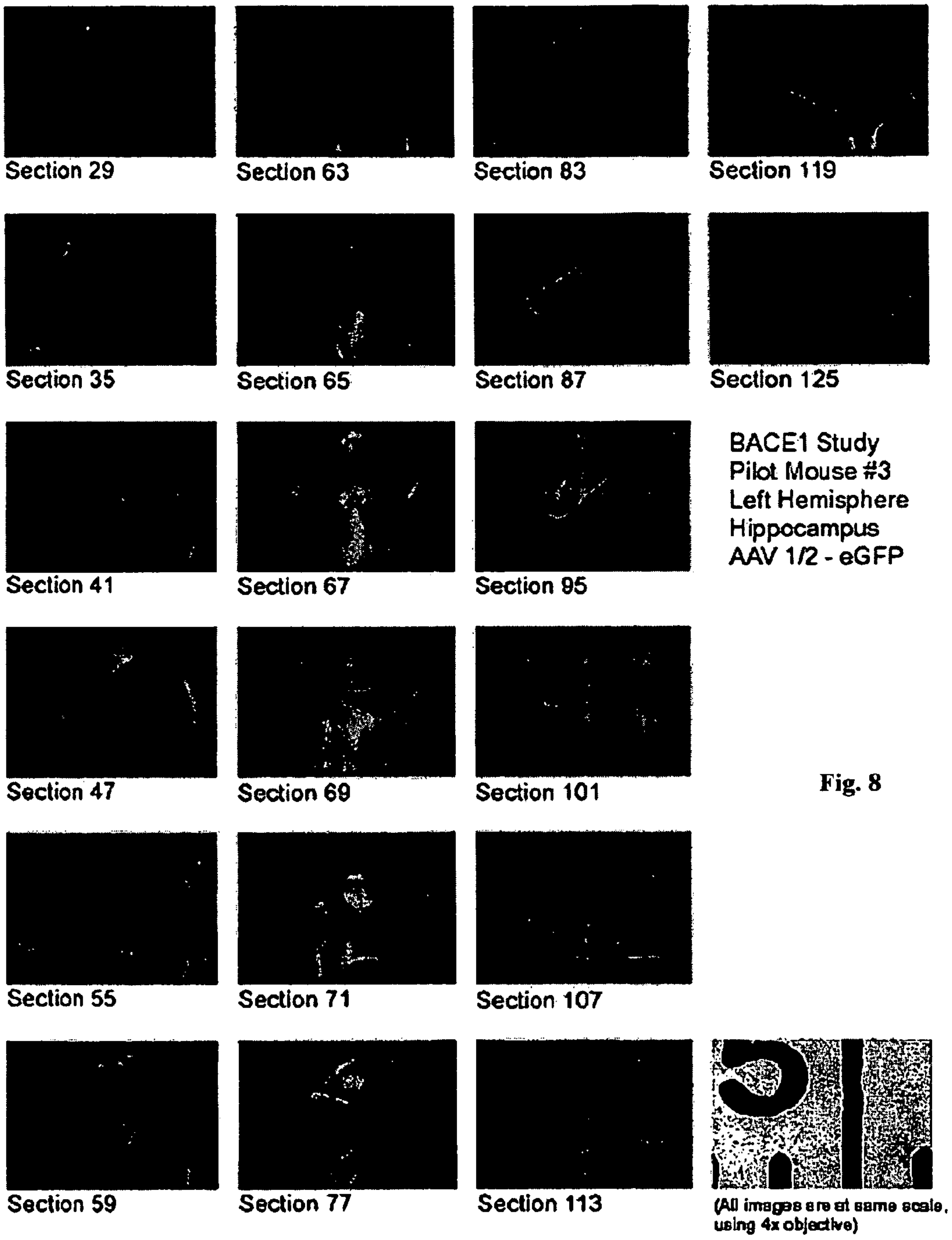
FIG. 8 contains photographs of multiple brain tissue sections throughout the left hemisphere of this mouse number 3, from section 29 (lateral) to section 125 (near the midline of the animal, in the saggital plane) from administration of the AAV vector encoding for green fluorescent protein.

FIG. 8 contains photographs of multiple brain tissue sections throughout the left hemisphere of this same mouse, from section 29 (lateral) to section 125 (near the midline of the animal, in the saggital plane). This figure shows that injection of AAV vector serotype ½ at a single point results in expression of the delivered reporter gene throughout a wide region of hippocampal tissue, ranging from section 35 through section 107. These sections span 2160 microns (2.16 millimeters) of the lateral extent of the mouse brain hemisphere. Thus, this figure shows that injection of AAV vector at our stereotactic coordinates can result in distribution and expression of the delivered genetic material throughout a substantial portion of the volume of the mouse hippocampus.

Neurosurgical method: The details of the neurosurgical method used to deliver our therapy to the Tg2576 mice are as follows. After the induction of surgical anesthesia using isofluorene inhalation, the mouse was placed in the stereotaxic frame and its head was immobilized using the ear bars, incisor bar and anesthesia mask associated with the apparatus (MyNeuroLab, St. Louis, Mo.; Benchmark™ Digital Stereotaxic). The patency of the mouse's airway was verified. The fur on the head was clipped, and betadyne was used to sanitize the scalp. After the depth of the mouse's anesthesia was verified (i.e., unresponsive to tail and paw pinch), a midline incision 1.0 to 1.5 cm in length was made in the skin over the skull in the saggital plane. The skin was manually retracted and membranous tissue covering the skull was scraped away with a sterile #11 scalpel blade. A Hamilton syringe (Hamilton Company, Reno, Nev.; Model 88011) was placed in the syringe holder of the stereotaxic frame, and the tip of the syringe needle moved to the bregma point on the mouse's skull; (the intersection of the rostral, medial-lateral bone suture and the midline suture, identifiable by visual inspection). The needle was then positioned to the following stereotaxic coordinates on the left side of the skull: AP=−2.30 mm, ML=−2.00 mm. The corresponding point on the skull was noted visually through the surgical microscope. A dental drill with a sterile burr bit was used to erode a burr hole at this site through the skull bone. The syringe needle was again positioned at the bregma point, then moved to AP=−2.30 mm, ML=+2.00 mm on the right hemisphere of the skull. The site was noted visually, and a burr hole made at this site.

Once the burr holes were made, a Hamilton syringe was loaded with 5 microliters of AAV vector (AAV-antiBACE1-MB1749 or AAV-control at 1.3 to $3.9\times10^{12}$ genomic particles per milliliter), positioned from bregma to AP−2.30, ML−2.00, then lowered until the tip of the needle pierced the dura membrane covering the brain. Next, the needle was lowered to 1.25 mm below dura and left in place for 2 minutes. Then, the 5.0 microliters of AAV solution was injected into the hippocampus via the Hamilton syringe at the rate of 0.333 microliters per minute using an automated syringe pump. At the conclusion of the 15-minute injection, the needle was left in place for 2 minutes. Finally, the needle was slowly withdrawn from the brain at the rate of about 1 mm per minute. Once the needle tip was clear of the dura, the injection to this site was complete. Injection to the site in the right hemisphere proceeded in the same manner. Following completion of both injections, the incision in the skin over the skull was approximated using forceps and the skin closed with silk sutures. The skin was swabbed with alcohol and the mouse removed from the stereotaxic device and placed in a clean recovery cage. Sterile saline (0.5 mL) was injected subcutaneously at a site on the back to aid in hydration, and diazepam (1-2 mg/kg) was administered to prevent the occurrence of seizures during recovery. Upon complete recovery from anesthesia, the animal was returned to standard housing.

Experimental design for In Vivo Testing in Tg2576 Transgenic Mice: Six heterozygous transgenic and 10 age-matched wildtype controls from Tg2576 litters (obtained from Taconic Farms, Inc., and University of Minnesota) were injected with either AAV-antiBACE1-MB1749 or AAV-control at 12 months of age using the above procedure. Half of the mice received bilateral injections of AAV-antiBACE1-MB1749, and the other half received bilateral injections of AAV-control, in a 2×2 design:

| | Treatment Administered | |
|---|---|---|
| Number of mice Genotype: | AAV-anti-BACE1-MB1749 | AAV-control |
| Tg2576 heterozygote | 3 | 3 |
| Wildtype | 5 | 5 |

(4) Testing for Behavioral Effect of Anti-BACE1 siRNA Treatment in Tg2576 Mice:

In mammals, the hippocampus is a brain structure that is essential for the formation of new memories. In human patients with Alzheimer's disease, the loss of memory formation capabilities that is symptomatic of the disease is presumed to be due to the effects of the disease on the patient's hippocampus, among other brain structures. In mice, the hippocampus is involved in the formation of memories for spatial place or location. Compared to wildtype controls, the Tg2576 mouse has previously been shown to be deficient in hippocampal-dependent functions (Stackman et al, 2003). To show that our anti-BACE1 treatment of the Tg2576 mouse has a beneficial effect on their Alzheimer-like disease, we used a contextual fear conditioning procedure as an indication of hippocampal-dependent memory formation in these mice.

Methods: The contextual fear conditioning procedure is well-established method in the published research literature, and it has been determined that this method provides a measurement for hippocampus-dependent brain functioning. The details of the following protocol were adapted from Dineley, et al. (2002) who have used this method with various Alzheimer's mice, including the Tg2576 transgenic strain. The procedure is a behavioral test that is performed over two successive days. On the first day, the mouse receives training to associate a cage context and auditory cue with a mild electric foot shock. On the second day, the mouse is placed in the same cage context as the first day, but no shocks are administered; rather, the amount of movement (or conversely, behavioral "freezing") of the mouse is observed and quantified by instrumentation. The mouse is returned to its home cage for an hour, then placed in a novel apparatus and again its amount of movement (or "freezing") is quantified. The specific behavioral testing procedure we used to test our Tg2576 mice and wildtype control mice was as follows:

First Day (Training):

1. The mouse was placed in the fear conditioning apparatus and left free to explore it for 180 seconds.
2. The following was repeated five times:
   a. An auditory cue (white noise, 80 dB) was presented for 20 seconds.
   b. During the final 2 seconds of the above 20 second period, a 0.3 mAmp foot shock was administered to the mouse through the floor grid of the apparatus.
   c. There was a pause of 40 seconds before the next presentation of the auditory cue.
3. At the end of this time period (total of 8 minutes) the mouse was returned to its home cage.

Second Day [24 Hours Later] (Testing):

1. The mouse was placed in the fear conditioning apparatus and its mobility (or conversely, behavioral freezing) was observed for 300 seconds (five minutes).
2. The mouse was returned to its home cage for 60 minutes.
3. The mouse was placed in a novel apparatus that differed from the conditioning apparatus in its flooring (solid plastic versus wire grid), visual cues (color and pattern of walls), and odor (a citrus-scented solution was used to wipe down the plastic flooring). The mouse's mobility (or "freezing") was observed for 180 seconds (three minutes).

The key measurement derived from this procedure is the percentage of time in each observation condition that the animal spends motionless, i.e., behaviorally freezing, which mice naturally do in fearful situations. Context-dependent conditioning is indicated by the difference in percent freezing in the trained environment, versus the novel environment (which is used as a baseline). To the extent that the animal has formed a specific memory for the spatial context in which the shocks were given, the percentage of behavioral freezing in the trained environment (measured on day two) is large relative to the percentage of behavioral freezing in the novel environment (also measured on day two).

Results: The Tg2576 mice and wildtype controls were tested using the above protocol at 15 months of age, which was three months post-surgical treatment with either AAV-antiBACE1-MB1749 or AAV-control. The behavior of the mice in the trained and novel environments was video recorded and automatically scored for behavioral freezing by software designed for this purpose (FreezeFrame™, Actimetrix, Inc., Wilmette, Ill.). The results were found to be insensitive to changes in the adjustable parameters used by this software. The following parameter values were used for the scoring in the reported results: 1) lack of motion by the animal was defined as video-frame to video-frame difference (computed from pixel values by the software) of less than 15 pixel values, and 2) freezing by the mouse was defined as a "bout" of lack of motion exceeding a full second in duration.

Figure 9:
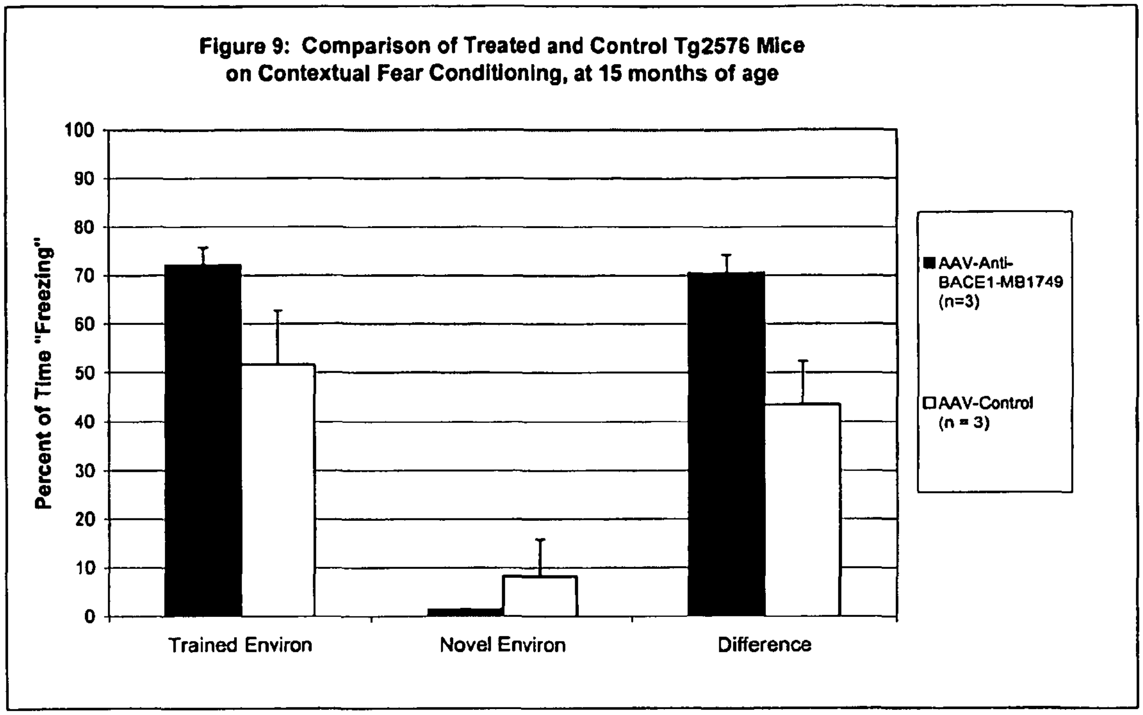
FIG. 9 is a comparison of treated and control Tg2576 mice receiving contextual fear conditioning at 15 months of age after those mice had been neurosurgically treated at 12 months of age with an AAV vector encoding for anti-BACE1 siRNA or an AAV vector encoding for a control siRNA expected to be inactive with respect to suppressing BACE1 mRNA.

At 15 months of age, the difference in the percentage of behavioral freezing in the trained environment versus the novel environment exhibited by Tg2576 mice that received the AAV-antiBACE1-MB1749 treatment was significantly greater than for transgenic Tg2576 mice that received the AAV-control treatment ($p<0.05$, see FIG. 9). Conversely, there was no effect of the AAV-antiBACE1-MB1749 versus the AAV-control treatment on the extent of context-dependent freezing exhibited by the wildtype mice (mean 37.58% versus 19.74%, $p=0.325$, n.s.).

| Difference in percent freezing in trained minus novel environment at 15 months of age | | | | |
|---|---|---|---|---|
| Group | Tg-antiBace1 | Tg-Control | WT-antiBace1 | WT-Control |
| Mean | 70.60% | 43.47% | 37.58% | 19.74% |
| StDev | 6.32 | 15.43 | 32.01 | 20.57 |

Overall, the heterozygous Tg2576 mice were more susceptible to fear conditioning than the wildtype mice. However, the AAV-anti-BACE1-MB1749 versus the AAV-control treatment did not alter the behavior of the wildtype mice, but it did alter the extent of contextual fear conditioning seen in the treated Tg2576 mice. These data support the conclusion that the AAV-antiBACE1-MB1749 treatment has improved the ability of the heterozygous Tg2576 mice to form context-dependent memories, and it has not changed the comparable ability in wildtype mice.

Figure 10:
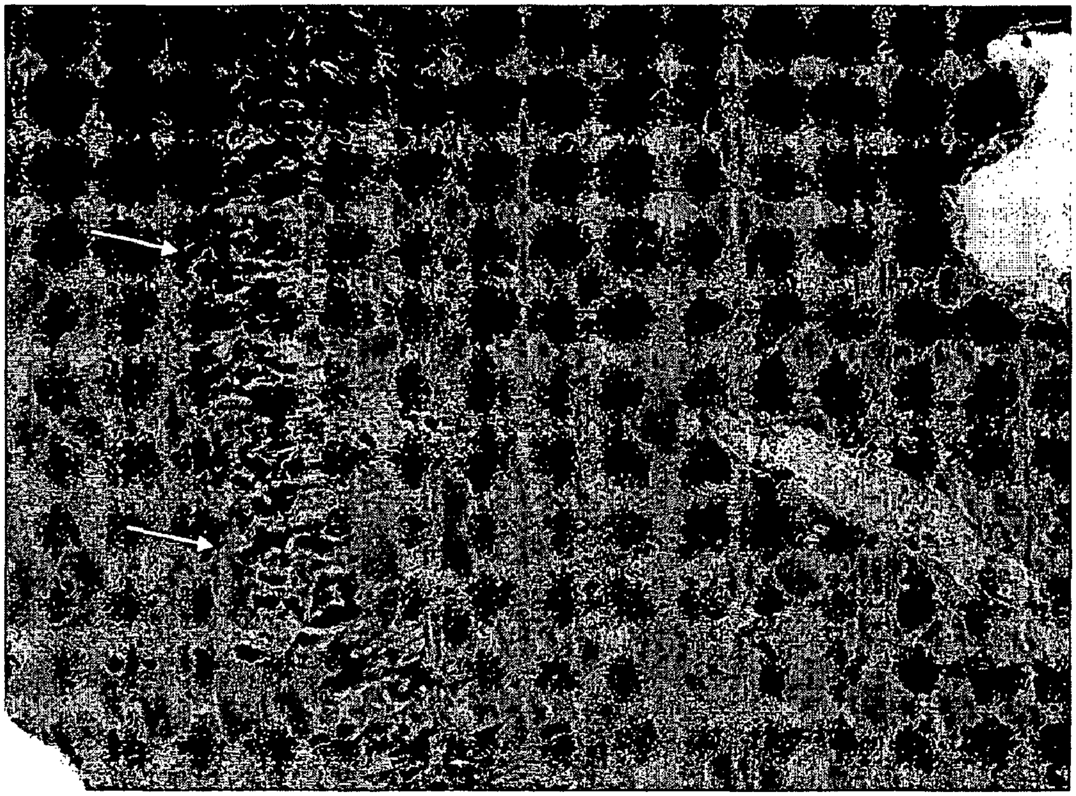
FIG. 10 illustrates immunostaining for BACE1 protein in normal mouse hippocampus.

(5) Histological Analyses of the Effects of Anti-BACE1 siRNA Treatment in Tg2576 Mouse Brain Tissue Once the mice that have been treated with AAV-anti-Bace1-MB1749 or AAV-control have attained the age of 19 months, they will be euthanized and their brain tissue examined to determine the effect of the treatment on level of BACE1 protein in the treated regions of the hippocampus, and the effect of the treatment on the extent of beta-amyloid plaque formation in those regions. The treated regions will be identifiable based on the expression of green fluorescent protein in the neuronal cells, similar to as shown in FIG. 7 and FIG. 8. The level of BACE1 protein will be identifiable based on immunohistochemical staining using standard methods, with an anti-Bace1 primary antibody, and a peroxidase-conjugated secondary antibody for visualization. FIG. 10 shows an example of this staining method. In the figure, the cell bodies of the neurons of the cornu ammonis region of a mouse hippocampus are clearly visible, showing that BACE1 protein is detected by the antibody staining method, and that BACE1 protein is normally present in the neurons of the untreated mouse hippocampus.

In our treated animals (heterozygous Tg2576 or wildtype mice receiving AAV-anti-BACE1-MB1749) we expect that the amount of BACE1 protein will be reduced in the regions expressing the GFP reporter gene, and that also in these regions in the heterozygous Tg2576 mice, there will be fewer beta-amyloid plaques.

Summary of Example 4: We have demonstrated the usefulness of using viral-vectors encoding for an siRNA sequence that results in the silencing of the expression of beta-amyloid cleaving enzyme in mammalian neuronal cells. This viral vector, called AAV-antiBACE1-MB1749, encodes for an siRNA sequence that is 100% homologous between the mouse and human species, (that is, the mouse and human nucleotide sequences are identical). As such, this same AAV-antiBACE1-MB1749 is the biomaterial component of the treatment for human Alzheimer's disease patients that is one embodiment of our invention. We have shown that this treatment can have a positive effect on a behavioral aspect of the disease manifested by the Tg2576 transgenic mouse model of Alzheimer's disease.

Example 5

Treatment for Treatment of Huntington's Disease Using RNA Inteference Targeting the Huntington Gene As another example embodiment of the invention, we have identified siRNA sequences that suppress the expression of Huntington mRNA in cultures of human cells. Furthermore, in order to conduct studies to verify the safety of suppressing huntingtin protein expression in the large mammalian brain, we have cloned and sequenced the first 846 nucleotides of the sheep gene that is homologous to the human Huntington gene, and have identified siRNA sequences that suppress the expression of Huntington mRNA in cultures of ovine cells. The steps involved in this work included (1) in vitro screening of candidate anti-human-Huntington siRNA sequences for efficacy, (2) cloning and sequencing of the first 846 nucleotide region of the sheep Huntington gene, and (3) in vitro screening of candidate anti-ovine-Huntington siRNA. These steps are described in detail below.

(1) Screening of Anti-Human-Huntington siRNA Sequences for In Vitro Efficacy:

Identification of candidate anti-Huntington siRNA sequences: In order to identify an siRNA sequence that is effective at reducing the expression of Huntington mRNA in human cells, we analyzed the human cDNA sequences for the Huntington gene available in the Genbank database (National Center for Biotechnology Information, accession numbers NM_002111.3). The analysis consisted of identifying sections of the cDNA sequence beginning with two successive adenine nucleotides (AA) or with a cytosine and adenine (CA), and comprising those two nucleotides plus the nineteen successive nucleotides. These candidate sequences were tested for possible partial matches to other sequences in other genes, using the BLAST software program provided by the National Center for Biotechnology Information website (http://www.ncbi.nlm.nih.gov/BLAST/), and sequences with a high amount of partial matching to other genes were eliminated from further consideration. Candidate sequences with an extreme percentage of guanine or cytosine (G or C) nucleotides in the sequence (e.g., greater than 65% or less than 35% of the 19 successive nucleotides were G or C rather than A or T) were also eliminated from consideration. From the remaining candidates, the following were selected for laboratory screening from the table below:

| Item | SEQ ID NO: | Name | Starting position within human Huntington cDNA (Genbank Accession NM_002111.3) | DNA sequence corresponding to the therapeutic siRNA | Method used for production of siRNA for in vitro screening |
|---|---|---|---|---|---|
| 1 | SEQ ID NO: 41 | HD0188 | 0188 | AAGATGGACGGCCGCTCAGGT | in vitro transcription |
| 2 | SEQ ID NO: 42 | HD0358 | 0358 | AAGTCCTTCCAGCAGCAGCAG | in vitro transcription |
| 3 | SEQ ID NO: 43 | HD0813 | 0813 | AAGGTTACAGCTCGAGCTCTA | chemical synthesis |
| 4 | SEQ ID NO: 44 | HD1066 | 1066 | AAGGTTTTGTTAAAGGCCTTC | chemical synthesis |
| 5 | SEQ ID NO: 45 | HD1639 | 1639 | AAAGGCAAAGTGCTCTTAGGA | in vitro transcription |

-continued

| Item | SEQ ID NO: | Name | Starting position within human Huntington cDNA (Genbank Accession NM_002111.3) | DNA sequence corresponding to the therapeutic siRNA | Method used for production of siRNA for in vitro screening |
|---|---|---|---|---|---|
| 6 | SEQ ID NO: 46 | HD2060 | 2060 | AAATTGTGTTAGACGGTACCG | in vitro transcription |
| 7 | SEQ ID NO: 47 | HD2714 | 2714 | CAGGAAATACATTTTCTTTGG | chemical synthesis |

Production of siRNA candidates for in vitro testing: We made double-stranded RNA corresponding to the HD0188, HD0358, HD1639, and HD2060 siRNA candidates by in vitro transcription from custom DNA oligonucleotides and other reagents using the Ambion Silencer™ siRNA Construction Kit (Ambion, Inc., Austin, Tex.; catalog number 1620) following the procedure recommended by the manufacturer. The custom DNA oligonucleotides used to produce our specific siRNA were as follows. The siRNA target sequences are listed in capital letters, while other oligonucleotides needed for the purposes of the in vitro transcription method are listed in lower case letters.

| siRNA | SEQ ID | Sense oligonucleotide (DNA) | Antisense oligonucleotide (DNA) |
|---|---|---|---|
| HD0188 | SEQ ID NO: 41 | aaGATGGACGGCCGCTCAGGTcctgtctc | AAACCTGAGCGGCCGTCCATCcctgtctc |
| HD0358 | SEQ ID NO: 42 | aaGTCCTTCCAGCAGCAGCAGcctgtctc | AACTGCTGCTGCTGGAAGGACcctgtctc |
| HD1639 | SEQ ID NO: 45 | aaAGGCAAAGTGCTCTTAGGAcctgtctc | AATCCTAAGAGCACTTTGCCTcctgtctc |
| HD2060 | SEQ ID NO: 46 | aaATTGTGTTAGACGGTACCGcctgtctc | AACGGTACCGTCTAACACAATcctgtctc |

We ordered chemically synthesized double-stranded RNA corresponding to the HD0813, HD1066, and HD2714 siRNA candidates from Ambion, Inc. (Austin, Tex.). The sequences we specified that this supplier produce for us were as follows:

| siRNA | SEQ ID | Sense oligonucleotide (RNA) | Antisense oligonucleotide (RNA) |
|---|---|---|---|
| HD0813 | SEQ ID NO: 43 | GGUUACAGCUCGAGCUCUAdTdT | UAGAGCUCGAGCUGUAACCdTdT |
| HD1066 | SEQ ID NO: 44 | GGUUUUGUUAAAGGCCUUCdTdT | GAAGGCCUUUAACAAAACCdTdT |
| HD2714 | SEQ ID NO: 47 | GGAAAUACAUUUUCUUUGGdTdT | CCAAAGAAAAUGUAUUUCCdTdT |

In vitro application of the siRNA candidates to cell cultures: To assess the effectiveness of each anti-Huntington siRNA candidate in suppressing Huntingon mRNA in vitro, HeLa cells (American Type Culture Collection, catalog number CCL-131) were used as the test system, as these cells express a detectable level of Huntingtin mRNA. The HeLa cells (ATCC) were cultured in Minimum Essential Medium with Earle's salts, L-glutamine, 0.1 mM non-essential amino acids, 1 mM sodium pyruvate, 10% fetal bovine serum (Gibco) at 37° C. and 5% $CO_2$. For transfection with the siRNA candidates, $4.3\times10^5$ HeLa cells were plated in a 25 $cm^2$ culture flask containing 7 ml of growth medium without antibiotics one day before transfection so that they were 50% confluent at the time of transfection. The cells were transfected with 840 pmol siRNA using Oligofectamine transfection reagent (Invitrogen). The siRNA candidates generated by in vitro transcription were tested in one set of experiments, while the siRNA candidates generated by direct chemical synthesis were tested in a second set of experiments.

Assay of the effect of siRNA candidates on Huntington mRNA levels in cells: To determine the effect of siRNA candidate on Huntington mRNA levels in cells, RNA was isolated after 36 hours of incubation. The cells were harvested from the culture flasks with 1 ml of Trypsin-EDTA (0.25% Trypsin, 1 mM EDTA.4Na, Gibco) and the cell numbers were estimated by a cell count using a viability counter (Beckman coulter). Total RNA was isolated from the cells using the RNeasy mini kit (Qiagen) and gDNA was removed using on-column DNase treatment (30 min) After isolation, absence of gDNA was confirmed by PCR. The absorbance of wavelength 260 was measured to correct for the amount of RNA. Reverse transcription took place using the iScript cDNA synthesis kit (Bio-Rad). Subsequently, two real-time PCR's were carried out using iQ SYBR Green supermix (Bio-Rad), one with Huntington primers and one with the GAPDH primers. Standard curves were generated by amplifying the following numbers of DNA control molecules (in triplicate) in a 25 μl reaction: $1\times10^{10}$, $1\times10^{9}$, $1\times10^{8}$, $1\times10^{7}$. $1\times10^{6}$, $1\times10^{5}$, $1\times10^{4}$ and $1\times10^{3}$. The DNA control molecules were chemically synthesized (Life Technologies) and had the same sequence as the PCR products.

Quantitative real-time PCR assay results: To confirm absence of genomic DNA a real time PCR was carried out using SYBR Green. Only the positive control yielded a significant signal, showing that all RNA samples were free from genomic DNA carryover. All RNA samples were diluted to the same concentration before continuing with the reverse transcriptase reaction, then 2 μg RNA of each sample was reverse transcribed to produce complementary DNA in a 40 μl reaction. Finally, real-time PCR reactions were performed on each sample to measure the amounts of Huntington mRNA in each sample. The amounts of GAPDH mRNA in each sample was also measured in parallel PCR reactions, as a baseline for normalization of the relative amounts of Huntington mRNA measured.

The results for the first set of siRNA candidates (generated using in vitro transcription) were as follows:

| Sample | Average amount of Huntington mRNA measured (in 3 replicate samples) (molecules per reaction) | Average amount of GAPDH mRNA measured (in 3 replicate samples) (molecules per reaction) | Relative amount of Huntington mRNA (normalized to amount of GAPDH mRNA) | Relative suppression of Huntington mRNA |
|---|---|---|---|---|
| HD0188 | 2.24E+04 | 3.03E+07 | 7.39E−04 | <0% |
| HD0358 | 1.40E+04 | 2.32E+07 | 6.03E−04 | 13% |
| HD1639 | 1.70E+04 | 2.70E+07 | 6.30E−04 | 9% |
| HD2060 | 1.34E+04 | 2.34E+07 | 5.73E−04 | 17% |
| Untreated control cells | 1.53E+04 | 2.15E+07 | 2.65E−03 | =0% |

The results for the second set of siRNA candidates (generated using direct chemical synthesis) were as follows:

| Sample | Average amount of Huntington mRNA measured (in 3 replicate samples) (molecules per reaction) | Average amount of GAPDH mRNA measured (in 3 replicate samples) (molecules per reaction) | Relative amount of Huntington mRNA (normalized to amount of GAPDH mRNA) | Relative suppression of Huntington mRNA) |
|---|---|---|---|---|
| HD0813 | 1.07E+05 | 1.7E+08 | 6.29E−04 | 76% |
| HD1066 | 1.89E+05 | 2.3E+08 | 8.22E−04 | 69% |
| HD2714 | 8.49E+04 | 2.1E+08 | 4.04E−04 | 85% |
| Untreated control cells | 6.09E+05 | 2.3E+08 | 2.65E−03 | =0% |

In the above two tables, the relative amount of Huntington mRNA is computed by dividing the average amount of Huntington mRNA measured in the sample by the average amount of GAPDH mRNA measured in the sample. The relative percent suppression of Huntington mRNA is calculated by subtracting the relative amount of Huntington in the sample from the relative amount in the untreated control cells, and expressing this difference as a percentago of the relative amount in the untreated control cells. (For example, (2.65E-03 minus 6.29E-04) divided by 2.65E-03 equals 0.76, or 76 percent suppression, by HD0813).

As these tables show, all of the latter three candidates (HD0813, HD1066, and HD2714) produce substantial suppression of Huntington mRNA in HeLa cell cultures, while the first four (HD0188, HD0358, HD1639, and HD2060) are essentially ineffective at suppressing Huntington mRNA levels in HeLa cells. Coincidentally, the three effective candidates were tested in these experiments using chemically synthesized siRNA, while the ineffective candidates were produced by in vitro transcription. However, we already have experimental data from our development of anti-BACE1 siRNA that indicates that the method of production of the materials for the screening is not the cause of the effectiveness of one set of siRNA versus the ineffectiveness of the other. Therefore, we conclude that HD0813, HD0166, and HD2714 are each effective siRNA targeting human Huntington expression.

(2) Cloning of the Sheep Gene that is Homologous to Human Huntington

Because we intend to establish the safety of suppressing huntingtin protein expression in a large mammalian brain prior to treating humans with our invention, we have undertaken to identify siRNA candidates that are effective at suppressing expression of the sheep huntington gene. The sequence for the gene in the ovine genome that is homologous to the human Huntington gene is not currently available in Genbank or other publicly available genome sequence databases. Therefore, we have cloned and sequenced the first 846 nucleotides of the sheep Huntington gene, and established by computer alignment of our sequence with the human gene sequence (NM_002111.3) that we have identified the DNA sequence corresponding to the start codon through the first 282 amino acids of the sheep huntingtin protein. The source of the sheep genetic material was from samples of flash frozen sheep brain tissue (cerebral cortex, striatum, and cerebellum) harvested from laboratory animals that were being used for unrelated medical research purposes (testing of cardiac devices) and that were euthanized less than one hour prior to the harvest of the brain tissue. In addition, sheep genetic material from the OA1 ovine cell line (American Type Culture Collection, catalog number CRL-6538) was used as a source for clones used to confirm the results obtained from the brain tissue sources. In each case, the total cellular RNA was isolated from the source material, then used to generate cDNA, from which a portion of the Huntington sequence was amplified using PCR. Cloning and sequencing of the amplified PCR products was conducted using standard molecular biology procedures

.

The obtained sheep Huntington gene sequence is as follows:

(SEQ ID: 48)

```
ATGGCGACCCTGGAAAAGCTGATGAAGGCCTTCGAGTCCCTCAAGTCCTT
CCAGCAGCAGCAGCAGCAGCAGCAGCAGCAGCAGCAGCAACAGCCGCCAC
CGCCGCCACCCGGCCCGGCTGTGGCTGAGGAGCCGCTGCACCGACCAAAG
AAAGAGCTCTCAGCCACCAAGAAAGACCGCGTGAACCACTGTCTGACAAT
CTGTGAAAACATCGTCGCGCAGTCTCTCAGAAATTCTCCAGAATTTCAGA
AACTTCTGGGCATCGCTATGGAACTTTTTCTGCTGTGCAGTGATGACGCA
GAGTCAGATGTCAGGATGGTGGCTGACGAATGCCTCAACAAAGTCATAAA
AGCTTTGATGGACTCTAATCTTCCGAGGTTGCAGCTAGAACTCTACAAGG
```

-continued

```
AAATTAAAAAGAACGGCGCCCCGCGGAGCCTGCGCGCGGCCCTCTGGAGG
TTCGCCGAGCTGGCTCACCTGGTCCGGCCTCAGAAGTGCAGGCCGTACCT
GGTGAACCTGTTGCCCTGCCTGACGCGCACAAGCAAGAGACCCGAGGAGT
CCGTCCAGGAGACGCTGGCTGCAGCGATCCCTAAAATTATGGCTTCTTTT
GGCAACTTTGCGAACGACAATGAGATTAAGGTTCTGTTGAAGGCTTTCAT
CGCGAACCTGAAGTCCAGTTCCCCGACTGTGCGGCGGACCGCGGCGGGCT
CAGTGGTCAGCATCTGCCAGCACTCCAGGAGGACGCAGTACTTTTACAGC
TGGCTGCTCAGCGTGCTCCTAGGTTTGCTGGTCCCCGTGGAGGAGGAGCA
CCCCACCCTGCTGATCCTCGGCGTCCTGCTCACCCTGAGGTATCTG
```

The alignment of this sheep sequence with the 5' end of the coding region of the human Huntington gene sequence is shown in FIG. 11.

(3) Screening of Anti-Sheep-Huntington siRNA Sequences for In Vitro Efficacy

As a further step in the development of a therapy for Huntington's disease based on our invention, we have identified several candidate siRNA sequences targeting the sheep Huntington gene, and have screened them for efficacy at suppressing sheep Huntington mRNA in ovine cell cultures. In identifying candidate sequences, we did not limit the candidates to those that begin with two adenines (AA) or a cytosine and adenine (CA) but also allowed candidates beginning with guanine and adenine (GA). These starting nucleotides are shown in the right column of the table below in lower case letters.

| Item | Name | SEQ ID: | Starting position in sheep Huntington sequence | Starting position of the (partially) homologous sequence in the human Huntington gene (NM_00211.3) | Amount of homology of sheep to human sequence | Ovine Target Sequence |
|---|---|---|---|---|---|---|
| 1 | EB1 | SEQ ID NO: 49 | 205 | 643 | 18/21 | gaAAACATCGTCGCGCAGTCT |
| 2 | EB2 | SEQ ID NO: 50 | 328 | 766 | 19/21 | gaATGCCTCAACAAAGTCATA |
| 3 | EB3 | SEQ ID NO: 51 | 603 | 1041 | 18/21 | caACTTTGCGAACGACAATGA |
| 4 | EB4 | SEQ ID NO: 52 | 628 | 1066 | 18/21 | aaGGTTCTGTTGAAGGCTTTC |
| 5 | EB5 | SEQ ID NO: 53 | 367 | 805 | 18/21 | aaTCTTCCGAGGTTGCAGCTA |

We ordered chemically synthesized double-stranded RNA corresponding to the EB1, EB2, EB3, EB4, and EB5 siRNA candidates from Dharmacon, Inc. The sequences we specified that this supplier produce for us were as follows. Note that for the purpose of the chemically synthesized siRNA, the target sequences are the 19 bases shown in the right hand column of the above table, omitting the first two nucleotides (aa, ca, or ga).

| siRNA | SEQ ID NO | Sense oligonucleotide (RNA) | Antisense oligonucleotide (RNA) |
|---|---|---|---|
| EB1 | SEQ ID NO: 49 | AAACAUCGUCGCGCAGUCUdTdT | AGACUGCGCGACGAUGUUUdTdT |
| EB2 | SEQ ID NO: 50 | UGCCUCAACAAAGUCAUAAdTdT | UUAUGACUUUGUUGAGGCAdTdT |
| EB3 | SEQ ID NO: 51 | ACUUUGCGAACGACAAUGAdTdT | UCAUUGUCGUUCGCAAAGUdTdT |
| EB4 | SEQ ID NO: 52 | GGUUCUGUUGAAGGCUUUCdTdT | GAAAGCCUUCAACAGAACCdTdT |
| E35 | SEQ ID NO: 53 | UCUUCCGAGGUUGCAGCUAdTdT | UAGCUGCAACCUCGGAAGAdTdT |

Using methods comparable to those already described for screening of anti-BACE1 siRNA candidates, we have co-transfected HEK293 cells (and in separate experiments, HeLa cells) with these siRNA candidates, and with a plasmid containing the sheep huntington gene sequence and green fluorescent protein (pTracer-sheepHD). Forty-eight to 72 hours later, we harvested the total cellular RNA from these cells and measured the level of sheep huntington mRNA relative to the level of GFP mRNA in the cell samples, using quantitative real-time reverse transcriptase PCR. The results of four independent experiments are as shown below. The values shown are the percent suppression of ovine huntington mRNA obtained in the cells treated with pTracer-sheepHD and one of the siRNA candidates, relative to the amount of ovine huntington mRNA found in cells transfected with pTracer-sheepHD but not treated with any siRNA.

| Percent suppression of ovine Huntington mRNA | HEK 293 Cells | | HeLa Cells | | Average percent suppression |
|---|---|---|---|---|---|
| Item | Experiment 1 | Experiment 2 | Experiment 3 | Experiment 4 | obtained |
| EB1 | 48.4% | <0% | 7.00% | <0% | (no reliable suppression) |
| EB2 | 76.0% | 67.1% | 53.3% | 47.9% | 61.0% |
| EB3 | 85.1% | 45.7% | 69.7% | 81.0% | 70.4% |
| EB4 | 88.1% | 88.3% | 93.8% | 92.9% | 90.8% |
| EB5 | 23.8% | <0% | 94.3% | 40.3% | (inconsistent data) |

From these data we conclude that EB2, EB3, and EB4 are effective siRNA sequences against sheep huntington, with EB4 being the most effective at suppressing the expression of ovine huntington mRNA when expressed from a plasmid transfected into HeLa or HEK 293 cells.

Using the EB4 sequence targeting sheep Huntington mRNA, we can make an adeno-associated viral vector for delivery of DNA encoding a short hairpin sequence corresponding to this siRNA, and deliver this vector into the brains of sheep by stereotactic neurosurgery, in the manner of our invention, to establish the safety of this therapy for Huntington's disease prior to application in human patients.

SEQUENCE LISTING

<160> NUMBER OF SEQ ID NOS: 82

<210> SEQ ID NO 1
<211> LENGTH: 21
<212> TYPE: DNA
<213> ORGANISM: Homo sapiens

<400> SEQUENCE: 1
aaccaagagc ggagcaacga a 21

<210> SEQ ID NO 2
<211> LENGTH: 21
<212> TYPE: DNA
<213> ORGANISM: Homo sapiens

<400> SEQUENCE: 2
aattcgttgc tccgctcttg g 21

<210> SEQ ID NO 3
<211> LENGTH: 21
<212> TYPE: DNA
<213> ORGANISM: Homo sapiens

<400> SEQUENCE: 3
aaccaagagc ggagcaacga a 21

<210> SEQ ID NO 4
<211> LENGTH: 21
<212> TYPE: DNA
<213> ORGANISM: Homo sapiens

<400> SEQUENCE: 4
aattcgttgc tccgctcttg g 21

<210> SEQ ID NO 5
<211> LENGTH: 21
<212> TYPE: DNA
<213> ORGANISM: Homo sapiens

<400> SEQUENCE: 5
aaccagtacg tccacatttc c 21

<210> SEQ ID NO 6
<211> LENGTH: 21
<212> TYPE: DNA
<213> ORGANISM: Homo sapiens

<400> SEQUENCE: 6
aaggaaatgt ggacgtactg g 21

-continued

<210> SEQ ID NO 7
<211> LENGTH: 145606
<212> TYPE: DNA
<213> ORGANISM: Homo sapiens
<220> FEATURE:
<221> NAME/KEY: misc_feature
<222> LOCATION: (1)..(145606)
<223> OTHER INFORMATION: LOCUS AF163864;145606 bp;DNA;linear;P
RI 24-JAN-2001
DEFINITION Homo sapiens SNCA isoform (SNCA) gene
ACCESSION AF163864
<300> PUBLICATION INFORMATION:
<308> DATABASE ACCESSION NUMBER: AF163864
<309> DATABASE ENTRY DATE: 2001-01-24
<313> RELEVANT RESIDUES IN SEQ ID NO: (1)..(145606)

<400> SEQUENCE: 7
aattttcctt gaaaaacata gatgtccagt tctatctctc atattttttc ttttcataga 60
gatatggcac tttaggatta atttaagctg caaacagcag aaaaatgcaa aataacagtg 120
gcttaaatga aatagaaata ttttatctct tgaaaaagtt ctgataaaga cagtcaaatg 180
ctagaagggc aactgtgttc cagaaggttc tcaaggagcc aggctacctc taacccactg 240
ctctgccatc tctaattcat gtcgtatgtc ctcagggtcc acaatggcag taagaacgct 300
cctcatcata tctgtgtttc aaatagtaga atggagagaa agagaagaaa aggaggcatt 360
aaggaaggtt ccagaagctg ccatttgaca cttctgttaa catttaattg gccaaaattt 420
aatctcatat cgcataagct gtaagagatg ctggaaaact tatttgtctc cactctacat 480
ggacattatc agagtatttc tcaacagaga ggtctatgta ataatagtaa aaagtaagag 540
tggacacaaa cctagtcctt tacctttcag tagaagtaaa aatgctatat taatatttac 600
tctctctctc tctctctctc tctctctctc tcatttttgg ttttgacaat caaattcagc 660
taaatatgat tgaaactaaa atcaaggaaa atgcattata ctctgttgtt atggtaactg 720
gaatggtgaa atgtgtggat tattttcaca ccttcaataa tatgtttcta accatatatt 780
ttttaaaaat tgctgcaggg tttgcttaat gaccagagta taaaggcaca tttttttctc 840
agttggcaaa aacacagttt tgacaaattt gacaagtttt tgtagatctg taatttattt 900
gatttaatta aattttcatc ttgttttcac aatgagttat tgaaaataaa atctaaagct 960
ttaaacagga aaattttaaa tttgaatttt cttggttgaa ctacttatac ttttcacttt 1020
caattcacta acagaataaa tacatcattc cactgaatat gagccatcca tacaaagagt 1080
ccatgaccaa atgcaatgtc actaggtatt taaagtaacc tataaattat gttctgtctc 1140
attgtccaca aaatattaca acctgcatat ttggaaaaac attttgttca tgatatgtac 1200
atatatgagg catgcatatg gataaataca tataaagttg tgaaaattag gcaaatttta 1260
tattttcgtc cactcttgaa actttcattt ttcaaaaaca aaatttaaaa tgctaacttt 1320
taaaataaat gtgccatagt agcacaatat gttaatattg gggaaaactg catggaaaat 1380
atacagaaat gcttcatact ttacaattct tttgtacatc ccatattatt tcaaaagtta 1440
aaagttttaa atatgttcag tcttgaaatg tatcagaaat gtttatctaa agttttgttg 1500
gtgttaagat taatatatta gtaatattac acacagaaag acagaaggta aaagtaaagt 1560
tagtttgaat atgactgtca ttttaagtca ttaacattta actttaccaa cttcatctca 1620
agttggccca tatcactgcc caacttaaac acatggctac atgcagcagg taaagtacat 1680
ggcaggacta ttgagatatc aaggagtcac tgtgtgtcag gaaatgataa agttccccag 1740
cgtctcctca cctgtgtcag gccgacttag ggaaaccaca ttctacgttc ataaagagtg 1800

-continued

```
atctgcgggc ttgaaaggca agtaagcaga aagaagtgtt tatcccagca attcatgaaa   1860
atgttgaaaa aaaagaaaaa ctaagtcagc tttccttaga acccaagttt cggcctgcct   1920
tttaaaattt tctctatcaa agctgccacc tttttccag atgctcaaga taaaacactc   1980
aacacagaaa tgcatgattt tgttgctgag ataccggttt gttgtttaca ctctgccctc   2040
ctatccattg caccttccag ttccgcttgc tctcagtctc cacctctgat tgctacttac   2100
acaatttatc ccatgaaaca ccatcagatt attccagcac acaccagtat ctctgggcct   2160
tccctggtgc actgcactct ctcctttcca cagagcctgt ggaaagagtg gcacagtagc   2220
tggaggggca cacagggtac agagcacctt tccccaccca actcttgcgg tgctgtagac   2280
ctgaggtggt accatgaagg aaacatggac agttgagacc acatgcaaga gcccagacac   2340
acggctcaag ctcccagggt cagtgatagt gtatagctag ctgggaaccc tgcactggcc   2400
ctgtgttcaa catgagtggg tcaccctaaa agacatttca gcgtggttct gcctaccaaa   2460
tcttgcaaag aaatacctct ccactcagtg agaagtgatc cactagccag gctgccctcc   2520
tagacctgaa ttaaccatag agtcccagaa ttattctata ggcttgagcc ccagcattct   2580
gtggggcatc tggttgaccc cacaggcagc agggctagga agtctgagag tagcatctca   2640
aaagggtgaa gaggctggcc cacaggggtc ctgttcaggc tgagagtgca gctcctgaaa   2700
agcactgcaa accctgaagt tcccagcgtg ggagggaggg cgatttggag aattgtgagg   2760
aaggcattcc aaagtgctac ggtgcccaag tgaagactta cgtcgagaag aaatagaaaa   2820
atgacagctt ttccccaagt ggtaacaaga attagctaaa ccaagcctaa ttgtatattc   2880
ttcccaattt taacccattt attaaatcac tgaagctctc ctgagcagaa taaggggtag   2940
ggaaagaatt cagaataatt cagggaaaat gcctcctcat gaaaactcta aaatttggaa   3000
aacggttggt tcctagtaat cgagatagct atattttcct tcacttacca aaatgaaact   3060
taggaagttc attctctttt actcctaatc tgcaaatacc ttagtccagt gaacaaatgt   3120
gaaccgaaag agccaatctt tcaaaataca acctgagtgg ctaaatgggg ctatgtttta   3180
aatagaggca agtggccatt tgctgactaa agatcacaca tgtatactct gagttccctg   3240
aaaacctaca gctctgctca actttgggac ttccagagct cacctgatct accaatcagg   3300
cctggactgc ttcaaccaat cagggctcag ctgtatcaaa caatgggaac tgagcatttg   3360
cataaacaaa cctgactgga aacttgggtg ggaacttttg ccataataac tgaaccctct   3420
cttggttctc tggatcacac cttcatttta caccaaaagc tttgaatcac ggtttgcaaa   3480
ctgttcactg gaataaagtc tctttcttcc aaattccttt tcagagaact tttgttcaca   3540
gtccctatta tccgagataa atctgtaagc aatatgtatg tgatggaaaa tgtttcttcc   3600
ttcctcccca actttcaatc cttgttcttt tctaatcatc ttatagataa tgtctaagaa   3660
attggcttat ttaagttaaa agttttgact tccttactac tcatttgaaa gtacaaaata   3720
cctcagttgc acatgcctac ctactacgtc aacagtgtgc tgctgcatat taaaagagat   3780
ccaatttcaa atcacctaga aaaggctaaa tcttactttt tcttgcttta gatgacctct   3840
ctctatatat aaggctgata tcagccacaa acctcccctt ccttgtgaga ggagggcagc   3900
cttcaaactg aagttcagag cattgttgta caatattcct gaggtatatt gctccccata   3960
ggattgggat ctgtgccata gaacctataa atgggattta cacaagtttc tgttattgtc   4020
cagggaataa attttggacc acaaaagtga aatatataat tcccaatgcc ttttaaatgt   4080
ataaatatgg acagcagctc agtgcacttt tcactggatt aacagcatgc tgctatattg   4140
```

-continued

```
cgatactgcc aaaaaagacc ttatatttca aagcagaata cattagtcct agaaaaggag   4200

aagagcagct ctagggtatg tccatgatcc ctctgtgaat ctattgtctg cttcattgcc   4260

tgaggcagaa caaaagagca cgtggccaag aatgaggctc tggatcagcc cagcttgggt   4320

cctcggcctc aaactatggc ctcagcgaca gtttcctgat ttgcggagta aatactactg   4380

tgagtatcca acacaattca gaggattgaa tgaggttaat taacttaatt aacaagtatt   4440

aattaattaa ttaaaaacac taggtcacag cctgggccat aataagctat caataaacac   4500

ttactattgg tgttagcaat ctttactttt atttaagtga tgtaattact ccaatgtact   4560

ttatttgagt gatggaatta tagatatata tttataactt atataagtgt aagtagttac   4620

acttttggaa tatacttata caagtactta tataggttat attaaagtat atatttataa   4680

catatttata ggattaatgt aagaatattt tttataaaat gatctaacat gctaaaatat   4740

agaaattaat tagtaaaatt ataatttact ttagcttgtg tttatttgac accaactacc   4800

tggacattta gtccatttac tgcagtactt ctccaggtat gattcttggg ccagcaccat   4860

cagcattacc tgggaaatga gttagaaatg cacattctca ggccccacca caggcccata   4920

taaaaaccat ggatttagtg tatctagaag gacaaaaatc aaaacactta gcttcattca   4980

ggaaaaaaat aattctgata ttgatagata cctctcttca cttttaaaag tttcttctta   5040

tagaaaccag atctgattgt attgttaaaa ttaaacttgt aaattttttc acaacgaatt   5100

tcctgtatgg tggtctatgt ttggggaaat actcatcccg gaactcaact gtacagggtt   5160

gggcatgttt tacatacaag tgtatgtctc tcttcttgtc ttccttctcc cttgaaccct   5220

agtctccctc cctgcctttt cagaagtttc cccctggagt tctcagccta ttctctttta   5280

tctttccatc caaacgtagt caccaatata gtcctctttt ctctctcaat ctacacagca   5340

gaagcctcca ctgctgcttt agaatccaga gatatttcca atcccattat ccccaaagat   5400

gaagtctctc ttaaaaatcg agattctcta ttttagtagt ggtggctctg tgttcatgct   5460

gttccctctg cctagaacag catttcttca tattttcaca tatttttaca gcacatggca   5520

cataaaaagc acacaataaa caccaacatt ctgagttaaa aatgtgaaat gtcttttcct   5580

gcaaaaataa tatatgcctg gtgtttgtcc cagttcaata cacatttatt gactgcctaa   5640

tactttgcag gcattgaaca aagcatgggg tagaaataat aacagtattt tctccccaca   5700

ctgaagtagt gtgcactcta caaataggga agatatatat atcttcctta tattatatat   5760

atttatatat ataaatatat atttatatta tttatatata tataaacata tatatataaa   5820

tagattactt tcacataatg tcacaggtgt agcaatagga gagtacacac agtggcttgt   5880

gaatactgag gccaacttga gagatcagaa aaggttttta ggagaaggtg atgaagggct   5940

gaatatattt taaaactgtt aaatgtgttt tcaaagggca ataaacaccc atatgttcca   6000

taaatattat aaacagcatg cttattcaag ttagttcaga ttatgttttc aaaagcaaaa   6060

tagatttaag tcacacttat tctttccttt aaataaaatg ttcttcaagt taaaagtatt   6120

atgaagtatg tctgggaacc attttcttgt tggaggccct taacatcttc acatattccc   6180

aaatcagaaa ttagcaaacc attttgacat ctccctcttc ctcaattctc tcatacaagc   6240

atccctaagt catatccatt gcatttccaa tgtttttcaa attatttttt cctttaacat   6300

ttgtattgtc agtgccttat ttttgcatct cctaatttct ttctagataa catcctaatt   6360

ttttccccca aatctagttt tcatcccctc caaatatctg caagatatca cagtgctctt   6420

taagcaaaac aaatcggatc acatttttct cttatttaaa tcttttatta ttatgctcct   6480

ctaactagga tgaatatgca tcccagtttg tccaaatgta gatattccag ttttatactt   6540
```

-continued

```
gctgactagc ataattgtca ggagtgtctc ctttcactct cagaagtgcc tgttctgaat   6600
tcaaaattat atagttagcc ttctcattgc cttcattatt ttgttttaat tcaataatct   6660
tacattaaaa tcttcattta taatgtgagt cctgccatta agagatgcaa gattgctctt   6720
acacccggct ttaccctttt acaatttgag ttcatcaaaa tcatggatta tgtcttaaaa   6780
acaactagta tttaacacca tgcctgccat tgaataggca tgtaatgatg tttattaaat   6840
tttaaatagc tacatttaaa attgaaggtt ttgttattaa tcatattcta tgtgaaacat   6900
ccttagatta ttgaaagcat ccatatgctt ttcgacattc ttttatatat atatttttat   6960
tatactttaa gttctaatgt acatgtgcac aatgtgcagg tttgttacat atgtatacat   7020
gtgccatgtt ggtgtgctgc acccactaac tcgtcattta cattaggtag atctcctaat   7080
gctatccctg ccccatcccc ccaccccaca acaggcccct gcatgtgata ttccccttcc   7140
tgtgtccaag tgttctcatt gctcaatttc cacctatgag tgagaacatg tggtgtttgg   7200
tattttgtcc ttgcgatagt ttgctgagaa tgatggtttc cagcttcatc catgtctcta   7260
caaaggacac gaactcatca tttgttatgg ctgcatagta ttccatggtg tatatgtgcc   7320
acatttttctt aatccagtct atcattgttg aacatttggg ttggttccaa gtctttgcta   7380
ttgtgaatag tgccgcaata aacatacatg tgcatgtgtc tttatagcaa catgatttat   7440
attcctttgg gtatataccc agtaatggga tggctggatc aaatggcatt tctagctcta   7500
gatccctgag gaattgccac actgtcttcc acaatggttg aactagttta cagtcccatc   7560
agcagcataa gagtgttcct atttctccac atcctctcca gcacctgttg tttcctgaat   7620
ttttaagatc accattctaa ttggtgtgag ataatatctc gttgtggttt tgatttgcat   7680
ttctctgatg ggcagtgatg atgacccttt tttcatgtgt ctgttggctg cataaatgtc   7740
ttcttttgag aagtgtctgt tcatatcctt tgcccacttt ttgatggggt tgtttgtttt   7800
tttcttgtaa atttgtttga gttctttgta gattctggat attagccctt tgtcagatga   7860
gtagattgca aaaatttttct cccattctgt aggttacctg ttcactctga tggtagtttc   7920
ttttgctgtg cagaagctct ttagtttaat tagatcctat ttgtcaattt tggctttcgt   7980
tgccattgct tttggtgttt tagacatgaa gtccttgacc atgcctatgt cctgaatggt   8040
gttgcctagg ttttctccta gggtttttat ggttttagat ctaacattga agtctttaat   8100
ccatcttgaa ttaatttttc tataaggtgt aaggaaggga tccagtttca gctttctaca   8160
tatggctagc cagttttccc agcaccattt gttaaatagg gactcctttc ccaatttctt   8220
gtttttgtca ggtttgtcag agatcagatc attgtagatg tgtggtatta tctgagggct   8280
ctgttctgtt ccattggtct atctctctgt tttggtacca gtaccgtgcc attttggtta   8340
ctgtagcctt gtagttttgg tgtggatgtc ctttctgttt gttagttatc cttttgacag   8400
tcaggatcct cagctgcagg tctgttggag tttgctggag gtccactcca gaatctgttt   8460
gcctgggtac cagcagagcc tgcagaacag cgaaaattgc tgaacagcaa atgttgctgt   8520
ctgatcgctc ttctggaggt ttcatctcag aggggtacct ggctgtgcga ggtgtcagtc   8580
tgcccctact tgggggtgcc tcccagatag gctactcggg ggtgaaggac caacttgagg   8640
aggcagtctt tccattctca gatcccaaac tccatgctgg gagaaccact actctcttca   8700
aagctcttcg acagggacat ttaagtctgc agaggtttct gctgcctttt gtttggctat   8760
gccctgcccc cagaggtgga gtctacagag gcaggcaggc ctccttgaac tgcggtgggc   8820
tccccccagt ttgggcttcc tggccacttt gtttacctac tcaagcctca gcaatggcga   8880
```

-continued

```
gcgcccttcc cccagcctcg ctgccacctt acagttcaat ctcagactgc tgtgctagca   8940
atgagcaagg ctccgtgggc atgggaccct ctgagccagg cgcaggatat aatttcctgg   9000
tgtgccgctt gctaagacca ttggaaaagc gcagtatttg ggtgggagtg acccgatttt   9060
tcaggtgccg tctgtcacag ctttgcttgg ctatgaaagg gaattccctc accccttgca   9120
cttcctgggt gaggcaatgg ctccctgttc ttcgggtcat gctcgatgtg ctgcacccac   9180
tgtcctgcac ccactgtcca ataagccaca gtgagataaa cccagtacct cagttggaaa   9240
tgcagaaatc accagtattc tgcgttgctc acactgcaag ctgtagactg gagctgttcc   9300
tattcggcca tcttggaact gccctcactg actcaacatt atttttaaca tgtttattta   9360
cacatttata aaatgatcac tgagtactta atacataatc tagttgagca atgtcctggt   9420
gatgcttgga tatgagaaaa tgaaaaaaca aacatctaat tacagatgct cctcaattta   9480
cagtgatgtt atttctcgat taacctatca taaattaaaa atattgcaaa tcaaaaatac   9540
acttaaacac ctaacttatc aaacactata gcttaagctt ttcctaactt aaaatgctca   9600
gaacactcac attaacctac aaatttggac tcctacattt gggtaggcta atgtaagtat   9660
tctgagccct ttaaggcagg ctaggctaag ctatgtttgt gcatgacaca aagcccattt   9720
tacaataaag tgttgaatat ctcaggtaat agtattatat cacatatcaa tagcccagga   9780
aaagatcaaa atttaaaatt ttaagtacaa tttctactaa atgggcatca ctttgacacc   9840
attgtaaagt caaaaaatca taagtttggg atcatctgta aatgagggca caattcccac   9900
aagaagattt cagaatcaga ttcaagatat tgtgaggaca caaaagagga agttatcaac   9960
tctcagggag tggaggggaa aaaacggctt tatgaaagaa atgacttttg ggcagtcttg  10020
gaagataagc aattgtaaat aatcagtaga actgcagtag gacataagac gagccatgga  10080
ttagcctaga caggttacat agaggtcaga gctcagagga gattattggc cagtccttgt  10140
aaacaacgat gagtgtctaa agagtgtcat gtaagagaaa gagagaaaca gtataaaaat  10200
tcataaaagt cagcctggta gcagtgtgac aagcgtactt aaagaaaaag acacttgccc  10260
taagtcaaca aagtttattt cagaataaga attatattaa tatataggca tctgaattca  10320
atagtatttt tgccaaaatc aaggcataat gtgtaaaaat gtattcattt atatcccacg  10380
ttgattgaag tcatttcttc taattttcag gttttagctc tgcctatgca cgtggatgag  10440
acctaggtct caatcaaggt ctggcagttc agaaggtcaa gtcagaccat caaccatggt  10500
agctacttca ttgaccagcc tcacctagaa tgagtataac tgtgaagctt ttcaattttc  10560
tttattattt tagccatact gctatcatta ggatatttga cctctccaaa cttcacgttg  10620
aaatttgatc cccaatgttg aacatggggc ttcatggaag gtgtttgggt aatgggggca  10680
gatccctcat gaatagatta atcccctcct taggcatggt gatggtaagc gaattctcac  10740
tctattagtt accaagagag ctggttgtta aaaagggctg ggcctggtac ctctctcccc  10800
tctccctctt gcttcctttc tcaccatgca atctctgcac attccagctc cccttcacct  10860
tctgccatga gtggaagcag cctgagacac tcaccagatg cagatggcca attttaaact  10920
tttttcgaaa tcagaattgt gagccaaata aatatttttt ctttataaat tatcagtgtt  10980
ctttactagc aacacaagtg aactaagaca catactgtgt ttgctttctc tttcccatcc  11040
cttaatctga gtagaaatta taactttgac aaattcaatc attaaattta ctccaaaagg  11100
tggtaaacta attcaaaact ttctcctccc tcacattagg ccagaattgt atgatatctc  11160
tggcaacatc ttctcctttc cactcctttt agagtaaaca gagatgaatt tatgcattgg  11220
ttgcctgtac gtggtatgag aacatccttg gcctcagttt acttcgttca gatttcatca  11280
```

-continued

```
gttgctagta gcttttgctg atatgtgaat gttctgtgct tattaagaaa ggttattatt  11340
gtggtaacaa aatctacctt taaatctagc gttataaatt caattatttt actgttgatc  11400
cctttaaatt caccatattc catgaataga aagtgtctag gacttggtcc tgtgggaatt  11460
tcttatttta agtaaacact gagtgctaat gcatgtcagc tctcctcttg ccattttgag  11520
attttcaaga tcttgctagc tttgaaagtt gaattgggtg aaataaaaat gctgcaatat  11580
taaaaaaatt taaatctcaa agacctcaag acatagttca agacttttaa aagttcaagg  11640
gtttgtcaat aaataataaa gaatcatttg ttgctttaac aaagaacagc aaaggatgtg  11700
taacataact ggaacattca ataatggctc tatcaaattc ctaaaataag cttaaagaaa  11760
cataagatct acatattaat atttatgact gtttctgaaa aggatatgag ttaaaatctt  11820
tcccaacagt tgatattaaa caaaatgttt gtccaaacaa aaaaacagaa atttaattgt  11880
atttttaatt aaaatgatgt aactcatatt atatgccaat taaaaaaataa agggaaccac  11940
tgggggattg gtcatttaaa aaactgatat aggggctggg cgaggtggct catgcctgta  12000
atcccagcac tttgggaggc cgaagtgggc ggatcacctg aaggcaggag tttgagacca  12060
gcctgaccaa catggagaaa ccctgtcttc tactataaat acaaaattag ctgggcgtgg  12120
tggtgcatgc ctataatccc agctactcag gaagactaag gcaggagaat cgcttgaacc  12180
tgggaggcag aggttgtggt gagccgagat tgcaccattg cactccagct tgggcaagaa  12240
gagtgaaatt ctgcctcaaa acaaaacaaa aaactaatat aggtgatgaa aattgtggct  12300
gttgttataa attgttactg gtcaatgagt ttactacaga aacgtgtaca cacacgtata  12360
caataaatgc tatatattac atgaatttga aaaataatat gcattatggg acagcaactt  12420
caacttttca cagattttaa atgcaaacat ttgaaaaatg aaggaagaag agaatataga  12480
agtggagaag gagctgggga aaaaggaaag gaaggaaatg agaaatacac cttggataaa  12540
caaactgata agttggtgca ttttgaaaag agagttggat agagaactga accatattgg  12600
taactggaga tatgactcat tatttcatgt aatgatggta ttaagcacca actgggctaa  12660
gaatgcatta aaggaaaaaa cataggcatt ggaaacagga gagctgcgtt caaatcctgg  12720
acctatagtt aaagctccct aaggactcac tttccttatg tttcaagtaa gagggagaga  12780
ggtactcatt attcttacct taaaggttaa tgtggggggt taaatgctaa gaggcaagaa  12840
acatattgct tgctacaatt agtgctaaaa aatattaccc cttttcttac tcaatttgag  12900
aggtgctagg ttcttaacat ttgtgcattt tcttgtttgt tttacatata ggcagaggaa  12960
aggcaagata ccatctttag tcatttaaat ctatgatttg gagaaaagat gttttcaaag  13020
tatccttgct cattgacttt gctatactag acagtatgag tattagcttg cagactttat  13080
gagtgtaata ataaaacaga attctatgca tctagaagta taagcagaat ttttactgag  13140
taattttaaa actttttttg ctattgttca gatcagctta gtccaaattt tttaattagt  13200
tattgaggta gagactaaaa tgtactttct cttacattac atactgaaaa tattattgca  13260
tgtttgatta gttaatatgc atattattaa ttattgtagg tagtaagaaa actgatctaa  13320
aatctttgtt tactcaacct gtttatcatg gtcttaagga actttttgta aactgcttta  13380
taattttact gtcatatatt cagaatagtc ttattcaaat acatccaaaa cactgagtat  13440
atcaataaag tctttcaaaa accaggaaaa aatagtgggt ttttccaaag atagaactta  13500
atataagaat ttctgtaact gtactgaagg actgccaaag gacataatgg agtaacagaa  13560
agattaataa attcagaaag cagggatctc ccataaaaga agagcaatga aagatagagg  13620
```

-continued

```
ttggggttat taaaaccaaa aagcttaaag ccatacctct gtagagttgg cacttatact  13680
tctgaggtga ggtgctggca cctcaggggg catgaggtga agccttgagg agcttcagtc  13740
agatgcatga ggaaggggca ctgcatggat ggctggtgct ggttactcag atgctcaggg  13800
gaggagtccc acattgttgg gcctcagaga tctgaggaga ggatgctgca ttcgaggtcc  13860
cggaatccct gaggggagct tatatggttt ggctctgtgt ccccacccaa atctcatctt  13920
gtagctccca tagttcccac gtgttgtggg agggacctgg tgggagatag ttgaatcatg  13980
gggtcgggtc tttcttgtgc tgctctcatg atagagagta agtctcatga tatctgattg  14040
ttttaaaaat gggagtttcc ctgcaaaagc tctctcccct tgcctgctgc catccacata  14100
agacgtgact tgctcctcct tgccttctgc catgattgtg aggcctcccc agccatgtgg  14160
aactgtaaat ccattaaacc tctttctttt gtaaattgcc cagtctcagg tatgtcttta  14220
tcagcagcat gaaaatggac taatacagta tattggtacc aggagagtga ggcactgttg  14280
aaaagatacc ccaaaatgtg gaaatgactt tggaactggg taacaggcca gggttgtaac  14340
actttggagg gctcagaaga agacaggaaa atgtggaaaa gtttgaattt agtagagatt  14400
tgttgaatgg ctttgcccaa aatcctgata gtaatgtgga caataaagtg caggctgagg  14460
tggtctcaga tgaaaatgag gaacttgctg ggaactgaag caaaggtaac tcttgttata  14520
ttttatcaaa gagactggtg gcattttgcc ccgccctcga gatctgtgga actgggaact  14580
tgagagagat aattcagggt atctggcaga agaagctcct aagcagcaag gcattcaaga  14640
tgtgacttgg gtgctgttaa aagctttgaa ttttaaaagg gaagcagatc ataaaagttc  14700
agaaaatttg cagcctgaca atgtgataga aaacaaaatc ccatttttctg agaaattcaa  14760
gctggctgca gaaagttgca taagtaacaa gaaaccgaat gttaatgccc aagacaatgg  14820
ggaaagtgtc tccaggacat gtcagaggtc ttcacaacag tcccttccat cataggtctg  14880
gaagcctagg agggaaaaat ggttttgtcg gccaggccca gagtccctgt gctgttgtag  14940
gctagggaca tagtgcccta catcccagct gctccagcca tggctgaaag aggccaatgt  15000
agagcttggg tcatggcttc agagggtgca agccccaagc cttggcagct tccacatggt  15060
gttgagattg caagtgcaca gaagtcagga agattgaggt ttaggaacct ctgccaagat  15120
ttcagaggat gtaaggaaag gcctggatgc ccaggcagaa gttttctgca ggggtggggc  15180
cctcatggag aacctctgct agggcagtgc agaagagaaa tgtggggtgg gagccccata  15240
cagagtccct actggggcac ctcctagtgg aactgtgaga agaggaccac tgtcctccag  15300
aacccagaat ggtaggtcca ccgacggctt gcaccatgtg cctggaaaag ctgcagacac  15360
tcagtgccag cccatgaaag cagccaggaa ggaggctgta ccctgcaaag ccacaggggc  15420
gaagctgccc aagactgtgg gaacctacct tgtgtgtcag agttacctag atgtgagaca  15480
tggagtcaaa ggagatcatt ttggagcttt aagatttgac tgccccactg gatttcagac  15540
ttgcatgggg cctgtagctc ctttgttttg gccaatttgt cccatttgga atggctatat  15600
ttactcaatg cctgtacctc cattgtatct aggaagtaac taacttgctt ttgattttat  15660
cataggtggt atcataggtg gaagggactt gccttatttc agatgatact ttagactgtg  15720
gacttttgaa ttaatgctga aatgagttaa gactttgggg gactgagaaa acatggttgg  15780
ttttgaaatg tgaagacatg agatttggga ggggccaggg gtagaatgat atggtttgtc  15840
gctgtgtccc cacccaaatt ttatcttgta tctcccataa ttcccacgtg ttgtgggagg  15900
gacctgatgg gagataattc aatcatggga gtgggtcttt cctgtgctgt ctctcatgat  15960
attgaataag tttcatgaga tctgatggtt ttaaaaatgg gagtttccct gcacaagctc  16020
```

-continued

```
tctcttcttg cctgttgcca tccatgacat gctcctcctt gccttccacc atgattgtgt  16080
ggcctcccca gccatgtgga actgtaagtc cattaaactt cttgcttttg taaattgccc  16140
tatctcagct atgtctttat cagcagcatt agaaaagatt aacacaagag caataagaat  16200
gtttctggac atgtagaaag aagttaaagg ctggaaccaa ttgctgtcac tggaacaaag  16260
gaagatggct ggagtgcggg tgccactaac agtaacaatt atcaaataag aaggatcaaa  16320
cgccttttct cccgcctttt actgtcttct aaagtcatta attggcagaa tatcatagaa  16380
agccagatgg tacaggaaca taatttgtag accttagccc cagtgccaga gagaaagggg  16440
aaaaaaatag acttaaagag caatggcttt gtaactagca tactgacatt ttgtaagttt  16500
agaaaactct tattttatca gttttgttct gcaaattcac ttatttagtt attaacatgt  16560
gttgtttttg tgataatcca tcaaaaagaa ctgagtatct ggtgtttatg gaaagcaaac  16620
taatatctga gtataatttt catttcaatg ttaaatgtct ttatttaaat acagagaaca  16680
gtcgactatc atcatcattt caactgatta tccaactatg acatctagtt gtaaaacaga  16740
aattaattct cagaagttat tactttctat caaaccttaa atattcatca ataagataca  16800
tcttttctag gaccctataa aatgattaat aaatttatta ttattattta ctgtacaaat  16860
attctgctgt tatttattaa aacagaagta ttccatatcc tgaatcagta caatgttaat  16920
ctcctctgtt tactatgtcc atggaaaaat gtgccagtga tttgattagg accataaata  16980
tttgtttttg tattcagagt cccttcatgt tgtcaaaatc cttactgcct gtataatcat  17040
gtttattcct tgtgattttg ttcgtttttt tttgtttttg agacagaacc ttgcgctgtc  17100
acccaagctc ctggagtgca gcggcatgat cactactcac tgcagcctcg acctcacatg  17160
ttcaagtgat cttccccccct cagacccccca agtagctggt actacaggtg catgccacca  17220
agcccagcta atttttaaat tttttgtaga tacaggatct ccctttgttg cccagacagg  17280
tctcaaattc ctaggcccaa gaattcctcc cacctcagcc ttccaaagtg ctgagattac  17340
aggcatgaga caacatgccc agccctggca ttcaatttca gcatctataa aactgtattt  17400
attttaaggt tcctcttgaa tcacaattta tccactgagt atacatatca ggacacaaaa  17460
cacactctat cacaactgga aggacaggaa atttggagaa tatagtataa aactaatgta  17520
gtaacaagag tagcctaatt tttcccaaag ggtccatgaa ttcacaccct actggacagc  17580
tgctctcaag ttttcatttt tttcacagag tgttcaataa ttctgtcatt gaaaagtgtt  17640
tctgccagga ttgatggtgt gaaataaaat ttatgggagc cattgctttg gactgagatc  17700
ttgcactagg cccaagggac cagacaaaaa tagtgactca tgttacagtc ccacattatc  17760
aagccaaaac taagttgttt gtctgacctt cctagaaatc aagagagtaa gagacaatag  17820
ccaaatccct agaggagcca gttttagcta gcatgataag gaagtcccct ctgctttaac  17880
ttttataagg aaagaacctt tgaaataaga aatctacttt ttgctctctg tttctgcttt  17940
ccttggcctt ttactgtata taaaaccaaa ctcctctgct cagcttatca aaaaactcat  18000
tatattatat agaatgaagt gtagcctgat tctagaatta cagataaaag ccaattaaga  18060
cctttaaata agttgtaatt ttgtcttttg gcaacagttt ctgaactgag tctgggaaat  18120
aaataatcca acaaccaggt aaaaggaata gagaaagatg agtgaattcc ttaaagctgt  18180
cttttctcat tctggtaagt tccttcactc tactaaaata aataattcta ccacctggat  18240
aaatttggtt ccttaatgga aaaataatat catcagtaaa agtggaaact ctgggtaaga  18300
aaacggaaat aattaaaatg cctaaaccaa ctttattgtc attaaaatat caaacagatg  18360
```

-continued

```
aactagaatg attcaataag atttcaaatc aactgttagc agtcttttca tgtagaaaga  18420
agtctgcatt taggaagccg ttgaaagaaa ttgctaagct ctaaggacag gtcctgtcca  18480
gaccaaagca ggcccctagc cctaacaggg atcccttggg taaggagacc atttgctgca  18540
ataagaaaaa atgacatcaa aggagaggct gagtgctatg atctgaagat cagcaggtga  18600
ggaatctctt gggaatctcc tggatgcttg ctctggacac aaggcaggca ctggagatgt  18660
aaagaaatgt gtggccctca attgttcaac aaatagccat cagttcaaac tgaatatgta  18720
ataacgcatc ggtctgcaat cagaatttca aagcccagag aaatacattt aaaagatcaa  18780
tcctttagaa tatagcaata ttctttattg tctatgccct gtttagcaat caaccttcca  18840
cattttctac tgagttttct agacagctta gaatgaaagt cctacagggt aagaagttca  18900
agagttaatg gatgcttttg ttcttccagt tggttctaat aagagtggta aaatacaaca  18960
gcatattctt tataatttga ttttaatcca attttgtaca ttctcagacc taaacattgt  19020
ttaccacact aattattttt gaagttaacc tcccctcaat accctttttta aagagtgagt  19080
gctgaaatta taacagccat atgatattga tgaggctgct tttagagcct caaattcaac  19140
tccagaaatt tatttttagt tgtgcatatt tattgtaaaa tatttgtagt gccagcttat  19200
gttttctatg tccagatttt gttctccacc ttctgaagcc cacagagtgt gaaacaagca  19260
tttacaatgg agatgatggt gctaatttta tgtattttat tccctggcat atttgattgc  19320
aatagagtag acaaaaggat ggattagtag ctatgatctc tctctctctc tctctctctt  19380
tctctctctc tctctctctc tatatatata tatatacaca cacacacaca cacacacgga  19440
aggcatcaga tatctcatgt gtgtatacac atacatatat ataggatata atgatttatg  19500
tgatatatat gtgaggtaag tcttcatgtc ttccataggt atagtaccag ttggttaatc  19560
ttgggccagt catgtagctt ctacaaactt taggctttct ggacaaagca gtatataatg  19620
ttcattatgt agctatgcca aaacaaaggt caaaataaag aaagattcta cctagagcaa  19680
aagagaattt atatatataa attttatatg caaattatat acagctttat atacaaatat  19740
aaatatcacc ctgatgtagt agtttgctag gattgccata acaaaatgct acagactgtg  19800
tggttaaaca acagaaattt attttctacc aattctgaaa gctagaagtc tgagatcaat  19860
gtatcagcgg ggttggtttc ttctaaggcc tctctccttg gcttgcagat ggctgtcttc  19920
ttccagtgtc tttatattgt cttctgtgtg tgtgtgtcag tgttctaatc tgctcttctt  19980
ataaaaatat cagtcagatt agggttcact ccaaggtaag aactgaagag catgctcttt  20040
tctttgatgg ggacaagtga ctctatctag acataagtct ttggagagca gtctctcaga  20100
tgctgaccct ctctacaatg gagagagcgc atggcatggc ctgctaagct acttctctgc  20160
cattctgcta ggcaggtttc aggccctgac aatataagac gtgagcctct actcatcttt  20220
ggataagtct ctctgcatta ttgcaaatac aagaagcatt ttgtagctgt gtagtaaaga  20280
gaggagaaca cttgcaatat tctcagtcaa gattctcaac tccctgaaga aaaacagtgt  20340
attttacata aattcatgct gttataatta cattatataa aaagattatt aaccaaatat  20400
tgtacatatg aaaacagagt tgaaagctct tcaactattt caactgatga ctcccaagat  20460
ggacctgact gtactgatat aatctgatgg atttttattt gaagctattc taacagaact  20520
atattttatg gtatggaaac gaagagaatt gttttaggga agagcatgtt taatgttttc  20580
aaatattttt gtctctgact taaattttgg cttttctagt ttgtttcaaa ttttcacact  20640
tgggtcaatt ctcttttgct ctaggtagtt ttttttttta tcttgacttt gttttggtgt  20700
atttctgcct gactggaaaa gtttttgtaa ccccactttc ttttcatccg attagtagct  20760
```

-continued

```
cttctgtgtc catagataaa tatatccttt acttctgtga gcattatttt ggtatatgta  20820
tttttgttcc agttaggaaa agagcagcaa aatgattttc tttcttgttt tcttcctaaa  20880
acttgattta gaagctaagt gggagcagcc ctttcacaca ccatcatggt agttatttac  20940
gtgcattagc gcgattcatt ttcacaaatt tatgagatgg ttaaagttaa ctttcatttc  21000
ttaaagagag agaacaagtg gagaaaaagt tcaactgcag aggcttgaga ttgtattgtg  21060
tgttgcttaa gaagaaatat ggagtcaaag tgcctcatca tttaccagtt gtgtgacata  21120
tcacaaaaag agggagtgta accagccaaa aatttaactt ggacaattgg attggtaaaa  21180
actttttatg ggatatgcag gaatacagtt cttaaaattt tataagatgg cataaaattt  21240
atttctttga taaatgatat tttcttaaga tatctttcta gaaatggaat tgctgagtca  21300
agatgcatat tgagggattt tgatacatat ttttaaatta ccttttagaa aaggtaattt  21360
ttagtaggaa agtagaagtt tatctcctat tgctaggcat actgattttt ttctttttct  21420
tatctgcatt taatcacttt tctttaatga gcatatacta cttgtataac agaaaataaa  21480
ggatgattat atttgggaag tgtcatgtca gattgtcctg tccagtttga aatccacttt  21540
gacttttaat ctaccttgag atgttatttt agctccctac aggttaaggg cataatccaa  21600
gatgattaag gagattgaat tctcatttaa ttgattgttg ccacagacac ttacacagag  21660
ataaagtcat taaacacatg tctcttttac atttgaaaag acatggcaaa taattttact  21720
gctttcttta gtatacataa tgtcataata ttgtgagtgt gcatgtgtat accattctgt  21780
ctatatctta atgatctaga atgtatatgc tactttctta catgcaaatg agctgtacat  21840
atttgagtaa tattggtgac ttttttatat aaatcaattt ttccttttga tgattacatt  21900
atacgaagat gtttgaatgc tgtttttttct ttgttatgtg tatgcttata tctgtgaaac  21960
atctagctag atgtcctgca ggaatcagtt ttacatatgt aaacaggcat atttctgcac  22020
tctaaatttt gataattaaa ataattcgta actttattat tcaactctca agtgtttaat  22080
agccattact aacaaaaatt tctctttgtg gctaatctga ttacttggaa tctttttat  22140
tgtgaccaaa aaaagcaacc ctgcacatac aactttaact tcaatatttt aatgacgaaa  22200
tttaaggata atttaaatag aaatggactc agaaaagaat cagtaagact tagtgaagga  22260
tcattgtcta ttatagagaa gttgatttaa gattaactta ttagtaatat ttaacatata  22320
taaagaatta ttagactggg tatatagaca agcgttttat tcttggaaga caaaaagaag  22380
aaaaattgaa ttcaaccgat gtatacgaaa ataaaaagta acagtaaatt aaaaatagat  22440
aattaaataa atatatgata cagtataacg ttttatagcc aagatgatgt tacaaatcca  22500
tatttattga catggatatg tttttatact aaagtgttta tcaaatagcc attaagagat  22560
aacttctttg aataatttgc tttctaaatt tcttaactac ataaatttcc agctttatat  22620
ggaacaccaa gttttcaaac cattagtgat gtgcttttta tatggtgtta aaaagtttct  22680
ttctttcttt tttctttttc ccccaagatg gagtcttgct ctgtcgccca ggctggagcg  22740
cagtagtgcg atctcggctc agtgcaacaa ccacctcctg ggtacaagca attctcctgc  22800
ctcagccccc caagtagctg ggattacagg cacctgccac cacgtccagc tgatttttgt  22860
atttttagta gagacggggt tttaccatct tggccaggct ggtctctaac tcctgacctc  22920
aggtaatctg cccacctcag cctcccaaag tgctgagatt acaggcgtga gccaccatgc  22980
ccgacctaaa aagtttctta aacgtcactt tatactctca aattatctag aaaggaaaac  23040
gtattagatt cctggatatt ttggatattg taaggaacat acttatttgc tgtatatact  23100
```

-continued ctgtttgtaa cagtattgta acttcagttc aaaacaatac acaaaacatt acaagttccc 23160
gtgatatttt aaaaattcat ttattttctt cctttctgaa tacaaatgct gttcagtctg 23220
ttgattcttc actaatctga aatattaggg actgatttct gaattggata ttcattctga 23280
agcctttcag agccactggc acaaagggtc tgtcaaactt ggaacaccat ttgttgtatc 23340
attttatttc tttctcttgg caaatccaca taattcatac aggactatgc cagtgtcttt 23400
tgaaagaaac aaggtttaag aaagtaaaaa tgttaataaa gatagtgaat gttaattctg 23460
tcattgttac tgtatttctt caagctgtgg ctgcaaactg ctttgagtga tgttattgta 23520
actcgcacat tagggagaga aagagatgtt tggtagattt ttaattaatg atccctatca 23580
atgctccttg agctttccca ctctatctct ccacaacttc catccctggt tggaaatttt 23640
ttgcttaccc atactaagtg agagttattg atgggaaggc atcagatatc tcacgtgtgt 23700
tgctggtggg atgggagact gtggaggatg ggaacaggtg gaaatctact gcaatggaaa 23760
aaaaaaaaag catgtcctag gacacccaaa acatggaggc tagataataa caatagctac 23820
ttgtactgag agcttccact ctgcctggct ctttgctatg agccacatta ttcattcctt 23880
acaacaatca aacaagacaa gtaaaatatc atgcccattt tttaatgaga aaactagaga 23940
ttagagaggt tatagatact tgctctgagt cactagtaat gagtagtaga gctttaataa 24000
gtccctgaat ttaggttgta tctagtacat ttactcttag aagtctatca tgctcaccag 24060
agttgcagag ttgcgtgtat ttcttgggct cattaatgtg tttttttctt tctaaaacta 24120
aagtcatttg aacttgttag attttgaaat atttaaatat cttttctatc tggctttaac 24180
atctttaatc ttggaatctt gcatgccttc atattcttag gaccacgaaa ccacaggaat 24240
atttaaaatg atatctagtg gaaacaatat gaagttggcc atggggtcaa attagagaat 24300
ctgaatacta tgcttctcct tgattgctct tcccatttct tcagagtaac cctattcccc 24360
catctcatgc tcaccccctt tccaaaatca tacataatga tctcccaaca ggatgcatta 24420
ggctttctct actctaccca ctatgaaatt acacaagaag cctatcgcaa tctcactacc 24480
tcgtctctct cacaggttta cagaaggtga gaggaaggtg cagatagaga ataagaagca 24540
ggtggctcca gcatcaacat tacatcaccc cttgtgttca caacaaatat ggaatattat 24600
ccaaagataa taaacgttgt attttcttaa cttaaacaca ttaaatcagt cctctcttta 24660
atcacttgtt aatgggcagc atctttattt tcatgccatt ctactctgct gtctttgcta 24720
tagcacaagt ttaccacata ccatacctaa aaattcagtt gttctatggg ggtaaacaaa 24780
gtctaggtta agcatatatt tcatagaatg ttaatctata gcaaaattaa tgaattaaat 24840
ccagataaaa gaatcctatt atggtctggt aaaatattta tatttcactt agcaaagaga 24900
aaacaaaaca tgaatattgt agttatgaac agaatatgca tgttagtaat gcttccaaat 24960
atgttattac ttcataactt catatttctt atgaggtaca agccattcaa ttagtttaac 25020
gttatattca gagaggctaa agatttactg aagaccatgc tgtccatcaa taatgaaaag 25080
aaaaattaaa aaaactttat tttaacttct agttcccttc tttgtacttg agcagctttc 25140
cctccttaag aatacagacc tagaacatat gcaatatcac tatcaatatt atgtgtaatt 25200
aaaagttcat tggatgttta ctgtgttcaa ggcattttaa ggagtgacaa gagttaaaca 25260
tatagttgta attcaaaatg acaacgaaat tagtttacag ttttcttttt ttgtaggtag 25320
taagaaatca tctcccccta ttgaggaata ccaatataga aaaggcaaaa ctttaaatat 25380
gaatgaactg tttcataata acataagttc ttcttgattt ccattgtcac atccaaattt 25440
gaaggctatt tctaacacag ctgggttcta cctttttcct tctcactctt taccacaccc 25500

-continued

```
aatctgtgag gcttcagaca caaactgcta attcaggaga caattgtgcc ttctgtaaca  25560
gtttctgcta aattgtctca gctctgccac ttaaaatagc taggtgatct cagcatatca  25620
ccaaaactct tggagctcag tttctctgtc tataaaagtt acataaaatg taattgatct  25680
gcttgttatg actaaataac atagtacatt agtcctttgc caaaggacta acaaattacc  25740
aaataaaagt ttggaatcat gttaaacgtt tataagaagt acaactgtcc agaaataatt  25800
ctctcacatt ggtctgttgt aatgagacct aaaatatctc attttattta cctctttgac  25860
ttaaagcact aggtctcaag gaggtcatgg ttatactata aatatgtcat gtgaaataat  25920
atattaaata attgttgtaa tactctattg agatactagt tgtaaagagg cacaatggaa  25980
aacttatact attaacagta gtaaaaagaa acaacaaaaa gcaataaaaa acaaaacacc  26040
cattcatgca acgacatgaa cgaacctcac aaatattata ctgagtaaaa gaagtcagac  26100
aaatataaaa caaagtttat actacgtgat tagatcttta tgacattcta gaatatgcac  26160
atgaaggtac aaggtaactg tctggaatga tgaaaatgtc ctgtgtcttc aaaatagtgt  26220
gggttacact aatgcatggc tttttcaaaa ctgatttaaa gggacacaac atctgagcat  26280
ttccctaggt gtaaattaca ctgcaatttt aaagaatcat ctaatgatat tgtggttatt  26340
tttaaacagt ccttaaattt tgtggatgca tactgaatgt ttacagcgga aaagatatat  26400
ataaagcttg aatttggtaa aaaaaaaaaa aagagggagg attggtagtg ataaagtgag  26460
tggacttatg gatgagacat gatcagccat gcattgaaaa aatgtaaaag ttggatgatc  26520
ttcacatgag agtcctttat tctgtctact tttgcatatg tttgaatatt tcccataaca  26580
aaaagttgaa aatagagtga tcacatgagt taatctccta atttacaaaa aagaaaactg  26640
gaaacagaag gagaacaaaa cttgttcaag gtctcaaagc cagacagcaa actagctccc  26700
aagtccaacc ttcttgctcc ggtcctaagc aaacaaaaaa tattaatatg agctactgca  26760
ttaaggaaag tctgcttttc caaagggcag accaatagtt caaggaagag tttaaataat  26820
aaatatttgt gatcttactt tcatgctttt ctattttcca ctgaacacat atgcattatc  26880
ttctatatgt cttttatgta taatcatttg cttcctgttc cttgtggttt taaagttgtt  26940
ttgtatgttt aaatttgatt ttactcaaat ttcagaaccc aaattagcgc aagaatcaga  27000
caaagcataa ctttctataa atataaaaac aattaaaaaa aaaacataca gcaaaaacga  27060
gttgttgttt ccccccctcct cttccagtgc ttaactaatc ttccgaatcc aggcacagaa  27120
agcaaaggct ttctgctagt gggaggagct tgcttctcca ttctggtgtg atccaggaac  27180
agctgtcttc cagctctgaa agaggtgaaa atgtgttaag cgatgcaaaa attgtcttga  27240
agttcgcgtg tgtatgtctg tgtgcatgtg cgtgtggtgg gtggggggag agaaaagggg  27300
gtgtcaattc tgagggcaac gagaatcaga agtcagaaag gtgagtggtg tgtagcatct  27360
ccctttcaga aggggctgaa gaagaaattg gatatgatgg tccggtaggc taaatcacgc  27420
tggatttgtc tcccagataa agggaggtct gcaaagtaag tcccatttct agagcgaaaa  27480
gccttaggac cgcttgtttt agacggctgg ggaatattta ttccttgttc cactgatggg  27540
aaaatcagcg tctggcagga gctgattggt ggaaaggaaa atggtgatag tggcgtggaa  27600
agaggatttg ctgagccttc tcctgcctcc tcaacctgtg actcttcctt agtagtctcc  27660
ctttcaccct caggaccctt tccggctctt cctagattaa gagcaaacga aaaccttgaa  27720
gatatttgaa ctaaagcgac ccctaacgtt gtaacctgtg accgtgatta aatttcagcg  27780
atgcgagggc aaagcgctct cggcggtgcg gtgtgagcca cctcccggcg ctgcctgtct  27840
```

-continued

```
cctccagcag ctccccaagg gataggctct gcccttggtg gtcgaccctc aggccctcgg  27900
ctctcccagg gcgactctga cgaggggtag ggggtggtcc ccgggaggac ccagaggaaa  27960
ggcggggaca agaagggagg ggaaggggaa agaggaagag gcatcatccc tagcccaacc  28020
gctcccgatc tccacaagag tgctcgtgac cctaaactta acgtgaggcg caaaagcgcc  28080
cccactttcc cgccttgcgc ggccaggcag gcggctggag ttgatggctc accccgcgcc  28140
ccctgcccca tccccatccg agatagggac gaggagcacg ctgcagggaa agcagcgagc  28200
gccgggagag gggcgggcag aagcgctgac aaatcagcgg tgggggcgga gagccgagga  28260
gaaggagaag gaggaggact aggaggagga ggacggcgac gaccagaagg ggcccaagag  28320
agggggcgag cgaccgagcg ccgcgacgcg gaagtgaggt gcgtgcgggc tgcagcgcag  28380
accccggccc ggcccctccg agagcgtcct gggcgctccc tcacgccttg ccttcaagcc  28440
ttctgccttt ccaccctcgt gagcggagaa ctgggagtgg ccattcgacg acaggttagc  28500
gggtttgcct cccactcccc cagcctcgcg tcgccggctc acagcggcct cctctgggga  28560
cagtcccccc cgggtgccgc ctccgccctt cctgtgcgct ccttttcctt cttctttcct  28620
attaaatatt atttgggaat tgtttaaatt tttttttttt aaaaagagag aggcggggag  28680
gagtcggagt tgtggagaag cagagggact caggtaagta cctgtggatc taaacgggcg  28740
tctttggaaa tcctggagaa caccgggtgg gagacgaatg gtcgtgggca ccgggagggg  28800
gtggtgctgc catgaggacc cgctgggcca ggtctctggg aggtgagtac ttgtcccttt  28860
ggggagccta atgaaagaga cttgacctgg ctttcgtcct gcttctgata ttcccttctc  28920
cacaagggct gagagattag gctgcttctc cgggatccgc ttttccccgg gaaacgcgag  28980
gatgctccat ggagcgtgag catccaactt ttctctcaca taaaatctgt ctgcccgctc  29040
tcttggtttt tctctgtaaa gtaagcaagc tgcgtttggc aaataatgaa atggaagtgc  29100
agggaggcca agtcaacagg tggtaacggg ttaacaagtg ctggcgcggg gtccgctagg  29160
gtggaggctg agaacgcccc ctcgggtggc tggcgcgggg ttggagacgg cccgcgagtg  29220
tgagcggcgc ctgctcaggg tagatagctg agggcggggg tggatgttgg atggattaga  29280
accatcacac ttgggcccgc tgtttgcctg aggttgaacc acaccccgag tgagcagtta  29340
gttctgttgc ctacgccttt ccaccatcaa cctgttagcc ttcttctggg attcatgtta  29400
aggatacccc tgaccctaag cctccagctt ccatgcttct aactcatact gttacccttt  29460
agaccccggg aatttaaaaa aggggttaat cttttcatgc aactccactt ctgaaatgca  29520
gtaataacaa ctcagaggat tcatcctaat ccgtggttag gtggctagac ttttactagc  29580
caagatggat gggagatgct aaatttttaa tgccagagct aaaaatgtct gctttgtcca  29640
atggttaaat gagtgtacac ttaaaagagt ctcacacttt ggagggtttc tcatgatttt  29700
tcagtgtttt ttgtttattt ttccccgaaa gttctcattc aaagtgtatt tttatgttttc  29760
cagtgtggtg taaaggaatt cattagccat ggatgtattc atgaaaggac tttcaaaggc  29820
caaggaggga gttgtggctg ctgctgagaa aaccaaacag ggtgtggcag aagcagcagg  29880
aaagacaaaa gagggtgttc tctatgtagg taggtaaacc ccaaatgtca gtttggtgct  29940
tgttcatgag tgatgggtta ggataatcaa tactctaaat gctggtagtt ctctctcttg  30000
attcattttt gcatcattgc ttgtcaaaaa ggtggactga gtcagaggta tgtgtaggta  30060
ggtgaatgtg aacgtgtgta tttgagctaa tagtaaaaaa tgcgactgtt tgcttttcca  30120
gatttttaat tttgccctaa tatttatgac tttttaaaaa tgaatgtttc tgtacctaca  30180
taattgtatt tcagagaaca gttttaaaaa ctcatagtct tttaaaaaat aatcaagaat  30240
```

-continued

```
attcttaaga atcaaaatca ttgatggatc tgtgatttct tttaccatca tgaaaaatgt  30300
ttgtcaattt taatccattc tgatttttaa aatatgactt tgatatgccc ctgtgatgtg  30360
tataaagaga cctatttgtg gccctaaaat ggaaagaaca gattagtctt tgataaagtt  30420
acttcatgtg atcatttggt ctctgtgaac actgaggaca gagaaaagtg cttgagggct  30480
gctactaatc tctcagaaac atttgtatag ttcatccatc aaatgacaca catactaaaa  30540
gaataaagaa attgatgctt attacctact tgttcctaaa gttccacctt ggggtataca  30600
cccaaactct gactctcttt tctgtaactt gaactgtatt caattgagtg ttattttaca  30660
aaccactctg aattccttgg aaaagaatag acacacactc tcatccacag gcatagacac  30720
acacactcaa cacagacaca ttgcccattc ttcctctctt ctttctcctc tgagcttttt  30780
cacattctct ggtggcaact atagcagtaa gagtcacagg atgaacagtc aggtggagga  30840
tgaccacatt gagttgccta gctgaaacat gtgctctgtc tatgtctgca aagtgaaaga  30900
aagctacact atctcttcaa catagatcag tgggggaaat tttatacttg ggatgattta  30960
tatgaatgca tctcatcaaa gttcacaaca catttttttt ttcagttttt tattttcagt  31020
ttttagagtc agggccttgc tctgtcgccc aggctggact gcagtgatgc tatcatagct  31080
cactgcatcc ttgaattcct gggctcaagt catgccccca cctcagcctc ctgagtagcc  31140
aggattatag gcatgtgcca ctgcctcatt atttagactt ttcttatgtt gacttaatct  31200
tcccacaaat cttcaattaa attacttttt ttctacctta aaacatattt tcagaaagtc  31260
attgaaatag ggtgttacaa gaggaaaaaa ttgatgagtt aattttaaat attttatgaa  31320
gtgtgaatta taccttttta gatggaattt ggaatactga atcagtgaca tgcagtttat  31380
cagtatcttt ccgtttgtcc tcagatttcc aagttctgca agcacaagtt gctttgactt  31440
agttaccttt taactgttca ttgaaatcat tttcaatgtc tctcatggca tttaacacat  31500
agcacattct ataaattatt tattggttac attctgagtt ctaattgaga gttgaactta  31560
cacacagaat ttaagataaa aaatgaccat gtgaagacac aatagtatag tccagggatt  31620
ggcaaaattt tgggtaagga atcagatagc acgtatttta agccatgaga tctatgtctt  31680
ggccaggtgc cgtggctcag gtctttaatc ccagcacttt gagagcccga ggctggtgga  31740
tcacttgagc ccaggggttt gagaccagcc tgggccacag ggtgaaaccc tgtgtctaca  31800
aacaacgcaa aaattagccg ggtatggtag catgcacgtg tattgccagc tacccaggag  31860
gctgaggtag gaggatggct tgagccatac agctcactgc agaggttgca gtgagccgag  31920
atcgagccac tgcactccag cctgggtggc agagtgatac cctgtctaaa aaaaaaaaaa  31980
aaaaaaaaat ctatgtctca attctgctgt tgaagtgtga aggtagtcat aaacaataac  32040
tagtgtggct gtgttccaat aaaacttcat ttatcaaaac aggtggtggg ctggaattgt  32100
cttgtatgtt gtagcttgct gactactgat agagtggaaa gaacatgcac taatcacaca  32160
aaccaaagtt ttagttgaga ctacatcact tatcaccttt agggtcttgg ggaagcgtac  32220
ttaacatctc tgagcatcac ttccctgatt agtaaaaaat atgatttaga aaacttcaac  32280
taccttgcag tttttgtgag aatgtcataa taagacagga catatgaata attgagcaca  32340
cttttatata taggaaccat ggttattatt atcaaataaa ctctccaacg gaataattac  32400
tttgccaaca cgttttccat ttattctttt atccttcatt acataactag tttgaaaggt  32460
tggaggcgac caaagaccat tttataattt cacttatggc cgaagatgtt tggtagaagc  32520
ctcataagaa aagtaatctc attcctttat aagaatatac ttttaacaac tactttttaa  32580
```

-continued ctcattgaat aactacctta atgatcagtg ttatttttat gggttttgtt ccctccattt 32640
ttgttatctg catacaccaa ttttcaatca acatacttca atttaataga caaaaatttc 32700
ttcaaatgac tcagaaatta attagatcta aatccaaaag cagaaagatt taattatctt 32760
tatataatgc tcagtaatat aaatgcaata aatacaagaa aatgatgatc tttgagtgtc 32820
ttccaatgcc actctgctca ataagcagca gtggccatca gtgaaattga tagcaaattc 32880
tcaagtcaaa atgtgcttca cctcactaag ctgacaaagt caacataaca tgcacaacag 32940
ggataactga gttctcaaaa ctctcaggta ttacttctga ccttcttctc cactctgtgc 33000
tcttttgagg ttgggaagac aagatagggt gtgtgtggga cacctccgct cagggaagcc 33060
atcagctctg gtgtccctac agcatttata ccttgctagt cacataacca cttggcacct 33120
attttgtagg tgtatgttat caattacaga ttactcataa attaaaggct aaccatcaat 33180
tacagattat tagtaaataa ttatgacctc aaagaacaac tgattggttt gatacatggt 33240
aaccttatga ggactctcat ttatctcgtt tttttaagtt atatacctat ctctttgggg 33300
ttgcactaca aaaatataaa atatgttgca taagatattt ataaaaaata attaattata 33360
agttctagtg gtgtggttta gtggcattct tttttttttc tttttttctg agatagggtc 33420
tcaatctgtc acttcactcc aggctgaagt gcagtggtgt gatctcggct cactgcaacc 33480
tccgcctcct gggttcaagt tattctcctg actcagcctc ctgagtagct gaaattacag 33540
gcacgcacca ccatgcccgg ctaatttttg tatttttagt agagatgggg tttcaccatg 33600
ttagccagga tggtctcgaa ctcctgatct catcatcctc cgacctcggc ctcccaaaat 33660
gctgggatta caggcgtgag ccattgcacc cggcctagtg gcattctttt ttaaaaataa 33720
atttaattgt gtatatttag ggtatgcaac atgatgctat cagatacatt agacactaaa 33780
aaattactat attgaagcaa attaatatat tcataatctc tcatagttac ctttttttgtt 33840
gtttttgtgg caagggcagc taaaatccac ttatttatca tgaatctcaa atatagtaca 33900
attttatcac ctacagtcct catacattag atctgtacac ttgttcatct tacacatctg 33960
ctacttgctt ggatcctatg gcctatatgt ccctattttc tacctacttt tccaccccta 34020
ttaaccctgt attttacgta gtctctgtat atttgaattt tgtttcaagc ttccacatat 34080
atgtgagata atgtaatatt tttctttctg tgtttggctt atttcactta gcataatttt 34140
gtctgggttc atccatgttg taaatggtag gatcttgttt ttttagggct gactgatatt 34200
ccattgtatc tatgtaccac aatcttttta tctacctatc tatcagtaga cactttagtt 34260
gtggctatta tgtttttctt tttttctttt ttggagacag ggtcttgctg tcacccaggc 34320
tgcaatggag tggtgttatc atagctcact gtaacctcaa acttctgggc tcaagagatc 34380
ctcctgcctt ggcctcccaa gtagctggga ctacaggcat acattaccat gcctggctaa 34440
tttttaatat tttttgtaga tatagcatct cactctgttg cccagactgg tctcaaactc 34500
ctaattcaaa tttagaatag agtatgacaa ttctgtaaaa tataaaaaac atgtccactc 34560
cgtataggaa gttatacaat gagaagaaga caaacactat ttacattact cttgataagt 34620
tttttacaaa gaaataaaac actttaattt ctaatgtttt aaattctggt ttgctaaata 34680
aataaatatt agttttagtg tttttaaaat tccttatata gttataagtg atcttcctgc 34740
ctcagcctcc caaagcactg ggattccaag caagagccac tgtgttgggg cccttggaaa 34800
cagatatgct gaaatctttt cttgtggatc tacacccaga agagggattg ctgggtcata 34860
tgctactcta tttttaattt ttcttttatt tttagtgaat atgtaataat tgtatataat 34920
tgtgggatcc agaattatat ttccatacat gtatacagtg tgtgataatc aaattagggt 34980

-continued

```
aattaacata tccattacct gaaacattta tcattccttt gtggtgggaa cagtaaaaat  35040
taaaaattct ctcttctaga tttttgaaca tatgcaataa actattgtta agtatatcac  35100
cctacagtac tacagaatgc tagaactcat tcctcatatt tggctccaat ttcatattct  35160
ttaaccaacc tctccatatc ctcccctccc tcttaccctt gtcagcctct aataatcata  35220
attctactct ctacttctat ctcattgtct ttgatttaga atatgtttca taatttaacc  35280
aaaggtcaaa ttcttaggta ctgctaaggc aaagaacaaa gatcgcattc cagctgttag  35340
acatttctta ctactagtca tttttaagac aacatggggt gcaggtggtg aggatgagag  35400
atagagattg aaacatattc tcttaaatat cagctgttct cactctgcat agttccagca  35460
caaacaaatt ccaggtacta tggttagtta aataacacca gcccctaaca acacaattca  35520
aatttctgtt accacagtat accgaaagtc attgcataaa gtacaaactt tgctgctaac  35580
tcttcagcct tcaaatcatt acataaataa cagaaaccca ttataatcag tgacaaaacc  35640
acagcacttc tttcaaagct ttttggagat tggttgcttc acatctgtta tgcagttcat  35700
acagacagca atgcccggac ttgtgtggcc acattgtctc ccagtggtga gcccatgtga  35760
tgtttcacaa aaatgcgcaa tcaaaagagg aaactggcca gcaaagatga aagagtagca  35820
aacaaaggaa gtgaaacatt ctggaagtaa aatttgaatc aaacataagt tgatgtatac  35880
aggaagtagc caccctgagg atgttgtcac tgctgcaatt caggagactc taaatatgca  35940
gtcagaggaa cgtagtgagg tgaaggtatc cgtataatgg ggaaagaggt tgtgataaag  36000
agtgaaggtg tcccagagga agcgatgctg aaaaatacac cttatgttaa atacactgtc  36060
agtatatcat gacattaaag tgcaaatgat aacattttgt aaactgatcc aaacttaaaa  36120
aggagtatga taattctgta aaacataaaa atcatgccga ttccataaat tatacagtgt  36180
gaattacact gaaaaatcca acattagaga ggatatgaat acaatttttt acaagcataa  36240
ttttaataat acacataata attatttgta ttcaagttta gtaatggtca aggtttggaa  36300
gaaattctga tcctgtgtag agaccctagt ttgaatgtgc ttatagccta ttattacatg  36360
tgtaatgtta cataaattac ttaactcaga tttttaattt catcagctat ttaaaatggg  36420
cataatataa ctatattaag tggatgttat gaagattaaa taagatgata tgtaaaatgt  36480
gtttttgtt tgtttgtttg tttgtctgtt tgttttttg agacagagtc ttgctctgtt  36540
acccaggctg gagtgcagtg gcacaatctc ggctcactgc aagttctgcc tcccgagttc  36600
atgccattct cctgcctcag cccctcccaa gtagctggga ctacaggcac ccgccaccac  36660
gcctggctaa ttttttgtat ttttggtaga gatggggttt caccatatta gccaggatgg  36720
tctcgatctc ctgacctcgt gatctgccca cctcggcctc ccaaattgct gggattacag  36780
gcatgagcca ctgcgcccag cctaaaattt tttttacata atgggtgttc agcacatgtt  36840
aaagccttct ctccatcctt cttccctttt gtttcatggg ttgactgatc tgtctctagt  36900
gctgtacttt taaagcttct acagctctga attcaaaatt atcttctcac tgggccccgg  36960
tgttatctca ttcttttttc tcctctgtaa gttgacatgt gatgtgggaa caaaggggat  37020
aaagtcatta ttttgtgcta aaatcgtaat tggagaggac ctcctgttag ctgggctttc  37080
ttctatttat tgtggtggtt actggagttc cttcttctag ttttaggata tatatatata  37140
ttttttttt ttctttccct gaagatataa taatatatat acttctgaag attgagattt  37200
ttaaattagt tgtattgaaa actagctaat cagcaattta aggctagctt gagacttatg  37260
tcttgaattt gtttttgtag gctccaaaac caaggaggga gtggtgcatg gtgtggcaac  37320
```

-continued

```
aggtaagctc cattgtgctt atatccaaag atgatattta aagtatctag tgattagtgt  37380
ggcccagtat tcaagattcc tatgaaattg taaaacaatc actgagcatt ctaagaacat  37440
atcagtctta ttgaaactga attctttata aagtattttt aaaaaggtaa atattgatta  37500
taaataaaaa atatacttgc caagaataat gagggctttg aattgataag ctatgtttaa  37560
tttatagtaa gtgggcattt aaatattctg accaaaaatg tattgacaaa ctgctgacaa  37620
aaataaaatg tgaatattgc cataatttta aaaaaagagt aaaatttctg ttgattacag  37680
taaaatattt tgaccttaaa ttatgttgat tacaatattc ctttgataat tcagagtgca  37740
tttcaggaaa cacccttgga cagtcagtaa attgtttatt gtatttatct ttgtattgtt  37800
atggtatagc tatttgtaca aatattattg tgcaattatt acatttctga ttatattatt  37860
catttggcct aaatttacca agaatttgaa caagtcaatt aggtttacaa tcaagaaata  37920
tcaaaaatga tgaaaaggat gataatcatc atcagatgtt gaggaagatg acgatgagag  37980
tgccagaaat agagaaatca aaggagaacc aaaatttaac aaattaaaag cccacagact  38040
tgctgtaatt aagttttctg ttgtaagtac tccacgtttc ctggcagatg tggtgaagca  38100
aaagatataa tcagaaatat aatttatatg atcggaaagc attaaacaca atagtgccta  38160
tacaaataaa atgttcctat cactgacttc taaaatggaa atgaggacaa tgatatggga  38220
atcttaatac agtgttgtgg ataggactaa aaacacagga gtcagatctt cttggttcaa  38280
cttcctgctt actccttacc agctgtgtgt tttttgcaag gttcttcacc tctatgtgat  38340
ttagcttcct catctataaa ataattcagt gaattaatgt acacaaaaca tctggaaaac  38400
aaaagcaaac aatatgtatt ttataagtgt tacttatagt tttatagtga actttcttgt  38460
gcaacatttt tacaactagt ggagaaaaat atttctttaa atgaatactt ttgatttaaa  38520
aatcagagtg taaaaataaa acagactcct ttgaaactag ttctgttaga agttaattgt  38580
gcacctttaa tgggctctgt tgcaatccaa cagagaagta gttaagtaag tggactatga  38640
tggcttctag ggacctccta taaatatgat attgtgaagc atgattataa taagaactag  38700
ataacagaca ggtggagact ccactatctg aagagggtca acctagatga atggtgttcc  38760
atttagtagt tgaggaagaa cccatgaggt ttagaaagca gacaagcatg tggcaagttc  38820
tggagtcagt ggtaaaaatt aaagaaccca actattactg tcacctaatg atctaatgga  38880
gactgtggag atgggctgca ttttttaat cttctccaga atgccaaaat gtaaacacat  38940
atctgtgtgt gtgtgtgtgt gtgtgtgtgt gtgtgagaga gagagagaga gagagagaga  39000
ctgaagtttg tacaattaga cattttataa aatgttttct gaaggacagt ggctcacaat  39060
cttaagtttc taacattgta caatgttggg agactttgta tactttattt tctctttagc  39120
atattaagga atctgagatg tcctacagta aagaaatttg cattacatag ttaaaatcag  39180
ggttattcaa actttttgat tattgaaacc tttcttcatt agttactagg gttgaatgaa  39240
actagtgttc cacagaaaac tatgggaaat gttgctaggc agtaaggaca tggtgatttc  39300
agcatgtgca atatttacag cgattgcacc catggaccac cctggcagta gtgaaataac  39360
caaaaatgct gtcataacta gtatggctat gagaaacaca ttgggataaa tcagctgcta  39420
tcataatcat tcctcttcca catcagataa atgaattaac tttttgaata gggttattta  39480
atataaagtg cttaagtcta attatgagaa gaaataagat aattacactt caatggttaa  39540
agagagggag aataatttgc atattatgcc tgatgtaaaa tgtttattat gggtacatat  39600
taagtgctaa ctaatcgtta attgttcttg ctacaagtct taatgcaggg aaacaagaaa  39660
ttattacata gtacctaata ttatcttcta atattaaaga aacaatttcc cctaaattca  39720
```

-continued

```
tcccattagc ttttttttt cggtggggca ggggagaaat acagacttca gtaaacttgg  39780
gccgggaact ttctacctac aaagttcaaa taaaataaat tatcctagtt agataatatc  39840
aatgaaaaat ccaccaactt aaatcctggc tgtttgatct caggaaatta tttcagttat  39900
caacttaatg catcatatta tagaaatata tgaaaatgtg tttaattaaa cttactgaat  39960
gatatgtttt ttaaggtact ttaaaaataa acctatgata taaagttact tatttttcat  40020
gcaagtatag tataaagaaa tttctaacac tggagatttt ctgaaggttt tgattcttat  40080
aaatttatta catcataatg aacaaaacta attttcaaca tattatgatt taaatttcct  40140
tagtaaattg ttttaaattt attttcttta aatccatatt tacatatgta tatttaaata  40200
tacatattta cttgtataac aattcaaaac catatattaa ttttataatt ttgtttaatg  40260
tcaaaggtta gatttggcta tatctattct aaaagttgct atcacatttc ctttttggaa  40320
ttttattttt aaagtagcta aagtcaaata taaacctatt atttatatta atgcagacat  40380
tagaggtaga cactaaattc gttttagtat attctaaatt atttattatc tactatgaaa  40440
taatataaag aaaaataaag cagaatccct gatttcaaag aactcagttg ccgaaaaaca  40500
gttaccattt attagaccca aaatgtacta atatgagtgt gtctcttttc cttttgtttt  40560
gtcacccgtc atttggaatg tcagtgagta gagagatagt gtgaaaggcc ctcaagggga  40620
aaaatagagg ttaaaggtca gcagagaccc tactagagaa atcagttcta cagaaatgtt  40680
tttaaatgtg tcgattattg ctacatgtac actctgtcat tttgtaatgt agccatttta  40740
tttatgatta taataataaa acaacaaaat tataataatg tgtagagtac attttactgt  40800
gcagtgtatt gcattaaaac tagattaaaa tttatacata tataaaaggt tatctagata  40860
ttataaaatt tatggctgga tctgtaaaaa attcaaaacc tatttttaat cttgctttga  40920
gattttataa caagaaaatg ttcgtttcaa gcaaaatttt caattcacgt ccttgaaaag  40980
gaaaaaaatg acaacttgaa acacataatt gactattttt aaaggatcaa catttcagaa  41040
atgttttaaa acataagatt ttcagtacag cttttcgctg gcatttaaat cgaactttga  41100
attgtaaata gctcttactc ttaaggagac atcagccata tccttagaag tggcacggag  41160
ttggtaggta gttgtacaaa attctagcct aaaagacaaa tagggagcaa cactactgtg  41220
gaccctttct ggtcttgggc tgtgtggcta tgtcaggctt gcccacattg cctgaactaa  41280
ggagaaagcc tcttgtcctt acagaccccc ttagcttaca tagtctattt gaaaacgaat  41340
tgctttgtcc acaccattta aatattggct tcaggccggg cacggtggct cacgcctgtt  41400
atcccagcac tttgggaggc tgaggcgggc agatcacgag gtcaggagat cgagaccatc  41460
ctggctaaca cggtgaaacc ctgtctctac taaaaatata aaaaaattag ccgggcgtgg  41520
tggcgcgcgc ctgtagtccc agctgctggg gaggctgagg caggagaatg gcctgaaccc  41580
gggagtcgga gtttgcagtg agccgacatc gtgccactgc actccatcca gcctgggtga  41640
cagagcaaga ctccgtctca aaataaataa ataaataaat aaataaataa ataagtaaat  41700
attggcttct tcaactggtg agatgaaaac tatacaatag tcatgtgaat agcactaaac  41760
agctgacatg gtgtaactcc tctcagactg aggcttatct ggggagtaca aagcatgtca  41820
agaaaatgtg ccttcatttc cttagatgag tgtccccatc ctccactctc ctccactgtt  41880
ctcctctctg cttctatgat atcaactttt tttttttct ttagattcca catgagtgag  41940
atcatgtggt tgtttgcctt tctgtttctg gcttatttaa ctgaacaaga aagtttttga  42000
catgaaatta aacttctgct tgtaaactca attcaaacta tttacactgt cttctcaaaa  42060
```

-continued

```
atgttaactt attttaataa atctactgaa tgaccgtatc tcattttgtt ttatgaaaag  42120
aaattgtaag ggtgctcaat agcctcttca ttttcatact gtctagctcc tgtgctccta  42180
ttaaaattac tgcaaattta gctttttaag aacccctttgt ttcactacct gaagttctat  42240
aaaaagatcc aagttccttc acaaccgttt cttatgctgt tattcgtaca tatgtgataa  42300
taccacgtct gaacacgtag ataataagta ggggctgggt gcggtggatc atgcctataa  42360
tcccagcact ttgggaggct aaggcaggtg gatcacctga ggttaggagt tcaagaccgg  42420
cctggccaac atgatgaaac cctgtttcta ctaaaaatac aaaaaataat aataataata  42480
attagccagg tgtggttgtg ggcacctgta atcccagcta ctcgggagac tgaagcagga  42540
gaatagcttg aactcaggag gcggaggttg ctgtgagctg agattgtgcc attgcattcc  42600
agcctgaaca acaagaatga aactccatct caaataaata aataaataga agtatgtatt  42660
gtgttgctta gaaggtgtgg tggaaattaa cttgctgagt gagatcaaag gattggcact  42720
gaattgaaat aaagaaatat tcatgctgag tctggttcaa atataactgc acctgtaaga  42780
attgctttct gtaaactttc catagtataa accaaatcca aatcactcat ggctttacat  42840
tcctgatcgt taaacttgaa gcacttttta atactgcatg actttagcca aaatatctta  42900
gccaagattc aatgtttggt tgaaccacac tcacttggac atcttggtgg cttttgtttc  42960
ttctgaccac tcagttatct atggcatgtg tagatacagg tgtatggaag ccgatggcta  43020
gtggaagtgg aatgatttta agtcactgtt attctaccac cctttaatct gttgttgctc  43080
tttatttgta ccagtggctg agaagaccaa agagcaagtg acaaatgttg gaggagcagt  43140
ggtgacgggt gtgacagcag tagcccagaa gacagtggag ggagcaggga gcattgcagc  43200
agccactggc tttgtcaaaa aggaccagtt gggcaaggta tggctgtgta cgttttgtgt  43260
tacatttata agctggtgag attacggttc attttcatgt gaggcctgga ggcaggagca  43320
agatacttac tgtggggaac ggctacctga ccctcccctt gtgaaaaagt gctaccttta  43380
tattggtctt gcttgtttca ggcattaacc cagataaatg ccatgcaaat tttataatta  43440
ttatgattgt ttcaatttct ggaagaaagt taatgaaaca aaaaatgtag taaaatgcca  43500
aaggaacagt gacatttcag aaagaatgag ggctttcatg ttaattgtaa gtcttggaat  43560
ttctcttcct tggagtaaca aatccctttg tgcctaattt cctaatttcc aaaataaagt  43620
tcttttactt atttctttat agtgacatca tctcttatta aatggcatat ctgcatatta  43680
cataacagtt cattgccaaa tacatatttg tgggaaatga gagacttaaa atacatacca  43740
accagagata tagttttgag gtagatttta aaattctgag aagaattttg actgaatttt  43800
tttgacaaac atgggacacg aataagatta taccaaagat attataactt tcattttaaa  43860
tatggaacta atacagtatg aggtgtcaac aacgttgaag tttcacaaac atcaccacaa  43920
cagcaaaata atttttgctt tttccctgcc acaatgacct ccttgctatt tcttgaataa  43980
atcaagcata cccttgccct gacacgttct tggggaggcc tgccctaatc tatataaaat  44040
tggagccatt cttctcacct ctggtattcc cagtctccct actttttttc cttctttctt  44100
tctttttctt tttctttctt tctttccttc tttctctctt ttctttcttt ctttactttc  44160
tttcctttct ttcttttccc ttccttcctt ccttcttccc ttccttcctt tctccctttc  44220
tttctttctc tttttttcttt cttgcttcct tccttccttc tttcctttttc tttcttttcc  44280
cttccttcct ccctctctcc ctcccttcct tcctcccttt ctttctttct cttttttctt  44340
tcttgcttcc ttccttcctt ctttcctttt ctttcttttt cctttctttg ccaaagtgtt  44400
attcaccttt aaatataata cataatgtgc ttactttaat gtatgatttt tattttattt  44460
```

-continued ctcccttcta gaatgtaggc accatgagag tgaaatatat ttattttgtt cattgatatt 44520
tcacaagtgt ctgggagagt ttccaactta cagtagacaa ttaacaaaca tttattaaat 44580
taaggaggga aggaagtgag taagcacaac aactttcatt tctgggtctt ttataatcat 44640
atgcttagta taagaacagt gctattcagc tatccaaaag ttacaatcaa aatgattttg 44700
gatgaatatc ttgaaaattg tgagaaagaa gttttatttg ctggcaaact attctgggtt 44760
gtttccactt catgtaatcc taagtagcag ccttaccttg atagcccatt aaaactctga 44820
taataaaaag gcagaacaaa aatatctgtg atatatttag atttactaca tgtacttaca 44880
tgtctagtgt ctggtgcaat ggatgctaat gatggcaaat ccttactggg cttctagtga 44940
agttcttcag ctaatgcttg aatgcatggt tggtcatggt ggtacccctt tgtacaaaat 45000
atgcttttca aataatctta ttagggataa taattatatt aattcctggt ttccatctaa 45060
aattttaatt ctatttatag cttcgtaaga tttcacaagt taagagggac ctcagattaa 45120
attagtacac aggcaattaa tcagttttgt gtctccgacc cttttcacgg gctaatagaa 45180
gctatagacc ctcttagctt cagaaaaatg tgcactcaca tacgcacatc aaagagctta 45240
atgggaagtc cattgacaga ccctctgttc agatcaatct tctgattgta gagatgagga 45300
aacagaaatc tacagaggaa gtgggtagtc caagattgca cagtcatttg gaatagactg 45360
gacaccagta gtacttttcc agccactata tcacttcccc aagcacttcc tcaaaactta 45420
ccttcctttg ggtctttata cattcagtta tggacaacta gatttaacta gaggatttta 45480
ttgcttcaga atattaagca acagggaaac atgtaccgtc ttttattcac ctgcatttaa 45540
ggcatacaat ataaattgca aatggagcat gaaagtgctt aatcttttac aaaactgggt 45600
ttgctttcca cccatctaaa aatacttcta tttattttaa tatttaaagc agaaatctaa 45660
gtgatgtgac aaaattaatc atttggagat atttccctta taggtagtat agtttcttac 45720
tgatttctaa tatgaaaatg aagccataga acctagaaat tgcagcatag ttgtggaaat 45780
aaacattgga ctgagagtga aaatggctag tcttcctctc tgctcataca ccacctgact 45840
ggataacctt ttgcagatct cctaaaagtc tttctcataa aatgaggaag ctctactaga 45900
aaattgttga agtctaattt agcaataaag ttctgagttt ctataataat tcaaagaata 45960
ctctaataaa tgtctgcaat tgtggtcaca tctatgggat gctaaaaaat ctggatggtt 46020
tcaatgaaag tatttaattt gttcattatg aactttgaaa taatttattt catttttaa 46080
actttgatca aaatgaccct ggtaaataga aataagcaaa ctctttttgc ttgaaatgct 46140
tattaatgac tgcattgaga cactcattca tcattcaaga aagaatgttt gctcacactg 46200
tgccagaaac ttggaggaag agggatgtga caagtagggg tactggatgt ctagcttgta 46260
gaagtggatt aatggctctg cttttaagat caggaacact gaaagggagt aatggcaccg 46320
gttttcacct ttcatgccct ttgagggtat ctggtccatc accctctagt tgatgaggga 46380
gggaaagttc cctctccctt cacaaatagg tggaaattaa atgacataat tctgaacaac 46440
caataaatcg agagtaaatc aaagcagata cctgttttgt taatttgatc atatgaatgt 46500
agctgccctt agtaataatt tctaagtata agactagtta aaggacaaat gagttatctt 46560
gaattataag attttgtttt acagaacaat attaactctt gtgtttagta cattagaata 46620
atagatattt tgatccatat ttttactcat gtgcacataa gaagttatca gtcatacaat 46680
tcatttcttg aagttcatac ctttcattgg cagagtagaa acaggttaaa agtgcactgg 46740
cagaaatttt aagtgcaaag caacagtgat gttatataga gaaaatttat atttcctact 46800

-continued

```
tctattgaag aagaaagatc tgcttgttct aagaatattg tacaaagaaa gtgacttgaa  46860
tcagcgttat tctgtaatgc tactatgcgt gcagtgtgga gtagccacta gaacacttgg  46920
tctatcccag ctcctcaaca gtgtcttgct tgtggctggt gctcaaataa atccttgctg  46980
aactaatgag catctctttc atgccacatg gaatgctcta aaagagttgg atcctgaagt  47040
ttttatattt ttgtaatttt ctggagtgtt agagagcaaa agtcctgaat aaactgtgaa  47100
gccactgcct gacaaataat acagcagtca gcttcgttat catatcccat tgagacacga  47160
cttatctaca tgatgattaa tagttttcac gcaagaaata agcttgaaat gtctgttgcc  47220
ttgggtactt aaaacatcca ggttcagcga tgttatttat tgttgttcaa aatcagaatg  47280
aagttcctaa gcaatgccat tttggaaaaa ttacatcaat atattatgaa caactttttt  47340
taaatcttga tttcaaatgg attgacacgt gtatattctg taataatcct gacttaattc  47400
ataaaaggat agctagccag ttgtgtgcta gatgaataaa aaaaaagcag gttttaaaat  47460
gtcaggtttg acatcgtgaa tataatatct aagtatcctt ttactcattt cctttgactt  47520
actatggctg tcatgttggg cttcatgaaa atttattttt aaacacttga gtgttatgga  47580
ccctctgatt aaatgattaa tcagatgatg tatgttgcca tcagctgaat catttaatgt  47640
tgatttcaca aacaagcaca ggtcacaggc aacatttcag atttctttga agaagcacac  47700
acaggtcaca ggcataatct taaaataatt ttataacaag gtagtaataa gagatgtcag  47760
gactggagaa atattttaat ttatagtaag ctttcccctt aagtgtctaa taattgttaa  47820
tataatacat tgcctcaaat aattaaaagt ttggttcttg tccttgtgct tgacttcaga  47880
agataaccag atgactatta ggtatattta gacctaaatt aaaagctttg agacacaatg  47940
aattgcctga tttgtatttg tgtttcgagt ggcatatact attactggca ctataatctt  48000
agattaaagc atactgtgat tattaaagaa aaatttaaga ttgatttgtt tctaaaggta  48060
tgtaacagtg acattttgca atgtggtatg taaaagttgg tatttctcac tcatatgaga  48120
gcccactaat ggtacataaa ctgtccccac ttagaaacac aattattatg gcctttcttt  48180
gtatctgaca aaatttcact gggttcaaga tggatgaata gtgaattcta atgaccctta  48240
atcctgtaag gttctaggtg ggaaagtact ctgtaattat gtataaaatt ataaggaaaa  48300
taggcttact gctatgtttt cattaaaaat cattaactga gtacttaata tgtgccagac  48360
actcagctgg gcaccatgag aaatacaaaa ctgagtaaca tatgggtggc tcctgccttc  48420
aagaaatggg cagttcaggc cgggagactg acatatttac cctgggaaaa agggagcagc  48480
tgtggtctct gagaacaata tggtttgtta caagtatata tccatcatgg aaaaaaagag  48540
atttatctta gaaatgagag aggctgatgc tctcaataaa tatcatacat taaattgtgt  48600
ttttgtcagt agactgaaat tacctcacat acacgcacag atagtagcca tgatatttta  48660
gctgcttaga tatagagaca aatacttcca cccaaatctt aggatcagtg gttaatagtc  48720
tgtaagcatt acaatcccac aacatatgca tgactataca tccaatttta atattcaaag  48780
aactgattgc gatgatagtt ttgtttgtca aagaaatgta ttataggatg agtgggatag  48840
aactgcatca cgttacacca acaaataggt ttaaatcata tttgtgcact tcccttgttc  48900
cttcataaat gtttaacata gcttaaaatt ctgtggactg caacgtgaga gcaatgacca  48960
cacttctgtg aacccatttt tactgtgcat gtgctaacgt ctattgttag tattccttca  49020
cttgcaaaga tggcatgata attttgctgg tttcattaat gagatactgt taaatgtagg  49080
atgacttcaa acttagttgt attgtaaaat tatttttaat tgtatacatt taagttgtac  49140
agcatgatgt tttgagatac ttatctttat ttatatatat atataatata cacacgtata  49200
```

-continued

```
taaaagtgat tcctacattg aagcaaatta acatacccat catcatatgg ttatctttgc  49260
tttttttacta tcagtgccta aaatctactt tcttgaaaaa ttaccagtat gcactacaat  49320
attattaaca ataatcttca tgttgtacat tagatcttta gacttactca tcttacatga  49380
cttaggtttg tttttacctc tactaccatc tgagccatat ttccactttg taatttgata  49440
ataaacttgg aaaaatagca cttatatgtt taggtgacgg gcataaatag gataagatgt  49500
gtttatatat tattccatat atcttgtctc caactacaat gataaacaac ctgtttgtcc  49560
ctaaaaagta agaaataact tgacttttct gccccttcaa gcataggctg ttagctttta  49620
agttttaggg agacattgat gatgctattt gctttatcaa gaggaaattg tcaaaagagg  49680
tcttttggtt ctcaaactat tcaaagtatt taaaaatcag gacaaaatat gtttacgtga  49740
tattcaaggg tacagaaatg aggtaaatga gatgccaatt gtatttgtca tgcaaatata  49800
taattatgtg tatgagagtt agatgataca tctcatcaat ttaattgttc ttctacaagg  49860
agaaaatgaa caatttgtca actcgtatat gaagtaattt ttataagaaa ttttattaaa  49920
acttttaaca acatttggat ttttaagttg caatttaaat atccccttct accaggtgat  49980
tctggaatca ctaagcagtt acctgtgaaa attccaaagt agcatttaat tcttattaat  50040
gtcatagtga acactaatgc aaagaatact gagccagaaa ttatgcttgt tgaataaata  50100
gattatttat tgaacaagta agtgaaaaaa tggaaataaa gaacagatat atattttatc  50160
ttcctgctta gatgtgggac tgtcctactt ttctctggtg ttcacaacaa caatatgata  50220
aatctaattg gaattcagtt cataggaatg aattcagtta cattatggat tgtgatgaat  50280
aatgtacact tttaatttaa tgaaatcaaa tagattttaa ctatctatgc ttacaatggg  50340
gtgacataag tctgacaatc cttaatatca agtcatctcc aattcacatg tatacacact  50400
tttttctat ttggctattg ggaatcctca caaaaatcga aaattgccct ttcagtgtac  50460
gttacggtat ttcatgccac acagattttc tgaggttgta catacagctt tgccttgagg  50520
ttccaatttt tgctcagtgg attgagtata tattatttgc tatatatcag aagaggcatg  50580
tgcttcctac ttatgtcacg taactttggg attaatgtaa ttgtcctaca aagcatagat  50640
agatagaaat acttcatcct taatttctaa tattatgaca tatctaaagt aggcaccttt  50700
aaaagataat ctccactaaa tacgaatgac tgcttatagt ggcaattcat ctttcatggt  50760
agtcctccta caaaggtata ctaacattta tgagtttgaa acaaaggcaa ttcacaagtg  50820
ttctgctaga gatggtctat atctgctgtt tgatccagca tgatggccag ctggccctcc  50880
tgtgcatgac ggctcgtggt ttaactgcac cattttgttt ggtcatatac agggaaaaca  50940
tggcatggtg tggagggcat gggcttgaat tcagggaaca gagagttggt cttctctctc  51000
tcactctact ggatgatgtc atctcccctc tctaagcatg agttttctta tctgtgaaat  51060
aaaaatgttg aattaaatga gttcaaaatg ctttcagtct gtgtttaata gcttgaatct  51120
taagacaatg tattcaatta tgcgttgcca gatccctggc aactcatgta acctttctaa  51180
accatagcta ctcatctgta actggccagc caactgccca gggttggagt gtgaatgaaa  51240
taagataatg cagacaaaag atttttaaaa attgtagtgc attatacagt tgtaatattt  51300
tgccaagaac ttacattttc tctaagaagt gtgtcgatac atgatcacag aaaatctttt  51360
ccatattcct ttgtagtttg atgatattaa gtaagtaaat tgtataacac aaagagggaa  51420
aagcatcact gaacatgccg ttttatttag ctaaataaaa tgtaatcact attagttttc  51480
ctctgatttc cccaaagtca tgtgattcca ttgagtatta tgcacatggt ataattagaa  51540
```

-continued

```
tggattctct gctcaaataa ttttgggaaa catttaaatt aacaaagttt aaaagtatct  51600
ctgttaagct gaagcaaatc tcaaaggcct taatattgta tgtaagagga atagttacca  51660
tctttcctaa tgcctctttg acgccaaacc catggagaat agttctaggt gttcagtaaa  51720
acacagattt gggatgccac aggttaattg gaactgtccc ctgcaatctt tttctctttt  51780
tcttaataat ggctgattgc aggtcctaga tgaaagacat ttagagagat tatcaggact  51840
cagcatccca tatcagaatc cattctttta tagtcatttt ctgttacatt tcttgggaca  51900
acaccaaaga aatgaccatc ttcattcaca taggctttgt accaaatgct gacaaagatc  51960
cttggtgacc tagatggggg caggtctaag tagattgcag ctgtaaaatt ggctgatgaa  52020
tgatctcagc cccttttact cacactcaaa ggcaggacag tccattaagg ggaaggaggg  52080
cagagttttt ccttaggcca attccctatg ccagaacttt ttagaatgga agcatttcca  52140
gaggagaaac aaccccaagc acagttcaaa gccccctcct cccaagttca tttgaaagtg  52200
ggatggttta tctgcaaagg gggaaaagat gagggatagg gacgggaata tccctaccct  52260
tcagagagtc tggtttcatc ctgcactttt actgcacagc cacaaatgcc ttggggtgaa  52320
tctacaatat gatacatcat atggtctaaa cgtgcctggc tgatcctctc taatacttca  52380
ggggtctaaa agggataaca tgctctcctg ttactcaccg actctgtccg ccatatttca  52440
cccagccagc cactgccttc acttccgtcc gaggcctaat ctgagcccat gggaaaccta  52500
agaaccccta ccacaactgc ctcaactctt gggaatcagg gtgtatgggg gtgacaggaa  52560
gtgagcatac attctccaac ttgatatgtc agccccccacg tctgtatgaa tgtttgctca  52620
cactgtgact gccggccttg ctcctcaggc tgcatcctac cagggagtaa gacccaagtc  52680
cttcctgctt tcagacaaca ccaagcctca tgagtcccca ctcagaggaa ggaccagaga  52740
caaactctaa tgttccacta atacttccct tcttattact ttccttgaaa atcccttctc  52800
cctctttctt tttatacttc gctaatgaaa ggtaatgaaa gggtctggca cttggaattt  52860
agaattgata catggttttt aacccgcgga cgtattccac aataaccctt gcatcttcta  52920
ctaagatgtg ggctaggaag ggaccagcca gttcccaggg tcacagtgcc tcagctgatg  52980
tttcatattt tcagcaactt tatgttagag atgtccatca atcagaacaa tatggttaga  53040
gaataaacta ataaaagtca cttttgagga catgttggaa gtctatcaaa agcattgaaa  53100
ttatgcatgc tctgaccagt cgcatgtcta agaatttaaa tatgatcata agtttaaata  53160
tgaagatgtt tatcacagaa ttgattataa aacaaaattg aaaaaaatag tgctagaagt  53220
ttgatcatag ggacctcatt aaatgcatta tggttgatcc atgcagtggt ttgctgaaca  53280
gccattaaaa tgttgtagaa taattattaa tggtgtggaa ggatgctatt gttgcagtat  53340
gtgaaaagaa caaattacaa agcagtttgt gcagcataat atttttattt tttaaaaacc  53400
tgtatgtggc ttatgtacat ataaagacgt ggaataaatg cacaaggtac tcagtttttc  53460
tcagtgaagc ccattttgca ttttgggctg ggtaattctt cgctgtggag aactctcatt  53520
cattgtagga tgtttacaag ccctgggcct tacctcttta acgccagtag gcaccccccag  53580
catggcaaca agcacaaaat ggtctctctc atattgccct tgaggaaatt ttgcaactaa  53640
gtaactatta ctgggtccta gattacagtc tggattattg cgttcctttc ttatttttat  53700
tttctccaat tccctttaat aagcatgtac tggattcata aaaaaacaac ataaatggta  53760
attacaatat tccgcactgg ttaaaactta tgtaaataag cattctgctg ctttagccac  53820
aattgcaatt tatgctcctt ctctttctta agttcccagt tcccacgtac attcattcga  53880
ctgattcaaa agtcatttta gcttgataga ctcttaaaag ttagagttat catttctgct  53940
```

-continued

```
atttattctt tcaattatcc atttgtccac ccatccatct gatccatttt gttgatgcat  54000
gctgtgtata aaatactaca ccagcctggt gcggtggctc acgcctgtaa ttccaggact  54060
ttgggaggcc aaggcgggtg gatcacctga agtcaggtgt ttgagaccag cctggccaac  54120
gtggaaaaac cctgtctcta ctaaaaatac aaaaattagc caggcatggt ggcagacgac  54180
tctaatccca gctacttagg aggctgaacc aggagaatcg ctcgaaccca ggagatggag  54240
tttgcagtga gctgagatca tgccaataca ctccagcctg ggtgacagag caagactccg  54300
tctcaaaaac aaacaaaaaa aatacaatgc caagcatcat aaaaaatata gtgatatata  54360
agacctattt gttgtgctct aggcattgac atctagctgt caaccattaa tatgtgtagg  54420
agtctatcta tcaatattat ggactgtgct tgaagacttc ttccccaatc tttttctctt  54480
cccattaagt ttgaagtgag gttttctgag tgaagtatca tagtacatac agtctcatta  54540
tttttcaaaa atctctggtt atagtacatt tctttccttt atccccttg ttcccaacta  54600
tcaaaccatt ttggatatcc agtattggta tccagtatta ttaaaaagca aaacagagaa  54660
ctattaacaa aaaaatttgt aggagtaatt ggttgtatgg tatccagtac tattagatag  54720
taaatcagaa aattattaac aaaaatttta gacgaataat ggattgtctt gcccaagtga  54780
attgagtgat ttagttgttc tttcattttt agcaagtaca gctgatcatt tgaggcctta  54840
ctcattgttt gattttgcaa attcttacta ttataaatgt tttgggctct gagaaagctg  54900
ttgtcttaat ctgtttgtgc tgttataaca aaatacatga gactgggtaa tttacaaaca  54960
acagaaattt atttctcata gctctggagg ctgggaactc caagatcaag gcatttgtct  55020
tcaggttcag tatctggcga gggccggttc tctactccca agatggtgtc ttgtcactgt  55080
atcctccaga gggccaaatg ctgtgttctc acatggtaga gagatagaaa gggccaactc  55140
actccctcaa ggcctttcat aatgttacca attccacttg tcagggctct gcccccgtga  55200
ctttattacc tctgcaaggc cccaccactt aatactatca cgttggttat tacgatttat  55260
cacatgaatt tcgaccatac tagttgccat cctttcattt tcatatatcc ttaaaacttt  55320
gcctttctca ttttaatgta ctttatccac agtatgccaa cttttcgata cttttgttaa  55380
cctgtctgac gatatatagg aaactgtaaa agtgcagttt ttgatacact ctttagctgc  55440
ccgtttactt ctactgtcgt tagagaaccc catccatagt gcatgtgttt attttgtgta  55500
tgaacaaaga ctttatatat agtttgggtc atttttattc attagtgctt cccttataat  55560
ctctgaatac cattttatta gtacatactg ctattcttaa tagtaactag catgcctgat  55620
catcccaaat gtctaggttc acattttaaa ataagttata tctttgggct taacagttta  55680
ttgaaaggta acaaggattg agtcatagtt gtatgttttt ggaagtagaa ttcaactgta  55740
aatagaaatt ggttgtttag atctcactat atatgaaaaa atgaaggctt taggagaaaa  55800
tctccccaaa gtacccattt ttcatgtgat aaatatcatg aaatgatttg agaaaaaaat  55860
gtatatttgt tacagctaac aaatatttgt gttttttatt cttcatggag agaatgaaat  55920
ttcttctctt ctttacacat ttctttttct tattagaaac taattggtgc ctttataaaa  55980
attaactgca gagcactaac gtgtatatat aagtattatg tagggtgtag ggtatgttca  56040
gggtatggtg tgtgtgtgtg tgtgtgtgtg tgtgtgtgtg tgtagctgtg tgtgtatata  56100
atgaaatata tggtagtgtt gtttcagaaa tctgcttggt cttcccagag ttcattcatc  56160
ttataaattc atctacattg atctctattt ttggaatcca tgaaatgttt tttggcagta  56220
cttcctttaa tatagtgtgc tggaaatctg gaaatttcta gccagattag ttacaaaaaa  56280
```

-continued

```
ttagccagtg gttttgcact ctctatagaa tcaaggccca aggcctactc ttgttactca  56340
gggccttgtt ttatctggcc tctttctttt cagccatata gctctcaaat actcaacaaa  56400
attcttcatt ctaggtagac aagtatcttc aaaatacttc ccaattatct aataactgtc  56460
ttaccactaa gaaggctttt atgtctcctg tctgaatttt atccatgcaa aaaagtccag  56520
cccaagcctc cagaactcca aaaagttatc cctaactgct gaaacacagt aatttcacta  56580
tgtgaaattt cactttggtc tcctagcatt tgcagatata ccatacatat ccttgatcct  56640
tttcctttca tacctttttat atctaaccct taagctaata attttaccta cactgtaatt  56700
caaaatgtat ccccagtctt accatgtctc ccttctctac tgttaccacc ctaggctagg  56760
ccttcatcat ttctcacctg gactccttcc ctaacctctg aactgatctg cctgcttcca  56820
cttagacacc caacctagtc cattcttgag cagtcggaat aattctttta agaaagaaac  56880
cagatcacat ccccctctgc tcccaaccat ccagtgacct cttatcatac atagaatgaa  56940
atgcaaatct ttactgtgtt ttaaaggccc tacattatct ggccctcagt aacttcttac  57000
ttcctatccc ttttctcctt gtatgccacc ctccaactac actctaacta cactgtcttt  57060
ttccctgttc ttcagacctg ccaaccatat tttcactgct caattaatat gtagaaaatg  57120
aattgttcgt taaatgtaga ctgtttcctt cttaaagcaa agataaatga cattgtcttc  57180
aaaaacaact aactgcccag aattcctgat tttaatttta aaaagacaaa ctgcaagaat  57240
gtgttaaaca gtaaggaaac aattcactac ttcagaattc tatatgattt cactgcacgt  57300
tagtaatttt gtatattata gaatatgagg gtattctaat aaacttaact ctatgctgta  57360
tacttatcat gatagctcat tttcttatat gtttataaca gcactactta ttgtacatgg  57420
atacgtggga aataaattaa ttttctcctt aagaacaaag caaccatttc actcatgaga  57480
taaatcttga agatttaaaa actacttata attaattata cattattcat ataatgttaa  57540
gtattttctt agtaaaccac ataatttaga atggcaattg gacagatggg cagaaccaca  57600
tgcatccact attaggcagt tggtgagcat aagatgccag aaagaagatt aggaatatca  57660
aggcagggag cttccgatcg ctcttgaaaa cattgaccct tcactcctca ctctccacga  57720
tgcatttcct ttgaaaagta atgccttcca aaacaaagtt ctctgtttta tatctaaact  57780
tactcaatag tttctcatgg ttattgatat ataaaaaata aagtaaaatg tttaggcaga  57840
ccaaaagaag aatttccccc tccctctgcc ttttatgcca aggtgacagc tatgaaatgt  57900
acagtacgtt tcctctgcaa ggaatgtagc agtgttccat tgcaagaaga tgagagggag  57960
agaaaggttg cacgctgagg aatatagtgt catttgtcac tgcctagact catcagctgt  58020
gtggaactct gagaggcacc aggcttcttt atttatttct tcagaaactt cagcaaaaaa  58080
gatttcatta ggagcagaga aaaatgtgaa aaacgaatta gcttttgtga tggggagtag  58140
tcatctctga atattgatca agattaagag ggttgtcttc gtaacttctt ttatccatag  58200
tctatactga tttaactaga aaactaattt caggtggtat ttcgggtgtg gcagatcttt  58260
atagtaaatg aagaatctag tcaaatctac tgaaaaactc tgcttacttt aatgtttgat  58320
ctggttgaaa ccattttagc ttaacaatcc ttcctctgaa acagggaatc aattgatatc  58380
ctacagcaaa attatgtgga agggccatta gcttcacatc caatgcaaat tttgcctgtg  58440
tttactcttc cccaatccaa aatatatcag atcctagatg ccagtgaaat cgtttgagct  58500
agatggcttg agggtcatag ctttttttcat ttcctgttct cagacctctt ataattgata  58560
gaataaaatc agaagagccc tagagctgtc ccacctattc tgcctcacaa aagtagaagt  58620
aatggcaacc actatcatag ggatcatgct cacctttttc ttaccagaca aatttggata  58680
```

-continued

```
ttagcttgaa attaatacct tccttaaaat gttggaattt ggttatatgc gaaattttgc  58740
tctatttatt cattatattt tgtatggaat tatttttgcc ctatattttc acttaagtgt  58800
tctctaccca agattttaat tgaacccaaa tcagccagac acacagacat ggattttgct  58860
gccaccaagg ttaattcttc ttttaaagtt aacttttaaa atttggtaaa atatagcttt  58920
gaaaatttgc attcgtctag tgtttgttat gtatttcccc cttttgtttg attatatgtc  58980
tatattttc ttgtagaaat tgatttttaa cctgcttttt atgttagctt ttatgagctt  59040
ctgtctgaat tctgaatatg tctttcttaa tgtcttctaa atgtttcttt ctggattatt  59100
aaaagattta ttaggctttt aataattata tttgttacct tagggaatgt gtttgaaaat  59160
attttaaatg gaattgccag ttaacacagc attgaacttt ttcttgttag agatacattg  59220
ttttctaggc attttattgg gagagaagtt agtatgatat aatgtctttg gctgatatta  59280
actcttctaa gatgcattgt ttctgagaac accattgtct gatttcattc agggaaattt  59340
cacacaagcc agtagagtca atactttttt caagacctgt taattgatat atataaaaac  59400
ttgccattgt ttacatgccc atttcagatc ctttatgtga cctaagctag aaatgcattt  59460
taacagcatt tgtttttcca aaaatattta tttatttatt tattatagag acagcgtctc  59520
tctatgttgc ccaggctggc ctcgaactcc tgggctcaag caattctcct gcctcggcct  59580
cccaacagtg ctgggataca ggtgtgagcc attgtgccag gcccttgttt ttattttttt  59640
taaacattgt attttgaaag gggtttgaag gtgatcccta gatagcaacc agtaatgatt  59700
cgagcagcaa aacaatctaa aaagtaattt tataagaaaa tgcagaacat aaatgagccc  59760
ataaaaaatt atattaggtt ctatttacat tactaccttc tttcacatgt aatatttcac  59820
taacatttaa tgaatttctg tgcagtgcca tataccatta tgaattctag gatagaagaa  59880
tgagtgagaa atgttcttag gccttaggaa gaaggaacaa gcatctctgt gtaatagtta  59940
tttcaactct tcttttacac ctcattccca tattaaatct cagaaaagct aaagtaatag  60000
ctatcccaga tctattttag actccagaca cttacttcaa tgtcttgttc tccttatcag  60060
actggaatca ttccaaacct cttaacttct gggcaaccat gataatgcga cagaaaggac  60120
actaaatctg tcgcaaattt atcttgatat tctatccagt cttacttggt actgaaggtc  60180
acaagtaaaa taaggtggtt gttttttgtt tgtttttttt ttttttttga cagaagagaa  60240
aagaacactg tgagcacaga gtgaatgtct aacattgatt cttgagtagc aggaattctc  60300
tatgcgagag gatctctatg caaaaagatc tcatattcta gcacaattta aggatctcta  60360
tgcaaagata tcccatattt tagcattatc aataagctat ggggtaatat attgtatgtg  60420
gtgtggcttg aattctagaa atttgatttc tagaaatggt ccctgtagtt aaggatatat  60480
aatgtggccg tctccagttt tctatgagga ataggaaaat actatcatta ttagctgtgt  60540
gaccatggac aacttgcttc gttcttcagt tgcatcatct gtataaaata agaataagaa  60600
aatttacatc tgcaaggtgt gatggagatc acatgggata attgtggtcc cagagcctgg  60660
cacaaaaggg cttaatattt ataatcctcc ccatttctcc gtatactcta aaggaagttt  60720
attgcttatc aaattgtgcc gtggttagtt gtacagcttc cctgccaaat tgtaaactcc  60780
aacactaatg tgacgttaca ttttatatag tgctatgatt ttcaaattgt ttgcataatt  60840
tcaaatacac agtaaattgc tttttattag tataattatt gctattgtca atattattat  60900
tacaacagct tcacagtaag atgggcagaa aaaaatttaa tttccatttt acaaatgcac  60960
ttttgaggct cacagaagtc aaatagacca aagtcacagg gctagtgagg gacccagaag  61020
```

-continued

```
aaacaaattg taattcactg attccaagtt cagtggttgc cttactgcat cataaaggct  61080
attacacaat ccaggtgtat catatgattc ttgtctatat attcatacat atcagaaaaa  61140
gtgttctact caaaattgct agcaatcaac agatactgat agtcattagt acttaaatct  61200
ttatcaaatg aaatattaat acccatgaaa gagaggacaa tgaaaggttt gtatcatttg  61260
tatgtcacaa gtcaactttt ttcaatcact cattattagt ttaactgtaa aaaattattt  61320
acatttagcg tgaaactttc ctgtattctc aacatatttc cttcggtaga aaagcaaacc  61380
tccagttctc tgttctttgc ttggatactt gccagtttgt aactcagcta tcaaacagta  61440
aagctcacaa aacacttatt aaaatgacta aaatccaaaa caccaagagc acagcatgct  61500
ggtgagatgt ggagcaacaa gaactttcat tcattcacta atgctggcaa tacaaaatgg  61560
tacagtaact ttggaagata ggttgacaat ttcttacgaa gctaaactat acttaacata  61620
tatatttgtc cattttcaca gtgctaaaaa gaagttcccg agactgggaa atttataaag  61680
gaaagaggtt tatttaattg actcacagct cagcatggct gaggaggcct cagaaagctt  61740
ataatcatgg tggaaggaga aggggaagca aggcacctac ttcacaaggt gacaggaagg  61800
agaatgaatg caggaggaac taccaaacac ataaaaccat tagctctcgt gagaactcac  61860
tcgttatcat gagaacagca tgggggaaac agctctcatg atctagttac ctccacctgg  61920
tctctccctt gacatgtggg gattatgggg attataattc aagatgagat ttgggtgggg  61980
acacaaagcc taaccatatc accatatgat ccaaaatcat gctacatgat attcacccaa  62040
aggaaatgta aactgtgtcc acaccaaaac ctgcacatgc acgtttatag cagctttatt  62100
cataattgcc aaaacttgga agcaaccaag atgttcctca ataggtgaat gaacaaaaag  62160
actggcacat gtactcaatg gaatattatt cagtgataaa aagaaatgag ctatcaagcc  62220
acaaaaacac atggagaaaa cttaggtacg taagccagtt tgaaaggttg cattctatat  62280
gattccaata tatgacattc tgaaagagac aaaattctgg agacagtaaa aagatcagtg  62340
attgcctggg gctctgagaa agtgcagagg gatgaatggg tgaagcacat ggcatgttta  62400
ggacagtgaa actattctct atgatactgt catggtggat acatgacctt ataccttttgt  62460
taaaactcag aattttacaa tacagagtga attctaatat aaactatgga ctttagttgt  62520
aataaggtat caatgttatt tcataagttt taataatgta ccacactaat gcaaaattat  62580
aataataggg gaattggggg aagggtaatg gagtatatgg gaatgcactg taatctcagt  62640
acaattattc cacaaaccta aaacttcttt caaaaataca agctattggt caggtgtgat  62700
ggcttatacc agtaatctca gcactttggg aagtcaagac cctcagatca cttgaggcca  62760
ggagttcgag accagcctgg ccaacatggt gaaatcctgt ctctactaaa aatacaaaaa  62820
aaaaaaaaga aagaaagaaa agaaagaaag aacagaagaa atgaaagaaa ggaaagaaag  62880
aaagaagaaa agaaagaaag agaaagagag aaagaaagaa ggaaagaaag aaacagaaag  62940
agagaaagaa agaaagaaaa agaaagaaag aaagaaagaa agaaaagaaa gatgcggttg  63000
ctcatgcttg taatcacaac tactcgggag actgaggcat gagaatcgcc tgaactcaga  63060
aggtggaggt tgcagtaggg tgagattacg ccactgcact ccagcctggg tgacagagca  63120
aggctctgtc tcaaaaaaaa aaaaaaaaag ctattaaaaa tatgtaaagc tcagtctaga  63180
tacagtacca gaatagtagg aactttattt cacctgtcct acaaattatg gttgtgtgcc  63240
acttgggtaa aactcagaat ccaaatatgt gaatgtaaga tttatgggga aattatttgt  63300
atttcaaaat aatccttaat gaatgcactc cttctaaagt agccattaat aaagcagtta  63360
atgtttcatt taattataga ttaatgtaca taagatatgc caggaatgca attaggaact  63420
```

-continued gggaaggggg tgttattcta ataacttcca catagcattg tgagacattt tctgctttct 63480
tcaaatttca tttaattaca ttttaaacaa atatttttgt gagcctatta tatagtcctt 63540
cgctagcact gaggagacat gctttgtgac cttggtgatt tcacattcaa atttcccttt 63600
cacctacact cttccttgtt ttttcatgcc tgtgtagatt gtaaattctt cctcagatta 63660
agacatttta ttcacctttg taacatccac agtatctagc acaatcagtg ccttcaaaaa 63720
caattggcct caagaattga ttgactcaat gagtgactga aagactaaat taataagtac 63780
acatctattt gtacttccct gcttacttat aaggtatgac aatgaaatac tgagacagtt 63840
atacattact tacggactca atctcatttc tttacaatct ctattcttct tttttgagta 63900
taatgttatt ttacaattcc actaacttgt cactctttat tataaattca tatctccatt 63960
tcacctgaga ataataaagg caaggaagta ttttaaatga tcttgttttt tataactagc 64020
attcattgag caaatcaaag tatgaaaata atataggtgt cagtgattat tataaagttg 64080
tatgcacaaa acattccaat gattggggcc aatacagaga aaacatctca atatttggaa 64140
ttttgctttt ctgtaaatac tttgatatgt acttacatca tatcaattat aactcctgct 64200
gaaaacaaac agtgcacaca aatttggtag ttggaggaga ctttataaag ggactaatta 64260
cgaaggttta gaccgggtta ggaaaaacac atggaatagt gcaatacttt aggatggcaa 64320
cagcgagcac cgttataacc actaggccaa aatgaactaa atgaacaggg agattaccat 64380
ttatcagaaa aagagggaga aaggaaggag agatgaccaa gcaagtccta tgtgaagacg 64440
gctgcctgac ttgagctgtg tgatctttgg actgatacca cctgcctgca ctggcctagc 64500
agggcgagaa tagtcaatat ctggaaaatg gatcacctga ccttactttc ctccctccct 64560
gtttcctctt tgtggtgttt ccactggcca aactcacagc gtagacaaaa ggagtgcatt 64620
gatgtagcag tggttctaat ccagggccaa ttgtgctccc agggaacatt agtggttatc 64680
acagctcagg ggaggaaggg agaggagtgg agtgctacta tgattcactg agggattttt 64740
ttaaacatct acaatgcaca ggacatcctt ccacaacaaa gtatccagtt aaaaaatgtc 64800
attactgcca aggttgaaaa accgtggtgt agtcagtaca attcatcttc tccaggcaca 64860
gtgcaggagt ggggtggagt gtctgaaggg gaagaaggaa gaaaccagca caccccacaa 64920
aagtaaccaa tgcaaatacc aaataggaaa agacagcact taaaatacaa aagtctcagg 64980
aatatatctg atagtgtttt atggaattta ttaaaattta gcctggagtg agtaatattt 65040
agcaagccag gtttgtcttt agagaaatcc ttgtggggtt tatacaacga tttattaaca 65100
aagggcacac acaatactca tattacagtc agtctggtta tgtaaaacat gggcaagaat 65160
gtaacaggac aatgtgatgt attcacaaag gattttagga ctacacagat aatcctctaa 65220
tgctttcact tacgtactat gaaaggctat agtttgcata gtgatatagc cacgtaagat 65280
agtaaacttg acattcatgc agctatacat gtttgcacac accaggatgc atgccctttc 65340
tacctggttg atttttttatt cttttattaa tctctaattt attccccaga acactctcca 65400
taaaaacttt ctcacaactt aaatctttaa tctattgtgt ggatttctga ctcattctcc 65460
aagcttttcc tcttccctcc gcaatgcctt atagtcttat gactatttat ccctttgcct 65520
acatttctag ccagatctct tgcctgatac acactctcat atttctcttt gcacgctaca 65580
catttttatt tagatatcac actactactt tgatttcaac aggtctcagt ttaacttaat 65640
ttttccttca agcaaggagt cccttcatat cagttatcac cattggcacc agaatttttc 65700
ttatgacttc ccatgaccta caatataaac catataaatc actgatgcct ccatagttcc 65760

-continued

```
ctccctctca aatttagcca taagatgatt ttaggatcct tgttttttcc aatctctctt  65820
tcattctctc ccccatctct tccattatga aggtttggat aggacacaac tcatgcctag  65880
attagtgcaa tagatgctga gcctgtgcag cggtagttta gctttctctc ctggttaact  65940
ttaactgcca catatatcac ttcacacgtc atttttcatt caaacgtatt taactggctc  66000
ttcattcata agaagctgga atttgtcgtt tgactgatat tttaaagatt ttatattttt  66060
tctccatcct cgttctaatg ttgtatcttg tgtcatttgt tcattcataa acttaagact  66120
tagctaacca ctgagcatcc aggaaattca gtatctatca tgtgaattct ctaatactgg  66180
ttgatccatt gtcaccagag catagcaggc ttctcctgcc tttatgtatg tttgtcatat  66240
agttcatgcc taaaattctt tcttaaatct taaattccta agatacacac ttttgcccaa  66300
gatcacagta atctctgcca taatctctgc tggaatctgt tcactgtgtt gctcctgctg  66360
aacttcttac agatgacttt ttttcttttt ggtttccctg gtatctagta taatttctta  66420
tataggtact caataaatgt ttcctgttga tctctacacc tactctgtac aataccatag  66480
tgactagaca catgttgcta tcaagcattt caaaagtagc tagcctgagt tgagatatag  66540
gggtaaaata cacaacagat ttcaagacat attatgaaaa aaacccataa aatttctcag  66600
taattttttt atagattaca tgtagaaact ataacatttt gaataagttg tatcaaataa  66660
aatataaaat tcacccggtt ctttttaatt tgttaaatgt ggtggctaga aaatttaaaa  66720
ttacataatt ggctcacaga ataattataa tggatggtat tgctttagat caagtttgtc  66780
taacccgtgg cccatgggcc acaagcggcc caggatggtt ttgaatgaga tccaacacaa  66840
atgtgtgaac ttccttaaaa cattatgaat tttttgtttg ttttgttttt gttttttttct  66900
catcagctat catgagtgtt agtgtatttt atgcatggct caagacaatt aattcttctt  66960
caaatatggc ccagggaagc caaaagactg gacaaccctg ctttagatag taaagcatat  67020
gagtagttaa tgtgtactat aagcagtgtg atctgataga ctatttaatg ttgtttgatg  67080
gtacattatt caagtcgatt attatgtcta cctatgcagt ttaacgacgg taatgagaga  67140
gggcagcttg attacaggtc ttatcttttg actaacttgc taggccacct gagaaggacc  67200
caaattatct gaatgcttaa ctcaactaat ttgtattcac ttgaagaatt tcaaggatgt  67260
ttatatgcca tcaacttgct ttaaattttt tctctcagtg aaaatttttc ttaaaatgag  67320
tatgtggtat tcaaatttat ccttgttttc tatgattatc ttttcatagc actgtggttt  67380
ccaggaacct tttttttttt gagatgcatt ctacatgtaa ctattgcaca gtttgcatgt  67440
agtaaggttc attattcttc tacttttcca aacacctggc atgtttactt gaggttggta  67500
caccttgtat cccagatttt gctgttttta acctaaatat tgaatatttt gattaaacat  67560
tatggaaagt ttaaatgggt caagaaaaat agcttttctt cccatgaaga acaatacggc  67620
ataggagtta agagcataga tttaaagtca gaaaacctgt gctgcctact tgtgcaaagt  67680
cacttacatg ctgtacttct gtttcttcat ctgtaagttc taccccctagg tatttactta  67740
agattaatgg aagcatatgt tcatacaatg acttgtacag aattattcac gatagcatta  67800
ctcttaatag ctctaactgg taacaacaca ataatcaatc aacaattgtg ctgtattcat  67860
acagcagaat actacttagc aacaaaaatg gaatggacta ctgataacct caacaacatg  67920
gatgaatctc aaaactatca tgctgtgtga tgccaggcac aaatcagtac atactataat  67980
tccagaaaag acaaatgtca tccatagtaa caacaagatc catgcttgct ggaggtagag  68040
gcatcagttc agtcattcag gaagctgatt ccaagatggt gttagaatta caaccatcca  68100
caagagattt attgcaggca atagctatga aaggtagaaa gagaacagga gaaaaaccag  68160
```

-continued

```
gcaaggaaaa accacaatgt agttgtgata tcacttcaaa gggaggcaga aggaaggaga  68220
attgggtagg aatagccaca gattacagtg cagttacaag aaagtcttgg cttccaacaa  68280
aggttacttg ttgaggagtc atgcattagg cagacatgtc tgggctgtag tttccttgct  68340
gctcccagtc attggctgga ggccagtctg ggttcctgtg ctgtggtgga tcccattgct  68400
gctgcagcag gaggccaata gcactcctgg cagctaattg gagagaaaag atccaagagg  68460
tgtaccttca tggctacccc catggggctg gggtggaggt ggaggagaag gagaaggaat  68520
taactagaaa aaggcacaaa ggaaaattgg ggaaaataat gaagatatat gatttctcaa  68580
ttgtggtggt cgttacatgg gtttattaat gcatcaaaac tcaagaaatg tacatttaaa  68640
atgagtgcat atgattgtaa gtgaattata cctcaatata gttaattttt taaaaatcat  68700
agatttcttt atatttaatg catgaacata aacctaagac actcctccac tccaaaactt  68760
aattaccttg tgatcagcag agcagaaggt actttgtgat atataggtag agaagatgaa  68820
gtcttgtgac atttaacaag ggacaggaaa atggaccttg tcctaagtta ccaaactgca  68880
aaaatatcac ctacaaaggc tattcataac atacattttc aaggggggtta caatatttgc  68940
ctactataaa attttggatc tgtaaagggg ttaaattatt tgtgcagggg aataaacatc  69000
aaagaaacat taagaggtcc agagaagtaa aataggaagg gtcttttggc tagaggagat  69060
atttaacttt cagaacatgt ggaattaagt tgtattgatt atgatctgat cttcttcccc  69120
ctaaatttga tcctcttcct gtaatctatt gtttccatca tcttcaactc ttccctttcc  69180
ctctcccttg tccctcagtt ctagtcaatc acaaagtcct acagtttcac tttctgtata  69240
ccttatttct ggaattcatc tctagacttc aaaatatata tatatatatt tttttttgag  69300
atggagtctc gctctgttgc ccaggctgga gtgccgtggt gcaatctcag ctcacagcag  69360
cctctgccac ccaggttcaa gcgattctcc tagttcagcc tcctgagtag ctgggattac  69420
aggcatctgc caccacgcct ggttaatttt tgtattttca gtagagatgg ggtttcgcca  69480
tgttggccag gctgatctcg aactcctgac ctcaggtgat ccacccgcgt cagcctccca  69540
aagtgctgga attacaggtg tgagccactg cttccagccc aaaatatctt aagtagataa  69600
ttgcacgact aatctctgct tttctctccc agcagccttc caaattcatg tctcacagct  69660
gacagagttg ttcctgcctt cagattcatg acctggctct gtgttccagc tcaggctttc  69720
tctctcatat cacctcttgc ctctctgttg cccccatatt ttcccctctg gttggttggt  69780
gctcctttgg aaccctctgc atatcttttc aagaatatta tgacttatta tgcctataaa  69840
ctttgtttaa ttatttattt ctaaaatttg acagggaact ttccgaaggc aggtattgtg  69900
tctttctcat ttaaaagcaa attctcgcct ggcatggtgg ctcatgcctg taatcccaca  69960
ctttgggagg ctaaggtgga cagatcactt gagcctagga gttcatgacc agcctgggca  70020
acacagttag accaaaaaaa aaatatatac gaaaattagc ctggcatggt ggcacacccc  70080
cgtagtctca gctagtctgg tagctgaggt gagaggatca cttgagcctg gatggttgag  70140
gttgcagtga gctgtgattg tatcactgca ctccagcctg ggcaaaaaag taagatcctg  70200
tctcaaaaaa aaaaaaaaaa aaaattagtg aatcctcagt gtttaaaaag tccataaaca  70260
tactaaacat agaagacctc caaatgaaat taatcaatta ttatttagtg ggttgcttct  70320
cttttgtttt aatatagttt taacaaagag taaaagttat gatcttttta tatgtaaaat  70380
aaataatgcc gggtttgaca taaattttag gaaaactaga gacgctactt cctaaaaatt  70440
ttctttctat aatcttccta aatatttttc cataaagtac aaaataatag aaaaaaatta  70500
```

-continued

```
agagattgag tatcctttca ggaagtgata tgacaaatag ggttcgagaa ctatttgaat  70560
tctcaccact tttcataagg gcagatctca agttaaattt ttctattcga atttaaatga  70620
ctttcactgg aataccatta cagaaaagct tctgtgttta gatggcaata tggagtttct  70680
tttcttggaa tattaattga aggagaagtc ttaatttttt aagtctatat ctccgtatat  70740
atttgaacct attttatatg ttagtccttc tctttagtaa ccttcatcca cagtgaacaa  70800
gatttaccct tacctttaag cagtagcggc tactttatgt gaagtgaaca gctgcttttt  70860
ttatctgcat ctagacatca agtagtccag agtcctttct aacaccctag caatagaagt  70920
aagaatattt tgaccattcc atgacttgat gatacttcta gtaataatac tgtattatta  70980
aaaacaaaca aacctttgtg cagtggtaat tgaagcagtt ccttgggaac atgtattaag  71040
tactttttag cagttaagtc cactctctgt aggttaagga atatttaaat aaaataatgt  71100
ggcaaatgag ttcaagatga taaatgcgat gagaactaaa acagctttaa ttttatgtgg  71160
gaaataaata gaggaaaagt acattacagg gctcctggac ttatttcttt cttcaaagtg  71220
tttctcctag cgaatattat tactattttt tctcttaagt aaaaaataca caaagtatga  71280
atctacacag gataataata ttgaagttaa ggatgatgtc tcctccttca ctctccaaaa  71340
tactatttac ttggcttcat ggaaatctct ctcactccaa ttccaccgtg tcaactgagg  71400
tcttctgttc tttctctccc tatagcatat tcctgttaca taaatcctaa actgtgtcgt  71460
gttagtcaca cactgtaacc tctagataag cgcctgtcca gaggttctca atcagagcct  71520
tgcaaatatg tattaaatca atgggtcatc ttcagtgtct cagtgggccc ttggatatgt  71580
tttgcagact gctgtgagta tgtagggatg tccagtatcg agggaagtgt ggatggcttt  71640
cattggttct tatagggctg aagaacacat agagcagtaa gcacttctac tgtagggaga  71700
gatcgagctt ctcccatccc cactgctggc accaccacca ccctacaccc catttgagt  71760
tctgaaagtg aatccttgag aaagaacaca caaaacaacc atcataatag tgggcacagc  71820
tgtgggtggt agaataacat tcccaagctt cttttcctac acatgattaa tattaattca  71880
gcaaacattt attcagctcc tacttttaaa caggcactat tctaggtact aaagacatag  71940
aggcaaagca tacaagactc tgcctttgtg aaacaattaa gaaataagta aaaagaaaag  72000
aaacagaaaa ggcaatttgg atagtgtcag gtgctataaa gaaaacaaaa tgccatttta  72060
ataaataata ataatacaat gttttcatac tatgtgctag acactatgct agtaggtatt  72120
tatagacata acctcaatta atcctcaaaa tggcatgttg atatcaatac cccaagttta  72180
catatgagac ttaagatgtc tgagtatatt cccccaggta acaattaata tgcacaataa  72240
aactttttgc tcattcattt attaacctat gttgattgag tacctatttt gtgtcaggca  72300
tcattttaag gcacctggat atagttatga acaaacaaat aaaaatctct gccctcaaat  72360
aattaatatc tcacagaggt taggcaaaat ataatcagaa aataagtata acgtatagga  72420
tgccagatca tgaaagaagc tatgaatggc atcaagaagc tggaaaaggc aaggagacag  72480
attttctcct agagtctcca aaacagaaca cagtcctgcc gacaccttaa ctttaggcta  72540
gtgagacccc tattggactt cagacttaca atcccacaat gtaataaatt tgtggtaatt  72600
cagtagggga acaatagaaa actaatacga tatcaaaaca aattatatca tagaacaaga  72660
aaatgtaatt gtgacaaata atacctacaa aaatgttgta aatgctaggc aaataatgtg  72720
tttaaagcac ttaggccaat gttcaacgta aagtaattca tgctataata tcatcatcat  72780
cattaccaat atttaggggc tctaacaaat gatgtacgtg taagcagatg taagaaaatt  72840
tccttgctga agaggaggta ttaatagagt atataacaat agataacaaa ttccaaataa  72900
```

-continued aggcaaacta aatgttttat tggattaaat ttaattttaa aaactacaag aggccgggcg 72960
cggtggctca cgcctgtaat cccagcactt tggaaggctg aggtgggtgg atcacgaggt 73020
caggagatcg agaccatcct ggccaacatg gtgaaacgct gtctctacta aaaatacaaa 73080
aattagctgg gcctggtggc gcgtgcctgt aatctcagct atttgggagg ctgaggcaag 73140
agaatcactt gaacaaccaa ggagtcggag gttgcagtga gccaagattg tgccactgca 73200
ctccagcctg gcaacagagt gagatcccgt ctcaacaaca acaacaacaa caacaacaac 73260
aacaacaaaa ctgtgagatc catggtgggc ttttaagagg aaaatgcaag ctaaggtttg 73320
tttagactct gagtactgca tgtgtaaaaa taaaggcatg atgaaaagat caagagatta 73380
gagtgatact ttttatctac tagtgtcaga gtcatgacca ggggattggc tatgagaata 73440
cataagctgt gccaggagta atccaaggag attgtttcaa tttggaagag tgtccacaga 73500
atgattctca tactagacgt tgggctattg taaagaaagt tggtaggtac tccatcgcta 73560
ggatcatatc agggagaaat tgaacaggat ggccctaatg accctgttgt acccctagct 73620
tatggattag gcaagtcact tctactcgta taccctgttt ccccatttgt aaataagagg 73680
atgtgttact ctaaggatct ctaagattct ttgcagttgt taaattgcat agctctccac 73740
tgattccatg gtggaaattt gctattctat tacaaatatt ctaaatgtat gagatatcag 73800
acatactcat ttaaaaaaca aaatacaaaa aataagtatt ctacaaataa acacagataa 73860
tgtttaaatt ctatatgtct ttgtttctct tcagaagcat ccaaaataca aaccatctaa 73920
gaggcaagaa aatgtcgtga tgttcctagt gcaagttaaa aagatttgct ttcctcaagt 73980
cggaaagccc ttctcatttt tgaggttttt ttcttctttt ttttttcaag tgaaagcatt 74040
ttggaggagt caatatccat ctttaaaggt agccaggtca catgtataca tatgtaacta 74100
acctgcacaa tgtgcacatg taccctaaaa cttaaagtat aatttaaaaa aaaaagaatt 74160
taaataaaaa aagaaaatca gagagaaaaa aaaaaaagat gcatgtgcac cctgatacta 74220
ccatccatag tgatacggtt tggctttgtg tccccaccca aatctcatct tgaattgtaa 74280
cccccatgtg ttgagggagg gaccttatgg gaggtgattg gatcatgggg gtagtttctc 74340
catgctgttc tcatgatagt gaatgagttc tcataagatc taatggttta aaatcatggc 74400
acttcctttt gctctctctt tctcctgcca tgtgaggtgt gccttgcttc cccttcccct 74460
tctgctatga ttgtaagttt cctgaggcct cctcagctat gcagaactgt gagtcaatta 74520
aacttctttc tttataaaaa aaaaaaaaaa aaaaaaaagg tagccaggta aaaattactt 74580
gtttccagga cattttcacc tgaaagaagc attgtcatat aacatagaag caagaaatcc 74640
agtagtgggg gttatttaaa aatagctgga aaatttcaat cagcatgagt ttgaagcaac 74700
aatttatcat caccttttat ggtgggtggg gttaagaaca tttcagcggg caaagtggtg 74760
gtgatgggga agagacacca ggggaggtga ttcccattgc attgctttgt aaacagaggc 74820
acaggttctt catttttgtc acacaaaatc acagctatgc agaatttatt aatttattct 74880
tctgagacaa gaaaaaagcc accaaaggaa accaacagct tgctcctctc acactggggg 74940
aaccgtatga gagacttatc tatccctgac tttaattttg acctgaggag agctcctctt 75000
aaggaaaaca aattaattca atgactatac tacttaatca ttgaccttta tttaataaga 75060
gatttttcca taggatatgc tgagctgtct cacttacatc agttgtgtct cctgaggtgg 75120
gtgacaggag accacaaata ttgcatagca cacaaatcgt taatagcagc tgtataccaa 75180
accattacct aaatatgtag agtacaattc attctcacta atgtcagaga gcatgctata 75240

-continued

```
aaatggtgaa tccggacagc tgaagatact gaataataac ctctattttg aacaagttta  75300
cagtgttcca atcagtaatt aaattgatac ctgatgaata tatgtgtgtg tatgtattca  75360
tagcagagat ggttttcctg agataaggat tttgttattc ggataggctg ctgctggaat  75420
tgtccttcta cccttgtttc tttgtcctta gtcatcactc atacctcttt ccactcttct  75480
gccatcactt ttgtcaccaa agtcatggtc ctttccccgc cgattgctgc tgcaggtcta  75540
gggcaccaag acttaggcag cactcaccat gtgccaagaa ctggaccaca ggtaccatcc  75600
agcattgctc atggagactc tgtccctttc tgtaggacac cctcctttta gctagcaacc  75660
cctccaccac ctagagcctc tggacctctc attttaatat taagaactag gaaaacttac  75720
cgctgagaat aactagtaca actagaactg gtagagaaat ctgggtctct tgggaatgga  75780
tttttaggct ttattgatta gaggtgtatt aataatgcag tgttatagtt tcatgacata  75840
acgaataaaa aagttcattt tggacttgcc tttcagctcc ctaggagcta aaagacgtat  75900
ttaatgtaac ttgtgtggtg gaaataagtt ctttttcag gcaaaagatg tgcaaaccca  75960
tctggggaag aaacattaaa aactaaggag acagtgtcct agataactat gttcttttcc  76020
tgttttagtc taaaataatg attagttttc ttatatatct tcatttgtct tggttccttt  76080
tagcccaatt taataatatt attgcagata ttgatgaaaa cctttacctt cctcttaatt  76140
catcaaagta cttgataaaa tttatacata gtacattaat tgggaggttt ttatgagatt  76200
aattaatata atgaactgat gttgaaatta tttaaaacct gaattattat tgtattaagt  76260
aggacactta atacagttaa tcagttctgt ctttattcat ttgtgagaat ttttggcaag  76320
ctattgtgaa tattcaggga agggaatgta tttttagcag gaatcttata cctcctacat  76380
agaaatgaag catttactga aacatccatg aaacaaaatg tttctgaatg tgtactatac  76440
acttgttata agccccttt cttctgtagc tatattttgg agaaaaatct ttgctttgac  76500
aaaaaaaatt atgttgactt acacatatat tttataacta agcagtgttt ggtttgtgat  76560
aaaggataca aaaatataaa aatgttcagc acacgtaagt aaggccttgt tgacaatgtg  76620
agttatgcta ctggatactc aaaaggaaca ttcagtgttc tcaggtggtc tctagactgt  76680
ctcaagccta ggaagatatt ttataagcaa aggaataaga gaaggaagat tcagatttaa  76740
tccaagtgaa gaattcagtt ttgtgtgcct tatcctgtta ttttgagagg cagccaaaag  76800
atgctggtca gcaaggagaa ttgtaagttg ggcagccaac tctgatttct caacctctta  76860
gctgttttct taaactcaga atttttaatg aatttaaatg tccatatcag gtagactttg  76920
gggatgcttt taccagtgat tttcagaatg ttactttctg gcatttcttt tcacgtagca  76980
ttatattaaa aatgaattca ttcatccacc ttcccttgtc cttactaatt ttccctccta  77040
ctcccttccc ccttgttctt gccatgggga catgcaaaca ctggtggttg atgtctgagc  77100
aaggctgctg acagggggag gaaggagatg tcaagcagag gtcaatggca gtgtgcccag  77160
cagcctagga agtaggaggg aaaagagaga gagacagaga tggtggatga aagagaaagc  77220
caggatgatt atggtggtta tgatacttgt catgctgaac acccaattga gcacccaata  77280
agcacataat aatttaatca tcctctggct tggatggcag tgttctatca gtgttgactt  77340
cctggttgtg acagttttac agtgttagtg tagaagagaa tccttgcttt agagaggtac  77400
ttactgaagt acttagggtt aatgcaccat tgtgctggaa aaagatacgc acacacacgc  77460
acacacacac acacacacac tcacacacac gcacaaatac atccatgtgt taggcagagg  77520
gagcaaatga ggtaaaatgt taataattag gaattctggg tgaagtggat agagggactc  77580
tttgactgtt cttgaaactt ctctatacat ttgatctgtt tcaaattctt cagaaaatca  77640
```

-continued

```
aactacaaaa acttaattca tttagtgaac atctactgaa catctgtata ttaaatagtg  77700
ttaaatgaat gtcaattaaa atgctcaaac acagtagagg ttgattctca ttcacataag  77760
tccatggtag gtgtttttgg caggtgggtg agtttctccc ttagggagat tgaggaaccc  77820
agactcctcc caagttgcag ccccaccgtc ttctgagggg atgcatccat acccacttcg  77880
aagtagcata cattatttcc tttctcattc ctttggatac cagccacaat ttattcaagg  77940
tagacagaaa attgtagtat atagccatat gccctgacaa agaagggaga acagattttg  78000
gtggacaact agcaaactct gatacaatct gttattaagc actgtgtgtg gatagatgct  78060
aactagaagg agattatctt cccttcagca aatataaact gaatgccgtt tatttggttg  78120
aaactaagct agatcatggg agtatagaaa ttttataaga agacatagtc acttctgtca  78180
gtgagctcaa gaagaattag tatgcggaat gtaatcatac ctacaggggg cttgtgccac  78240
ttaagtaaaa tgaaacatta ttttgagtac aatttagcaa taaatgtact acgagatcat  78300
taaaaatcat gtttgaatgt tattgtgtca aggatgggaa aaagactttt gggttgtaga  78360
cttgataatt atagttaaaa acagttttta ttcttgttta gtcttatttt ttatgtttaa  78420
acatatttat acttgctaac atttatactt gctaagtaaa gactgttttt acaaccatga  78480
caagaacaaa acatattagt aatgcaaatg ccacatttcc tacaatcaac taatcacact  78540
aacatatttg catggaagaa tcactgggat tgatctggcc acgtgtgtag tcatgcccaa  78600
aatgtgaagt ccatctgttt tgcaattttt tttaaccact gttatccaaa tgctccttgg  78660
attttttta ttagtggata tattttggag gtcagacacc ctcttggcta gatcatcacc  78720
tttataacaa atatatatac tattctcatg gaaatatatt tagacgttgc cctactggga  78780
attttttca agtaattaat gtacagcttg tgcaacagct tgatcttggc ttcatggaaa  78840
taattcactc ttagcagcat ctaatgccac aaagcattta tggatgtcag ctcagaactt  78900
acttttattt atctctgagt tacttttttt tttttttttt ttttgagaca gagtctcact  78960
ctgtctttgg cttgtcccta acctcttaac agacttaata ttaagctcca tttcactcag  79020
tcgttctgtt gtcatataaa tgagacattc tacaagcata gtttttagtt tctgccagag  79080
catcatacaa cattgtgagc tatgatgaag ataaagacct agagaagata tttaatatga  79140
agttcattat ctaatatttg gtatgtgtgg caaaatagca atctactgct tggttctgct  79200
gtaatctatt tacccaccca tcccatcttt ctttcaattt aaaaggataa tgattttagt  79260
cacgattata cataaaccca ttaccatagg caataaacaa tggggcaaac cattggtccc  79320
atagttggag tgtggtctga agtgtgtttt ggtggagaga gatctatgtc tggagatagc  79380
taacatggat ttggatccca gatctgctcc tacctgttgc tgtgcctgtg accaaatcat  79440
gtgatctctc tggtttcagt ttacttgtga ataaagtaaa taccttcatc aacacctgtt  79500
tttgaataca atgtttttct gtaatttttg cttcttataa tgttataatg atcatcctta  79560
catctaaatc ttggtttaca ttttcatcaa ttcttttgga aagattggag aagtaaattt  79620
tggagatgta tgtcggctat taaaaatgtt taattttta attaaaaatt aaaacgttga  79680
aaaatcctga tgcaaaataa atgcattatg cttagtgaac tcttctcatt tcgaagttta  79740
ttcaccttct tgtttttgca agtttcctga aaaatgcata taaagtcact aagttagcag  79800
aactttataa aattatataa ctatatataa tcttttgata tcagtgaagc cagctgatcc  79860
tatagaaata atgtaggaat tataatcact agcacataat ttaagagtcc tgtggtctta  79920
ttcatgttat ttaccctctc tgaatcttac atatagtaag agggttatta tacataatat  79980
```

-continued

```
gtgtacatgt atacaggtaa gtaagtatat atgcttatgt gtaaaagcag agttattgtg  80040
agagtcaaat ggaaatgtga aagtactttg tagtttttta ttactattat taatttttaa  80100
taaaatggta acattcattt aataatcatt agttttaact tcagattgta ctggatttcc  80160
tctagtattt cttaagatta gtgaataaag tatttctcct aataaatata ttgactactg  80220
tctttcgatc aaacatatta ggtatatttt tacagtagca tcaggcagtg aaaatttgaa  80280
gctctttata gaggactgat ttatgatgaa aaggaataac atgaacaaat ggaattatat  80340
gaagcttccc cagaaatatc taagaggggc caattttaag aaatatctga cttctttttc  80400
atggacattt caaaataaac ctaactcata tggtacagtt tttaagaggg aaaagaaaaa  80460
accatctgag aatctctgga attctgccga aagtatcact tggcatttta ttctaccttc  80520
tggatgcagt tgattgacag tagtgttatg atgccagggg tatagtgact agaaaaagaa  80580
aaccagggaa ttcagtgttc ttgctcatga agaacagctt ggttctttaa aaacaatgag  80640
attttgccac cccatctcac aaacctatga tttgtgagaa caatcccttt tgtgttgcaa  80700
gacttttaca tttctcttcc cacactatat tagaagaata aacattgctt cataagtacc  80760
gattgatagt ctcatttcat atttttaaaa tagagttact ttaaggttaa atttttcatg  80820
tagattaaaa tgactaagta accattcaca tatttcaaat aaaatatatt tttactacaa  80880
aaggaaaata actagattct taagtgttat agtcaagtgt aattgagtaa tatgaattct  80940
aaatgaattt ctaagatctg ctcagctttc actactttag gaaggaacaa cttaagaaaa  81000
attttaataa agatatctct tcacacacat ggcagtgttg tacttagaga acatgaccca  81060
aaatttttta tgactgcata ttgaattcct gatactcttg ggaagctcca aaagcaccag  81120
tggagtttcc agatgtaact gtggctgcag acccgccagt cccggtgttg gaagggatca  81180
ttataggctc ttgtgtgcag actcatcttc agacccagag gaattaaata acttgcccaa  81240
agtcgcacaa ctttctcatg gtaggttggg cactagaata aatattgctt tttcttaaga  81300
gttttagcct ccgtattatg aaatcttcta tgttctgctg atgatatctc ccttcttcat  81360
ctgttttcta tttttaagca atggaaatac aaacttgcaa ctccccattt ccaacacaac  81420
ttagaaaaaa caatatttaa agaaaaaatt acaggcatct catctccttt acctgacaga  81480
tgcttgatag taatggcctc tagataggga tgacatctaa tataaatgtg tcctttcaag  81540
tcaagctttc tctgttcatt agtagaaata ttgtatatca agtgtgcaaa aattttcttc  81600
aacagggagc tttgtttccc tccttttatt ataacaatct gagctttgtg gtcccagggt  81660
ctcctagtgc ctgtctttag gtctgtttat tcacatgaag aaagcatgtc atatagtatt  81720
atctaagact caggctgctt atgcatgatg acagaagggt tcccaggcac aaacattcat  81780
ccatgcattc atccatccac ctattcatcc attgatttgg ctgataatta ttgactactg  81840
ttgagttgcc ctcagattta gtttctgtcc ttctgccatg gggaaatatg gggttaagcc  81900
acaacatact cttctcttct ttttctgcac cttcttagta tatttagttc cattttgtct  81960
agccctgcct ctgacttctt tgttgtactt caggtttttt atcattgaaa gttatttctg  82020
gatcatagat cattctcttg gtcactttgc ttgttcactt ataaaattaa ttcagaaaaa  82080
atgacccaca gtaattactg taaatcacag accataaact ataatactgt atattgtatt  82140
atagtacaga aatatttata ctttaaaatg ttttaaatat agatattata aaaagatatg  82200
tctcatataa gtaatataaa tacttttttta ttacctcttc tctccctatt ctccaggcca  82260
gtgttttaaa aatccatctt tatatgtcca tcctggaaaa aactcatgat cataaatgag  82320
tttctcaata gagtttataa gcccacagtt gaaacacaat tgtcttagca tccatttagt  82380
```

-continued

```
tgtcatactt ttaagattta atggcaaata ttatgttttg tttcttcaaa agaaatattt  82440
taaaatttta gtaaaggcag ttagagaagg tagagataat ggactgttta atcctacttt  82500
tcatcccaca agtgaacaaa aaaatgataa aacatttttc ccaaaatgta gctttaacta  82560
tacttaaatt tggactaaaa tgggagatat cttttctact attgaaaagc cgtgtctgta  82620
gattaatgct aaaatcgggt gtaaaagcaa aatttgtttg gcttgattgc caatggccca  82680
ttcatttggc tacagaaaca atagcacata gcaacagata atgatgtgag atcacctagc  82740
tcaagtaaga gtgtctgatc cgtcaaaaat atatacatca agattcaaaa gaaatgtgtg  82800
ttttctcaag tcatctctgt aaaaatacat taaatagagg aatagaagtt tgactttgaa  82860
aatacattgc agacccaatc cgtctttcct attttctggt gaaaagtatc aaatatgtgg  82920
aacctggaac tgctattctc cttcttaaaa atctttctta atattctatt gataactggt  82980
gcaagcctaa ctttttgtct tacccgattc ttctcacacc aaagtgatag gaccttcagg  83040
tagcctttgg atagaagata aataataatt taactattga tggaagttag tattagaatt  83100
agacttggaa gtctatggaa taaaatgatt ctacaacaat ttgtacttca gacattagta  83160
taacaaaaca tgtttgcccg tgcatgcgga aacaaccaat ttcatgtgga tgcttatatt  83220
cacaaaggag taaccacctg gggtttccca ctgttgctcc agagaaaact agcagcagga  83280
gaacttctct gaaggtatca agacatcttt aaaaaacact tgttaagtgt tggttcagct  83340
aaagcaggga gttttcagtt agtaatggct tttaaaaatt aaaacaagtt tagcatgtag  83400
gtcattaacc ttgaatcact gtcatgatta ttattaacca tctgttctca aatcgaaaga  83460
tatttttctt ttctagatca catttattct cacattgctc aatttcacta tatatcaaga  83520
catgaaaact gtaaaaatca caccttctac attattattt ttattgaaaa attcctaatg  83580
aaacagtgcg ctctgggata gagaaaggaa ctaactgaca ttttgcttct taacttgttt  83640
ttatgcaagt tctaagtggt ttctggccat gtacataaaa gacaaatatc tggaaaaaaa  83700
actagcagaa gtcagttatt tggctctatc tactttgaga attatgttat ataaatgtta  83760
ggaaattttt tgtaatattc ttatttagaa atgaaatata aaaagtttta aaaatatcta  83820
aggacagtat acagtcctaa agtaaagctg ttaggtaaat gctacacaat cctcttatta  83880
cagagtcact tacctgagaa tataagaaga gggcctcttg tttaagagta aatgtgagct  83940
gcaatcagga ttctgcactc atttggacac ttagttttgt ttttccatga ctggtgttgc  84000
ctgttactga gacacctacc tgtcatgtga ccacagctta tgttacaatg tgtctagtca  84060
gacttagaga tgtgtgaaag agcagtacct agacgggaaa ctatgggtct ataaaggttt  84120
tgccttcttg ggcggagttc aaactaggaa gccacaaaac ttccagttgc attttcacag  84180
attaatgaaa tatattttac acttttcctg aaagatattt tatttgtgca aaccttgtta  84240
caaagtacag ccagttgatt aatcgatgaa gtgatttgta gtggattctt atattttgtg  84300
taagggtata tgtgaggccc tatatatgag gctttctata taatgaagta taattcagtt  84360
cagcatttca attcagcaat cacttattgg gcctctactc agttgccttc agggctttat  84420
aatttaattg ataaagggag gttaattaat taattataac aacagatcgc ttaatagtgt  84480
aactactaat ttaattaatg acaaataaca atacattaaa agaaatgcat taataaaaat  84540
aatatattgg tgttatagac aataattttc tgattaactt tattattatt atttcaatag  84600
cttttgggga gcaggtggtt tttggttata tggagaagtt gtttaggtat gatttctgag  84660
attttggtac actcataacc tgagcagcat acactgcacc caatgtgtag tctttcattc  84720
```

-continued

```
ctcaccttcc tcccaccctt cccctcaagt ctccagagtc cattatatca ttcttatgcc  84780
tttgcatcct ttagtttagg tggcagttat aaatgagaac atgtaatgtt tggttttcca  84840
ctcctgagtt acttcactta gaataatggt ctccaactct atctacgtag ctacaaatgc  84900
cattattttg ttccttttta tggctgagta gtattccata gcatccacac acaccccccct  84960
atgctttata tatatatgta aatatatcac attttcttta tccactcatt ggttgatggg  85020
tatttaggct ggttccatat ttttgcaatt gtgaattgtg cagctataaa catgcatgtg  85080
caagtgtctt tttcatataa tgacttcttt tcctctgggt agatacctag gagtgggatc  85140
gctggaacaa atgattgttc tacttttagt tctttaagga atctccataa cttttccatg  85200
gtggttgtac tagtttacat tcctaccagc agtgtaaaaa aatgttccct ttttaccact  85260
tccatgccaa cgtttatttt tttatttttt aattatggca attcttgcag gagtaaggtg  85320
gtatcacatt gtggttttga tttgcatttc cctggtcatt aaagatgttg agcatttttt  85380
catatgtttg ttggctgttt gtctatcttc ttttgagaat tgtctattca tgtccttagc  85440
ccactttttg ataggattat ttgttttttc ttactgattt gtttgagttc cttgtagatt  85500
ctggatatta gtcctttgtc agatggatag tttgcagata tttctcccat tctgtgggtt  85560
gtctgtttac tctgatgatt atttcttttg ctgtgcagaa gctttatagt tttaggtccc  85620
atctatttat ctttttgtt gttgttgcat ttgcttttgg tttcttggtc atgaactctt  85680
tgcttaagcc agtgtctaga agagttttac caatgttatc ttctataatt tttaaggttt  85740
tgggtcttag atttaagtct ttgatccatc ttgagtggat ttttgtataa gttgagagat  85800
gaggatccag cttcattctt ctacatgtgg cttgccaatt atcccaacac catttgttga  85860
ataggatgtc ctttccccac cttatgtttt tgtttgcttt gttgaagatc agttggctgt  85920
aagtatttag ctttatttct ggattttcta ttctgctcca ttgatctaca tgtctatttt  85980
tatagtagta ccatgctgtt ttcctaacta tagtcttgta gtatagtttg aagttgggta  86040
atctagtgcc tccagatttg ttattttttg cttagtcttg ctttggctgt atgggctgtt  86100
gttttgttcc atgtgaattt taagattttt tttcttgttc tttgaagaat gatggtggca  86160
ttttgatggg agtcgcattg aatttataga ttgtttttgg cagtgtgctc attttcacaa  86220
tattgattct gccaatccat gaataaggga tgtgttttca ttagtttctg ttgtctgtga  86280
tttctttcag caatattttg tagttttcct gtagagatct tccacctctt tggttaggta  86340
tattcctaag catttttttt ttttgcagct gttgtaaaaa ggctcaggtt cttaatttga  86400
ttctcagttt tgttgctgtt ggtgtatagc actggtactg atttgtgtac attgattttg  86460
tatctggaaa ctttactgaa ttaacttatc agatctagga gctttttgga tgagtcttta  86520
ggttttctag gtatacaaac atatcatcgg caaagagcaa cagtttgact tcctctttag  86580
cagtttggat gctctttatt tctttctctt gtctgattgc tctggctagg atttccagta  86640
ctatgttgaa tagaagtggt gaaagcaggc attcttgtct tattccagtt ctcgggggaa  86700
atgctttcaa attttccccc gttcaatata atgttggctg tgggtttgtc ataagtggct  86760
tttattacct taaggtgtgt atcttatatg ccagttttgc tgagggtttt aatcataaag  86820
caatactgaa ttttgtcaaa tgctttttct gcatctattg agtttatcat atgatttttg  86880
tttttactcc tgcttatatg gtgtatcaca tttattgact tgcatatgtt aaagcaaccc  86940
tgcatccccg gtatgaaacc cacctgatca tggtggatta tctttttgat atgctgctgg  87000
attcatttag ctagtatttt attgaggatt tttacatctc tgttcatcag ggatattggt  87060
ctgtagtttt cttttttgt tatgtccttt tctggttttg atattagggt aatactggct  87120
```

-continued tcatagaatg atttagggag gattccctct gtctctatct tttggaacag tttcaataga 87180
atttgtacca atttttcttt gaatttctga tagcattcac ctgtgaatcc atctggtcct 87240
agactttttt tgtttcctga catttttct attattgttt cactctcact atgcattatt 87300
ggtctgttaa taatttctat ttcttcctgt tttaatctag gaggtttgta tatatgcagg 87360
aatttgtcca tctcttcttg gttttctagt ttgtgtacgt aaatgtgttc acagtagtct 87420
tgaataatct tttttatttc tgtggtatca gttgtagtat ctcccatttc atttctaatt 87480
gagcttgttt agatcttttt tcttgttttc ttggttaatc ttgccaatgg tctattgatt 87540
ttgtttatct tttcaaagaa gcaggttttt gtttcattta tcttttgtat tgtattttgt 87600
gtttcaattt tatttattta tttatttatt tttattttta ttttttgaga tggagtctca 87660
ctcttgttac ccaggctgga atgcaacagt atgatcttgg ctcactgcaa catctgcctt 87720
ccaggttcaa gtgattctct tgcctcagct gcccgagtag ctgggactac aggtgcctgc 87780
caccacacct ggctaatttt tgtattttta gtagagacgg ggtttcacca tgttggccag 87840
gcaggtctca aactcctgac ttatggtgat ccgcctgcct tggcctccca aagtgctgcg 87900
attacaggtg tgagccacca cactaagact caattttatt tatttctatt ctgatctttg 87960
ttatttcttt tcttctgctg ggtttgggtt tgctttgtct tgtttttcca gttcctagag 88020
gtgtaagctc agattgtcta tttgtgctct ttcagacttt ttgatgtaga tatttaatgc 88080
tatgaacttt gctcttaaca tggcttttgc tgtatcccag aggttgtgat aggttttgtc 88140
attattattg ttgaattcaa atatttttaa aattttcatc tttcttgatt tcattgttga 88200
cccaaagatc attcaggagc agattattcg atttccatgt atttgtatag ttttgagggt 88260
ttcttttgga gttaattttt aattttattc cactgtggtc tgagagaata cttgatataa 88320
ttttgatttt cttaaattta ttgagacttg ttcatatggt ctgtcttgga gaatattcca 88380
tgtgttgatg aaaaggatgt agttgttggg taggattttt tgtaaatatc tgttaagtcc 88440
atttgttcta gggtatagtt taagtccatg tttctttgtt gactttctgt cttgatgacc 88500
tgtctagtgc tgtcagtgga gtactgaagt cccccactat tattgtgttg ctgtctatct 88560
catgtcttag gtctagtagt gattgcttta taaatttggg agcccaagtg ttagatgcat 88620
atacacttaa gattgtaaat ttttcctgtt gaactaatta ttttatcatt atataatgtc 88680
tctctttgtc ttttttaatt gttgttgctt taaaatcttt tttgtctgat ataagaattg 88740
ctattctttc tcactttgag tttccatttg catggaatat ctttttccac ccctttacct 88800
taagtttatg tgagtcctta cgtgttaggt gagtctcttg aagacagcag atacttggtt 88860
gatggatttt tatccattct gccattctgt atcttttaag tggagcattt aggccattta 88920
cattcaacat tagtattgag gtatgaggta ctgttctatt catcatgata gttgttgcct 88980
caataccttc ttgttgttgc tgttgttaat tgtgttatta ttttatgggt cctgttaaat 89040
ttatgcttta aggaggttct attttgatgt attcaagtta ctgtttcaag atttagagct 89100
ccttttagca tttctcagtg ctggcttggt agtggcaaat tcagcatttg tttgtctgaa 89160
aaagacttta tctctctttc atttatgaag cttagtttca ctggatacaa aattcttggc 89220
tgataattat tttgtttaag aggctaaata tagggcccaa tctcttctgg ctagcagggt 89280
ttatgctgag aaatctgcta ttaatctgct atgttttctt ttataggata cctgatgctt 89340
ttgcctcaca gctcttaaga ttctttcctt catcttgact ttagacaacc tgatggctgt 89400
gtgcccaggt ggtaatcttt ttgcattgaa tttcccaggt gttctttgtg cttcttatat 89460

-continued

```
ttggatatct agatctctag caagactagg aagtttttct tgattattcc ctcaaataag  89520
tccttaatga ccccactata taacatgaaa tatctgttat tggtactgag gtgctggcca  89580
caaacaattc tgtgtgtcct gaaaactctt cagaatattc gtcatcttta gcacttgtta  89640
tcttagtgtt tgggcttggc ttagagtgat acatctcata acagggcaac agaaagaacc  89700
aggaaccaag atttatataa cataagtcag taaaactaga ggcaccagag gtttacattt  89760
acattaggtt acattttcta acaggtagca aagcacatga atgaagttca gtggaaggcc  89820
ttcctcagga atccagtaaa aaccaaacat acacacacac acacggacat ccgtgaggca  89880
ggaagggatg tccactatag tacagacaag catcctggaa ggccatcaag gagtaggtgg  89940
gtttcagttg cctcaggaat gtggcatgga cccaaactaa gtgagtacag atacttgtca  90000
ttgaggagaa gattcaaaat agcatcctag gtgtaaaaac tgaggcacct ggggcagggg  90060
aactaggtct ctggaatgtt ggcttaaaag caccccctctc aggaaaggcc tcatatgcca  90120
tgcagggggt tatatatgtg ttgtgggaca cagatggcaa ggagataatt ctatgcacca  90180
ggctccacta ctaacaggta aacagaccaa cattaacaga gacttaggta aaaaggtagg  90240
tgcccagtgg tcagttctca ggcacttcca agatgcacct aacagaaatg taacttggtg  90300
tctattgtgt cctaggtcta acaactgaag agaagtgaat tagtacctct tgtggacaga  90360
gaaacagggg cagagaccca ttacaaagct gtctcagata ggcatttgaa gctgtttaag  90420
tatgtagagg cttaagtcag gctggttctg aaatgtgaga gagggttaag cttcatggga  90480
aatcagcagg gtagtttgct attttttatt ataaccaatc tcacaatagt ttgggacatc  90540
aaatatcaaa ttgttgggaa tatttatcca tattagtctt tttgccacta atatttaaaa  90600
atagtttaca atatacaaca aaaagttgta aaatttccat ctccacttaa tcgatcttat  90660
gtaacccata caatacatca aatgtccttt ccccacttta tgttttttatt tgctttgtca  90720
aagatcactt ggctgttagc atttgggttt atttctaggt tctctattct gttttattgg  90780
tctgtgtgcc tatttttata ccagtgccat gctgttttgg tgactatggc cttatagtat  90840
agtttgaaag caggtaatgt gatgcctcca gatttttctt tttgcttaat cttgctttgg  90900
ctatgtgggc tctttttttgg ttccatatga attttaggat tgttttttct agttctgtga  90960
agaatgatgg tggtattttg atgggaattg catttaattg tagatttctc ttggcagtat  91020
tacccaggct tttcttattt tggcaccctg tgctgctgtc tccttttcct tctttctgct  91080
tctcttaacc aactgttacc tacacttcaa tactttctga gggcaattca tcctccagta  91140
agtctccctg aatcttctct tccttccctg gcttattata tatccttcct cttggttccc  91200
atagcaccta tgcacacttc tgtcattgca cttgccaatt tgttttataa tgatctgctc  91260
atctgtctcc tcacttagac tatgagctca ctgagagcaa tggctgttgc attcacctta  91320
tatcctcaac accattctga aggcaagaga aagaataccc agaggtggag ctgggaagct  91380
ggttgtccaa gtagtgaatg actctagttt gaattgaact ctatagccag tgggcaatgt  91440
ggatgtgttg acagtttttt aacaggggac tagtgaaaac acattttggg tttagaaaaa  91500
attgcaagtc tgatgacata cataggagaa gagattagag ataggaattt cacttcagaa  91560
atttaaccac aagagcaagt gacagatcac ggaagtctga accagactat aaatgtgaga  91620
atagagaaaa aagttaacaa tttgggtgtg aaagggcgag ggagagaggt gtgaagaatg  91680
actaagtgtg gatctgtttt taaggattga atggaaattt gagcatttta gctaatcagg  91740
cctaatattg agcaaagcaa aactcttgca aattgttatt tcaagtgtgg gctgagaaaa  91800
tgaaaaaata taaattctca cgttataacc tcttccgtgt gtctgatttg atagaatcca  91860
```

-continued

```
gccccattgc ctccaaattc cattgcatct tagaccagca aacacaagtg aattctactt  91920
aaccccagaa ttctgtatga aaatcttact gccttttttt ttctaatcat gtgtcaaagt  91980
gtgggaagaa cttttattta tgttttaata aattgtcagt ataaccattt ttacttgaaa  92040
atattataat ttttcaagta aacaaattgt ttctctaagt tgaaaatttt atgatggaat  92100
aaaagtattt ttcctcaaaa cacatagaaa ttttacaaca atattttaga gttaactaaa  92160
tgtttcttta gtagtttagt cacttaaaaa gtgatatgat tatgaaaata cttaaacttt  92220
gtcttttaac tatttctaat aatgctattg gtataatttc atatttttat actgatcttt  92280
tctccaaact ttagtaaaac atacttctgt aaacccctgc ccacaaaact gaagtccaca  92340
tttacttctg aatgactgat aagtttgtaa aagtatgcat gaatttcgtt attaaattaa  92400
agtttttatt atattttatg cacaatggta taaattatta aattaatttt caagcttata  92460
gaacattgat aaagattgtc attagaaaac cctgagttga ttgttataca ttacataacc  92520
tttcattggt ggattagtga atatgttata gggtgaccat gaatccaaag aatcaaagct  92580
ggctacagca aacagagggt caaaaggata tggaactatg catgatccag caaaacactc  92640
aatatctgtt ttcctggaat gttaaaagac aaagaagaaa acttggggaa cactagatgc  92700
atatagttct ggttctttaa gaataaaaat atgggccggg cccggtggct catgcctgta  92760
atcccagcac tttgtgggag gccaaggcgg gtggatcaca aggttaggag ttcaagacca  92820
gccaggccaa catagtgaaa ccctgtctct actaaaaata caaaaaaaaa ttacaaaaaa  92880
aatacaaaaa aaaaaatagc caggtgtggt gacaggcacc tgtattccca gctacttggg  92940
aggctgaggc aggagaatca cttgaacccg ggaggcagag gttgcagtga gccaagatag  93000
tgccactgtg ctccagcctg ggtgacatag tgagactctg tctcaaaaaa aaaaaaaaga  93060
ataaaaacaa gaatggtcag agtcctagta ccttgtccag tgtagtgctg ccttgagatt  93120
gcattgcaat ctgtctgaga gatagtaaaa gaaagtgata ccttccttag ccctgtttct  93180
ctttagacta tgctttcccc tctccaagtt aatatctctc agtctaaagc ctgggaaaag  93240
gtgccaattt tgtttttctt tcttcctcac acctcctaga agttacactg ggacactatt  93300
actttttcc aggctttggc catgtgtatt gttttggaga gtcaacttcc ttttttcttt  93360
cattctgcaa atagttttga gctgtcactc tgtactaggt gctataaaac ttacaggtgc  93420
attttacatg cctatttcct ataggccacg atttaacaaa atgttcataa atgagaatta  93480
ggagtgcatg tattgaatca ccacacatta actgaacagc tttcattggc cagagactat  93540
attgacagtg gagattcaaa gataaactag agaaatctca tgcttaaata actttctata  93600
ataaattata taagagaagt aggttcaggg atcttgggag ctcagaagca ggatgagtta  93660
aacaaaagtt ggattttgcc tttagcttgg tttcattatc ctgaaggaag agcctgaaat  93720
atagtgtagg gtgcaagtag tatatgtggg tggcaatctc gggaaacagg agcatgtgat  93780
gaataaggag aaaaagccaa tataaaggta ctgcattgag ggcaatgagg gctctaattc  93840
tctgcacctt ctcaagcatt gtgcagattg gttttctgga ttatcagcct gaaggacaaa  93900
acgaagaaac agccattagc tcctgtctcc cattgtctga gagctgccac taggatatta  93960
acttcctgaa attctgcaga aatctcctct tactttggca ctggagatgc ccatacgcag  94020
aaagcaaaaa ggcacagcat atttaaggaa gctcataaga aacagtgcat ccagaagtgg  94080
cgagaattgg aggaatggac atgagactct aagaaccagc gcctttgatg ttccttttga  94140
tctgttatgt agctcttctt gtacacaggt gagcaaaggc atgctggaca aatggattca  94200
```

-continued

```
catgtgctaa agcatggggc aaaaaccaca tattaattca ggaaaagaca agatgcgtgg  94260
ccctctctgt ctctgtctaa gggtgaatta aagaggggat atatgtacag agtggcaggg  94320
caggacttga gataagaagg ctaggtgggt gctctcatgc tagtagcatt atagtacagg  94380
tgatgagaag ctcctgaaga atcatcttaa catttgtatt ttagagcaac agtattgagt  94440
tctgacttag agacagcaaa actaaagaca gaaagactat tttgattatt aatgatgtag  94500
atataagaat atcgtcaatg tgaactaaag catgaagcta cttatgatat atcattaaaa  94560
ggatttaact gattggagac aaacgagagg gatggggaaa agaattcatt tgtttttagt  94620
tgctcttttt ttcctactta ttcctttgtt ccgagtgtga ataaactttg taaactttta  94680
tactaaaaca ttctgctcat tcatacttat ttctttgatg aaacaaggaa acccttgtat  94740
agttataaac gtgtgaatca atttaaatat taggaaattt ttttaaataa agctagtttt  94800
ctgaagggga aaaacttggt tcaatttttt gctggcaatc tgctttgtga tttttgaaca  94860
tgatatctac atctagactc atgttttgct agctggaatt ttttttcaaa ttaacgctac  94920
cattattata tgctttacta tttagctttt gcagccttgg aaatctatga ttaatacaaa  94980
taattctcta tggcaatttt aaaaatacat gtaaaagcct tcaatctaca ttgctactgt  95040
gtcgtagcac aaaaaaagaa aatgtgatca aattttaata aaatctacaa tttattccct  95100
tctaaataca gtcctagctc aggagaaagg aagctatttg tatttttcag aatcaaattt  95160
ccctaaatga atatagagaa agaattataa ctgaaatatt gttgaaacag tggtcatctc  95220
aaatctgaag gtcattccaa aaaagtttct gagttttcat tgcctcaatc taaaagttgg  95280
ccttttttggt aatagatgaa agtaaaataa ttgaaagggt ctgttgcagt tttggaatat  95340
cttgaaaata tagtagagtg aagccttctt cccttaaata aaagacaagt tgctgattgt  95400
tttctttcta gccagataag aataatgcct tctttctctt gttagtctta acacctcact  95460
tgttactatg tgtcagaaag gcgagacacc ataaatggag atactactga tggaggtcat  95520
ctgacatggg gctggtaggc agtgggaaga ctggtatgga cacaggtggc ttaggggttg  95580
gggaatgata tggaactaag gaaatgataa ttagcagaac ccagtgtgca tgtgtgtgca  95640
ttcgtgtgtc cgtgtatgtg tgtactgtag cacaatgcaa gaaagaaaaa acaaggcaga  95700
cttttcataa tttcagggat aaataaatcc tttatcactt catgtagaat attggctact  95760
tggaggtata tctaaacgta aatatataac tatataacta catgctaatt aaaaacatac  95820
aaagaagaag tgcctaaaga attacaacag aaagtggcat agtgattatt agagttaata  95880
taatataaat aaggccaggc atggtggctc atgcctataa tcccagcact tttggaggtc  95940
aagttgcagg gatcacttga ggacagggga tagagacaag cctagccaac atggtgaaac  96000
ccatctctac taaaaataca gaaattagct gggtgtggtg atgggcgctg gtaatcccag  96060
ctactcaaga aactgaagca ggagaattgc ttgaacccgg aagctggggc tgcagtgagc  96120
caagatcgcg cactgcactc cagactgggt gacagagaaa gacccggtct caaaaaatta  96180
aaaaatagta taaataatat ttcaaaacac aagtctgtta agataaaagg tacagaggaa  96240
tggtgagatg acttttttat ttgtgtgata agggactgtt ttctgtgatt gtgagaaaga  96300
ccaggagtta agaaaaagtg gccatcaata aatcagccac ttatggggaa gaaccataaa  96360
ccactctcag atgaaataca aatgcagtca ttatttaata ttattggaat atttgtatta  96420
gtttttggta tgtgctgcta gtgctggtac attttagtag tcaattaata ttttgttaat  96480
cttaatttct aactaaattc cagagtgaaa tggaaataat aatgaaaaaa ttttatttac  96540
aaaacagatt ttgttttttt ctgttaagaa tgatacacag ttgtccttca gtagccatag  96600
```

-continued

```
gggattggtt tcaggacctc ccttgggtac taaaatctgc agatgcctaa gcccctgtta  96660
taaaatggct tagtatttgt atataaccta tgcacatcct ctcatatact ttcaatcagg  96720
ggtccccaac cccagggcca tgaccagtac tggtccatag cctgttaggc tgttcgatac  96780
caggctgcac agcaagagct gagctcctcc tcctgtcagc tcagtggtgg cattagattg  96840
ccataggagc acgaacccta ttgtgaactg cacatgtgag ggatctaggt tgtgcgctcc  96900
ttatgagaat ctaatgataa atgtaatgtg cttgaatcat cccaaaacca ttccccttcc  96960
cctcaccatc cctgtccgtg gaaacatttc ttccagaaaa ccagtccctg gtgccagaaa  97020
ggttggggac tgctgcttta aataatctct agattactga taatgcccaa tacaatgtaa  97080
attctatgta aatagttttt atactatatt gtttagagaa taatgaaaag aaaaagtcta  97140
catgttcagt ttaagtgttg ataagtgtgt agagaaaagg gaacccttgt acattgttgg  97200
tggaaatata gattggtgca gtcattatgg acaatagtac ggaggttcct aaagaaatta  97260
aaattagaat tacctaagac ccagcaatcc ctcctctgga tgtacccaaa ggaaataaaa  97320
tcatcacctc ataaagatat ctgcactgct atattcattg cagcattatt tacagtagcc  97380
aagatatgga aaccacctag gtatgtgttg gtgcatgaat ggataaaaga aactgtggta  97440
tatgtatata caatggaata ttattcagcc ttaaaaaagg agaagaccct gtcatttgcc  97500
acaacatgca tggacctgga ggatattaag ctgtgggaaa taagtccaac acacatccac  97560
acacaaaatt gcataatctc acttatatgt ggaatctaaa aagaaaaagt tcaaatataa  97620
agttagaata aaacagtggt taccggccgg atgtggtagc tcacgcctgt aatcctagcc  97680
ctttgggaag ccgaggtggg tgaatcacct gaggtcagga gttcaagacc agcctgacca  97740
acatggtgaa atcctgtttc tactaaaagt acaaaaatta gccgggcata gtggcaggtg  97800
cctgtaatcc cagctactca ggcagttgag aaaggagaat cacttgaact caggaggcat  97860
aggttgcagt gagccgagat ggcgccactt cactccagcc tgggcaaaag agcaaaactc  97920
tgtctcaaaa taaaaaaaca aaaaacacag tccacacact ggttaccatg agtgaggtgg  97980
cagggaggag attgggagat gtagatctaa ggatacaaag tagcagatat gtaggaggaa  98040
ctaaaaagct gacatgcagg atgacaacta tagttagtaa tagtgtattg tattcaggat  98100
ttttgctaat tgagtagatt atagctgctc ttgccacagg ggaaaaagtg ggtaactacg  98160
tgagatagac aatggatgtg ttaatttttg tcactataat aaccttttca ccatatacat  98220
tcatcttata acagcatgtt gtttactgta aatatataca ataaaattta tttttaaata  98280
tctgagtatg atttgatgat ttgtgaaaat agagtgaatt ataataattt taaatgtaag  98340
ttaatgttat tagaaaagaa acagaaagaa cataccacac agaaagtctg tctgaaggat  98400
ctttgttttc tccaccaata caagtgttca ttgattcaga ggtggattat gagatatgac  98460
cataaaacaa aaatttcaag ggaaatatat tttattcaat gaaaaattct caacacaact  98520
gttatatgcc agtaaacact atatctttta aataacaggt catatctatt atatttaaaa  98580
ttcaaggaga gactacatta gagatgctat tagatcaact tctaatttca aagatttcta  98640
agatatggaa cagttactcc ttatacaaat taaaaaagca aatgctgaag aaattcagct  98700
acatggatac accatgaggt ggaaagatgc tccataactc ttagttaaac tgcactaatt  98760
acacataaaa ggaaaatgtt tcatttcact gtaatttgga aaccaaagaa agaaaagact  98820
gaatttttac atactgttaa agagattgcg tatctgttct aagtttaaga cagaggcaaa  98880
atgtatttta ttcatttgtc ctgcaccgtt tagaaataaa attcaacttc cttttaattt  98940
```

-continued

```
tttttaagaa taaaaaactc agtctaagga aagtcttaaa gttttcattt taagtgatcc  99000
actgttctag aagtttaata ttttgtttaa aatgtttatg ttctgtattc caccaagtct  99060
agttttaaaa caaaacaaac aacaacaaaa tacttctcta acttggagtt taaggtgaaa  99120
gaaaccaatt acgtggtttg gaaatgtcac actttcatc tcttttttaa aaaaattttt  99180
aattcaggac agaaattgta tggatttagt gtaagtcttg ggatctcaca agtgtcagta  99240
tttcactctc ctccatatct tgatagcaat aacttgaaat aggatctcag tagctcaagc  99300
aatactgggc tctgagagtt ggttaaaaat tatttggctg agcgcctgtt gctgagggaa  99360
gaactaatct cgagcatatt tttggagcca aataccaaat tgtttgtgct tagcaacaca  99420
gcaccaggct tgcccttcag aatgattcta gaccaaatgc cagaaatgct ctggttctga  99480
ctacagagtt ctattcacaa atgacaggag gcaagaggtc ctcctcactt tcagaagaaa  99540
ggtcctttgc tttcttagtc aatggtagga aaaccattgt ggttttcatt gcattacata  99600
atttttaagg tgattacttc aataagaagt gctctgtgta tatgtgtgtt tatagacgca  99660
ttttttaaac actggagaat ttctgaaagt agtacaaacc ttgtaatgtc aagtagatgt  99720
gggaaaaagg gagtttacaa cattctctcc tgacattgct ctcctttggc atctgcattt  99780
ttaaaatgtt aaaaatgttt aaaaacgtgt gcttaacact taatttggtg atagttgctg  99840
ttaccaaggc aactctgtaa ctccacccag ataaaaataa atcttgaaga tgagtttctg  99900
tgtctctgag caaatatttt tgtgaatagt agaagcagag aaagttaaag atacctgagc  99960
ttttgatctt tactagtttt atagatatgt ttatagttat acatttttat tcatacattt 100020
tagataaata actttgtaaa gcaattgatt cttcttgtaa aaatcaagta tattcttaat 100080
agactgataa actttctttt tttgagacag agtcttgctc tattgcccag gctggaatac 100140
agtgccatga tcttggctca ctgcaaccta cctctgcctc ctgggttcaa gcaattctcc 100200
tgcctcagcc tcttgagtag ctgagattac aggtgcatgg taccacaccc cactaatttt 100260
tgtattctta gtagagatgg ggttttgcca ttttggccag gctctgagaa actttttaag 100320
gtctcttttg cagccagcta tttgtctacc ttatttcatt cttaatctca ctagccaata 100380
ttttttctgt ttaagtgctt tcagcaaata ttaaatgctt gtgccttcag tcttatcctg 100440
tggaaacact ggtaatgaca aaaacacata tttcaaccta atatacaata gaaacagaat 100500
gccagttatt catggaggag aagaatagac ttctgtattt aaaataacat tttgctctgt 100560
gttttaaaat cattcttcct tcatcaattg taagcatctt gactataatt tatacaccta 100620
aagataaata attcagtagc aatgataact gaaaacagga cacatacaat gaactagcta 100680
aattaccata cattctcatc catttcaaaa atagctctgt actttttttca gattttgtta 100740
gaagaatatt caatacaaat ttttattcaa tgaacacttc agatgtcaag attgttaccc 100800
acatggacaa cagtaaccta ggtaaagatt ctgcagccag gcgtggtggc tcacacctgt 100860
aatcccagca ctttgggagg ctgaggcggg cagatcatga ggtcaggaga tcgagactat 100920
cctggctaac atggtgaaac cccatctcta ctaaaaatac aaaaaattag ccaggtgtgg 100980
tgtcatgtgc ttgtagtccc agctgctcgg gaggctaagg caggagaatc gcttgaaccc 101040
gggaggtgga ggttgcggtg agccgagatt gcaccactgc actccagcct gggtgacaga 101100
gcgagactct gtctcaaaaa aaaaaaaaaa aaattttata cctgggctct gtgctcacca 101160
gcagaagggg taacatggct tcttaggaca accttacttg accatttact tctttgacac 101220
taggggtatt cttagatcag caggtccttc cctccactta tgcacatgag gctcacagag 101280
agtctgggag gcagggaatt tatgattgga aacagtatac tttttatcta agaaattatt 101340
```

-continued

```
aatgtcactg cattcaagtg attaacacca tcaatatctt caagactaag gggattacat 101400
gatgtgtaaa attagaaaac tgtcatctac tagtggctag gcactttaat tatattaagc 101460
atgcaacaag agaactcttc aaatgaatcc atctctcctc tgtattattt ccaacccttg 101520
gatccccatc tgtttctgca gacaacagct atgctgctga atgtcttaat ggtttgctgc 101580
cccaactagc ttcaagatac tgcaggtcaa gcatagcatc ttactcttcc ctgcatctcc 101640
agcacctctc agaatgttgg tcacatagaa gatgtttgct gaggagttga ataagaatat 101700
gtacaaggga cacaattagc attgtttaaa aaagatgtaa caagataggg taaaggaaag 101760
ctttggagga taaatcttta gaacaatcaa taatatcttc tcctctgttg gttagttgcc 101820
cttcaatctc agccactgaa tcaaatacaa cataattact attctgatat gttcttgaat 101880
cgaatatcca ataataagat attcggatgc atagccatgt ctaatatcaa agcccatgct 101940
tttcgctatt attgtactcc atacattagc ttccaaattt atttgcaatc caaatattaa 102000
aagcaagtca taagcttagt atcgccaatg tgatactaag tatccactta ctaaacttta 102060
ttttcaaaat gtggttttat ctcagtttaa tgaacacggc atgttttaat ttacactttc 102120
atattatata gtaagggcgt ggttacagat atgttaattt cctgtgctgc ttcacaatga 102180
tggaacataa tagcaaatga aactgttaat ttgcagatac ccataggcct ttggtgtctg 102240
aatagaaata aacacaccta caactgagag aggaagcatg tgaagcattc cagtgaacag 102300
aggccattta ttcagtcaca gacacaggag aaaaacaaca attaaaaaaa aatctctgat 102360
gaaaagttca taaaaagttc actcagttta agcatatgtc ctataactac ttaaaataga 102420
gttcttctta aatatcattc tttgctgttt ttagatttct tctgcctgta tcaaattaat 102480
agaacacagc atacttttaa tttgctctgg tttcttagtg gggcatttat taaacacatt 102540
aaaacaatag tctcagggtt ttactgctga tgttaaagtt ctgctttcct acttaccaac 102600
tgtgtcatct taaggcacat actttgcctc tctctcaaat ctcccaaatg gagaatgata 102660
agaatacgta cctcaattaa agaagctata acaagtagaa tgtttggaaa agtgccgggt 102720
acaccataag cccactatga gtattggatt gtattacctc tgaaagctgc agaatggaat 102780
tctcaaagtt atatgtccct aaaatcctct taagtgacag aaatggagaa attagcagtc 102840
tgtctaagag agcttttcta gagtctgggc atatgttttt aggacaagac agttcagctt 102900
cagcttaaaa tgagagagca cgtctgtgtc cttactcctg ggtgccaggt ttcttgtccc 102960
catcttaaga caaataattt tggtggagaa gaggcagtct ctttgatttc gctctaaaaa 103020
ccttttctgg aggaggtaga cactctccac ccccgttttg agactcatgc agctgaggat 103080
gactggctga gtacaagcaa ttgttccttc taagcagttt caattcttat aacttgtgga 103140
gatattctta agtccagggg attttgtgta tggtggattt ttattacaaa gtcctgtact 103200
tcataggaac aaaataattc aaagtcagga accagatcaa agccacaact cagatatggc 103260
accttgagaa gttcatttgt atttcacttg cataaaaacc ctcaccactg ctatctgatt 103320
ttcacaaatc attcaacagc tatccatgaa gcacccactg tgtgtctggt ctctgtgtca 103380
gtccctggct tcatgtgtct ttccttctgt accctgactc cccaactcat gaacacatga 103440
agtaaaaaaa tgaaaatctt tttctgacct ctcttcaaaa tcactttttt caaaacaaac 103500
acctctcacc tgctcatcct ccagccagta aatcacaggg gcctagaaat gtcacttaca 103560
aatattttct gattctgtcc ctcccttcaa gcttgccaac attatcacag tttagggcct 103620
gctcatcttt cccccaatct ccaattagat ctctccacaa tgcaattctg cacattccct 103680
```

-continued gttacaaccc ttcaattatt tcccagccca tccaaaataa aatctaagcc tcttactaac 103740
acattcagga actctgtggc ctacggtttt ctacagacta attttccagc agttgacttc 103800
cagtgcaagt gaaaacctag tgtcatgcct gcatgataga taaatttgaa gctgaagagc 103860
ccaaatgtat agaccatgcc atgaaaggtt tatagtcatg acacagtggc cctatagtac 103920
agtgcttgaa gctggctctc tactgtcaga cagaccactt gccagccatg agacctgggg 103980
caaaatgcct taatttttat gtgcctcaag ttctcatgtg agatgagaat aaaaattacc 104040
cctatttcat aagatttgat aaagtgttta gcataatacc tcataacaat tgcaattcag 104100
tggtggttat tattataaag aaaagatgat taactttatc ttaatgttta acttgttctg 104160
atagttattg atctatagct ttgatatgga ggtttgagaa tgacctggaa agaattggcc 104220
acaatgattg aagatagtga tacaagaata aaagatgact gcaaaatgta aacctgcaat 104280
aacagaaaga atgaagtcac tggtctcatg ggaactgata tgggagaaaa aaacagatca 104340
aaaggctatt catgttttgg gcctctttgt caaaatggaa atgagaaact ggggaataaa 104400
aattaaagca attctagcat ctggttttaa cataattctt atccctaaaa agaatctata 104460
agaaactccc aaaatgacag gcagccgtgg gtagcattgc atttcaagta atcttttaat 104520
tgttaaaatt taagtttcca acatgaacat aaaattttca acctaaaaga aatgagttcc 104580
aaatctgaga caagtgaaaa aggataaagc ctactagggg gtaaattcca tctctttaga 104640
gatctagtac ccaatttagc aatgtccaat caagccttta actactacat ttgaacacct 104700
catcatttca aaatgttact taatgatgcc aattaactgt acaatgtctc tgcatagcac 104760
atagccctaa aatgatttgt gcaatgttac tgtcagtaaa actgaactac agggaatgct 104820
catattctat gtcattatat acagaaatgc aatatcaata aagtgatatc tgttggtatt 104880
agaaaaaagt gaaaattttc atatctttct attttctttt ttcctcaatg ggatgctctt 104940
gttaaagata gctctgcata gtaaggtttg tataaacatt atttagctaa agttaaaagg 105000
ggtaacatac tggttctagc acagatatta aaacaaatta gtttgtaggt agggcagcaa 105060
tcaattatat tactaaccat agctttggtc cttttatcct ttcccatttg attttacaca 105120
gtgggatgtt aaaggttgaa tgtctttggt atctataaac ttaattgaaa gctgttattt 105180
gtttgtttaa gtctgttgat ttttataatc ataattttac tcctatagat ttcttgtagg 105240
agtactatat gaatttatgt tgcactgaat tttgttatgt tatacaaatt aataggcttt 105300
tatttatgga aagctactat tgatctgtca tttcttaaaa aattactaaa aagtgttaaa 105360
actttaaatg ttggagagtt tatattttaa aagttacatg ctagaaaaac atgatgtctg 105420
agtatattag aagttataga taattcatct gtcaactata aaactctcca acactgcctt 105480
tctttaatga ataatatgaa atttagcagt gaaaatgtga caatgtacaa tcctaaataa 105540
atcaacaaat ttagagatgt acctctaaaa ccattgtaaa ttcaacagtg taattttcca 105600
ttggactttc acttattcat tcattaaaca aatgtttgtg agtgcctgca atgtatgaga 105660
cattgtactg aagctaggca gtgtgagtta tcatatggga ttatccttta aatacttctg 105720
agggcaaaaa aaaaaaaaaa aagaagagaa aaggtgtgag gaaagataaa gggttaattc 105780
attaaaaaat aacacttgag gactgttttc tttgcaaggc ataaagttat caccctttca 105840
aacagtagat atttcacatt taggatgcga gactccagtt ccaacaaagc tcattgcaca 105900
gctgctaccc tgattaaact gctacatgaa ctctgagcaa tgtagcatgg tagccgcatg 105960
cttctgcttg catgatggtt aattccttcc attctcatta gtgattttct gagctttgaa 106020
attctgatgg tacctaggat ataaagcata tttatctaac tgaaaaacag ataattagat 106080

-continued gtaacataaa atatgaatgg ctttgtcact ttattgtagc agagaatgaa tgtgggataa 106140
attaaagctg atgctagaac atatgcctat tttttagctg gaaaatttca agatttatgt 106200
actttgggct tgagaaagaa atggagttta ttttttatgc actgacatct cttttttttt 106260
ttttttggaa gagctctctt aggaatgaat ggtatgtaaa tacagtagga atgtaattat 106320
agattttcct gacccagttc ctaaataata gatatcattt cagaagtgcc ccaatacctg 106380
accttttgct ccaagccata tcaaagcaca catctagtct acttttcact ctcattccta 106440
gccactatga caatactatt cagataaaac ttctagtcct ctacttatgt gactcatacc 106500
aacttgacct tacgatagtg actgggggtg catatctagg ttcatgctgt ttgtccatta 106560
ttatggtttt gtgagaaaag gcaaaatttc taggtaaagt gttatgagga cgaataatcc 106620
accaggcaac caactgaccc tttcatttgc catcttgtca cttcaaacag ctctccagaa 106680
cctgcagcca gcacagacca aagtcaggtt tgtctcctct tctgttgatg aacaaaggtt 106740
gattccatat cgtggctatt gtgaatagtg gcagtaaaca tggcagtatt gtatgaaaat 106800
atcacagata gcccttaaat atgtgcaact atgatgatct atcaaaatta aaaattaaaa 106860
tttattttta aaagttcagt tagaaagctt gtagttcctg gcaaactact acctttctcg 106920
gcaaaagaat ttgatatctc ttaaatattt tctgcctaat gctgatagat tgtatttaca 106980
tattccatta atgcaataaa taaaattaca ccaaaacatc agcattattt atttccaggg 107040
gcatctctca aaataaattc ctccaaaatt cacaaaacca aaaccaatgt gaaattgtac 107100
tcagggatgc aaatgtagcc cagtgaagca tttgcccact tgtttggtat tattgaagca 107160
caattagaaa aatgtgcaat gtatgcccaa aaattctata ataagggcca ggcgcggtgg 107220
ctcacacctg taatctcagc attttgggag gccaaggtgg gcaaatcatg aggtcaggag 107280
atcgagacca tcctagctaa caccatgaaa cccagtcttt actaaaaata caaaaaattg 107340
gcccagacgt ggtggcggga tcctgtagtc ccagctactc gggaggctga ggcaggagaa 107400
tggcatgaac ccaggaggca gagtttgcac tgagcctact ctccagcctg aacgacagag 107460
cgagacccca tctcaaaaaa aaaaaccata ataagaactt tttaatatac tatattataa 107520
tgtaaaaaga ctagatgtca aacaaattag gtgatgggaa ggaattgagg gagaatttta 107580
gactaagcaa ttgagcagca cctgtttttc accacaaatc tgttacatgt attgctcaat 107640
tgtgctgaat ccatattggg tcctggtggc tatgtaatag tctctttctt ggataaatgt 107700
ttgtcctctc ttatggttta ctaatggtgt acagaacagc attgaatagt ggttatttcc 107760
tatgacttcc tagatatctc tctcataatc ctgaatgttt taaagatcat tcttagatag 107820
agtacagcta gacacgaacc atagtggaaa tcaggtagac aaaatttaaa aggagtctta 107880
attgaaggtc attttattgt cctcagtatt aatcttactt aaaacaaacc tgtcactgag 107940
cagaactcaa aacaccagag ccctttgcca aatgtgattt tttacaacag gagcgctggc 108000
agttgagagg agtattctgt cacacttgag agaattcgag tccctgaaga tttatatgaa 108060
tgcttagcta ttatcgaacc atctcttcac agatgactta gtaaatgtct gcctttgcat 108120
cagataatgg cttacaagtt aatctcctct tgctccctgt tacacacata tacaccttct 108180
tcctaaacag ctcataaggt gaaagaaaga ctcagatttc tgactatgta attgataata 108240
tcacacggac tgcctgctca tcatctgcta gtcacattgg cagagttgac agttttggag 108300
acactgaaga cagtgcatat attaggaaat aagcagtttc ctgatataaa ttttcttgta 108360
gtttataaat tacatagcat ttattattcc ctcatatttt ataacattta ataatagaac 108420

-continued tgacacatat attcatttta aactcaattg tgtataataa ctatcatagc aacccttcag 108480
tgcctaaata tcaaatcttc cattcctccc atgaacatct tgaatatata ggtactgtgg 108540
ttagctccaa caagcttttg gttagaattc attgcactga tacatagaca ttgttttaaa 108600
ggcaatttca aatcaaagct gtcagctgtg aatcaagcac accttaaaaa gtgacacatt 108660
tgtcactaga ttccagcctc tcaaattact gacacgcatc ctttttatgt aaagatgaca 108720
ttgttctttc ctgatatatt gcattcctca tgaatttctt atagtcatag aatttttata 108780
aaccatttca gaatcgctga aataaacatc aatattttta actttttcat tctgtcaaaa 108840
atattgtatg cagagatatt gctgtaagtg tgtatacctg tgcttaagag actagggctg 108900
aagagaagta atcaaccgaa ccactggtgt aaatgtgcgt cacattttta gtgactagaa 108960
attgaaataa ttccaacaaa tttatgtgct ttgggcttga gaattcagac tgccttaggc 109020
taagataaaa atcttttcct ggtactatat accttctttt attgaatgac tacctggctc 109080
tttctattat atatgcagat tttgtacctc tggtcatctt tgtaaatggt gcctaaaaga 109140
tatttgaaga ataagtgacc agcaataaga acaaatgtct atacaaaagc accctttagt 109200
tggatgtaat tcactacttt gagttgttaa taacctctaa ggatgacagt agctattagt 109260
tgaataaacc attatgtcta ttattagaac actagatagt ttataagtcc aaacaatgca 109320
taaaatacct atctcatgtt accattgttt aggttaccag ataattgttc tgtccaatta 109380
ttccacttaa tttttttgctt gcccattagc taaatggcaa gataaaattt gtcaaacggg 109440
ggggaatgta ttgaaaatgc tagacaacta cacttaaaat gaaaacaggc caggcgcggt 109500
ggctcaggcc tgtaatccca gcactttggg aggccaaggc gggtggatca cctgaggtcg 109560
ggagttcaag accagcttga ccaacatgga gaaactccat ctctactaaa aatacaaaat 109620
tagccgggca tggtggcaca tacctgtaat cccaactact ggggaggctg aggcagaaga 109680
atcgtttgaa cccaggaggc ggtggttgca gtgagccgag attgtgccac tgtattctag 109740
cctaggcaac atgagcgaaa ctccatctca aaaaaaaaaa aaaaaagaaa gaaaagaaaa 109800
caaatgcata atttgcaaat attattttta tattgtatgt tatctagggc ttctaaatgc 109860
attcttctta taagcctagg tttgcaataa cattcattta gaattgagta attttaaata 109920
taatatttta taaaataaaa tataataatt tctcttaatt ctttgaaaat attaaattaa 109980
aagggggttg caaactctgc attccacatt tccatcccaa catttaattt tagcaatttt 110040
gtagtctgcc taaaatgcaa tccatcattt actgtttaga aaatagggaa tgtacacaaa 110100
ggcctttcag ctttccctga actccataaa aatctttttg cttctttact gccccccttt 110160
gtcaggagtt ctgaggaact gtttttttatc ttaagtctca caaagcattt aggagaatat 110220
ttaaacttaa attcttttaa aacttatgtt caggacaaag taacattgta tgcattggtg 110280
tcatatgtat ttaaattttg aaatttttaa tactggcaaa atgaggtttc aattttaata 110340
taaattattt aacaatctta aatcattaaa tatattactt aatatattta atatatctaa 110400
acagtcacaa ttttcccata ctaataatca taaaaaatct tacccaatgg tcatatagat 110460
atacttaatg gagttttggg ggggtatttt tgtatattaa aaaattcata tatttgcctt 110520
acttagaaga actgattaaa tgaaagtata atattaacaa acatattgtt attttatatt 110580
tgcatttgtg ataattatat ttgaaacgtt caagattttc caatgaattt cttttgcatt 110640
tgcgtatttg tgccttttta ttataaaaat aggtggcttt ttagttccac tgcataagtt 110700
tcaacatagg tctacaaata gtgcatcttt ttgaagttaa tcattataat cacaaattga 110760
agttgcctga gctccaattg gagtctaaat ggatgactga atcttattat tcgaaaccca 110820

-continued ctgttgctac acaatatggc cacacaagag agtacacaag acccgtctga ttcagcctca 110880
gtgccataaa tattttaatg gtttcgttgg aatctggaaa tggagctcac cacaggagat 110940
gcttcttcct ttgactctca ttattatttc ctttacaaat taattaataa aaacttagat 111000
gctaaattag cacttgatga aaacttatat agccttgaca ttttgattct gtgagtgaat 111060
aaaaatactt ggagaaataa aaatcctaat catgttcagg aatacccaca aggtaacaag 111120
tacattttta aactttaaaa acatttatta ttcatgataa aacatgttgt gtgatttaaa 111180
tataaatttt tattatttgc tttaacttat ttccggatta aaaagtaaat gtttacctag 111240
ctgttctaaa tggtaatcct catgattaaa acagcaattt gtcatatttc agttacaaat 111300
gatcttttat tattagttat agaacataag tttcttcatt gactgaggcg atgtttcaag 111360
tagataaatc tgttaaaaaa attgtggtca tattctgtta aattctcata ccaggcaatt 111420
tgtttgatat tcaggaaaaa cctagccact gaccaaaaac tctacctgcc ttctcagttg 111480
tatcctcttg gacttaaagg ggactgggaa agttataaga tggttcatga tagtccatca 111540
acatcccaag aacaaaaaca gatgttgtac tgacagcatc atatgatcat atgcatgtaa 111600
gagcacattc atattgccaa atcagttgga atttttcacg gttgaaagtt aaatgaaatg 111660
cttagatgta tgagtcatcg gagttaaaga caattacagc cagatttatg gctgtgctaa 111720
aataaagcta gttagaaaac agaccaaatt ccatgacgat accaagtctg actaatgatt 111780
caccttaaat ttcggagcaa catttatcct cacttgtttg tttatttgac aatgtgccct 111840
tatccattaa gtaactagga ggaagggaaa agcactacgt gggtgagtga caagacactg 111900
acactgattt gtgactttgg ataattcctg gatgctgtta tctgttttgg catagagatg 111960
gatctgtaac tgctaataat tgccgactgt gaccatccca gaggccattt acttaaccca 112020
ggtatttcag acctgacagc ccgaggataa acacgatttc cctccatcac taacttcatc 112080
tgcagggcct aagcctcctt cacagtctct ccagtgattt attggcatct ccaagggtat 112140
ctcacatgtg ctgaagaaca aatctgctca ctttcatctg cttggtttc ccttttgaaa 112200 tctgctgctt taaaattact aagggaggaa tcatgcctgc tgctaccctt gccagtgacc 112260
ttgcagtttg tgccctgatt gttccaatta ccacaatcaa aacagaagcg tttgcagtta 112320
ctgcagtgct ctctctgtgg atgtcaggtc tgactcagag agccaggctg gggaacagcc 112380
atttccactc ttgtacctct gcaaaaggac ttccatgttc cgtaaacaga ctcccacctc 112440
tcatttcccc cccaagcaaa gcatcataaa ttagagagca tgtaacggga aagaaaatcc 112500
attagccatt tgggttcagt cagacaagcc agctcatgga aagtttatac aggaaggtca 112560
catttcaatt gagatcagga gggtgaaagg gtccagctgt gtgatgagag agagaatgtt 112620
cgggaatgtg gaacagaggt atccaaggca gaacaaactc gtatatgaag gctttaaggg 112680
tgtgcaaatc tagcatattt tatgacataa aagagtcctg attagctaga atatgatgaa 112740
tgtgagaaga ggtgaaggct ggagatagga aaaattattc cagatcttat aagctatagt 112800
aagaaatttg catattatat atagacttgt gggaagccat tggattttgt aagaaggaga 112860
ttaacattat cttatttatg ttatttgtga tttataaccc caaatgtgcc agatacaaac 112920
aaaccaaaaa taataataat aataataaga agaagaacaa caacagcaat ggaactgtgg 112980
tgatggtttt ggtcacaaaa tgcatatata tctatttttc acaatgcaaa aatatttcat 113040
tatttcaaat tttaacataa atgtgggtat gcatgagctt acaaatcttg aagtttattg 113100
gggaatattg gtgagcatgg tttttattgc atggtcacaa cttactaatg ggaaacatct 113160

-continued gaatacctat tgagttaatg catgcacatt tttattttcc tggaatactg agaaaaaggt 113220
tgctacataa tgtcttgata gcttctaagt catggctcaa aagtgaatgt ggaatctgct 113280
aatcggaatg gactcagatt cagccaagtt ctcaaaaaca tttgctttca tagatgtctt 113340
caagaaacaa ggagtcttga atttaaattg tgaagtgtct atcttagaat agagagattt 113400
aaaatctgac tgtattttgt ttaaaaaagc ctatataact gtattatata aaattattta 113460
tactacagtt aaaaaaagaa tcccatccta tttgtgccta aataagtgcc tgcttgtagc 113520
atgaaaacta tttgttgagg gtccttagat cctcagagca tgctgtgaaa gtaggtacaa 113580
ttgttctttc tatataagcc tcttaagata acagataatt gccagaaata cagcacacag 113640
tacaaaatta ccttgtttta cttttgccac aaaaaacaat ttcttttggc tttgagcaat 113700
aaagtccaat gatttttttc ctttcaaaat atcttcctcc ctctccataa gttttatatt 113760
tattcacgaa ggaatattcc aatatcggat gtttttgtct gtgtctcttc ctggaacaaa 113820
tgttaattaa tctctttggg tttgtatgtc aagtggaggg gtggggattg gggacaggtg 113880
atagttgtct agggagttaa cttcatctct ataggagagt ggatagacgc tgtatacgaa 113940
aagctcttga aaagggaaat acagcagcca cttcctcagg gcttccatgg tggtcagact 114000
ccttgattgc tttagattaa ctctggcttt tgtccttcgg aggccaccag attgggtgga 114060
tagacattgt ccttgctgtt cttttgacct acctacttgt actttagggg aaaaaaatgc 114120
ctgtaatagg ttaaatgctt tctcaaagat caccaaagta tataacacat ggcaaataga 114180
cagagaaatg agacagtata atcagtataa tttataaaag taccttacag caggatccca 114240
tgggatatgg gtttttttta aaaaaaatct acctaatctt ttcattgaac tcctattcag 114300
gattcattat attgaatatg gctcagagac ctggaaaatt gtttccacct ttttaattta 114360
ttcaccatca tttatggaag ttttcaagga cgtttactta cctacctcag ttaacagatt 114420
gtactacttg ggaagtctat aaatatgagc ttaaagcatt ttctgagttt taaaataatt 114480
tagattgtgt agaatgttaa aactaaaaga ggaaaaaatt attcagttcc tcagttgaac 114540
ctagcaattt atcttttcac agtgtgctca agtatagttt ttgaaaagta aagaagatgg 114600
tttttataca aacataaaca catttcaaag attttattca actaattaat tagtagtgga 114660
gccaataagc tggtaagact ggtttaaagg aatatctgag gaataaagat ttatagaaac 114720
agtcaaagaa attctaaaga gaattgacta atagatataa atctagtaaa tatttgatta 114780
ataatagcag taacctatgg aattatgttt tctactgagc ataaatgagc atgaatctct 114840
ttgggtttgt atgtcaagtg gaagggtggg gattggggac aagtgatagt tgtcaaggga 114900
gttaacttca tctctatagg agagtggata gatgctgtat aagaaaagct cttgaaaagg 114960
gaaataaagc agccactgca catctgcaca tataacctgt agatctgggg gctctaataa 115020
aaaagttaat ggcaatgtca aaatctggtg ttttatctta gataacttca tagtcattga 115080
ttgagcccct taaaaataac atttaaagga catgtagtca ttctgtttct ttattgccaa 115140
gttttcagca atttttctca tgagaatgag tgctaagaaa cttttggtgg agcgtggtgg 115200
ctcaagcctg cagtcttgca ctttgggacg ccaaggctgg ccaattactt gagatcagta 115260
gtttgagacc accctggcca acatggtgaa accttgtctc tactaaaaat acaaaaaaaa 115320
aaaaaagtgg gatgtggtgc atgcgcctgt aatcctggct actctggagg ctgaggcacg 115380
agagtcactt gaacccggga ggcagaggtt gcagtgagcc gagatcctgc cactgcactc 115440
cagcctgggc tacagaggga gactccatct caaacaaaca aacaaacaaa aaagaaactt 115500
ttaaaatata acaatagaga cattacatag gcccacaaaa ccacctccaa aaaagcattc 115560

-continued tatcacctgc aagaaagcat atatatatat ctgcttttgt gtatatatat atatatatat 115620
atatctgctt ttgtgtatat atatatacac acacacacac acatatgtgt gatatcagca 115680
tgtgtattta cacatatatt ttgtgcatgt atatttttaa ctaaaaatgt gctaggagtt 115740
agatatgaac tgattttgga ggaggtgata tgctgtagag agagagaatg ggagaatagc 115800
agtattataa tctctctcca ttgtattcag tttttttctt tgtctgaatt tttaatagaa 115860
gtcagccaga agatgttagt ttctgggaaa tgtgttgaga tttacagtca aatccagaga 115920
gaactagagg cttatgagta aataagtaaa ggttatgcag agaaagtatt ctttttcctg 115980
tgtaaacttg aatattggcc aggcgcggtg gacacctgta atccagcact ttgggaggcc 116040
aaggcgggtg gatcgactga ggtcaggagt tcatgaccag cctgtccaac atggtgaaac 116100
ccattctcta ccaaaaatac aaaaattagt gggtgtggtg gcaggatcct gtaatcccag 116160
ctactacgga ggctgaggca ggagaattgc tttaacctag gaggcggagg ttgcagtgag 116220
ctgagacagc gccattgcac tatagctacg gcgataagag tgagacttca tctaaaaaaa 116280
aaaaagaaaa gaaaaccttg aatatttctt gtacttgtgt tcaaatcata cagttatgaa 116340
agtttacccc tagctgttac acttaaaatg tacttctgaa atatacagag agatgataca 116400
gactattaat gagttccact aaacttttaa tggtttagaa aatacaaata ttttcttatt 116460
tttctggaat tccagccatt aatgtaaaac attggtttca acataaataa cacactggca 116520
tgcacatatg cctaagcatg ggcccccaca catacagaca ttctgaaaga ccacttttta 116580
aaaatattca gtaccgtata ttgtgcattc cttctttatc cacatactta agctgctgca 116640
agcatcccat tgataacacc agtaataaaa gatgggacca tcagtaatga gatttgaaag 116700
ccccttttgc aagaaagtaa ggactagaag gtggaaatca ctctgtctta gagtcatatg 116760
gattggggct ttgctagaag tgtgtgctct cagggaaagc tgccttttta ttttctccag 116820
agaaaagcct ttttgtcagt aaaagaagat gtatcatcca atgcatatgt aaaattctaa 116880
acagcagata aaacaacatt cactattaat ctctgcaaaa gaagatatat tgaaaaaatc 116940
ctcaagtgtc cctctttggg tttctttgtt atatattaaa gcagttatct ttagatgcat 117000
gagaatcacc tgaagacctt atttttaaaa ttcagattcc tgtcagttca ctcccaaaga 117060
ttccgattca gtagttaaga gacaaagcct aggaatgtga atttacaatc aacacctcag 117120
gtgatagcca tgcatgttct taatgctcta ctactatcta tgcataaaag gaagataaag 117180
ttttaaaaac ttgaaatgtg gtataacagt ttagtattga ataatataca tttttactta 117240
ttgtaacaaa ttatgatatc tacttggggc aacagtatct tttattttgg atctgaatcc 117300
taattttggc taggtatcac tgagggattc ttagtctaaa acaattaaat ggagttagtg 117360
gtttttttta gtaactcttg attttctgtt tttttccatt ggcatcttac aaaatttatt 117420
cattcatttt tcccttttttc acttggcatt atttgttaga cagtggacaa aagaactata 117480
gaaagtagag aagcatgtga tgttgtcctg ctcttagatt ctcgcaactc aggagaggac 117540
attcgcttac accaatcatc tcaaaacatg gcagtttatg ctgaactcag tccaatggga 117600
gagcatttga ctgagcacat agggagagaa gttagctctg ttgaaggata atcaacgaag 117660
aattcttagg aaaggtacag tcattcattg aatatttgct cggcacttac taggtgcata 117720
tgtgcactaa gatctaagga tgggctgatg aagaacccag gtcccttttc ttctagtgga 117780
catgcagact ggcctaaaaa aaaaaaggta actggaaaat ggataaggaa actgagtcac 117840
tcggtttatt tattatcact cggtttattt gcttttgttt gtattttcat tttgacacag 117900

-continued cacagtgtca tcttaacgca tcctccaaag tgaaggatgg ggtggataac actttagttg 117960
gcatttctgt agccaggagc caggatcttt ctcccataat tgcattaacc tgggaaggca 118020
ccctctaggt agatttgtat agcaccctgg ttaatcaatt atcagtttac ttcttgtctc 118080
actaagcttt aacaccttac atttatgaag cagtgtaaat ataactttag catcttgatc 118140
acagcaagca cctgatttgt attttttat tagctcaagt gaaatcagat cagagaagta 118200
cattacaggt cataaaatat gtgcaaattt cataatgacc tccttttaaa atgtgcaaaa 118260
ataagattgt taaggcacat tccagagcct tggggggtgt gtgtgtgtgt gtgtgtgtgt 118320
gtgtgtgcgt gtgtgtgtgt gcttgtcttt tgagaatatc tgtatatcag aaaatttggc 118380
tgagaagcaa tcttcttctt agtggttctt tttctctttt gaaaataaag tactaaaaat 118440
acttaaagat gcagaacagc aacctgttcc cagtgagact ctcgtttaat taatgtggtg 118500
atctatatag agaaaaggga caattgcaaa agtccctcaa taattatcta accacagtct 118560
ttaggtaatt acagcagaaa gattttcaag acacaaaaca ccctggaaaa tttgacctct 118620
tattttgatt caggcctttc atttcttaaa tattttcttt aatgttgatg tttatgcttg 118680
acaaggtcag cctaatgcca gatgaatccc tggaactcaa aacattgctg aattcacagt 118740
tgaaggattt taatataata taccagcttt taaaaatcct acagtgagaa taacaggact 118800
gaataaaaaa attaagaaat gctcaggtag aaataaatag agaaatttag aaaaaaaata 118860
aaacgtattc aaaataagta ttaagcattg gcaaagaaaa aatagtagca gacaattaca 118920
tgttccattt gtaaagatga ttattaatta gtggtcttgc aaaacattgg agaaaatttg 118980
ctgaaccatc acattcataa atattaaaac cacccattag tgaaaatctt tttactaaac 119040
ttcacaactg atagtcaaat aatgttcagt ttttctccat tgcaataaaa aataaaggct 119100
tttgccttca gatcagtctc tggccttat taattcagtc agccagaagc cacatggaaa 119160
tattttgttt tgttaaaagc cagcttgccc tcatgatctt ttaaaatctt ttaaaaatct 119220
tccatcagcc ctctccctga cttgaattat ggcagtgctt tctaaactgg taaactcaat 119280
ctccttggtg tgcctcaaga tagagtacat aaaccctcct tagaaattga gctctcaatt 119340
ctaaattgca ctctccatga gagcaagcaa gaatgctttg ctttgtatta agtggtcaca 119400
atattaaata taaccataga cagcactgta ttttctaaac accttatttt cttttaatga 119460
ctgacataaa ttagatcata agtatacaaa tgcatatctg ttgtattttt cagcaccatg 119520
tgtttttttt tctttttct gagttatttt cctgctttcg gcagcctttt ctctcaggtg 119580
ccttgtgatc cacagtggtg tgtgttcaca ctaaccaaag caatagtctt acctgccaga 119640
aatagctgtg acatttaaag agaggtccag gggaaggcac agtgcttaac atccaagtct 119700
gaagagctaa tagtgaaatt ggggcatcag ctacagagag atttagggga agtaacaggc 119760
aggttaaata ttttatggaa atgatttctg ttctgtatat gattgcaatt aacacatgtc 119820
aatctgtttc attaatttgt taactcatct attatgctat gccatgaaga aaataaaatt 119880
ggagttcttt attttttga gatggagtct cactctcttg cccaggctgg agtgcagtgg 119940
caggatctca gctcactgca atctccacca cccaggttca agcgattctt ctgcctcagc 120000
cacctgagta actgggacta caggtgcgtg caaccatgcc tggctaattt ttgtattttt 120060
agtagagatg gggtttcacc atgtgggcca ggctggtccc aaactcctga cctcaagtga 120120
tccgcctgtc ttggcctccc aaggtgctgg gattacaggc gtgagccacc gcgccccgcc 120180
acaaaactga agttctaagc ttcagtttag atgctcacta aatgcttgtt ttgcaatacc 120240
tgactgtaac tggcaggaat atgttttgaa agtcctcatt ttccaggtat gcagatgaaa 120300

-continued tataggggca ttatctacta tgtcaaatta taatgattta tcagtggcac atgaaagtcg 120360
cctcacattt cttaatcagt gatataccat tatgtcatgc caccttttaa tgtaatatgt 120420
ttacatcttt ctttagatgt aagcattcat ttagttcatc acggtggctt tcacacttac 120480
tccaagaacg ctatgagttc ctttgatgtg ctcaagtctc ctgccccagg gagaaaggga 120540
gtggtgagca ggaatcgctt taatctattt acacagatat tttcttttcc atttatttta 120600
aaggaatttt ttttaactta atgagtatgc agtgacggtg gtgatgatga tgatactaag 120660
gtttaaatga ttagatagtc aaatctgggc tggaattgta atactgtttt gacttttaat 120720
cttagagaag ctccagtctg cttattttct gggcataaac acatgagaac aataacacag 120780
ttctgttatc tgaatgttgt tatattttgt ttgaaacatt cagtgacttt caaatattgt 120840
atttgcctaa gaaaattcaa cagagtcaga cattctcttc caggttaaat ttggtgagtc 120900
tgctaggaaa ataaattttg tgcactggtc attctgatct agtggacgtt ctaataaaag 120960
cacctttgtg ctgcctacgt cttcacttta aagataagat acctgggtac tcgacaccaa 121020
attatagttt gagatctcaa aaatgggata gggaaaccac agctcaaaaa caaaaatact 121080
agcactggaa aagatagaac tagtgaagat gaatcattct ctagacttta aattcagaga 121140
tatcaaaatt aagaaaaagt aggaggaata aaaaaagagg gtaagcaaaa caatataagt 121200
ttgtatagca agagggtata aagcaaatac aatatttttc agaaaaatta aataaaaata 121260
gatttacata acattgtttt taatctcaaa gatcaaattt caattttcat ctcattttaa 121320
aacccatatg cacagtctcc tttatataca tcagttgggt gtcaaagtga cttttttctt 121380
gtttccaaat acagttattt ttaaaattta attgtatgat ttaggaattt gaaagcaagc 121440
cagtttgcac acacatatgt tattatatgt gtgctttaga cttggttttt agttaatgta 121500
acatgacagg gccacctgag ttatttgttt acaaactagc tggaaagcca ccctggagga 121560
gaaacctggc aacaaaatgg tctgcagctt tgttattgtt atctatagga ttggatgcca 121620
ttattgctgt aaaatagttc acaagaactc agtctatggg aaagactcaa aaattctttg 121680
cctgttaaag aaaaatcagg atattggact ggttagttta actaaaaagt gatgatactc 121740
agattctgct tggattcact gcttctcagc agttgttttg tttctttcta attgatattt 121800
tatttttcag agaacccatt ataaaactct tcttcttccc ttaaaatcac aaccacacaa 121860
cagcaattaa aacatgcttt gacgtaagac tgatatggtt ttaaacccag cttgactatc 121920
gaatttttta ctttaggcaa aacacctctg acatttatgt cttatcgtca gtaaaaaggg 121980
gtgattaaca gttttacaag attattcaat aaataaatat aaattcctcc ttttccttcc 122040
tttcctttct tcatcttcag catctgcatg ccataagctc attttagttc tctggactca 122100
tgttaacatg tcccaccttt cccaaattaa acatcatctc tgttattggc tccattcttt 122160
tcctctcatt tgagacaatt ctttatcaac caacaccctc tctgctctgt attgtgaaac 122220
tctgctccta ctacattaac agtctcttgg tttctttaaa aagaagacaa aacaattaaa 122280
gaacagaagc aaaaaatcta ctcaaatccc caattgttac cctcaaaatt aattgtccca 122340
cccctagctt tctcattgca caactctttg tcaaaatgtt ttctaccatc acagccttca 122400
atgatctttc tggttccttt atctcctgaa gtctgacttc tacctccatc tttttctgga 122460
ctattcaaca cactttgaga aaaaacatac ttttgttaaa caggtatgca tccctgaagc 122520
ataaaataca tagtactgaa agtgcacatg tgtggttctt cccatttttt ttacagcact 122580
tgaaactgac aagtagtagt accaattact tagtaaaaga cctttttcat ttcatttctg 122640

-continued aaatattgtt attttccttt ttcatcttcc atctctgact acacctccaa ttttacctct 122700
ttgctgcctt ccttcctaag aaagttcttc atgcaatgcc atcttgtttt tcttcacttg 122760
cctctttttc tcactttaat tttatgaact ctgatgactt acctctgtag tgtaactact 122820
caaaatatgt atttctgaag tctcaactcc aatctcatat tttcaactta tatttatgga 122880
ggcatctcag actcaaccta cctaaaaaat ggcttatctg ccctaaaatc tactttgttc 122940 ttttttctc tactgctaat aattatcttc ctagttggtc aagctcaaaa cctaatcatt 123000
tttactcctt gtccctgtgt cagctgtcca cattcaagca gcgtatcatt tctgcacatt 123060
tttcaagcaa gtcagtaact gccttttgtt tgggactgtc ttttcatata gtgaacagcc 123120
ttggaagata gaaatcattt ctccttctaa aacaaaaggc aggtgtgctt gcagccttgg 123180
atagaggtag tgcctctttc taaagcaaag ggacatcttt actggccatt ataaaatatc 123240
catgtttcct gagctctgcg ttcctctttt ctaatgcaac ccactgagca tgtaggtgtc 123300
acctgagctt ttctgtggga attgcggctt gaggaatcag tgcaagaaaa tcatgatact 123360
cttgctaatg ctattaatgt gagtagtaaa gttaattgtc tctgacccag cactattgtg 123420
tctttgccca gcactcaaaa gactggcagg cttgcaagta ggacaaaatg ttagattttt 123480
cacagttctt ctgcttataa gtacttgtta aaaccaatta aaacacaact tgtagtttgc 123540
acctataatt ttgtagcatt tgcttcttat ctatgtcact aggatgtgct tagtgacaga 123600
cccatctatc atctattact caagtttttg gctgtattcc taggcaacag agagaagggg 123660
aacaaacaag aggacctgtg cacagtttga gaaaggcaaa acaccgagct taattgcaga 123720
cttgaatgta gctagcaaac gaagtaaggc aaaaggttcc tttttttttt ttttagatgg 123780
agtctcactc tgtcgccagt ctggagtgca gtggtgctgt ctcggctcac tgcaacctcc 123840
gcctcctggg ttccagcgat tcttctgcct cagcctcccg agtagctggg actacaggca 123900
tgtgccacca tgcccagcta acttttgtat ttttagtaga gacggagttt caccacgttg 123960
gccaggatgg tctcaatctc ttgaccttgt gatccgccca ttcggcctcc caaagtgctg 124020
agattatagg tgtgagcctc cgttcccggc caaaagtttc catttttttaa atagttgggt 124080 ttttagtttc gattctttcc aaaaaaaggt tttcttaaaa aaataaaatt agcaataaga 124140
tgaaatataa caacaatata atcttattaa gacaatatat gatatacatt tatcaaaata 124200
cttatatttt caaaagtgct taaaataatc tagcacatag tagatgctca gtaaatattt 124260
gatattatga ctgtgcatgg gtcattatag gctactttat gtatatcatt tcatttagta 124320
caacatcact ctgaaaaatg ttttattgtt accgtttttc agttgaaaca tttacgttgc 124380
tcaagatctc actggtacca tctactatta ggtcagtctg ccaccaaatc tcatgctctt 124440
aaatgccctt tttctcctga gcttccaaca aatagtgtac tgtatataat tgttgaaggg 124500
aggggactgt gagacaaaat atttagagtg aatgtgtagc cacaatttca gttcctcaac 124560
aaagtgataa aattaggaat catcctcaat atatattctt ccaacacaca cacacacata 124620
cacacacaca cacacacaaa taccacaagc ccacttgaat gcaccccacc tacacattgc 124680
aaccatagag acaattgcag cattaaatac agaatattct gtgtgttgtt tgtttgttct 124740
ccctttgcta caaaaatcag aatttctact caataaacag caaagggaga tacaaatgaa 124800
ccaaattaaa gaaggaaaaa atgttgaaaa aattatatac agaactatgt attgatttat 124860
tgagagttca gtaatgtaat ccagaaataa tggatgcctt aaaagtaatt aaaagaatgc 124920
aaataaacat ttagtgccaa ttaaagaaaa agaaatacaa cattagacaa aataaaagat 124980
attcatttga tgcaatgagg aaataatctt ttattcctct ttaaattctc tgtggaataa 125040

-continued ggcatggtta taaataaata aacatctgcc ccatggactt aatggatcgt tatattttat 125100
tgcgataatc ataatgaaat tgttgggagg gattagtatc tctagtgtaa tgctaagaaa 125160
gataaagcct gtgcccaggc aaaagctttc ttggttggtc aaaaggtttg aagacatttc 125220
aaactattct aaaacaaaca aacaagcaaa caaacaaaaa acatacaatg tctttgccac 125280
atatttagga aacaaaatga acaatttatt tctgacaacc tcatagtctt tgttctgtca 125340
gaacaataat ggaaaggtct aaaccagaaa atgctatgca ttgaatttat aataaactat 125400
tttttcctgt aacaaaaaat tgataaactt gatatttgca gatttaatga ttatgtgttt 125460
aaaaaaaatc tggtttttgc ccttgcaaaa aatcatatat atacacatag atatgtatgt 125520
gtgtgtgtgc atagtatata tatatgtata tacatatata tacacacatt tatatatata 125580
aacatttcct ttaacctcct attttattcc aataaaaata ttggtattag agatagttct 125640
gatatttcat catgaatagt taacattgca tttggaaagg attaattttt ttgaaacgta 125700
attttacctt aataagtagc ccagcgtaat attttagtaa ttacacagat tttttttca 125760 agacatttga caactaatat tgcataatag ttaagagtgt gggctttgga gccagacttc 125820
ctatctctgt tcattcactg ataaaatgga gacagtagta acttcctcaa agagttgttt 125880
tttaagatca aataatgcat ataaaactct tgaaatggta ccaaatacag agtaagcacc 125940
aaataaacat taactgttat tgttattcca tgtccgaata acacagaaaa gtaagaattt 126000
taatatttca tttgaatgac cttttaagga tacacctagc ccattatctt tcttgataat 126060
cttgtaagat gattcctttt ttatctccga tctgttgagg catggataga ggttttcaga 126120
gaaaacattt tctaggtaac tgaaagaaag tagcaacaac aaactgtgac aaaacttaac 126180
aatgagagaa tttacaagat agaataattg caactccttt tgaaatcaac cactatggtc 126240
ctctggctgg gatagctaag caaagatatt ccagcctgaa ggttgagatc tacttgaaga 126300
gttttctatc cagattgtga gggcccctca aacttcactt agtatctgtt tctattagta 126360
tggaaacttc tggaaccttg tggtatcaca ttcacttgac tactttattc ctgctctagc 126420
tatcttaaag cctttcttaa tcttttatct tttagagaag atacttctag gttttaaatc 126480
caccgatctt gaagctattg ccttcactct ctgcttcaga gcccatcctt ttgtatatga 126540
gtagtttgtt ttgcctaaag tactttctcc cagtcagatt ttaagtccag tttctcatct 126600
gtttttgaga gcaaactcct gggccttggc tcactaacat cttgacagca tatttcttct 126660
ttcctatggg cttttcagca ttccctgggt ttttctaaaa tatgaaagca gactctttat 126720
ctcttacttt gtcaaagcct accctcccca ctgatttctc acccagttgc tagttttaag 126780
acctgcctct ggccgggcgc agtggctcac gcctgtaatc ccagcacttt gggaggccaa 126840
ggtaggtgga tcacgaggtc aggagatcga gaccatcctg gctaacacag tgaaaccctg 126900
tctctactaa aattacaaaa aaattagcca ggcgtggtgg tgagcgcctg tagtcccagc 126960
tactcgggag gctgaagcag gagaatggcg tgatcccgtg aggcagagct tgcagtgagc 127020
tgagatcgcg ccactgcact ccagcctggg cgacagagcg agactctgtc tcaaaaaaaa 127080
aaaaaaaaaa aaaaaaaaaa aaagacctgc ctccaaatat cattgtattt gcaaacatga 127140
aatgacttat tgattctgag ctcagcacaa gagcaaacct ttctcagctt gacccatctt 127200
cacatcgtta atgtcttatt cagtcactac ccaaggggct gaccttcaag attctaatcc 127260
atgaaagctt aaaatagtaa acaaatttga atatagttta acatacataa taaattttat 127320
ttctagaaga ggaggatcag cccttagaca tgaaaagtaa aaatagttta ttcccagatt 127380

-continued

```
tccctttgtg cattagtata ttcaaccgag tctatccaag taacaggaca aaaaaagctg 127440
gcagttgttg ctgcgctgtg aagtcttatt aggtgagtca gctaattata tggcactacc 127500
ataaatacag caggcactgc cctgcttgtt aggcttgcca aggaaaataa ggatttaaag 127560
cagcatacta cctctttgct atataatgac attttcttct taaaaatgat tttgcaccaa 127620
ttcctgattt atccaccaat tattttttaa tttatggttg aatgtattta aacctgaatt 127680
cagagataaa actagtaaat agctccccaa aataacccca aatatattta atatattagc 127740
tttactctct cctccactgc caaaccttta aaaactgaaa taaattgttt ttatttcatc 127800
ttttctcttt ttctctctct ctaaggtgat tgccaagact aaagaaacag ctagaagggc 127860
aaaagacaag aaaatcagta agatagtaac agattatcca aagtagagca cggctcaggt 127920
gcagtggctc atgcctgtaa tcccagcact ttcggaggct gacgcaggag gatcacttga 127980
gtccaggagt ttgagaccag cctgggcaac ataatgaaac ttcatctcta taaaaaaaaa 128040
aaatttaaat agccgagcat ggtggtgtaa gcctatagtc ccagctattt gggaggctga 128100
ggctggagga tcacttgggc ccaggagttg gagactacag tgagctatga ttgtatcact 128160
gcattacagc ctgggcaata gggcaagacc ctgcctctaa acaaaagata aacaaagtag 128220
agcataaatg gcttctaaat atatgttatt tatgtgtaag actgggttct ctaaaggtat 128280
catttaatta aaatagattt gcattctcaa tctgtaggta tggattatgt ataatgtatt 128340
taagatatga cttacagcgt tcaccaatgt gactattccc aagtgatcca gatggctgat 128400
gacatagtaa tttgtacatt tgctgagacc tgatctgagt aggtatgtaa cataactgag 128460
ggagagcaag tccatttgcc gaaagaaagc ctagcatatg acccaggagc cacatcttca 128520
ctcagccttg ttgctaggtt tggcttagca tatataatag catagcatgt ataatttatg 128580
acaaaaaatt atactttgca ctttttaatt agaacattca aaatgatctc aggaagtggc 128640
accagagatc atcagtggtc tactgtactt cgtgtgtatg tgtctgtgag tatgtatgtg 128700
tttgtgtgtg ttcccacatt ctaaggcatg tcttttacag gttagtagaa aatgttgata 128760
gaaaattata gatttcaaca tctaaaacac agtaggtcac tacattgtta aaacttggaa 128820
ttttttatct tgttgtaaag tcaggccaac caaacctaaa atactgctac attgaaatag 128880
tgcaaaatat tcaaaatact atagttatag atttggtagt aggactgtac cagacctgtc 128940
actctataca agacttatgc cttgcccttt cacttacctg ttccctttta catctatctt 129000
actagatgta atgctataaa ttatatttct aatatattat aatttatcat gtattataat 129060
gtatcaaata ttacaaatta tgttgcaact ccccttacct ttcgtctgca tattgcctca 129120
gaaagaacag atggatccaa cagacttcaa ccacaggccc ttagtgacaa atagctctta 129180
atgctgggct tgccactttg atgcatttct aaagttatag aatgttaaat gcaccaagtc 129240
ctttggtcat tttatttcta ccttagatct aagccataac tatactttcc caaaaattaa 129300
agtttgaatt ttaacttaac catatataat tggaaaagga ggttgggttc gttaagtgta 129360
attttatcat gctttattat cctttgggca ttggatacag cagaacatgc caatttctat 129420
ggcttctcat gtgacagaat atacttacta ggatgcaatt aaatactcct cagagtatgt 129480
aaacaataaa tgtaatcatt acattatttt tatattgttc tttcttatgc ataatagtaa 129540
gactgaaaat atagtgttat ttctgaaata tgcatattgt tttgcttttg atgattaaat 129600
aacattgtcc aaagttttag gttttttgaa atcttatatt ttttaacaaa atatctagcc 129660
tttccaaaac aagacctcaa taattcgttt aagacccaga gttgttcctc tccacataga 129720
tctcttaaaa aggcagagga tttatgacct caagagaaat cagagtatcc aaagtttgct 129780
```

-continued ttaattcaat gttttaaaaa taaaattcct tagattttat caaaaattga gattagtttg 129840
attttgaatc agatgccctt tgctccccac cccaaaatgg cattatgagc agactaggaa 129900
ttgataatag aaaattgaac atatgaaata tatctttacc ttgcttttta acaaggtatt 129960
catgtctatc gccttcattt ttaagtgcat caataaaata catggtaatt ctcttagtga 130020
aatatactat ctacactatg tacacactcc cctgtctgag gtagagaagt agagaatatt 130080
cacatttttg aaacgtctat gctattttta tttaaatacg agttctgggc ttgatttcat 130140
tttggaacac gggtgtgtgc ttaagttgaa ccttttttc ctcttaagtc aaagttcttt 130200
tttagtttct tcttttatct ttttggctac tatctctctc cttcatcctc ctggtgtgag 130260
ttgttgagtg aaggtattaa ttccattatt tgaggctaag tgacattgtt caataatgca 130320
gcaaaacaat ggttctaccc aaaatatctt caagtgtaaa agcagtgggc aaaagagaaa 130380
gtgcgcttct gctgctttga atgtttaagg ctgtgaaagt tgatcacaca aattgggtca 130440
ttcttgttat acccaactaa aacaatcaag aagcctggga ggaaaagcat tcaagaaaca 130500
tcacattgct ccaaaagtgt aattttctac aagtccgcat gctgaggctg cctgttgtaa 130560
cctgggacca attttttctg taactgctga aaaaacttgc tgcagctcta ggactaattt 130620
tgcccaccac tgtcactcac caattgaagc ttactagctc cccagaacct ttctagtgcc 130680
aatgaacttt ctcaaagagc agcgtgtatc atttctcttt ttcagaacac ctccaacctc 130740
ctctttgttc tttgggtata ccaaagacca accagccttg aatttcaatt tttcttccca 130800
cataaaagtt ttaatttaga aatgtatctc tacatttcta actttgacaa agcatagata 130860
ccagataatt gatgaaacct tgctatttta acgatcacca tggattactt cccagtgtct 130920
tcagataacc ctcaacattt gccaacattt gatggacttc aaaatgagca tatctttttt 130980
aaaaaaaatt attcacactg acagcaagta cattggtata ctctatatta aattatacca 131040
cagggtttac aaacaattgg tgatgtcggg cagtggtttc caaggaacat acttaacaag 131100
acactcacaa ggccctacaa acctgcattt ttaacaaggg ccctagatga ttctagaaga 131160
gtgtggtttg gaaagcaatt tttgccttta ttatgtgtca ttttaaatat atttaaaatt 131220
aaagttataa gtcatagaat tgaataaaga taatttcctt acagaaagta ttactaggta 131280
tctaaataca atatggttca aaacaggaaa tttaaaaaga ttatgtaaat tctgtagttg 131340
tattcctaaa gacagtagct gaaatttttt cctacttctc cttgtatcac ttccctttc 131400 cttcactttc acttccctgg aattgtactt cccaataagc tattagcagt gaaggaagct 131460
tcgtctcatg atctgtttta tagagcactt cagctgggac gagtacgaaa tgataatcag 131520
ttatatcagc tattcaaccc tacaggttta tttaaaaaga acttgaataa gctttttagg 131580
gagaaagagg tcagtctcag ccatttctgt ttcctaatat agcttttaag tctttcctta 131640
ttagcaatga gggtcattcc attgtaattt tttgataacc atttttcttt ctgtgtgtca 131700
aatgcagata taagatactg aactgagtct atttcactgt tcgtaaaaca atcccatttg 131760
aaaaaaaaaa gtctacagct attccaggga tagggcctag tagagagaga ataaaaggta 131820
ttttcttact atgtctctat atcctaccct gtaggttctc ttattaagca tacaggcata 131880
taccaaaatc cagacgtttt tctcatttat tttattgccc taacatattc tgggttaata 131940
taatatcata atgaaaattt gagaaaaaat tgatttttc aaaagtgttt aacatttgtt 132000
atattggtag tttttttct tgtttgtggt aaaaataaat agaaggtgca cttcacacct 132060
tcaagtatga ttatattttg aaaacaagtc atgaatactc ataaaatgca aattttaatg 132120

-continued ttcttttttt gttacagcca aactatatta ggcacagttg taaattggag ttgaaattta 132180
atatttcttt atagataaca atgtttttag aaataggttt atgaaacagt aaatatacag 132240
gtatagggat aaaattgtgt ctgatggtca tatgaagtgt ttgttgttat attctccttg 132300
gaatagctgc caaatatttt agtatgctta aaatctacga atgtgataga gtcaacaaat 132360
ttagatcaca tattcagaaa aacatagtta gagaactaac tattgaaatg agcatacagc 132420
agtcttcctt tatctacagg gatacattct gaaacccccca ctaggacacc tgaaattgcg 132480
gatagtagca aaccctacat atactgtttt ttccaatgct tatgtaccta tgaaaaagtt 132540
taatttataa actaggcaca gtaagagatt aacaacaata actaataaca aaagagaaca 132600
attataataa tatactgtaa taaaagttat gtgggtatgg tctcgctttc tctttccctc 132660
tctctctgtc tctaaatatc ttagtatttt ggggttgcaa ttggtggtgg gcaactgaaa 132720
ccatggaaaa caaaaccacg gataaaagga gactactgta tatacttttt aaaactgatg 132780
aaatattaaa ctcatgtttc ttctatatcc cacccatttc ccccacccaa acctagatag 132840
atatcttatt tgatctgtaa acatttaatt aatttgtaaa agttaagaac tttttgaagt 132900
aaaactgcaa tatatcatca cacctaaaga aataaacaat aattcttaaa tatcaagtca 132960
gtgttcaaat ttccccaact acctcatatg tgttttccat ttgcttatgt agggttccca 133020
atgagaatga aataaagttc ttaggttgca attggctaat gctctctcac ttctacttta 133080
agcggcaggt tcccactaac ttctttttag ttgcaattta cttattgaaa ttagacgtat 133140
tctttgtctt gtgtagtttc tcacagtgca aaatttgctg attgtagcca ctgttgtaag 133200
caatgaacat gtttttcacc accttatatt tgctgtaagt tgtcagtgat agttaaatgt 133260
taatcaaatt caaattcgga tcacgtaggg cttttctttt tttgttttct ttttctattt 133320
atatatttat ttatttattt tgagacggag tctcactccg tcaccaggct ggagtgcaat 133380
ggtgtgatct gggctcactg caatctccac ctcccgggtt caagtgattc ccctggctca 133440
gtctcccgag tagctgggac tataggagaa ccaccacgcc cggctaactt tttgtatttt 133500
agtagagatg gggtttcacc atgttggcca ggatgctata gatctcctga cctcaccgat 133560
catgtaggac ttcaattgtc gaacaaacga acctttaata gcagttacac cattaggatg 133620
acctgatcca acatcgaggt cgtaaaccct attgtcgatt tggactctag aataggattg 133680
tgctgtcatc cctagtgtag cttgttccca cttgatgaag ttattggatc agtgaacaat 133740
agcccactta aactagtaca gtcttagttt aagatggtga tgtgtatgta cttccatcag 133800
agggcacata atacagtaaa tcctcactta acttcatcaa tagtttctgg aaactgtgac 133860
ttgaagcaaa acaacatata acaaaaccag ttttaccatt ggctaattga tataagcaag 133920
aattaagtcc tatggcaaat ttctggacac aaaaacacca tcaaactcct aaataaagat 133980
aaatcacttc tgacattaaa cattgaaatt aatgtgagct atatatacgt ttaagaaaga 134040
ttaatacaaa caagtcaaat aacttaccta attatttcgg tggaggccgc aggtggttgg 134100
agcctatcct ggcagctcag ggagcaatat gggaacccac cccggacagg acgctgttcc 134160
attactgcag ggtgctcttg tacacaccca ctcacccagg ctggaaccat gcagacacac 134220
acactcacct aacctacaca tctgtgtaca tccttcaaag ttcagccaaa taacatataa 134280
acaaatccag taatatccat cagtcttagt tccgtcataa caactccttt ttgatcatca 134340
aacaacaaac agggtaggtc tgccatattt acttgtctgg tccatatcaa aattttctaa 134400
caaattatat tagaaaatca aatctctgtc agtttcaaaa tcatggaaaa aaatttgcct 134460
tatttccctt atacttggat atcctaacag taatctaaat attaatgaga aagttaatga 134520

-continued tgtcgtttcc ttctccctgt tgtaaagaag gttttgctgt cccgtttgat cactaagact 134580
aattgacact cagaaaaagc ataggaaact tctcagcatc acaaaagctc tgtcatctag 134640
agaagctagg acttgagctc aagtcctgtg acatggaagg ccttgtgcct agccatcctg 134700
cagcagaggc gtatctacca agaagtgaaa cactacgaaa acagtatgtt tactccacat 134760
tttaaagtga ggtagtttgg ggtggttcat attttattta atttatatat tatttggatt 134820
ttttttagtt tataaaaagg gcattggcaa gggcagaatg atctgtaagc ttctctgccc 134880
acctaccata agcatgatct ttagtgtgac cttttcttac tgttagccat tttcttatac 134940
ttctgcgtcc ctgtcagtca cttccatgtg aagacatggg gaagcttttt tacatcagac 135000
atgttgttga aaatcagccg cgttggctga gggattattt gatctctttc tccaagtccc 135060
tttaggctca cattgcctct ctgttctttg aattttcact tacctttatc ttcttataat 135120
tactttgctg aaataaatgc aaagcaacaa aaggtattta gtgaagaata ccaacaaagc 135180
catgaccatt tcaggctgag ttttgtagta ttctttgtct aggaagagat acctagaaaa 135240
attttctgac catgtatttg attattttcc ttcaatatgt atagtctcag tcttcaaatt 135300
tcagaaaaga atttgtttct tcattgtcat ttaaaattaa tgtgttaaat atgtatgctt 135360
ttacattata agtggttata aaagttaaac acttagaaaa aaagtcaaaa taacatacat 135420
actatccaac aaaataactt tcatatttta ttgtgttttc ttccaaactt tttacctttg 135480
cgtctgaatt ctgtgtaggt tgtatctata atatagacaa cactttatag cctgctaaat 135540
attataccat aaataggtag ttgttacata attctcaggt aatagtaata caggtcttta 135600
tcataatcta ctgagtagtt gaatgataat ttttttaag acaaggtctc cctctgtcac 135660
ccaggctaga atgcagtggc atgcacatgg ctcactgtag cctctacctc ccaggctcaa 135720
gtgatcctcc tgcctcagcc tcccaagtgg ctgggactgt aggcatgtgc caccatgccc 135780
agctatttat ttgtattttt agtagagatg gggtttcatt gtaacagccc aggctggtct 135840
tgaactcctg gactcaaatg atccacctgc ctcagcctcc caaagtgctg aaatcacagg 135900
agtgaaccac tgcacccagc aataattttt taactcttca ttattcattg aacatttagt 135960
taacaattct aaaaatttg tttcctgctg tcattgatct tgtgaaaaat atctttggac 136020
tatagctgtg gattatttcc taaatagtaa attacttgag caaaaagttt acatactttg 136080
agggttgata acccatgttg ccgcaatgtt tccccggagg cattgtggag tttagaatgc 136140
cagtagtaat attaaggtgt gccattttca agatccgtgg ccaacatccc tatatgtaag 136200
atttttccaa aacatggttc tgatttttaa aagtgaaaaa tgctacttca tcatgttctt 136260
tttgtgcttc ttactttaaa tattagaatg aagaaggagc cccacaggaa ggaattctgg 136320
aagatatgcc tgtggatcct gacaatgagg cttatgaaat gccttctgag gtaggagtcc 136380
aagctgaatc tttctaacaa gacagtacca aaaacctgtc attgtcacat ttctctttca 136440
ttagtgctta gtgagaatca tttgctctct acatgctcat tacgtggaca acttgcaagt 136500
taagaatagt ttttacattt ttaaagggtc cttaaaaaaa aagaggagga ggaagatgaa 136560
gaagaggaag aaaggatgta aaagaaatca tatgtagtcc acatagctta atatacttac 136620
tacttgaccc tttacaggaa aagtttacta acccctgcat tagagaatat atttttagaa 136680
actttacatt ctaaaataaa tttctaaatg gaaagttagg gaaatcaatg gaatgccaaa 136740
ggaaggttat tattttttgc catacatgtc caatgggatg acgcatagta aaataaaagt 136800
tacccacaca agttatagaa taaaaagata aatgcatgat ttgcgacaat tgatatattc 136860

-continued cagtataatg ttttaaacaa cacaatatga ttgttaattt tattttgatt gaaaatgaaa 136920
gtatctttaa tagaaaatgt atcaaaaggg aaattagaaa atactgttag atgaataaaa 136980
ctggcccaag aagaaacagt aaatctgaat agatttgtaa cacagcgaat agattaaatt 137040
agtaataaaa aaaaaaacct acctgcaaag aaaatcccag gccgagatgg catcactggt 137100
aaattctacc aaacatttaa agaggaatta atactaatta gttaacacca attaatatct 137160
cttacaaaac agaagaggag acatttccca actaattttg tgagaccaat attaccctga 137220
taatcaaaac caaacgaaga tatcacaaga aaagaaacta tataatggct ccattaaaaa 137280
ttgagttcaa gtatgttgta gtttggttat gtattattcc tcacggcatt attaaaaggc 137340
atgtcgagga tgggcacagc agttcacacc tgtaatcccg cactttgtga gccaaagtgg 137400
ccaggttact tgaggccagg agttggagac cagtctggcc aacatggtga aaccccatct 137460
ctactaaaaa tacaaaaatt agccgggcat ggtggtacac gcctatggtt ccagctactt 137520
gggaggctga ggcatgagag tcacttgaac ccaggaggca gaggttgcag tgagctgaga 137580
tggcacccct gcactccaat cttggtaaca gagcaagact gtctcacaca gacacacgaa 137640
aggcatattg ataataattc aacttataga aattgagatt aaattgtttg tttgcctaat 137700
aagaatttcc aatattttgg ggtcttttat gcaagacaca gtactaaaca caatggaaaa 137760
ctatagagta attgacatta ccaggacata aggagtttac agtctggtag gtttgatgaa 137820
aaaaaataga aattcattca ttcatttctt cattatgatt cctttaacaa acataattga 137880
ttgtcttcga tgtaccaggc atcacaggag caaaaatata taagacatac taaaaagtaa 137940
aacattttaa agatctgttt caatcaatca ggagaagttt tattgaggag gtaatgttga 138000
tctgggtggg aaaaggtaag agatatagta ggtcaaaaca aacagaggac attctggcac 138060
aagggaatat cagaagcaaa ggcatgtatg tctgagcatg caaatggata tgtctgagaa 138120
cagtgaataa ttatgactca agcttaggaa caaggaaaat ggtgatagat tgaatttgca 138180
gctatgggtc aaagacaagt tatagagtat taggataatc ttgtcatttc agcttgtatt 138240
ctattcagaa aacaacttga gttattgaag ttatgcttat ttgtttgttt ttaagcagaa 138300
tcctgatatt attagagttg ctctttagga ggaataatct gatcccttta attaaatcca 138360
ttaatatttg tgttgtggat gctatccaga tactgtatgg agagcttgag gtttgaaata 138420
caagtaataa ttgaagccat agatgaagac gaaattttca actgggagag tgaaagtagg 138480
gaaaatgtat cttgccttca aacatcttaa tttccttctg agaattagag catcttagtc 138540
tggaaaaggc tttatagaca gcttgatttt gttctcacat tttacaggtg aagaaactga 138600
gaaccagaca gtccaactta tttgtcctac caaactaggt atatgatcat taaatggtgc 138660
atccggatca gaacctagat attttaactc tgactactac tgtaattcac ttttatatca 138720
gacaagaaag acacaactat taaaaataag ataatatttg ctgcagaata tttgcaaaaa 138780
cattgattgt aaattttagt gtaagtgggg agccatttcc tatctcattg gctgtcagtg 138840
ctgatgcgta attgaaactt atactaacag tgtgtgctgt ctttttgatt tttctaatat 138900
taggaagggt atcaagacta cgaacctgaa gcctaagaaa tatctttgct cccagtttct 138960
tgagatctgc tgacagatgt tccatcctgt acaagtgctc agttccaatg tgcccagtca 139020
tgacatttct caaagttttt acagtgtatc tcgaagtctt ccatcagcag tgattgaagt 139080
atctgtacct gcccccactc agcatttcgg tgcttccctt tcactgaagt gaatacatgg 139140
tagcagggtc tttgtgtgct gtggattttg tggcttcaat ctacgatgtt aaaacaaatt 139200
aaaaacacct aagtgactac cacttatttc taaatcctca ctattttttt gttgctgttg 139260

-continued ttcagaagtt gttagtgatt tgctatcata tattataaga tttttaggtg tcttttaatg 139320
atactgtcta agaataatga cgtattgtga aatttgttaa tatatataat acttaaaaat 139380
atgtgagcat gaaactatgc acctataaat actaaatatg aaattttacc attttgcgat 139440
gtgttttatt cacttgtgtt tgtatataaa tggtgagaat taaaataaaa cgttatctca 139500
ttgcaaaaat attttatttt tatcccatct cactttaata ataaaaatca tgcttataag 139560
caacatgaat taagaactga cacaaaggac aaaaatataa agttattaat agccatttga 139620
agaaggagga attttagaag aggtagagaa aatggaacat taaccctaca ctcggaattc 139680
cctgaagcaa cactgccaga agtgtgtttt ggtatgcact ggttccttaa gtggctgtga 139740
ttaattattg aaagtggggt gttgaagacc ccaactacta ttgtagagtg gtctatttct 139800
cccttcaatc ctgtcaatgt ttgctttacg tattttgggg aactgttgtt tgatgtgtat 139860
gtgtttataa ttgttataca tttttaattg agccttttat taacatatat tgttattttt 139920
gtctcgaaat aatttttag ttaaaatcta ttttgtctga tattggtgtg aatgctgtac 139980
ctttctgaca ataaataata ttcgaccatg aataaaaaaa aaaaaaaagt gggttcccgg 140040
gaactaagca gtgtagaaga tgattttgac tacaccctcc ttagagagcc ataagacaca 140100
ttagcacata ttagcacatt caaggctctg agagaatgtg gttaactttg tttaactcag 140160
cattcctcac tttttttttt taatcatcag aaattctctc tctctctctc tctttttctc 140220
tcgctctctt tttttttttt ttttttttta caggaaatgc ctttaaacat cgttggaact 140280
accagagtca ccttaaagga gatcaattct ctagactgat aaaaatttca tggcctcctt 140340
taaatgttgc caaatatatg aattctagga tttttcctta ggaaaggttt ttctctttca 140400
gggaagatct attaactccc catgggtgct gaaaataaac ttgatggtga aaaactctgt 140460
ataaattaat ttaaaaatta tttggtttct ctttttaatt attctggggc atagtcattt 140520
ctaaaagtca ctagtagaaa gtataatttc aagacagaat attctagaca tgctagcagt 140580
ttatatgtat tcatgagtaa tgtgatatat attgggcgct ggtgaggaag gaaggaggaa 140640
tgagtgacta taaggatggt taccatagaa acttcctttt ttacctaatt gaagagagac 140700
tactacagag tgctaagctg catgtgtcat cttacactag agagaaatgg taagtttctt 140760
gttttattta agttatgttt aagcaaggaa aggatttgtt attgaacagt atatttcagg 140820
aaggttagaa agtggcggtt aggatatatt ttaaatctac ctaaagcagc atattttaaa 140880
aatttaaaag tattggtatt aaattaagaa atagaggaca gaactagact gatagcagtg 140940
acctagaaca atttgagatt aggaaagttg tgaccatgaa tttaaggatt tatgtggata 141000
caaattctcc tttaaagtgt ttcttccctt aatatttatc tgacggtaat ttttgagcag 141060
tgaattactt tatatatctt aatagtttat ttgggaccaa acacttaaac aaaaagttct 141120
ttaagtcata taagcctttt caggaagctt gtctcatatt cactcccgag acattcacct 141180
gccaagtggc ctgaggatca atccagtcct aggtttattt tgcagactta cattctccca 141240
agttattcag cctcatatga ctccacggtc ggctttacca aaacagttca gagtgcactt 141300
tggcacacaa ttgggaacag aacaatctaa tgtgtggttt ggtattccaa gtggggtctt 141360
tttcagaatc tctgcactag tgtgagatgc aaacatgttt cctcatcttt ctggcttatc 141420
cagtatgtag ctatttgtga cataataaat atatacatat atgaaaatat gtatttggtt 141480
tctgcctcca gttcttacaa agagctccta aaacccttgt aatttcctga gtagtagggg 141540
tgctagggtc atcttttgtt ctaatatttg gtctttgact ctgctttctg acagagctcc 141600

-continued

```
ttagtccctg ggtgagagta gcatcttctc ttctaatgaa gtgactcttg ctgggttcct 141660
ggatgggggc tggtcaccag aaaggtcaag ccatgataag aagcttgaag cttttggccc 141720
cattcacatc ttctggggac gggagagaag aggagctgga gattgagtta ataagcaaca 141780
atgcttccat gatgaagact ccataaaaat ccctaaaaga caggattcag agtgctttga 141840
aataggtgaa catgcagagg tgctgggaat tgtggtgtgt ccagagaagg catgcaagct 141900
ccccacgcct cccccatacc tttccctgtg catctcttcc atctggctgt tcctgagttg 141960
tatcctttta taacaaactg gtaatctagt aagcaaactg ttttcctgaa gtctgtgaat 142020
cacactagca aattatcaaa cctgaggaga gggccgtgga gaccttggat ttgtagacaa 142080
gtcaaacaga agctatgagt aacatgagga ctcattgctt gtgattgtca tcttcagtgg 142140
gaaggggaaa aatcttgtaa aactgagtcc ttaacctgtg ggtcaatgct aactccaggt 142200
agatagtgtc cgatttgaat tacgggacac ccagttggta gccacaaaga atgggagaat 142260
tgcttggtgt agaaaacaca ccccacacac acatgtggtg tcagaaatga accggaaata 142320
ttgtgttccg gaaatattga gtgttgtgag tgagtgtata gaaagaaaaa cagcgtttcc 142380
ttttcactac tagattaaaa caaacacact catgcattca cacatctcaa agacaactat 142440
taattctcaa agacagtgct gtctaaatcc atactgagga agaaaacaca ttttcttttc 142500
aaatctgtaa acctgacaga ctgcctctgt ccacacacta atggaactct gtgtttcatc 142560
tgaaatgtgt tcatcccact ttgttctttc tgtcttgggc agggcaagag tgcaacaggg 142620
ctgacatttt catatgagct ctgtccctgt tattggctat actttagaca aattattatg 142680
tgtcaaatat agatgtaagt gatttatcaa tattaagtca tttaattctc aaaacaacct 142740
taataggttc cattatgatt ctaattttac acataagcca aaggaggcac ccacaggcta 142800
gataactttc ccacggccac acagctagta agcggcagag ccaagaggcc caacattaca 142860
gcaccacagt ctgtgctctc agccccttgg ccacatagtg tcagagtgag gacacacagc 142920
tatttaagaa aacttccaga agtctaggaa atggggtgat agccccactt ttctaggtat 142980
aataattaga tatttgtttt tcttcaggta cctaaagaaa atttactaga gtttgagcct 143040
ttagtaagtt ttgctagtac atctgttttt cttcaggtgc ctgaagacaa acatatacac 143100
acacacacac acacaaacac acacaaaatg tgtatctata tatatgtgta cacatatctc 143160
tcatctctat atatatgtct ctgtatatct atatatctat aaacatatct atatctatag 143220
atacatatag agagatttct tttttttttt ttttgagatg gagtcttgct cttgccacct 143280
aggctggagt gcaatggcac aatctcagtt cactgcaacc tccgcctccc aggttcaagc 143340
gattctcctg cctcagcctc tcgagtaggt gggattacag gaacacacca ccttagcccg 143400
actaattttt gtatttttag tagagacagg gttcaccacg ttggccaggc tggtctcaaa 143460
ctcctgacct caggtaatcc acctacctcg gcctcccaaa gtgctgggat tacaggtgtg 143520
agccaccatg cctggccaag atttctaatt ctaagagaaa ttagcacctg ataggtattt 143580
ccttgtaaat aaaccgggca tatcctgatt atagaactaa gttaattatt ttccgtggaa 143640
gatacgaatg ttgatgcaat aagagcagca gtctacagta aggtgggctt tgtaattttc 143700
tgtgttgaat catggcatgg gtacttggct tatgtcaaat agacaaaaaa atataaatta 143760
aggtataact gggattgtca attatacata tttagtaatg gaatgaatga atttataaat 143820
agatagtaaa gggcatgaat taagaatcta taggtataaa taatattagc aacttaatat 143880
tgtataataa agtttgattt tctaggtgta gttgattgat gcagtaatgt tcgttttatc 143940
ctttgagtaa gcctagaatt gaagaaccca aaatgcaata gaatagatat aacattgaaa 144000
```

-continued ctattcctaa atatgatttt agttccaatg ttctttgtgt aattacctaa gcttttcttt 144060
aatgtttttg ctgctactac agtatcctta attatttgaa atcttatatt ggaagcagtt 144120
aaaccacatt ccttcaaaga gcccttagtt tgagcctcta gtaagttttg ctagtataat 144180
ttggttttaa aattggctag aattgcatag ggaatttcca taacgtatag ttgatctgca 144240
actataggtt aacatactag gatggcttct cttatgaacc ttatgaaaat acatcctcag 144300
attccctgga aggtcagtga ccagaaatcc tcgttgtttc tatggcaaca cagcaagata 144360
tggtgccttg gaaatgtgct gcattttaat taggttcctc tagggcttcc taactgcctt 144420
ttgcaggtaa actaaatatc agattgcctt ttatcttgca acaaaatgaa acctaaccca 144480
tgtctgtaaa tgtcaaagct aagctgtgtt ccagtaaagc tgaatccaaa caaatatagt 144540
agcaagtcat gtttttatct tagaaaagaa tacaatactc tttacctaga atagtcaagg 144600
atgctgctta atgaggtagg ttagagtaat agagactatc ctgaactcca aaactattaa 144660
tagactatgg aacttcgact cccatttatg tctcttacta cttaatatta gtgtctctgt 144720
ttccttatat gtaaatatgc aaatgataaa aatagtgcct catagcattg ttgcatgcat 144780
taagtgagtt aatgtaagtg gaatacttag gactgcctgg ctgatagtaa gtgatctatg 144840
agtcaatgat gctatttatt agtagtagta ctagtacagc acactgtatt tttaaaggta 144900
aataagaaat aacaattttt ttaaatgttc atatacattc acatgtcttc ttttaatata 144960
aaatagcaat caagatcagg ataatggtag agatattttg gagacacaag gcagaagcta 145020
tttactaata gctaggggag cattttacta gtttactaac caatattact atacttatgt 145080
gtacttagca gaatatcacc tagcaccaaa aagaaattaa gaaagtgtaa cttactgaga 145140
agtgaatatg caccaactcc ataaacacta tgtttatgga acacatctaa ctttagactt 145200
agctatactc atcgactcac atatcttctc atccaagtgg gatgtgttta atatttacca 145260
tatattcata agttcactga gtattgttct ggtaactaga aaaaaaaaag gacaagcata 145320
tataagtaaa actcactgat ttaaaacaga gtattatcaa ctacaaaaga aaaaaaaaac 145380
cacttgaacc tccactgatt tctcaaatct catttatttc ccattatctt ccctcatacc 145440
tcttgcattt atttggttaa atttcttttt gatccaaaag gaagcaatgt ttacctgaca 145500
atttctactt tatgccagaa caacaaatgt accagcaatt acaatatttc caagaaaagt 145560
attgtttgtt ttctcttcat gtctttggtg agtctctcgg aattag 145606

<210> SEQ ID NO 8
<211> LENGTH: 4349
<212> TYPE: DNA
<213> ORGANISM: Homo sapiens
<220> FEATURE:
<221> NAME/KEY: misc_feature
<222> LOCATION: (1)..(4349)
<223> OTHER INFORMATION: LOCUS DRPLA;4349 bp;mRNA;linear P
RI 13-MAY-2002
DEFINITION Homo sapiens dentatorubral-pallidoluysian atrophy
(atrophin-1)(DRPLA), mRNA. ACCESSION XM_032588
<300> PUBLICATION INFORMATION:
<308> DATABASE ACCESSION NUMBER: XM_032588
<309> DATABASE ENTRY DATE: 2002-05-13
<313> RELEVANT RESIDUES IN SEQ ID NO: (1)..(4349)

<400> SEQUENCE: 8
acgccatact ggacgccaag tgggaggaac ttcaaggctg tcccctgcgg gcctcccgct 60
ctgcttctgc gaaggtttca ttgaaaacag atcctgcaaa agttccaggt gcccacactg 120
gaaacttgga gatcctgctt cccagaccac agctgtgggg aacttggggt ggagcagaga 180

-continued

```
agtttctgta ttcagctgcc caggcagagg agaatggggt ctccacagcc tgaagaatga    240
agacacgaca gaataaagac tcgatgtcaa tgaggagtgg acggaagaaa gaggcccctg    300
ggccccggga agaactgaga tcgaggggcc gggcctcccc tggaggggtc agcacgtcca    360
gcagtgatgg caaagctgag aagtccaggc agacagccaa gaaggcccga gtagaggaag    420
cctccacccc aaaggtcaac aagcagggtc ggagtgagga gatctcagag agtgaaagtg    480
aggagaccaa tgcaccaaaa aagaccaaaa ctgagcagga actccctcgg ccacagtctc    540
cctccgatct ggatagcttg gacgggcgga gccttaatga tgatggcagc agcgacccta    600
gggatatcga ccaggacaac cgaagcacgt cccccagtat ctacagccct ggaagtgtgg    660
agaatgactc tgactcatct tctggcctgt cccagggccc agcccgcccc taccacccac    720
ctccactctt tcctccttcc cctcaaccgc cagacagcac ccctcgacag ccagaggcta    780
gctttgaacc ccatccttct gtgacaccca ctggatatca tgctcccatg gagccccca    840
catctcgaat gttccaggct cctcctgggg cccctccccc tcacccacag ctctatcctg    900
ggggcactgg tggagttttg tctggacccc caatgggtcc caagggggga ggggctgcct    960
catcagtggg gggccctaat gggggtaagc agcacccccc acccactact cccatttcag   1020
tatcaagctc tggggctagt ggtgctcccc caacaaagcc gcctaccact ccagtgggtg   1080
gtgggaacct accttctgct ccaccaccag ccaacttccc ccatgtgaca ccgaacctgc   1140
ctcccccacc tgccctgaga cccctcaaca atgcatcagc ctctccccct ggcctggggg   1200
cccaaccact acctggtcat ctgccctctc cccacgccat gggacagggt atgggtggac   1260
ttcctcctgg cccagagaag ggcccaactc tggctccttc accccactct ctgcctcctg   1320
cttcctcttc tgctccagcg ccccccatga ggtttcctta ttcatcctct agtagtagct   1380
ctgcagcagc ctcctcttcc agttcttcct cctcttcctc tgcctccccc ttcccagctt   1440
cccaggcatt gcccagctac ccccactctt tccctccccc aacaagcctc tctgtctcca   1500
atcagccccc caagtatact cagccttctc tcccatccca ggctgtgtgg agccagggtc   1560
ccccaccacc tcctccctat ggccgcctct tagccaacag caatgcccat ccaggcccct   1620
tccctccctc tactggggcc cagtccaccg cccacccacc agtctcaaca catcaccatc   1680
accaccagca acagcaacag cagcagcagc agcagcagca gcagcagcag cagcagcagc   1740
agcatcacgg aaactctggg cccccctcctc ctggagcatt tccccaccca ctggagggcg   1800
gtagctccca ccacgcacac ccttacgcca tgtctccctc cctggggtct ctgaggccct   1860
acccaccagg gccagcacac ctgcccccac ctcacagcca ggtgtcctac agccaagcag   1920
gccccaatgg ccctccagtc tcttcctctt ccaactcttc ctcttccact tctcaagggt   1980
cctacccatg ttcacacccc tccccttccc agggccctca aggggcgccc taccctttcc   2040
caccggtgcc tacggtcacc acctcttcgg ctaccctttc cacggtcatt gccaccgtgg   2100
cttcctcgcc agcaggctac aaaacggcct ccccacctgg gcccccaccg tacggaaaga   2160
gagccccgtc cccgggggcc tacaagacag ccaccccacc cggatacaaa cccgggtcgc   2220
ctccctcctt ccgaacgggg accccaccgg gctatcgagg aacctcgcca cctgcaggcc   2280
cagggacctt caagccgggc tcgcccaccg tgggacctgg gcccctgcca cctgcggggc   2340
cctcaggcct gccatcgctg ccaccaccac ctgcggcccc tgcctcaggg ccgcccctga   2400
gcgccacgca gatcaaacag gagccggctg aggagtatga gacccccgag agcccggtgc   2460
cccagcccg cagcccctcg ccccctccca aggtggtaga tgtacccagc catgccagtc   2520
```

-continued

```
agtctgccag gttcaacaaa cacctggatc gcggcttcaa ctcgtgcgcg cgcagcgacc   2580

tgtacttcgt gccactggag ggctccaagc tggccaagaa gcgggccgac ctggtggaga   2640

aggtgcggcg cgaggccgag cagcgcgcgc gcgaagaaaa ggagcgcgag cgcgagcggg   2700

aacgcgagaa agagcgcgag cgcgagaagg agcgcgagct tgaacgcagc gtgaagttgg   2760

ctcaggaggg ccgtgctccg gtggaatgcc catctctggg cccagtgccc catcgccctc   2820

catttgaacc gggcagtgcg gtggctacag tgccccccta cctgggtcct gacactccag   2880

ccttgcgcac tctcagtgaa tatgcccggc ctcatgtcat gtctcctggc aatcgcaacc   2940

atccattcta cgtgcccctg gggcagtgg acccggggct cctgggttac aatgtcccgg   3000

ccctgtacag cagtgatcca gctgcccggg agagggaacg ggaagcccgt gaacgagacc   3060

tccgtgaccg cctcaagcct ggctttgagg tgaagcctag tgagctggaa cccctacatg   3120

gggtccctgg gccgggcttg gatccctttc cccgacatgg gggcctggct ctgcagcctg   3180

gcccacctgg cctgcaccct ttcccctttc atccgagcct ggggcccctg gagcgagaac   3240

gtctagcgct ggcagctggg ccagccctgc ggcctgacat gtcctatgct gagcggctgg   3300

cagctgagag gcagcacgca gaaagggtgg cggccctggg caatgaccca ctggcccggc   3360

tgcagatgct caatgtgact ccccatcacc accagcactc ccacatccac tcgcacctgc   3420

acctgcacca gcaagatgct atccatgcag cctctgcctc ggtgcaccct ctcattgacc   3480

ccctggcctc agggtctcac cttacccgga tcccctaccc agctggaact ctccctaacc   3540

ccctgcttcc tcaccctctg cacgagaacg aagttcttcg tcaccagctc tttgctgccc   3600

cttaccggga cctgccggcc tccctttctg ccccgatgtc agcagctcat cagctgcagg   3660

ccatgcacgc acagtcagct gagctgcagc gcttggcgct ggaacagcag cagtggctgc   3720

atgcccatca cccgctgcac agtgtgccgc tgcctgccca ggaggactac tacagtcacc   3780

tgaagaagga aagcgacaag ccactgtaga acctgcgatc aagagagcac catggctcct   3840

acattggacc ttggagcacc cccaccctcc ccccaccgtg cccttggcct gccacccaga   3900

gccaagaggg tgctgctcag ttgcagggcc tccgcagctg gacagagagt gggggaggga   3960

gggacagaca gaaggccaag gcccgatgtg gtgtgcagag gtggggaggt ggcgaggatg   4020

gggacagaaa gcgcacagaa tcttggacca ggtctctctt ccttgtcccc cctgcttttc   4080

tcctccccca tgcccaaccc ctgtggccgc cgcccctccc ctgccccgtt ggtgtgatta   4140

tttcatctgt tagatgtggc tgttttgcgt agcatcgtgt gccaccccctg cccctccccg   4200

atccctgtgt gcgcgccccc tctgcaatgt atgccccttg ccccttcccc acactaataa   4260

tttatatata taaatatcta tatgacgctc ttaaaaaaac atcccaacca aaaccaacca   4320

aacaaaaaca tcctcacaac tccccagga                                     4349
```

<210> SEQ ID NO 9
<211> LENGTH: 13994
<212> TYPE: DNA
<213> ORGANISM: Homo sapiens
<220> FEATURE:
<221> NAME/KEY: misc_feature
<222> LOCATION: (1)..(13994)
<223> OTHER INFORMATION: LOCUS SEG_HUMHD;13994 bp;DNA;linear P
      RI 12-FEB-2001; DEFINITION  Homo sapiens huntingtin (HD) gene.
      ACCESSION   AH003045 REGION: 316..14309
      VERSION AH003045.1  GI:663286
<220> FEATURE:
<221> NAME/KEY: modified_base
<222> LOCATION: (4781)..(4782)
<223> OTHER INFORMATION: a, c, g, t, unknown or other
<220> FEATURE:

-continued

<221> NAME/KEY: modified_base
<222> LOCATION: (6665)
<223> OTHER INFORMATION: a, c, g, t, unknown or other
<220> FEATURE:
<221> NAME/KEY: modified_base
<222> LOCATION: (11228)..(11229)
<223> OTHER INFORMATION: a, c, g, t, unknown or other
<220> FEATURE:
<221> NAME/KEY: modified_base
<222> LOCATION: (12691)
<223> OTHER INFORMATION: a, c, g, t, unknown or other
<220> FEATURE:
<221> NAME/KEY: modified_base
<222> LOCATION: (13136)
<223> OTHER INFORMATION: a, c, g, t, unknown or other
<220> FEATURE:
<221> NAME/KEY: modified_base
<222> LOCATION: (13145)
<223> OTHER INFORMATION: a, c, g, t, unknown or other
<300> PUBLICATION INFORMATION:
<308> DATABASE ACCESSION NUMBER: L27350
<309> DATABASE ENTRY DATE: 2001-02-12
<313> RELEVANT RESIDUES IN SEQ ID NO: (1)..(614)

<400> SEQUENCE: 9
atggcgaccc tggaaaagct gatgaaggcc ttcgagtccc tcaagtcctt ccagcagcag 60
cagcagcagc agcagcagca gcagcagcag cagcagcagc agcagcagca gcagcaacag 120
ccgccaccgc cgccgccgcc gccgccgcct cctcagcttc ctcagccgcc gccgcaggca 180
cagccgctgc tgcctcagcc gcagccgccc ccgccgccgc ccccgccgcc acccggcccg 240
gctgtggctg aggagccgct gcaccgaccg tgagtttggg cccgctgcag ctccctgtct 300
attaatttcc ttcttttttt tatttttaga aagaaagaac tttcagctac caagaaagac 360
cgtgtgaatc attgtctgac aatatgtgaa aacatagtgg cacagtctgt caggtaattg 420
cactttgaac tgtctagaga aaacttgaca gtttctcttc tttttttgct tagaaattct 480
ccagaatttc agaaacttct gggcatcgct atggaacttt ttctgctgtg cagtgatgac 540
gcagagtcag atgtcaggat ggtggctgac gaatgcctca acaaagttat caaagtaaga 600
accgtgtgga tgatgttctc ctcacttcca taaatctctt gtgatttgtt gtaggctttg 660
atggattcta atcttccaag gttacagctc gagctctata aggaaattaa aaaggtgggc 720
cttgcttttc ttttttaaaa atgtcttaat gcaaccctca ttgcaccccc tcagaatggt 780
gcccctcgga gtttgcgtgc tgccctgtgg aggtttgctg agctggctca cctggttcgg 840
cctcagaaat gcaggtaagt tgtacactct ggatgttggt ttttagaatg acttgcgttc 900
ttttgcatac acaggcctta cctggtgaac cttctgccgt gcctgactcg aacaagcaag 960
agacccgaag aatcagtcca ggagaccttg gctgcagctg ttcccaaaat tatggcttct 1020
tttggcaatt ttgcaaatga caatgaaatt aaggtatgat tgttgcctca ggtcacaaac 1080
atgttttatc tacttggact tttgcttccg taggttttgt taaaggcctt catagcgaac 1140
ctgaagtcaa gctcccccac cattcggcgg acagcggctg gatcagcagt gagcatctgc 1200
cagcactcaa gaaggacaca atatttctat agttggctac taaatgtgct cttaggtaag 1260
gtggaggcat atgagtggaa gagtctgtta agatgtcttg cttccacccc cacaggctta 1320
ctcgttcctg tcgaggatga acactccact ctgctgattc ttggcgtgct gctcaccctg 1380
aggtatttgg tgcccttgct gcagcagcag gtcaaggaca caagcctgaa aggcagcttc 1440
ggagtgacaa ggaaagaaat ggaagtctct ccttctgcag agcagcttgt ccaggtagga 1500
gcacagggtt tactctagga actgaccaga acacctgtgt ttctctgttt ctaggtttat 1560
gaactgacgt tacatcatac acagcaccaa gaccacaatg ttgtgaccgg agccctggag 1620

-continued

```
ctgttgcagc agctcttcag aacgcctcca cccgagcttc tgcaaaccct gaccgcagtc   1680
gggggcattg ggcagctcac cgctgctaag gaggagtctg gtggccgaag ccgtagtggg   1740
agtattgtgg aacttatagg caagttatta gcaaggtcta cacttacaaa ctttatctgt   1800
cactttctgt gatttgcagc tggagggggt tcctcatgca gccctgtcct ttcaagaaaa   1860
caaaaaggtg attatttcag aaatcagagt cttgtgttaa aaggaatgtt ggtacattat   1920
ttactaggca aagtgctctt aggagaagaa gaagccttgg aggatgactc tgaatcgaga   1980
tcggatgtca gcagctctgc cttaacaggt agttctcact agttagccgc tggtgtggtt   2040
tgacaaatga gtgtttctct gtcttcagcc tcagtgaagg atgagatcag tggagagctg   2100
gctgcttctt caggggtttc cactccaggg tcagcaggtc atgacatcat cacagaacag   2160
ccacggtcac agcacacact gcaggcggac tcagtggatc tggccagctg tgacttgaca   2220
agctctgcca ctgatgggga tgaggaggat atcttgagcc acagctccag ccaggtcagc   2280
gccgtcccat ctgaccctgc catggacctg aatgatggga cccaggcctc gtcgcccatc   2340
agcgacagct cccagaccac caccgaaggg cctgattcag ctgttacccc ttcagacagt   2400
tctgaaattg taagtgggca gaggggcctg acatctttta attctcacag ccccccttga   2460
accgtttagg tgttagacgg taccgacaac cagtatttgg gcctgcagat tggacagccc   2520
caggatgaag atgaggaagc cacaggtatt cttcctgatg aagcctcgga ggccttcagg   2580
aactcttcca tgggtatgtg gactacaggt gatgcgctac aaacacttaa tcttgatttc   2640
tctgttttta aagcccttca acaggcacat ttattgaaaa acatgagtca ctgcaggcag   2700
ccttctgaca gcagtgttga taaatttgtg ttgagagatg aagctactga accgggtgat   2760
caagaaaaca aggtgaggga cataggcttg agacgacttg gtgacaaaca agtgtcattg   2820
tctcctttct agccttgccg catcaaaggt gacattggac agtccactga tgatgactct   2880
gcacctcttg tccattgtgt ccgcctttta tctgcttcgt ttttgctaac agggggaaaa   2940
aatggtgagt acaaaagggg atgtgcacag ttgactgaag gtggcttggg tgatttcttg   3000
gcagtgctgg ttccggacag ggatgtgagg gtcagcgtga aggccctggc cctcagctgt   3060
gtgggagcag ctgtggccct ccacccggaa tctttcttca gcaaactcta taaagttcct   3120
cttgacacca cggaataccc tggtatgtta aaagttcaca tctgatgtgc tcgttccatg   3180
gctgagcaat ttatctccac agaggaacag tatgtctcag acatcttgaa ctacatcgat   3240
catggagacc cacaggttcg aggagccact gccattctct gtgggaccct catctgctcc   3300
atcctcagca ggtcccgctt ccacgtggga gattggatgg gcaccattag aaccctcaca   3360
ggtaacggcc agtttttcag ctgtgttttt tatgatgttt gttgcttgtt cttctggtta   3420
ggaaatacat tttctttggc ggattgcatt cctttgctgc ggaaaacact gaaggatgag   3480
tcttctgtta cttgcaagtt agcttgtaca gctgtgaggg tgagcataat cttctgtgga   3540
accatttctt gtcctcttgc cttggacctt gtgttccaga actgtgtcat gagtctctgc   3600
agcagcagct acagtgagtt aggactgcag ctgatcatcg atgtgctgac tctgaggaac   3660
agttcctatt ggctggtgag gacagagctt ctggaaaccc ttgcagagat tgacttcagg   3720
taagtgagtc acatccatta gatttcatga tttcattgtt aaatgtgctc ttttgttagg   3780
ctggtgagct tttggaggc aaaagcagaa aacttacaca gaggggctca tcattataca   3840
ggggtaagca gtttattttt gtgagatgct gtttgtttat ttttattatc cttctctcta   3900
aagcttttaa aactgcaaga acgagtgctc aataatgttg tcatccattt gcttggagat   3960
```

-continued

```
gaagacccca gggtgcgaca tgttgccgca gcatcactaa ttaggtattt accaatattt   4020
tatctctttt ccttttaagc aaattaacct tacttttgtg ttaggcttgt cccaaagctg   4080
ttttataaat gtgaccaagg acaagctgat ccagtagtgg ccgtggcaag agatcaaagc   4140
agtgtttacc tgaaacttct catgcatgag acgcagcctc catctcattt ctccgtcagc   4200
acaataacca ggtatgctga cccagtggca tcttcacatt gtattttaag tctctatatt   4260
tttgttatta gaatatatag aggctataac ctactaccaa gcataacaga cgtcactatg   4320
gaaaataacc tttcaagagt tattgcagca gtttctcatg aactaatcac atcaaccacc   4380
agagcactca cagtaagtct ctttcttgat gcctcttact gaggtgtgat tttattgttt   4440
ctttcttctg agtttggatg ctgtgaagct ttgtgtcttc tttccactgc cttcccagtt   4500
tgcatttgga gtttaggttg gcactgtggg tatgtatttt cctcagtata tattaatagt   4560
aatttgactt tgcaaatgtc tgcttccaga ggtgcctcca ctgagtgcct cagatgagtc   4620
taggaagagc tgtaccgttg ggatggccac aatgattctg accctgctct cgtcagcttg   4680
gttcccattg gatctctcag cccatcaaga tgctttgatt ttggccggaa acttgcttgc   4740
aggtactggt actgagttga aacagggact ccggagaggt nntgtctgtg cccatatcac   4800
agccagtgct cccaaatctc tgagaagttc atgggcctct gaagaagaag ccaacccagc   4860
agccaccaag caagaggagg tctggccagc cctgggggac cgggccctgg tgcccatggt   4920
ggagcagctc ttctctcacc tgctgaaggt gattaacatt tgtgcccacg tcctggatga   4980
cgtggctcct ggacccgcaa taaaggtaat gtcccacttg ggtgctggat tcatattgtt   5040
ttttgttttt gtttttctat tttaggcagc cttgccttct ctaacaaacc ccccttctct   5100
aagtcccatc cgacgaaagg ggaaggagaa agaaccagga gaacaagcat ctgtaccgtt   5160
gagtcccaag aaaggcagtg aggccagtgc aggtaggaaa cagcgtgggg aagggaggga   5220
caagtttatc ttttgtgtgc atatttttaa agcttctaga caatctgata cctcaggtcc   5280
tgttacaaca agtaaatcct catcactggg gagtttctat catcttcctt catacctcaa   5340
actgcatgat gtcctgaaag ctacacacgc taactacaag gtatgggcct ctgcatcttt   5400
taaaaatata accgtgtgtt ctctccttca ccttcccaag gtcacgctgg atcttcagaa   5460
cagcacggaa aagtttggag ggtttctccg ctcagccttg gatgttcttt ctcagatact   5520
agagctggcc acactgcagg acattgggaa ggtttgtgtc ttgttttttc tccttgggtt   5580
gtcgcttaat gtctgacttg tctttctaca gtgtgttgaa gagatcctag gatacctgaa   5640
atcctgcttt agtcgagaac caatgatggc aactgtttgt gttcaacaag taagagcttc   5700
attcttttcc tcttctgtta ttgttgatgc ctcatttttt tcactgtagt tgttgaagac   5760
tctctttggc acaaacttgg cctcccagtt tgatggctta tcttccaacc ccagcaagtc   5820
acaaggccga gcacagcgcc ttggctcctc cagtgtgagg ccaggcttgt accactactg   5880
cttcatggcc ccgtacaccc acttcaccca ggccctcgct gacgccagcc tgaggaacat   5940
ggtgcaggcg gagcaggaga acgacacctc ggggtaacag ttgtggcaag aatgctgtcg   6000
ttgctctgct tccctttat tcccatttgg cagatggttt gatgtcctcc agaaagtgtc   6060
tacccagttg aagacaaacc tcacgagtgt cacaaagaac cgtgcagata aggtaaatgg   6120
tgttgtttgt ggatgtgaac tcattctttc tttcttttt tcttttttat agaatgctat   6180
tcataatcac attcgtttgt ttgaacctct tgttataaaa gctttaaaac agtacacgac   6240
tacaacatgt gtgcagttac agaagcaggt tttagatttg ctggcgcagc tggttcagtt   6300
acgggttaat tactgtcttc tggattcaga tcaggtttgt cacttttatc tttcatccat   6360
```

-continued

```
catattgatg taaattttat tttccttcct gtaggtgttt attggctttg tattgaaaca   6420
gtttgaatac attgaagtgg gccagttcag gtaatagcat tttattattt tagatttttt   6480
aaggatctaa atggatgttt ttgtttctag ggaatcagag gcaatcattc caaacatctt   6540
tttcttcttg gtattactat cttatgaacg ctatcattca aaacagatca ttggaattcc   6600
taaaatcatt cagctctgtg atggcatcat ggccagtgga aggaaggctg tgacacatgg   6660
taacnggaca cacctttcac tgtcgtcttc ctgataaggg taccctttttg tccccacagc   6720
cataccggct ctgcagccca tagtccacga cctctttgta ttaagaggaa caaataaagc   6780
tgatgcagga aaagagcttg aaacccaaaa agaggtggtg gtgtcaatgt tactgagact   6840
catccagtac catcaggtaa gaggaatgta tgttggaact gtcgtgcaga ctttctaatt   6900
gtgcacgctc ttataggtgt tggagatgtt cattcttgtc ctgcagcagt gccacaagga   6960
gaatgaagac aagtggaagc gactgtctcg acagatagct gacatcatcc tcccaatgtt   7020
agccaaacag caggtttgtc cccgcagcct tggcttgttg ttgtagaaat gtttgtggtg   7080
tctaattcca cagatgcaca ttgactctca tgaagccctt ggagtgttaa atacattatt   7140
tgagattttg gccccttcct ccctccgtcc ggtagacatg cttttacgga gtatgttcgt   7200
cactccaaac acaatggtga gtctctcgcc tggctcagca gatgaagctg tgacttatgt   7260
attatgttta ttttaggcgt ccgtgagcac tgttcaactg tggatatcgg gaattctggc   7320
cattttgagg gttctgattt cccagtcaac tgaagatatt gttctttctc gtattcagga   7380
gctctccttc tctccgtatt taatctcctg tacagtaatt aataggttaa gagatgggga   7440
cagtacttca acgctagaag aacacagtga agggaaacaa ataaagaatt tgccagaaga   7500
aacattttca aggtatgctt tctatctgag cctataacta acttcactgt catctttttt   7560
ctttcttgga aggtttctat tacaactggt tggtattctt ttagaagaca ttgttacaaa   7620
acagctgaag gtggaaatga gtgagcagca acatactttc tattgccagg aactaggcac   7680
actgctaatg tgtctgatcc acatcttcaa gtctggtagg tgaatcacat tagtcttcct   7740
ggagtaaaga catttctcct taactttgtt tctaggaatg ttccggagaa tcacagcagc   7800
tgccactagg ctgttccgca gtgatggctg tggcggcagt ttctacaccc tggacagctt   7860
gaacttgcgg gctcgttcca tgatcaccac ccacccggcc ctggtgctgc tctggtgtca   7920
gatactgctg cttgtcaacc acaccgacta ccgctggtgg gcagaagtgc agcagacccc   7980
gaagtaggtt cataatgccc cacagcccag ggccattgtc aatgcatctg ttgctccttc   8040
tagaagacac agtctgtcca gcacaaagtt acttagtccc cagatgtctg gagaagagga   8100
ggattctgac ttggcagcca aacttggaat gtgcaataga gaaatagtac gaagaggggc   8160
tctcattctc ttctgtgatt atgtcgtaag tttgaaatgc ctgtaaacgg ggttgaaatg   8220
aatctctcat catatttttc cttagtgtca gaacctccat gactccgagc acttaacgtg   8280
gctcattgta aatcacattc aagatctgat cagcctttcc cacgagcctc cagtacagga   8340
cttcatcagt gccgttcatc ggaactctgc tgccagcggc ctgttcatcc aggcaattca   8400
gtctcgttgt gaaaaccttt caactgtacg tcttcatcct gccgactatt gccagatctt   8460
ttcttctttt ccttcttgct gttagccaac catgctgaag aaaactcttc agtgcttgga   8520
ggggatccat ctcagccagt cgggagctgt gctcacgctg tatgtggaca ggcttctgtg   8580
cacccctttc cgtgtgctgg ctcgcatggt cgacatcctt gcttgtcgcc gggtagaaat   8640
gcttctggct gcaaatttac aggtattggg aagagaaacc ctgatattga ttcaaacaca   8700
```

-continued

```
ctaatgtgtt tttgtctatt agagcagcat ggcccagttg ccaatggaag aactcaacag   8760
aatccaggaa taccttcaga gcagcgggct cgctcagagg taatgctgga aacacaggtc   8820
gtccttgtga ctgtaatttc atttttattt gtattttaga caccaaaggc tctattccct   8880
gctggacagg tttcgtctct ccaccatgca agactcactt agtccctctc ctccagtctc   8940
ttcccacccg ctggacgggg atgggcacgt gtcactggaa acagtgagtc cggacaaagt   9000
aagtgtccag cgtgtctgca tgggaggctg ttccccttat ccattttttt cttcccagga   9060
ctggtacgtt catcttgtca aatcccagtg ttggaccagg tcagattctg cactgctgga   9120
aggtgcagag ctggtgaatc ggattcctgc tgaagatatg aatgccttca tgatgaactc   9180
ggtacggggg gagcagtgga ggcaaggaat cgtttgttaa cctttaatgc tctgatttca   9240
ggagttcaac ctaagcctgc tagctccatg cttaagccta gggatgagtg aaatttctgg   9300
tggccagaag agtgcccttt ttgaagcagc ccgtgaggtg actctggccc gtgtgagcgg   9360
caccgtgcag cagctccctg ctgtccatca tgtcttccag cccgagctgc ctgcagagcc   9420
ggcggcctac tggagcaagt tgaatgatct gtttggtaat taaaattaaa atttatctta   9480
ttttagcacc cacccacgag gtccttctgt ttcaggggat gctgcactgt atcagtccct   9540
gcccactctg gcccgggccc tggcacagta cctggtggtg gtctccaaac tgcccagtca   9600
tttgcacctt cctcctgaga aagagaagga cattgtgaaa ttcgtggtgg caacccttga   9660
ggtaagaggc agctcgggag ctcagtgttg cggcattctg tgactcggta cttcccttta   9720
ggccctgtcc tggcatttga tccatgagca gatcccgctg agtctggatc tccaggcagg   9780
gctggactgc tgctgcctgg ccctgcagct gcctggcctc tggagcgtgg tctcctccac   9840
agagtttgtg acccacgcct gctccctcat ctactgtgtg cacttcatcc tggaggccgg   9900
tgagtccccg tccatgaacg gtgggttcca ttcttctctt tgttctgttg taattttagt   9960
tgcagtgcag cctggagagc agcttcttag tccagaaaga aggacaaata ccccaaaagc  10020
catcagcgag gaggaggagg aagtagatcc aaacacacag agtaagtctc aggacccatt  10080
tttttcttac aaaagtcctc tcttaaccgt tgcttgttta gatcctaagt atatcactgc  10140
agcctgtgag atggtggcag aaatggtgga gtctctgcag tcggtgttgg ccttgggtca  10200
taaaaggaat agcggcgtgc cggcgtttct cacgccattg ctcaggaaca tcatcatcag  10260
cctggcccgc ctgccccttg tcaacagcta cacacgtgtg cccccactgg tgagtctgct  10320
cgttccttgc agaagaccag atgatgtcac ttccttttca tcttctcagg tgtggaagct  10380
tggatggtca cccaaaccgg gaggggattt tggcacagca ttccctgaga tccccgtgga  10440
gttcctccag gaaaaggaag tctttaagga gttcatctac cgcatcaaca cactaggtac  10500
tcttggggcc tctccttcag gtcacccact ctctcatgta agatttatat ttgtaggctg  10560
gaccagtcgt actcagtttg aagaaacttg ggccaccctc cttggtgtcc tggtgacgca  10620
gcccctcgtg atggagcagg aggagagccc accagaagta aggccacacc ctgtgctggt  10680
tggcacagct cttgttacat gtgggctctc cttccaggaa gacacagaga ggacccagat  10740
caacgtcctg gccgtgcagg ccatcacctc actggtgctc agtgcaatga ctgtgcctgt  10800
ggccggcaac ccagctgtaa gctgcttgga gcagcagccc cggaacaagc ctctgaaagc  10860
tctcgacacc aggtttgctt gagttcccac gtgtctctgg gaaacactct ttaccttttt  10920
tctaaaatgt aggtttggga ggaagctgag cattatcaga gggattgtgg agcaagagat  10980
tcaagcaatg gtttcaaaga gagagaatat tgccacccat catttatatc aggcatggga  11040
tcctgtccct tctctgtctc cggctactac aggtacctga gggaaaggga gcgggggagc  11100
```

-continued

```
gggatcaaga ctcagggtgc tggtgttcac aggtgccctc atcagccacg agaagctgct  11160
gctacagatc aaccccgagc gggagctggg gagcatgagc tacaaactcg gccaggtcag  11220
tctcgcgnnc ccgccgcctg gcctcacact gagcagtgcc ccgtttctgt ggcaggtgtc  11280
catacactcc gtgtggctgg ggaacagcat cacacccctg agggaggagg aatgggacga  11340
ggaagaggag gaggaggccg acgcccctgc accttcgtca ccacccacgt ctccagtcaa  11400
ctccaggttt gcagatggcc tttttatttt taacagtgga aaatacccat ctcgcatatt  11460
ccacaggaaa caccgggctg gagttgacat ccactcctgt tcgcagtttt tgcttgagtt  11520
gtacagccgc tggatcctgc cgtccagctc agccaggagg accccggcca tcctgatcag  11580
tgaggtggtc agatccgtaa gtgagccttc ccattcccct cacacccctt gccctcctgg  11640
ttttccacat ctccagcttc tagtggtctc agacttgttc accgagcgca accagtttga  11700
gctgatgtat gtgacgctga cagaactgcg aagggtgcac ccttcagaag acgagatcct  11760
cgctcagtac ctggtgcctg ccacctgcaa ggcagctgcc gtccttggga tggtaagtga  11820
caggtggcac agaggtttct gtatgcagca gcttttgtct gtgtgtgcct aggacaaggc  11880
cgtggcggag cctgtcagcc gcctgctgga gagcacgctc aggagcagcc acctgcccag  11940
cagggttgga gccctgcacg gcgtcctcta tgtgctggag tgcgacctgc tggacgacac  12000
tgccaagcag ctcatcccgg tcatcagcga ctatctcctc tccaacctga aagggatcgc  12060
ccagtgagtg ggagcctggc tggggctggg gcgctgagcc tggatgctgt ctcccgtttt  12120
gagctgcgtg aacattcaca gccagcagca cgtactggtc atgtgtgcca ctgcgtttta  12180
cctcattgag aactatcctc tggacgtagg gccggaattt tcagcatcaa taatacaggt  12240
gagtgggccc tggctgtctt cctctgcatt tgacacagag gcctttgtcc ctgtgcagat  12300
gtgtggggtg atgctgtctg gaagtgagga gtccaccccc tccatcattt accactgtgc  12360
cctcagaggc ctggagcgcc tcctgctctc tgagcagctc tcccgcctgg atgcagaatc  12420
gctggtcaag ctgagtgtgg acagagtgaa cgtgcacagc ccgcaccggg ccatggcggc  12480
tctgggcctg atgctcacct gcatgtacac aggtgagcat gtacacggtg cccataaggc  12540
cataaccttc gtactgaaca cttttgttac aggaaaggag aaagtcagtc cgggtagaac  12600
ttcagaccct aatcctgcag cccccgacag cgagtcagtg attgttgcta tggagcgggt  12660
atctgttctt tttgataggt aagaagcgaa ncccatccct cagcccgttc agtctctgac  12720
ctgcgtccct cctcccagga tcaggaaagg ctttccttgt gaagccagag tggtggccag  12780
gatcctgccc cagtttctag acgacttctt cccaccccag gacatcatga acaaagtcat  12840
cggagagttt ctgtccaacc agcagccata cccccagttc atggccaccg tggtgtataa  12900
ggtgaggttg catgtgggat ggggatggag ttgacactca ggcgcctgct tgctcttgca  12960
ggtgtttcag actctgcaca gcaccgggca gtcgtccatg gtccgggact gggtcatgct  13020
gtccctctcc aacttcacgc agagggcccc ggtcgccatg gccacgtgga gcctctcctg  13080
cttctttgtc agcgcgtcca ccagcccgtg ggtcgcggcg atgtatcctc tctggntccc  13140
tggtnctggc ccgccggcct ttttccttaa ctcctgcacc agcctcccac atgtcatcag  13200
caggatgggc aagctggagc aggtggacgt gaacctttttc tgcctggtcg ccacagactt  13260
ctacagacac cagatagagg aggagctcga ccgcagggcc ttccagtctg tgcttgaggt  13320
ggttgcagcc ccaggaagcc catatcaccg gctgctgact tgtttacgaa atgtccacaa  13380
ggtcaccacc tgctgagcgc catggtggga gagactgtga ggcggcagct ggggccggag  13440
```

-continued

```
cctttggaag tctgtgccct tgtgccctgc ctccaccgag ccagcttggt ccctatgggc  13500

ttccgcacat gccgcgggcg gccaggcaac gtgcgtgtct ctgccatgtg gcagaagtgc  13560

tctttgtggc agtggccagg cagggagtgt ctgcagtcct ggtggggctg agcctgaggc  13620

cttccagaaa gcaggagcag ctgtgctgca ccccatgtgg gtgaccaggt cctttctcct  13680

gatagtcacc tgctggttgt tgccaggttg cagctgctct tgcatctggg ccagaagtcc  13740

tccctcctgc aggctggctg ttggcccctc tgctgtcctg cagtagaagg tgccgtgagc  13800

aggctttggg aacactggcc tgggtctccc tggtggggtg tgcatgccac gccccgtgtc  13860

tggatgcaca gatgccatgg cctgtgctgg gccagtggct gggggtgcta gacacccggc  13920

accattctcc cttctctctt ttcttctcag gatttaaaat ttaattatat cagtaaagag  13980

attaatttta acgt                                                    13994
```

<210> SEQ ID NO 10
<211> LENGTH: 118777
<212> TYPE: DNA
<213> ORGANISM: Mus musculus
<220> FEATURE:
<221> NAME/KEY: misc_feature
<222> LOCATION: (1)..(118777)
<223> OTHER INFORMATION: LOCUS AF163865;118777 bp;DNA;linear R
OD 24-JAN-2001
DEFINITION Mus musculus alpha-synuclein (Snca) gene,
complete cds. ACCESSION AF163865
<300> PUBLICATION INFORMATION:
<308> DATABASE ACCESSION NUMBER: AF163865
<309> DATABASE ENTRY DATE: 2001-01-24
<313> RELEVANT RESIDUES IN SEQ ID NO: (1)..(118777)

<400> SEQUENCE: 10

```
gaacctcaga cagctgacag aaagtcctcc aattctgagc tacaggagtg aatctgctac     60

tgaaaacaca ggcagagcag acacgctgct gtagacacag aggaagatga cagggacagg    120

aagatgtaga cactgatagc aattagctaa ggagattcat ttcttttttc cctaaccagg    180

caaggaccct gactagaaga cattttgttg ttgaaacatg ttgttgaaga tacagttttg    240

gggatgtatg tgagaaaatg aagagtaaac ctgaatttaa caagccatgg ctttgggtct    300

ggtaccatga cgaagcataa gttacagaat actttctcgt tgccgttttt tggtttgtaa    360

attcagtcct tcaaatatcc atacatactg ggctcttgag aacccatgaa gaaaggatgg    420

aatacttggt gtttatgcaa acttatttaa tacctactgc aaagttcaag tcaaggctta    480

atgccttgac tactttcaca atcagccact acttattgga ttgggtggtg aaaacatggc    540

tgagacatct tgtagtcata attttttttt aaagaaaagt acctgatcct tcttagaagg    600

gggaacaaaa tacccatgtg gggagataca gagacaaagt ggaacagaga tgaaaggaaa    660

gaccatctag agactaccct acctggggat tcatcctata tagagacaac aaatccagac    720

actatagtgg ataccaacaa gtacttgctg acaggagcct gttgcagttg tctcctgaga    780

ggctttgcca gtgtctgaca aatacagagg tggatgcttt cagccaacca ttggactgag    840

cacagaggcc ctaatggagg ggctagagaa aggacccaag aagacgatga ggtttgcaat    900

cccataagag gagcaacaat atgaaccaac cagtaacccc agagttccta gggactaaac    960

caccaaccaa agagtataca cggagggact catggctcca gttgcatatg tagcagagga   1020

tggccttgtt aatcatcaat ggaaggagag gcctttggtc ctgtgaatgc ttgatggccc   1080

cagtgtagtg ggatgccagg accaggaagc aggagtgagt gggttggtga gctgtggggg   1140

atcaggaaaa gggataacat ttgaaatgta aataaagaaa atatctatta aaagaaatta   1200
```

-continued

```
ccccttcatgc tgtcaaacac cttttagttc ctgtaatcag gcttcctggt tcttctttct   1260
tccccttttg acacagactc tatgtccaca aggctagcct gactgttgca gtaattctct   1320
gaccaaatct ctcaagtgct gaaatcatag gcactaacta ctaggcctgg ctctaacact   1380
ggatttttaa gatcctataa atcctggaca ctttaaactt ctattttact cagaattttg   1440
ttggagaacg tactgtgtgg gacacaaatc actgctatag tgtttccaga aatttgaaga   1500
atactgagtc ctgttatgtg gtgactgaat ggagctgtga cctcctacaa agtagagctc   1560
aaggttctac attctctgtg gggtctccag taattccatc attgcaatgg actcctgcca   1620
ggaccatagt ttcagaatgg agtgtagaaa ataaatagta caacatctgg gtaagaaatt   1680
tggagaaaca tgatggagcg cttcaaagct gtctacacac acacacacac acacacacac   1740
acacacacac acacacgtga tcatgatgca ttgagagtaa gaataacaac attgctaaag   1800
agagtttgtg ggtacagaag agaaagagaa aaatgcttaa attaaacatg caaataaaac   1860
ttcatttaag aagtttgcag aatgaatctc caagctctaa agacaaatat tatccaaaac   1920
tactatgctg gaatgccagt caacacaggg gccactgggc aagttttctc taatttaaac   1980
aaaaccaaaa accaaaccaa accaactaat taaccaaacc aaaatcccaa ccaaccaact   2040
aaccaaacaa gcaaacaaaa atcctggaac aacatgagag cccaaggact gtgaatagaa   2100
tctcaatatt caaggtgtat ttgggaagct ccagcaagtg agctaagacc acaaggcaga   2160
ccagggaggg ataaagagac agtctctcta gatcaatctc taaacagtca tagatacaaa   2220
ctacacaggg gcttactagg ccacagttta aatttcacac aaaaaacaaa attcattgaa   2280
aagctgatcc cttagagtat gtaaaaattc cttgtttctg ctctagttgg cagtgtcatg   2340
agccttatca actggatggt gcagggactc catgttacac aatgtttttc ttcttctatt   2400
tgtttctaaa atcagtggtg agatcaggca catttttaaa aacatgacca tactcttgtt   2460
cattaccttc tcaagtaaaa aaaaaaaaaa acctatgatt tggcgggttc tgattatgga   2520
gggctgaaat agtaatatca gtcatgaaca gctgagagca ctggtttctg agcctctgat   2580
tgaagcttta gaatcctgtg tttggatgta taatattaaa gaaacaatag tcataagcct   2640
cagcctgtac tcaagatagt tttaaatgtg tggttatttg ctggtatgta tgtccgtgca   2700
gcatttctgt gcctgatacc tgtggaggtc agaaaagtgt gttggatttc ctgggattgg   2760
agttacagac aattttgagc tgccatgttg gtactgggac tcaaatccca gtcctctgca   2820
agagcagcct gtgcccttat ctgctgagcc acctctctag ccccattata acaagaattt   2880
ataaagctga tgacctattc catgtatccc ctagttcatt gcattgtgag agtgaataat   2940
ggtatttgta gataggttga aattataaat gtatttccta ttggttcatc atgagccaga   3000
catacagctt ttccaagatt taggttccct ggataaagcc ctcagtcata ttatcagcta   3060
tcaatgtaat gttatgttgt aaatataaat attagcccta gtacactaag gtagccacga   3120
gaagacttgc tgtgtcttaa acaagagaaa tttgttttct cacagttctg gaggttagaa   3180
gtctaatatc agatgtcagc agggttgatt tattctagtg ctgctgtcct tggctcacag   3240
gccactgcct tcacagtgca gcctctatgt ctacttctaa tgtattctag cctactcttc   3300
ttgtaaatac atcaatcatg gtagatttgg gcactcttca atgacacatt ttaaccttta   3360
tgtcctcata ctgagggtaa gaacttcaac acacagttgt aaaaatttat ttgtaagtca   3420
tttacttaaa aagtttttaa taacaaaatt tttcgtgtga atataacgca ttcagattac   3480
tctcatcttc cactgtcttt tatttaccct ttactcttat caaatctcac tgtcatcccc   3540
ccccaaaaaa aactcttttc cacatttatg tctttttgtt ttgtgaccca ttgagtttaa   3600
```

-continued

```
atatgtccat ttatgtgaca atgaatatgt gaccattgga tcctggtgag cttactagtg   3660
ggtacacagc taaagacaat gactttatgt ctttcaccat ctatcaatag caaacaatta   3720
atcatggaga ggtaggggca catacaccct tctactggtg gtacataatt aacaggcaca   3780
gtcttgaata gatccagtgc caagaacttc agctgctgta agctcatgat taaaatggct   3840
gtattatggc ctgaagatta tgttttgtac tctttctcca taacatttag catattatat   3900
tcttcccctc ttcagctttc attccataaa ctttagatgt actggttcaa atgtcctgtt   3960
tagggatgaa atatggagac aaagtgtgga gcagaaactg taggaaaggc catccagaga   4020
ctatctcacc tgaggatcca tcttgtatat agacaccaaa cccagatact attgctgatg   4080
cccagaagtg cttgctgaaa ggtgcctgat atagctgtct actgagaggc tctgacagag   4140
cctgacaaat acaaatgtag acgctcacag acaaccgttg ggctgagcac gtaggtccct   4200
gataaaggag ttagagaaag tagggttagc aaccccatag gaagaacaac aatatcaacc   4260
aaccagaccc cccagagctt ccagggacta agccacctac caaggagtac acatagaggg   4320
acacatagct caggctgcat atatatgttt ttcaggcatc aatgggagga gaggccctcg   4380
gtcctatgaa ggctggctgg atgccccggt gtaggggaat tggagggcag ggaagcagaa   4440
gggtgtggat gggttgggga gctccctcat agaagcagag gagggggatg ggataggggg   4500
tttcaggtgg ggatcaggaa agcagataac atttgaaatg taaataaaga acatattccc   4560
cccaaaaaga caaatatcac atcacacaca cacacatgtg cacacacaca cacacacaca   4620
cacacacaca cactcagaga gattgagaga gagagagaga gagagggaga gagagagaga   4680
gagagagagg tgcagagagt ggaagaggca gtttaaccag gacagttgaa cagagacagg   4740
ttgcacaaag agaacaagct agacacagaa gacagaataa accaagggat gagaaagagg   4800
cagagtagaa catattgcca aagttagtat caggtcaagc agagcaattt agaagaggcc   4860
gagagagaga agccagaatg aatcaatcag tgtggagagg attttgagcc ataacagctg   4920
agttgaacca tgtagagtta aaaaagaaca agagagggtg agcttattca tcattaagtc   4980
ttagaggctg aaaatattct agacctagat aatactgtat ggagggtaga agcttccagg   5040
actaggccta tgttagcaga gagaggcagt aagcctctga tatgacaatt acattaggtg   5100
aaaaatagtt acaattacat ttaggtagca tgttttcatt attcatcagc tgacagacat   5160
ttagaccgtt tctatttcat ggctattatg aatagagaag aaattaacat ggatgagcaa   5220
gcctctctga agtggaatat agagttcttt gggaatatgc ccaggagtta tacagcgtga   5280
tgatatggaa gacctacttc ttctcttttg tagaaactct acattgattt tcatagtgaa   5340
tgcttcccct tttctccaac catcattaaa ttaatgtttg cctttcccaa gtctgtacta   5400
gaatttgtta tttgtccatt tgtcttagac atcctgagtg ggtaagact ggggcctcca   5460
gtctcttgag ggttaggtgc atcatctctg tatgaacaca gccttggcag tcctctactg   5520
taagtgtttt gggggcctca tatcagctga tatatgctct cggtttggtg gtccagtttt   5580
tgagagatct tgggggtcca gattaattga gactgctggt cctcctacag aatcaccccc   5640
tttctcagct tctttcagtc ttccctaact cggaaacagg ggtcagctgt ttctgtccat   5700
tggttggttg caagtatctg catctgacac tttcagctgc ttgttgggtc ttctggtctg   5760
tggtcatgat aggttggtcc ctttgtgtga gcgctccata gtctcagtaa tagtgtcaag   5820
ccttgggacc tccctttgag ctggaatcca ttttggacct gtcaagggat cttcttcagg   5880
ctcctctcta tcttttctca aatgtatagc taataaatat tttgaaaatt tccctcagtt   5940
```

-continued

```
ttcagaatgt ctcttcacac aaaggatggt gttcttttaa gcttcacagc cctatttgtg   6000
agttattctt aatatctgtt caactgtgtc ctgttccaca acctataagt tgaggtatat   6060
tttctttctc ctctgaggaa tcatgttatc agatttgtgt tgaggtgctt ggagttggat   6120
tttgtacaag gtgaagtaga agaatctagt ttcacttttc tacacattgc tattcagttt   6180
gaggaacata attgaactat tctgaactga gattctctaa actgaacaga actgaattga   6240
actgaattga aatctctatc cttccctgat gtttaagtag cctctttttc ctgtctgttc   6300
ttgtgagagt taggcatatc ttatttgtgt ctcattctgt aaaatctttg tctgtacctc   6360
aattagatat cactgtttgg gattaaaggt atgtacaaaa gatatgtcta aatcccagcc   6420
agggaaatta aatgtatgtc tactctgcat tccagtagaa ttatatcttt gtatgtgatt   6480
ccttgcccaa gcacccatgt tgcttgatta aaacctctac aacatttatt ccaagatatt   6540
ttattttttc tgtggttatt gtcaccactt aatttgatga cataattatt aaaataatta   6600
ctctccccct gaggaagact gagctacacc atctctatgc tagctcaaga catacttcct   6660
actggcatga ggattctaat tgactcccta tcttctgaat tcagagtgag ttatatatga   6720
cacacgatat tcattaacac aattaaagga taagtatgaa tatttggtag tttttaatgt   6780
ggtcaacagc atccaacaat gacaggagag tttgaaaaaa tttcatagga aaattgtcac   6840
tggtttttaa ttaacactta aaaggtgtaa cattttttttt atgctattaa gctctattcc   6900
aaaaagtgtt aagttcattt tgtctatttg ggaaaaagaa gaggtagaaa atatcttgag   6960
aagaaggaat attgtgatca caaggctaca gtgaaatggg ccatgtccac tagagtagta   7020
gaggaaaagt aatagaggaa attatcatgt attgtaaaaa tgacacttta ttatcagcaa   7080
ggtggagcag tagaatgttt gtatgctgcc tagataggaa tgaaagagca tgcttctttc   7140
tttgatggga acaaatgact ttgtacagaa acattttcct ggagataggt ctctgagatg   7200
tggaaccttc cctagtgaaa aggaccatgt ttcctgctgt gctgccatga atatttttag   7260
tcttgctcat ctttggctaa gcctcagtgt ttgtggatac cagatgcatt gtgcaggtgt   7320
gatgtggaaa caggaaatct gactacttgc catattctca aacatatttc ttatctccct   7380
gaagcaaaag tagaacataa aacatttctg ctatcaccta ttctaattaa atgcatatat   7440
aggattattt attaaaaata gtatttatga aaaaggctga aagctctgtg atttttcagt   7500
taactccttt atgcacatgg ctatactgct gatatctgat gaatatgtgt ctgatgctat   7560
ttgtgttcat cacttttctg ttgccgtgac aatataccac aaccaaagca tcttatagaa   7620
ggaagagttt atttggctta tggtttctta tgaagatcct gaaagtaaag gaagccctga   7680
aaaaccattg tgtgaggctt tgaaaatgaa gcctgggtta cagtagatcc caaaggcttt   7740
agagattcca aagccttaca cagtggtctc tcagggcttc ttttcctttc agtatcttca   7800
ttcaggatga acttgccaca tatagcatgg cctcagaaac tctctcaaac aatggagaaa   7860
actccatgag cccttaactc ttaaaaaaca aacttccaca atattcatgg aaattatgat   7920
attcttggac attaatctat ctctgaagat gcatcttcca ttagagtcta taaaaaggta   7980
aacaagagaa aacaaggcag agaaaaaaaa tagataaagg taagtggcca aaggtttgta   8040
aacaacactg agccaaaaat tcctggcctg gaaatgagta gagtaaccag atcataagga   8100
tggtcagaat ctcagatgtt taagtgaaac tgtattctcc tacataacaa aatcattccg   8160
tgtcagcgcc aacatggctc caaagagtca gatctggtca acagccaaat ccttaagaaa   8220
tctagctcca agttcatttc caactgacta gaggtaaatg ttatgctttc ttctgagtaa   8280
ttttctctaa atgatttaaa gaaagggtga agataattta gaactcaaat taaaggttac   8340
```

-continued

```
taaacaaaat tcaaacttca ttttccagtt ctttttcagt ttgtttttta aaaatataat   8400
tatatcattt ccacttttct tttttctttc tccaaactct cccatatagc caatttgctc   8460
gcaaattaat tgcttcctct ttataaaact gttattacaa ttttgcatat tatcattttt   8520
aatactttat agtatctgca ataacaataa ttaatataaa cataatacta atatataata   8580
tatattttcc tatacataaa accaccacct ccttggactg tataatgtta ctgtgtgtac   8640
atgttttgag ggttggtcat ttggtattgg aaagatcttc cttggggagc attatttcta   8700
ccattctcat cactccttag gaacctacaa ttctttgtgt agggtttgag gcctcttcag   8760
cccccattca cattagcatg cgtattggtg tgttccttgg ttgggtcatg tttaggcacc   8820
catgaggatg agactttggg tatagtttct tacatttctg ggagacacag ttttacagca   8880
cactctgtgc tcctctggct cttatagtgt ttctgctccc tttccagaag ggccttcaag   8940
cctaaaggaa ggacctgtgt tgtagttaca tcagttgggg tgtggctcta caactctgaa   9000
ttttaattgg ttctggtttt ctgctatagt ctctgtctgt tgcaaagtga agtttcctca   9060
atgagggagg aatgagaatt atacttatct ataaatataa tgacatacat ttcaaatgta   9120
gttagagatt ataattgttt gtaggctctc caatgttcat gactttgcaa gtcctgggta   9180
gttggctagg tttcaatgac cagacatgtt ttctcccttg ctgtgcaggt cataaattca   9240
atgagagcta ttggttgtca cgaaggtatg catgccactt atacacccca agggttatca   9300
ctccatgctg gtcacttgtg tttcacaggc atatatctgg gtagaacaag gggttgcttc   9360
tcacctttgc tagtgtacat ggcaccttct ggtactgaaa gctactcctt agggaggagg   9420
cttttaggtc agttccagct tagggcctct gtgctccgtg tttgaagtac atattgtcat   9480
cagcaataac aatttacctt ctacttctga aggacaacca aaagaaataa tatcagtaac   9540
gtataatgta ttctgtgtct cttctataat cctgaccaat aactcaaaag aggatttctc   9600
actcatcaac ccctgtaagt atcgttgttg ttttgttttg atataattgc aatatttcac   9660
ctctcttttc ctctcttcaa gttttccagt atacctctcc caggtctcct tcacattgaa   9720
tgttctcttt ttctttaact gttattgcat aatatatgta tatacatatt tattcttcag   9780
tataacctac tcagcctgag agtgaataat gctacttgaa tgtatgtttt cagggctgac   9840
cacttggcac tggacaagca atttgtatgc tcttctctac agagatcata tctcctgcac   9900
ccagcttttc tcagttacct attgtccttc atgtagcatt gaggtctcat ggacttttcc   9960
ctgtccactt tgacatttcc ccttgtgcta accttgttca gttcaggttt gagtagtcat  10020
gaatgtgaga cttcatgggt atagcttctg acattattag cagacataat ctcatgcaaa  10080
ctttcttgat cctctggctc ttacaatctt tctgtttcct cattcataaa tgtttctatt  10140
gggactgggc tctaaaactt tgtattttga ctggttgtag cttttctgta gtggtctcta  10200
tttgtttcaa agaaaagatc ccttataagg agcaaagtct atacttatct gtgggtataa  10260
caacaaatgt ttgtagattg tagttaggga ttattctggt ttagtaaatt agtggttgta  10320
gtttctcctc caacatccat gacttcacta gcactgacta gttcactagg ttttcaggta  10380
ccaggcatgg tttctctctt gctgaatgac tcatacccac aattagaggg ctgttggtta  10440
atactcacaa gtatgcatgt gactcctgca tgcttttggt tatcatggac cctgatgcca  10500
ctgaaacaca ctaacatcac cttttttat tttatcgctt tcaagaaaca gaaaataggg  10560
tctctttagg gagcttgaaa ccttggtttg tggagtattg tttgaggaca cccttccctt  10620
catttcaatg caaagtagac ctgtccttaa tggtgtaaaa cttttaaata attacagcct  10680
```

-continued

```
tccttctgtt gctttggcag taacataaac atactgttgg tctttttctc tctaaactat  10740
acattttgta tttctgcccc agttgctctt tctttcatta tagatctgca taagtgttat  10800
agtacaacca ttccacagat tcatcattat gttgtcttac aatcacttcc actaaagaaa  10860
ttcatccttt acttttcaat tgagtctcag gcaagtattc tgctcaggac atgagcagaa  10920
ggtggccaca aaccatgatg aaaaaatgaa tagcctccaa cacacttgct gttaacgtcc  10980
ttcattcctt ctgaaacctc ttggtccagg cttctacagt atttatccct ctcagccctg  11040
ctgtcttcca atcttctacg agaaggacct tttcatctct gctcatagca ttcatctgcc  11100
tttcgctttc aatgtttaca ttcctccaaa ccccaaaatg attgggttct tcacagaaat  11160
agccaacttt tttggtacca acttctgttc tcatttcttt tctattgctg tgaaagacac  11220
cacagccaga aagcaacttt ggaggcgaac ctttatttca gcttgaaggt tatagtttat  11280
catcaaagga agtcttggca gaaactgagc cagaggccat ggaggagtgc tacttgctgg  11340
cttacttcca gaatcacatt cagctacctt tctttcttac atgtcccaac ttcattgttc  11400
acagtagact aaactctttt acatcaatca tgaagcaaga aaaccactac atatacaccc  11460
acaggccaat ctcacaggta tcagttaagg ttctcccctt ctcagacata tctcaattca  11520
taacacgttg taagcacaac cagcacacta ttcaaacaga tttgcttagt gatgggggaa  11580
gcaaaaggaa ctgtcttaga ctgatatgct tgcaatgttt tcaaatagct tcatctctgg  11640
actaaatttt gggttttttt tttgtttgtt tatttcaaat gtttatattt ctttaatttt  11700
gtaatgtaaa tatgctgaga aatagtatat agtatttgtt gaagagcttt aattcaatct  11760
ccttgaactt catatccaga tatcaatcac tttttataaa attatatttt cttttgccct  11820
aaatacgtga cctaggaatc agtataaata taataaaatg taagtataaa tgcaagcatt  11880
tatgtgtcaa tagtctttgg cctcttagtc aattctttct ttctttcttt tttgtttgtt  11940
ttcttcaaga cagggtttct cagtatagcc ctggctgtcc tggaactcac tctgtagacc  12000
aggctggcct tgaactcaga tatctgcctg cctctgcctc ccaagtgctg ggattaaagg  12060
catgtgccac caaagcccac tttcttagtt agttcttgtg gctgcttaaa catggtttca  12120
tcgctagttg gaaataactt acttgccaga gtaagattaa tggagagttt gtataatttt  12180
tcttcttttt cgccaattag tatcactctg gaaacatatg cagatctgct tattaactgg  12240
gcaaatttca attgggcaga catattttat tatatatatt ggtttcacct aagaaaagca  12300
cagcaatgtg aatactctct tttttctttt gtttgtttgt ttcctgatat atattgcata  12360
agctaagtgg gtcacccatc atcacaacac ttgtttgtat gctttaggtt gctatatgct  12420
ttaaaaaact ctgggaccag aatggttggt catgtcctaa tggatgaaac accttttcac  12480
ataaagagtg ggtgacttag atagatacct gagcaaaaat tttacatgga caattgcttt  12540
ggcaaaaaaa ttatggaaag tgcaggatca ttatcaacag tttataaaat ggtaaaacat  12600
gtttcttgga catatgtcaa cattctgagg atgtatattt tataatcatc aaggaaagat  12660
tgtcttttaa tataaaattt tagtcaaatt taaaaatttg tttgtgagga agactgatac  12720
catattgagt ttaatttttc tatcatcatt gatctaattt ttttcaacta acagtaaaaa  12780
tgaaccattc tatatgtatt gtatgaagtc tgttcatttg tcacagaaac tcatgttgat  12840
ttcccatctg tctttagtgt tattttaact acttaaataa tctctataca taagaccaca  12900
gcacaagata attaaggagc tagaatgctc attcacttaa ttattgccca acacacttac  12960
agagctccat tttacatttg aaaaatttgt caaattgttt tactctctct ctctctcttt  13020
atatatatat atatatataa aaggtgtgtg taatagtatg tgtgtagtat atgtatgtgt  13080
```

-continued

```
gcaaatgtgt tttaatatgt atagtctatc actctctatt ttcagtatca ttaaaaattt  13140
tatgctattt ctttgcttga gaagaaactg cacatttgag taaaataagt tggatttttt  13200
ctttggataa ttacattgtg tgaagatgtt taaataagtg ttttttcat atgcacatat  13260
taaagatcat ctgtgaaaca tctatatttg ttatgaatta aaaagacaaa tatttagaaa  13320
gccatatttc tatagtctag gctttgacaa gtaaagtgag aatccatagc tctgttcttt  13380
ccatcttgag catgacacac acacagtctc tttgtaaatt actcaggctt tcttattctg  13440
atataaatac aaacacaaaa taacttgtat tttgatgaga aaactgaagt ggaacttaaa  13500
tataaatgga cttgaagatg ctatatttag aagctaaagt attactttgc ccctaatttc  13560
attttctaat ttgtttaatc acttgttcca tatttgatat ggaataacaa gctttcacaa  13620
tactgatgat gcattttata taatgttgta ggcaatcgtt tcaatgctac tccatacttt  13680
caaattgtct aaacaggtaa aaagtattag aatctctgag cgcctgctgg acatgctcct  13740
tttattgact ttctgttatt tatttccttg aaaggcataa taaccaaatc aatactgtca  13800
gaaaaatata aatcctcttg gtatgctatt ttatccactt atttttccct ctgaaaataa  13860
atattactga aaaatatatc tgtcttatta atctgcccag ttttgctcac aaaagatatt  13920
ataagttgga tttcataact tttctatctg gttggaaata ttttacatcc tatagtaaga  13980
taaagctatt gatggcagtc acagacatct caggtatctt gtgaatgaac taagaaatga  14040
ttcaaggctg caaataagac ctgaccaaat taaaagaaat gcttcctagt tcaccctaaa  14100
catcagttta cataaaaatc tccactcatc gtactaaaga gacagtttag taattaagag  14160
ctcaaattgc tcttgagatc tgagttcagt tttgagcacc tacatcagga ggctcaaaca  14220
tcctgtatct cctgcttcag gtgaccttat acctctaggc tccttgagca ctggattcat  14280
atttatacac actaaagtaa acattaaaaa catgcagtca tttttaagaa tgcactcagt  14340
tgaattattt ctaagaacac tcttatttct gtcattacac aatacacata aaatacctgc  14400
cctattttac agagattaga gaggtgaggt gctagctcta actcactgct agttcatagc  14460
agcacacagg tccatctagc ctctgagttg tatgtggaca ccctgtctca gatttatgtc  14520
ctgctttctg gagttgagtg catttctggg gttcatcagt atgatctttt tcctcatttt  14580
gaaataaata aatttcttat attccaaaat atcaaatgta ttttctattt ggttttatag  14640
tctttaagtc ttgaaatcat ggacatcttc attttcatag gactacagca atggttgtga  14700
tgtttagaaa gacatccaac tgaattattc acatatgcca tgctattttc ctgtggccaa  14760
agttaacacc tgttcttcat tgttgttcat taccctctga gcgtgtggaa taatagaata  14820
aactgcacaa gaggtcaaat taaagatttt cttcagacac tacattccct cttcattgat  14880
tctttttct ttttaaattt agtgtcccat tattgttctg tctcaagttt aaatctttga  14940
aaatgaaata tgattatcat cttaaagcca tatattggca gcttctctgc tgcatatccc  15000
atataagatt gtaagataca tatatgcaga tttcagcagc acatgtctca tgtaattaca  15060
gaagatgaag gagggacagg cagatactaa gaagcacata atactaagca tattatgtct  15120
gtactcagtt aagcccatta aatcaacgct ttccaccctt ttaatcactt tgcgaccatc  15180
agcttccttc tcaccatgac atttcactct gctttctttg taatagtgta ctgttaaact  15240
caggacaaac ctcaaaactc acttgtctca tgggaaatca aagagagtgc aggtcaagta  15300
tatatttgcc tagaacatta atctacagca taattacgtg attaagctca gttaaatcaa  15360
tgctattagc atggcaaaat attagatttc actcgtggga gagcacctgc acacatcact  15420
```

-continued

```
cacatgtccc attaagttgc tctgccttac actacaggct ttgagtttaa actttaagtt  15480
ttaaagtgat tttcagaaca aggctttgat actaatggag gtgcgggaca gaaaggagaa  15540
aacaacagga atgtccagtt cctctctttc ttacagaggg ctgcagctcc attataaatg  15600
cagagacaag aacccacagg ttgatcttag aaaccgtcag catagtttga aaagctgctt  15660
actgtgctca gagtgctttg aagtgtgtat agaataaagc agaaatataa taataaatca  15720
aaatggtgaa aattatttta caattttatt gtagtctttt tgtaatctgt gcatgtgtgt  15780
gcgtgcatgt gtgtgttcat gcatatgtgc aagcatgaat gtgtgtgtgt gtgtgtgtgt  15840
gtgcatagaa agaatttccc aacaccaaag aacgctgata cagatactcc aaatataact  15900
gatatgtgtc ttcatgtgta cctcagctcc cgattttcca tgttcatatt cacatttgag  15960
ggcgatttgt aacacagctg ggtcctacct tgttactttc catccctgct ctgggagact  16020
tcacagactg gtttacagtg atagaggatt gtgccttctg gaaaagccta ctggattatc  16080
tcatatctga ctctgatgtg atctgagtcc aatgcactct cagagctcca gtttccctgt  16140
ctagaaaagt gacacaaaac taaacttatc cccttgtgat gattaaacgg ttcagcacct  16200
ctgttctttg ccagacataa agcacagtgc acagatgtgg agttatggag ccattgtagg  16260
aagcacaact atcccagtga gtccttcgtt gctcggcagt tgggccttaa agtatctgac  16320
attttatttc tcttttaact gaaatcccaa ggcttaagag gagatccctg tgaatttata  16380
aatatgtcat atcgggaaat atattaggta gttgtcactg cagtctatcc aactaactga  16440
attttatggg tcactgtgaa aatgcattat tggcagtaat aaaagaagaa aagaaactaa  16500
taaactagtg atttatgcaa cagcataggt gaactaacac atcatgctga ctggtataaa  16560
caaaggccat atactccatg gatatgtaca gaatcaaata gaattataaa catagttcaa  16620
agggatgaaa catttccttt tatcttttga gatttcactc aggtcagata actggccaga  16680
ctgtgtgact gaagataata gaaaccagac agtgctgatg ttaggagcaa caccctgacc  16740
agtaccgctt agttttgcat gcaatgagtg ttctagatat tgaaatagtc tctctttaaa  16800
atggtatgct atcacttgga ctttttcaaa atctgcagac acaaaatcag agcagttcac  16860
tctataaact ataattcaat gtagaatatc atttgatgcc atcctgggta tttcagtcat  16920
tctcacattt attaatgtgt gctagaatgt tcccagatgg aaaaacatga aaagcttaaa  16980
tctctagaag gagagaagtc gatagtgaca gagtagccat gctgaaggca cagaatgatg  17040
cttgtggaag ctggtgatat ttatgtagga atcttagtct cacaactgta aatatgttta  17100
aatgttttac attctaaaat tttagaggag aggtgtcatc tcaattcact ttctcttcta  17160
taatagaaaa aaaaaaaacc tggctaaata gaacataact tggtaaagtt ctgagaggca  17220
gaaaaccaac gcccagacgc aaccaaaaca ggcctggcaa aacattatcc cgaggaaacg  17280
tttgtgtcct ctcatctggc tttagactat tgacaaatag accccaagaa attggaagtc  17340
ctccaggaat ttgctgaggg aaggaaaagg ctgaagcctt gtgtcaatta cagggtgagc  17400
atgtctccca ggaagaaata tcagatatca gatacttagt cagacctcct tgcagaagag  17460
actggagcgg agacagagac agtagctgga agcacacttt gacctactgc ttagtcatac  17520
atacatcctg acctctatct aaacaagatg aacttggggc actaaacctc tgttcctctt  17580
cttaacgtgg ccacattgaa ttactcccat ttctagtatt tcactattta tatgtcactt  17640
tacctggctg gttgaggaca ggtgtcctaa cttggcagga tggggatgct agagcccagg  17700
atctaaccct atctactgca gaggtgccac cttttccttt aatttcaagt aaacatggta  17760
tgtgccacta gtgtgtagga aggttgattt ttaaagggaa taagaattga aggcgttgct  17820
```

-continued

```
taaacagtta atttctgtca cattacttgt actctgcatt tgtggtttta tctgcctcct  17880
tcctttatag catgccaaac aagctgcttg tcccttgttt caaatgcttt tttagacttc  17940
aatttattta tttatttatt tatttattta tttatttttc aggattcaga agtcaactga  18000
cttcaaggat cagagaaagc attccctcct acgacccccc cccccttttta atacagtaaa  18060
cgcttgattt agcttccagt gcccaacaca agttcagaat acaagaaagg aaaagcaagg  18120
cactctgctg ggggaggagc ttggcactca aatccactct gctataaaac agtggtattc  18180
tgctcatctc agagagaagt gggaacgtgt taagtaacac agaaattgtc tcaaagcctg  18240
tgcatctatc tgcgcgtgtg cttggattgg aagaagagtc tgttcgctgg agctccacgc  18300
agccagaagt cggaaaggta agaggtgtgc aaaatctgcc attaagtagg gactaaggaa  18360
gaaactgcct gtgatggtcc cagagggtga atcccacagc cgctaccttc ctatcctgta  18420
actctatagt aagccacttt ctcaagtgca aaaaagcctt gaggcagctg gttttcgacg  18480
gttgggggat atttattcct tgctccacag atggggaaaa aaaaatcagc gtctggcagc  18540
cgctgattgg tggaaaagaa aatggtgata gtggagtggg aatgaggatt tgctgagcct  18600
ccccctgctt cttcgacctg taactcttcc ttagtcggct cccctttgca cccagaaccc  18660
ttttagactc ctccggggta aaaacaaatg gaaatcttaa gctgtgtgaa caaaagcaac  18720
cccaagggtg tgtgctccct ctccattgcc tggctccgca cacagaccat ttcaggcggt  18780
ccagctctct ggtgtggcat ctgggctcgt cctggaggag ggggtcgcct agaggaactg  18840
ggaacagact gaggcaggga aggagggggg tggggcagga gaggcgccag ctcaagttca  18900
gccacgataa aactgagggc cctctgaact cgaggggagg ctcaggccgt cctctcttcc  18960
ttccatccgg gggaatgtgc tccagatacc cacagccctc acgcaccgca cctccaacca  19020
acccgtcccc tccctaggaa gaggagcgaa ggcacgaggc aggcgagggg cggggagagg  19080
cgctgacaaa tcagctgcgg gggcgacgtg aaggagccag ggagccagag cgcccggcag  19140
caggcagcag acggcaggag accagcaggt gttcccccctg cccctgcctg cccttgcctc  19200
tttcattgaa attagattgg ggaaaacagg aagaatcgga gttcttcaga agcctaggga  19260
gccggtaagt acctgtagat ggggcagctc tggggatctt agctagccgg agcaaagagc  19320
cgggacgcct agagaagacc aactacagct gctttggcgg tggggactgg gccagtgcgt  19380
ggaaagtaca tcactcggct ttcctttcgc tggagacatg cccttccatc ctgtcaaagc  19440
ccgagggaaa ggccaggttg cctgtggcat ctgcttttttc aagcggaaac gctagggtgt  19500
ttcatgttga gtgctggatg gtggaagctt agtgctgggc attgggtgga atttgagcat  19560
ccaactttca tgctccaacc ccaggcattt cagcttcttt ctgtagagga agaagggtgc  19620
ctttggccca tgattaatag aagtgcagag gacagtaggc aacaggtgat aaagggttaa  19680
tgagcatggg gtgcagggtc ttctagagga ttccagctga ggacagagct tcttggttgg  19740
gtggtgctca agtgagactg ctcaagtgta tggacagcgc ctgctctggg cagatagcag  19800
gcaaagagct agtggtgggc agaaggtctt gcaagattag aaaggctggg cttcaagcag  19860
ttccctactt ctagattaaa cagttcccct cccttccttc tccaaagact gactcctctc  19920
tgggtctttt atcctcttgc ccccactcca tctctgtacg cccacctccc atgttccttt  19980
tctagatagt ctttttactt tgaatgtaac ctttgggccc tgggaacttg atggggtaga  20040
ggatgcccac ctccccttct gcaactcttc ttctgaaata tgtatgtaag agcagtcgaa  20100
tgatcaaact agatccatcc catccttaag tgacatgact ttttcctagt attgagtgac  20160
```

-continued ataactcaac aatcaatcaa cactgtgccc agcaccccca catcccccca cccaagaaat 20220
cacacttaca ccaggacttg ggggaaggca tactgatttt tccccctcaa tttcctttct 20280
ttctctagct gttttaaacc ttattattat tattttttta cccaaatttt ctaattcaaa 20340
atgtattctg tattctctag tgtggagcaa aaatacatct ttagccatgg atgtgttcat 20400
gaaaggactt tcaaaggcca aggagggagt tgtggctgct gctgagaaaa ccaagcaggg 20460
tgtggcagag gcagctggaa agacaaaaga gggagtcctc tatgtaggta ggtagtgaca 20520
ctgtgactaa tgaattgggg tggctggtgt gtggtgtctg attcgtgtgc atcacagctt 20580
ctcagaagag tgacagctgt gtggaggtga gagaatatga acctgcatat tagctctcag 20640
aaacaaacag ggacaatgtt ttctgtcctt agattcatta atcttgttat ttatgtaggt 20700
tttttatttg gttttctgtt tctgtgtatg aatacactga attttaaaaa ttggcaaccc 20760
atgaaaaata accaagaata tgcttatgaa tcaaagacat gtatggcagt aagcctggtg 20820
gcatttggga agtggaggcc caaggaccag gagttgatgg tcatcttcag ctacacagag 20880
aatttgatgc cagcctgaac tatgtgagaa cacacacaca cacacacaca cacacacaca 20940
cacactcaca ctctctctct ctctctctct ctctctctct ctctctctct cacacacaca 21000
cacactcaca cacacacaca atacacacac acacactctc tcttacacac acacatacac 21060
acatacacac atacacacac acacatacac acacacacac actcacacac acacacaaag 21120
aaataaagaa ataaaggaag gaaggaagga aggaagaaag aaagaaagaa agagaaagaa 21180
agaaagaaag aaagaaagaa agaaagaaag aaagaaagaa agaaagtgag ccacaagtac 21240
tcatgggact ttgatttctt tcatcatcac tataggtaat acctgctaag tttaataaat 21300
tataaagctt taaacaatag ttttgcataa ttttatttta caactgtgaa aatacaactc 21360
ctttgaccct caaatagaag aaagaaagca agtcttcttt ggtggatctc cttttaggga 21420
tcacttggtc agtgggaaca gcgggactta aggaacttca gaaatgtttg tttagttcac 21480
ctgtcagaga tcatacatgc tgaacagtaa gaggttgata tttagtgcca ttttctgcct 21540
gactgtacac attgaaagga aggccaacac tccctttctc tgtctttccc tgtgttaaat 21600
tggctgtaac tttacaaatc ccttctagta ctttcatgga aggaatagac acccatgcac 21660
acatgcttat ccccagcaga gacacaggtg cacatgggag cacagttgca gggttcatct 21720
acctctcttt cctcctgtga acactgtttc caccttctta ggagggcatc tctcttggtg 21780
gaagactcag ggtaaacatt caggctgaaa aggagcagaa caggtggcaa aagtgatgca 21840
gatgctaccc agagtaccaa tcgggggaag ccatgctgac cctccaaacg atcagtgagg 21900
aattgatact tgtaaacatt ttcatgaatg tgtcttttca ttgaagtttc tagcagatca 21960
cctttcctaa ttcttcacag aataatttta cattgaatta attctctttt tctacttaaa 22020
acatcctttc agaaagtctt gtaatgagta ttgtaagaga agggtgtcaa tgagctaatt 22080
ttagagtgtt ttttttttaa tgaattgtga agtataatgt tttagataga attcagaata 22140
taaaagcagt aatttgtaga tttggggaaa aactcaattc ttccacaact acaggcttgt 22200
gactgatttt tttttttttt acttcagttg cttaagaaac atatctgtag atcactaatt 22260
taaagcaaat ttagaagttg ttgaatatta atttagtata ttactctttc tggataataa 22320
atggattttg tcaagcagaa cacttctttg tttttattgt taattttgag tttgggcaaa 22380
taaagtgatt atatttttca aagattaatt ttgttggtct ctgtgaggcc attatattga 22440
aagtgtaatt ttaatatgtc taatattatt aaaattatca atgtctgtta ttatatttaa 22500
aacatgttta attaatcaat tgcttattat gttctggaat ctaattaaaa gctgaacaca 22560

-continued

```
tgcatagagt ttgggatgaa gagtaatgtg tgaagataag aatgatagct cagatatttg  22620
tcaacttctg ttaatgttcc aacacatatt agaaaatctg tcatagataa tcagctgtac  22680
tgttggctat actgattatt gcttagataa tcaactgtgc tgttaaagta tgaaaacaac  22740
cataggcaaa aaacagtgtg actctgcctc tgtctttatt gactcagaga ctatagagaa  22800
atgaaaggaa tgtagactct ggacttgact tgatacagac agaaatttaa ttcaagccac  22860
atgatttctg cctttagcat ctgcaggagg taacttgata tctttgagtc tcctcccctt  22920
tttcacatac acatagttca taaaaatgca actgctttgt aaagttacta aagttatgta  22980
gttaaggtag taactgagtg cactttcata tttaggaaac ttgaatcttg tcagagaagt  23040
tgttcaatct atctgttact cagtcaacct aatttcttac tttttatcca agatatgaaa  23100
ctattattaa tacctaacct gaaggattag aaataatctg gactttggac atagctcccg  23160
tggcacagtg cttgtctgcc agcatgcagc cctgggttct attcccgtac cagaaaaaca  23220
aaagattaaa aataaaaggt tagaagtaat caaagaaaaa caatgtaaac ttcagcactt  23280
atggctgaaa aggcttggca gaagtctcat ctcatctcta ataacaaatg ccttggacaa  23340
ctgcctttca atgaattgaa gacctgccat actaatcagt gtgctgattg tctctgtgat  23400
atttgcacaa aaaattcaat taacatattt tagcttcata atcaacagtc tcaatggcgt  23460
gatgtataat tataaattga atttaaagtc aaaaagtttt cttcacttca tgttagtttt  23520
attaatacta taaagaaaat caccttcaag ttctgtttca ctgcctggtg aagagctgtg  23580
gtcacacatc taactcctaa gtctcacatg tgagacttaa ctacatgttg ctaagtagtc  23640
agcatataaa ccaatgatat gactcatttc tcacattcct cttaggtccg tatccttgta  23700
atattccaaa taaacaagac agggtggggt ggaaggcagg gtacatttct aggctcagag  23760
aagccattat tatattgttc cccagcttcc atatcttact tcttatttgc tacttgatga  23820
ctaatttttt tttgctatat cttatcagtt agatctcacc tgtaaactga agataaacta  23880
tcatttataa cttagctgat aattaggata acaaaggtga gaggtatggt ttgagataca  23940
gggccttcaa gactcatttg tctttcatta aagaggcatt ccatgatttt accaaacgtc  24000
aaattctctg ttactgctga ggcaaagaag acagacaaga gaccagccag tgagcattag  24060
ttttccttgg tcatgctttt tttttaattg ggtattttat gtatttacat tttaaacgtt  24120
atcccctatt ctattctaaa ccccttccct ggcttctatg agaatgctcc cctgccaccc  24180
atatactttc acctcacggc cctggcattc ccctacacta gcgaatccag ccttcacagg  24240
tccaagggct cttcttctat tgatgccaga caatgccatc ctctactaca tatgcagctg  24300
gagctatggg ttcctctatg tgtacttttt ggttggtggt ttatgggagc tctggagggt  24360
cttgttgatt gatattccta tggggtttca aaatggttgg cttccagcat ccgaatctgt  24420
attgatcagg ctctagccga gcctctcagg agacagctgt atcaggctcc tttcagcaag  24480
cagttcttgg tattagcagt agtgtctggg tttggtgtct gcaaataaaa tgaagccttt  24540
ccttcagtct ctgctccact ctttgtccct gtgtctcctc tagacaggag ctcttaaagc  24600
ttgttgtagt gaagatgata cagaagagtt gagttctctc acgcaagctg ttctactact  24660
tgtgcagggt gccctgccca ccaccatttc cagttgtgat gtgaatagca cctgtctcat  24720
aaagcacaac ttaaacacct gtgattgcag tgcataaatt aatagtaatt attcgaggta  24780
caaactttac tgctagcact tcaccctaaa aattatcgca aaaataatga aagcccaatg  24840
taattggtga ctacattaaa ctacttcttt cagaatttgt ccatgagctg ccactttcca  24900
```

-continued

```
tctgttacaa gatttgcaca aaaagcagca cctgtgggtg tgctgtcttt tgtaacctgc  24960
taataaatcc gtgtgatatt tttacagaca cacatctcag aaaggggaaa ctgaccagct  25020
gaggtgaagt cacatcaagg caataaagtg caaaatcctg ggagcaattt gtttatagaa  25080
aaataacagc tgaatattca gattgcagaa atgtaaattg aatatttaat aattttggaa  25140
atagcaattg gttcataccc gggttagtgt atatcaactt gaaagaaagt agagctagca  25200
tatgtggtct ctagtgtagt cctagatagt atgtacacac ttcagggtca ggaggtaaat  25260
gtacaagctt acactgagga ttgtgacata tcagaagcca ttgtctcaga ggaagtaatg  25320
ccttcttaac cccatgctaa aagaactatc agagtcagat cgcggcatga agagttgtgg  25380
tggtttgaat aggaatgcca cccagagtct catgaacctg gtaccagcca gtggtactgt  25440
ttgggaagga atatgcagtg tagccttggt agccgaggta tgtcacaggg agaggcagtg  25500
aaggtttaat agccacccat cattcccagt gtactcttgg tcccctgctt ttggatcaat  25560
atgcaagctc tccattgttc ctgctgccct tcccttccta ctccactgtg gattctaaca  25620
cacccaatgt tttaggacat gaaaaagata cccacaccgt aaaggcatat gcaatgagaa  25680
gaaggcaagc tttgttgaaa ctacttaata agcacattgt ttttgcaaaa attaaaaatt  25740
ctaaactaca aaatataaaa taaatattag ctttaacatt ttatcatttc ccaacatact  25800
tgtgtttaat aatttgactc atagcccccct caccatccac tgcttataca gtttccccat  25860
tcattgttag gttctgtaca ctgatcagct cagcttgtcc tcacagctct acagtccctt  25920
gcaaaatgag cagtgcctat gaaatgcatg cagacagcac ccatgcagaa cacatatccg  25980
ttcctgctaa caagtgtgcc tttctctctg cgctgcttct agtgcggtga tctttcctgt  26040
gctttcagct tcagcttctc cttcagaggc atttgtatgg gtaagaacaa gagtttgcac  26100
catgtctgta tcatgcattc aacagtactg agggctttac ttcaacgatt tccttttatt  26160
cttttgccaa gatcatgatg cagatttcgt taacctttag tgaagtgaag agttaaatct  26220
ggactctgta tcggggtggg ggtgggtggt tctttatttt caaaataaaa gttcctacat  26280
atgctttttt aattaatgag ggtttaattg actcctttct aaaatattat tttaaataaa  26340
atagacaaaa attctcttaa ggctatatgt atatatcttc aaaactattt actaaataat  26400
ttaacatact tttgtacatg tacttaggtt atcttattga tcatattatt cagcttgtag  26460
aaatgcacat ctgaatttta agcaattttg gaattagaaa ttacctcata gttagtgttt  26520
gtcaacttga caggaagtag agatatgtgg gaagaggaca taacatttga ggaaatgtct  26580
acctctgatt tacccatagt aatgtttgtg aggatatttt cctgattgac aactgatgga  26640
ggagcaccca gcccactgtg ggtggcacca cccctaggca ggtatttttg agtgttataa  26700
gaaagcaggc tgagcaagat atggagagca aaccagtgag cagcattttc ccgaggtctc  26760
cacatcagag cctgcctcca ggttcctgcc atgcttggag tttctacttt tggttccctc  26820
gataatgaac ttccaaactg gaagctgaga aatctccttt tccacacttt gtgtttggtc  26880
acagtgttca tcaccaaaca gaagactttg attggcaagt tagttatgta cagggaatgt  26940
ttactctaaa tgttggtatc tgtactttat gactgagcag ttggcttcta ggaagctatg  27000
tatatgatat agtttttgta ctagtttttt ttcctcttct tgttttctgt ccatgtagca  27060
agacattttt tttcttctca aatagtgcat ttttaaaatc cactatttta aagttttaaa  27120
attccccccc ccccacatgc tggcctaagt ctttttcagc ttatatgtcc tcatgtcctt  27180
tttatccttt gcattcttct gtgtctagat aagattattt tagttaatgt tcctctctcc  27240
atctctttag tcctttcttc cttggtttct tggtaatatt ggggatcaaa tttaggtcct  27300
```

-continued

```
taaacatcag aaaacagtgc tgcactaaga actatgtctt tatccctata ggatagcttt  27360
cacttaaaaa tgtgtatttt tatatgtatg tatatataat atgcatgtat attgtatata  27420
tatacagata tataaaaatt ttatgcatgc agataaaatt atcagtattg attgtacaaa  27480
gtgagaggcc tcattatgat gtgtgggtct ccccttcctt ggaggtaatt ggcaactggc  27540
ctaataggct gaggggagca gaggcggttc aggcttcaga ctaccataag tatgatggat  27600
tgacttctgg gatcagcttt agtgagacat aacaacttag acagtgctag ggatttctgg  27660
gtgggtgtag attattggct aggttcgagg tgctgaggat gtgtcattta aagaaagagg  27720
aattccagga attattggga gagaggttgt tgaatctgta atctggccat tgacaacatg  27780
attgtcttta taggtgaggg acatagaggc ctgatgccac agcaagtaga ctaagaatag  27840
ggagagagtg atcctaactc ctgcctgtct aaggatgaga tttgtcagca tcttgatccc  27900
gtctcactct tgctccaggc tagctctgct ggctgcacat tctcacaatg atcttcccac  27960
agatgcattt aatatacaag gttatagcca cccttctatt actagttttt tattattatt  28020
tgtagagata atgcttttta tatttttatt tgctttgtta ttcctgcgct ttcatttttg  28080
ttgtgtatac tcattgttca tggttccatt ccataaggac atttttatat aagtatatag  28140
aacacgattt ttcacaattc atgaatgtat tttgatcata actcctctcc tttattcttt  28200
ctccccccttg ctcttcctct ccacttcttt agtaaagccc agctgctttt gcgtactttt  28260
tatcactcta tgcatatctg ggagaaaaaa tgatgctatg tttttctctg tgagctgggt  28320
catttcattg aacatgatga tctgactttt tccctacaca tatcataatt tccttctttt  28380
ttatttccga ctacaagtca attatgaaac ccagtgtgtg gagaattctt aaaaagtaag  28440
aaataaaatt tccagccatg ccacttctgt gcaaccacca gagccaccat acaagaatga  28500
tgtactgcat accatgcata tttgactatt caaccataga gtgttatgga agcaacccag  28560
atactcacca gtggatgact ggaagaagag actctggtat aaatcaaaac cagagttttt  28620
caaatgaacc ttaaatctcc aaactattta atcaaatggt ggtcattata ctgaaatttt  28680
aagcattaga aagattattt ttaaaatgat taacaaactt acttttaata atatgtgcaa  28740
tagctatttc tttgtttagt aatggctcaa ggcataggtg aaattcttat cttacataca  28800
gtcctagttt gaaagtaaca tgctgttact taataattat gcaaatcact taattatgat  28860
ttttagtttc cttatgtatg aaatgggtat tgaatggctg catcagagat gatgtgaggt  28920
caatctgtac caggggttgg gcagacgctg atatcttctt tcctctccct tttttgttgt  28980
ggattgtgca gtctctgctc tgttgtgctt ttacagcatt ctcaggtctg cacagagaat  29040
cttactatgc ctgtgttatc ttccctttcc ttctctctgt aaattgatga agaaagcatc  29100
aagcaagggt tatgtaaaga gtcgttatgt tttgtgcatt gtgttttatg ttttatctga  29160
taaataaagg cacaaaactt ttaccagtgt tgcctctggt gcagttccca tccatgttca  29220
cattgtgtgg tcaagctaca catatctgtt gcctctaaca tatgtcagat ctttatgata  29280
ttaaccactg aagcttgtag ccttttgaga tccacagtgc ccagttgctg tctattatct  29340
cccaggtgga acagcacagg agcttcatac tgctgactaa ctcaactggc tacccactaa  29400
accctctcca ggcttccctc ctgaactcaa cctggatagg ctggtggtag ctttcctctg  29460
gggtggtggc cagatccccc ccactttagt gatttctgag tgtgattggt ggttgttagt  29520
cttctgaagt tatctttgta cattcccttc tgaatattga gaatttttaa ttggctgctg  29580
taaattgaag gacagtttaa tatttatgcg ttcaatttct ttgttcttta ggttccaaaa  29640
```

-continued

```
ctaaggaagg agtggttcat ggagtgacaa caggtaagct ctgttgtctt ttatccaggg  29700
gtgatatgcc gaatgccttc taggctaaat taacttgatg cttatacttc aagatataag  29760
tgtaagagcc attgtctaca gaggaacatg ggtcaattta tttttttatg tatctaattt  29820
ttaattttgg tatggtgaga tggagtttag ctacacaagc cagaacagct tctgcttcaa  29880
tcttctaaga actgggagta caggtatcac caatggacct tgcatattgg ctttgtttaa  29940
agtttaatgt ttatgcaatg aaatattttt aagtagacaa atatggatta aaaatgtata  30000
gcccaatatt ctaatggcta agaatgacgg atttagattt gtcaatggta tttaattcta  30060
ataatttggt atttgggtag taggctaaat aaataaaata taatgatgct attattaatt  30120
taaatatttg atgtaaacat ttctttagta tttagtattt ataccatcag ttatactgat  30180
tagatatttc ctctgtgatt aacaatcctt tttagaaaat atacttagta gtgtgttatt  30240
tttaaaaagc tgtatatttt tattttattt gtatccactt gtcatatctt caaaaagatt  30300
ttcaataaga ctaaaataat aaatattgaa ctaatatgac taaaattata atgatcaaaa  30360
atgacaaaga caatgaattt actgtgggag gaaaagcaac aggagaacaa taagaaggga  30420
aaaaccaaag agaaaatgat aaacataacc aagctgccaa agcttggtgg tagctaaagt  30480
tccttatgtc catttgccat gcatcagact accttaagtg ggaaaagacc tgtcaggaat  30540
gaacttgata tgatcaggaa ccttggccat gacaccacat aacaaagcaa atgcactgca  30600
taagatagca tcacacagtg gcaacctgtg tcttccagtg gctctttccc aagaatcatt  30660
tgctggccat ggaggaaaag aactcattct ttttagcaca ctgataaaga ataatgatgc  30720
taaagcaaca ctgaagccca ggaacaagac ccttttggaa gttcacaatg gtgaggactt  30780
ctttcagttg ctgtcccaca aaaagtgcag atagcaagag agtaagcaga ctgattggtt  30840
cctggaagct gaaacttagg cttgactctc ataagacaga taagacaggt acagagtgct  30900
ggaggcccac atccagagcc acgatgttcc agcttccata gttgagggag aaggaactgg  30960
tgagattcag agtctattgt ggatgcattg ttctctattg acaactttgg aaatttttaa  31020
tattccctga atgacaagga tataaagcat gagtttttat actgtgtgga aaagagagtg  31080
ggggctggag gagcaagaga ggtcagaggg gtgtggaaag tttctgcagt aggcaacatt  31140
ttagaaatat tttctagaaa ataattgtca gcaagcttgc atttccatag ttttataatg  31200
ttgacaattt acatgccttt tatatatcct tttagtctat taaggaactt gaaatgctcc  31260
acagtaggta aagacacatt atataatata acccaggatt cttgaatatt tactactgaa  31320
agttcccttc catatttaac tgtatcaaat ctagtgttaa caaaacacta taagagacac  31380
gtttttgttt gtttgttttt tgttttgttt ttgtttttgc tttttgggac agggtttctc  31440
tgtatagccc tggctgtcct ggaactcact ttgtagacca ggttggcctc aagctcagaa  31500
atctgtcttt gcctcccaag tgttgggatt aaaggcatgc acctcccggc tataagagac  31560
actgttaagc agcaaggaca cagtggtgtg gttgtggcac cttgtaccac cattctacca  31620
gtttagaaac ctgacagtaa tatataatat caaatatact gtcacaatta gtcagactat  31680
gaagaaatgc attgtcaaga aaggccacag taagtgctat ctctccccat cacatataaa  31740
taaattgcgt aatttattga gtagtatttg tgctgctcaa aagttaagaa tttaggaaca  31800
ttttgaattc tggactttca aagaagtgcc actacatatg tttgaaatgt tacttagaag  31860
ggataataga agtgactttg ggaagtgagg tcacagagct agctggcttt gatactgaaa  31920
ttgtatagca atgctcagac ttgacactgc acctggctgc aatgttttgt gtccactcac  31980
ctcaatgcaa accaaatcca attcacttgt tgctatgtgt tataattaaa ctcccaatat  32040
```

-continued

```
tttctaattt ctgcactaaa ttcatattca gtgtttggct gaaacatgtc tcttctacct  32100
tgctgtcttg tttcttcaga ctcctgttac ctatgatata tgtgtctata gaagttgaca  32160
gctgctagaa gtggaattat taaagtctct gtcacaccat catcttttac tctgttgtca  32220
ctcttgattt tcttaagtgg ctgagaagac caaagagcaa gtgacaaatg ttggaggagc  32280
agtggtgact ggtgtgacag cagtcgctca gaagacagtg gagggagctg ggaatatagc  32340
tgctgccact ggctttgtca agaaggacca gatgggcaag gtatggctgc ctgttttatg  32400
ctcagtaata accctggaca ccatgtcctt gcatgcatca tagagcatgc acatgatgca  32460
cactgtgggg aacactgcct ttaaagggct cttattttga tgcactgatg tccttgggaa  32520
atgtcatgca cacaataacc ctgattgttt tagtttctgg aagaaagata tagaactaaa  32580
aaaacgtagt aaacactaag agaccagtga catttcagaa agaataaccg ctttcatgta  32640
aatggtaggt ctggaattcc tctttatagc aatagcaagc attttcatga gtaattttta  32700
cactgaactt agccaaaagg ttgagaagca atcatgagta atttctaaat tttcagaaag  32760
aagatctttc atttgattta tttggaatga catcatctct tattaaatga catatttgca  32820
tatcatgtaa caactcattt ccaaatatga ttttgccaac tgggagactt aaagttcata  32880
ccaaacacag atcatggttt catatggtga ttcttacatt ttcagaattt taaatttgct  32940
tctggataaa tatgaggctg cagtgacata ttctaggtat aattttccta tcaaatgtta  33000
aaggaacaga aaatgaggac ccctggaaga tgacgtttca caaacctcat gatcttacag  33060
taggatgagt tttgcatttt tatgtcacat gtacttttat actttttttg agagattcca  33120
gcttcccccc aaaaaagccc atctcagttt ctcttgctct gggtctttgt taaatgacat  33180
cttccttgca atgcctaatt tatttaaagt tggaaccatt ctcacccatg aaaaccataa  33240
cctttctatt ctaatttctt cttgtttgat aaagtgtcat tgcatttaaa ataaattaaa  33300
taatctactt gttttgagta tgttattttt ctttgtctat gtaggcacta tcataatgta  33360
aatatttatt ttgcttgttg atacttcatg tgtctaggca agttcctaac tacaaattca  33420
gtaatgaata agagcttatt aaggatcgaa agaatggata aatgacaatt ttctaaggat  33480
taataatcat atacatggtg taaaaccttt ggctattgac tgatccaaaa gttgtaatca  33540
aatgggttct gaagtagaca tcctgaaaca caaaagaaag atactttcac ctgtgggcag  33600
actactatgg gtcttctcta tttcactcat cctaggtggc agaacaaacc atggatagtg  33660
gattgggaaa ctgaggatgt acatttcata gacagttcta ttgttaggga aattaaatgt  33720
aacccaagat aatctaggaa gtgttcagag aagtgctcag ctgatgtcaa catggactga  33780
tcaattcagc tctgctctga gtgcaatatg cttttgtggt aacgtcattt ttgtggtaat  33840
aactatatca atgcctattt tccatttgac attgtaatca tatgtttatc tttatcatac  33900
ttaaaatttt aagagacttc agattagtat caaggagtct agaattacag gttctttgac  33960
aatctagtga aaacaaggga acctcttgtc agaaaaacac atgatcacac atatacaaca  34020
aagcaccaaa ggaaggccat caacagaccc tcaatttaaa accaactcct gatgaggaat  34080
gtggaatttg tagaggggaa gtgagtgtca agttcctgca gtgactggag ttacccgatg  34140
accctcacac acatctatct gagttggcaa gatgtgaagt gttttaataa accgtttgtg  34200
acttataatg catgttttaa gtgcagacaa agtgacatca cttgcccagc tgtgtcacca  34260
atacatacct tcctttgtct actgattgaa ttgtgcaata ctagagttag tggaaaacct  34320
tagtgctttg gaatgtataa aggctgggaa gcatgtctca ttccatttcc cactttgtct  34380
```

-continued

```
gcacctaaaa catgcattat aagtcacaaa cggtttatta aaacacttca catcttgcca  34440
actcagactt attttctacc ttttataata acaatccata ttttagtatt ctaaagcgga  34500
aatctaccag tgttacaaaa tgaaacattt gcagatattt ctcctagagg aattaactct  34560
gggctcctaa aattttctaa tataaaaatg aaaccataaa cagaaattgc agtaaaaaaa  34620
attgggataa aaccctgttg gtttggggtt agatggttga tcttcatagt atactggtca  34680
tttggtagct atgaaagctt gtgctaagcg cccaagacct atccttatgt aatggggagc  34740
tctgagtttt gctaccttac caaaaagctg gtaaagccca atttagaaat gaattctgaa  34800
tatctacaat aactcaagga atacacaaat aaatgccagt aattgtggcc atattacttg  34860
attcaaaaca tatccacagt ttaaataaaa ttggatttat ttctaaagaa atttgaaata  34920
ttttatttca tctttcagat tctaattaaa attatcttgg tgaaaagaaa caagcatata  34980
tttgttaaat tttttaattg attgttagtg accccaattg gcccatttgt aacaaataat  35040
gattgtgtct cgtgtgtgag aaacttggaa gaacagggat ttgaccaata gctctcatat  35100
actaataaaa ggctaataga agggattagt cacactatct tggtggttgg gtctcaagga  35160
ctagcttttt ttttttttgt aaagttttat tcatttattt tatgtatatg agtacagcat  35220
tgctttcttc agacacacca gaagagggcg tcagacccca ttatagatgg ttgtgagcca  35280
ccatgtggtt gctcagaatt gaacgcagga tctctggaag agcagtcagt gcccttaact  35340
gctgagccat ctctccagtc ctgttcccag ctttaataag acaattaatt atatttatgt  35400
tatttatctt tatctatttt tctgaataac taactatgtc tgcctagcac tgagaaggag  35460
ttcaatgatg attaattata tctatctttt attatttatt ttaatttaaa ataacaataa  35520
aatttaaaat gattactcta caaaaaagta gaatatgtca taacacatgt taacagtaga  35580
atgttatatt aagtatacat acaaccacaa actgttatag caatcaaggt aattaacata  35640
atcaatgact tcaatgactg tggtggcagt caggtattat taactgcaag aactgtgtca  35700
catgttaagt ttcaagggca ttccctccct cccagttcct tacccctgat aacttatgag  35760
caacatcttg ccatttcttc caccttctag cccctggtag ccacaaatct aacctgtttc  35820
tatggacttg atgttttctt agaatatatt ctacatagat gagagatacc aaagtatata  35880
gctttgttcc tctggtttac tttgcattgt ataatgtcct caaggcttat ccatgctgtg  35940
gcaaatgtaa ggatttccct gtctgtatag accttttgaa ggcttaataa tattgcattt  36000
gtacacatat gcacacatct ttacccattt agctgctaat tactctttgg catgtttgca  36060
catcttaact attctgcggg tttctttctt tatatctacc aattcgagtt tcagactata  36120
tggtagctgt gattttagtg tttgaggact tgcactcagt cttagtagtg actcagttat  36180
atttttagca gaggtgctaa agcttccctg tcctctacac cctcaattct tgccgtgggt  36240
tgtccttttg atgaccagtc taatggcgat aggtgataat agatcattgt ggctttgaat  36300
tgtttttact tacgggttag tgaagaattg ttttcataca gcccttggct atttgtatgt  36360
cttctgtgat aagtgtcttt ccagccaatt agttcagtgt gtgtgcatgt gtgtgtgtgt  36420
tgtttttggt gtgtttatat gtgatatgtg tctgttgtgt gtctgtggta tgtagagtat  36480
atgtgtatgt gcattttatg tgtagtttgc atgtgtatat gtatgtaaca tgtgcatgtg  36540
agtttgtgtg tgttatgcaa attcacttgt ctgaacaggc atgtatagag tccatagatt  36600
gacattggga tattttttca gtcatttgtt tcaggatcca tttcctagtg ttgaatttac  36660
aggtgtgcac tgtcacgtgg cttttcacgt ggatcttggg gatccaaatc aaggacatgt  36720
gtttacacag caagcatgtt actcagagag ccaactctaa agcttctttc gtcgattttt  36780
```

-continued ttctcttaac caaaatagat ttttttatac agaatattct gaatatagtt tccctcctcc 36840
aactcctccc agttctcccc catctcccct ctcatttgta tccataccct ttctgtgtct 36900
cttagaaaac aaacaggtat ctaagggata ataataaaat tagataaaac gaaaacaaac 36960
agaagaaaag cagtgaaaga aaaagcacaa agaacacaaa tgaatgcaga gacatacgtt 37020
tacacacaca ggaatcccat attaaccaca agaatggaag cggtgataca tgcataaaga 37080
cctgtaagtt aaatacagtg ctctgacaaa atattagaag agaaagaacc tccaaagatg 37140
ccactgacgt aatttctct ttggcatcta ctgctgggca tgcagcccat ggcttgttac 37200
tccagtgagt cttgcttgga gaaaccaagt ttttatttgc aagtggttat ggattggagc 37260
aagcttctag tgagggctga aggcatgtgt ccacttctcc tttcatctct aggactccat 37320
ctggtgcagc tgtgcaggct ctgtgcatgc tgcctcaggc tgtgtgagtt cctctgtggc 37380
catgtttaga ggccttgttt ccctggtgtc ttccattccc tttggctctg atactatttt 37440
tcacttactt tctttttgtt gagcactgaa caaatacata gtttgcaaat tgtttctcct 37500
ctttacaggt tactcctgta tcttgatagt agtctaattt acagtggaga agctgtcagt 37560
ctgatgcagc ttctatgtat tcccactcta gccagtagat tttgagtttt accaccaccc 37620
ccaaatattg ttcagaccaa tgttgataca ttttcctttg cactttatta taatagtttt 37680
caagtgttga atgttgtgtt tgagcttttg gctgttcagt tttcccagca atgtctattg 37740
atgatgtcct agagctgctt tccccattgt gtgattttga cacttttgac atagcttgcc 37800
tgctgttgag tctgtgggtc tacagttctc tgttccagtg cacacattat gccagtacaa 37860
tgctgttttg gttactcaag tcttgttacg gatttttaaa tctggcattc tgatgcctcc 37920
aggttgaatc tgaaattttg atattattgc ttgtttctta aggtggcttg gatatttaaa 37980
gtcctctgat ttgactcttg tgggtttagg gtttttgact atgtctgtaa aatgtttcat 38040
tttagtttgg ggaagaggca catcccatct ctaagtcatt ttggcgacgt tggtaattct 38100
tcagatccat gaatacaggt tttctttcca tttacctctg tctcactttt taaaaaatca 38160
atgttttata atttttagtt atttaggctt taaaacctac gttcgattta tttctatgta 38220
ctttttattg acactcttaa tgctcttgac actatttaag tggaattact ggtttctttc 38280
ttagttagat atctgtgtaa aactgattct taattttgcc tattgacttc atatcttgaa 38340
actactttat ttattaattc tatttggtgt aatatttaga ttctttacat gtacatatca 38400
atttaccat ataaaacata tgtatatatt attactgtac tataaacaat caggcataaa 38460
cacttaatga tataaaacat ggaagatttt agaagtgact cagtacttgg tagatctgat 38520
ctacaatgtg ctatgtgtaa aagcttatca gttgttacaa actcattcag ttgattgtta 38580
cagtggaaac tgactaatat gagttgacag aaatataagc tagtagtggt tttatgtaca 38640
gcatataaaa ctagtcccca ttttcacaga gagaacgatc tgcttgtacc aagaatgttg 38700
aacttaggaa gttactggcc tccatgctgt tgagtaatgg cacagtgttt acaatgcaaa 38760
gctagtcact gagcatctgt ctgggacatc tggcctgtct gtctgcttaa tggtgttctg 38820
tttgggccta ctatttaaac caaccattgc taaataaatg gacatctttt tagttccatc 38880
tagagtgctc tgaaaagttg tagctaaata tttaaaaaat gttttgaaaa tgagtgaagg 38940
actgagtcaa ttgtggagtg tgctgccttg catatatgac attgctctgc ctcttatcct 39000
gtgcttttag gtatcaatct attcacatga taactcatag ttttcacaca ggtaagcttg 39060
aagcaccaaa gatcaggagt gttaattatt tttctccaga gtcagaagaa agtgctgaag 39120

-continued

```
cattgataat cgtgaaacat tcatcattag attataaata attttttaaa tttatctgtc  39180
tggtcaactt tatttttttt tggattgcat tttattttat ttagttattt ttttacactc  39240
cagattttat tccccccacc ctgtccaccc tccgactgtt ccatatccca tacctctact  39300
ttacccactt gtcttcacaa ggatgtcccc cgccctcacc caaccagacc tctaaattcc  39360
ctgaataaaa ataatgtttg aaaaccttaa tttcaagaca gaataaaaca catgcagtct  39420
ataatcattt cttgattgat aagaagagag ctaaccaaat gcagaaagaa cagtgtcatg  39480
tttggcatgg tctttaatga tcatgacatt cttctccctg cttcctgttg gcacgattga  39540
tgagcgcagt gttgtgcaca ttaagtccta aacactgaaa ctgactttga tcagatgata  39600
tatgctgcct ctaggtgagt gatttgatca caatctcaca aagaatccac aggtcatagg  39660
caacattttg catttctcta aggaaataca tatattacag gtggaatcaa aggtgaggat  39720
tagtgaaaca ttttccttta ttttaagatg ttttccttca gtgtttaata atgaccaatg  39780
caataagttg tgtgaaagca ttagaactcc aagttctgtc tgttcagtcg aagatagtca  39840
ggacagtatt caaacctaaa tgaaagcttt gtgatacagt gagtgatctg ctctgttgtg  39900
gtagtggagt ctgtgagcag cattggaatc ttaaagtatg ataataccc tcaaaggaat  39960
aaacacaatg ggcttacttg atctgtttca aaatcagtga tgttccatat catcagtagc  40020
atttttgcaa tgtgatccat ctaagatagt atttttcact aaaaggagaa catgctaatt  40080
gtgtacatta tccttgctta gaaacaacag gggaatgcca gggccaagaa gtgggagtag  40140
gtgggtgggg gagcatgtgg gggacttttg ggatagcatt ggaaatgtaa atgaaataaa  40200
tacccaatta aaaaaaaaga aacacacatg ttgagtggtt gtattgtaca taaatgtttc  40260
actgctctta tatgtatgga gaggaattgt gaatcttagt gatttctaat cagggaaatt  40320
tctaaaagga aaagaattct gtaattgtaa ggaaaaatag ccttactgga cttttgtttg  40380
ttgtaattcc aaagcactga gtcatttgct aatatgtgat tggtatccag atggatcagc  40440
aagaaatgca tgaatcatga atgcatgttc cctgtgttat gtatgtagac cactgagggc  40500
aacagacatt atccctagtg aaaaacagtg agtatagtat gtatattccc taagcttata  40560
tctattatag aaagagttaa gtggcttttg ttagaaatga aagagaattt gtattattcg  40620
aaataaatac taactctgat gagtgttaac ctgggttttt gtgaatagca aatgaagtag  40680
cttcagacaa ataataacca taatatttca cctgcttgac acaagaacac aaactttttc  40740
cactcaagtt ctatgttcag tggtttataa tctgtcagca tgaaaccttc agcaacatag  40800
acatgaataa aaatgtttaa aggccagact atggatgatg ctctttacaa aagaaattgt  40860
aaggccagca tggtagtatg actttaagca taccagtgga caaatacaag ctatactatg  40920
caaatctgtt tattttctca caagtgctgg cagaggttaa tattctaaca agtgctaata  40980
cagtttcatg aattgatttt taaatttttt attggttatt ttatttattt acatttcaca  41040
tgttatcccc cttcctggtt tccctgcata aaacctctac tccatttcct ttccccatta  41100
cttatatgag ggtgtccccc ccccactccc accttactcc actatcattc tcctacactg  41160
gggcattgat ccttctcagg accaagggcc tcccctacca ttgatgccag acatggccat  41220
cctctgctac atatgaagct ggagccaagg gtccctccat gtgtactctt ggattggttg  41280
tttaatcctt ggaaactctg gggatctgg ttggtggatt tgttgttcta attggtctta  41340
gttgtataca tgtgaacatt tattgctact gtcctttcac ataaaaccat tgtataatat  41400
tttatagggt ttcatttgag ctgctactat tatgtttaag atgatttcaa acttacatga  41460
ttttatggaa tttatttatt aaagggatta aaaatgatac atatgcgcgc gcgcacacac  41520
```

-continued

```
acacacacac ataccacatt tctacaatcg aacaagttaa catgcctgct atctcacaga  41580
gtacttctct ttgtttttta gtaacagaag ctaaaagtta ctcttttgga aaattgcttg  41640
catacactct atattaggta ttgtctttac attcctgagc tcgccagact tgctcacaca  41700
gttgactgta ttctttttaa tatctttgca catctaactt gtatttttac tttgtaatga  41760
aatggcaaac tcttcatatg gaggcagaat ctgattataa tgtgcttatg tgacagtcac  41820
tagtcttatc ccaaattcaa agagtaagaa ataatttgat tagttccttt tttggatgta  41880
ggctttgact agaaacatag cttgtattgc tacttatcaa aataaaatga cagaaaatgt  41940
cctatagttt tccaaatatt cacaatacac aacaattcag gacataagtc aattactgat  42000
atttccctcg acaatttcag gaataggaat aaataagacc agttgtgttt gcattgggaa  42060
tatatgatta tgaaagtggg aattagatgc tatcatgaat ctgattattc tattaggtga  42120
aaatgaatta tcaattccta tataaggtaa ttgctccata agaaacttta ttaaaatttc  42180
taattacact ttaattttta ggtatacttt aagaatccac cctactccct ggtgtagtgg  42240
aattattaaa catatttgta atattttcat ggtagtattt aatttccttt agagctataa  42300
tacatagtaa aacaaacagt gtagtctgaa atgagtgaat agataatgat gaaataagtg  42360
aaaaatgcga aaaattatgt acatttcaat ttccttttta aaaaaatttt attaggtatt  42420
ttcctcattt acatttccaa tgttatccca aaagtccccc atacccaccc ccctactccc  42480
ctacccaccc actccccctt tttggccctg gcatttccct gtactgaggc atataaagtt  42540
tgcaagacca atgggcctct ctttccaatg atggctgact aggccatctt ctgatacata  42600
tgcagctaga gacaagagct ctggggtact gattagttca taatgttgtt ccacctatag  42660
ggttgcagtt ccctttagct ccttggttac tttctctagc tcctccttcc tttctgcctc  42720
atctttcatt cgtattttct tattcaaaca ataggactaa tttgtttgga actcagttca  42780
acaaatgaat acagttgcag gtctgtgtat gcaaggagta aaatgaaatt tacattttaa  42840
ctacacttgt gaggggatgt gtttgaaaat tcacatctct atttgattat tgggtgtcca  42900
cacacacaaa tgagaaacaa tttaaatatg ttatatgatt tcctgtcatg caaccttatg  42960
gagtgcgtac tcagcttagc ttggacactt taagctttgt tcagtaattg tatgttatct  43020
gataagtctc tgggggtagg catgtgcttc ctacttatgc tacctagctt ggaattaatc  43080
tatctgttat acaaagtcta aaatttacta gaatatttca tctttaatct aattttataa  43140
caaatgtaag gcagatacct ttcaaaatat ctctgctcaa actaacagaa ttgcttatag  43200
tagcaatcat ctgtccatgg aggacagcca ctgtaagatt gacagagagg tagttcttac  43260
atgttctgtt agagctactt catacctgct actcaatcca ctttgatagc ctgatcttta  43320
tccccagggt ctggtttata tgccctattt gctcaagcat atagaaagtg tggctgggta  43380
agagggcagc tctgtacttc atggagtgtg gcattatctc tttcaccatg ctgtatgagg  43440
tcaccacact gctttgagca ctgacatttt tatccatgaa atagaattgc tgaatgaaat  43500
gagctcaaaa tgttttgtat ctcgattcag tggcttgaaa tttaggacag ttgtttttca  43560
attatgcact gccagacccc tggcaactca tttaaccttt ctgaagaagc gtttatcctc  43620
tgtaattggc cagccaactg cagagttgga atgagaagga aatgtagcag caaaggcaaa  43680
caatcaaatg gactgtggca taattgtgat atttttctat aaagaatctg atgtttctat  43740
ttatatcttt ggtttagaca tgtgattatt gagatgactt tttttttttt tggtgtggtt  43800
tggctttatt aagtggttta acaccaaaag gaatacactt gagagagggg atctctttat  43860
```

-continued tgggcttaat aaattgagtc acattctttg tcttagtttt ttttttttcca tgttgatctg 43920
attaaaatcc tctgacttaa gcaacttgaa gtagaacagt tttctttcac acacagatca 43980
tggatacagt acatcatggc agggaagcag aggcagcaga aacatgaagc gtcaagtcac 44040
ttacaaaaaa aaaaaaccta gtcaagtaca gagagtgacg attgctagca attcagtcat 44100
ggcctttttt atatataatt caagatccta gtctaggaca tggtgttact cacagtggac 44160
tggttttccc aattcagtta tctaatcaac ataacctctc acaggcattc ccagaggcta 44220
atctcctagg tgatcctaga ttccatcaaa tttacaattg aagttagcaa taacacctct 44280
gttacattga attaaatttc tcaaaaccaa ttttattaaa ggttttatta aatgttatct 44340
tcatgtttta attagaaagc atcctgttca aaggattttg agaacactgg tataaacaaa 44400
gttttaaaat ttatctttta aattgaaaat gccaagtact tagcattata ttgcaagggc 44460
ataattatct ttcttagtgt ctcttcacac cagatgcata gagaataatt ctaagtactc 44520
atggagcaca tatacaagat ggcctgagta atgaccgttc tcactctgtt ttccttgtct 44580
tagtaatagt ctttttagat cccagataaa aggacactca gaacaagtga atgatctctc 44640
agcatttcat atcacaatct attttttgga gacacttttt aaaacattct tgaaagaagg 44700
acaaagacat aattcctgtg ttccatgtaa ggttttccat caaatcatgg aaaagattct 44760
gatagcctag atgatgagag tccagctaga ccagctatga aattctcctt gctctcttct 44820
ctctttgtgg tgagccagcc tacacttcct ttcaacacct aatttggacc cagataacct 44880
aggaatctgc cattgcagtg ttgaatctca tgaactgagg ttagtgtggg aagggcacaa 44940
tgctctctgc tgatgctcac atgttgagca tgtctgtgtc acaggttaaa aatgcagtga 45000
tagaagcatc cctgagtaca cacggtacac tggcggaaaa gcactgcaag tatgcctctc 45060
cactcagtgt attttgtgtc taagagttta acagctctag atttacatat aaggttattt 45120
atcaaagcat tggtaatgat acatttctta aatgctggaa acttggcaat agccactagg 45180
ctaaatacat gatggcttat cccctgtaat aattatttca acagaaaggt acagaagagc 45240
aatgggtgac ataataggtt gttcttgctg cattaagtga aaatatgagg ttatagaaca 45300
tattaaagtt tgtaaacact tttgttatta aaaacaaaca tgtcatgtga tgtctgtgtg 45360
tatttctaag cagtcttttc atttaattac aattagaaat taaaggtaca acattttatt 45420
ttacttgttt gtccaaatcc caactttaat tgatttataa aataatttta cctatgtagg 45480
acattaatgc agttattaat atgactgtga ccattgctgt ttattcattt acttagccac 45540
acatatatgt gttggcctac ctaattcata ctatgtgttc tactttgcac caagtattat 45600
aactgtaggg atgtagaagg ttgatttcca ggacccagtt cattgacatc aatcatcttg 45660
tctcctccta gtatgaaata agacttgttt tgttttcttt gttttgtttt gttttgtttt 45720
ttcgaagcag ggtttctctg tgtagccctg gctgtcctgg aactcactct gtagaccagg 45780
ctggcctcaa actcagcaat ccacctgcct ctgccttcca agtgttggga ttaaagatgt 45840
gtgccaccac tgcctggcga aatcagattt cttttgtgaa gttctgaagc ttttaatcat 45900
taaaaattcc aacctggaat agttctttta tatattatta ttattgataa taattatcaa 45960
atcaatatga aataccattt cagcaattct ctttcttgtt ggcttatgat aattgcatgg 46020
cttatccaaa taccagaaca cacttgaaca aaaaatttct aagagcaaag aattgtatta 46080
cctgagtggt taatttaatg gctcatgtat atttgacaag aatttctgat cttctgagcc 46140
ctgataatta actggctttg ctgattctta tctttggact ctgagagaga gctatcctca 46200
tagtcagtat atgctagggt aacaaaacac atgcaattga gtaattcttg aaaaacagaa 46260

-continued

```
tttacttatc acattgtaaa gctgggaact cagagatcta gacgagtttt gtgtcctgga  46320
gaatctcatc tttgttctga gatgacatct tgttactgtg tcctggagga gagcattttc  46380
aaggtgaata gaactgaagg ggtaaaactg tccccttgta cagcacaaac cccacatggt  46440
accattacct gtaaagagcc ctacctcaca attgggacat tagtgacgac atttcaagta  46500
atgggttttg gggatattca ggtcataata gctattatct ttattttcat gtaccattag  46560
aatgttagct tcttcttttt attaatatca ttcacagtag ggagaaatcc ctgtattaaa  46620
taccattccc tgtgtgcttg ttatccactt tggtaagaca cagaaagcca caaaagcaca  46680
ctctggaact ttgctttcgt catttcactc ccagtagtta gacacatcca tagtgtatgg  46740
gtttatttta caactgaaca ggaatctcac atgtcatgtg ggagtttttt taactataca  46800
tgcttgtatt tgaaagcaac atttaactgt gcattttcct ttggaaataa caccttccaa  46860
aacaatttc cccagctcaa atcgaaacat acacaatgtt tcctgtagta attagaatat  46920
aagcaagaaa atgaaactct gaggtaggca cagaaaaggt ttcatgttcc ttctgccttt  46980
attgccttta actagtcata caggatgcca gtaaaaaaaa aaaagtaaat tccttgaaaa  47040
ggaatacttt agtttactta atgacaagga tgagagagac agagacagaa agagaacaca  47100
tatacacaca actctctagc tctctctctc tctctctccc tctctctctc tctctctctc  47160
tctcacacac acacacacac acacacacac acacacacac acacactcag aggatgtgta  47220
ttaaggacta caaatgagat tgtgctgctg tgatgaatgg gacagtgtga ttttatcact  47280
ggactctgca gttcagtgga accctgtagg tcctgctgaa accctaggct gcttaaattc  47340
ttcagcaatg atactttcat tgtacaaaga gacatgtcaa aacacatttg cttttgtgat  47400
tctgagtatt cacttctgaa attaatcaat gttccacaag gaaaactgtg atttccttta  47460
tttatagctt gtaataatct agctagatat ttctcatttg gaggcatatc ttcaatttta  47520
acaaatcatt gtattacaaa agcatattca aaattcccaa gaaatttacc ctactgcact  47580
gtttgttctg gttgaaaaca ctgtaggtag gtgtcttagt cagtgttcta ttactgtgaa  47640
gagtcattat gaccatggca agtgttataa tgaaactctt aaaactgggg cttacttaca  47700
gattcagagg cttagtccag tgtcgttatg gcagggtcca tggcagcatg cagatagcca  47760
tggtgatgga aaatagctga gagttctgta tccaggtctg cagccagtag gaagagagaa  47820
agccactgga cctcgcttgg gttactaaaa cttcaaagct ctctactagt aacacttcct  47880
ccaataatgc cacacctcct aattctgtta agtagtgtca cttcctgatg agtaaatatt  47940
caaatataaa tatctataga gctattctta ttcaaaacat agttagcaat ttctctttgg  48000
tgggagagaa tcaactgata cgctatagca caaccatgtt caatgctgtt acctgtatgt  48060
ccaaggcata ttttgtgtgc acttattcct tcattcaaaa cacacctgtg gtatctggag  48120
gccagtgaga attatgtgag caagatgttt gagagacaca gtctttcacg tctgtacttg  48180
cttgaccctc atctaagtga cgttgttaga gaagtccaaa gctggcgttg tagcattctg  48240
ctgccacagg tcatcatcca caccttatcc tactctattg ggataattac ttggaattaa  48300
aaccaatcta atttgtaggg gaattggtta tgcaaataat cagcttagat tttctggat   48360
ttattcacag tatttaatgt gtaattattt ctgccctcac ttttacatgt tctttaccca  48420
gcattttaac caaacctaag acaggctgca tgtgcacatg ggcaggtttt ttttgtgttt  48480
tgttttttgt ttttgttttt tttttctgca atcagaacca ttttttcttg gaaaattaat  48540
ttcaaaatac attcagtcag aaaaaaaagt gcttataatg tttgtctggt gtttcacaag  48600
```

-continued

```
agctgccctc atgtcctact gcttacatat ctatagtttc catataaagt ttcattttct  48660
acgggctttt catgttagtt cctctaagtt ttctctcaat ttgaaatttg ttttcctcaa  48720
tttctttcct atgtgtttct ttttggataa ttgaaagaag atgcacaatt tcttaattct  48780
tatatttgaa ataattgaaa tgtgttttaa aagtcatcac tgttactata acacagtttt  48840
ccacaagagt tctatctttg gtttttgtgc atttcagtgt gcctggctga tgttcagtgt  48900
cctaggatgc gctgaaatgc tatggcatca tttcatccag ttatatttca catgagctgg  48960
tagagataat cctttagtcg ggacctattg atgcctagat ttttaacagt gtcatacttt  49020
acctgtctta gcatgttgtc ctaagataca agaatgatta agatgtattc ttagatccag  49080
gataatgagc atagcatctc catggaatac ctctttctct tattttctgt tgaattccca  49140
tactaaattc aaaaattaac cgaaaggtag agtttcctca gtctgtctta acacacgaca  49200
ttctgtgcag tgctggtttc tcctgtccac agtggaatca tctcaaactt cttaactctt  49260
gggcagccat gaagatgaag gctaagacac taaatcttcc acaaatttat cttgctcttc  49320
tgtctactct cacttttact ggcagtggca aatagaattg aggttgttaa gagtctgttg  49380
ttacttattt aatagaagga aaaagtaaaa cagtattatt gctacagagc cttgatcaaa  49440
accaagactc aaggaagtac aaatccttgt acttccagta agagcatctg gcaaagagac  49500
ccaagatttt ggcaccatcc atatgctatg tgataatgta tgcatatggt gtggttttaa  49560
gaaattagaa ttctaaaata gtttgtatag tcaggctatg taatgtcgct ttctctagtg  49620
tcctgcagaa agtgagagtg ctctcattag gtacctggtc aggaacaaat tgcttcattc  49680
ttcagttatt taataatgga aacttaaaaa aacaaaaacc caaaaacatg ttttagaggt  49740
gtggtgataa atgtcctagt gcctgccata taagagctta gagattatag acttggtatt  49800
ctttcgaggg ctagatattt taatgcttta tcctgacatt tatcaaattg cacttcggtt  49860
ggtgagtgtc acattaccct gacaaattat taacattata aagaaaggac tgtcaccaat  49920
gagtcaatat aatttttata gtgttttata aatttcatat tttgtataac ttaaggtgca  49980
tgggatattt attaatttct atttgttgtc aacactaatg ctacataaaa tgtaatgtaa  50040
tttattttg caaatacatt ttaaagtctg taaaaaggac ccaaatatac tccaaatctc  50100
ataaatggta agtgaccctg aaagacaacc tactgagatt tagtgacttg aaagtccatg  50160
tttgcatgac tcatcagaag tactgtacct caaagaattt catcttaagt catagaagtc  50220
tcatgaatat agtcatatgt atcgcaacat gcggcctttt actcaaaaat cctaacagtt  50280
aacaaatcta tatcctatga aatatttaaa ccagtagaaa atgggtagtg aaagatttat  50340
atcttgtcta cgtagaagtc aaattttaaa agtcacccat taaaaatctt agtttagcct  50400
ggcgtggctg tgcacacctc taatccatag cactcgggag gcagaggcag gtggatttct  50460
gagttcgagg ccagcctggt cttcagagtg agttccagga cagccagggc tatacagaga  50520
aaccttgtct caaaacaaac aaacaaacca aaaaaaaaaa aaaagaaaac aaaacaaaaa  50580
tcttagttta actactttga tattccctgt atttaacatt ttgcctatca gtagtatcta  50640
ttcatttctt tagtgcttga ttggaacagc aaagaaagtc tatatgacag ctagccacct  50700
gaaaagctca ctatataact gctggatgac caaatctata tcagagaggg gtggttagga  50760
agagaaaccc aagcattgca tctgtataca cagagcatgt tttgtcattt tggaatacag  50820
tttggatgtt tcttttcgtg tttgtttgtt tgtttgtttt tacaaagcta actctgtata  50880
tgatccaaga gtcaaaatca ttggtatttg cttgcttgag ttgaataccct atgtttacat  50940
gtgaacctgc aaataattgg taccagcttt atctgcagtc caccaaacat ggaagaagtc  51000
```

-continued

```
aagaactttt ttaataagga aacacaatgc atccattttg tggaatttta ttcagtgatg  51060
attaaaattt gagccatgat agcacaaagg cacatggagg aaattaaaat atatatgcca  51120
aatgaaataa gacactcttt agactatgaa ccaaggatgt gatgatatat aaaaatgtga  51180
tcgttttgga atgccaaaat tctgaggaca gtaagaaagc aaagcaatag ttgcaggggc  51240
ctctggagag gtggaagact gtgtggtcaa acaacaggat gggagtgggg tacaactagg  51300
cagggaagtt attatgacag catggttttc tatggtaggc atttgctgac tcatataaaa  51360
caaggaggtg ccaactgtga tcttcagtga tgttatctca attctcatta acaataggaa  51420
ctttcaagtt cgtaactcag taaggcaaga taataacgtg ggattgtaac atctggaaat  51480
cctctttatt gctgtgtgat tattctgccc aaagtgtcta taaaaacaat gtatcagaag  51540
ggtgtaaaca catgaaactc aagaagaaca aagaccaaag tgtggacact ttgcccctta  51600
aaattgggaa caaaacaacc atggaaggag ttacagagac aaagtttgga gctgaggcaa  51660
aaggatggac catctagaga ctgccatacc cggggatcca tcccataatc agcctccaaa  51720
cactgtcgcc attacataca ctagcaagat tttgctgaaa ggaccctgat atagctgtct  51780
cttgtgagac tatgccgggg cctagcaaac acagaagtga atgctcacag tcagctattg  51840
gatggatcac agggccccca atggaggagc tagagaaagt acccaaggag ctaaagggtc  51900
tgcaacccta taggtggaac agcaatatga actaaccagt accccacaga gttcatgtct  51960
ctagctgcat atgtatcaga agatctagtc ggccatcatt ggaaagagag gcccattggt  52020
cttgcaaact ttatatgcct cagtacaggg gaacaccagg gccaagaagt gggagtggct  52080
gggtaggggg gtggaggtga gggtatgggg gacttttggg atagcattgg aaatgtaaat  52140
gaggaaaaca cctaataaaa taaaagggtg taaactcttg agtatcgaaa tttccagagt  52200
gctcagagcc tcatttgtac cctttaccat cctatctcat gctgttggat tcattgtggt  52260
aagagtataa atgtaaatat gtaggtttaa aatgtatggg aaaatatttg tatatcaaaa  52320
ataatctcat tactacacag gctggacgta ggcctcctgc acatatgtag cagaaatgca  52380
gtttaatctt catatgggtc cctaactatt agagtcaggg ctaccccaaa agctgatgcc  52440
tgtaagtgga atatgttctt ctagctgggc tgtcttgtct ggcttcagtg ggagaggaag  52500
cacctagcca tgaaaagact tgagtgccag ggtgaggagg acatccaacc actcagagga  52560
gaaggggtgg gggaggcttg gacaagtgtt gtgggagggg attgcagtga gcaggataca  52620
aaagtgaaca agtaaataaa taaatacaac tgtaattttg ttactacagc gttcctcaaa  52680
taaagaggag cagaacatgt caaatgagta ccttaaccac ggaagactgg tgggcatcag  52740
ctacatctgt agctggagcc tgagagaagt gtttactctg atagctccac acaaaactga  52800
agcactggga agagattttt gtcttctccc ttcagacttc atgtaacctg gatgcattca  52860
ataagtattt gttgtggcat tgttgagtag tccctttata ggcactgtaa aggtttctta  52920
gtgacactga tggtttaata ctcaggttta atgtccagtc cctatatagt cttaattgct  52980
tgtcttgctt tggaggataa cacatcttcc tcaggctcag actgcatctt acttgcactt  53040
gcacttctac agtattgatc tcatttcaca ggcacctata atgcgtggac tcatgaaatg  53100
atcccataac taaaggagta gccagacata tatttctcct tgcttgtttg tttataacat  53160
tagacaggtg aatgctacag aaggtatttg ctgcccatgg cctcagggca tggcctcagg  53220
tcatgacctc agggtcgact gccttagggc acctctgggt gcccttgtag cagtgctgtt  53280
ttgcaaagcc catgatgagc cactccttat tataaacacg tatttcacat gagaatgata  53340
```

-continued

```
aggtgagttt ttaataatct ttctaattaa acaaataaag gtatgaaagg aactgaaatg  53400
tttagtgcat gattactaca aggctgtatg cactaacatc ccagtgtcta gggccaagat  53460
ggagagaact tagtaactat ctacaatttt tcttttctct aaatattgcg atatatactt  53520
tctctgtatt tattataatc cccgtaagaa cagatggcct gcacagatta gacaacttca  53580
ttaagtgaca aattgtggag gttggtaata aaagaacctt acagcaacca gttaatcagg  53640
agaggtcatc ataaagagaa ggaagagagc tagggagagg gatggatttg gagaagggag  53700
gacaacagag aggtcatgag agcaggggaa gcaaatagca agccctgtgt gaaaatggcc  53760
ttctgactgg gcttgccatc tgtgaaatgc ctgcttaccc tgggcctggc aggtagtagc  53820
ctaggactgt ctggaaacag attgcctcac ctcatatgac cttccccatg ccctctttat  53880
ggtgcttcat ttggccaatg tcttataatt gtgtagacat gaagcagcat ttagacatag  53940
agtactttat gtaggacagg tttctccaaa gggactcttc gagtgcacct caatccatga  54000
gagagatgta tttcccaaca ttctctgcat agaagctaag gattctctgt ccaacctcta  54060
gtggtcagaa tacatcctat gattcagtca actgtttaga tgttaatagt gtaagtctca  54120
acaagcccca gtgcagtcca tatggttctt ctctgggcat ggcaggagta ggtggttgcc  54180
agtgtctgaa acataaaaca ggtgaaaaca gacctgcgga gagacagcag gaaaaataga  54240
agacagctcg caagtacatc tggtggtgtt tatgagattt attaaaattc aacaaggagt  54300
gcttaacatt tagcaaatga agtttgtctt taggaaaatc cttgtgggat ttatacaagg  54360
atctgttaat aaagggcaca tacaacactc ataatacagt cagacatgtt atgtaaaaca  54420
ggacaagaaa gtaataggat aacagagtgt ttgcacaagg gattttgtga tataacacat  54480
gattcttcag ccttcgctct gcacttttag aggctgggat ttgcatagtg atgcagccac  54540
acgagacagt aaccttgaca tttttgcagc tgtacatatt tgcacacacc aagacacata  54600
gtcttcctgt ctagttacta tttgattctt ttgttcatct cttatttatt accaaaagta  54660
gtgttcacaa aactgtttct cacaatttaa gcttttaaat catggtgtga attacagaca  54720
ttttatccaa gtttaccttt ttcagcagaa atgccatatg ttctcaaaac catttatcac  54780
tttatttaca attctagcta ggttgtttgc ttaatatttc ttagcataca ccacatatgt  54840
ttactttgat actccatttc tgcctcaaat ggtcaaaaag ttcaacttaa tctttttcct  54900
caaataagca tttctacctt atccatcaat aacgttgcaa acagtatttt actgtgatcc  54960
ataacacaaa tcacagatgt atttgaggtt tgtaattctg cttctctctc caatataatg  55020
aacctaggtt ctgtctttac aactctgtct tccatcattt tcattcagaa ggtttggatg  55080
agactttgca tggagagtgt aggagaccat caacttgtct acctgcttgg cctttccttc  55140
cagttaactc ttagctgcct ttgtccctag ccacatcatt tcctgtgaac acagactttc  55200
ccaggtcctc atgataaggc agagtttctc ttaagcttct gcttttctcc atcttcattg  55260
tgtgcattgt gtgaccttct gtcatttgtt tattcacgca tttgaatgag ctaattattg  55320
aagatccaag atagtaccct ttctaacaca gtggctaata agtacttctt gttgatctct  55380
atagttttct gcctaaggca tttgtaattg ggttgatatt gctttctaac ctttagaact  55440
gagatgcagt tgtagcacac acttaactga tagataggtc aaataggttt ctacacacaa  55500
tctcaattgc gacataggtt aaataggctt ctggccacca cattacaaac tacaaagaaa  55560
cctacttaat ctatctacca atggttgtat gtggaatctg tgtaagagta tcaagaaatt  55620
ttatgttatt taaaagacat gtttctatgt cttagacatc cagtacactc tttataccca  55680
cacctcacaa tttaacattt gacacatttg gagtctatca atgtatcaac tttatatgat  55740
```

-continued

```
gctgcaagat agtgtaacca tcttcttatg cctattgtca gcactgcaag gtaccctctc  55800
taaatccttt cattattaat cttcttcatt aatactttgg tatatgatga ttatgaaacc  55860
tttgcttggc tattcaaaaa aattaattaa gcaagtagga taaagttttc agaagcagaa  55920
gtctaaaaag aacaacagca attgaggact ggaagaggac tcttgttata caaatgtgag  55980
gaatttaact ctgaatcaca cgagctaatg tggactcagg tatagcactg tgtgtctgta  56040
ttcctaggtc tctctcatat gatggacata ccatctttgt tgtggctaga gaaatggctc  56100
agtcttcagc tccttgggta ctttctctag ctccttcttt ggggggccct gtgatccatc  56160
caatagctga ctgtgagcat ccacttctgt gtttgccagg cactggaata acctcacaag  56220
agagagctat ttcagggccc tgtcagcaaa atcttgctgg catatgcaat agattctggg  56280
tttggtggtt gtatatggga tgtatccctg gatggggcag tctctggatg gtttttcctt  56340
ctgtcttagc tccaaacttt gtctctgtac ctcctttcgt gggtattttg ttccccatta  56400
taagaaggac caaaatatca acactttggt ctttcttctt cttgagtttc atgtgttttg  56460
caaattgtat cttgggtatt ttaagtttcc aggctaattt ccacttatca gtgagtgcat  56520
accatgtgtg ttcttttgtg actgggttac ctcactcagg atgatatcct ccagatacat  56580
ccatttgcct aagaatttca taaattcatt gtttttaatt gctgagtagt actccattgt  56640
gtaaatgtac cacatttttt gtatccattc ctctgttgag ggacatctgg gttctttcca  56700
gcttcaggct tttataaata aggctgctat gaacatagta gagcatgtgt ccttattata  56760
agttggaaca tctttgaaat gtaatgaaga aaatatctaa taaaaaagtt ttggcaggta  56820
aaagaaaaag gcttaattaa taattcaata atataccatg gtcttaaaac aaaacaaaac  56880
aaaacaaaac caacaaaaaa agaaacttag aaagatttcc tttcctaaag ttgggatata  56940
tcttttccct tttatccttt caagtcacag gagttgtagg agtcactcca agtatttgaa  57000
gacagagcaa aattacttgt ccagaggaca tcttcatctg tagattctgt ggccatatag  57060
cacagaaaaa agaaattcag tgatgggtat gtttataaag actgaggtga aagcaatctt  57120
gagaggatag tgtgttgcca ccttgtcaca tgtttgatac taagagcatg tcactgatcc  57180
aagtggtgac attctaaatc acagtggtgt ttattattaa ttctttctgt gaggaaacaa  57240
aaaagctacc agtggacatc aagttgccct cttcatattc agaggatggt gtgacttcct  57300
atcaatcaga gaccactgtt agaggaatca tgtccaccta atggccaggc tacttgatct  57360
ctatctcagc ttcattagca ggttttttc tctctcttt tgacatgtgg aactgtcata  57420
tgaaacagga atgaagtggt cacagcatta gaaggtatac agaccttgag taagagctgt  57480
gtgcttgagc attaaagtag tcctgactcc tgtcagaaga cattctagaa agtactggat  57540
tcaggcaggc tacagacatt gcctagcaac tattttttgg ccagcttgta cttctgttaa  57600
caaatgatta tttcctgagg ccagaatttc gtcccttcga tagactatct ctgaactttt  57660
tgtttttctt tgtttcatag ttcttgagta tcactctgtc ctctgaagtc acttcttccc  57720
tagcagcagg ccatcagcat tgagttcctc tccctgttca ttgccactaa gtaaagttat  57780
gatgaagaac ccgtgtatac tacccatcag gtgtacatgc acactgcttc actttctaaa  57840
agccagctcc cctctgcagt gacacctcct ttacaccatc actaagttct tcccccatac  57900
agggcctcag agcttcttgt aatatgaatt aggaaggctt aatactggca aggatattaa  57960
gttcaactag aggtggtaga gaaatgaggg tcttgagagt ggatttttgg aatcatgagg  58020
ggcaaggaca cagcattaag tcttataata aatttaaaag gattattttg ggcttttctt  58080
```

-continued

```
gggaattaaa cacaccctta ataaaaattc tcaggtgaaa aaagaaattt ttttcagatt  58140
aaagacttgg taagtacata ttagggagaa gcacatttct aacttaaaat tcatgctttc  58200
gtcatgttac attaggaaac acgattggtt tgtatatcct tatatctgtg ctttcagttg  58260
aaactaacag cattattgag ggaaacaaag aatttttttt cctttactgc tagcctatca  58320
aacctctcaa tgaaatttta tgcatagtac agtaatcaag agatttttgt caatatttaa  58380
tacaatggat agatgcagaa attattgaaa atccaaatta ttattttgtg aaccatggta  58440
ccgatgttca ggcctgcctt catgcatttg tgagaaattt tgacaagctg ttgtgagtgt  58500
tcaccaaagg gaacacactt ttggcaggac ccttgcattt cctacatgga cagaaagtgt  58560
ttactgtgaa acaactgttt ctcgatgtgt actgtcctct cctaatttaa gcataaacct  58620
cttttcttcc tgaatgtaga gttcagagaa aggatttgtg atgacccaaa gtcttgactt  58680
aaagagatat tttataaagc agtgctgtgg ctcataataa aaagctgtaa gatgctaaat  58740
gccaagcata cagaaataag acattgccag ccatctgact tttgcaactg gatgatttaa  58800
aagaacattt gttgatctca agttgtcctt agaccatcct agttctaaca agatccaaag  58860
tgaaatgtga atgtctgcgt ttggtttctg atagggatgt ttttttaaaa aatattttta  58920
ttaggtattt tcctcattta catttccaat gctatcccaa aagtccccca tactctcccc  58980
ccaactcccc tacccaccca ctcccacttt ttggccctgg tgaaaaactg attttcaaat  59040
cattctggca tgactttgaa agcatacctg ttcaacactt tttccttgtt cttctacctg  59100
ccctttgata tttctaacca cccccatatt ggtatgggga tatgaaaaca ttagtgcctg  59160
gtatctgaac aggcctgctg aacaggaaaa aatgaaatta agtcatgtaa aggtgagtgt  59220
ccagaagcca cagaagtagg aaaggaaaga aagaggtgtc tgaacagtgc tgaaagaagg  59280
tatggcttca gactgtctgt cacaccaaaa attaatggaa caaataataa gtagaataat  59340
tttaacattg tctggctttc atagtggtgt tgtggttggt attggctttc tgactgatga  59400
gaaattttat gttgtttgca tagactagtc ttctttccag gggatacatg ttgaaagggt  59460
tacgtcccat catctacctt gctacacaca caacacacac acacacagat agagagagac  59520
agagacagag agagacagag agaaacagag agacagagag agacagagag agagacagag  59580
agagagacag agagaaagag agagaggaag aggaggagag aggaagaagg agagagatgg  59640
agtgagggag gaagggcaag agagagaagg agagagaggg gaaagggaga gagtgtgtca  59700
atgaatagat aaatgaggta acatgtttat gattagagat tctgagcaat gtgggtataa  59760
tgctccttaa aaatattatt gaaacttttc tgtgggtttg aattttgaat taagtaaaac  59820
ttaaattaca aaataagtat gattcactga atctcctata aaaaaagatt aattataata  59880
aagacaaagt gggtgttttg gaaagtggga actttctaag caaagaaatt taggcagcca  59940
atttctctcc tgctactggg tactgcccta tccaagagtg tgtccatcat tctgtcctgt  60000
gcttgtagta gcgcatatca tttgtttttc cataccatga gctctgattc ataatctaag  60060
gaggctggaa aaatgtcctg ttgtgtacat gtcagacaga gaaaggagaa cagatttttg  60120
gcagatcact agaaagccac aataagcccc ctatgaagca caatatgggg tctgatacca  60180
gaacctttcc tcaagaggag agctgatcat ctttcttttg tttgaaactg ggctaggaat  60240
ttaacaagaa gataccgttc tgtcagtgag atcacaaaag gtgaatgtgt gaaaaataat  60300
aatgcctatt caaaactagt acaatttaaa taaaatggaa cattctaaag tacaatttag  60360
caataaattg ctgtaggcag gctgaaactc atcattaaat acatcatgtc aaggagaaaa  60420
agatgagttg cagaaatagt aattgctaaa acagttaccc cccttttttg tttaaagata  60480
```

-continued

```
tttatacttg tcaacattca agattgtaat tttaaaacca cagtaagaaa acatgttatt  60540
aatgaaagtg ttgcattttt tcacaggcag caatctgatc accttggttg ctctgtacag  60600
aactgacctg gccatgtatc tagccatgac cagaatacaa ggatgcccat ttgtgctgca  60660
gatttccacc cactcacatc caattcctcc tcacatagtt ttactagtgg catattctga  60720
ggccagactt cctcttggct agaacataac cctttaaaca aatctatatg ctattctaat  60780
ggaaatatct tcaggcattg ccctactggg catagattca agtcagcttg tgggccagct  60840
tgaacttggc ttcttgtatg tggtttgcct ctagaagcat ctactgccag caggacactg  60900
gcagcctttg tgaatgtaag ctcagaactt tcttccaata tacgttatct tttatttgaa  60960
atagtttttg gacttatgaa ggaaatcaaa attattatgt gggtaagtaa attatatgaa  61020
gaagactcag ttaagtgtct atggtgactt atcccttact tttcaataaa ctttttagat  61080
tccttttcac ccaggccttt tgtcgctacg tcgtgagcca agtgttcata gactagtttt  61140
taatagacta tcaaacacaa ctgtgacatt atgtagaagt aaaggcagga ggacttgggt  61200
tttaggtaaa ctggaatata cagtaagttt aaggccaaca aagactacat ggtgaggtcc  61260
tggaggtcct gtctccagag aacaaaaagc aaaaacaata gcaaaaaaaa aaatcccaaa  61320
aacaacaaaa aatacaagga aagagattta acattatcat atcatctaac ttttggcatg  61380
gtagcaacat aatagtagta gctctactat agtctgttac ccatcactgc ttgtgatttt  61440
acaagatcca caagtatata caagatgaag ttcacagatg caactgcacc aaccacaagc  61500
actttgggta gaatatggca gtatcctagc agggagaatt tatgctcagg cagctaacaa  61560
gtgattaaat ccaagtctgc ttttgctctc ctgcaatgca gtgaggaaat cagatagccc  61620
ctttgccctc tgtttatttt gaattaaact ttatccactc aatttttaaa aatttactag  61680
attaattaat gttttatata ttataaatac agttttgttg gacatctttc ctaatatctt  61740
aactggtcct tgggaaaatt tatagtaaat aatagaagta caaaattgcc actcaaagta  61800
ttgtaaattc ccaatggata aattcatgtt tagtaaacat ttcacattta atatttgttc  61860
actttttcat tttcacgata tttttttcta aataagtgcc tgtcaggtca tgaaaatgcc  61920
agtaaaatct catgaaatca tttatccata aacaatcttt tgatgttagt gggctagttg  61980
attctatcaa aggaatttag agattatcag tagcacacag ttttagaatt ctagggtctg  62040
attgtgttac acctcctgtt agagtctagt tatagcagaa tagttgctgt caatatcttg  62100
ttgctgccaa tatcttgtaa ggcagtgtgt ttactggttg gaaacatgta aatctaacca  62160
ctttataagc agtaatagtt tttatagttt gaccgttatt aattttttat taataaaata  62220
tataacactt tcaatttcag ttatatatat atatattcag tcctctttaa tacatcataa  62280
cacttgtcaa tagctatgat ttatttatta tattgtgtgt atgcgagtac cagtatgttc  62340
attacatgtg tgtatgatcc ctgcagaggc cagaagaggg tgtcagatcc cagggaacta  62400
gagttgcaga aggttgtgga ccacagtgta ggttttggga acagaactca gattcttgcc  62460
aggagcatca agtgatttca taactgctta gccatctgtg tagccttgtt ttttctattt  62520
tttggagtat gatgtgtttc aaaatacagt atctaaatct gtagtccagg atagcttgag  62580
attcactata caggcttccc cctagactca agcaaatagt attggtttta actaagctac  62640
atttaaaaaa tccatttgcc agtgtgtttt agttgaacat atagacttac ttgaagcagt  62700
ccctagacac agatcagttc atggctcaat tccaagatgg gtctcatatg gtgtatgata  62760
aaaggaaagc agtacaagaa atccatctga tctttggagg cttgtagaaa ggttaacttg  62820
```

-continued

```
acatcttatc ccaccttctg gtgcaggtag gtaactgaca cagtgatatg atgactgggc  62880
atgatggacc cagaaagaga aagctagata atagcatgat gtcccttcag aagagcagct  62940
tgtttcatac aaaacaatga aaaaattatc acctgttgat ggagaaatgg ctcatcattt  63000
acgatgactt gctcttcctg caatgaacct ggcctcagtt cccagcaccc acatggtgat  63060
tcacaactgt ttgtaactac agttctaggg atactacatc ctcttctgat ctctatggtc  63120
attaggcatg tgcatcacac agagacacac aatcagggca aaacatatac atacataaaa  63180
ggaaaataaa cttttttca cattgaaaaa atatttacct catccccact tgtacaagaa  63240
atatgtgtcc aataccattt gtattgtaga attttatact gtttccctat actgtcttat  63300
acaagtaaaa cctaaactag ataatctgat aatcttattt tatatatttg aaattctttt  63360
tagattgaat ctctgttttc agattaaaat gagtaactac acatatattc caaacaaaat  63420
aatttgtaaa agaagcatga ttatttttaa gttttataat tgagtaaata gcattgactc  63480
tgaatgagtt attaaagttt ttcttaattc tcatttattg ggaaggaacc atcaaagaaa  63540
cgttttactt tacactcatg gcagtttttt gattagaaaa taatttctta ttacatatca  63600
aattcctaat attttgtgca agcttcaaaa gatgccaatg aaatttccag aacaagagtt  63660
cagaaacaac tgtctacatt caggtaggat gcacactgtt ctttatgttc agttttatct  63720
ctagatccag atgaactgaa ttacagtcag tcaactagac agggaaaatg agcatctgca  63780
cagctctagc tttggctgat ggagccaact tactacatag cttcctgtgt tgtggtatca  63840
tcaaatattt aacttctgtg atatttcttt gcctgttgcg taagtttaac caacaaaaac  63900
acatttccca ttgcccatcc caacatgtaa tagcagcaat tatttaaaaa tcatagtcat  63960
ttgctcttta tgtctacaag acaatacttg ttagtacatt caatataaat gttttctttc  64020
acaccaaggc agtttcctga ttcattagag ggaattttgt atctgagcag aggaactctc  64080
atgttccccg ctttcccttg ttataacatt ctgagctcca tgaccatgta ttattccagc  64140
tccatgtttg gacacgggtg aaggaagcat atcacatgtt cttcctaaga gacttagact  64200
aagtatgcaa aagacccaaa attttcgaag gtccaagtcc ctatctgttc ataagctcat  64260
ccctagtcat tcattgcttc agctgctgtt tttggaccag tattgagtca acttcacatg  64320
cagtttctcc ctttctacca tgaccatttg tacatcctct ttgtttcatg gtttaatcct  64380
gcaaaagtat atatttactt ttgtttggcc taatcttgac cataacctag attgtacttt  64440
agacttctta ctctttaaaa ttttaaaatg tgcagcataa ataattttct cctactttga  64500
ttaatccaaa aactatttcc aaggtcatta taaaaggtcc caaattatga gttccaatat  64560
tatggtcagt agacctattt gtgctctata acagtgttat ataatatttt aataggaata  64620
ttagaacgga aatgggcctc atgtgaacaa tgtgttttat attactccct tccccattta  64680
tcatgcctgg tatatgtgag tatgtatgta tgtatgtatg tatgtatgta tgtatgtgtg  64740
tattttttat gtattgttat gtatatacaa gtgatatata tatatataat atatatgtgt  64800
gtgtatatat acctttatgt atgtatatac acacacacac acatatatat atacatacac  64860
acatatatat atatgtatat atatatgtgt atgtatatat atatactgtg tgtgcattca  64920
ggtgcatttg tgtgtggagg catctatgtc tttggcaatg attctcatag aattttttga  64980
aacattgtct ctcactgaat ttggaattac tgtttcagct agactggctg gcccttgaac  65040
ttcttcaaag ccccctgcac tgggtttata aacacatcta tgccagcttt tggttgtatg  65100
gtaggtatac aagttcattt cctccttctc ttcagcaaac actttaccca ttcttcataa  65160
ttcctatgct ctaagccaag atattttttt cttaatgtgt ccaccatggc aaaggctcag  65220
```

-continued

```
aattataaat gtgtttctcc aaaaccctca gttaagaata tggctgccta attatgcatt  65280
taactaatag gcttctgaaa ttaataacca atataatatc gtggttcact aagacaaata  65340
tttgtagatt ttaataaagg caggtaatga agctaaagtt aaagaaaacc ttcaatacta  65400
tttatcactg tttgtgaaca aaatatgatg aaaatatttt gcccataaca taacactgcc  65460
ttaactatat ccatcttgac tcaaagagat agaaatccgt tctgtcactc acagtatatg  65520
tttgcagatg aatgctagaa ctgatcacag atgggaaact aggtgtgcat tgcaggggct  65580
caggtatagg tcacaactct atcagtctct gaacatcatg acacaggtag gaagaccagg  65640
aagaaatgtg ttttgtttca ggcctctata atgaaaagtg aatgtgaaaa ctcaaaactt  65700
caccttgaaa agcctctgta tatcttatat gtttttccca tttcctggtg aataggtaga  65760
atacagggaa caaaaaccac tgctctcatc ccagtatcag cccagactct tttcccagta  65820
cctcatctca cagatattcc tccattcctt cctccccttc tcctctgaga atagggagcc  65880
ccacttctcc ctataacctt acccccaacc cctggcacat caaatcacag caggtccatg  65940
taaatcccat cccactgagg ccagataagg cagctcagct aggggagcag gatccacagg  66000
caggcaacag agtcaggggc agcccctgtt ccaaaccatt ctcattccta gtaatgctgt  66060
cctagcacta tgctgatgac tggaccaaac atacaatttt tgttcttact tgactcttac  66120
aacttcaaaa attaacagtg taaatttcca gttagctttt gattttaaga caagctaatt  66180
agtgaagaat taggcacaga aatctacata ataaaataat tacagaaaaa gaaagtatct  66240
aaggtcagca ttagtatggc atcttatttt ctgtctgtca tggggaaaca agcaattcca  66300
tatggatcgt agaggtcaga aagaggcact gctgatccca cactgctgtt ctatctagca  66360
caagcagcaa gagactctcc aaagcccagt aagcaaaagc gccctgctta tgttggctcc  66420
actaatgcag ggaatttcaa atgatggatg aattaaaaaa tttgaaagag gttccgcctg  66480
acagccactc atctgtgata tatcctttgc tgtcacgatg attagccatc tgttcctttt  66540
ctagatctta cccatccact atcattacca tccaccatca ctatctacta ctaaaaccat  66600
taaagcacat ttaaagatgt gaggtctagg aatggtatct ttaaggtagc atatatgtcc  66660
agtgtggtag cacgtgctca ggataggtcc tgagttctat cctccagcac catcaaacca  66720
caaaagataa aaaatgaaga tgtatgaact atatacttta ttagcttcta tctattacta  66780
gcaatacaat gtcacactcc atggcagtgg aaggaaggag ataccaggca tgccacttga  66840
caagttttta gacttgtgac tggtttcagg ttatgttcat aaaagacaca tggaaaggaa  66900
aagtagttaa atttgtgtgt ttggatggat ttactttgag gactgtggtt atgaagcact  66960
tgtttctaga ttatttcctt ttatccaaag tagaagggac ttaaaattgt ctacgttagt  67020
agttctcaac ctgtacctgt ggattgcaac ccctttgtgg tcacatatca gatatctaca  67080
ttatgattca taacagtagc aacattacag taatgaagta gcaacaaaag aatcttatgg  67140
ttgggggtca tcacagcatg aggaactgta ttaaagagtt gcagcatgag gaaggttgag  67200
aaccagtggt ttaaggtcag tgtacagtcc caatttgaag cagcacagat gcaagtgctc  67260
ttgggtaact tctacatggt tgttttactg tagttactga tctaactgtg aaaagtggtc  67320
agcctgttgc agactgaatc tgaatagaaa tcacaatttt gcatactctt ggtttcataa  67380
ttcctttatg cacatccttc tgagaccctg gttgtactac actactacca cttgggccta  67440
gagcccctct cactgtgaaa gaatgattgt atccttgggg agctataaag attatgactt  67500
tgtgaattaa tctcaaatca gggagccaca ggacttccaa ctttattttc aaatatgtgt  67560
```

-continued

```
gaactcccct gtgagatggt ttatcgaagc ctttgggagg tgcagccatc tgattgacca  67620
gttatcttat ttgcaattga ctcttttatt ttatatgaag ctctgtttgc taagaaggac  67680
aattcaatca gcagtcactc atagaactac tcagttgatg taatgaataa agagacatta  67740
gggtcagtga aatgactcag tgggtaaaga aacattctgc caagtctgct gacccaggtt  67800
tgatacccta ggatcgacat agttgaagga aggaacacta ttccaccagt tgtactttga  67860
cctccccatt ctcactttag cacatatgca tgcccatact aaataaatgc aaagtttaag  67920
agaaacacca agacttattc aacaaattta ataacttatt agaatactca agtacacagt  67980
caaagaaaga agttatatta tggattaata gcaaaacaca tactgagtgt taaaaattat  68040
atactggagg agaatgggga agggtagatt gagagctaga catatacaac agagtgaact  68100
ttcatctggc ccttcaaaat tcttagtatg aaaaggaata gggacttgca actgaaaaga  68160
actctaatgg caattcataa aaactttagg gtagaattta gaagagggaa ttaaaatttt  68220
aagtctacaa tcaattcata caacaatctc tttatataac agtgtttttt gtacactgaa  68280
tactgtgcaa atattttgta aaaggtatca agaactattc tgttaacagt ggcttgcata  68340
taatcagaca agatggcata catactctac ataacgcaca tttgtataaa acataaataa  68400
attgtaaaaa caatagccta cacactatat ttttaaagta gcattttctt atttttgtaa  68460
taaataagat ttttgagatt tagcttattt agccaactaa tcattgacct ttttataagc  68520
agatgtagta attcttaaag ttcccaatta aaataaaatg caaagttttt gctattggtt  68580
ttgatacact gactccaaac catatggtag tataaagata tttcttgaaa actctgaaat  68640
cttttcattg tcttctctta gaattgtttt atgactgttc ttctttaaca gtgtagatga  68700
atgaatgaac atccaaaatg aatagaccaa gcagcccgtg ttagaaaatt cattagtttt  68760
actggattcc actgaggact ggacaataag tggcaaaaca tatgaatgca gttctgtgga  68820
agcttcctca ggatttaaat aaattcaagc aacacacaca cacacacaca cacacacaca  68880
cacacacaca cacacacttg tgtacaggga ggagagccat tgtattagaa aatgcaacct  68940
ggatggccat cagggtgtga atgtcagcta ccacaaaata tatcagactc aaagctgaac  69000
aggcaccagt actttttatg gagaagaacc aggatggcct caaactcacg attacccgtc  69060
tcatcctccg gaacactggg attataagta tacgccacca catttggtga aagaaaggac  69120
ttgttttgaa tttctgtatg aatgaagttt caaaagaatg caattaagta cgagatcaaa  69180
tttagaagaa agatttgatc taaaaaatac aactaaatga gaaaaggtgg ataggaaaaa  69240
gcacagtatg cattctttat tgtgttgctt tcacgatgtc aaaaacaaat taaataggct  69300
agtaaaatgg aaaggccatg aacaaatgtt ccttgtagta tagaatatac tagactatct  69360
cttctatata aattgattta aaattaatga caaacttggt ttcaattcaa ccagctcatt  69420
ctaaaaagtt gaaatataca tatgtgtgtt tgtgtgtgta caaatgaata tataatgtat  69480
ataatgtaca atgtgcatat acattgtata catatatatg ttagaatgat gggtgtaatc  69540
atgtatttat atttttgaat aaattctaaa cataaccaaa ttccagaaca acttagcagt  69600
actaagaatt actgattaca ttaaagttta tttataatca atacacaaag atattaatgc  69660
atgtaattct atcagtattt atgtttctga tgttataatg ccaatgttta tttcacatac  69720
gtttgaatat tgtttaatat tatacatatt ctaaatatag taccaaatga tatttttatt  69780
tacattaatg agaaaatgta agtcctggtg aaattctgtg aaaaaagtta tgtatcagtg  69840
aaaaatggta tggaacaact ttctttcagc tccaaaaatg gcaatacttt tccctttatt  69900
caataaagag tatttttaag tagaaaagtt aaaaaaaaaa aacgggattc tagtcagaca  69960
```

-continued actcgaaata tatgggtcag agtaacagta tctctggaat gcaggcttaa aacctgacta 70020
agatcagaga cttgagtacc atacagggtt ttatgtgtgt attgtctgat aatggcaaaa 70080
gaagatggtt ttaaaaatga ctgattcata agcaagtcaa cattaagtga aacttgaatg 70140
gaaatttagt tttctagtaa taagcattta gataataagg agtgccttat tattattaga 70200
tattaagctg gtaccccctg tgccttggct atgactctga aatgaataga atgaagttac 70260
agttaacaga gatgcagagg cagacacttc cctgtgctac ctaaacaggt acttagtgta 70320
ctttgaacct tatttctgac aggtctgaga tgtaaaagga gggaaaccag tgagcccagt 70380
gattctagcg ttgccgtgaa ctgctcagag gtagtttgtc attgcacaga gctgttctca 70440
taatagttat gatcccaagc cttaaattgt tgggaactat gttactgttt atttgttgtt 70500
gttttttttt ttttcctcta ccctctggtt aaaatataat tttgatgcat cagcatagtt 70560
atgaagggga cttactagca agtgcttttt aacactgata tttgggtctc ctggattcta 70620
tgaaagtcat gtctccttaa ctactttatc tcctgcactg cgccctcccc cccatatcca 70680
cagagcatct gaatggtcac tcgtggccat gctccagagg tgagtgatgt acacacgggt 70740
ggagaatcca atttaaaata gcatgagaat gtagaagaga caaaggagca ctgcaggagc 70800
atgtgcagat ataagtgctg gaagtcccca gactgctttc tccagacttt ctcagctcct 70860
ggtgttgctg cccactctgc tgccctggtc cttaccttaa ccagctccct tatatgcttc 70920
catgttttat ccttcactaa gtctctttct ctctggttct ggatgcttag atgttcttcc 70980
atttggttcc atgtcatatg gtcatttctg tttctgcagc agctaaactg ttggataatg 71040
gtttgcaggt ctgactccca agtaccactg tgagctcatt aacaatggct gccatctcct 71100
tgtatcctct gcactatacc agcagatgaa gttggaccat gggctgtatt ccatggtgaa 71160
tgagtgctct gtgctggttg gaaccctata gcaatagaca atgtgaatac attgacagtg 71220
ttttgttgtt gttgctgctg ttgctgttgt tgttgttgtt gttgttgttt ttggcaagat 71280
actcacttca gggttttaag aacatgaccc aacctgttaa aaatcaataa attcagacag 71340
aggatttttt agttaagagt taaggtacaa atgagagatc actgaaggtt ttaagcagac 71400
tgtaaggtaa gaagggaaga aagttcccaa agtatatgct aggagctagg gctccagtgt 71460
aaaggatggc taaacgtggg tctgttttaa ggggtgtaca aacatatttg ggctaagaag 71520
gcccaatatt tactttcgaa tgagggaaaa tgcttgtgac ttaacaggtt gcctgttcaa 71580
tgaactaaaa aaatgtaaac tcttactcca taatctcttt aatatctcac ttttgccaaa 71640
ggaatctaac cttattgcca ccaaatccca ctgaactcct agacgagcaa aaaaaaaaaa 71700
aaaaaaaaaa aaaggggggg gggagttcta ccaatcccca tgacattctg caattttcta 71760
attatagatt gaaaaagagg gttgaattca tttcatggga cattcactgt gtgtccctac 71820
aggatgctga gccataattg acccacacat gtggtgtgtg atatttgatc agggatccta 71880
ggctggaaag acagctcagt aggtaccttg caaacacaag gatttggatc cacagaactc 71940
aattttaaaa agctggtcat gataacacac atgagtgatc cccgctctaa aagacaagga 72000
tagtaagatg tctgggtttc ttggctaacc agcacaacct acttggcaga ttccaaacct 72060
gctagagata ttgttggaaa gaaagttctc aacagaatct gaggaacaac accagaaaca 72120
gtctacatgt ctacacacac ctatcatccc cccacatcca catatacaca tgtacatgta 72180
tacctataga taaacattac cctcccccac acttgaaaat acacatatac acaacattca 72240
ttttaaagac acaggctaca gttttcactg tcttgggcat tgctcattct tttttgttaa 72300

-continued

```
gaaactgcca atgccattcc ccttgctaat aaatgttata aactgtggtc acattatgct  72360
gcagtagaaa tgccagagac tcttcctttc tactagtatt ctgatgtgtt tattcagctt  72420
cctcccacct cctctatccc tgtttaccct tcatagtgtc tcatgacagc tttctactct  72480
ctatatcttt gaaataaaga ctttaccaac attttaataa tttttttcat ttgccgtttt  72540
tatttttatc tttttaaaat tattattagt tattttcctc gtttacattt tcaatgctat  72600
cccaaaggtc ccccataccc acccccccaa tcccctaccc acccactccc ccttttttggc  72660
cctggtgttc ccctgtagtg gggcatataa agtttgcaag tccaatgggc ctctctttgc  72720
agtgatggcc gactaggcca tcttttgata catatgcagc taaagacaag agctcccggg  72780
tactggttag ttcatattgt tgttccacct atagggttgc agttcccttt agctccttgg  72840
gtaaattctc tagctcctcc attgggggcc gtgtgaccca tccaatagct gactgtgatc  72900
atccgcttct gtgtttgcta ggccccggca tagtctcaca agagagagct atatctgggt  72960
cctttcagca aaatcttgct agtgtatgca atggtgtcag catttggaag ctgattatgg  73020
gatggatccc tgcatatggc aatcactaga tggtccatcc tttcgtcaca gctccaaatt  73080
ttgtctctgt aactccttcc atgggtgttt tgttcccatt tctaggaagg ggtaaagtgt  73140
ccacactttg gtcttccttc ttcttgaatt tcatgcgttt ggcaagttgt atcttaagtc  73200
ttgggtatcc taagtttctg ggctaatatc cacttatcag tgagtacata ttgtgcgagt  73260
tccgttgtga ttgggttact tcactcagga tgataccctc caggtccatc catttgccta  73320
ggaatttcat aaattcattc tttttaatag ctgagtagta ttccattgtg taaatgtacc  73380
acattttctg tatccattcc tctgttgagg agcatctggg ctctttccag cttctggcta  73440
ttataaacaa ggctgctatg aacatagtag agcatgtgtt cttattacct gttgggatat  73500
cttctggata tatgcccagg agaggtattg tgggatcctc cggtagtact atgtccaatt  73560
ttctgaggaa ccgccagact gatttccaga gtggttgtac aagcttgcaa tcccaccaac  73620
aatggaggag tgttcccctt tctccacatc ctggccagca tctgctgtca cttgagtttt  73680
tgatcttagc cattctgact ggagtgaagt ggaatctcag tgttgctttg atttgcattt  73740
tcctgatgat taagggtggt gtgactctaa ctaaggaagt gaaagatctg tatgataaga  73800
acttcaagtc tctaaagaaa gaaattaaag aagatctcag aagatggaaa gatcacccat  73860
gctcatggat tggcaggatc aacattgtaa aaacggctat cttgccgaaa gcaatctata  73920
gattcaatgc aatccccatc aaaattccaa ctcaattctt caacgaatta gaaagggcaa  73980
ttggcagatt catctggaat aacaaaaaac agaggatagc aaaaagtctt ctcaatgata  74040
aaagaacctc tggtggaatc accatgccag acctaaaact gtactacaga gcaattgtga  74100
tcaaaactgc atggtactgg tatagtgaca gacaagtaga ccaatggaac agaattgaag  74160
acccagagat gaatccacac acctatggtc acttgatctt tgacaaggga gctaaaacca  74220
tgcagtggaa aaaagacagc attttcaaca attggtgctg gcacaactgg cggttatcat  74280
gtagaagaat gcgaattgat ccatttctat ctccttgtac taaggtcaaa tctaagtgga  74340
ttaaggaact ccacataaaa ccagagacac tgaaactcat agaggagaaa gtagggaaaa  74400
acctcgaaga tatgggtata ggggaaaaat tcctgaatag aacagcaatg gcttgtgctg  74460
taagatcaag aattgataaa tgggacctca taaaattgca aagcttctgc aaagcaaaag  74520
acaccgtcaa taggacaaaa agaccaccaa cagattggga agggatcttt aaaactgtac  74580
tacagagcaa ttgtgatcaa aactgcatgg tactggtata gtgacagaca agtagaccaa  74640
tggaacagaa ttgaagaccc agagatgaat ccacacacct atggtcactt gatctttgac  74700
```

-continued

```
aagggagcta aaaccatgca gtggaaaaaa gacagcattt tcaacaaatg gtgatggcac  74760
aactggcggt tatcatgtag aagaatgtga attgatccat ttctgtctcc ttgtactaag  74820
gtcaaatcta agtggattaa tgaactccac ataaaaccag agacactgaa actcatagag  74880
gagaaagtag gtaaaaacct cgaagatatg ggtacagggg aaaaattcct gaatagaaca  74940
gcaatggctt gtgctgtaag atcaagaatt gataaatggg acatcataaa attgcaaagt  75000
ttctgcaaag caaaagacac cgtcaatagg acaaaaagac caccaacaga ttgggaaggg  75060
atctttacct atcccaaatt ggatagggga ctaatatcca atatatataa agaactcaag  75120
aaggtggact ccagaaaatc aaataatccc attaaaaatg ggctcagag ctgaacaaag  75180
aattctcacc tgaggaatac cgaatggcag agaagcacct gaaaaaatgt tcaacatttt  75240
aataatttta atacagtcat ttattgtaac aaccatttca aaaacacttg tttccttaga  75300
atgaaaattt taactagata aatgtggtta tccatgaaaa tattaaagaa tatacaatat  75360
acattatatt attgtatata taatatggta tagcacatga tataacacac acacacacac  75420
acacacacac actttacaaa aatgttaaaa aataatacca cacagaatgt tgtgagaaaa  75480
tagcattagt gtctgactca tcttctcata cttttagaaa taaaattaaa gttcttcaca  75540
ctttgtgtaa agcccaaaag gttcagccct aaggaaaact tgaaatttgg gtgttaaata  75600
agccaccagt ctaaaagttg gacatttctg aattaaggct catgcctcat ttccaccaag  75660
tgctgcttca aaacaaaaca gtgataatgg ccacaaaaaa cctctggcaa ctctaattta  75720
aggtgacgta tactgatgaa tgatttattt atcttagaag tgccaatatt tcactctttt  75780
ccatgtcttt aaagcaactg aaatagtttc atgagcacag gcataactgg attcttggat  75840
ttggggagaa atgatttggc tatgtgcctg ttgctgagga aagaaactgc caacactgag  75900
gatgtttcta aagccaagtg ccaaattgtt tgtgcttagc atcatgtatc aggctggccc  75960
tgcaagatga ttccattcca aaggtcagaa atactctgcc ctgtttccag aattttattc  76020
agaaattgga aatagagaca gcttcaaaat agtacacatc ccatcttctt ctcagaatga  76080
gggctttgat ccaagccttg ctatgtaaaa tgcatgggag gaagaggaac ctaatacaaa  76140
ctttgtttat tctatccgcc attgctgttt tcatcttcag aagaattctg ctttttggtt  76200
tagtggtaat aacttgtacc aagtcgatgg caactccacc cagataatga tgagtttgtg  76260
agaacatatt tttcacatgt ttgaagaata gagctacata gggttgaatc tgccttgcaa  76320
tttgatcttt atcagtttta tggaggcata tctccatgat taccccctgtg tatgtttact  76380
ttaattagat aaataaccag aaaccaattg ctccctcact tatgattatg tgtattctcc  76440
atggagtgag agacaatagc tagtagccat ttgtttacct tcttactttc ttactctcac  76500
tacccagtat ttcctaatta aagctatcag cagccaccat atgcctgtga catgagtctt  76560
actctgtgga aacaccatga tcaaacaaac aaacaaacaa acaaacaaac aaacaaacaa  76620
caggttgcat tctcagcagt tgcagaaaaa ctcactttct tttgcatttt caacttgttt  76680
ttacattaat cacaaacatt aacagtctaa caacataatg tgttcactta aagataaaca  76740
acacagcagt tgttaactga aactcagatg tcaacactgg gttaagagaa ttatggtggg  76800
tttaccgaaa agttgaaaga gagaattgtc tcagtgaggt gtggccttca actggaagca  76860
ctgaagccag acaattagag ggaagattca aaggaggtgc tctcaggatt taagtcacca  76920
tgtctcagtc ttcagaagaa tgtgcagctg accaaggcca gacctgtgaa gagacccaga  76980
aactacaggt tgcagcagcc tccatcgatg ttgaggagcc atgttcctca cctcatctta  77040
```

-continued

```
tggctactag tctgaaggac cagaccagtg aggagaccca agtctccaag gatgtggagg  77100
aaccatgttc ctcttctcaa cttcttatgg ctagcgacca ggatgattct gaagatgaga  77160
cagccagtac ttccagtgat cttcagcatc cctatgactc ttcaagcgag tctactgagg  77220
atcttgatga ccaagaagtg cagggtagcc cagtcattcc accagatcag tcagatagca  77280
cagatttacc tgtgatgact gtagatggga aagttgattt cttggtgaat tacatgctgt  77340
acaagtatca ggtgaaagag gtgatgagta tgaatgatat aatgacactc attgtcagag  77400
aggatgaaga tcgttttcat gaaatcctca tgagagcttc tgagcgcatg gagatggtct  77460
ttgggctgga tgtgaaggaa gtagatccta tcaaccattg ctatgctctc tttatcaaat  77520
taggtctcac ctatgatggg atgcgcaatg atgagtacag ctttcctaaa actggtctcc  77580
tgatactcat cctgggtgta gtctttatga agggcaaccg tgccactgaa gaggagattt  77640
gggaagtatt gaatccaatg ggaatctatg ctgggatgac tcatttcatg tttggtgacc  77700
ctagagagct gataactgat gagtttgtga gggagcaata cctggaatac cagccaatag  77760
ccaatagtga tcccatacag tatgaatatg tgtgggggct acgggctaaa gctgaaacta  77820
gtaagatgag agtgttagag tttgtggcca aggttcatgg gtcagaccct actgtgttcc  77880
tttctcagta tgaagaggca ctgattgaag aagaagagag aacccttacc atgctattag  77940
agcatgctga ttcaagttct acttctggtg aaagttctag tgacacaagc agcaacttct  78000
ctcaggtcta gtacagtcag agatcagttc cttctgtata atttacagag aatttttaaa  78060
cttgcgggga aagatgtacg acctagattg tatagggaga agggagcgtc ttagctgcat  78120
agttctaatt tgtataagca ccatgccatg tttttcattg tttgcccttt atatatgaaa  78180
atacttacac ttaaaagcat tgttgtttag tttcaaaatc tcaacttaat accattcaca  78240
aatttaataa gagcgttgtc ataacataaa actaattggg aaataatccc atctatctgt  78300
acagttatct ggaatagtta aacatgcgtt ttctaagctt ctacctttta aacagctttc  78360
ttctaattac tccctttgta cctttccatt tctcagtaaa attacatgct ctatgtggag  78420
ttgtttactt tatagttgcc aataaaattc aagaaagttt aaaaaaaaaa agagagaatt  78480
atggtaattc ctctcaaaaa aaaaagtgtc tcaccattat tttctcacat cttattagaa  78540
gggtatctaa caagatccgt aggtatgtag agccagcaag catctggctt ctcatctctg  78600
tggtggaagt aattaaagta ggaagtgccc attttgactc tgctgtcagc agaagagaac  78660
acactagact tgttagtgca gccttagcca ggccatctac ttccatgaca tgggataggt  78720
ataaattagc atggccatcc tttcttgtct ttgtagttca tacagaatcc aggaagcaac  78780
acatttagga gtaggagttg taccattttt gcataggaaa tgtacagttt cagtgtcaat  78840
gcagggaatt actatattta taaaaatcac agagtccctc tggctggtgc tttttagtca  78900
aatatgaaat gagtagtatt ggaattacaa gctggcatca cttccgtcat tggagacctg  78960
tttctgcagt cacagctgct aaaacagctt catgattcct ttactacgag ctttgtggtc  79020
ctgcagatga aggatatcat agtacatttc ctgcatctct catgacactc gtgatcagca  79080
tataagactt ttcttttgtc gagaattaaa taagaatatg gccaaggaac agaattagta  79140
ttgtgaagaa ggtgtaatga gataagataa agaatgattc agagctgcca atcatgtatc  79200
cctcttgctg ggttcattgt ctctctatct caggcattga atgaaacata ctcttgttcc  79260
tgactataaa atcagtaata taaaacaacc aatttaatag catttagaag agactcaata  79320
gaccggcagg gagaagactg tatccactga tttaaaatat gtattatgat accataaatt  79380
ttaaaaagaa aggaaggata gtcttataaa ttcctaagtt tgatagcaca taagggctga  79440
```

-continued atggtgatca cttgggtccc ctttaccttc attggttctt tgcatcttca cctcgagcaa 79500
ttgattgtgt ttcgcttgtt tgggttctct gcctttctcc acactccatg atttttttca 79560
aaactgtctt ctgttcccct tcttgcccac attgtaaaca tgtgaagtag aaaagtgaaa 79620
gtgattttgg tgtcttttct tcagaatcat tatgttttcc agcaagaact aacactgaaa 79680
gctacctgaa acacaaataa attaatagaa ttgagccata cagtcatctg tatataaagg 79740
tgtaacgtaa aagggccact atataggaag gcagagtcag cataaggctt gatttaaaaa 79800
aatggcagaa caattatccc tttgatgaga tagacttaca tcttacaagt gtagtcatgc 79860
tacatcataa gttgacctca ttttctaaat tagtcagagg agcataactt ttttttctgt 79920
ctttcatttt ttttgctttg tttttgtttt tctagacagg gtttctctgt gtatcactgg 79980
ctgtcctgga actcactctg tagaccagac tggcctcaaa ctcagaaatc tgcctgcctc 80040
tgccttccaa gtgctgggat taaaggcatg ggccaccacc attgcccggg tcgtctgtct 80100
tttctaagta tgcttcctcc agtacatgta atgtttctcc ttttttccca tattttcctg 80160
ttctgggcag ctgttaggat ttacagattg cttgcttgcc tttggttatt tcctgttgcg 80220
ctgtaataaa actgccctct tttaataaac ataggctttg cttgacttca gaacctgttt 80280
tagatgtgtg tttccaaaaa ggttcccatc tgtattctta gaccccttat gtcttgcatg 80340
agcacattct tccccagttt gtatactaaa gatacttggt tgaacccatg tttgtttgga 80400
acatatttat ttcatttgga ttctgagttg ttcctttgct ttacctagtg gagcagagct 80460
tatgggaccc cagagtcttt tctggataag ctttcttcca tgaagcaagg cttctgggat 80520
tttataagat gttctaagga aaattcagtt taaaatgaga cgttatgttg atgtgataaa 80580
ggtacaaatt tatgacaact actttattgt tgccagttaa gaaccacatt gtaaacatac 80640
cccctagaat acatttaatt ccatagcact taactatatg tccctacaag taaggtatga 80700
cactcttctg tatataaagg catcctcata atctttatca tcagtgtttg gtaaacattt 80760
acctgttcaa attctgcttc atggtgagaa tttttattca gaaatataac aaactaatta 80820
aatccttttt tgacaatttt ctgtattatt taaatacatc atactaaaga ttttagtata 80880
ttaactaaat aaagattata atattattta aagtaagccc atcaatgaat aagatatata 80940
cgcacatagg gaccccttag tcacagtcta gtagactcag gcttctcatt gtttcctttt 81000
ccatcctttc cttttctagt tgatacctat gagtttgcag gtttgttgtt gaaggaagtt 81060
gctcctgaaa gactctgtcc aggccaacag tggccacaag agcagggcca gatgcaagtc 81120
tctcttccag ctctacagtg atagttaaga tggctgccat cttaccctcc acagctactg 81180
tcaaccatct gaactagcag ttccacatac atctccccta agcttgctta cattaagatc 81240
agcatctcct tttccctggt ctctagttag atctttccat attatatttc caactacaac 81300
ttttaaatgc tttctcaaaa ccttcaaaac attgtaaagc atattattaa caaacccagt 81360
ttgtcattgg tctaacttca ttttcttctg ctgctacttt tccagcaact agcttccact 81420
gcaagtaaaa ttttactatc accaacacat gagaggtaaa catgaagcca gaggagtctg 81480
tatgtgtatt ttgtgcaata agttggttca tggccattac accaaatgcc tggttgtact 81540
ggttgacaac tgtctttcta ccagatagac tgtttgccca ctgtgcgatc ttggacaaca 81600
tttaaatttt tgtgtttctt agcttttttta catgtgacat gaggataaaa attactccta 81660
cttcatcaga tttaaataaa gtgttttaac ataataccta ccctataaca attcagttca 81720
atgatggtat catgaagaga aaacacatga ctttaattga attttagagt tctgatgtgt 81780

-continued

```
gtgtgtgtgt gtgtgtgtgt gtgtgtgtgt gtgtgtgtgt gcatgtagat ataaaatatg  81840
aaccagagga ttacctggaa ataactggaa acagaatgac agaatgtatg atagattcgg  81900
aatgaccata gaattaatat ttgcaaataa atagtagaat gattccactg atcttttgga  81960
aactaaaaga gagaagaata tttcaaacag ctttcagtgt ggctttctgt gatgctctct  82020
gtctgctgct tctgctgctg caaaataaag cttccctcct ccccccttatg agcagtgaga  82080
gtgacacttc cctgtgggtg ttgggataac tatttagaat gcagcgagga attacattgc  82140
ttagaaacgt ggcaatagaa cttctcttct agggtccatt aagtcaccag acacaggtag  82200
tgggctgatc ttacagtaac caagcatgaa tctccccata tttagcaggc catgagccaa  82260
ctaggagacc agtatagaaa tctatagcca gcaagaaggc agagaacaat tgactcttgc  82320
ttgcttgtcc ccatcaattc atttacaaac agcccatata ccaaaggtgc tggagacact  82380
gtggaagagg gggtagaaag acaatgagac cagaggactc agtggtttgt tagcatatgg  82440
ggtcttccta ataaaatgca aaaggggtat ggagagggga gtgtgagtga atatgtgcat  82500
atgaccagat acagtgtatg aaattctcga agaattaaat tctcaatata actcccaact  82560
gcaggctaga gagttattct tagacccaca gataagtgta gcccttacca ttcatcatag  82620
aaagccacag ttaaaagcca tctaaattgc tttttccctc tatcatgttc cagaagctca  82680
gtgacatcat tattcccccc catttacaaa tataaattct atagtatttc catttttttaa  82740
aatttcctgt tttcggtgtt tattgtttgt ttgcttgtat gggattcttg ttgttgttga  82800
ggcagaatct ctctacgtag ttctacctgt cttataacta cttgtgtaaa ccaggctgac  82860
ttcaaacaca cagagatctt cctggcctct gcctcctgaa tactgagatt atagatgtgc  82920
agtgccattt ccagctactt attttcaaaa ggctgttcat attttggtgc ctgtttctgt  82980
caaactccaa gtgagaagat ttggattaag aattatagcc cctttccatc tggtttgcac  83040
ctaattctga tcctaaaaca aagtaagctt cttttcaaat tatcttttat ttatcaaaac  83100
catggtttaa atttccagca tgaatataca atttgccatt taaaagtaat gtttgaaagt  83160
tgtgacagct gaccagagac aaggcctact gaaggtgagt tccagtgctg tggagggaga  83220
ggtcatgaat ggtcttgatg aagcttattg catgcaagat catcacaact tcagaaaaga  83280
ccttaagatg ccaactaact atgttattgc tggggttcag agagcctaaa atgtggtgtg  83340
gattgtattg gcaatgtaac taaagagcaa gaatgttcat attttatgtg attttaaagg  83400
tattaagtat caatgaacta attctttcaa gagcagagat aaatgaaaca ttttatcttt  83460
ctgttttcct tcttactctc taggaggctc atgttgaaga caagtctgaa taggaatgct  83520
tgtagaagca ctcattaact aggattaaaa tagctagcat ggattcacca cagaccttac  83580
agtaattggt ctgcaagcca ttcaatcctg ccaccataac attagtcctt tttaaatttt  83640
ttaaatttta tttatcaatt tcaatctgat tttacatagt gaggttttca aatttcaatg  83700
tctttggtcc ctgcaagctt tattgaaaga tatattcatc tatccagggc taatggtatt  83760
tataagcata actgtactca catggatttc ttaagaggaa caatacataa aatttacatt  83820
acaacaaatt ttgtgaagac tttatataag tgtgcctcag cttatagaaa gtatagatag  83880
aaagtttaat ggctatcaac atcatagact ttatgtttgt aaagttaaca agaaagtcta  83940
cactataaag cgataataga taattataca taaagtatgt aactaatacc aacttccttt  84000
aataaattgt agggaatttg gcagtaaaat tacagcaatg tgctaaccta gtaactcaat  84060
cactgtgtat cacctctaaa attcatttta aattcaacag tataatttct cataagcaat  84120
ggcttactca ctcattgaac aaatgttgag catttgtgga gacatagtac ttattctagc  84180
```

-continued

```
caggtatgtt gttatgtggg ctcattttgt atatacagaa tataagaaat tatctgagaa  84240
aagacagagt taaagaattc aacagtaatg cttgagagtg gttattgttt ggcaaggcac  84300
ccagctgtcc tttctagaga gtaacaactt cagcattggg atgagaaatt ctcacttctt  84360
tgtacctcac tgaccagggg tgagcagagc tgctcagaag ctctcttggt gcctaatacc  84420
ctccattctt gttagtgatc tgaaactctg gaatctccca cagttcccca ttcatagagc  84480
ctgtttatct aagtgaaaaa ataagaataa aaaagggtgc tgtaacaaat acacaagaaa  84540
tatgaacggc gttctcaccg tgttcttgta gaaatgtaat agaaatttaa gctgatgtta  84600
ggtgacaatt aaaatctggg aggtgttttg tacactatca cctctttggg atgagatctt  84660
atgaatgagt gatgtctagt agaaaagacc tgtaatcata ggttttgttg accctttttcc  84720
tagataatag acgctgtctt agaagcgcca ctaacctctg atattttcct ccaagacctc  84780
tgcaaacctg tattctgctt attgtacatt gccatggcaa tactgtctag tctgcccatc  84840
caggtcccta ttcatatgac tcacttggct gctccacagg agaggagtta gcttcaccta  84900
accagcacca ctgtagcttc caggaaggga catgggaaag aatagcctgc caactagcca  84960
gcaggcctgc tcgtcccctc tttacttcta atagcaactg cagggctata gccagcacag  85020
atcactgtta atattaaaag cttgtgaatc atggcaaatc atcgtctttt atggtcagaa  85080
agaatgatgc ctcttataag tcttttctgc ttaattatgg tagaaggttt ctacatgttc  85140
ctctaattat agcaaatata atcagactaa agcttggtag ctaatgctat acttatagga  85200
agtgtacaga acagtgaata atgtagatgt tgataatata cacatgctaa agtatcctct  85260
aagaaaagaa ggcagtgtcg caaatgaaag taatttaagt gaaagtgttc ctatgaagaa  85320
tcattgtcgt cacaagcctg gcaacatatg aatgtataat ccctgtggtt ccttctgtga  85380
taatatgaac tcgatcttct tacttccata aaggaatgac aagccaagct ataggaacaa  85440
gaaagcaagc aaggcacaca agtattgcct actttttctt ttcttttctt tttttttgtg  85500
attacactgt cagaactcag caaatgccta tatcccctgg tagcctttaa caggaacatt  85560
ttcattgtct ctgtcataaa acgactgtat gtcacatgga ttgagtgaaa ggaaggcact  85620
gagtaagaac tgtggattct gaatatcagg atatcctgtt tttacgccaa ggctctttgt  85680
taaccatctt gatcaatgat gccaaactag tctagattta ggctgtgaga taaacatttg  85740
ttcttgtata cagttccccg atcatggcca aaggacagca tgaacagagg tgaaggctct  85800
ggtttcccag acagtggtct cattatctct tttgcatgtt ttaagggtca ttcttaacta  85860
cagcccaaga ctcttgataa cagggctcac gtagaataat tgcaggacag gtttagtata  85920
gtatcatttt tcatcctcca atgctaatca gattgaaaat aaacctgtca ctgagcagaa  85980
gaaacaaggc caaggccatt tgctgcatgt gatcttttca cactggcttg ctgagtttca  86040
gatgattttt ctgtcacact ccaaagaaca tgagtccctg aagacttttg tgaaggctta  86100
gctattatca agccattgcc tcatggatga cttcataaat gtttgctttt gcatcaggta  86160
atggcataca acataatttg ttcctgactc cccactatac acacatatat ctcctttgac  86220
attagctaat aaaatgacag agagacgttg atttctgact gataatatca caagagctcc  86280
ccacacactg tctcctacaa atagagtgga atttacagtt ttataatgtc cttaacattt  86340
ttctttcaaa tgattatatt taaacatcta acatttatgc atacatttat agcaaagcat  86400
ttaatttcag caaccttcct gctcctaatt aagcagtcat ttactctata gaaataagga  86460
gtatatcaat ctcaaaggcc atctttcaac atgctcacac ttgacactct tgtttcattt  86520
```

-continued

```
acccatgttt tctgtcacag gttctgatgg attaatttct gatttctctc aaagcctacc  86580
aaaaattttt ttatcataaa atcatttaga gtggttattt ttaggaataa ttaatattgt  86640
atgcttgtga aaaatataga tatttaaaat aaaatattag agttaataaa ataaaataaa  86700
ataatcatat aatgtgtttg tttgataaaa ttaagcttaa acaatatttt atttattaaa  86760
tttacatatt ttcttatata tatttaatat atctgttcac agtgttctta taataatcat  86820
caaatacccc tctcagtggt catataaagc aaattttata aatttctcat ttctgttatt  86880
tatccaccaa taatgtatat gtcattgtcc ttctatataa cactcctgcc tagtggttat  86940
ataaagtatg ctttgtaaca ttttctctct tttaaaattt acacatcaat aattcatata  87000
ccgttgttcc tccatatttg taagtgaagg ctccagaccc tcttcagatg ccaatgattg  87060
aggtagcatc gtcatcactc tatatctata ggacatagtt ttagaacccc cttccaatgc  87120
ccatgagtca aatgttatca tccatttgta cctataagaa atggctccaa cacccccctt  87180
gagaggccag attgaaattg cttgaattca ttaaactgta taataaatac tttcaacttg  87240
tatcttccta caaacttaca ttatagtacc taatacaagg taaatgtcat gtaagtagtt  87300
gttataatgt atttttatgg acttttggtc tagcattgat atcaatctat ggcttcacaa  87360
atgaataaga ttctttgctt tgattaatta cagttgcatc ttttccttct gtgggtgtgt  87420
ttgctgtttt tggagggtac taggttgtag aacagtttgg taatattttt gtctgttaga  87480
ctggtatctc aagcaccagg ttctatatcc aatctgccct tgtgtactct ctatggcaag  87540
tctttatcca acagcaaacc actctgatat taaagaaagt ggtggctaaa tccacatact  87600
tgttaggtgc ttattagttt gaggagtcaa gtgacttcag aagtactgtt taattagtag  87660
ggttatgatt ggaaagggaa aagagagttc agaaatgatg ggaaacgagt gacacgtatt  87720
agattattag ataggaatta gaggaggagg atatgtgtgt gggaataatt gatgcaaagg  87780
ggagaaatgc catgtatgtg tggaggttag agctaggaga ctaaaaggag taggtaaaaa  87840
tacgtactca gatatcataa accaggtcag ccgctgatct ttgggagatg tggcaataag  87900
tgggaaaggt acagaaagaa ggaaaacacg gaaaagaaag tcggaaaagg aaagacgatg  87960
agggagataa ggaagacaag caggaggaga agaaaaggaa gagagggaga gaaagaatgc  88020
caatcagtaa caggtggaga gtgaaggggc ctgggttgaa ggctacttca tctactagac  88080
tgtaaagaca ggaaatagct gtgcagagag aagagctaag cagaaatagg aaatctctgc  88140
cagatatgtt actggtggag agatatggac aatataagga aatgaggcaa ctggcttgag  88200
tgctgttttt tttttttttt ttttttttt ttatcatcct agtggatctg gggcttaggc  88260
ttccttggtc ctggtctttg ctttatctct gttgagttta actggtccag ccgtcttttg  88320
tactcacatt tctccttgca tttggagttt cttgactatc ttttgtgaac tgtggatagt  88380
gtggatgcaa actcttccaa actgagttgc tgtgattttt tgtctttttt tttaattagg  88440
tattttcctc gtttacattt tcaatgctat cccaaaggtc ccccataccc accccccccca  88500
atcccctacc cacccactcc ccctttttgg ccctggcgtt cccctgtact ggggcatata  88560
aagtttgcaa gtccaatggg cctctctttg cagtgatgtc cgactaggcc attttttatg  88620
atcaacagag gagtctggct ttgtggtgcc caaatgactg ttttgagctt gcctttcctc  88680
acggggttgc tgatgatggc ctgagcagca gtcacagcaa acttcctttt taatatctgt  88740
acaagcacag cttttgtaga ttctttgata ggaacctgca gtccactttt ctggagtgtg  88800
atagaaaagg caactgagtt ggaagctgtg ttgaatttag attcagctgg aaatccaggg  88860
taatggcaaa gaaggtgtgt gcatccaaca attgactttt gttagtatgt tgatcaagtc  88920
```

-continued

```
aatacagagg ctagagaagc tgagcatcat taaatacttc tatttacttg tttttcctaa  88980
gtaaggatat gttttagcat ggcttctaat caccattctg tcccagttta atatatttaa  89040
atatatatac ttacttggat ctcattaata tatttaaata tatatactta cttggatctc  89100
attgaattga aaaccacagt tctatatgat aactaattgt ttataattta accagataga  89160
tgaaatgaaa atatattatt aacatgtgta tataatactc agcttaaaat gaggggggga  89220
tgtctccatc aatgtcctcc cctcagatct tagggaaccc tgtggaataa aaagcagaaa  89280
gaaccagagg agctggagga caccaggaga acatgcattc tgaataaaaa aaccaggctc  89340
atgtgagatt gaataaccaa gcacagggcc aacatgggcc aacactaggt ccccggcata  89400
catatcacag cttccagttt agtgctttta tggttcttca agtgtgagaa tgagtgggtc  89460
ttgtgccttc tcctgggttc ttttcattct attggtttat attgtgcaac attgatatga  89520
tcatttttgt tttatgttat tatattttat ttgctatatt ttattattat ctcttagaag  89580
cctgttcttt tctaatgaaa gacaaaaggt ggctctagat aggaggagta gaggatgggg  89640
aaaatgtaat caggatagat tgtgtgagga aagaatctat tttcaacctt aaaaaagtgt  89700
gtcctgatat tttgtattta tatcataata atcatgtctg aaacaagcag tcaagttcta  89760
attagtttct tgtgctattg tatatttttg cttttgggac ccacatagac ttgtaaacag  89820
cgttactatt tttgaaattc accataactg caaactgaag ccgtcttcac tgccctggga  89880
gcctgactgg atgtctgagc cttatctttc caaaccctct actgctgtac aatatggtca  89940
cataggtgca tacacaagcc tgttggactc agtctccaag ccataaatag tctgttgaat  90000
ggcttaattg gagtctagaa atggagctgt tcacatatca tgcctctttc tttgaatccc  90060
attaccttcc ttatgagttg atgaacaaaa actgttaaca gttgaagtct tcaagatctt  90120
tgtatttaga ttcagtcagt gaataaaagt tcccagaaat taaaaaatgc cacccatgat  90180
tggcaactat ctttattttt gtcttaatcg tgtctataat tatctttaac aaatgactga  90240
ctgcatgtgg gcatttgttc ctgtagagga tatcaaacat ggttttgaaa catacaaaga  90300
tttggtgttt attgtgaaac atattaaaca cactttaaaa tcaaactgat tgcttaaatt  90360
taattttaga ttaaaaaatg acaattcttg agatcaaaaa aagcaattca ataactcgat  90420
taaatataaa ctttattcct aacagctatt cagctttata taaacttatc actgactgat  90480
gatgttatag caaatatgtt tttaaaatga atagttatgc tgtgttcatt ttcttttttt  90540
tttgatgtgc actctgagct tagtgctttg tcttttacta gtttattaat ttatataaat  90600
attaatgcaa aataaatcat aataagatca tgtagtaata catttttttca agttattcta  90660
gatttttagt tttttttttaa attaggtatt ttcctcgttt acattttcaa tgctatccca  90720
aaggtccccc atacccaccc cctcaacccc ctacccaccc actgcccctt tttggccctg  90780
gcgttcccct gtactggggc atataaagtt tgcaagtcca atgggcctct ctttgcagtg  90840
atgaccgact aggccatctt ttgatacata tgcagctaaa gacaagagct cccgggtact  90900
ggttagttca tattgttgtt ccacctatag ggttgcagtt ccctttagct ccttgggtat  90960
tttctctagc tccttcatta ggggccgtgt gacccatcca atagctgact gtgatcatcc  91020
acttctgtgt ttgctaggcc ccggcatagt ctcacaagag agagctatat ctgggtccta  91080
tcagcaaaat cttgctagtg tatgcaatgg tgtcagcatt tggaagctga ttatgggatg  91140
gatccctgca tatggcaatc actagatggt ccatcctttc atcacagctc caaattttgt  91200
ctctgtaact ccttctatgg gtgttttgtt cccatttcta agaaagggta aaatgtccac  91260
```

-continued

```
actttggtct tcattcttct tgaatttcat gcgtttggca agttgtatct tatatcatgg  91320
gtatcctaag tttctgggct aatatccact tatcagtgag tacatattgt gtgagttcct  91380
ttgtgattgg gttacttcac tcaggatgat accctccagg tccatctatt tgcctaagaa  91440
tttcataaat tcattctttt taatagctga gtagtattcc attgtgtaaa tgtaccacat  91500
tttctgtatc cattcctctg ttgaggggca tctgggttct ttccagcttc tggctattat  91560
aaataaggct gctatgaaca tagtagagca tgtgttcttc ttaccggttg ggacatcttc  91620
tggatatatg cccaggagag gtattgcggg atcccataac cccattaaaa aatggggctc  91680
agagctgaac aaagaattct cacctgagga ataccgaatg gcagagaagc acttgaaaaa  91740
atgttcaaca tccttaatca tcagggaaat gcaaatcaaa acaacactga gattccactt  91800
cactccagtc agaatggcta agatcaaaaa ctcaggtggc agcagatgct ggcgaggatg  91860
tggagaaaga ggaacactcc tccattgttg gtgggattgc aagcttgtac aaccactctg  91920
gaaatcagtc tgtgttcatt ttctaaaagc ataattaatt tgacattaaa ggaaacatct  91980
agtgaccgaa tatatactcg gccatagcca ctgcctctca aagatttcct attttactta  92040
gagtaggtca atgaagatat aaaatggttc aagttaactg acattgcaag aaaaactatg  92100
accctagaat cctgtgcatt gaaaggatca tgcaatacag agatgagtgc caattcctac  92160
tgtcacatca gttgcaggtt tccattgttg aaagttaaat ggatgcttac atgtactcca  92220
tcatggagtt aaagacaatg acaatggcat gtctgtacta aaagaaagct ggttaggaac  92280
agatgaaatc ccgactgata gagtttcact agttattcag cttatgtgtg tcttcccttg  92340
tctgttcaac agctgaccta tagctgttta gtagtgagta ggggagggct gagcaatgag  92400
tgtgtacctg acaaggcact gaagtaggtt tgtggctttt cataatctta gacactatgt  92460
tggtatagag atggatctgt aactgctaat cattgactct ttccatccca cagctcattt  92520
ccttaccccg aacatcttca aacctagtag cttgagacta aacatgtttt tttttttttg  92580
ttttttttcat tgtaaatgct atctttgggc aacaagcctg cttcccagac cactagcgat  92640
ttattagcat ctatcagctt atctcataca cttgagaatg aataagtttg ctttgacctg  92700
cttggctgtc ctttttgaaa ccagctacct atgagttact cagagaggaa tcatgcaagt  92760
ctgttcccct tgctaatgac ctagtttctt gtgtctggag tattccagct ggagagtcct  92820
ctgtggatag cagtgcaatc cttcatgcca ggctggaaat aagcactgct tccttaatct  92880
ctcccatagt tacttacatc tattgtgatt ttgtgaatgc aggcacatac atatttttca  92940
aattattata aaataacagc atatgagata tgaatgtaat acagcccatt ttatatatag  93000
gttatacaga aagcctgcat ttcaatgtgg aacatacaga caaagaatca aaccatatca  93060
caatagcaga ctgtcaggga tggtcccatt agattgtagg attgacatat tcaaagcaga  93120
aaaattcctg tatgaagttc gaaaagattt gagaatcttg tgtcttaact tcatgaaact  93180
gcagtctgag ggtagatgga ttaggtcagt tatagcaaga ataaaatttt aatttttgtat  93240
atacacttgt taatatttta tgaaaagaat tattattgtc tagcttaaga catattttac  93300
ttataaccag ttctaatcca gaaacaaact tggacaccaa tactgggatg gtagtggcca  93360
gcagggtccc aaaatgcatg tatatgcttt atacagatgt aaagctcttt tactactttc  93420
cttacgaatt tatacatgca tatgtttgtg aatgctaaat tttattggtg atggttgcta  93480
aaatgatttc cacttactaa taagaaacat atcactcttg agctaatgca tgcacttctt  93540
tttttaacct tcttagaata ctggaagaag aaattacttc aaagtgtaca taagggcttt  93600
caagtaattt tgtgactaga gagggtataa atggttggtt tatggcttca aaaccatcac  93660
```

-continued

```
tgaaagcaga tgtatagtat ggattccctt acctccatcc attctctaga tgatgagtat  93720
ctgggcttgt tccattgcct atgcttgaga agggagatga agggaggaag agagatactg  93780
agagaacaat ggagaaagaa atcaaatagc tcacgttttc tctcatatac agaatctaga  93840
tttaaatata tattgctcta agtatgacag gaaaatacaa gtgaagcatt ggggaagaag  93900
agaggtgtcc gtatgaagga gagaagggtt aaaagaggac aatggggaga atatgatcaa  93960
gtacagtgat gtaaacctag ggaaatactg taaggaaatc aatcacttca catgctcact  94020
taaatattta atttaaaagt gaacttggaa tttaccaatt gaaatagact cagaattccc  94080
acattctcaa agcatttgct ttcatgggtt gcttcaagta gcaagacatc tttttaaagt  94140
gttgaggaca aggctgtaga ttttgctgta taaaaagatg ctgaaagaaa gaaagaaaga  94200
aagaaagaaa gaaagaaaga aagaaagaaa gaagaaaaga aggaaggaag gaaggaatta  94260
agaaaaaaga agctccgttt acaccagtat tacatgactt tatttacaaa tggatactat  94320
tctgtctttc tgctggcagc tttactgtct gcttgctcaa tcttctactg atctccttgc  94380
tagactttag acactttatc catttgatgt aatcttctca gaagaccaag gctgcagtta  94440
cagtccacat tcaatatctt attcttttcc tttattttga acataagtaa cacttgtctc  94500
taagtaacaa ggtcaaggtt tttgctttat ttctgcctcc ctcaaaacat ttctcttcct  94560
ctctacaagt ttcaaactta ttcacaaagg aatattgcaa tacggatgct attgtccgcg  94620
tttcttcctg gaacaagtgt taattgatct ctttgggtct atgtgtagag aggagttggg  94680
acctaggaaa ggtattatct ggggagttcc cttgtccttg gaacagaaca aagagatgct  94740
gcctacaaag gctttacctc cccagggctt ctctgtggct agactcaatt acagctggag  94800
aagctgtggc ctatgtgctc ccaaggccat ttgacaagat agtcagctgt ttattcttgt  94860
ttcttccctt gtacctgtac tcctcagaaa aacattcttc gaataagtga cacatttaat  94920
ctgcaatctt caaagggcat agtgtgttca aacacaaaaa taaatgagac aatgcaattt  94980
ctgaaatcga cttacagcga tatcccatgg gagtgtactc caaaccatcc acccaggctc  95040
attgctcttc taggcaagag ccattacaga gagcacagct ggaaacctgg aaaacagctt  95100
tccctagcat ttgtggttgt agagcttttc ttacctactt aggtgacatt atagtactta  95160
cagagtctat aaatagacta agatattttt tgaggttaaa acagtttaaa ttgtacagat  95220
tattagaact aaaaaaggaa aatgattcca ttacacttga ccttagttta cgggttgctc  95280
tccttagact agatgaagca tttttcaaaa gctaaaaggc tgtggcgatt gcacagaagc  95340
aaaaacaaca catatcatag acgttatctg attatttaat ggacaggtgg gaagattgaa  95400
acactgcttc ataagacctg aagtgggtta gccagtggga agactgataa gcattatcta  95460
gggttgaacc tgtgctttct actgcagaat actacaagtt acttataaaa ctgtgaggtg  95520
gtagggctct aatcagtcaa atagttatca gggcaatgcc tgagtcagtg aagttcttgc  95580
cattcacaag acaaatacct ggctcctgta cagccagcct atgctagtca gagtcccagg  95640
ctaaacagac accttgtttc aaaaaacaaa ttgtacatat cctgaaaaaa tgacactcaa  95700
ggttgccctg tggcctgcac ccccaccacc cccagacata catgtgcaca catataaata  95760
aaagagaaaa aaatagtaaa attgagggca tgctttggtt ccctagttct aatgtccatt  95820
ttctcatgaa actgaatgct gacaaaactt gacaaaagcc aagaatcaca cagggtctca  95880
gaacaacctc tcaaaaagca tgcctaactc aagtgtgacc taaataggct tcttaagtac  95940
ctgcatctta cctatatcta acatacaaag ttgcccgttg ataaccactg tggaagaagt  96000
```

-continued

```
gccagtcttt agagatgcaa tctgagagtg acagtataat gatccattgt gttatctgtt  96060
tttgttcttc taaatattta atagaagttt gtaagaagat gtattagttt ctgagcaatg  96120
tgaccaaatt taaagccaaa tctagaggac actttcgatt tcagaataag atgtcaaatt  96180
aaaaaaaaat ttcatatgta aagcaatatt tgtgtgtgtg tgtgtctgta tacaatcaat  96240
tataaagttc ccacatgtct gtaatagctt tactgtagta ttagaaagtg tgtaatgcac  96300
actgaatgaa ttcaatggta ctttctatta ttttgaaagt aaaagtattt ccccatcttc  96360
ttgaaatttc agaccataag gtgaagactg gtaagtggtt tctgccatac tggcttgctg  96420
tcccctaagc atgaagccac acatgaatgt gctctgagag gccctggggt ctggtagctc  96480
agaatgaagc cttgcttcct aatcatcctc tgtaatggag agctctgggt taatcatctt  96540
cagagtaagt gtaatccttg atgacaccta ctgagactga gctaaagttc tgtaaaggga  96600
acttaaaaaa aaaggggcca ttccacgcta gtgccggcta ctctctgacc ccggcagtct  96660
cgctacctcc atggctagcc ccatgtagca accttacatc tcgtggttct ctttttgcag  96720
attgtaaccc gataaaataa aaactctaga ggcttgtgat ttattaatca gatttatatt  96780
agtaaattct caacccacaa aatgcctgca caatgaactc aaaactcaat taatataaac  96840
acaagctaca cccctagatg aggcacatga accctactta ttatttaatc acctatgtaa  96900
gaaatcccca atacttaccg ctcccaggac tgtttgcttc tggctcctct tcctctccta  96960
ctggttccat cttatctctt cctctccccc cccctttttt ttctcttggt ctctctgtcc  97020
tcatctctaa aatcctcagc ccactttcct tgtctactgc ccagtcacag gctctcacct  97080
tatcttgtaa ctgtcctcac ctgcatatag acagcagcct tcaaagttct cagtgtgttt  97140
ctgacaagga ctaaatcttc agaaatgtgt caatgtaagt cctctgccct acagcccccct  97200
ttattgtcaa gattctgtag atttaaacct tgcccacata actcatcttc tggcaatttc  97260
tgagaaactg tgccttctgg taatgtcaga agctacaccc ataaagtctc atcaatatga  97320
ctgcctaaac atgaactgaa caatgacaat gaaatgctaa actggaagga aaagagccca  97380
tgggatctca actctacaca aagaactata ggcagctaaa gaaatctgat aatgagagaa  97440
atagtcttcc ccagggaaga gcacaacaac tggctatcca ataccagaca gctctgaaaa  97500
tgcacacata agtaacatta taaagactga agaatattat atttagaaat atgtatagta  97560
tatatataca tgtacatatg tgtatgtaac aacaatgaat gaaaaaggtg ccattagttt  97620
gaaaaggagc aagaggggggt atatgggagg ggttagaggg aagaaaggga agtgataaat  97680
gatgtaatta tattaaaatc tcaaaacaga aaagaacaac tcaatatcaa caatgcgcat  97740
gtttttccta tgatataaga aaatcatata tgcttaggac agtagttcct tttaaaattc  97800
agccacaaat cactgagagt ttccagttta aaaacagtta aattgtctca catatttatg  97860
ctttccattt tcaattttca gtttaaaatt gagaaaaact tataaaagtt gcagataatg  97920
gtatgtgatt tccttatttt taagatcttc atcaccatat tggaataaag gcttttatgt  97980
actccagaac tgtccatcat ggcactctat gtggaagggt acttgcatta gcacataggg  98040
aagaaataat tccattagaa ccaaggttga ctctcatctg tagaatctaa gaatagggaa  98100
caccattggg ttactcttct catatccctt ttcttcttgg ggcatatctc ccagccttag  98160
cacaaaggac ttaggagagt aggtgaggga agggagtcca agtttatcag tcaagtaaca  98220
cattactata acataggcag cctctgaatg tctctgggaa atatgcttta atgctcatct  98280
taccatcaca ttgttatccc aagagaagcc cttgggctag atgtgggcca gtctccagtt  98340
gatcacttca gttctcagct cactcctcat cttgctgtgc tttctcacct gacagtggtg  98400
```

-continued

```
atacagtgtg aagacaattt tagccacttg atgacagcca gcacctggtt cacatgtcta  98460
tgctagttca aatgaatcag ccagaaagta tattagaatt catcaaagat gtgtgaattt  98520
caaaatgacc tatttcttta aaatgtgtaa aagtacaatt gtgaaggctc attctagaag  98580
attctttcct ttgcttctcc ctttttcctt aaatctctga gtgagaaaat gtagctgaga  98640
agcaggcttt ttatcttaat atctccccaa ctctgttaag aaataaaaga ctaaaaataa  98700
attactttaa gattcagagc agcaacctgt ccccagtgaa gctctcttaa ttaatgtggt  98760
gacctgtgta gagaaaaggg acaactgcag agtctctcag taattatcca accaaagctt  98820
cagataatta cagtagggag gtttttgaga cacaggacat cctgaaaact tgaacttcct  98880
tgttgactta ggccttctat tcattcatgt tggggtttgt aattgacaaa gtcagagcat  98940
atcagaaact cacacattac taaagtctct gtgtttgtac ttgacaaaga cagcacatat  99000
cagaaattca aacactacta aagtctctgt gcgagttctc aacagaaaat aaagtgcctc  99060
ataaaatggt ggaaattagg ggattagcta aaggtaaaat tgagaagtgc tcgtgcagta  99120
ctgagtaatg tgggccagat aaaagatata ttttatatag actataagat atattagaca  99180
gcaaattgag aactgttgtc aaagattgat accagacaac aatatgttgt attcataaag  99240
agtattcttc agcactccaa taatgggcag tgttggaaaa tctttccaag gtgctgtatt  99300
tatgaatgtt caaactactc attagctaaa tttccttttg atttaaactc ataattggta  99360
atcaaaataa atttcaattt ccccctttgc ggctttaaaa aagtggaatc tcagtggcct  99420
tcaggtgact cactggactc gtacattcag tcaatctgaa accacataaa tggatttggt  99480
ttcattaaaa ccatttcgcc ccagtggctt tctaagccta taaaaaaacc tgctctcagt  99540
gacccagtct aacttaaatc acagcagtgc tttctcaaaa caataaatgt tatcttttcc  99600
atgggagtca agatgagaag ctaaaatcac cttagagacc aagctatctc atagatgtcc  99660
tgtccttcaa taaagaaaga atatttgctt tgcactgagt ggccacagtg ttcattttag  99720
ccacagacca tgcatgttct ttttggcaca gctatgtagt aggctacaag atggaaggct  99780
tatattgact gttctcagta ctctcctcat gtctcctggg ttgctctcct gctttggtag  99840
ccttttctca caggtgcctt tgctgcacag tactgtgtgt tcattaagca agagagtcat  99900
tgtttcttcc agaaagagaa ggcctttaaa agaaagggtc tgtggcaaca atggcctgta  99960
acatgcaaag cagatgaaat gataagttaa agagtggttt gggagcaatc cgtagcagct 100020
ccatttcaaa tacagtcaca aatggttgca tgtaatgaac aataacgctc ctcaactagt 100080
tgcagcagat tgctgactca tccggtacat attttgatgg tatatgaaga aaataaaggg 100140
aaattctaaa ttttctaggt gtgctgttga tatgcagcat attgggtact cagtcaaatt 100200
gtaatttatc agtgcaatgg acgtggcctc attcattaat cagtagcagt ggattgtatt 100260
atgtatgtct tttggtagaa atatgactta gtttactgct gtggttttca cacttgttcc 100320
agtgaatcgt atagatacat tttatgtgtc taagtcatat aatccagcag aggcaggtgg 100380
atatctgagt tcaaggccag ccttgtttac agagtgaatt ctaggatagc cagggttaag 100440
cagagaaacc ctgtcttaaa taatcaacca accaacaaac aagatatttc tcccccaact 100500
ctatatatcc tcccaaggag tctttgatgg gggcagcagc tagcacaaga ggtggtatgc 100560
actgcccctc cacactgctg ggctttcaca cccatcacat ttgtgctacc tacatcatga 100620
tcaatctgca cagattgaat gttcaagtac tagacacaaa attatgattt aaggaatgaa 100680
taataagcaa gaagagccac agtttcaggg gaaaatgcca gcattcaaca aatgtcacta 100740
```

-continued ggaaatagct cagaattgag agttatcaaa agcaagtgat agaaccaata tgcattctat 100800
ctatttgtga aaatctcaag gagtaaaaat gaaatttaat taaaaaatta aagtagcaag 100860
aatgtatcaa attcggtaag tcgaatagta agtttctcta gagagataat acaaaaaaaa 100920
accaatattt gctcagaaca aataaataaa aacagatcca tttgtgtttc atttcaaaaa 100980
gcaactctca atttttaaag ttcattgtgt aaaatcactt ttgtgtaagt caattttatg 101040
ttcaaatgat attttttctt ttagatcttt gttggttttc ttttacatcc aatattttaa 101100
tacaggaatt taattcatga atttgatagg attatatttt gcatatgtgt tacacatgtg 101160
tttaacttgt catttagtag ctgtgacatt gtagggcacc tgactccttt atgtcccacc 101220
tagctgaaca tgctccttgg agaattgttg ctgttacttt ggacagtatt ttttcattat 101280
aaatacaaac agtctgtatg ttattttgtt cttaaaagat taataatttt tactgtcttt 101340
aatttttaga gaaaaatgaa gacatcaggc tgactgacta acccctaaat ggcaaggccc 101400
aggttctatt tgttatgctc cacttcttcc tcaacaatgc ccaggtccca ttagttacac 101460
attgcctctc tcagcagttg gctaatttcc ttctaattta tttttcagac tccattatag 101520
aacttttcca attacagcta catctcagca cttaagaccc atgctttggt ttaacatttg 101580
cacggctgca gactgagctt gaaggccatc actgtcactc cagagataga gatgtactct 101640
caagttttac tactctaaat aagataggtt gaattcctgc ttcacagggt tacttggtga 101700
ataaatgaat ccccctttct cttttgcttt cttattctgg atcttatcag tttcaatgag 101760
aaaagaaagg gtgtgtcatc tttggactct cccatcaggg tagaggacta ttgcttatac 101820
attagccaga gatttatgtt tgttggctca gctgcagact tatttctctg aactttaacc 101880
acctgtgacc ctggaactta cttcctattg taaccatcaa tttccagctc caatgaatgc 101940
tctttgcatg caggcagctc ctgccagtga taacagccct ctgtaggaca ccaagactag 102000
gacccatagc taccatggct agtgttgtag ccttctgaaa cagttcttcg ttactattct 102060
cctcatctct aaagcactgt gtcatagttc caggattgtt tgggttgtca gctgttgaca 102120
gcatccagga tacaaggtct aagtcatctt catgcctggg ggcttcctgg aacttgcagt 102180
ggaggtaggt gtgcagctta ttgtatctag ctccttacag ccttcatggt cttcatgacc 102240
tctgctcccc gtcatctctt ctcagctgtt ctctggagct tttcagcctc tctcttcact 102300
gctgtgcagc tgttctcctt tcttttgttg ccatatcagc tactctactg atggctaatt 102360
gactgacagt cggtcactca gacagggtac cagagaaatt ctagcagctg tcagttagcg 102420
aggtacactc cacaccaacc cattccatag tttatttaaa agaaaagcat gcgtcaaaat 102480
agtgttcagg ataaaggctt atcataaata ttactgatgt tttaatggta tttagcaatt 102540
tctaaatctg cccagtgcct cagttacagt ggcctccttc tcttatttgt ctttaaaaca 102600
cacttatagg ggctggggac aaaaaaaccc acacacttat atatctgata tctttaatgc 102660
atcatttatg gtaggtttga agaagcatct ccgacaatgt ataccagaca ggatttatgt 102720
gccctgaaat gtcttttttt ctatagctag taacagtccc tgtcttgatg atcaatcaaa 102780
cacaaattcc aataactggt caatgaaaac atacatataa gtaacattat atggagtcaa 102840
caggctatgt tagaaatgta tatctatata caaatacatg tgtatgtgtg acataatgat 102900
gaaaatatga cctcaaattt gaagtagaac agagggtggt atatggaagg atttagagga 102960
agaaagggag aaatataatt aaattataat ctcaaaaaat attaaaaaat gctaaaaaac 103020
caatcagttc atccccttc tttctaacac ttatccagat tcacacagtc ttggaatcca 103080
cagatctcac atttctgcat attttaaaca aggcaccaat tgctttcgct tgggtctgcc 103140

-continued ttcatgagga tattagcaca atgatcagcc ttgaaaggta gaagtagttt ctcctcctga 103200
gtcaaagaca gatgtgagtg tgtagcctta gtcagatgct cggtttatag tcattcctta 103260
taatttaaaa aaaatctgga ttggtgagat ggctcagtgg ttaagaacac tggctgttct 103320
tccagaggac cctgttcagt tcgcagcatt cacatggcag ctgacaactg tctgtaactc 103380
catcccagag ggtttggctc cctcacatag acatttgagc aggcaaaaca tcaatgcaca 103440
tgaaaataaa tcttaaaaga tgctatttcc ttaagttcca aagttctctt ctatcatgaa 103500
cccagtgact gggagttttg gtgtctttaa actttcctgt gagaattggg acgttccctg 103560
tggctttggg atttccatgt gagatctgtg ctctggctcc tgctattttc ataaacagtc 103620
atgtaacttg tctcaaaatt ttgtattttg tttcaacttc tatagtattg atcttgacaa 103680
atgtgataat ttacaagtag tacaaaacca aactgtggac aacttttaag taatcattgc 103740
caattcaaat gaagtaaatt atagctactc catcttcatt tttaatatgc aacctgtcca 103800
acataaggtt tcgctgtcat gtgcacctga tcctcatgtc ctgcagccat tctgcaggtc 103860
actgccagac tgatttacct gaaaccaatt ttcaccttat agctgtcagt caaagcatgg 103920
tggttattaa atgtgcaagc cctgttggca agtgttcccg gtactcatct acctccaatt 103980
cccattagcc cagggacagt atcacttttc ttctgccata ttttgtccat gatatatccc 104040
gtgtttagtt ttcccagcta gcctcaaaat attgagattc aatactgatg tttctgggag 104100
taatcgctcc tcattttgaa tgtgttattt ttacgtctca gtgccctaga ccaaggttat 104160
atagtcttct gtttttttcag atctcacatt ttatttaatt ttctagaatt gatagtttga 104220
ggtgaaactt atgtttcact atatactttg caattattga cctcattcac agtatataca 104280
aatgtttata ctgctaattc ctccttcttt tgaagaacca atatgctgat attagtagga 104340
acactgtaga tttgttggca ttaagcatag atctcatcaa ggagttagaa tgtagagaaa 104400
caacattttc tattcaattt catgaaagtt ttttagtttt tctgctacat aaaaatacaa 104460
tgttcttatg acttgatcaa ttcttcatat aaaataactt aaagtctaca ttttcagaag 104520
tcttataacc tcttaaccca caaaatatat catggttttc aaatctggct actatgcggc 104580
gagttgctgt cataagcatt aatactgtgt gataattaat tgtcagcttt aagacagtaa 104640
ccttactttc tgtgctgtgc ttatgtcaca gttgtgtctg tccaatataa gcaacataca 104700
gtttcgtaga gagtacatta ggtcttctgg gagtttgaag acagagactc aaagaaaaag 104760
tcatgctttt cagagagttc ttaacctgct ttacttaaag agaaccagtg actgaaatat 104820
taagagctgt tttcttggca gcatcataag aatcaataaa agactactca ttctccagaa 104880
ccaaggctgg aaagttgtcc caccaagtgc tttgttgtca cctcagctct ggctgctgtg 104940
ggtaagcctg caagtgaagg atcctggcag ctgcacttta gtttctgctc tgtgcctttg 105000
tctcacacca ggtgcttcct acccatggct agggcttcag cacctgttcc tacagtctac 105060
acctaaattc ctgggcagct gagaggtggg gatatggaat atgtgtccca ctttgacaaa 105120
gacaaacatt gaggttttgt agagtctcaa atgaaactaa ttggtgaaag cagacaaaaa 105180
gtttctatta taaaaagata aaaaatgaag cctattctga agaaaaactt agctacaact 105240
tgataatata aaaataataa gtactcatta attaaataat atgtgtttat taaaatacgt 105300
aaacaaatta gatgctatcc gagtacatag ggtctcagta aatattctgt tatataacta 105360
tgtactggtg attactggct actctatgtc accgtgttta atatctctaa tgtcacaggt 105420
accatttgcc acatggcaag tcagttacca aatattttgt ttagagcagg gaggggtata 105480

-continued

```
ctttatccag agtttccaat caacccgtca tatgtgcagt tttgaggaag ggactctgac 105540
acaaggtgct tggagtggtt ttgtaaggaa gcttttattt gttccataaa gtgataaagc 105600
tggccatttt ttacagatgt acttctctgt cacatacgca tgcactctca ccacagaaga 105660
gtgcctgcag ctactgctca cattcataaa gatgctcaca ttgtcttatt acagatactc 105720
tgtctgtggg aaactgagaa ttcctgttga acattcataa gtagatctaa aggaaccatg 105780
ctgaaggaag atccattgag aatgttgagc agagctgtgg attgacttat tgagagtttt 105840
ataatgtgtg taatccagaa ataatggatg ctttagaagt aattaaaaga ctataaataa 105900
acacttagtg ccttaatata aagaggagaa agacaacatt gagctcatca gctgtgatga 105960
cgaagtaatc tttctcttta aacgctatgt gaataagtaa gcaaactaca cttgatgact 106020
agatacagca tctgcctcat ggacttaatg gatcatgatg ccttattata ataatcaaag 106080
tggacataaa tgcaggggct taagagggat taccaccttc agtgctcagc aaagctttgc 106140
tccttgtcag caggggagaa gaaagcactc aagtgatgat aattcaaact attctagttt 106200
gaagttccta gtggcagaac ctccaataaa atggcttact acaaattcag aagataacat 106260
tgtctgagca gctctcttca ttagaagcaa tgtgttcatt gccccctaaa taaaaaggtc 106320
catttttgta cttggcaaaa catcaggcac acacacacac acacacacac acacacacac 106380
acacacacac acactcaact cccttagctg tctgagatta ctcctcttga tgcaaatagt 106440
aacaagcttt aattaatacc agaggtagtt gaggtactca gacattaatt atacctcatt 106500
catggaatct ggcttaatgt tttattatga aaggtttatt tacaagaagt gtcacaaaat 106560
acaacataat aattaggagg gcagactttg gaaccaggtg tagtctgttc tgcagtgggt 106620
aaaatgggaa tcataatggc agccttctct aaggactagt ttgagttcag gtaaagttta 106680
taccgtcttt ggaatgtgtc cagaccccaa taaagcacca aggagagtct ggtttgttgt 106740
tattattgtt gtttttaaac tgtggtttat ttataagtaa gatgggcaag aaatcatttg 106800
gtagcatttg cttttaatta ccttaatttt ttttaaaatt taacttagtg tattaattta 106860
cttagtttta aaatcaagcc tcactctata tttcatcctg acttgaaact tactaggtaa 106920
aaatgggtgg cctcaagtcc ttggcattcc tgcttgagtc tccaagggca gtattacagg 106980
catgaagcac catgacaggt tttgccttgc atatcaggtt tctttataat ctagtttaga 107040
gttccccttt atcactaatt tgtccaaaca gatttgaagt tcccagaaat actctaagtt 107100
tagaaaagtg accactggca cgatgtgaca atatttaact gtgacagtat tttcaaatcc 107160
ttctgaagtg tattgctgtg atctgcgtgg ccctacttcc tcagtgctga tgatcccatg 107220
gagacactga tagcacagtc actttaatag gctggggccc agtgaggaac ttttccttct 107280
agatggtaga cctggtagac ttcacttggc ctcagctcac attcttgctt cagctttctt 107340
aaagcctttt aatcactcag ataagaaaga catagcctcc ttgtgtacta taaagaacat 107400
atctaataaa aaaaaagagt tcttggtttc atatctattg atttctaagc cttcagtcta 107460
tgtcagaacc tcacaactct tgtcattttt ttggatacaa gcatcttgtt ttgcctgaag 107520
catttttcat cagtcttata gtaagataga ctatccacca tttctttctt tgtttaaagc 107580
aagcacccgt gccatggttt gctaaagtgt gaatgttccc tcttttttc cttcaaattc 107640
ttcaccattc cgtaaggtct tctaaaatga aagcatcaat cctgttttat agatggccaa 107700
agtctacctt ttttattcag ttactgattt taggacttcc tttcaaagac cattgcatta 107760
atgaacagga tgcagccttt aaaagtccaa tctatacatg tttaaagtaa tagtaaaaag 107820
aacctcatgt atacatgcaa tcatacaaaa atcatacatt ccctcaacag tcctaaagca 107880
```

-continued ctggaaatgc aggttattct caggtttcca ttgtgtgtga gtatttccac cagaacatat 107940
tcaaataaca ggaataaaag ctggcagtgg ttgcctcgct gtgtaggctc attagatgag 108000
tcagctaatg acagggttgt gcattcaaaa gggcaggcac tctgccactt accaaagaga 108060
atgaggatta agatagcatg ttacctcctg aaaactagag ttaaaaatgc ttttgcctag 108120
atacctactt agtgtgccaa gtgttttata caactgggtt tttgataatt gattaaaacc 108180
ctcttaaaag attcttcaag tatatttaat atattatctt gctttttcct tgtctcccaa 108240
aacttttaaa agaatgaggt aaaggagtgt ttatctattc tctgtactgt tctgtccctc 108300
taagagacta aatcactgtg ccagagggga ggagaacctg agcaatcaga ctttcaaagc 108360
agaacacagg cacatgttca atgagaagag gagtacacgt catttccatg taggactaga 108420
ttctccatga atgccactga actgtataaa aatttataca cataaaaatt tattgtattc 108480
acaatctgaa aagtgacccg agaagagtgt gttttcggca ttgcttatca gtgttcccta 108540
actttgctat tccagtgtga cacatgcaat tgatggcata gcaatttcct gttcactgag 108600
gaaatcttgc tagatgtaat gaagctggat gtgccataat aaatgagggc agataagtca 108660
ctctgatcag caagtagcct ttcagatgag ctaggaaact cctatcttca gtcagcttgt 108720
ggctagtcat tttgttgtgg ttgtggttgt taaaatcagg ctgtagttat ggttttgttt 108780
tatggtttta aaaactcaac tactgaaccc tttagtttta atatatatat taatatatat 108840
atactctgta tcaccatgta tatgtatatg aatatagggt gcctggtata gggtttgcct 108900
gttagtagat atatataggt taaagataat ctggaagtag tttttcccag gttccacaca 108960
ggcagagtca tttggagaca tggaactgag agtagattag cttgtctaat cagcaagctc 109020
caaggatcta cttgtcctta atgcccatca ttaacctgcc gcccactctc cgctgccaca 109080
tatatacaca tatcctatcc agagaataca agcacacgct actctacttg gttgctcatg 109140
catagaaagg ggcatttttc atttttcaag ggctctctcc ccgcctaatg ttttcatata 109200
gaacaaagcc cctccaagtt gtaaattgtt tatgatggtg aatatctagg ccagggcaaa 109260
aattggcaac agaaaaggct gaatacatgg taaatatctt gtttgtttgt ttgatttttg 109320
agacagggtt tctctgtata gccctggctg ttctggaact cactttgtag accaggctgg 109380
actcgaactc agaaatccgc ctgcctctgc ctcccgagtg ctgggattaa aggcatgcac 109440
caccatgccc ggcatatggt aaatatctta cacttatgtt ctaacaagtg tttttttttt 109500
atttctgcca agttcacttt tttaatgtgt ccatataata catggctatt tctcttagta 109560
aaatgtgctt tgtaatatat atatatgcac ttccctacgt gggaaatgaa gtatatggtg 109620
tgtacacttt ttctattaaa tttacctaac cgttttacac acacaaacac acacacacac 109680
acacacacac acacacacac acacacacat cttctaatta ctctctccct aacaccatta 109740
tttttctttc atccctatta agaccttact cccaccattg ctactagtcc cttccccaga 109800
ttcatggatt ttggttttgt gactcatttg gtttagtcag accttttttct gtgaactttc 109860
gattgagact gcacatcagt acatgatgtg atcttcagtg ggtataaaac tgaaggcaat 109920
gatttaccct tgccccaaat catcagtagt aagtagtata gcagtgacag ggtcatctga 109980
gtccttctat ctatttctga catttgacag gctcatattt gtgtatatac aaaatattta 110040
tgcatatatt tgcatatatt aggcatatat ttatgcatat acagagcaag cacctgtagc 110100
ttctataagt tcatgattga aattcctatg atttgccatg gaacactatt tcttcctttt 110160
ggcccttaca atctttctgc tgccccttct tcactaccta ctggtcctta gaagagacag 110220

-continued gataagtgta gtgtttatac ctgagcacta atactctgcc ttttgtaacc tggaaccacg 110280
tgtctctaca tttaccattg ttcactgaaa ggagaggttt atcttattaa ggctgaaagt 110340
agcttttgtt ccatgctact gtgacagaca acaaagagga atggcaagaa cctgtactgg 110400
ttgaggggtt tacttgtgtc tttgtgatga acagtcctgg aatttgggtt ttggtataat 110460
aaaatgactt ccaggacaaa ttttgttcag cctgtacttt ttttttaaa tagatctatg 110520
ttatttttta tttaaaatgg aattctggga tgtattttat attagagata cttaacacag 110580
taagatgtat gcttaaataa accttgccct atcatgtcaa agttctttta aatgtctgcc 110640
tttttcttta tggctgttgt tttctccatc tttatgatct attgagcaaa tgtgttactg 110700
tatttattaa tgggttgatt aatattacct gacattataa caaaatactg gtctcatcca 110760
aaacatatgt ttagcataag agcagtggga tcagatcttg acctgctgct ttcagtgttg 110820
taagtgtaga tatcaggtac ttgtttagcc cttacatttg aaaaaatacc atatactctt 110880
ccagctgtct ttcagaaacc cagttttcct ttagctcctt gtaaattttg aagcagagat 110940
caccttttat tttcctgtat ttatattggt agatagaaca ttgttatttt cttatattaa 111000
atgtcactgt ggaggtgaca aatgattgct gacagtggat agtaattacc agggtcaatt 111060
gtaaattttg gtcagttctg atcttaaatt ctgtttacgt gaataatctt tgttttctgt 111120
attgcaacat tgccaccaag aattatcctt tacaaaatac tttgttgtaa acatcagtga 111180
agattatgat gcaagctatg catggggagg taagatgtat actatacatg ggagccaagt 111240
agcatgcaag ttagggtaca gtctatgcat taggggccag gaagtttcaa gacatttatg 111300
agggttgggt aggatggaaa ctgtacatga aaagaccagg tagcatgaaa gctatatttt 111360
aggaactaga aacatgcaag atatatgtgg aggtggcagg taggatataa actatgcatt 111420
tggagtccag gcagaatgga aacatgttag aaggattcaa gctatgcatt aagaaccaga 111480
cagaattcaa gtgataagga gggggtatgg aggggggggt agtgggatac aagctgtgca 111540
ttaaatgcaa tgtgacctgc tggctatgca ttaggggcta ggtaggatgc aggatataca 111600
gtaaggacca agtagcatgc attaaagtcc aggtagtata cgagtataca agctacacaa 111660
aagaagctag gtggtattgc agcacagatc tctctgaaaa agaggagata catatttgat 111720
atccttgata cagaattttg acgatcttct ctgcaggaaa aatggtggat gcgagcctgt 111780
cttttgtatg gccactaaat ctgtaccaac accttgacct gtactagatc ctctatcttt 111840
gcccttttgac aggttttgcc cacatgcagg ttaccagtta gtgttttttt gtttgtttgt 111900
ttgtttggtt ggttttttt tgtttcgttt tataggtcaa gacacttgct tttttattta 111960
gacagcatct ctcttctttt gagtatgtat ttatatttta aatgatacag ttctctgttc 112020
acagataaac ttatggacac atccgtggtt tcacttttat tatagaaatt atggatcctt 112080
tatgatttta tggaaccctt gcctacaaat taagctgtga atttttaaaa aaatctttga 112140
taaatttgta gctggagctg tgagtccctc catgtgtact ctttggatgg tggtttagtc 112200
cctgggagct ctgggggtac tggttgcttc atatcgttgt tcctcctata gggctgcaaa 112260
tcctgtctgc tccttgggtc ctttctctag ctcctccatt ggggaccctg tgctcagtcc 112320
aatggttgac tgagagcatc cacctctgta tttgtcaggc actggcagag cttctcagga 112380
gacagctata tcaggctcct gtcagcaagc acttgttggc atccacaata gtgtctggct 112440
ttggtgactg tatgtgggat ggatctccag gtggagcagt ctctggatgg ccttcccttc 112500
tggtcatcaa taggaggaga ggccgttggt cctgtgaggg ctcaatgccc cattgtaggg 112560
gaatgccagg accaggaatt gggagtggat gggttgatga gcagggggga gggagagagg 112620

-continued

```
atatggggtt ttcagcaggg aaaccaagaa agggtagata cttgaaatgt aaataaagaa 112680
aatatctaat aaaaatatta agcacacata caaaaaaaac tttgataaag ataactcctc 112740
aagatttgtg gaacacggtg tttcctaaat gaatgccagg agagtacaat ctttagcaca 112800
ggaaaatgta gtactaagaa acacaaacac gtatactatg tttttaaaaa gaaaccaaca 112860
attattgatt tacaacttgg atgattttat gattaaaatt gacatgaagg gattttaatt 112920
gattgtattt catggtaaac ccaggaagga atttctaagc aacattcagc attatctgga 112980
tgaactctga agggcaaaca cagttatccc cttatacaca tggacaccca cagcctgtga 113040
catcctcttc tactaatgta ggaatatcag agttaggagc ccccagggtt ggcctttcat 113100
attgtcttat ccagtttata acataaatct cacaagttac attggaaaat gcactgaaga 113160
ggtggtttac tatatttcct tcctatgagc tgtataaaaa tcacgtaaac atcagtgaga 113220
ggggtccatt gtgtcacttg ctcctcccag ttatatacaa atgaaaagat ctctttgctg 113280
tcttttctca acacagttag ttgatgctca ggagtggtgg taacatgccc agagtcacaa 113340
aagataactt aggctggaat tgtaatgtgc atcctatgat caagttctgg ggctgaacta 113400
ccacacaacc aaaacctgga ttcttatact accatgtaaa atactgttac tctacatttt 113460
gaagtgaggt gatttgggga cagtttaaga cttatttaac ttataaacaa attggcctct 113520
ctgggtttgt aaccagagat tgttgatatc tatacagcat gataggatga tctgtaaggt 113580
gccctgccaa gctaccgaaa gcatgacctt cagagtctga ccttgcctta gtgtcaactc 113640
ttatttcttc cctctgccca cctgtccatt atgcctatga taaaagcaga gggagatagc 113700
atttacagtg agtatattgc ccacagaagc tgagcatcct ttgatctcat tgaaatagac 113760
catttagcct ctagttgctc tttgagtatt tgctgaactc tgtcattcaa taattacttt 113820
ggtggaacaa atggaaaaga acaaaagatc tttgatgaag gatacaaaaa agctccatca 113880
tgtcaagctg aatgctaggg tgtctgcatt gtggagagat aatctgaaat tttgtccaat 113940
catatctttg ttttggtttt ggttttggtt ttacttcaag tacatataat ttcaaacttc 114000
agctttccaa agagaactat ttctttggca gcatttaaga atgaattatt ggggctcaaa 114060
atatagctca ctgtttaaga acatatgtat ttttcttcca gaggactcta gtttataatc 114120
tagcacctat atggagaatc acaaggatct atagctccgg ttccagggaa tgtgatgccc 114180
tcattattca ccacacatgc acatagtcca cacacatact cacaaataaa agaaaagaaa 114240
acaatgaatt ataaaacaca tgtactttac cttttaaaat ttaggaaaaa taaataataa 114300
tgataatttg tcaatatttg ttttactttt ttggaacatt tttacttttt cattgaaatg 114360
ctatgtgggt tctgtctaca aatgacatcc tgttaaacat tacaccaaaa ataagctatc 114420
cttattagag aattggcaaa tgatttcaga aaagttttga atacattact gttatttgat 114480
tcatcattac ccattgacta caaaccattg ttactatagc attgcgctta tggagagaac 114540
ttatggactt tagctttggc aacttccagt gtagttaatt acctgtgcaa aatatttgta 114600
ctctttagat tggtaaccca tgcatgcaca atgtttttc cagtggtttg gtacacttag 114660
aatccatcaa taatacagaa gaatgcactt ctgataacac ttcgtgcagc accttgaaga 114720
taaggtgtct ttttcaagct ggttttcaga agttaaaaca ctctcttatt gtgctttctc 114780
ttccctctct gtagggtgag gaggggtacc cacaggaagg aatcctggaa gacatgcctg 114840
tggatcctgg cagtgaggct tatgaaatgc cttcagaggt aaatgcctgt ataaagaaaa 114900
ctaagcaaaa cactttaggt gtttaatttg gaacacatac catcaaaacc ctgccactat 114960
```

-continued

```
cagatctctc tcacattatg gttggcatag ttcaatcaag aaaatatttt agagcaaatg 115020
attttaatct ttgtgggaga gggtaaggga tatagtaggt caaaattaaa acattctaga 115080
acaagagact ggtagtaaca aaggcatatg gaaatgtctg agtaacaacg ggcagttatg 115140
aatcatggtt agaaaacaga aaaatgacag attaaggctg aagacataac taaggtttta 115200
gacaaactgt agagccccaa gttaccatca tttaagttta tttttacatt tggaaaaaga 115260
agagtttgat gataggttta gtttaacagc acaatcctaa ttagagttaa ttttgaggaa 115320
ggctatcaaa ttcagttaca ttgggtcatt actgtcatga atgttatctg gattttgtcc 115380
aggaggcttg ggctttcatg tgaaagatcc ttcatggaag caattcatga aggtggagtg 115440
ttctaatggg ggagagaaag gcgaaagatg agctctggag gaggcttcat gcagcttacc 115500
taggtgtgca cagctcacac tgcagagcaa aggagagaat ccagagaccc tgccaattca 115560
cactgcagga ggagagcaca gatcaaatga tatacctaga attgggccta ataatctaac 115620
ggtgatgtcc tctataactt acagttgata cgtatgaaaa agccaataaa tgtcaatgac 115680
agataagttc caaacactgc tctgaggatc aattttatct gattgaaatg atgagccctc 115740
ccccactgtg aagcagacag ttgatatctg tcacttcact gacaaggcat gctgttatta 115800
ttttcttttc ctgatattag gaaggctacc aagactatga gcctgaagcc taagaatgtc 115860
attgcaccca atctcctaag atctgccggc tgctcttcca tggcgtacaa gtgctcagtt 115920
ccaatgtgcc cagtcatgac cttttctcaa agctgtacag tgtgtttcaa agtcttccat 115980
cagcagtgat cggcgtcctg tacctgcccc tcagcatccc ggtgctcccc tctcactaca 116040
gtgaaaacct ggtagcaggg tcttgtgtgc tgtggatatt gttgtggctt cacacttaaa 116100
ttgttagaag aaacttaaaa cacctaagtg actaccactt atttctaaat cttcatcgtt 116160
ttctttttgt tgctgttctt aagaagttgt gatttgctcc aagagtttta ggtgtcctga 116220
atgactcttt ctgtctaaga atgatgtgtt gtgaaatttg ttaatatata ttttaaaatt 116280
atgtgagcat gagactatgc acctataaat attaatttat gaattttaca gttttgtgat 116340
gtgttttatt aacttgtgtt tgtatataaa tggtggaaaa taaaataaaa tattatccat 116400
tgcaaaatct ttcctggttc cttttacttt agtaacaaaa tcatgcatat cgggaacatg 116460
aacatttaat gacaactgac acagtgaact ggaatgaaaa gttgcaacat gtcttaagga 116520
accgagggga tttagagatg gaacagcagg aaggattctc cagtgagatt gaacacagcc 116580
agctttatct acagttctgc tcagagctgt ggctgcactt gaggaaacac ttcattggaa 116640
ctaaaacgtg tgagggatag tgaactttta catattcata agacacatta gcatatcaga 116700
ggcaggccat tgaagaacct taatttggaa tttatggcat gtatatgtgt gtgtgtgtgt 116760
gtgtgtgtgt gtgtgtattt gtgtgtgtgt gtgtgtgtgt gtgtgtgtgt gtgtgtgtgt 116820
ataaaagaac ccaggaaata ccttaaaact cctcagggac cccaggcagt gggctatgta 116880
tatgatacct tagcaggtac gcaaaggtaa aagcaaaatg gaacaaaagg caatgtcaat 116940
ttgtgaataa cagggatttg ggaatatctt ttaggaaaag gtttctttag ataggcttaa 117000
ttacccatga atgaagacaa aaacttgact gactgagaaa ttactcagtt catcttccta 117060
attattcaga agaaaaccag caaagccaca gtgaaaacca cttgcagaga gtacactttc 117120
tgtaacgaat attgttgctc ctgtacggtc atgagtaatt gatgtgtgtt ggacagtgac 117180
aggaacagaa gaggagtggg agaccatgaa gatagcacca ctggaacttc cttctgccca 117240
gttgagaaaa tactatggag tgttcagttg catgtgtgct ttgaccctgg aaataggtga 117300
taactcctta tctaatttat gtttccttga agctgatgaa ggattcatta ttaaggtagc 117360
```

-continued ccagatggtg tttagggtac attatatatt taccgaaagt accctcttct taaaaaggaa 117420
agatacaaac agaacacaat caaattgatg acaatgacaa tgagcagtgt aggactggag 117480
gcagactgtg cttgaccttg agaactgcta ttgatgggta tggtattgta aagctcttct 117540
tctcttaagc agtgccacgc tgtcaatgtg cgaacagtta atgagttttt gctgtttagc 117600
tttcttttat cttaagagtg tttcactcac cacctaaagg aagctcctta gttcacacaa 117660
gccctggtag gagtccagcc cttgagaagt gcagtctgag gatgcctctt gactagagct 117720
ttagctttcc agatttaaat cccaagtcag agctgtttga tttgtaatga gtccacgaag 117780
gactttaaag aaagccgtcc acagcaggct tgggccccac aattggcagc actacacaat 117840
caaatgtaca ctttggaatt tcaacttttg ccttcttttc aaaagtctct tctccagatt 117900
gtaagatgca agtatacttc ataatttgta tagctatttg tggcataatg gaatttatac 117960
atagggtgtc atacaactag tacacttata atctattcag agccaggagg cttatggttt 118020
gagacactgt ctcaggaaac atattcagaa tgtttctgcc tctaattcct ggaggagtaa 118080
tttaaaagca ttgtgatttt atgtgccata tgattgctaa gtgtgtctct tattctaata 118140
actgatctat cgatatctat ctatctatct atcatctatc tatctatcta tctatctatc 118200
tatctatcaa tcatctatct atctatctat ctatctatct atctatctat atcatctatc 118260
atctatcgat ctatctctca tccgtggttt gcacatagct cccagtgcta agaatttctt 118320
aactcttgtt ctgatgaaat gcacacaatt tggcttctga agctggctga tgtataagag 118380
agaaaggact atatttacct caatcagcac aaggatggca gtagatatct ctgtaagaaa 118440
gaagagcaaa atgaagagct aacttagcta accaaagttt ggcatgatag atgaggagtt 118500
aggcattaag ggctaaaaat agtagaaaac tatattttta tgtttgaatt ttgtagaaga 118560
ataaacagtt ttatagaact atggttaact tcaaatgtca tatcacctaa tggaaatata 118620
ctgagagggc tgacaaatcc agtttgtatt tttcttgctt ctgttagtat tctttccttc 118680
ggagatgggt gagtattact tgagggtctt cagagatgga aaggtcagag agaaggagga 118740
aggtaggggg gagagagaga gagagaaaga gagagag 118777

<210> SEQ ID NO 11
<211> LENGTH: 4047
<212> TYPE: DNA
<213> ORGANISM: Mus musculus
<220> FEATURE:
<221> NAME/KEY: misc_feature
<222> LOCATION: (1)..(4047)
<223> OTHER INFORMATION: LOCUS Drpla;4047 bp;mRNA;linear R
OD 16-MAY-2002
DEFINITION Mus musculus dentatorubral pallidoluysian
atrophy (Drpla), mRNA. ACCESSION XM_132846
<300> PUBLICATION INFORMATION:
<308> DATABASE ACCESSION NUMBER: XM_132846
<309> DATABASE ENTRY DATE: 2002-05-16
<313> RELEVANT RESIDUES IN SEQ ID NO: (1)..(4047)

<400> SEQUENCE: 11
cacgacagaa taaagactcg atgtcaatga ggagtggacg gaagaaagag gcccccgggc 60
cccgggaaga gctgagatca aggggccggg cctcccctgg aggggtcagc acatccagca 120
gtgatggcaa agctgagaag tccaggcaga cagccaagaa ggcccggata gaggagccct 180
ctgccccaaa ggccagcaag cagggccgga gcgaggagat ctcagagagt gagagcgagg 240
agaccagtgc gcccaaaaag accaaaaccg agcaggagct ccctcgcccg cagtctccct 300
cggatctgga cagcttggat gggcgcagca ttaacgatga cggcagcagc gaccctagag 360

-continued

```
atatagacca ggacaaccga agcacatccc ccagcatcta cagcccgggc agcgtggaaa    420
atgactcgga ctcatcctct ggcctgtccc agggccccgc ccgcccctac cacccacctc    480
cactcttccc tccttcccct ccaccaccag acagcactcc ccgacagcca gagtctggct    540
ttgaacctca tccttctgtg ccgcctactg gatatcatgc tccgatggag ccccccacat    600
cgagattatt ccagggccca ccacctggag ctcctcccac acacccacag ctctaccctg    660
ggaatgctag tggaggtgtt ttatctggac cccccatggg tcccaaaggg ggagccgctg    720
cctcctcagt gggtgcccct agcggaggca agcaacaccc cccacccact accccaattc    780
caatatcaag ttctggggcc agtggtgctc ctccagcaaa gccacccagt gctccagtgg    840
gtggtgggag cttaccttct gcaccaccac cagcttcttt cccccatgtg acaccaaacc    900
tgcctcctcc acctgccctg agacccctca acaatgcctc agcctctcct cctggcatgg    960
gggctcagcc aatccctggg catctgccct ctccccatgc catggggcag ggcatgagtg   1020
gacttcctcc tggcccagag aagggtccaa ccctggcccc ttctccccac cctttgcccc   1080
cagcttcttc ctctgcccct gggcctccaa tgcgatatcc atattcatcc tccagtagct   1140
ctgccgcagc ctcttctagt tcctcctcct cctctgcctc ccagtaccct gcttcccagg   1200
ccctgcccag ttatcctcat tccttccccc caccaactag tatgtctgtc tctaatcagc   1260
cacccaagta cacccagcct tctctcccat cccaagctgt gtggagccag ggtccacctc   1320
ctcctcctcc ctatggccgc ctcttggcca acaacaacac ccatccaggc cctttccctc   1380
ctactggggg tcaatctaca gcccacccag cagcccctac acatcaccat caccagcagc   1440
agccacagca acaacatcat catggaaact ctgggccccc tccacccgga gcgtatcctc   1500
accctctaga gagcagtaac tcccatcatg cacaccctta caacatgtca ccctccctgg   1560
ggtctttaag gccctacccc ccagggccag cacacctgcc tccacctcat ggccaggtgt   1620
cctataacca agcaggtccc aatggtcccc cagtttcttc ttccaactct tccgggtctt   1680
cctctcaagc ctcctattca tgttcacacc cctcttcatc ccagggcccc caaggagcat   1740
cctacccctt cccaccagtc cctccagtca ccacctcctc agctaccctt tccactgtca   1800
tcgccaccgt ggcttcctcg ccagcaggct acaaaacagc ttcgccacct gggcccccctc   1860
agtacagcaa gagagcccca tccccagggt cctacaagac agccaccccg cctggataca   1920
aaccggggtc accaccctcc ttcagaacag ggaccccacc cggctatcga ggcacctctc   1980
cgccagcagg cccagggacc ttcaaaccag gttcaccgac cgtggggccg gggcccctgc   2040
cacccgcggg gccttcaagt ttgtcatctc tgcctccgcc acctgcggcc ccgactacag   2100
ggccgcccct gaccgccacg cagatcaaac aggagccggc ggaagagtat gaacctcccg   2160
agagtccggt gcctccggcc cgcagcccct cgccccctcc caaggtggtg gacgtgccca   2220
gccatgccag ccagtcagcc aggttcaata agcacttgga ccgcggcttc aactcgtgcg   2280
cgcgcagcga cctgtacttc gtgccgctgg agggctccaa gctggccaag aagcgcgcgg   2340
acctggtgga gaaagtgcgg cgcgaggccg agcagcgcgc gcgcgaggag aaagagcgcg   2400
agcgcgagcg ggaacgcgaa aaggagcgcg agcgcgagaa agagcgcgag ctggagcgca   2460
gtgtgaaact ggcccaggag ggccgtgctc cagtggagtg cccatctctg ggtccagtgc   2520
cccatcggcc tccctttgag cctggcagcg ctgtggctac agtgcccccct tacctgggtc   2580
ctgatactcc ggccttgcgc actctcagtg aatacgcccg acctcatgtc atgtctcctg   2640
gcaatcgcaa ccacccattc tatgtgccct tgggggcagt ggacccgggg cttctgggtt   2700
```

-continued

```
acaatgtccc agccctgtac agcagcgacc cagctgcccg agaacgggag cgggaagccc   2760

gtgaacgtga cctccgtgac cggctcaagc ctggctttga ggtgaaacct agtgagctgg   2820

aacccctaca tggggttccc gggccaggcc tggatccctt cccccgacac gggggcctgg   2880

ctctacagcc cgggccacct ggcctgcatc ctttcccttt tcatccgagc ctggggcccc   2940

tggaacgaga acggctagcg ctggcagctg ggccagcctt gcgtcctgac atgtcttatg   3000

ctgagcggtt ggcagctgaa aggcagcatg cagaaagggt ggcagccctg ggcaatgatc   3060

cactagcccg gctgcagatg ctcaacgtga ctccccatca ccaccagcac tcccacatcc   3120

actctcacct tcacctgcac cagcaggatg ctatccacgc agcctctgcc tcggtgcacc   3180

ctctcattga ccccctggcc tcagggtctc accttacccg gatcccctac ccagctggga   3240

ccctccccaa ccccttcttt cctcaccctc tgcacgagaa cgaagttctt cgtcaccagc   3300

tttttgctgc cccttaccgg gacctgccgg cctccctttc tgctccaatg tcagcggctc   3360

atcagctgca ggccatgcac gcgcagtcag ctgagctgca gcgcttggcg ctggaacagc   3420

agcagtggct acatgctcat cacccattgc acagcgtgcc actacctgcc caggaagact   3480

actacagtca cctgaagaag gagagtgaca agccgctgta gagctgcgat ccagacagca   3540

cccactgctc cttcatccag accttggagg accaccccaa ccttttgacc ccaccccacc   3600

cccagccgag gagagggtgc tgcccgcttg cagagctcct gcagctgggt agagggaggg   3660

agggaagaag ggacagacaa ggtcagggcc cggggttgtg tgcagaggtg ggaagtggca   3720

agggtggggg cagaaagtgc acagtatctt ggaccaggtc cctcctccta tcccctgctt   3780

ttcttctcct ctatgccgaa tccttggtgg ccactgcccc tcccctaacc cattggtgtg   3840

attttttca tctgttagat gtggctgttt tgcgtagcat tgtgtgctgc cccgccccat   3900

ccctgtgtgt gcaccccctc cctcggcgat atgtgccctt acccgtccca cattaataat   3960

ttatatatat aaatatctat atgatgctct ttaaaaaaca tcctgaccaa aaccaaccaa   4020

acaaaaacat cctcacagtt ccccagg                                       4047
```

<210> SEQ ID NO 12
<211> LENGTH: 10033
<212> TYPE: DNA
<213> ORGANISM: Mus musculus
<220> FEATURE:
<221> NAME/KEY: misc_feature
<222> LOCATION: (1)..(10033)
<223> OTHER INFORMATION: LOCUS MMU24233; 10033 bp; mRNA; linear R
OD 18-JUL-1995
DEFINITION Mus musculus huntingtin (Hd) mRNA, complete cds.
ACCESSION U24233
<300> PUBLICATION INFORMATION:
<308> DATABASE ACCESSION NUMBER: U24233
<309> DATABASE ENTRY DATE: 1995-07-18
<313> RELEVANT RESIDUES IN SEQ ID NO: (1)..(10033)

<400> SEQUENCE: 12

```
ggctgagcgc cttggttccg cttctgcctg ccgcgcagag ccccattcat tgccttgctg     60

ctaagtggcg ccgcgtagtg ccagtaggct ccaagtcttc agggtctgtc ccatcgggca    120

ggaagccgtc atggcaaccc tggaaaagct gatgaaggct ttcgagtcgc tcaagtcgtt    180

tcagcagcaa cagcagcagc agccaccgcc gcaggcgccg ccgccaccgc cgccgcctcc    240

gcctcaaccc cctcagccgc cgcctcaggg gcagccgccg ccgccaccac cgccgctgcc    300

aggtccggca gaggaaccgc tgcaccgacc aaagaaggaa ctctcagcca ccaagaaaga    360

ccgtgtgaat cattgtctaa caatatgtga aaacattgtg gcacagtctc tcagaaattc    420
```

-continued

```
tccagaattt cagaaactct tgggcatcgc tatggaactg tttctgctgt gcagtaacga    480

tgcggagtca gatgtcagaa tggtggctga tgagtgcctc aacaaagtca tcaaagcttt    540

gatggattct aatcttccaa ggctacagtt agaactctat aaggaaatta aaaagaatgg    600

tgctcctcga agtttgcgtg ctgccctgtg gaggtttgct gagctggctc acctggttcg    660

acctcagaag tgcaggcctt acctggtgaa tcttcttcca tgcctgaccc gaacaagcaa    720

aagaccggag gaatccgttc aggagacctt ggctgcagct gttcctaaaa ttatggcttc    780

ttttggcaat ttcgcaaatg acaatgaaat taaggttctg ttgaaagctt tcatagcaaa    840

tctgaagtca agctctccca ctgtgcggcg gacagcagcc ggctcagccg tgagcatctg    900

ccaacattct aggaggacac agtacttcta caactggctc cttaatgtcc tcctaggtct    960

gctggttccc atggaagaag agcactccac tctcctgatc ctcggtgtgt tgctcacatt   1020

gaggtgtcta gtgcccttgc tccagcagca ggtcaaggac acaagtctaa aaggcagctt   1080

tggggtgaca cggaaagaaa tggaagtctc tccttctaca gagcagcttg tccaggttta   1140

tgaactgact ttgcatcata ctcagcacca agaccacaat gtggtgacag gggcactgga   1200

gctcctgcag cagctcttcc gtacccctcc acctgaactc ctgcaagcac tgaccacacc   1260

aggagggctt gggcagctca ctctggttca agaagaggcc cggggccgag gccgcagcgg   1320

gagcatcgtg gagcttttag ctggaggggg ttcctcgtgc agccctgtcc tctcaagaaa   1380

gcagaaaggc aaagtgctct taggagagga agaagccttg gaagatgact cggagtccag   1440

gtcagatgtc agcagctcag cctttgcagc ctctgtgaag agtgagattg gtggagagct   1500

cgctgcttct tcaggtgttt ccactcctgg ttctgttggt cacgacatca tcactgagca   1560

gcctagatcc cagcacacac ttcaagcaga ctctgtggat ttgtccggct gtgacctgac   1620

cagtgctgct actgatgggg atgaggagga catcttgagc cacagctcca gccagttcag   1680

tgctgtccca tccgaccctg ccatggacct gaatgatggg acccaggcct cctcacccat   1740

cagtgacagt tctcagacca ccactgaagg acctgattca gctgtgactc cttcggacag   1800

ttctgaaatt gtgttagatg gtgccgatag ccagtattta ggcatgcaga taggacagcc   1860

acaggaggac gatgaggagg gagctgcagg tgttctttct ggtgaagtct cagatgtttt   1920

cagaaactct tctctggccc ttcaacaggc acacttgttg gaaagaatgg gccatagcag   1980

gcagccttcc gacagcagta tagataagta tgtaacaaga gatgaggttg ctgaagccag   2040

tgatccagaa agcaagcctt gccgaatcaa aggtgacata ggacagccta atgatgatga   2100

ttctgctcct ctggtacatt gtgtccgtct tttatctgct tcctttttgt taactggtga   2160

aaagaaagca ctggttccag acagagacgt gagagtcagt gtgaaggccc tggccctcag   2220

ctgcattggt gcggctgtgg cccttcatcc agagtcgttc ttcagcagac tgtacaaagt   2280

acctcttaat accacggaaa gtactgagga acagtatgtt tctgacatct tgaactacat   2340

cgatcatgga gacccacagg tccgaggagc tactgccatt ctctgtggga cccttgtcta   2400

ctccatcctc agtaggtccc gtctccgtgt tggtgactgg ctgggcaaca tcagaaccct   2460

gacaggaaat acattttctc tggtggactg cattccttta ctgcagaaaa cgttgaagga   2520

tgaatcttct gttacttgca agttggcttg tacagctgtg aggcactgtg tcctgagtct   2580

ttgcagcagc agctacagtg acttgggatt acaactgctt attgatatgc tgcctctgaa   2640

gaacagctcc tactggctgg tgaggaccga actgctggac actctggcag agattgactt   2700

caggctcgtg agtttttttgg aggcaaaagc agaaagttta caccgagggg ctcatcatta   2760

tacagggttt ctaaaactac aagaacgagt actcaataat gtggtcattt atttgcttgg   2820
```

-continued

```
agatgaagac cccagggttc gacatgttgc tgcaacatca ttaacaaggc ttgtcccaaa   2880
gctgttttac aagtgtgacc aaggacaagc tgatccagtt gtggctgtag cgagggatca   2940
gagcagtgtc tacctgaagc tcctcatgca tgagacccag ccaccatcac acttttctgt   3000
cagcaccatc accagaatct atagaggcta tagcttactg ccaagtataa cagatgtcac   3060
catggaaaac aatctctcaa gagttgttgc cgcagtttct catgaactca ttacgtcaac   3120
aacacgggca ctcacatttg gatgctgtga agccttgtgt cttctctcag cagcctttcc   3180
agtttgcact tggagtttag gatggcactg tggagtgccc ccactgagtg cctctgatga   3240
gtccaggaag agctgcactg ttgggatggc ctccatgatt ctcaccttgc tttcatcagc   3300
ttggttccca ctggatctct cagcccatca ggatgccttg attttggctg gaaacttgct   3360
agcagcgagt gcccccaagt ctctgagaag ttcatggacc tctgaagaag aagccaactc   3420
agcagccacc agacaggagg aaatctggcc tgctctgggg gatcggactc tagtgccctt   3480
ggtggagcag cttttctccc acctgctgaa ggtgatcaat atctgtgctc atgtcttgga   3540
cgatgtgact cctggaccag caatcaaggc agccttgcct tctctaacaa acccccccttc   3600
tctaagtcct attcgacgga aagggaagga gaaagaacct ggagaacaag cttctactcc   3660
aatgagtccc aagaaagttg gtgaggccag tgcagcctct cgacaatcag acacctcagg   3720
acctgtcaca gcaagtaaat catcctcact ggggagtttc taccatctcc cctcctacct   3780
caaactgcat gatgtcctga aagccactca cgccaactat aaggtcacct tagatcttca   3840
gaacagcact gaaaagtttg gggggttcct gcgctctgcc ttggacgtcc tttctcagat   3900
tctagagctg gcgacactgc aggacattgg aaagtgtgtt gaagaggtcc ttggataccct   3960
gaaatcctgc tttagtcgag aaccaatgat ggcaactgtc tgtgtgcagc agctattgaa   4020
gactctcttt gggacaaact tagcctcaca gtttgatggc ttatcttcca accccagcaa   4080
gtctcagtgc cgagctcagc gccttggctc ttcaagtgtg aggcccggct tatatcacta   4140
ctgcttcatg gcaccataca cgcacttcac acaggccttg gctgacgcaa gcctgaggaa   4200
catggtgcag gcggagcagg agcgtgatgc ctcggggtgg tttgatgtac tccagaaagt   4260
gtctgcccaa ttgaagacga acctaacaag cgtcacaaag aaccgtgcag ataagaatgc   4320
tattcataat cacattaggt tatttgagcc tcttgttata aaagcattga agcagtacac   4380
cacgacaaca tctgtacaat tgcagaagca ggttttggat ttgctggcac agctggttca   4440
gctacgggtc aattactgtc tactggattc agaccaggtg ttcatcgggt ttgtgctgaa   4500
gcagtttgag tacattgaag tgggccagtt cagggaatca gaggcaatta ttccaaatat   4560
atttttcttc ctggtattac tgtcttatga gcgctaccat tcaaaacaga tcattggaat   4620
tcctaaaatc atccagctgt gtgatggcat catggccagt ggaaggaagg ccgttacaca   4680
tgctatacct gctctgcagc ccattgtcca tgacctcttt gtgttacgag gaacaaataa   4740
agctgatgca gggaaagagc ttgagacaca gaaggaggtg gtggtctcca tgctgttacg   4800
actcatccag taccatcagg tgctggagat gttcatcctt gtcctacagc agtgccacaa   4860
ggagaatgag gacaagtgga aacggctctc tcggcaggtc gcagacatca tcctgcccat   4920
gttggccaag cagcagatgc atattgactc tcatgaagcc cttggagtgt taaatacctt   4980
gtttgagatt ttggctcctt cctccctacg tcctgtggac atgcttttgc ggagtatgtt   5040
catcactcca agcacaatgg catctgtaag cactgtgcag ctgtggatat ctggaatcct   5100
cgccattctg agggttctca tttcccagtc aaccgaggac attgttcttt gtcgtattca   5160
```

-continued

```
ggagctctcc ttctctccac acttgctctc ctgtccagtg attaacaggt taaggggtgg   5220
aggcggtaat gtaacactag gagaatgcag cgaagggaaa caaaagagtt tgccagaaga   5280
tacattctca aggtttcttt tacagctggt tggtattctt ctagaagaca tcgttacaaa   5340
acagctcaaa gtggacatga gtgaacagca gcatacgttc tactgccaag agctaggcac   5400
actgctcatg tgtctgatcc acatattcaa atctggaatg ttccggagaa tcacagcagc   5460
tgccactaga ctcttcacca gtgatggctg tgaaggcagc ttctatactc tagagagcct   5520
gaatgcacgg gtccgatcca tggtgcccac gcacccagcc ctggtactgc tctggtgtca   5580
gatcctactt ctcatcaacc acactgacca ccggtggtgg gcagaggtgc agcagacacc   5640
caagagacac agtctgtcct gcacgaagtc acttaacccc cagaagtctg gcgaagagga   5700
ggattctggc tcggcagctc agctgggaat gtgcaataga gaaatagtgc gaagaggggc   5760
ccttattctc ttctgtgatt atgtctgtca gaatctccat gactcagaac acttaacatg   5820
gctcattgtg aatcacattc aagatctgat cagcttgtct catgagcctc cagtacaaga   5880
ctttattagt gccattcatc gtaattctgc agctagtggt ctttttatcc aggcaattca   5940
gtctcgctgt gaaaatcttt caacgccaac cactctgaag aaaacacttc agtgcttgga   6000
aggcatccat ctcagccagt ctggtgctgt gctcacacta tatgtggaca ggctcctggg   6060
cacccccttc cgtgcgctgg ctcgcatggt cgacaccctg gcctgtcgcc gggtagaaat   6120
gcttttggct gcaaatttac agagcagcat ggcccagttg ccagaggagg aactaaacag   6180
aatccaagaa cacctccaga acagtgggct tgcacaaaga caccaaaggc tctattcact   6240
gctggacaga ttccgactct ctactgtgca ggactcactt agccccttgc cccagtcac    6300
ttcccaccca ctggatgggg atgggcacac atctctggaa acagtgagtc cagacaaaga   6360
ctggtacctc cagcttgtca gatcccagtg ttggaccaga tcagattctg cactgctgga   6420
aggtgcagag ctggtcaacc gtatccctgc tgaagatatg aatgacttca tgatgagctc   6480
ggagttcaac ctaagccttt tggctccctg tttaagcctt ggcatgagcg agattgctaa   6540
tggccaaaag agtcccctct ttgaagcagc ccgtggggtg attctgaacc gggtgaccag   6600
tgttgttcag cagcttcctg ctgtccatca agtcttccag cccttcctgc ctatagagcc   6660
cacggcctac tggaacaagt tgaatgatct gcttggtgat accacatcat accagtctct   6720
gaccatactt gcccgtgccc tggcacagta cctggtggtg ctctccaaag tgcctgctca   6780
tttgcacctt cctcctgaga aggaggggga cacggtgaag tttgtggtaa tgacagttga   6840
ggccctgtca tggcatttga tccatgagca gatcccactg agtctggacc tccaagccgg   6900
gctagactgc tgctgcctgg cactacaggt gcctggcctc tggggggtgc tgtcctcccc   6960
agagtacgtg actcatgcct gctccctcat ccattgtgtg cgattcatcc tggaagccat   7020
tgcagtacaa cctggagacc agcttctcgg tcctgaaagc aggtcacata ctccaagagc   7080
tgtcagaaag gaggaagtag actcagatat acaaaacctc agtcatgtca cttcggcctg   7140
cgagatggtg gcagacatgg tggaatccct gcagtcagtg ctggccttgg gccacaagag   7200
gaacagcacc ctgccttcat ttctcacagc tgtgctgaag aacattgtta tcagtctggc   7260
ccgactcccc ctagttaaca gctatactcg tgtgcctcct ctggtatgga aactcgggtg   7320
gtcacccaag cctggagggg attttggcac agtgtttcct gagatccctg tagagttcct   7380
ccaggagaag gagatcctca aggagttcat ctaccgcatc aacaccctag ggtggaccaa   7440
tcgtacccag ttcgaagaaa cttgggccac cctccttggt gtcctggtga ctcagcccct   7500
ggtgatggaa caggaagaga gcccaccaga ggaagacaca gaaagaaccc agatccatgt   7560
```

-continued

```
cctggctgtg caggccatca cctctctagt gctcagtgca atgaccgtgc ctgtggctgg   7620
caatccagct gtaagctgct tggagcaaca gccccggaac aagccactga aggctctcga   7680
taccagattt ggaagaaagc tgagcatgat cagagggatt gtagaacaag aaatccaaga   7740
gatggtttcc cagagagaga atactgccac tcaccattct caccaggcgt gggatcctgt   7800
cccttctctg ttaccagcta ctacaggtgc tcttatcagc catgacaagc tgctgctgca   7860
gatcaaccca gagcgggagc caggcaacat gagctacaag ctgggccagg tgtccataca   7920
ctccgtgtgg ctgggaaata acatcacacc cctgagagag gaggaatggg atgaggaaga   7980
agaggaagaa agtgatgtcc ctgcaccaac gtcaccacct gtgtctccag tcaattccag   8040
aaaacaccgt gccggggttg atattcactc ctgttcgcag tttctgcttg aattgtacag   8100
ccgatggatc ctgccatcca gtgcagccag aaggaccccc gtcatcctga tcagtgaagt   8160
ggttcgatct cttcttgtag tgtcagactt attcaccgaa cgtacccagt ttgaaatgat   8220
gtatctgacg ctgacagaac tacggagagt gcacccttca gaagatgaga tcctcattca   8280
gtacctggtg cctgccacct gtaaggcagc tgctgtcctt ggaatggaca aaactgtggc   8340
agagccagtc agccgcctac tggagagcac actgaggagc agccacctgc ccagccagat   8400
cggagccctg cacggcatcc tctatgtgtt ggagtgtgac ctcttggatg acactgcaaa   8460
gcagctcatt ccagttgtta gtgactatct gctgtccaac ctcaaaggaa tagcccactg   8520
cgtgaacatt cacagccagc agcatgtgct ggtaatgtgt gccactgctt tctacctgat   8580
ggaaaactac cctctggatg tgggaccaga attttcagca tctgtgatac agatgtgtgg   8640
agtaatgctg tctggaagtg aggagtccac cccctccatc atttaccact gtgccctccg   8700
gggtctggag cggctcctgc tgtctgagca gctatctcgg ctagacacag agtccttggt   8760
caagctaagt gtggacagag tgaatgtaca aagcccacac agggccatgg cagccctagg   8820
cctgatgctc acctgcatgt acacaggaaa ggaaaaagcc agtccaggca gagcttctga   8880
ccccagccct gctacacctg acagcgagtc tgtgattgta gctatggagc gagtgtctgt   8940
tctctttgat aggatccgca agggatttcc ctgtgaagcc agggttgtgg caaggatcct   9000
gcctcagttc ctagatgact tctttccacc tcaagatgtc atgaacaaag tcattggaga   9060
gttcctgtcc aatcagcagc catacccaca gttcatggcc actgtagttt acaaggtttt   9120
tcagactctg cacagtgctg ggcagtcatc catggtccgg gactgggtca tgctgtccct   9180
gtccaacttc acacaaagaa cttcagttgc catggccatg tggagcctct cctgcttcct   9240
tgttagcgca tctaccagcc catgggtttc tgcgatcctt ccacatgtca tcagcaggat   9300
gggcaaactg gaacaggtgg atgtgaacct tttctgcctg gttgccacag acttctacag   9360
acaccagata gaggaggaat tcgaccgcag ggctttccag tctgtgtttg aggtggtggc   9420
ggcaccagga agtccatacc acaggctgct tgcttgtttg caaaatgttc acaaggtcac   9480
cacctgctga gtagtgcctg tgggacaaaa ggctgaaaga aggcagctgc tggggcctga   9540
gcctccagga gcctgctcca agcttctgct ggggctgcct tggccgtgca ggcttccact   9600
tgtgtcaagt ggacagccag gcaatggcag gagtgctttg caatgagggc tatgcaggga   9660
acatgcacta tgttggggtt gagcctgagt cctgggtcct ggcctcgctg cagctggtga   9720
cagtgctagg ttgaccaggt gtttgtcttt ttcctagtgt tcccctggcc atagtcgcca   9780
ggttgcagct gccctggtat gtggatcaga agtcctagct cttgccagat ggttctgagc   9840
ccgcctgctc cactgggctg gagagctccc tcccacattt acccagtagg catacctgcc   9900
```

-continued

```
acaccagtgt ctggacacaa aatgaatggt gtgtggggct gggaactggg gctgccaggt   9960

gtccagcacc attttccttt ctgtgttttc ttctcaggag ttaaaattta attatatcag  10020

taaagagatt aat                                                      10033
```

```
<210> SEQ ID NO 13
<211> LENGTH: 3616
<212> TYPE: DNA
<213> ORGANISM: Mus musculus
<220> FEATURE:
<221> NAME/KEY: misc_feature
<222> LOCATION: (1)..(3616)
<223> OTHER INFORMATION: LOCUS Sca1;3616 bp;mRNA;linear R
      OD 07-JAN-2002
      DEFINITION  Mus musculus spinocerebellar ataxia 1 homolog
      (human)(Sca1), mRNA. ACCESSION   NM_009124
<300> PUBLICATION INFORMATION:
<308> DATABASE ACCESSION NUMBER: NM_009124
<309> DATABASE ENTRY DATE: 2002-01-07
<313> RELEVANT RESIDUES IN SEQ ID NO: (1)..(3616)

<400> SEQUENCE: 13

ctcttcctcc actccctcca caggaagggc gtcacctgtc agattgcggc atcctggaac     60

agaatgaaag gatctgtgtt gaaacagcta cagtagggtt acagtagacc ctgagaaaac    120

agagtggact tcagcctgca cggatgagct tgaagcagga atggtttggg ttcaggcctc    180

ttacactgaa tttctctact gccacccttt ctactcaagc aacatcttac ggaaaagatc    240

tcccgggaag gaagtggctg cttgtggctt tgcactgtga tgaaggcaaa tggtacagtt    300

ttccaaagaa aatagaccaa aactttcttc ttgagaagaa acaaacctgc tgttggcaga    360

gggtatttct aacctctctg cgaaagaaag aaagacacca ccagaacctg ggcatcccag    420

ctgctgaggg aagtttccat ggtgaagtct cagggaggct tcctgggagc agagcatagt    480

gaatgctaat ccggagctgc cactgccagc ctaaagaacc cacgggagat gattccccat    540

gaagggcctg gatcccctac agaaatccaa tgtgactctc tgtttatcag actaaaacca    600

gagccggcca gccagtgaaa cagccaccgt ggagggggga cggcgaaaaa tgaaatccaa    660

ccaagagcgg acgaacgaat gcctgcctcc caagaaacgt gagatccccg ccaccagccg    720

gccctcggag gagaaggcca ctgctctgcc cagcgacaac cactgcgtgg agggtgtggc    780

ctggctcccc agcacccctg gcatccgcgg ccatgggggt gggcggcacg ggtcagcagg    840

gacttccggg gagcatggtt tacaaggaat gggtttactt aaagcactgt ccgcagggct    900

ggattactcc ccacccagtg cccccaggtc agtccccaca gccaacacgc tgcccaccgt    960

gtaccctcct cctcagtcag ggaccccggt gtctcctgtg cagtacgccc acctttcgca   1020

taccttccag ttcattgggt cctcccaata cagtgggcct tacgcgggct ttatcccttc   1080

ccagctgatc tccccatcag gcaacccggt caccagtgca gtagcctcag ctgcaggggc   1140

caccactcca tcacagcgct cccagctgga ggcttattcc accctgctgg ccaacatggg   1200

cagtctgagc caggcaccag gacataaggt tgagccccct ccgcagcagc acctcagcag   1260

ggctgcagga ttagtcaacc cggggtcccc tcctccaccc acccagcaga accagtacat   1320

ccatatttcc agctctccac agagctccgg gcgggcgaca tctcccccac ccatcccggt   1380

ccacctccat ccccatcaga cgatgatccc gcacacactc accctggggc cttcatccca   1440

ggtggttgtg caatatagtg atgccggagg ccactttgtt cctcgagagt ccaccaaaaa   1500

agccgagagc agcaggttgc agcaggctat gcaagccaag gaagtcctga atggggagat   1560

ggagaaaagc cggaggtatg ggcatcatc ttctgtggag ctgagcctag gcaaggcaag   1620
```

-continued

```
cagtaagtca gtgcctcatc cctatgagtc caggcatgtg gtggtccacc caagcccagc   1680

agactacagc agtcgtgata cctccggggt ccgtggatct gtgatggttc tgcctaatag   1740

cagcacaccc tcagccgacc tggaggccca gcagaccacg catcgagagg cctccccatc   1800

caccctcaat gacaagagcg gcctggcacc taggaagccg ggccacaggt cttatgcgct   1860

gtccccccac acggtcattc agaccacaca cagtgcatca gagcctctcc cggtgggcct   1920

accagccacg gccttctacg ctggcactca acctcctgtc atcggctacc tgagcggcca   1980

gcagcaagca atcacctatg ctggtggtct gccgcagcac ctggtgatcc caggtaacca   2040

gcccctgctc atcccggtgg gcagccctga catggacatg cctggggcag cctcggccat   2100

cgtgacgtca tcaccccagt ttgctgcagt acctcacacg tttgtcacca ccgccctgcc   2160

caagagcgag aacttcaacc cagaggctct ggtcacccag gcgtcctacc cagccatggt   2220

gcaggcccag atccacctgc cggtggtgca gtccgtggcg tcccccacca cggcgtctcc   2280

cacgctgccg ccatatttca tgaaaggctc catcatccag ctggccaacg gggagctgaa   2340

gaaggtggag gacctgaaga cggaggattt catccagagt gcagagatta gcaatgacct   2400

caagatccac tccagtactg tggagagaat cgaggagagc cacagccccg gggtggccgt   2460

gatacagttt gctgttggtg aacaccgagc ccaggtcagt gtcgaagtct tggtagagta   2520

tccttttttt gtatttggac agggctggtc atcctgctgt cctgagcgga ccagccagct   2580

ctttgatctg ccgtgttcca aactctctgt tggggacgtc tgcatctcgc tcaccctcaa   2640

gaacctgaag aatggctctg ttaaaaaggg ccagcctgtg gaccctgcca gcgtcctgct   2700

gaagcaggta aagaccgaca gcctggctgg cagcagacac agatacgcgg agcaggaaaa   2760

cggaatcaac cagggaagcg cccaggtgct ctctgagaat ggcgaactga agtttccaga   2820

aaaaatagga ttgcctgcag caccettcct cagcaaaata gaaccgagca aacccacagc   2880

cacgaggaag aggaggaggt ggtcggcgcc ggagacccgt aaactggaga agtcggagga   2940

cgagccacct ttgactcttc ccaagccttc gctcattcct caggaggtta agatctgcat   3000

cgaaggccga tctaacgtgg gcaagtagag accttgcgag cagcggaggc ccggggctct   3060

tttactgtct gtatccagat tactgtactg taggctaagt aacacagtat ttacatgtta   3120

catcctcttt aggtttgtat tctaaccttg tcattagagt caaacaggtg tgtcgcagga   3180

gactggtgcg tttgcattgt ctgcaagggt ctgttgagga gctggtgggt tggaggatgg   3240

tcagaaccat gtccatggag ctcccgggca tccttagtgg ccctgaatgt ggcttcatca   3300

gcccctgcct tctccggcag tgtgcagagt cgaggggcat cagttcccac tggtttcaag   3360

aacaaacaca gtgggaagta tcctgcaagg gagtgtctgg gtgcgtgtcc cttgtgaagg   3420

agtgcgagtg agggtgtctc tttctctgcc tctgtctccc tcacttgctc cctctcagtg   3480

tggggttggg ggacctgggt ttcccacctg caaagtcatc agggaaccca gcttccaggc   3540

attgtaggga gacatcagac aggcggatgg gaaactagtt tcaaagaacg tggttctctc   3600

caacatattt tacaat                                                   3616
```

<210> SEQ ID NO 14
<211> LENGTH: 1543
<212> TYPE: RNA
<213> ORGANISM: Homo sapiens
<220> FEATURE:
<221> NAME/KEY: misc_feature
<222> LOCATION: (1)..(1543)
<223> OTHER INFORMATION: LOCUS SNCA;1543 bp;mRNA;linear P;RI 05-NOV-2002
DEFINITION Homo sapiens synuclein, alpha (non A4 component of
amyloid precursor) (SNCA), transcript variant NACP140, mRNA.

-continued

```
      ACCESSION NM_000345: VERSION NM_000345.2 GI:6806896
<300> PUBLICATION INFORMATION:
<308> DATABASE ACCESSION NUMBER: NM_000345
<309> DATABASE ENTRY DATE: 2002-11-05
<313> RELEVANT RESIDUES IN SEQ ID NO: (1)..(1543)

<400> SEQUENCE: 14

ggaguggcca uucgacgaca guguggugua aaggaauuca uuagccaugg auguauucau      60

gaaaggacuu ucaaaggcca aggagggagu uguggcugcu gcugagaaaa ccaaacaggg     120

uguggcagaa gcagcaggaa agacaaaaga ggguguucuc uauguaggcu ccaaaaccaa     180

ggagggagug gugcauggug uggcaacagu ggcugagaag accaaagagc aagugacaaa     240

uguuggagga gcagugguga cgggugugac agcaguagcc cagaagacag uggagggagc     300

agggagcauu gcagcagcca cuggcuuugu caaaaaggac caguugggca agaaugaaga     360

aggagcccca caggaaggaa uucuggaaga uaugccugug gauccugaca augaggcuua     420

ugaaaugccu ucugaggaag gguaucaaga cuacgaaccu gaagccuaag aaauaucuuu     480

gcucccaguu ucuugagauc ugcugacaga uguuccaucc uguacaagug cucaguucca     540

augugcccag ucaugacauu ucucaaaguu uuuacagugu aucucgaagu cuuccaucag     600

cagugauuga aguaucugua ccugccccca cucagcauuu cggugcuucc cuuucacuga     660

agugaauaca ugguagcagg gucuuugugu gcuguggauu uuguggcuuc aaucuacgau     720

guuaaaacaa auuaaaaaca ccuaagugac uaccacuuau uucuaaaucc ucacuauuuu     780

uuuguugcug uuguucagaa guuguuagug auuugcuauc auauauuaua agauuuuuag     840

gugucuuuua augauacugu cuaagaauaa ugacguauug ugaaauuugu uaauauauau     900

aauacuuaaa aauaugugag caugaaacua ugcaccuaua aauacuaaau augaaauuuu     960

accauuuugc gauguguuuu auucacuugu guuuguauau aaauggugag aauuaaaaua    1020

aaacguuauc ucauugcaaa aauauuuuau uuuuauccca ucucacuuua auaauaaaaa    1080

ucaugcuuau aagcaacaug aauuaagaac ugacacaaag gacaaaaaua uaaaguuauu    1140

aauagccauu ugaagaagga ggaauuuuag aagagguaga gaaaauggaa cauuaacccu    1200

acacucggaa uucccugaag caacacugcc agaagugugu uuugguaugc acugguuccu    1260

uaaguggcug ugauuaauua uugaaagugg ggguguugaag accccaacua cuauuguaga    1320

guggucuauu ucucccuuca auccugucaa uguuugcuuu auguauuuug gggaacuguu    1380

guuugaugug uauguguuua uaauuguuau acauuuuuaa uugagccuuu uauuaacaua    1440

uauuguuauu uuugucucga aauaauuuuu uaguuaaaau cuauuuuguc ugauauuggu    1500

gugaaugcug uaccuuucug acaauaaaua auauucgacc aug                      1543


<210> SEQ ID NO 15
<211> LENGTH: 10660
<212> TYPE: DNA
<213> ORGANISM: Homo sapiens
<220> FEATURE:
<221> NAME/KEY: misc_feature
<222> LOCATION: (1)..(10660)
<223> OTHER INFORMATION: LOCUS SCA1;10660 bp;mRNA;linear P;RI
      31-OCT-2000
      DEFINITION  Homo sapiens spinocerebellar ataxia 1
      (olivopontocere bellar ataxia 1, autosomal dominant, ataxin 1)
      (SCA1), mRNA. ACCESSION NM_000332
<300> PUBLICATION INFORMATION:
<308> DATABASE ACCESSION NUMBER: NM_000332
<309> DATABASE ENTRY DATE: 2000-10-31
<313> RELEVANT RESIDUES IN SEQ ID NO: (1)..(10660)

<400> SEQUENCE: 15
```

-continued

```
ctactacagt ggcggacgta caggacctgt ttcactgcag ggggatccaa aacaagcccc     60
gtggagcaac agccagagca acagcagctg caagacattg tttctctccc tctgcccccc    120
cttccccacg caaccccaga tccatttaca ctttacagtt ttacctcaca aaaactacta    180
caagcaccaa gctccctgat ggaaaggagc atcgtgcatc aagtcaccag ggtggtccat    240
tcaagctgca gatttgtttg tcatccttgt acagcaatct cctcctccac tgccactaca    300
gggaagtgca tcacatgtca gcatactgga gcatagtgaa agagtctatt ttgaagcttc    360
aaacttagtg ctgctgcaga ccaggaacaa gagagaaaga gtggatttca gcctgcacgg    420
atggtcttga aacacaaatg gtttttggtc taggcgtttt acactgagat tctccactgc    480
cacccttct actcaagcaa aatcttcgtg aaaagatctg ctgcaaggaa ctgatagctt     540
atggttctcc attgtgatga aagcacatgg tacagttttc caaagaaatt agaccatttt    600
cttcgtgaga aagaaatcga cgtgctgttt tcatagggta tttctcactt ctctgtgaaa    660
ggaagaaaga acacgcctga gcccaagagc cctcaggagc cctccagagc ctgtgggaag    720
tctccatggt gaagtatagg ctgaggctac ctgtgaacag tacgcagtga atgttcatcc    780
agagctgctg ttggcggatt gtacccacgg ggagatgatt cctcatgaag agcctggatc    840
ccctacagaa atcaaatgtg actttccgtt tatcagacta aaatcagagc catccagaca    900
gtgaaacagt caccgtggag gggggacggc gaaaaatgaa atccaaccaa gagcggagca    960
acgaatgcct gcctcccaag aagcgcgaga tccccgccac cagccggtcc tccgaggaga   1020
aggcccctac cctgcccagc gacaaccacc gggtggaggg cacagcatgg ctcccgggca   1080
accctggtgg ccggggccac gggggcggga ggcatgggcc ggcagggacc tcggtggagc   1140
ttggtttaca acagggaata ggtttacaca aagcattgtc cacagggctg gactactccc   1200
cgcccagcgc tcccaggtct gtccccgtgg ccaccacgct gcctgccgcg tacgccaccc   1260
cgcagccagg gaccccggtg tccccgtgc agtacgctca cctgccgcac accttccagt    1320
tcattgggtc ctcccaatac agtggaacct atgccagctt catcccatca cagctgatcc   1380
ccccaaccgc caaccccgtc accagtgcag tggcctcggc cgcaggggcc accactccat   1440
cccagcgctc ccagctggag gcctattcca ctctgctggc caacatgggc agtctgagcc   1500
agacgccggg acacaaggct gagcagcagc agcagcagca gcagcagcag cagcagcagc   1560
atcagcatca gcagcagcag cagcagcagc agcagcagca gcagcagcag cagcacctca   1620
gcagggctcc ggggctcatc accccggggt cccccccacc agcccagcag aaccagtacg   1680
tccacatttc cagttctccg cagaacaccg gccgcaccgc ctctcctccg gccatccccg   1740
tccacctcca cccccaccag acgatgatcc cacacacgct caccctgggg ccccctccc    1800
aggtcgtcat gcaatacgcc gactccggca gccactttgt ccctcgggag gccaccaaga   1860
aagctgagag cagccggctg cagcaggcca tccaggccaa ggaggtcctg aacggtgaga   1920
tggagaagag ccggcggtac ggggccccgt cctcagccga cctgggcctg ggcaaggcag   1980
gcggcaagtc ggttcctcac ccgtacgagt ccaggcacgt ggtggtccac ccgagcccct   2040
cagactacag cagtcgtgat ccttcggggg tccgggcctc tgtgatggtc ctgcccaaca   2100
gcaacacgcc cgcagctgac ctggaggtgc aacaggccac tcatcgtgaa gcctcccctt   2160
ctaccctcaa cgacaaaagt ggcctgcatt tagggaagcc tggccaccgg tcctacgcgc   2220
tctcacccca cacggtcatt cagaccacac acagtgcttc agagccactc ccggtgggac   2280
tgccagccac ggccttctac gcagggactc aacccccctgt catcggctac ctgagcggcc  2340
```

-continued

```
agcagcaagc aatcacctac gccggcagcc tgccccagca cctggtgatc cccggcacac   2400
agcccctgct catcccggtc ggcagcactg acatggaagc gtcgggggca gccccggcca   2460
tagtcacgtc atccccccag tttgctgcag tgcctcacac gttcgtcacc accgcccttc   2520
ccaagagcga gaacttcaac cctgaggccc tggtcaccca ggccgcctac ccagccatgg   2580
tgcaggccca gatccacctg cctgtggtgc agtccgtggc ctccccggcg gcggctcccc   2640
ctacgctgcc tccctacttc atgaaaggct ccatcatcca gttggccaac ggggagctaa   2700
agaaggtgga agacttaaaa acagaagatt tcatccagag tgcagagata agcaacgacc   2760
tgaagatcga ctccagcacc gtagagagga ttgaagacag ccatagcccg ggcgtggccg   2820
tgatacagtt cgccgtcggg gagcaccgag cccaggtcag cgttgaagtt ttggtagagt   2880
atcctttttt tgtgtttgga cagggctggt catcctgctg tccggagaga accagccagc   2940
tctttgattt gccgtgttcc aaactctcag ttggggatgt ctgcatctcg cttaccctca   3000
agaacctgaa gaacggctct gttaaaaagg gccagcccgt ggatcccgcc agcgtcctgc   3060
tgaagcactc aaaggccgac ggcctggcgg gcagcagaca caggtatgcc gagcaggaaa   3120
acggaatcaa ccaggggagt gcccagatgc tctctgagaa tggcgaactg aagtttccag   3180
agaaaatggg attgcctgca gcgcccttcc tcaccaaaat agaacccagc aagcccgcgg   3240
caacgaggaa gaggaggtgg tcggcgccag agagccgcaa actggagaag tcagaagacg   3300
aaccaccttt gactcttcct aagccttctc taattcctca ggaggttaag atttgcattg   3360
aaggccggtc taatgtaggc aagtagaggc agcgtggggg aaaggaaacg tggctctccc   3420
ttatcatttg tatccagatt actgtactgt aggctaaaat aacacagtat ttacatgtta   3480
tcttcttaat tttaggtttc tgttctaacc ttgtcattag agttacagca ggtgtgtcgc   3540
aggagactgg tgcatatgct tttccacga gtgtctgtca gtgagcgggc gggaggaagg   3600
gcacagcagg agcggtcagg gctccaggca tccccgggga agaaaggaac ggggcttcac   3660
agtgcctgcc ttctctagcg gcacagaagc agccgggggc gctgactccc gctagtgtca   3720
ggagaaaagt cccgtgggaa gagtcctgca ggggtgcagg gttgcacgca tgtgggggtg   3780
cacaggcgct gtggcggcga gtgagggtct ctttttctct gcctccctct gcctcactct   3840
cttgctatcg gcatgggccg gggggttca gagcagtgtc ctcctggggt tcccacgtgc   3900
aaaatcaaca tcaggaaccc agcttcaggg catcgcggag acgcgtcaga tggcagattt   3960
ggaaagttaa ccatttaaaa gaacattttt ctctccaaca tattttacaa taaaagcaac   4020
ttttaattgt atagatatat atttcccccct atggggcctg actgcactga tatatatttt   4080
ttttaaagag caactgccac atgcgggatt tcatttctgc tttttactag tgcagcgatg   4140
tcaccagggt gttgtggtgg acagggaagc ccctgctgtc atggccccac atggggtaag   4200
gggggttggg ggtgggggag agggagagag cgaacaccca cgctggtttc tgtgcagtgt   4260
taggaaaacc aatcaggtta ttgcattgac ttcactccca agaggtagat gcaaactgcc   4320
cttcagtgag agcaacagaa gctcttcacg ttgagtttgc gaaatctttt tgtctttgaa   4380
ctctagtact gtttatagtt catgactatg gacaactcgg gtgccacttt tttttttttc   4440
agattccagt gtgacatgag gaattagatt ttgaagatga gcatatatta ctatctttaa   4500
gcatttaaaa atactgttca cactttatta ccaagcatct tggtctctca ttcaacaagt   4560
actgtatctc actttaaact ctttggggaa aaaacaaaaa caaaaaaaac taagttgctt   4620
tctttttttc aacactgtaa ctacatttca gctctgcaga attgctgaag agcaagatat   4680
tgaaagtttc aatgtggttt aaagggatga atgtgaatta tgaactagta tgtgacaata   4740
```

-continued

```
aatgaccacc aagtactacc tgacgggagg cacttttcac tttgatgtct gagaatcagt   4800
tcaaggcata tgcagagttg gcagagaaac tgagagaaaa gggatggaga agagaatact   4860
catttttgtc cagtgttttt ctttttaaga tgaactttta aagaaccttg cgatttgcac   4920
atattgagtt tataacttgt gtgatattcc tgcagttttt atccaataac attgtgggaa   4980
aggtttgggg gactgaacga gcataaataa atgtagcaaa atttctttct aacctgccta   5040
aactctaggc cattttataa ggttatgttc ctttgaaaat tcattttggt ctttttacca   5100
catctgtcac aaaaagccag gtcttagcgg gctcttagaa actctgagaa ttttcttcag   5160
attcattgag agagttttcc ataaagacat ttatatatgt gagcaagatt tttttaaac    5220
aattacttta ttattgttgt tattaatgtt attttcagaa tggctttttt tttctattca   5280
aaatcaaatc gagatttaat gtttggtaca aacccagaaa gggtatttca tagtttttaa   5340
acctttcatt cccagagatc cgaaatatca tttgtgggtt ttgaatgcat ctttaaagtg   5400
ctttaaaaaa aagttttata agtagggaga aatttttaaa tattcttact tggatggctg   5460
caactaaact gaacaaatac ctgacttttc ttttacccca ttgaaaatag tactttcttc   5520
gtttcacaaa ttaaaaaaaa aatctggtat caacccacat tttggctgtc tagtattcat   5580
ttacatttag ggttcaccag gactaatgat ttttataaac cgttttctgg ggtgtaccaa   5640
aaacatttga ataggtttag aatagctaga atagttcctt gactttcctc gaatttcatt   5700
accctctcag catgcttgca gagagctggg tgggctcatt cttgcagtca tactgcttat   5760
ttagtgctgt atttttaaa cgtttctgtt cagagaactt gcttaatctt ccatatattc    5820
tgctcagggc acttgcaatt attaggtttt gtttttcttt ttgtttttta gcctttgatg   5880
gtaagaggaa tacgggctgc cacatagact ttgttctcat taatatcact atttacaact   5940
catgtggact cagaaaaaca cacaccacct tttggcttac ttcgagtatt gaattgactg   6000
gatccactaa accaacacta agatgggaaa acacacatgg tttggagcaa taggaacatc   6060
atcataattt ttgtggttct atttcaggta taggaattat aaaataattg gttctttcta   6120
aacacttgtc ccatttcatt ctcttgcttt tttagcatgt gcaatacttt ctgtgccaat   6180
agagtctgac cagtgtgcta tatagttaaa gctcattccc ttttggcttt ttccttgttt   6240
ggttgatctt ccccattctg gccagagcag ggctggaggg aaggagccag gagggagaga   6300
gcctcccacc tttcccctgc tgcggatgct gagtgctggg gcggggagcc ttcaggagcc   6360
ccgtgcgtct gccgccacgt tgcagaaaga gccagccaag gagacccggg ggaggaaccg   6420
cagtgtcccc tgtcaccaca cggaatagtg aatgtggagt gtggagagga aggaggcaga   6480
ttcatttcta agacgcactc tggagccatg tagcctggag tcaacccatt ttccacggtc   6540
ttttctgcaa gtgggcaggc ccctcctcgg ggtctgtgtc cttgagactt ggagccctgc   6600
ctctgagcct ggacgggaag tgtggcctgt tgtgtgtgtg cgttctgagc gtgttggcca   6660
gtggctgtgg aggggaccac ctgccaccca cggtcaccac tcccttgtgg cagctttctc   6720
ttcaaatagg aagaacgcac agagggcagg agcctcctgt ttgcagacgt tggcgggccc   6780
cgaggctccc agagcagcct ctgtcaccgc ttctgtgtag caaacattaa cgatgacagg   6840
ggtagaaatt cttcggtgcc gttcagctta caaggatcag ccatgtgcct ctgtactatg   6900
tccactttgc aatatttacc gacagccgtc ttttgttctt tctttcctgt tttccatttt   6960
taaactagta acagcaggcc ttttgcgttt acaatggaac acaatcacca agaaattagt   7020
cagggcgaaa agaaaaaaat aatactatta ataagaaacc aacaaacaag aacctctctt   7080
```

-continued

```
tctagggatt tctaaatata taaaatgact gttccttaga atgtttaact taagaattat   7140
ttcagtttgt ctgggccaca ctggggcaga ggggggaggg agggatacag agatggatgc   7200
cacttacctc agatctttta aagtggaaat ccaaattgaa ttttcatttg gactttcagg   7260
ataattttct atgttggtca acttttcgtt ttccctaact cacccagttt agtttgggat   7320
gatttgattt ctgttgttgt tgatcccatt tctaacttgg aattgtgagc ctctatgttt   7380
tctgttaggt gagtgtgttg ggttttttcc ccccaccagg aagtggcagc atccctcctt   7440
ctcccctaaa gggactctgc ggaacctttc acacctcttt ctcagggacg gggcaggtgt   7500
gtgtgtggta cactgacgtg tccagaagca gcactttgac tgctctggag tagggttgta   7560
caatttcaag gaatgtttgg atttcctgca tcttgtggat tactccttag ataccgcata   7620
gattgcaata taatgctgca tgttcaagat gaacagtagc tcctagtaat cataaaatcc   7680
actctttgca cagtttgatc tttactgaaa tatgttgcca aaatttattt ttgttgttgt   7740
agctctggat tttgttttgt tttgtttttt aaggaaacga ttgacaatac cctttaacat   7800
ctgtgactac taaggaaacc tatttctttc atagagagaa aaatctccaa tgcttttgaa   7860
gacactaata ccgtgctatt tcagatatgg gtgaggaagc agagctctcg gtaccgaagg   7920
ccgggcttct tgagctgtgt tggttgtcat ggctactgtt tcatgaacca caagcagctc   7980
aacagactgg tctgttgcct tctgaaaccc tttgcacttc aatttgcacc aggtgaaaac   8040
agggccagca gactccatgg cccaattcgg tttcttcggt ggtgatgtga aaggagagaa   8100
ttacactttt tttttttta agtggcgtgg aggcctttgc ttccacattt gtttttaacc   8160
cagaatttct gaaatagaga atttaagaac acatcaagta ataaatatac agagaatata   8220
ctttttttata aagcacatgc atctgctatt gtgttgggtt ggtttcctct cttttccacg   8280
gacagtgttg tgtttctggc atagggaaac tccaaacaac ttgcacacct ctactccgga   8340
gctgagattt cttttacata gatgacctcg cttcaaatac gttaccttac tgatgatagg   8400
atcttttctt gtagcactat accttgtggg aatttttttt taaatgtaca cctgatttga   8460
gaagctgaag aaaacaaaat tttgaagcac tcactttgag gagtacaggt aatgttttaa   8520
aaaattgcac aaaagaaaaa tgaatgtcga aatgattcat tcagtgtttg aaagatatgg   8580
ctctgttgaa acaatgagtt tcatactttg tttgtaaaaa aaaaaagcag agaagggttg   8640
aaagttacat gtttttttgt atatagaaat ttgtcatgtc taaatgatca gatttgtatg   8700
gttatggcct ggaagaatta ctacgtaaaa ggctcttaaa ctatacctat gcttattgtt   8760
atttttgtta catatagccc tcgtctgagg gaggggaact cggtattctg cgatttgaga   8820
atactgttca ttcctatgct gaaagtactt ctctgagctc ccttcttagt ctaaactctt   8880
aagccattgc aacttctttt tcttcagaga tgatgtttga cattttcagc acttcctgtt   8940
cctataaacc caaagaatat aatcttgaac acgaagtgtt tgtaacaagg gatccaggct   9000
accaatcaaa caggactcat tatggggaca aaaaaaaaaa aaattatttc accttctttc   9060
cccccacacc tcatttaaat ggggggagta aaaacatgat ttcaatgtaa atgcctcatt   9120
ttattttagt tttattttga tttttattta atataaagag gccagaataa atacggagca   9180
tcttctcaga atagtattcc tgtccaaaaa tcaagccgga cagtggaaac tggacagctg   9240
tggggatatt aagcaccccc acttacaatt cttaaattca gaatctcgtc ccctcccttc   9300
tcgttgaagg caactgttct ggtagctaac tttctcctgt gtaatggcgg gagggaacac   9360
cggcttcagt ttttcatgtc cccatgactt gcatacaaat ggttcaactg tattaaaatt   9420
aagtgcattt ggccaatagg tagtatctat acaataacaa caatctctaa gaatttccat   9480
```

-continued aacttttctt atctgaaagg actcaagtct tccactgcag atacattgga ggcttcaccc 9540
acgttttctt tccctttagt ttgtttgctg tctggatggc caatgagcct gtctcctttt 9600
ctgtggccaa tctgaaggcc ttcgttggaa gtgttgttca cagtaatcct taccaagata 9660
acatactgtc ctccagaata ccaagtatta ggtgacacta gctcaagctg ttgtcttcag 9720
agcagttacc aagaagctcg gtgcacaggt tttctctggt tcttacagga accacctact 9780
ctttcagttt tctggcccag gagtggggta aatcctttag ttagtgcatt tgaacttggt 9840
acctgtgcat tcagttctgt gaatactgcc ctttttggcg gggtttcctc atctccccag 9900
cctgaactgc tcaactctaa acccaaatta gtgtcagccg aaaggaggtt tcaagatagt 9960
cctgtcagta tttgtggtga ccttcagatt agacagtctt catttccagc cagtggagtc 10020
ctggctccag agccatctct gagactccgt actactggat gttttaatat cagatcatta 10080
cccaccatat gcctcccaca ggccaaggga aaacagacac cagaacttgg gttgagggca 10140
ctaccagact gacatggcca gtacagagga gaactaggga aggaatgatg ttttgcacct 10200
tattgaaaag aaaattttaa gtgcatacat aatagttaag agcttttatt gtgacaggag 10260 aactttttttc catatgcgtg catactctct gtaattccag tgtaaaatat tgtacttgca 10320
ctagcttttt taaacaaata ttaaaaaatg gaagaattca tattctattt tctaatcgtg 10380
gtgtgtctat ttgtaggata cactcgagtc tgtttattga attttatggt ccctttcttt 10440
gatggtgctt gcaggttttc taggtagaaa ttatttcatt attataataa aacaatgttt 10500
gattcaaaat ttgaacaaaa ttgttttaaa taaattgtct gtataccagt acaagtttat 10560
tgtttcagta tactcgtact aataaaataa cagtgccaat tgcaaaaaaa aaaaaaaaaa 10620
aaaaaaaaaa aaaaaaaaaa aaaaaaaaaa aaaaaaaaaa 10660

<210> SEQ ID NO 16
<211> LENGTH: 1900
<212> TYPE: DNA
<213> ORGANISM: Homo sapiens
<220> FEATURE:
<221> NAME/KEY: misc_feature
<222> LOCATION: (1)..(1900)
<223> OTHER INFORMATION: LOCUS MJD;1900 bp;mRNA;linear P;RI 31-JUL-2002
      DEFINITION  Homo sapiens Machado-Joseph disease (spinocerebellar
      ataxia 3, olivopontocerebellar ataxia 3
      ACCESSION   NM_004993
<300> PUBLICATION INFORMATION:
<308> DATABASE ACCESSION NUMBER: NM_004993
<309> DATABASE ENTRY DATE: 2002-07-31
<313> RELEVANT RESIDUES IN SEQ ID NO: (1)..(1900)

<400> SEQUENCE: 16
ggggcggagc tggagggggt ggttcggcgt gggggccgtt ggctccagac aaataaacat 60
ggagtccatc ttccacgaga aacaagaagg ctcactttgt gctcaacatt gcctgaataa 120
cttattgcaa ggagaatatt ttagccctgt ggaattatcc tcaattgcac atcagctgga 180
tgaggaggag aggatgagaa tggcagaagg aggagttact agtgaagatt atcgcacgtt 240
tttacagcag ccttctggaa atatggatga cagtggtttt ttctctattc aggttataag 300
caatgccttg aaagtttggg gtttagaact aatcctgttc aacagtccag agtatcagag 360
gctcaggatc gatcctataa atgaaagatc atttatatgc aattataagg aacactggtt 420
tacagttaga aaattaggaa aacagtggtt taacttgaat tctctcttga cgggtccaga 480
attaatatca gatacatatc ttgcactttt cttggctcaa ttacaacagg aaggttattc 540
tatatttgtc gttaagggtg atctgccaga ttgcgaagct gaccaactcc tgcagatgat 600

-continued

```
tagggtccaa cagatgcatc gaccaaaact tattggagaa gaattagcac aactaaaaga     660
gcaaagagtc cataaaacag acctggaacg agtgttagaa gcaaatgatg gctcaggaat     720
gttagacgaa gatgaggagg atttgcagag ggctctggca ctaagtcgcc aagaaattga     780
catggaagat gaggaagcag atctccgcag ggctattcag ctaagtatgc aaggtagttc     840
cagaaacata tctcaagata tgacacagac atcaggtaca aatcttactt cagaagagct     900
tcggaagaga cgagaagcct actttgaaaa acagcagcaa aagcagcaac agcagcagca     960
gcagcagcag caggggggacc tatcaggaca gagttcacat ccatgtgaaa ggccagccac   1020
cagttcagga gcacttggga gtgatctagg tgatgctatg agtgaagaag acatgcttca   1080
ggcagctgtg accatgtctt tagaaactgt cagaaatgat ttgaaaacag aaggaaaaaa   1140
ataatacctt taaaaaataa tttagatatt catactttcc aacattatcc tgtgtgatta   1200
cagcataggg tccactttgg taatgtgtca aagagatgag gaaataagac ttttagcggt   1260
ttgcaaacaa aatgatggga aagtggaaca atgcgtcggt tgtaggacta aataatgatc   1320
ttccaaatat tagccaaaga ggcattcagc aattaaagac atttaaaata gttttctaaa   1380
tgtttctttt tctttttga gtgtgcaata tgtaacatgt ctaaagttag ggcatttttc    1440
ttggatcttt ttgcagacta gctaattagc tctcgcctca ggctttttcc atatagtttg   1500
ttttcttttt ctgtcttgta ggtaagttgg ctcacatcat gtaatagtgg ctttcatttc   1560
ttattaacca aattaacctt tcaggaaagt atctctactt tcctgatgtt gataatagta   1620
atggttctag aaggatgaac agttctccct tcaactgtat accgtgtgct ccagtgtttt   1680
cttgtgttgt tttctctgat cacaactttt ctgctacctg gttttcatta ttttcccaca   1740
attcttttga aagatggtaa tcttttctga ggtttagcgt tttaagccct acgatgggat   1800
cattatttca tgactggtgc gttcctaaac tctgaaatca gccttgcaca agtacttgag   1860
aataaatgag catttttaa aaaaaaaaaa aaaaaaaaaa                            1900
```

<210> SEQ ID NO 17
<211> LENGTH: 1735
<212> TYPE: DNA
<213> ORGANISM: Homo sapiens
<220> FEATURE:
<221> NAME/KEY: misc_feature
<222> LOCATION: (1)..(1735)
<223> OTHER INFORMATION: LOCUS MJD;1735 bp;mRNA;linear P;RI 31-JUL-2002
DEFINITION Homo sapiens Machado-Joseph disease (spinocerebellar
ataxia 3, olivopontocerebellar ataxia 3, autosomal dominant,
ataxin 3) (MJD). ACCESSION NM_030660
<300> PUBLICATION INFORMATION:
<308> DATABASE ACCESSION NUMBER: NM_030660
<309> DATABASE ENTRY DATE: 2002-07-31
<313> RELEVANT RESIDUES IN SEQ ID NO: (1)..(1735)

<400> SEQUENCE: 17

```
ggggcggagc tggagggggt ggttcggcgt gggggccgtt ggctccagac aaataaacat     60
ggagtccatc ttccacgaga aacagccttc tggaaatatg gatgacagtg gtttttctc     120
tattcaggtt ataagcaatg ccttgaaagt ttggggttta gaactaatcc tgttcaacag    180
tccagagtat cagaggctca ggatcgatcc tataaatgaa agatcattta tatgcaatta    240
taaggaacac tggtttacag ttagaaaatt aggaaaacag tggtttaact tgaattctct    300
cttgacgggt ccagaattaa tatcagatac atatcttgca cttttcttgg ctcaattaca    360
acaggaaggt tattctatat ttgtcgttaa gggtgatctg ccagattgcg aagctgacca    420
actcctgcag atgattaggg tccaacagat gcatcgacca aaacttattg gagaagaatt    480
```

-continued agcacaacta aaagagcaaa gagtccataa aacagacctg gaacgagtgt tagaagcaaa 540
tgatggctca ggaatgttag acgaagatga ggaggatttg cagagggctc tggcactaag 600
tcgccaagaa attgacatgg aagatgagga agcagatctc cgcagggcta ttcagctaag 660
tatgcaaggt agttccagaa acatatctca agatatgaca cagacatcag gtacaaatct 720
tacttcagaa gagcttcgga agagacgaga agcctacttt gaaaaacagc agcaaaagca 780
gcaacagcag cagcagcagc agcagcaggg ggacctatca ggacagagtt cacatccatg 840
tgaaaggcca gccaccagtt caggagcact tgggagtgat ctaggtgatg ctatgagtga 900
agaagacatg cttcaggcag ctgtgaccat gtctttagaa actgtcagaa atgatttgaa 960
aacagaagga aaaaaataat acctttaaaa aataatttag atattcatac tttccaacat 1020
tatcctgtgt gattacagca tagggtccac tttggtaatg tgtcaaagag atgaggaaat 1080
aagactttta gcggtttgca aacaaaatga tgggaaagtg gaacaatgcg tcggttgtag 1140
gactaaataa tgatcttcca aatattagcc aaagaggcat tcagcaatta aagacattta 1200
aaatagtttt ctaaatgttt ctttttcttt tttgagtgtg caatatgtaa catgtctaaa 1260
gttagggcat ttttcttgga tctttttgca gactagctaa ttagctctcg cctcaggctt 1320
tttccatata gtttgttttc tttttctgtc ttgtaggtaa gttggctcac atcatgtaat 1380
agtggctttc atttcttatt aaccaaatta acctttcagg aaagtatctc tactttcctg 1440
atgttgataa tagtaatggt tctagaagga tgaacagttc tcccttcaac tgtataccgt 1500
gtgctccagt gttttcttgt gttgttttct ctgatcacaa cttttctgct acctggtttt 1560
cattattttc ccacaattct tttgaaagat ggtaatcttt tctgaggttt agcgttttaa 1620
gccctacgat gggatcatta tttcatgact ggtgcgttcc taaactctga aatcagcctt 1680
gcacaagtac ttgagaataa atgagcattt tttaaaaaaa aaaaaaaaaa aaaaa 1735

<210> SEQ ID NO 18
<211> LENGTH: 5832
<212> TYPE: RNA
<213> ORGANISM: Homo sapiens
<220> FEATURE:
<221> NAME/KEY: misc_feature
<222> LOCATION: (1)..(5832)
<223> OTHER INFORMATION: ACCESSION NM_012104
VERSION NM_012104.2 GI:21040369
<220> FEATURE:
<221> NAME/KEY: misc_feature
<222> LOCATION: (1)..(5832)
<223> OTHER INFORMATION: LOCUS BACE;5832 bp;mRNA;linear P; RI
05-NOV-2002
DEFINITION Homo sapiens beta-site APP-cleaving enzyme (BACE),
transcript variant a, mRNA.
<300> PUBLICATION INFORMATION:
<308> DATABASE ACCESSION NUMBER: NM_012104
<309> DATABASE ENTRY DATE: 2002-11-05
<313> RELEVANT RESIDUES IN SEQ ID NO: (1)..(5832)

<400> SEQUENCE: 18
uccccagccc gcccgggagc ugcgagccgc gagcuggauu augguggccu gagcagccaa 60
cgcagccgca ggagcccgga gcccuugccc cugcccgcgc cgccgcccgc cggggggacc 120
agggaagccg ccaccggccc gccaugcccg ccccucccag ccccgccggg agcccgcgcc 180
cgcugcccag gcuggccgcc gccgugccga uguagcgggc uccggauccc agccucuccc 240
cugcucccgu gcucugcgga ucuccccuga ccgcucucca cagcccggac ccgggggcug 300
gcccagggcc cugcaggccc uggcguccug augcccccaa gcucccucuc cugagaagcc 360

-continued

```
accagcacca cccagacuug ggggcaggcg ccagggacgg acgugggcca gugcgagccc    420
agagggcccg aaggccgggg cccaccaugg cccaagcccu gcccuggcuc cugcugugga    480
ugggcgcggg agugcugccu gcccacggca cccagcacgg cauccggcug ccccugcgca    540
gcggccuggg gggcgccccc cuggggcugc ggcugccccg ggagaccgac gaagagcccg    600
aggagcccgg ccggaggggc agcuuugugg agauggugga caaccugagg ggcaagucgg    660
ggcagggcua cuacguggag augaccgugg gcagcccccc gcagacgcuc aacauccugg    720
uggauacagg cagcaguaac uuugcagugg gugcugcccc ccaccccuuc cugcaucgcu    780
acuaccagag gcagcugucc agcacauacc gggaccuccg gaagggugug uaugugcccu    840
acacccaggg caagugggaa ggggagcugg gcaccgaccu gguaagcauc ccccauggcc    900
ccaacgucac ugugcgugcc aacauugcug ccaucacuga aucagacaag uucuucauca    960
acggcuccaa cugggaaggc auccuggggc uggccuaugc ugagauugcc aggccugacg   1020
acucccugga gccuuucuuu gacucucugg uaaagcagac ccacguuccc aaccucuucu   1080
cccugcagcu uuguggugcu ggcuuccccc ucaaccaguc ugaagugcug gccucugucg   1140
gagggagcau gaucauugga gguaucgacc acucgcugua cacaggcagu cucugguaua   1200
cacccauccg gcgggagugg uauuaugagg ucaucauugu gcggguggag aucaauggac   1260
aggaucugaa aauggacugc aaggaguaca acuaugacaa gagcauugug gacaguggca   1320
ccaccaaccu ucguuugccc aagaaagugu uugaagcugc agucaaaucc aucaaggcag   1380
ccuccuccac ggagaaguuc ccugaugguu ucuggcuagg agagcagcug gugugcuggc   1440
aagcaggcac caccccuugg aacauuuucc cagucaucuc acucuaccua augggugagg   1500
uuaccaacca guccuuccgc aucaccaucc uuccgcagca auaccugcgg ccaguggaag   1560
auguggccac gucccaagac gacuguuaca aguuugccau cucacaguca uccacgggca   1620
cuguuauggg agcuguuauc auggagggcu ucuacguugu cuuugaucgg gcccgaaaac   1680
gaauuggcuu ugcugucagc gcuugccaug ugcacgauga guucaggacg gcagcggugg   1740
aaggcccuuu ugucaccuug gacauggaag acuguggcua caacauucca cagacagaug   1800
agucaacccu caugaccaua gccuauguca uggcugccau cugcgcccuc uucaugcugc   1860
cacucugccu cauggugugu caguggcgcu gccuccgcug ccugcgccag cagcaugaug   1920
acuuugcuga ugacaucucc cugcugaagu gaggaggccc augggcagaa gauagagauu   1980
ccccuggacc acaccuccgu gguucacuuu ggucacaagu aggagacaca gauggcaccu   2040
guggccagag caccucagga cccucccac ccaccaaaug ccucugccuu gauggagaag   2100
gaaaaggcug gcaaggugggg uuccagggac uguaccugua ggaaacagaa aagagaagaa  2160
agaagcacuc ugcuggcggg aauacucuug gucaccucaa auuuaagucg ggaaauucug   2220
cugcuugaaa cuucagcccu gaaccuuugu ccaccauucc uuuaaauucu ccaacccaaa   2280
guauucuucu uuucuuaguu ucagaaguac uggcaucaca cgcagguuac cuuggcgugu   2340
gucccugugg uacccuggca gagaagagac caagcuuguu ucccugcugg ccaaagucag   2400
uaggagagga ugcacaguuu gcuauuugcu uuagagacag ggacuguaua aacaagccua   2460
acauuggugc aaagauugcc ucuugaauua aaaaaaaaaa cuagauugac uauuuauaca   2520
aaugggggcg gcuggaaaga ggagaaggag agggaguaca aagacaggga auagugggau   2580
caaagcuagg aaaggcagaa acacaaccac ucaccagucc uaguuuuaga ccucaucucc   2640
aagauagcau cccaucucag aagaugggug uuguuuucaa uguuuucuuu ucugugguug   2700
cagccugacc aaaagugaga ugggaagggc uuaucuagcc aaagagcucu uuuuuagcuc   2760
```

-continued

```
ucuuaaauga agugcccacu aagaaguucc acuuaacaca ugaauuucug ccauauuaau   2820
uucauugucu cuaucugaac cacccuuuau ucuacauaug auaggcagca cugaaauauc   2880
cuaacccccu aagcuccagg ugcccugugg gagagcaacu ggacuauagc agggcugggc   2940
ucugucuucc uggucauagg cucacucuuu cccccaaauc uuccucugga gcuuugcagc   3000
caaggugcua aaaggaauag guaggagacc ucuucuaucu aauccuuaaa agcauaaugu   3060
ugaacauuca uucaacagcu gaugcccuau aaccccugcc uggauuucuu ccuauuaggc   3120
uauaagaagu agcaagaucu uuacauaauu cagagugguu ucacugccuu ccuacccucu   3180
cuaauggccc cuccauuuau uugacuaaag caucacacag uggcacuagc auuauaccaa   3240
gaguaugaga aauacagugc uuuauggcuc uaacauuacu gccuucagua ucaaggcugc   3300
cuggagaaag gauggcagcc ucagggcuuc cuuauguccu ccaccacaag agcuccuuga   3360
ugaaggucau cuuuuucccc uauccuguuc uuccccuccc cgcuccuaau gguacguggg   3420
uacccaggcu gguucuuggg cuagguagug gggaccaagu ucauuaccuc ccuaucaguu   3480
cuagcauagu aaacuacggu accaguguua gugggaagag cuggguuuuc cuaguauacc   3540
cacugcaucc uacuccuacc uggucaaccc gcugcuucca gguaugggac cugcuaagug   3600
uggaauuacc ugauaaggga gagggaaaua caaggagggc cucuggugu ccuggccuca   3660
gccagcugcc cacaagccau aaaccaauaa aacaagaaua cugagucagu uuuuuaucug   3720
gguucucuuc auucccacug cacuuggugc ugcuuuggcu gacugggaac accccauaac   3780
uacagagucu gacaggaaga cuggagacug uccacuucua gcucggaacu uacuguguaa   3840
auaaacuuuc agaacugcua ccaugaagug aaaaugccac auuuugcuuu auaauuucua   3900
cccauguugg gaaaaacugg cuuuuuccca gcccuuucca gggcauaaaa cucaaccccu   3960
ucgauagcaa gucccaucag ccuauuauuu uuuuaaagaa aacuugcacu uguuuuucuu   4020
uuuacaguua cuuccuuccu gccccaaaau uauaaacucu aaguguaaaa aaaagucuua   4080
acaacagcuu cuugcuugua aaaauaugua uuauacaucu guauuuuuaa auucugcucc   4140
ugaaaaauga cugucccauu cuccacucac ugcauuuggg gccuuuccca uuggucugca   4200
ugucuuuuau cauugcaggc caguggacag agggagaagg gagaacaggg gucgccaaca   4260
cuuguguugc uuucugacug auccugaaca agaaagagua acacugaggc gcucgcuccc   4320
augcacaacu cuccaaaaca cuuauccucc ugcaagagug ggcuuuccag ggucuuuacu   4380
gggaagcagu uaagccccccu ccucaccccu uccuuuuuuc uuucuuuacu ccuuuggcuu   4440
caaaggauuu uggaaaagaa acaauaugcu uuacacucau uuucaauuuc uaaauuugca   4500
ggggauacug aaaaauacgg cagguggccu aaggcugcug uaaaguugag gggagaggaa   4560
aucuuaagau uacaagauaa aaaacgaauc cccuaaacaa aaagaacaau agaacugguc   4620
uuccauuuug ccaccuuucc uguucaugac agcuacuaac cuggagacag uaacauuuca   4680
uuaaccaaag aaaguggguc accugaccuc ugaagagcug aguacucagg ccacuccaau   4740
cacccuacaa gaugccaagg aggucccagg aaguccagcu ccuuaaacug acgcuaguca   4800
auaaaccugg gcaagugagg caagagaaau gaggaagaau ccaucuguga ggugacaggc   4860
aaggaugaaa gacaaagaag gaaaagagua ucaaaggcag aaaggagauc auuuaguugg   4920
gucugaaagg aaaagucuuu gcuauccgac auguacugcu aguaccugua agcauuuuag   4980
gucccagaau ggaaaaaaaa aucagcuauu gguaauauaa uaauguccuu ucccuggagu   5040
caguuuuuuu aaaaaguuaa cucuuaguuu uuacuuguuu aauucuaaaa gagaagggag   5100
```

-continued

```
cugaggccau ucccuguagg aguaaagaua aaaggauagg aaaagauuca aagcucuaau   5160

agagucacag cuuucccagg uauaaaaccu aaaauuaaga aguacaauaa gcagaggugg   5220

aaaaugaucu aguuccugau agcuacccac agagcaagug auuuauaaau uugaaaucca   5280

aacuacuuuc uuaauaucac uuuggucucc auuuuuccca ggacaggaaa uaugucccc   5340

ccuaacuuuc uugcuucaaa aauuaaaauc cagcauccca agaucauucu acaaguaauu   5400

uugcacagac aucuccucac cccagugccu gucuggagcu cacccaaggu caccaaacaa   5460

cuugguugug aaccaacugc cuuaaccuuc ugggggaggg ggauuagcua gacuaggaga   5520

ccagaaguga augggaaagg gugaggacuu cacaauguug gccugucaga gcuugauuag   5580

aagccaagac aguggcagca aaggaagacu uggcccagga aaaaccugug gguugugcua   5640

auuucugucc agaaaauagg guggacagaa gcuugugggg uacauggagg aauugggacc   5700

ugguuauguu guuauucucg gacugugaau uuuggugaug uaaaacagaa uauucuguaa   5760

accuaauguc uguauaaaua augagcguua acacaguaaa auauucaaua agaagucaaa   5820

cuacuagggu ua                                                       5832
```

<210> SEQ ID NO 19
<211> LENGTH: 5757
<212> TYPE: RNA
<213> ORGANISM: Homo sapiens
<220> FEATURE:
<221> NAME/KEY: misc_feature
<222> LOCATION: (1)..(5757)
<223> OTHER INFORMATION: LOCUS BACE;5757 bp;mRNA;linear P; RI
      05-NOV-2002
      DEFINITION  Homo sapiens beta-site APP-cleaving enzyme (BACE),
      transcript variant b, mRNA.
      ACCESSION   NM_138972; VERSION NM_138972.1  GI:21040365
<300> PUBLICATION INFORMATION:
<308> DATABASE ACCESSION NUMBER: NM_138972
<309> DATABASE ENTRY DATE: 2002-11-05
<313> RELEVANT RESIDUES IN SEQ ID NO: (1)..(5757)

<400> SEQUENCE: 19

```
uccccagccc gcccgggagc ugcgagccgc gagcuggauu augguggccu gagcagccaa     60

cgcagccgca ggagcccgga gcccuugccc cugcccgcgc cgccgcccgc cggggggacc    120

agggaagccg ccaccggccc gccaugcccg ccccucccag ccccgccggg agcccgcgcc    180

cgcugcccag gcuggccgcc gccgugccga uguagcgggc uccggauccc agccucuccc    240

cugcucccgu gcucugcgga ucuccccuga ccgcucucca cagcccggac ccgggggcug    300

gcccagggcc cugcaggccc uggcguccug augcccccaa gcucccucuc cugagaagcc    360

accagcacca cccagacuug gggcaggcg ccagggacgg acgugggcca gugcgagccc    420

agagggcccg aaggccgggg cccaccaugg cccaagcccu gcccuggcuc cugcugugga    480

ugggcgcggg agugcugccu gcccacggca cccagcacgg cauccggcug ccccugcgca    540

gcggccuggg gggcgccccc cuggggcugc ggcugccccg ggagaccgac gaagagcccg    600

aggagcccgg ccggaggggc agcuuugugg agauggugga caaccugagg ggcaagucgg    660

ggcagggcua cuacguggag augaccgugg gcagcccccc gcagacgcuc aacauccugg    720

uggauacagg cagcaguaac uuugcagugg gugcugcccc ccaccccuuc cugcaucgcu    780

acuaccagag gcagcugucc agcacauacc gggaccuccg gaagggugug uaugugcccu    840

acacccaggg caagugggaa ggggagcugg gcaccgaccu gguaagcauc ccccauggcc    900

ccaacgucac ugugcgugcc aacauugcug ccaucacuga aucagacaag uucuucauca    960

acggcuccaa cugggaaggc auccuggggc uggccuaugc ugagauugcc aggcuuugug   1020
```

-continued

```
gugcuggcuu cccccucaac cagucugaag ugcuggccuc ugucggaggg agcaugauca   1080
uuggagguau cgaccacucg cuguacacag gcagucucug guauacaccc auccggcggg   1140
agugguauua ugaggucauc auugugcggg uggagaucaa uggacaggau cugaaaaugg   1200
acugcaagga guacaacuau gacaagagca uuguggacag uggcaccacc aaccuucguu   1260
ugcccaagaa aguguuugaa gcugcaguca aauccaucaa ggcagccucc uccacggaga   1320
aguucccuga ugguuucugg cuaggagagc agcuggugug cuggcaagca ggcaccaccc   1380
cuuggaacau uuucccaguc aucucacucu accuaauggg ugagguuacc aaccaguccu   1440
uccgcaucac cauccuuccg cagcaauacc ugcggccagu ggaagaugug gccacguccc   1500
aagacgacug uuacaaguuu gccaucucac agucauccac gggcacuguu augggagcug   1560
uuaucaugga gggcuucuac guugucuuug aucgggcccg aaaacgaauu ggcuuugcug   1620
ucagcgcuug ccaugugcac gaugaguuca ggacggcagc gguggaaggc ccuuuuguca   1680
ccuuggacau ggaagacugu ggcuacaaca uuccacagac agaugaguca acccucauga   1740
ccauagccua ugucauggcu gccaucugcg cccucuucau gcugccacuc ugccucaugg   1800
ugugucagug gcgcugccuc cgcugccugc gccagcagca ugaugacuuu gcugaugaca   1860
ucucccugcu gaagugagga ggcccauggg cagaagauag agauuccccu ggaccacacc   1920
uccgugguuc acuuugguca caaguaggag acacagaugg caccuguggc cagagcaccu   1980
caggacccuc cccacccacc aaaugccucu gccuugaugg agaaggaaaa ggcuggcaag   2040
guggguucca gggacuguac cuguaggaaa cagaaaagag aagaaagaag cacucugcug   2100
gcgggaauac ucuuggucac cucaaauuua agucgggaaa uucugcugcu ugaaacuuca   2160
gcccugaacc uuuguccacc auuccuuuaa auucuccaac ccaaaguauu cuucuuuucu   2220
uaguuucaga aguacuggca ucacacgcag guuaccuugg cgugugucce uguggcaccc   2280
uggcagagaa gagaccaagc uuguuucccu gcuggccaaa gucaguagga gaggaugcac   2340
aguuugcuau uugcuuuaga gacagggacu guauaaacaa gccuaacauu ggugcaaaga   2400
uugccucuug aauuaaaaaa aaaaacuaga uugacuauuu auacaaaugg gggcggcugg   2460
aaagaggaga aggagaggga guacaaagac agggaauagu gggaucaaag cuaggaaagg   2520
cagaaacaca accacucacc aguccuaguu uuagaccuca ucuccaagau agcaucccau   2580
cucagaagau ggguguuguu uucaauguuu ucuuuucugu gguugcagcc ugaccaaaag   2640
ugagauggga agggcuuauc uagccaaaga gcucuuuuuu agcucucuua aaugaagugc   2700
ccacuaagaa guuccacuua acacaugaau uucugccaua uuaauuucau ugucucuauc   2760
ugaaccaccc uuuauucuac auaugauagg cagcacugaa auauccuaac cccuaagcu    2820
ccaggugccc ugugggagag caacuggacu auagcagggc ugggcucugu cuuccugguc   2880
auaggcucac ucuuuccccc aaaucuuccu cuggagcuuu gcagccaagg ugcuaaaagg   2940
aauagguagg agaccucuuc uaucuaaucc uuaaaagcau aauguugaac auucauucaa   3000
cagcugaugc ccuauaaccc cugccuggau uucuuccuau uaggcuauaa gaaguagcaa   3060
gaucuuuaca uaauucagag ugguuucacu gccuuccuac ccucucuaau ggccccucca   3120
uuuauuugac uaaagcauca cacaguggca cuagcauuau accaagagua ugagaaauac   3180
agugcuuuau ggcucuaaca uuacugccuu caguaucaag gcugccugga gaaaggaugg   3240
cagccucagg gcuuccuuau guccuccacc acaagagcuc cuugaugaag gucaucuuuu   3300
uccccuaucc uguucuuccc cuccccgcuc cuaaugguac gugggguaccc aggcugguuc  3360
```

-continued uugggcuagg uaguggggac caaguucauu accucccuau caguucuagc auaguaaacu 3420
acgguaccag uguuaguggg aagagcuggg uuuuccuagu auacccacug cauccuacuc 3480
cuaccugguc aacccgcugc uuccagguau gggaccugcu aaguguggaa uuaccugaua 3540
agggagaggg aaauacaagg agggccucug guguuccugg ccucagccag cugcccacaa 3600
gccauaaacc aauaaaacaa gaauacugag ucaguuuuuu aucugggguuc ucuucauucc 3660
cacugcacuu ggugcugcuu uggcugacug ggaacacccc auaacuacag agucugacag 3720
gaagacugga gacuguccac uucuagcucg gaacuuacug uguaaauaaa cuuucagaac 3780
ugcuaccaug aagugaaaau gccacauuuu gcuuuauaau uucuacccau guugggaaaa 3840
acuggcuuuu ucccagcccu uuccagggca uaaaacucaa ccccuucgau agcaaguccc 3900
aucagccuau uauuuuuuua aagaaaacuu gcacuuguuu uucuuuuuac aguuacuucc 3960
uuccugcccc aaaauuauaa acucuaagug uaaaaaaaag ucuuaacaac agcuucuugc 4020
uuguaaaaau auguauuaua caucuguauu uuuaaauucu gcuccugaaa aaugacuguc 4080
ccauucucca cucacugcau uuggggccuu ucccauuggu cugcaugucu uuuaucauug 4140
caggccagug gacagaggga gaagggagaa caggggucgc caacacuugu guugcuuucu 4200
gacugauccu gaacaagaaa gaguaacacu gaggcgcucg cucccaugca caacucucca 4260
aaacacuuau ccuccugcaa gaguggggcuu uccagggucu uuacugggaa gcaguuaagc 4320
ccccuccuca ccccuuccuu uuuucuuucu uuacuccuuu ggcuucaaag gauuuuggaa 4380
aagaaacaau augcuuuaca cucauuuuca auuucuaaau uugcagggga uacugaaaaa 4440
uacggcaggu ggccuaaggc ugcuguaaag uugaggggag aggaaaucuu aagauuacaa 4500
gauaaaaaac gaaucccccua aacaaaaaga acaauagaac uggucuucca uuuugccacc 4560
uuuccuguuc augacagcua cuaaccugga gacaguaaca uuucauuaac caaagaaagu 4620
gggucaccug accucugaag agcugaguac ucaggccacu ccaaucaccc uacaagaugc 4680
caaggagguc ccaggaaguc cagcuccuua aacugacgcu agucaauaaa ccugggcaag 4740
ugaggcaaga gaaaugagga agaauccauc ugugagguga caggcaagga ugaaagacaa 4800
agaaggaaaa gaguaucaaa ggcagaaagg agaucauuua guugggucug aaaggaaaag 4860
ucuuugcuau ccgacaugua cugcuaguac cuguaagcau uuuaggucccc agaauggaaa 4920
aaaaaaucag cuauugguaa uauaauaaug uccuuucccu ggagucaguu uuuuuaaaaa 4980
guuaacucuu aguuuuuacu uguuuaauuc uaaaagagaa gggagcugag gccauucccu 5040
guaggaguaa agauaaaagg auaggaaaag auucaaagcu cuaauagagu cacagcuuuc 5100
ccagguauaa aaccuaaaau uaagaaguac aauaagcaga gguggaaaau gaucuaguuc 5160
cugauagcua cccacagagc aagugauuua uaaauuugaa auccaaacua cuuucuuaau 5220
aucacuuugg ucuccauuuu ucccaggaca ggaaauaugu cccccccuaa cuuucuugcu 5280
ucaaaaauua aaauccagca ucccaagauc auucuacaag uaauuuugca cagacaucuc 5340
cucaccccag ugccugucug gagcucaccc aaggucacca aacaacuugg uugugaacca 5400
acugccuuaa ccuucugggg gagggggauu agcuagacua ggagaccaga agugaauggg 5460
aaagggugag gacuucacaa uguuggccug ucagagcuug auuagaagcc aagacagugg 5520
cagcaaagga agacuuggcc caggaaaaac cugugggguug ugcuaauuuc uguccagaaa 5580
auagggugga cagaagcuug ugggguacau ggaggaauug ggaccugguu auguuguuau 5640
ucucggacug ugaauuuugg ugauguaaaa cagaauauuc uguaaaccua augucuguau 5700
aaauaaugag cguuaacaca guaaaauauu caauaagaag ucaaacuacu aggguua 5757

-continued

<210> SEQ ID NO 20
<211> LENGTH: 5700
<212> TYPE: RNA
<213> ORGANISM: Homo sapiens
<220> FEATURE:
<221> NAME/KEY: misc_feature
<222> LOCATION: (1)..(5700)
<223> OTHER INFORMATION: LOCUS BACE;5700 bp;mRNA;linear P; RI
      21-MAY-2002
      DEFINITION  Homo sapiens beta-site APP-cleaving enzyme (BACE),
      transcript variant c, mRNA.
      ACCESSION   NM_138971; VERSION NM_138971.1  GI:21040363
<300> PUBLICATION INFORMATION:
<308> DATABASE ACCESSION NUMBER: NM_138971.1
<309> DATABASE ENTRY DATE: 2002-05-21
<313> RELEVANT RESIDUES IN SEQ ID NO: (1)..(5700)

<400> SEQUENCE: 20

```
uccccagccc gcccgggagc ugcgagccgc gagcuggauu augguggccu gagcagccaa     60
cgcagccgca ggagcccgga gcccuugccc cugcccgcgc cgccgcccgc cgggggggacc    120
agggaagccg ccaccggccc gccaugcccg ccccucccag ccccgccggg agcccgcgcc    180
cgcugcccag gcuggccgcc gccgugccga uguagcgggc uccggauccc agccucuccc    240
cugcuccccgu gcucugcgga ucuccccuga ccgcucucca cagcccggac ccgggggcug   300
gcccagggcc cugcaggccc uggcguccug augcccccaa gcucccucuc cugagaagcc    360
accagcacca cccagacuug gggcaggcg ccagggacgg acgugggcca gugcgagccc     420
agagggcccg aaggccgggg cccaccaugg cccaagcccu gcccuggcuc cugcugugga    480
ugggcgcggg agugcugccu gcccacggca cccagcacgg cauccggcug ccccugcgca    540
gcggccuggg gggcgccccc cuggggcugc ggcugccccg ggagaccgac gaagagcccg    600
aggagcccgg ccggaggggc agcuuugugg agauggugga caaccugagg ggcaagucgg    660
ggcagggcua cuacguggag augaccgugg gcagcccccc gcagacgcuc aacauccugg    720
uggauacagg cagcaguaac uuugcagugg gugcugcccc ccaccccuuc cugcaucgcu    780
acuaccagag gcagcugucc agcacauacc gggaccuccg gaagggugug uaugugcccu    840
acacccaggg caagugggaa ggggagcugg gcaccgaccu gccugacgac ucccuggagc    900
cuuucuuuga cucucuggua aagcagaccc acguucccaa ccucuucucc cugcagcuuu    960
guggugcugg cuucccccuc aaccagucug aagugcuggc cucugucgga gggagcauga   1020
ucauuggagg uaucgaccac ucgcuguaca caggcagucu cugguauaca cccauccggc   1080
gggaguggua uuaugagguc aucauugugc ggguggagau caauggacag gaucugaaaa   1140
uggacugcaa ggaguacaac uaugacaaga gcauugugga caguggcacc accaaccuuc   1200
guuugcccaa gaaaguguuu gaagcugcag ucaaauccau caaggcagcc uccuccacgg   1260
agaaguuccc ugaugguuuc uggcuaggag agcagcuggu gugcuggcaa gcaggcacca   1320
ccccuuggaa cauuuuccca gucaucucac ucuaccuaau gggugagguu accaaccagu   1380
ccuuccgcau caccauccuu ccgcagcaau accugcggcc aguggaagau guggccacgu   1440
cccaagacga cuguuacaag uuugccaucu cacagucauc cacgggcacu guuaugggag   1500
cuguuaucau ggagggcuuc uacguugucu uugaucgggc ccgaaaacga auuggcuuug   1560
cugucagcgc uugccaugug cacgaugagu ucaggacggc agcgguggaa ggcccuuuug   1620
ucaccuugga cauggaagac uguggcuaca acauuccaca gacagaugag ucaacccuca   1680
ugaccauagc cuaugucaug gcugccaucu gcgcccucuu caugcugcca cucugccuca   1740
```

-continued

```
ugguguguca guggcgcugc cuccgcugcc ugcgccagca gcaugaugac uuugcugaug   1800
acaucucccu gcugaaguga ggaggcccau gggcagaaga uagagauucc ccuggaccac   1860
accuccgugg uucacuuugg ucacaaguag gagacacaga uggcaccugu ggccagagca   1920
ccucaggacc cuccccaccc accaaaugcc ucugccuuga uggagaagga aaaggcuggc   1980
aaggugggu ccagggacug uaccuguagg aaacagaaaa gagaagaaag aagcacucug   2040
cuggcgggaa uacucuuggu caccucaaau uuaagucggg aaauucugcu gcuugaaacu   2100
ucagcccuga accuuugucc accauuccuu uaaauucucc aacccaaagu auucuucuuu   2160
ucuuaguuuc agaaguacug gcaucacacg cagguuaccu uggcgugugu cccugugua   2220
cccuggcaga gaagagacca agcuuguuuc ccugcuggcc aaagucagua ggagaggaug   2280
cacaguuugc uauuugcuuu agagacaggg acuguauaaa caagccuaac auuggugcaa   2340
agauugccuc uugaauuaaa aaaaaaaacu agauugacua uuuauacaaa ugggggcggc   2400
uggaaagagg agaaggagag ggaguacaaa gacagggaau agugggauca aagcuaggaa   2460
aggcagaaac acaaccacuc accaguccua guuuuagacc ucaucuccaa gauagcaucc   2520
caucucagaa gaugggguguu guuuucaaug uuuucuuuuc ugugguugca gccugaccaa   2580
aagugagaug ggaagggcuu aucuagccaa agagcucuuu uuuagcucuc uuaaaugaag   2640
ugcccacuaa gaaguuccac uuaacacaug aauuucugcc auauuaauuu cauugucucu   2700
aucugaacca cccuuuauuc uacauaugau aggcagcacu gaaauauccu aaccccccuaa   2760
gcuccaggug cccuguggga gagcaacugg acuauagcag ggcugggcuc ugucuuccug   2820
gucauaggcu cacucuuucc cccaaaucuu ccucuggagc uuugcagcca aggugcuaaa   2880
aggaauaggu aggagaccuc uucuaucuaa uccuuaaaag cauaauguug aacauucauu   2940
caacagcuga ugcccuauaa ccccugccug gauuucuucc uauuaggcua uaagaaguag   3000
caagaucuuu acauaauuca gagugguuuc acugccuucc uacccucucu aauggccccu   3060
ccauuuauuu gacuaaagca ucacacagug gcacuagcau uauaccaaga guaugagaaa   3120
uacagugcuu uauggcucua acauuacugc cuucaguauc aaggcugccu ggagaaagga   3180
uggcagccuc agggcuuccu uauguccucc accacaagag cuccuugaug aaggucaucu   3240
uuuuccccua uccuguucuu ccccuccccg cuccuaaugg uacgugggua cccaggcugg   3300
uucuugggcu agguaguggg gaccaaguuc auuaccuccc uaucaguucu agcauaguaa   3360
acuacgguac caguguuagu gggaagagcu ggguuuuccu aguauaccca cugcauccua   3420
cuccuaccug gucaacccgc ugcuuccagg uaugggaccu gcuaagugug gaauuaccug   3480
auaagggaga gggaaauaca aggagggccu cugguguucc uggccucagc cagcugccca   3540
caagccauaa accaauaaaa caagaauacu gagucaguuu uuuaucuggg uucucuucau   3600
ucccacugca cuuggugcug cuuuggcuga cugggaacac cccauaacua cagagucuga   3660
caggaagacu ggagacuguc cacuucuagc ucggaacuua cuguguaaau aaacuuucag   3720
aacugcuacc augaagugaa aaugccacau uuugcuuuau aauuucuacc cauguuggga   3780
aaaacuggcu uuuucccagc ccuuuccagg gcauaaaacu caaccccuuc gauagcaagu   3840
cccaucagcc uauuauuuuu uuaaagaaaa cuugcacuug uuuuucuuuu uacaguuacu   3900
uccuuccugc cccaaaauua uaaacucuaa guguaaaaaa aagucuuaac aacagcuucu   3960
ugcuuguaaa aauauguauu auacaucugu auuuuuaaau ucugcuccug aaaaaugacu   4020
gucccauucu ccacucacug cauuuggggc cuuucccauu ggucugcaug ucuuuuauca   4080
uugcaggcca guggacagag ggagaaggga gaacaggggu cgccaacacu uguguugcuu   4140
```

-continued

```
ucugacugau ccugaacaag aaagaguaac acugaggcgc ucgcucccau gcacaacucu   4200

ccaaaacacu uauccuccug caagaguggg cuuuccaggg ucuuuacugg gaagcaguua   4260

agccccccucc ucaccccuuc cuuuuuucuu ucuuuacucc uuuggcuuca aaggauuuug   4320

gaaaagaaac aauaugcuuu acacucauuu ucaauuucua aauuugcagg ggauacugaa   4380

aaauacggca gguggccuaa ggcugcugua aaguugaggg gagaggaaau cuuaagauua   4440

caagauaaaa aacgaauccc cuaaacaaaa agaacaauag aacuggucuu ccauuuugcc   4500

accuuuccug uucaugacag cuacuaaccu ggagacagua acauuucauu aaccaaagaa   4560

agugggucac cugaccucug aagagcugag uacucaggcc acuccaauca cccuacaaga   4620

ugccaaggag gucccaggaa guccagcucc uuaaacugac gcuagucaau aaaccugggc   4680

aagugaggca agagaaauga ggaagaaucc aucugugagg ugacaggcaa ggaugaaaga   4740

caaagaagga aaagaguauc aaaggcagaa aggagaucau uuaguugggu cugaaaggaa   4800

aagucuuugc uauccgacau guacugcuag uaccuguaag cauuuuaggu cccagaaugg   4860

aaaaaaaaau cagcuauugg uaauauaaua auguccuuuc ccuggaguca guuuuuuuaa   4920

aaaguuaacu cuuaguuuuu acuuguuuaa uucuaaaaga gaagggagcu gaggccauuc   4980

ccuguaggag uaaagauaaa aggauaggaa aagauucaaa gcucuaauag agucacagcu   5040

uucccaggua uaaaaccuaa aauuaagaag uacaauaagc agagguggaa aaugaucuag   5100

uuccugauag cuacccacag agcaagugau uuauaaauuu gaaauccaaa cuacuuucuu   5160

aauaucacuu uggucuccau uuuucccagg acaggaaaua uguccccccc uaacuuucuu   5220

gcuucaaaaa uuaaaaucca gcaucccaag aucauucuac aaguaauuuu gcacagacau   5280

cuccucaccc cagugccugu cuggagcuca cccaagguca ccaaacaacu ugguugugaa   5340

ccaacugccu uaaccuucug ggggaggggg auuagcuaga cuaggagacc agaagugaau   5400

gggaaagggu gaggacuuca caauguuggc cugucagagc uugauuagaa gccaagacag   5460

uggcagcaaa ggaagacuug gcccaggaaa aaccuguggg uugugcuaau uucuguccag   5520

aaaauagggu ggacagaagc uuguggggua cauggaggaa uugggaccug guuauguugu   5580

uauucucgga cugugaauuu uggugaugua aaacagaaua uucuguaaac cuaaugucug   5640

uauaaauaau gagcguuaac acaguaaaau auucaauaag aagucaaacu acuaggguua   5700
```

```
<210> SEQ ID NO 21
<211> LENGTH: 5625
<212> TYPE: RNA
<213> ORGANISM: Homo sapiens
<220> FEATURE:
<221> NAME/KEY: misc_feature
<222> LOCATION: (1)..(5625)
<223> OTHER INFORMATION: LOCUS BACE;5625 bp;mRNA;linear P; RI
      05-NOV-2002
      DEFINITION Homo sapiens beta-site APP-cleaving enzyme (BACE),
      transcript variant d, mRNA.
      ACCESSION   NM_138973; VERSION NM_138973.1 GI:21040367
<300> PUBLICATION INFORMATION:
<308> DATABASE ACCESSION NUMBER: NM_138973
<309> DATABASE ENTRY DATE: 2002-11-05
<313> RELEVANT RESIDUES IN SEQ ID NO: (1)..(5625)

<400> SEQUENCE: 21

uccccagccc gcccgggagc ugcgagccgc gagcuggauu augguggccu gagcagccaa     60

cgcagccgca ggagcccgga gcccuugccc cugcccgcgc cgccgcccgc cggggggacc    120

agggaagccg ccaccggccc gccaugcccg ccccucccag ccccgccggg agcccgcgcc    180
```

-continued

```
cgcugcccag gcuggccgcc gccgugccga uguagcgggc uccggauccc agccucuccc    240
cugcuccccgu gcucugcgga ucuccccuga ccgcucucca cagcccggac ccgggggcug    300
gcccagggcc cugcaggccc uggcguccug augcccccaa gcucccucuc cugagaagcc    360
accagcacca cccagacuug ggggcaggcg ccagggacgg acgugggcca gugcgagccc    420
agagggcccg aaggccgggg cccaccaugg cccaagcccu gcccuggcuc cugcugugga    480
ugggcgcggg agugcugccu gcccacggca cccagcacgg cauccggcug ccccugcgca    540
gcggccuggg gggcgccccc cuggggcugc ggcugccccg ggagaccgac gaagagcccg    600
aggagcccgg ccggaggggc agcuuugugg agauggugga caaccugagg ggcaagucgg    660
ggcagggcua cuacguggag augaccgugg gcagcccccc gcagacgcuc aacauccugg    720
uggauacagg cagcaguaac uuugcagugg gugcugcccc ccaccccuuc cugcaucgcu    780
acuaccagag gcagcugucc agcacauacc gggaccuccg gaagggugug uaugugcccu    840
acacccaggg caagugggaa ggggagcugg gcaccgaccu gcuuuguggu gcuggcuucc    900
cccucaacca gucugaagug cuggccucug ucggagggag caugaucauu ggagguaucg    960
accacucgcu guacacaggc agucucuggu auacacccau ccggcgggag ugguauuaug   1020
aggucaucau ugugcgggug gagaucaaug gacaggaucu gaaaauggac ugcaaggagu   1080
acaacuauga caagagcauu guggacagug gcaccaccaa ccuucguuug cccaagaaag   1140
uguuugaagc ugcagucaaa uccaucaagg cagccuccuc cacggagaag uucccugaug   1200
guuucuggcu aggagagcag cuggugugcu ggcaagcagg caccaccccu uggaacauuu   1260
ucccagucau cucacucuac cuaaugggug agguuaccaa ccaguccuuc cgcaucacca   1320
uccuuccgca gcaauaccug cggccagugg aagauguggc cacgucccaa gacgacuguu   1380
acaaguuugc caucucacag ucauccacgg gcacuguuau gggagcuguu aucauggagg   1440
gcuucuacgu ugucuuugau cgggcccgaa aacgaauugg cuuugcuguc agcgcuugcc   1500
augugcacga ugaguucagg acggcagcgg uggaaggccc uuuugucacc uuggacaugg   1560
aagacugugg cuacaacauu ccacagacag augagucaac ccucaugacc auagccuaug   1620
ucauggcugc caucugcgcc cucuucaugc ugccacucug ccucaugggug ugucaguggc   1680
gcugccuccg cugccugcgc cagcagcaug augacuuugc ugaugacauc ucccugcuga   1740
agugaggagg cccaugggca gaagauagag auuccccugg accacaccuc cgugguucac   1800
uuuggucaca aguaggagac acagauggca ccuguggcca gagcaccuca ggacccuccc   1860
cacccaccaa augccucugc cuugauggag aaggaaaagg cuggcaaggu ggguuccagg   1920
gacuguaccu guaggaaaca gaaaagagaa gaaagaagca cucugcuggc gggaauacuc   1980
uuggucaccu caaauuuaag ucgggaaauu cugcugcuug aaacuucagc ccugaaccuu   2040
uguccaccau uccuuuaaau ucuccaaccc aaaguauucu ucuuuucuua guuucagaag   2100
uacuggcauc acacgcaggu uaccuuggcg ugugucccug ugguacccug gcagagaaga   2160
gaccaagcuu guuucccugc uggccaaagu caguaggaga ggaugcacag uuugcuauuu   2220
gcuuuagaga cagggacugu auaaacaagc cuaacauugg ugcaaagauu gccucuugaa   2280
uuaaaaaaaa aaacuagauu gacuauuuau acaaaugggg gcggcuggaa agaggagaag   2340
gagagggagu acaaagacag ggaauagugg gaucaaagcu aggaaaggca gaaacacaac   2400
cacucaccag uccuaguuuu agaccucauc uccaagauag caucccaucu cagaagaugg   2460
guguuguuuu caauguuuuc uuuucugugg uugcagccug accaaaagug agaugggaag   2520
ggcuuaucua gccaaagagc ucuuuuuuag cucucuuaaa ugaagugccc acuaagaagu   2580
```

-continued uccacuuaac acaugaauuu cugccauauu aauuucauug ucucuaucug aaccacccuu 2640
uauucuacau augauaggca gcacugaaau auccuaaccc ccuaagcucc aggugcccug 2700
ugggagagca acuggacuau agcagggcug ggcucugucu uccuggucau aggcucacuc 2760
uuucccccaa aucuuccucu ggagcuuugc agccaaggug cuaaaaggaa uagguaggag 2820
accucuucua ucuaauccuu aaaagcauaa uguugaacau ucauucaaca gcugaugccc 2880
uauaacccu gccuggauuu cuuccuauua ggcuauaaga aguagcaaga ucuuuacaua 2940
auucagagug guuucacugc cuuccuaccc ucucuaaugg ccccuccauu uauuugacua 3000
aagcaucaca caguggcacu agcauuauac caagaguaug agaaauacag ugcuuuaugg 3060
cucuaacauu acugccuuca guaucaaggc ugccuggaga aaggauggca gccucagggc 3120
uuccuuaugu ccuccaccac aagagcuccu ugaugaaggu caucuuuuuc cccuauccug 3180
uucuuccccu ccccgcuccu aaugguacgu ggguacccag gcugguucuu gggcuaggua 3240
guggggacca aguucauuac cucccuauca guucuagcau aguaaacuac gguaccagug 3300
uuagugggaa gagcuggguu uuccuaguau acccacugca uccuacuccu accuggucaa 3360
cccgcugcuu ccagguaugg gaccugcuaa guguggaauu accugauaag ggagagggaa 3420
auacaaggag ggccucuggu guuccuggcc ucagccagcu gcccacaagc cauaaaccaa 3480
uaaaacaaga auacugaguc aguuuuuuau cuggguucuc uucauuccca cugcacuugg 3540
ugcugcuuug gcugacuggg aacaccccau aacuacagag ucugacagga agacuggaga 3600
cuguccacuu cuagcucgga acuuacugug uaaauaaacu uucagaacug cuaccaugaa 3660
gugaaaaugc cacauuuugc uuuauaauuu cuacccaugu ugggaaaaac uggcuuuuuc 3720
ccagcccuuu ccagggcaua aaacucaacc ccuucgauag caagucccau cagccuauua 3780
uuuuuuuaaa gaaaacuugc acuuguuuuu cuuuuuacag uuacuucuuu ccugccccaa 3840
aauuauaaac ucuaagugua aaaaaaaguc uuaacaacag cuucuugcuu guaaaaaauau 3900
guauuauaca ucuguauuuu uaaauucugc uccugaaaaa ugacuguccc auucuccacu 3960
cacugcauuu ggggccuuuc ccauuggucu gcaugucuuu uaucauugca ggccagugga 4020
cagagggaga agggagaaca ggggucgcca acacuugugu ugcuuucuga cugauccuga 4080
acaagaaaga guaacacuga ggcgcucgcu cccaugcaca acucuccaaa acacuuaucc 4140
uccugcaaga gugggcuuuc cagggucuuu acugggaagc aguuaagccc ccuccucacc 4200
ccuuccuuuu uucuuucuuu acuccuuugg cuucaaagga uuuuggaaaa gaaacaauau 4260
gcuuuacacu cauuuucaau uucuaaauuu gcaggggaua cugaaaaaua cggcaggugg 4320
ccuaaggcug cuguaaaguu gaggggagag gaaaucuuaa gauuacaaga uaaaaaacga 4380
aucccuaaa caaaaagaac aauagaacug gucuuccauu uugccaccuu uccuguucau 4440
gacagcuacu aaccuggaga caguaacauu ucauuaacca aagaaagugg gucaccugac 4500
cucugaagag cugaguacuc aggccacucc aaucacccua caagaugcca aggaggucccc 4560
aggaagucca gcuccuuaaa cugacgcuag ucaauaaacc ugggcaagug aggcaagaga 4620
aaugaggaag aauccaucug ugaggugaca ggcaaggaug aaagacaaag aaggaaaaga 4680
guaucaaagg cagaaaggag aucauuuagu ugggucugaa aggaaaaguc uuugcuaucc 4740
gacauguacu gcuaguaccu guaagcauuu uagguccag aauggaaaaa aaaaucagcu 4800
auugguaaua uaauaauguc cuuucccugg agucaguuuu uuuaaaaagu uaacucuuag 4860
uuuuuacuug uuuaauucua aaagagaagg gagcugaggc cauucccugu aggaguaaag 4920

-continued

```
auaaaaggau aggaaaagau ucaaagcucu aauagaguca cagcuuuccc agguauaaaa   4980

ccuaaaauua agaaguacaa uaagcagagg uggaaaauga ucuaguuccu gauagcuacc   5040

cacagagcaa gugauuuaua aauuugaaau ccaaacuacu uucuuaauau cacuuugguc   5100

uccauuuuuc ccaggacagg aaauaugucc cccccuaacu uucuugcuuc aaaaauuaaa   5160

auccagcauc ccaagaucau ucuacaagua auuuugcaca gacaucuccu caccccagug   5220

ccugucugga gcucacccaa ggucaccaaa caacuugguu gugaaccaac ugccuuaacc   5280

uucuggggga gggggauuag cuagacuagg agaccagaag ugaaugggaa agggugagga   5340

cuucacaaug uuggccuguc agagcuugau uagaagccaa gacaguggca gcaaaggaag   5400

acuuggccca ggaaaaaccu gugggguugug cuaauuucug uccagaaaau agggugggaca   5460

gaagcuugug ggguacaugg aggaauuggg accugguuau guuguuauuc ucggacugug   5520

aauuuuggug auguaaaaca gaauauucug uaaaccuaau gucuguauaa auaaugagcg   5580

uuaacacagu aaaauauuca auaagaaguc aaacuacuag gguua                   5625


<210> SEQ ID NO 22
<211> LENGTH: 3880
<212> TYPE: RNA
<213> ORGANISM: Mus musculus
<220> FEATURE:
<221> NAME/KEY: misc_feature
<222> LOCATION: (1)..(3880)
<223> OTHER INFORMATION: LOCUS Bace;3880 bp;mRNA;linear R
      OD 07-JAN-2002
      DEFINITION  Mus musculus beta-site APP cleaving enzyme (Bace),
      mRNA. ACCESSION   NM_011792; VERSION NM_011792.2 GI:6857758
<300> PUBLICATION INFORMATION:
<308> DATABASE ACCESSION NUMBER: NM_011792
<309> DATABASE ENTRY DATE: 2002-01-07
<313> RELEVANT RESIDUES IN SEQ ID NO: (1)..(3880)

<400> SEQUENCE: 22

ccccagccug ccuaggugcu gggagccggg agcuggauua ugguggccug agcagccgac     60

gcagccgcag gagcugggag ucccucacgc ugcaaagucc gccuggaaga cccugaaagc    120

ugcaggcucc gauagccaug cccgccccuc ccagccccac aaggggcccg aucccccgc    180

ugaggcuggc ggucgccguc cagauuuagc ugggucccc ggaucgccau cguccucuuc    240

ucucgugcgc uacagauuuc uccugcccac ucuccaccgc cgggagcagg aacugaucga    300

aggggccugc agacucugca guccugaugc ccccgaggcc gcucuccuga gagaagccac    360

caccacccag acuuaggggc aggcaagagg gacagucacc aaccggacca caaggcccgg    420

gcucacuaug gccccagcgc ugcacuggcu ccugcuaugg gugggcucgg gaaugcugcc    480

ugcccaggga acccaucucg gcauccggcu gccccuucgc agcggccugg cagggccacc    540

ccugggccug aggcugcccc gggagaccga cgaggaaucg gaggagccug gccggagagg    600

cagcuuugug gagauggugg acaaccugag gggaaagucc ggccagggcu acuaugugga    660

gaugaccgua ggcagccccc cacagacgcu caacauccug guggacacgg gcaguaguaa    720

cuuugcagug ggggcugccc cacacccuuu ccugcaucgc uacuaccaga ggcagcuguc    780

cagcacauau cgagaccucc gaaagggugu guaugugccc uacacccagg gcaaguggga    840

gggggaacug ggcaccgacc uggugagcau ccccucauggc cccaacguca cugugcgugc    900

caacauugcu gccaucacug aaucggacaa guucuucauc aaugguucca acugggaggg    960

cauccuaggg cuggccuaug cugagauugc caggcccgac gacucuuugg agcccuucuu   1020

ugacucccug gugaagcaga cccacauucc caacaucuuu ucccugcagc ucuguggcgc   1080
```

-continued

```
uggcuucccc cucaaccaga ccgaggcacu ggccucggug ggagggagca ugaucauugg   1140
ugguaucgac cacucgcuau acacgggcag ucucugguac acacccaucc ggcgggagug   1200
guauuaugaa gugaucauug uacgugugga aaucaauggu caagaucuca agauggacug   1260
caaggaguac aacuacgaca agagcauugu ggacaguggg accaccaacc uucgcuugcc   1320
caagaaagua uuugaagcug ccgucaaguc caucaaggca gccuccucga cggagaaguu   1380
cccggauggc uuuuggcuag gggagcagcu ggugugcugg caagcaggca cgaccccuug   1440
gaacauuuuc ccagucauuu cacuuuaccu caugggugaa gucaccaauc aguccuuccg   1500
caucaccauc cuuccucagc aauaccuacg gccgguggag gacguggcca cgucccaaga   1560
cgacuguuac aaguucgcug ucucacaguc auccacgggc acuguuaugg gagccgucau   1620
cauggaaggu uucuaugucg ucuucgaucg agcccgaaag cgaauuggcu uugcugucag   1680
cgcuugccau gugcacgaug aguucaggac ggcggcagug gaagguccgu uuguuacggc   1740
agacauggaa gacuguggcu acaacauucc ccagacagau gagucaacac uuaugaccau   1800
agccuauguc auggcggcca ucugcgcccu cuucauguug ccacucugcc ucaugguaug   1860
ucaguggcgc ugccugcguu gccugcgcca ccagcacgau gacuuugcug augacaucuc   1920
ccugcucaag uaaggaggcc cgugggcaga ugauggagac gccccuggac cacaucuggg   1980
ugguucccuu uggucacaug aguuggagcu auggauggua ccuguggcca gagcaccuca   2040
ggacccucac caaccugcca augcuucugg cgugacagaa cagagaaauc aggcaagcug   2100
gauuacaggg cuugcaccug uaggacacag gagagggaag gaagcagcgu ucugguggca   2160
ggaauauccu uagacaccac aaacuugagu uggaaauuuu gcugcuugaa gcuucagccc   2220
ugacccucug cccagcaucc uuuagagucu ccaaccucga guauucuuuc uguccuucca   2280
gaaguacugg ugucauacuc aggcuacccg gcaugugucc cugugguacc cuggcagaga   2340
aagggccaau cuucauuucc ccugcuggcc aaagucagca gaagaaagug aaguuugcca   2400
guugcuuuag ugauagggac uugcagacuc aagccuacac ugguacaaag acugcgucuu   2460
gagauaaaca agaaccuaug cgaugcgaau guuuauacuc cugggggcag ucaagaugag   2520
gagacaggau aggauagaga caggaaggag augguagcaa aacugggaaa ggcagaacuc   2580
ugaucacuuu cuaguuccaa guuuagacuc aucuccaaga cagaagccca ucuggacuaa   2640
gagguaucau uccccaaugu gccugugguu guagucugaa cugaaaugaa augggggaaa   2700
aagggcuuau uagccaaaga gcucuuuuua acacucuuag aggaacagug cucaugagaa   2760
aagucccacu ggacagauga auuccuaucu uguuaauucu gucucucucu gcuucuucaa   2820
caugcuaagu ggcaccaaaa ugacccaacc ccaaggucuu aggugcccua ugggacaaca   2880
guuagaauau uguagggcua gggauggucu ucccagcaua gguucacucc aaccaaggug   2940
cuaaaaggaa cagacaggag aaguccuccu cucugaucca caaaggcaga gcccucaaga   3000
uucauccagc caggguuagg gcugaugcau uugccucugc cuggauuuug uuuuuauuuu   3060
cuuucuuuuu gcccaagugg guacaaaacg auaagcucuu uauggaauac ugagugggu u  3120
cauuccucuc uugcccucuc caauggcccc ucuauuuauc uggcuaagga aacaccacgc   3180
auuggcuagu auuaaacagc aacuguaaga uagagggcuu ucuguucuau gucauugccu   3240
ucaguaucaa ggcugccugg agaaaggaug gcagccucag ggcuuccuua cuuucuucuc   3300
cuuuccugac agagcagccu uucuguccug cucucugcug ccccucccaa uauaauccau   3360
ggguacccag gcugguucuu gggcuagguu guggggccca cacucaccuc uucccugcca   3420
guucuaacac gacagacaug aagccagugu uagugggaag agcuggguuu ucccaggaug   3480
```

accacugcau ccucuccugg uacgcucuac acugcuuuca ggcuggggac cugccaagug 3540
ugggacaguu gaugaggaag agacauuagc agggccucug gaguugcugg cccagccagc 3600
ugcccacaag ccauaaacca auaaaauaag aauccugcgu cacaguuucc agcugggucc 3660
ucuuccuugc ccucgcacug gugcugcucu ggcugaguag gaauacaccc acagacugcc 3720
aggaagaugg agacuguccg cuuccggcuc agaacuacag uguaauuaag cuuccaggau 3780
cacuaccaug aaaacgccgc auucugcuuu aucauuucua cccauguugg gaaaaacugg 3840
cuuuuucccc auuucuuuac agggcaaaaa aaaaaaaaaa 3880

<210> SEQ ID NO 23
<211> LENGTH: 1096
<212> TYPE: RNA
<213> ORGANISM: Homo sapiens
<220> FEATURE:
<221> NAME/KEY: misc_feature
<222> LOCATION: (1)..(1096)
<223> OTHER INFORMATION: LOCUS SNCA;1096 bp;mRNA;linear P; RI
05-NOV-2002
DEFINITION Homo sapiens synuclein, alpha (non A4 component of
amyloid precursor) (SNCA), transcript variant NACP112, mRNA.
ACCESSION NM_007308: VERSION NM_007308.1 GI:6806897
<300> PUBLICATION INFORMATION:
<308> DATABASE ACCESSION NUMBER: NM_007308
<309> DATABASE ENTRY DATE: 2002-12-05
<313> RELEVANT RESIDUES IN SEQ ID NO: (1)..(1096)

<400> SEQUENCE: 23
gaauucauua gccauggaug uauucaugaa aggacuuuca aaggccaagg agggaguugu 60
ggcugcugcu gagaaaacca aacagggugu ggcagaagca gcaggaaaga caaaagaggg 120
uguucucuau guaggcucca aaaccaagga gggagguggug cauggugugg caacaguggc 180
ugagaagacc aaagagcaag ugacaaaugu uggaggagca guggugacgg gugugacagc 240
aguagcccag aagacagugg agggagcagg gagcauugca gcagccacug gcuuugucaa 300
aaaggaccag uugggcaagg aagggguauca agacuacgaa ccugaagccu aagaaauauc 360
uuugcuccca guuucuugag aucugcugac agauguucca uccuguacaa gugcucaguu 420
ccaaugugcc cagucaugac auuucucaaa guuuuuacag uguaucucga agucuuccau 480
cagcagugau ugaaguaucu guaccugccc ccacucagca uuucggugcu ucccuuucac 540
ugaagugaau acaugguagc agggucuuug ugugcugugg auuuuguggc uucaaucuac 600
gauguuaaaa caaauuaaaa acaccuaagu gacuaccacu uauuucuaaa uccucacuau 660
uuuuuuguug cuguuguuca gaaguuguua gugauuugcu aucauauauu auaagauuuu 720
uaggugucuu uuaaugauac ugucuaagaa uaaugacgua uugugaaauu uguuaauaua 780
uauaauacuu aaaaauaugu gagcaugaaa cuaugcaccu auaaauacua aauaugaaau 840
uuuaccauuu ugcgaugugu uuuauucacu uguguuugua uauaaauggu gagaauuaaa 900
auaaaacguu aucucauugc aaaaauauuu uauuuuuauc ccaucucacu uuaauaauaa 960
aaaucaugcu uauaagcaac augaauuaag aacugacaca aaggacaaaa auauaaaguu 1020
auuaauagcc auuugaagaa ggaggaauuu uagaagaggu agagaaaaug gaacauuaac 1080
ccuacacucg gaauuc 1096

<210> SEQ ID NO 24
<211> LENGTH: 21
<212> TYPE: DNA
<213> ORGANISM: Mus musculus
<220> FEATURE:

-continued

```
<221> NAME/KEY: misc_feature
<222> LOCATION: (1)..(21)
<223> OTHER INFORMATION: Starting position within mouse BACE1 cDNA
      (Genbank Accession NM_011792) and corresponding human sequences.
      DNA sequence corresponding to the therapeutic siRNA starting at
      base 0803. The two 5' nucleotides AA are optional in MB0803.

<400> SEQUENCE: 24

aagggtgtgt atgtgcccta c                                              21


<210> SEQ ID NO 25
<211> LENGTH: 21
<212> TYPE: DNA
<213> ORGANISM: Mus Musculus
<220> FEATURE:
<221> NAME/KEY: misc_feature
<222> LOCATION: (1)..(21)
<223> OTHER INFORMATION: Starting position within mouse BACE1 cDNA
      (Genbank Accession NM_011792) and corresponding human sequences.
      DNA sequence corresponding to the therapeutic siRNA starting at
      base 1663. The two 5' nucleotides AA are optional in MB1663.

<400> SEQUENCE: 25

aattggcttt gctgtcagcg c                                              21


<210> SEQ ID NO 26
<211> LENGTH: 21
<212> TYPE: DNA
<213> ORGANISM: Mus Musculus
<220> FEATURE:
<221> NAME/KEY: misc_feature
<222> LOCATION: (1)..(21)
<223> OTHER INFORMATION: Starting position within mouse BACE1 cDNA
      (Genbank Accession NM_011792) and corresponding human sequences.
      DNA sequence corresponding to the therapeutic siRNA starting at
      base 1749. The two 5' nucleotides AA are optional in MB1749.

<400> SEQUENCE: 26

aagactgtgg ctacaacatt c                                              21


<210> SEQ ID NO 27
<211> LENGTH: 21
<212> TYPE: DNA
<213> ORGANISM: Mus Musculus
<220> FEATURE:
<221> NAME/KEY: misc_feature
<222> LOCATION: (1)..(21)
<223> OTHER INFORMATION: Starting position within mouse BACE1 cDNA
      (Genbank Accession NM_011792) and corresponding human sequences.
      DNA sequence corresponding to the therapeutic siRNA starting at
      base 3249. The two 5' nucleotides AA are optional in MB3249.

<400> SEQUENCE: 27

aaggctgcct ggagaaagga t                                              21


<210> SEQ ID NO 28
<211> LENGTH: 21
<212> TYPE: DNA
<213> ORGANISM: Mus Musculus
<220> FEATURE:
<221> NAME/KEY: misc_feature
<222> LOCATION: (1)..(21)
<223> OTHER INFORMATION: Starting position within mouse BACE1 cDNA
      (Genbank Accession NM_011792) and corresponding human sequences.
      DNA sequence corresponding to the therapeutic siRNA starting at
      base 0916. The two 5' nucleotides CA are optional in DhMB0918.

<400> SEQUENCE: 28

cactgaatcg gacaagttct t                                              21
```

-continued

<210> SEQ ID NO 29
<211> LENGTH: 21
<212> TYPE: DNA
<213> ORGANISM: Mus Musculus
<220> FEATURE:
<221> NAME/KEY: misc_feature
<222> LOCATION: (1)..(21)
<223> OTHER INFORMATION: Starting position within mouse BACE1 cDNA
(Genbank Accession NM_011792) and corresponding human sequences.
DNA sequence corresponding to the therapeutic siRNA starting at
base 1129. The two 5' nucleotides CA are optional in DhMB1131.

<400> SEQUENCE: 29
catgatcatt ggtggtatcg a 21

<210> SEQ ID NO 30
<211> LENGTH: 21
<212> TYPE: DNA
<213> ORGANISM: Mus Musculus
<220> FEATURE:
<221> NAME/KEY: misc_feature
<222> LOCATION: (1)..(21)
<223> OTHER INFORMATION: Starting position within mouse BACE1 cDNA
(Genbank Accession NM_011792) and corresponding human sequences.
DNA sequence corresponding to the therapeutic siRNA starting at
base 1231. The two 5' nucleotides AA are optional in DhMB1233.

<400> SEQUENCE: 30
aatcaatggt caagatctca a 21

<210> SEQ ID NO 31
<211> LENGTH: 21
<212> TYPE: DNA
<213> ORGANISM: Mus Musculus
<220> FEATURE:
<221> NAME/KEY: misc_feature
<222> LOCATION: (1)..(21)
<223> OTHER INFORMATION: Starting position within mouse BACE1 cDNA
(Genbank Accession NM_011792) and corresponding human sequences.
DNA sequence corresponding to the therapeutic siRNA starting at
base 1507. The two 5' nucleotides CA are optional in DhMB1509.

<400> SEQUENCE: 31
catccttcct cagcaatacc t 21

<210> SEQ ID NO 32
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: Starting position within mouse BACE1 cDNA
(Genbank Accession NM_011792) and corresponding human sequences.
DNA sequence corresponding to the therapeutic siRNA starting at
base 0683. The two 5' nucleotides CA are optional in SEC0683.

<400> SEQUENCE: 32
cagacgctca acatcctggt g 21

<210> SEQ ID NO 33
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: Starting position within mouse BACE1 cDNA
(Genbank Accession NM_011792) and corresponding human sequences.
DNA sequence corresponding to the therapeutic siRNA starting at -continued base 1722. The two 5' nucleotides AA are optional in SEC1722.

<400> SEQUENCE: 33
aaggtccgtt tgttacggca g 21

<210> SEQ ID NO 34
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: Starting position within mouse BACE1 cDNA (Genbank Accession NM_011792) and corresponding human sequences. DNA sequence corresponding to the therapeutic siRNA starting at base 2163. The two 5' nucleotides AA are optional in SEC2163.

<400> SEQUENCE: 34
aatatcctta gacaccacaa a 21

<210> SEQ ID NO 35
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: Starting position within mouse BACE1 cDNA (Genbank Accession NM_011792) and corresponding human sequences. DNA sequence corresponding to the therapeutic siRNA starting at base 2466. The two 5' nucleotides AA are optional in SEC2466.

<400> SEQUENCE: 35
aaacaagaac ctatgcgatg c 21

<210> SEQ ID NO 36
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: Starting position within mouse BACE1 cDNA (Genbank Accession NM_011792) and corresponding human sequences. DNA sequence corresponding to the therapeutic siRNA starting at base 2473. The two 5' nucleotides AA are optional in SEC2473.

<400> SEQUENCE: 36
aacctatgcg atgcgaatgt t 21

<210> SEQ ID NO 37
<211> LENGTH: 22
<212> TYPE: DNA
<213> ORGANISM: Mus musculus
<220> FEATURE:
<221> NAME/KEY: misc_feature
<222> LOCATION: (1)..(22)
<223> OTHER INFORMATION: Oligonucleotide MB1749A to construct the DNA encoding for a hairpin loop of RNA corresponding to MB1749.

<400> SEQUENCE: 37
gaagactgtg gctacaacat tc 22

<210> SEQ ID NO 38
<211> LENGTH: 38
<212> TYPE: DNA
<213> ORGANISM: Mus musculus
<220> FEATURE:
<221> NAME/KEY: misc_feature -continued
<222> LOCATION: (1)..(38)
<223> OTHER INFORMATION: Oligonucleotide MB1749B to construct the DNA encoding for a hairpin loop of RNA corresponding to MB1749.

<400> SEQUENCE: 38
ttcaagagag aatgttgtag ccacagtctt cttttttg 38

<210> SEQ ID NO 39
<211> LENGTH: 35
<212> TYPE: DNA
<213> ORGANISM: Mus musculus
<220> FEATURE:
<221> NAME/KEY: misc_feature
<222> LOCATION: (1)..(35)
<223> OTHER INFORMATION: Oligonucleotide MB1749C to construct the DNA encoding for a hairpin loop of RNA corresponding to MB1749.

<400> SEQUENCE: 39
tctcttgaag aatgttgtag ccacagtctt cggcc 35

<210> SEQ ID NO 40
<211> LENGTH: 33
<212> TYPE: DNA
<213> ORGANISM: Mus musculus
<220> FEATURE:
<221> NAME/KEY: misc_feature
<222> LOCATION: (1)..(33)
<223> OTHER INFORMATION: Oligonucleotide MB1749D to construct the DNA encoding for a hairpin loop of RNA corresponding to MB1749.

<400> SEQUENCE: 40
aattcaaaaa agaagactgt ggctacaaca ttc 33

<210> SEQ ID NO 41
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Oligonucleotide MD0188 to construct the DNA encoding for siRNA starting at position 0188 within human Huntington cDNA(Genbank Accession NM_002111.3. The first two 5' nucleotides AA are optional in MD0188.

<400> SEQUENCE: 41
aagatggacg gccgctcagg t 21

<210> SEQ ID NO 42
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Oligonucleotide MD0358 to construct the DNA encoding for siRNA starting at position 0358 within human Huntington cDNA(Genbank Accession NM_002111.3. The first two 5' nucleotides AA are optional in MD0358.

<400> SEQUENCE: 42
aagtccttcc agcagcagca g 21

<210> SEQ ID NO 43
<211> LENGTH: 21
<212> TYPE: DNA
<213> ORGANISM: Homo sapiens
<220> FEATURE:
<221> NAME/KEY: misc_feature

```
<222> LOCATION: (1)..(21)
<223> OTHER INFORMATION: Oligonucleotide MD0813 to construct the DNA
      encoding for siRNA starting at position 0813 within human
      Huntington cDNA (Genbank Accession NM_002111.3.). The first two 5'
      nucleotides AA are optional in MD0813.

<400> SEQUENCE: 43

aaggttacag ctcgagctct a                                              21

<210> SEQ ID NO 44
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Oligonucleotide M1066 to construct the DNA
      encoding for siRNA starting at position 1066 within human
      Huntington cDNA (Genbank Accession NM_002111.3.). The two 5'
      nucleotides AA are optional in M1066.

<400> SEQUENCE: 44

aaggttttgt taaaggcctt c                                              21

<210> SEQ ID NO 45
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Oligonucleotide M1639 to construct the DNA
      encoding for siRNA starting at position 1639 within human
      Huntington cDNA (Genbank Accession NM_002111.3.). The two 5'
      nucleotides AA are optional in M1639.

<400> SEQUENCE: 45

aaaggcaaag tgctcttagg a                                              21

<210> SEQ ID NO 46
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Oligonucleotide M2060 to construct the DNA
      encoding for siRNA starting at position 2060 within human
      Huntington cDNA (Genbank Accession NM_002111.3.). The two 5'
      nucleotides AA are optional in M2060.

<400> SEQUENCE: 46

aaattgtgtt agacggtacc g                                              21

<210> SEQ ID NO 47
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Oligonucleotide M2714 to construct the DNA
      encoding for siRNA starting at position 2714 within human
      Huntington cDNA (Genbank Accession NM_002111.3.). The two 5'
      nucleotides CA are optional in M2714.

<400> SEQUENCE: 47

caggaaatac attttctttg g                                              21
```

-continued

<210> SEQ ID NO 48
<211> LENGTH: 846
<212> TYPE: DNA
<213> ORGANISM: Ovis aries

<400> SEQUENCE: 48
atggcgaccc tggaaaagct gatgaaggcc ttcgagtccc tcaagtcctt ccagcagcag 60
cagcagcagc agcagcagca gcagcagcaa cagccgccac cgccgccacc cggcccggct 120
gtggctgagg agccgctgca ccgaccaaag aaagagctct cagccaccaa gaaagaccgc 180
gtgaaccact gtctgacaat ctgtgaaaac atcgtcgcgc agtctctcag aaattctcca 240
gaatttcaga aacttctggg catcgctatg gaactttttc tgctgtgcag tgatgacgca 300
gagtcagatg tcaggatggt ggctgacgaa tgcctcaaca aagtcataaa agctttgatg 360
gactctaatc ttccgaggtt gcagctagaa ctctacaagg aaattaaaaa gaacggcgcc 420
ccgcggagcc tgcgcgcggc cctctggagg ttcgccgagc tggctcacct ggtccggcct 480
cagaagtgca ggccgtacct ggtgaacctg ttgccctgcc tgacgcgcac aagcaagaga 540
cccgaggagt ccgtccagga gacgctggct gcagcgatcc ctaaaattat ggcttctttt 600
ggcaactttg cgaacgacaa tgagattaag gttctgttga aggctttcat cgcgaacctg 660
aagtccagtt ccccgactgt gcggcggacc gcggcgggct cagtggtcag catctgccag 720
cactccagga ggacgcagta cttttacagc tggctgctca gcgtgctcct aggtttgctg 780
gtccccgtgg aggaggagca ccccaccctg ctgatcctcg gcgtcctgct caccctgagg 840
tatctg 846

<210> SEQ ID NO 49
<211> LENGTH: 21
<212> TYPE: DNA
<213> ORGANISM: Ovis aries
<220> FEATURE:
<221> NAME/KEY: misc_feature
<222> LOCATION: (1)..(21)
<223> OTHER INFORMATION: Oligonucleotide EB1 to construct the DNA encoding for siRNA starting at position 205 in sheep Huntington sequence and starting position 643 of the (partially) homologous sequence in the human Huntington gene (NM_00211.3).
<220> FEATURE:
<223> OTHER INFORMATION: The two 5' nucleotides GA are optional in EB1.

<400> SEQUENCE: 49
gaaaacatcg tcgcgcagtc t 21

<210> SEQ ID NO 50
<211> LENGTH: 21
<212> TYPE: DNA
<213> ORGANISM: Ovis aries
<220> FEATURE:
<221> NAME/KEY: misc_feature
<222> LOCATION: (1)..(21)
<223> OTHER INFORMATION: Oligonucleotide EB2 to construct the DNA encoding for siRNA starting at position 328 in sheep Huntington sequence and starting position 766 of the (partially) homologous sequence in the human Huntington gene (NM_00211.3).
<220> FEATURE:
<223> OTHER INFORMATION: The two 5' nucleotides GA are optional in EB2.

<400> SEQUENCE: 50
gaatgcctca acaaagtcat a 21

<210> SEQ ID NO 51
<211> LENGTH: 21
<212> TYPE: DNA

-continued

<213> ORGANISM: Ovis aries
<220> FEATURE:
<221> NAME/KEY: misc_feature
<222> LOCATION: (1)..(21)
<223> OTHER INFORMATION: Oligonucleotide EB3 to construct the DNA encoding for siRNA starting at position 603 in sheep Huntington sequence and starting position 1041 of the (partially) homologous sequence in the human Huntington gene (NM_00211.3).
<220> FEATURE:
<223> OTHER INFORMATION: The two 5' nucleotides CA are optional in EB3.

<400> SEQUENCE: 51
caactttgcg aacgacaatg a 21

<210> SEQ ID NO 52
<211> LENGTH: 21
<212> TYPE: DNA
<213> ORGANISM: Ovis aries
<220> FEATURE:
<221> NAME/KEY: misc_feature
<222> LOCATION: (1)..(21)
<223> OTHER INFORMATION: Oligonucleotide EB4 to construct the DNA encoding for siRNA starting at position 628 in sheep Huntington sequence and starting position 1066 of the (partially) homologous sequence in the human Huntington gene (NM_00211.3).
<220> FEATURE:
<223> OTHER INFORMATION: The two 5' nucleotides AA are optional in EB4.

<400> SEQUENCE: 52
aaggttctgt tgaaggcttt c 21

<210> SEQ ID NO 53
<211> LENGTH: 21
<212> TYPE: DNA
<213> ORGANISM: Ovis aries
<220> FEATURE:
<221> NAME/KEY: misc_feature
<222> LOCATION: (1)..(21)
<223> OTHER INFORMATION: Oligonucleotide EB5 to construct the DNA encoding for siRNA starting at position 367 in sheep Huntington sequence and starting position 805 of the (partially) homologous sequence in the human Huntington gene (NM_00211.3).
<220> FEATURE:
<223> OTHER INFORMATION: The two 5' nucleotides AA are optional in EB5.

<400> SEQUENCE: 53
aatcttccga ggttgcagct a 21

<210> SEQ ID NO 54
<211> LENGTH: 1500
<212> TYPE: DNA
<213> ORGANISM: Homo sapiens

<400> SEQUENCE: 54
ttgctgtgtg aggcagaacc tgcgggggca ggggcgggct ggttccctgg ccagccattg 60
gcagagtccg caggctaggg ctgtcaatca tgctggccgg cgtggccccg cctccgccgg 120
cgcggccccg cctccgccgg cgcacgtctg ggacgcaagg cgccgtgggg gctgccggga 180
cgggtccaag atggacggcc gctcaggttc tgcttttacc tgcggcccag agccccattc 240
attgccccgg tgctgagcgg cgccgcgagt cggcccgagg cctccgggga ctgccgtgcc 300
gggcgggaga ccgccatggc gaccctggaa aagctgatga aggccttcga gtccctcaag 360
tccttccagc agcagcagca gcagcagcag cagcagcagc agcagcagca gcagcagcag 420
cagcagcagc aacagccgcc accgccgccg ccgccgccgc cgcctcctca gcttcctcag 480
ccgccgccgc aggcacagcc gctgctgcct cagccgcagc cgcccccgcc gccgccccg 540

-continued

```
ccgccacccg gcccggctgt ggctgaggag ccgctgcacc gaccaaagaa agaactttca    600

gctaccaaga aagaccgtgt gaatcattgt ctgacaatat gtgaaaacat agtggcacag    660

tctgtcagaa attctccaga atttcagaaa cttctgggca tcgctatgga actttttctg    720

ctgtgcagtg atgacgcaga gtcagatgtc aggatggtgg ctgacgaatg cctcaacaaa    780

gttatcaaag ctttgatgga ttctaatctt ccaaggttac agctcgagct ctataaggaa    840

attaaaaaga atggtgcccc tcggagtttg cgtgctgccc tgtggaggtt tgctgagctg    900

gctcacctgg ttcggcctca gaaatgcagg ccttacctgg tgaaccttct gccgtgcctg    960

actcgaacaa gcaagagacc cgaagaatca gtccaggaga ccttggctgc agctgttccc   1020

aaaattatgg cttcttttgg caattttgca aatgacaatg aaattaaggt tttgttaaag   1080

gccttcatag cgaacctgaa gtcaagctcc cccaccattc ggcggacagc ggctggatca   1140

gcagtgagca tctgccagca ctcaagaagg acacaatatt tctatagttg gctactaaat   1200

gtgctcttag gcttactcgt tcctgtcgag gatgaacact ccactctgct gattcttggc   1260

gtgctgctca ccctgaggta tttggtgccc ttgctgcagc agcaggtcaa ggacacaagc   1320

ctgaaaggca gcttcggagt gacaaggaaa gaaatggaag tctctccttc tgcagagcag   1380

cttgtccagg tttatgaact gacgttacat catacacagc accaagacca caatgttgtg   1440

accggagccc tggagctgtt gcagcagctc ttcagaacgc ctccacccga gcttctgcaa   1500
```

```
<210> SEQ ID NO 55
<211> LENGTH: 20
<212> TYPE: DNA
<213> ORGANISM: Artificial sequence
<220> FEATURE:
<223> OTHER INFORMATION: PCR Primer Sequence

<400> SEQUENCE: 55

tggtgttcaa tgcttttccc                                                  20


<210> SEQ ID NO 56
<211> LENGTH: 20
<212> TYPE: DNA
<213> ORGANISM: Artificial sequence
<220> FEATURE:
<223> OTHER INFORMATION: PCR Primer Sequence

<400> SEQUENCE: 56

gcgtcttgta gttcccgtca                                                  20


<210> SEQ ID NO 57
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 57

aagtagggca catacacacc ccctgtctc                                        29


<210> SEQ ID NO 58
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 58

aagggtgtgt atgtgcccta ccctgtctc                                        29
```

-continued

<210> SEQ ID NO 59
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 59
aagcgctgac agcaaagcca acctgtctc 29

<210> SEQ ID NO 60
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 60
aattggcttt gctgtcagcg ccctgtctc 29

<210> SEQ ID NO 61
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 61
aagaatgttg tagccacagt ccctgtctc 29

<210> SEQ ID NO 62
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 62
aagactgtgg ctacaacatt ccctgtctc 29

<210> SEQ ID NO 63
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 63
aaatcctttc tccaggcagc ccctgtctc 29

<210> SEQ ID NO 64
<211> LENGTH: 29
<212> TYPE: DNA
<213> ORGANISM: Artificial Sequence
<220> FEATURE:
<223> OTHER INFORMATION: DNA Oligonucleotides for producing siRNA

<400> SEQUENCE: 64
aaggctgcct ggagaaagga tcctgtctc 29

<210> SEQ ID NO 65
<211> LENGTH: 23
<212> TYPE: DNA
<213> ORGANISM: Artificial Sequence
<220> FEATURE:

-continued

<223> OTHER INFORMATION: siRNA strand

<400> SEQUENCE: 65
cugaaucgga caaguucuud tdt 23

<210> SEQ ID NO 66
<211> LENGTH: 23
<212> TYPE: DNA
<213> ORGANISM: Artificial Sequence
<220> FEATURE:
<223> OTHER INFORMATION: siRNA strand

<400> SEQUENCE: 66
aagaacuugu ccgauucagd tdt 23

<210> SEQ ID NO 67
<211> LENGTH: 23
<212> TYPE: DNA
<213> ORGANISM: Artificial Sequence
<220> FEATURE:
<223> OTHER INFORMATION: siRNA strand

<400> SEQUENCE: 67
ugaucauugg ugguaucgad tdt 23

<210> SEQ ID NO 68
<211> LENGTH: 23
<212> TYPE: DNA
<213> ORGANISM: Artificial Sequence
<220> FEATURE:
<223> OTHER INFORMATION: siRNA strand

<400> SEQUENCE: 68
ucgauaccac caaugaucad tdt 23

<210> SEQ ID NO 69
<211> LENGTH: 23
<212> TYPE: DNA
<213> ORGANISM: Artificial Sequence
<220> FEATURE:
<223> OTHER INFORMATION: siRNA strand

<400> SEQUENCE: 69
ucaaugguca agaucucaad tdt 23

<210> SEQ ID NO 70
<211> LENGTH: 23
<212> TYPE: DNA
<213> ORGANISM: Artificial Sequence
<220> FEATURE:
<223> OTHER INFORMATION: siRNA strand

<400> SEQUENCE: 70
uugagaucuu gaccauugad tdt 23

<210> SEQ ID NO 71
<211> LENGTH: 23
<212> TYPE: DNA
<213> ORGANISM: Artificial Sequence
<220> FEATURE:
<223> OTHER INFORMATION: siRNA strand

<400> SEQUENCE: 71
uccuuccuca gcaauaccud tdt 23

-continued

<210> SEQ ID NO 72
<211> LENGTH: 23
<212> TYPE: DNA
<213> ORGANISM: Artificial Sequence
<220> FEATURE:
<223> OTHER INFORMATION: siRNA strand

<400> SEQUENCE: 72
agguauugcu gaggaaggad tdt 23

<210> SEQ ID NO 73
<211> LENGTH: 55
<212> TYPE: DNA
<213> ORGANISM: Artificial Sequence
<220> FEATURE:
<223> OTHER INFORMATION: DNA Oligonucleotides for producing siRNA expression cassettes

<400> SEQUENCE: 73
ggtgaagctt gaccaggatg ttgagcgtct gccggtgttt cgtcctttcc acaag 55

<210> SEQ ID NO 74
<211> LENGTH: 54
<212> TYPE: DNA
<213> ORGANISM: Artificial Sequence
<220> FEATURE:
<223> OTHER INFORMATION: DNA Oligonucleotides for producing siRNA expression cassettes

<400> SEQUENCE: 74
cggcgaagct ttttccaaaa aacagacgct caacatcctg gtgaagcttg acca 54

<210> SEQ ID NO 75
<211> LENGTH: 54
<212> TYPE: DNA
<213> ORGANISM: Artificial Sequence
<220> FEATURE:
<223> OTHER INFORMATION: DNA Oligonucleotides for producing siRNA expression cassettes

<400> SEQUENCE: 75
cagctacaca aactgccgta acaaacggac ccggtgtttc gtcctttcca caag 54

<210> SEQ ID NO 76
<211> LENGTH: 54
<212> TYPE: DNA
<213> ORGANISM: Artificial Sequence
<220> FEATURE:
<223> OTHER INFORMATION: DNA Oligonucleotides for producing siRNA expression cassettes

<400> SEQUENCE: 76
cggcgaagct ttttccaaaa aaggtccgtt tgttacggca gctacacaaa ctgc 54

<210> SEQ ID NO 77
<211> LENGTH: 55
<212> TYPE: DNA
<213> ORGANISM: Artificial Sequence
<220> FEATURE:
<223> OTHER INFORMATION: DNA Oligonucleotides for producing siRNA expression cassettes

<400> SEQUENCE: 77
aaactacaca aatttgtggt gtctaaggat accggtgttt cgtcctttcc acaag 55

<210> SEQ ID NO 78
<211> LENGTH: 55

-continued

```
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 78

cggcgaagct tttttccaaa aaatatcctt agacaccaca aactacacaa atttg          55


<210> SEQ ID NO 79
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 79

tgcctacaca aagcatcgca taggttcttg tcggtgtttc gtcctttcca caag           54


<210> SEQ ID NO 80
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 80

cggcgaagct ttttccaaaa aaacaagaac ctatgcgatg cctacacaaa gcat           54


<210> SEQ ID NO 81
<211> LENGTH: 54
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 81

gttgaagctt gaacattcgc atcgcatagg ccggtgtttc gtcctttcca caag           54


<210> SEQ ID NO 82
<211> LENGTH: 53
<212> TYPE: DNA
<213> ORGANISM: Artificial Sequence
<220> FEATURE:
<223> OTHER INFORMATION: DNA Oligonucleotides for producing siRNA
      expression cassettes

<400> SEQUENCE: 82

cggcgaagct ttttccaaaa aacctatgcg atgcgaatgt tgaagcttga aca            53
```

I claim:

1. A medical system for delivering a small interfering RNA into a predetermined location in a brain of a patient comprising:

(a) an intracranial access device;

(b) a deliverable amount of a vector comprising a cassette encoding a short hairpin RNA and comprising SEQ ID NOS: 37-40 or the short hairpin RNA encoded by said cassette; and (c) a delivery means for delivering said cassette or said short hairpin to said location of the brain of said patient through said intracranial access device and further through a stereotactically implanted catheter.

2. A medical system of claim 1 wherein said intracranial access device is an intracranial access port.

3. A medical system of claim 1 wherein said predetermined location is the substantia nigra.

4. A medical system of claim 1 wherein said predetermined location is the hippocampus, the nucleus basalis of Meynert or the cerebral cortex.

5. A medical system of claim 1 wherein said small interfering RNA is complementary to the mRNA for beta amyloid cleaving enzyme type 1, or BACE1.

6. A medical system of claim 1 wherein said delivery means is injection from an external syringe into the intracranial access device which is an intracranial access port.

7. A medical system of claim 1 wherein said delivery means is an infusion pump.

8. A medical system of claim 7 wherein said infusion pump is an electromechanical pump.

9. A medical system of claim 7 wherein said infusion pump is an osmotic pump.

10. A medical system of claim 1 wherein said cassette is within a viral vector.

* * * * *